(12) United States Patent
Wu et al.

(10) Patent No.: US 11,760,761 B2
(45) Date of Patent: Sep. 19, 2023

(54) METHODS AND COMPOSITIONS FOR TARGETING PD-L1

(71) Applicant: Aligos Therapeutics, Inc., South San Francisco, CA (US)

(72) Inventors: Tongfei Wu, Boortmeerbeek (BE); Pierre Jean-Marie Bernard Raboisson, Wavre (BE); Francois Gonzalvez, Antwerp (BE); Antitsa Dimitrova Stoycheva, Half Moon Bay, CA (US); Jerome Deval, Pacifica, CA (US); Cheng Liu, Burlingame, CA (US); Qingling Zhang, Emerald Hills, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/444,947

(22) Filed: Aug. 12, 2021

(65) Prior Publication Data

US 2023/0065527 A1    Mar. 2, 2023

Related U.S. Application Data

(60) Provisional application No. 63/210,423, filed on Jun. 14, 2021, provisional application No. 63/066,689, filed on Aug. 17, 2020.

(51) Int. Cl.

| | | |
|---|---|---|
| *C07D 487/10* | (2006.01) | |
| *C07D 401/14* | (2006.01) | |
| *C07D 471/04* | (2006.01) | |
| *C07D 491/048* | (2006.01) | |
| *C07D 491/107* | (2006.01) | |
| *C07D 519/00* | (2006.01) | |

(52) U.S. Cl.
CPC ......... *C07D 487/10* (2013.01); *C07D 401/14* (2013.01); *C07D 471/04* (2013.01); *C07D 491/048* (2013.01); *C07D 491/107* (2013.01); *C07D 519/00* (2013.01)

(58) Field of Classification Search
None
See application file for complete search history.

(56) References Cited

U.S. PATENT DOCUMENTS

| | | |
|---|---|---|
| 2003/0199516 A1 | 10/2003 | Moser et al. |
| 2004/0167224 A1 | 8/2004 | Oazki et al. |
| 2005/0245527 A1 | 11/2005 | Ozaki et al. |
| 2008/0235883 A1 | 10/2008 | Lagrange et al. |
| 2009/0309488 A1 | 12/2009 | Kato et al. |
| 2012/0252789 A1 | 10/2012 | Stieber et al. |
| 2014/0117329 A1 | 5/2014 | Lee et al. |
| 2014/0225072 A1 | 8/2014 | Kim et al. |
| 2014/0353624 A1 | 12/2014 | Kim et al. |
| 2015/0014645 A1 | 1/2015 | Park et al. |
| 2015/0034919 A1 | 2/2015 | Kim et al. |
| 2015/0090962 A1 | 4/2015 | Kim et al. |
| 2015/0236264 A1 | 8/2015 | Kim et al. |
| 2015/0291548 A1 | 10/2015 | Sago et al. |
| 2016/0190482 A1 | 6/2016 | Jeon et al. |
| 2016/0276595 A1 | 9/2016 | Kim et al. |
| 2016/0308129 A1 | 10/2016 | Stoessel et al. |
| 2017/0012214 A1 | 1/2017 | Pyo et al. |
| 2017/0247320 A1 | 8/2017 | Yoo et al. |
| 2017/0327742 A1 | 11/2017 | Sudo et al. |
| 2018/0215711 A1 | 8/2018 | Lee et al. |
| 2018/0307069 A1 | 10/2018 | Kodera et al. |
| 2018/0307070 A1 | 10/2018 | Fujisawa |

FOREIGN PATENT DOCUMENTS

| | | |
|---|---|---|
| CN | 108794453 | 10/2018 |
| CN | 109265471 | 1/2019 |
| EP | 0409069 | 1/1991 |
| EP | 1972328 | 9/2008 |
| EP | 3540803 | 9/2019 |
| JP | 2009-242540 | 10/2009 |
| JP | 2010-059131 | 3/2010 |
| JP | 2017-037227 | 2/2017 |
| KR | 10-2014-0076170 | 6/2014 |
| KR | 10-2015-0111271 | 10/2015 |
| KR | 10-2015-0144590 | 12/2015 |
| KR | 10-2018-0053121 | 5/2018 |
| KR | 10-2018-0094468 | 8/2018 |
| KR | 10-2019-0007789 | 1/2019 |
| WO | WO 2003/084948 | 10/2003 |
| WO | WO 2008/097428 | 8/2008 |
| WO | WO 2008/151184 | 12/2008 |
| WO | WO 2009/036066 | 3/2009 |
| WO | WO 2009/148015 | 12/2009 |
| WO | WO 2011/072791 | 6/2011 |
| WO | WO 2011/091213 | 7/2011 |
| WO | WO 2012/014943 | 2/2012 |
| WO | WO 2012/070582 | 5/2012 |
| WO | WO 2014/097952 | 6/2014 |
| WO | WO 2015/063046 | 5/2015 |
| WO | WO 2015/086108 | 6/2015 |

(Continued)

OTHER PUBLICATIONS

"IUPAC-IUB Commission on Biochemical Nomenclature Abbreviated Nomenclature of Synthetic Polypeptides (Polymerized Amino Acids)* Revised Recommendations (1971)" *Biochemistry*. (1972) 11(5) :942-944.

(Continued)

*Primary Examiner* — Samantha L Shterengarts
(74) *Attorney, Agent, or Firm* — Knobbe Martens Olson & Bear LLP

(57) ABSTRACT

The present disclosure related to compounds that can be useful as inhibitors of PD-1, PD-L1 or the PD-1/PD-L1 interaction. Also disclosed herein are pharmaceutical compositions of that can include a compound of Formula (I), or a pharmaceutically acceptable salt thereof, and uses of or methods of using a compound of Formula (I), or a pharmaceutically acceptable salt thereof, for the treatment of PD-L1 related diseases including but not limited to liver diseases, cancer, hepatocellular carcinoma, viral diseases, or hepatitis B.

26 Claims, No Drawings

(56) References Cited

FOREIGN PATENT DOCUMENTS

| | | |
|---|---|---|
| WO | WO 2015/197028 | 12/2015 |
| WO | WO 2016/032120 | 3/2016 |
| WO | WO 2016/104165 | 6/2016 |
| WO | WO 2016/178463 | 11/2016 |
| WO | WO 2017/026272 | 2/2017 |
| WO | WO 2017/026479 | 2/2017 |
| WO | WO 2017/136556 | 8/2017 |
| WO | WO 2018/195321 | 10/2018 |
| WO | WO 2019/124345 | 6/2019 |
| WO | WO 2019/127008 | 7/2019 |
| WO | WO 2019/160882 | 8/2019 |
| WO | WO 2019/190101 | 10/2019 |
| WO | WO 2019/204609 | 10/2019 |
| WO | WO 2019/212290 | 11/2019 |
| WO | WO 2019/226991 | 11/2019 |
| WO | WO 2019/231226 | 12/2019 |
| WO | WO 2020/006724 | 1/2020 |
| WO | WO 2020/007322 | 1/2020 |
| WO | WO 2020/014643 | 1/2020 |
| WO | WO 2020/086739 | 4/2020 |
| WO | WO 2020/143385 | 7/2020 |
| WO | WO 2021/158481 | 8/2021 |
| WO | WO 2021/236771 | 11/2021 |
| WO | WO 2022/266236 | 12/2022 |

OTHER PUBLICATIONS

International Search Report and Written Opinion dated Oct. 8, 2021 for PCT Application No. PCT/US2021/045696, filed Aug. 12, 2021.
International Preliminary Report on Patentability dated Mar. 2, 2023 for PCT Application PCT/US2021/045696, filed Aug. 12, 2021.

METHODS AND COMPOSITIONS FOR TARGETING PD-L1

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 63/066,689, filed Aug. 17, 2020, and 63/210,423, filed Jun. 14, 2021.

FIELD

The present application relates to the fields of chemistry, biochemistry, molecular biology and medicine. The present disclosure related to compounds that can be useful as inhibitors of PD-1, PD-L1 or the PD-1/PD-L1 interaction. Also disclosed herein are pharmaceutical compositions of compounds described herein and uses of or methods of using the compounds for the treatment of PD-L1 related diseases including but not limited to liver diseases, cancer, hepatocellular carcinoma, viral diseases, or hepatitis B.

BACKGROUND

The programmed cell death 1 (PD-1) immune checkpoint expressed on the surface of activated $CD4^+$ and $CD8^+$ T cells controls an inhibitory mechanism to prevent autoimmunity. Engagement of PD-1 by programmed death-ligand 1 (PD-L1) expressed on the multitude of cell types, including macrophages, dendritic cells, mast cells as well as cancer cells induces T cell exhaustion resulting in reduction or loss of effector cytokine production (e.g. IL-2, TNF-α, IFN-γ) and upregulation of other inhibitory receptors and immune checkpoints (e.g. CTLA-4, LAG-3, and BTLA), or T cell apoptosis. High expression of PD-L1 is exhibited by many types of cancers to escape tumor immune surveillance and has been associated with poorer prognosis. PD-1-mediated immunosuppression is also linked to some viral infections, such as hepatitis B. There is an ongoing need for PD-1/PD-L1 therapies and improvements thereof for the treatment of disease.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

DETAILED DESCRIPTION

Hepatocellular carcinoma (HCC) is the most common form of liver cancer. HCC can be caused by a variety of conditions, such as alcohol consumption, cirrhosis, and viral infections that cause hepatitis, such as hepatitis B virus, hepatitis C virus, and hepatitis D virus. The inflammation, fibrosis, and cirrhosis linked with these conditions can induce malignancies in affected liver cells. HCC has relatively poor prognosis, with a five-year survival rate of about 30%, depending on if full surgical resection of the tumor is possible.

For early disease, surgical resection is used. However, most HCC are identified at later stages because of difficulties in diagnosing. Upon late stage diagnosis, the tumors are unresectable and most patients are given systemic therapies. The current standard of care in front line are multi-kinase inhibitors (including, for example, sorafenib and/or lenvatinib). Most patients are refractory or relapse from these treatments, and undergo second line therapies that have anti-angiogenic agents (including, for example, Regorafinib, Cabozantinib, and/or Ramicirumab) or immune checkpoint inhibitors (including, for example, nivolumab and/or pembrolizumab). However, most patients do not respond to first and second therapies, and the clinical benefit is poor, with overall survival not exceeding one year. In addition, biomarker driven therapies are lacking. Thus, there is a need to develop more tolerable and efficacious therapies for the treatment of HCC and related liver disorders.

HBV is a partially double-stranded circular DNA of about 3.2 kilobase (kb) pairs, and is classified into eight genotypes, A to H. The HBV replication pathway has been studied in great detail. One part of replication includes the formation of the covalently closed circular DNA (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of an HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Programmed cell death 1, or programmed death 1 (PD-1) is a 268 amino acid long type I transmembrane protein found as a surface marker on T cells and other immune cells. As an immune checkpoint, PD-1 serves to negatively regulate immune responses to prevent autoimmune disorder. PD-1 protein (NCBI accession number NP_005009.2) is expressed from the cluster of differentiation 279 (CD279) gene (NCBI accession number NG_012110.1) or mRNA transcript (NCBI accession number NM_005018.3). In some preferred embodiments, PD-1 is the human PD-1 protein, and CD279 is the human CD279 transcript or gene on chromosome 2. It should be understood that a person with ordinary skill in the art would view the terms PD-1 and CD279 as often nominally interchangeable when considering the nucleic acid (DNA or RNA) or corresponding translated protein, or the sequences thereof.

Programmed cell death-ligand 1, or programmed death-ligand 1 (PD-L1), also known as B7 homolog 1 (B7-H1) is 272 amino acid long type I transmembrane protein found as a surface marker on many different cell types. PD-L1 is a major ligand of PD-1 and results in inhibition of T cell cytotoxicity and cytokine production. Cancer cells such as HCC cells take advantage of this immune checkpoint by upregulating PD-L1 expression, resulting in dysfunctional anti-tumor immunity by proximal T cells. Viruses also have been observed to modulate the PD-1/PD-L1 pathway to inhibit immune host response. Hepatitis B virus has been shown to upregulate PD-L1 in infected hepatocytes, and PD-1 in associated T cells. PD-L1 protein (NCBI accession number NP_054862.1) is expressed from the cluster of differentiation 274 (CD274) transcript (NCBI accession number NM_014143.4). In some preferred embodiments, PD-L1 is the human PD-L1 protein, and CD274 is the human CD274 transcript or gene on chromosome 9. It should be understood that a person with ordinary skill in the art would view the terms PD-L1 and CD274 as often nominally interchangeable when considering the nucleic acid (DNA or RNA) or corresponding translated protein, or the sequences thereof.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. To the extent publications and patents or patent applications incorporated by reference contradict the disclosure contained in the specification, the specification is intended to supersede and/or take precedence over any such contradictory material. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amine and a di-substituted amine.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. In some instances, an alkoxy can be —OR, wherein R is an unsubstituted $C_{1-4}$ alkyl. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydropropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. In some instances, a haloalkoxy can be —OR, wherein R is a $C_{1-4}$ alkyl substituted by 1, 2 or 3 halogens. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a —C(=O)— group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

A "mono-substituted amine" refers to a "—NH$R_A$" in which $R_A$ can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NH$R_A$, wherein $R_A$ can be an unsubstituted $C_{1-6}$ alkyl or an unsubstituted or a substituted benzyl.

A "di-substituted amine" refers to a "—N$R_AR_B$" in which $R_A$ and $R_B$ can be independently can be independently alkyl, alkenyl, alkynyl, cycloalkyl, cycloalkenyl, aryl, heteroaryl, heterocyclyl, aryl(alkyl), heteroaryl(alkyl) or heterocyclyl (alkyl). A mono-substituted amine may be substituted or unsubstituted. In some instances, a mono-substituted amine can be —NR$_A$R$_B$, wherein R$_A$ and R$_B$ can be independently an unsubstituted C$_{1-6}$ alkyl or an unsubstituted or a substituted benzyl.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt (for example, ammonium or triethylammonium salt), an alkali metal salt, such as a lithium, a sodium or a potassium salt, an alkaline earth metal salt, such as a calcium or a magnesium salt, a salt of organic bases such as dicyclohexylamine, N-methyl-D-glucamine, tris(hydroxymethyl)methylamine, C$_1$-C$_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

COMPOUNDS

Examples of embodiments of the present application include the following:

Embodiment 1

A compound of Formula (I), or a pharmaceutically acceptable salt thereof, having the structure:

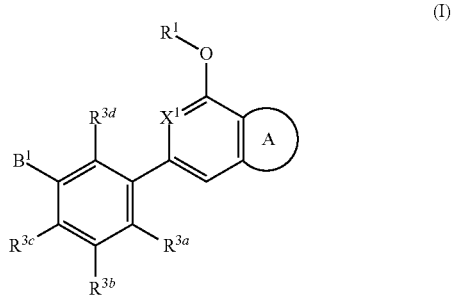

(I)

wherein:
X$^1$ can be N (nitrogen) or CH;
Ring A can be selected from:
 a monocyclic C$_{5-7}$ cycloalkyl substituted with R$^{2a1}$;
 a bicyclic C$_{6-12}$ cycloalkyl substituted with R$^{2a2}$;

a 5-7 membered nitrogen-containing monocyclic heterocyclyl, wherein a nitrogen of the 5-7 membered nitrogen-containing monocyclic heterocyclyl is optionally substituted with $R^{2a3}$, wherein a carbon of the 5-7 membered nitrogen-containing monocyclic heterocyclyl is optionally substituted with $R^{2a4}$ or $R^{2a5}$, and wherein when $R^{2a5}$ is present, $R^{2a5}$ is attached at a carbon atom adjacent to a nitrogen of the 5-7 membered nitrogen-containing monocyclic heterocyclyl;

a 6-12 membered nitrogen-containing bicyclic heterocyclyl, wherein a nitrogen of the 6-12 membered nitrogen-containing bicyclic heterocyclyl is optionally substituted with $R^{2a6}$;

a 5-7 membered oxygen-containing monocyclic heterocyclyl substituted with $R^{2a7}$ or $R^{2a8}$, wherein when $R^{2a8}$ is present, $R^{2a8}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens; and wherein Ring A can be optionally further substituted;

$B^1$ can be selected from:

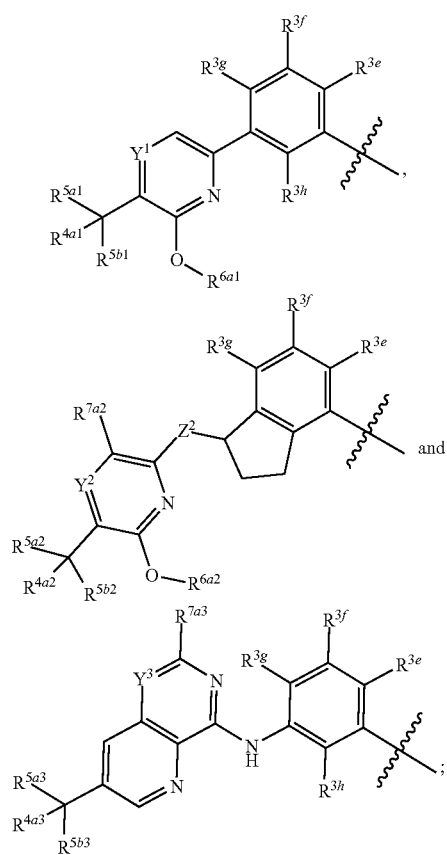

$Y^1$ and $Y^2$ can be independently N (nitrogen) or —$CR^8$, wherein $R^8$ can be selected from hydrogen, —$C_{1-4}$ alkyl, and —$C_{1-4}$ haloalkyl;

$Y^3$ can be independently N (nitrogen) or CH;

$Z^2$ can be O (oxygen) or NH;

$R^1$, $R^{6a1}$ and $R^{6a2}$ can be independently selected from —$C_{1-4}$ alkyl, —$C_{1-4}$ haloalkyl, -monocyclic $C_{3-6}$cycloalkyl, —($C_{1-4}$ alkyl)monocyclic $C_{3-6}$cycloalkyl, 4-6 membered monocyclic heterocyclic ring, aryl($C_{1-4}$alkyl) and —($C_{1-4}$alkyl) 5- or 6-membered monocyclic heteroaryl; wherein the —$C_{3-6}$cycloalkyl, the 4-6 membered monocyclic heterocyclyl, the aryl($C_{1-4}$alkyl) and the -5- or 6-membered monocyclic heteroaryl($C_{1-4}$alkyl) is optionally substituted with one or two or three substituents independently selected from halogen, CN, $C_{1-4}$ alkyl, $C_{3-6}$ monocyclic cycloalkyl and $C_{1-4}$ alkoxy;

$R^{2a1}$, $R^{2a2}$ and $R^{2a7}$ can be independently selected from amino, —N($R^{m1}$)$R^{n1}$, —($C_{3-6}$ monocyclic cycloalkyl) N($R^{m2}$)$R^{n2}$, -$R^{x1}$ and —($C_{1-4}$ alkyl)$R^{x1}$, $R^{m1}$ and $R^{m2}$ can be independently selected from hydrogen, —$C_{1-4}$ alkyl, $C_{3-6}$ monocyclic cycloalkyl, $C_{5-12}$ bicyclic cycloalkyl, 5- or 6-membered monocyclic heteroaryl, 4-7 membered monocyclic heterocyclyl, 8-11 membered fused-heteroaryl, 8-11 membered fused-heterocyclyl and -$R^{x2}$; wherein the monocyclic heteroaryl, the bicyclic heteroaryl the monocyclic heterocyclyl and the bicyclic heterocyclyl contain at least one heteroatom independently selected from O (oxygen), S (sulfur), C(=O), S(=O), S(=O)$_2$ and N (nitrogen); wherein the —$C_{1-4}$ alkyl is optionally substituted with one or two or three substituents independently selected from halogen, cyano, hydroxy, —$C_{1-4}$ alkoxy, —$C_{1-4}$ haloalkyl, —$C_{1-4}$ haloalkoxy, —C(=O)O$R^{Z1}$, —C(=O)NHS(=O)$_2$$R^{Z3}$, —C(=O)N($R^{Z1}$)$R^{Z2}$, —S(=O)$_2$$R^{Z3}$, —S(=O)$_2$N($R^{Z1}$)$R^{Z2}$, —N($R^{Z1}$)C(=O)$R^{Z3}$, —N($R^{Z1}$)S(=O)$R^{Z3}$, —N($R^{Z1}$)C(=O)N($R^{Z2}$)$R^{Z3}$ and —N($R^{Z1}$)S(=O)N($R^{Z2}$)$R^{Z3}$; wherein the $C_{3-6}$ monocyclic cycloalkyl, the $C_{3-6}$ monocyclic cycloalkyl($C_{1-4}$ alkyl), the 5- or 6-membered monocyclic heteroaryl, the 4-7 membered monocyclic heterocyclyl, the 8-11 membered fused-heteroaryl, the 8-11 membered fused-heterocyclyl and the 4-7 membered monocyclic heterocyclyl(CH$_2$) are optionally substituted with one or two or three substituents independently selected from halogen, cyano, —$C_{1-4}$ alkyl, hydroxy, —$C_{1-4}$ alkoxy, —$C_{1-4}$ haloalkyl, —$C_{1-4}$ haloalkoxy, —C(=O)O$R^{Z1}$, —C(=O)NHS(=O)$_2$$R^{Z3}$, —C(=O)N($R^{Z1}$)$R^{Z2}$, —S(=O)$_2$$R^{Z3}$, —S(=O)$_2$N($R^{Z1}$)$R^{Z2}$, —N($R^{Z1}$)C(=O)$R^{Z3}$, —N($R^{Z1}$)S(=O)$R^{Z3}$, —N($R^{Z1}$)C(=O)N($R^{Z2}$)$R^{Z3}$ and —N($R^{Z1}$)S(=O)N($R^{Z2}$)$R^{Z3}$; and $R^{n1}$ and $R^{n2}$ can be hydrogen, —$C_{1-4}$ alkyl, —$C_{1-4}$ halolkyl or $C_{3-6}$ monocyclic cycloalkyl (CH$_2$);

$R^{2a3}$ and $R^{2a6}$ can be independently selected from hydrogen, —$C_{1-4}$ alkyl, $C_{3-6}$ monocyclic cycloalkyl, $C_{5-12}$ bicyclic cycloalkyl, 5- or 6-membered monocyclic heteroaryl, 4-7 membered monocyclic heterocyclyl, 8-11 membered fused-heteroaryl, 8-11 membered fused-heterocyclyl and -$R^{x2}$; wherein the monocyclic heteroaryl and the monocyclic heterocyclyl contain at least one heteroatom independently selected from O (oxygen), S (sulfur), C(=O), S(=O), S(=O)$_2$ and N (nitrogen); wherein the —$C_{1-4}$ alkyl, the —$C_{3-6}$ monocyclic cycloalkyl, the —$C_{3-6}$ monocyclic cycloalkyl($C_{1-4}$ alkyl), the 5- or 6-membered monocyclic heteroaryl, the 4-7 membered monocyclic heterocyclyl and the 4-7 membered monocyclic heterocyclyl(CH$_2$) are optionally substituted with one or two or three substituents independently selected from halogen, cyano, hydroxy, —$C_{1-4}$ alkoxy, —$C_{1-4}$ haloalkoxy, —C(=O)O$R^{Z1}$, —C(=O)NHS(=O)$_2$$R^{Z3}$, —C(=O)N($R^{Z1}$)$R^{Z2}$, —S(=O)$_2$$R^{Z3}$, —S(=O)$_2$N($R^{Z1}$)$R^{Z2}$, —NHC(=O)$R^{Z3}$, —NHC(=O)N($R^{Z1}$)$R^{Z3}$ and —N($R^{Z1}$)S(=O)$_2$N($R^{Z2}$)$R^{Z3}$;

$R^{2a4}$ can be selected from halogen, —$C_{1-4}$ alkyl, —C(=O)OR$^{Z4}$, —OR$^{Z4}$, —N(R$^{Z3}$)R$^{Z3}$ and —$C_{3-7}$ cycloalkyl; wherein the —$C_{1-4}$ alkyl and the —$C_{3-7}$ cycloalkyl are optionally substituted with one or two or three substituents independently selected from halogen, cyano, hydroxy, —$C_{1-4}$ alkoxy, —$C_{1-4}$ haloalkoxy, —C(=O)OR$^{Z1}$, —C(=O)NHS(=O)$_2$R$^{Z3}$, —C(=O)N(R$^{Z1}$)R$^{Z2}$, —S(=O)$_2$R$^{Z3}$, —S(=O)$_2$N(R$^{Z1}$)R$^{Z2}$, —NHC(=O)R$^{Z3}$, —NHC(=O)N(R$^{Z1}$)R$^{Z3}$ and —N(R$^{Z1}$)S(=O)$_2$N(R$^{Z2}$)R$^{Z3}$; wherein R$^{m3}$ and R$^{n3}$ can be independently selected from hydrogen, —$C_{1-4}$ alkyl and —$C_{3-6}$ monocyclic cycloalkyl; and R$^{Z4}$ can be selected from hydrogen, —$C_{1-4}$ alkyl, —$C_{1-4}$ haloalkyl and —$C_{3-6}$ cycloalkyl;

$R^{2a5}$ and $R^{2a8}$ can be independently selected from —$C_{1-4}$ alkyl, —C(=O)OR$^{Z5}$, —$C_{3-6}$ monocyclic cycloalkyl and —(C$_{1-4}$ alkyl)R$^{x1}$; wherein the —$C_{1-4}$ alkyl and the —$C_{3-6}$ monocyclic cycloalkyl are optionally substituted with one or two or three substituents independently selected from halogen, cyano, hydroxy, —$C_{1-4}$ alkoxy, —$C_{1-4}$ haloalkoxy, —C(=O)OR$^{Z1}$, —C(=O)NHS(=O)$_2$R$^{Z3}$, —C(=O)N(R$^{Z1}$)R$^{Z2}$, —S(=O)$_2$R$^{Z3}$, —S(=O)$_2$N(R$^{Z1}$)R$^{Z2}$, —NHC(=O)R$^{Z3}$, —NHC(=O)N(R$^{Z1}$)R$^{Z3}$ and —N(R$^{Z1}$)S(=O)$_2$N(R$^{Z2}$)R$^{Z3}$; and wherein R$^{Z5}$ can be hydrogen, —$C_{1-4}$ alkyl, —$C_{1-4}$ haloalkyl and —$C_{3-6}$ cycloalkyl;

$R^{3a}$, $R^{3b}$, $R^{3c}$, $R^{3e}$, $R^{3f}$ and $R^{3g}$ can be independently selected from hydrogen and halogen;

$R^{3d}$ and $R^{3h}$ can be independently selected from hydrogen, halogen, cyano, —CH$_3$, —CH$_2$CH$_3$, —CH$_2$OH, —OCH$_3$ and —SCH$_3$;

$R^{4a1}$, $R^{4a2}$ and $R^{4a3}$ can be independently selected from amino, —NR$^{p1}$R$^{q1}$, —(C$_{3-6}$ monocyclic cycloalkyl)N(R$^{p2}$)R$^{g2}$, -R$^{y1}$ and —(C$_{1-4}$ alkyl)R$^{y1}$;

$R^{p1}$ and $R^{p2}$ can be independently selected from hydrogen, —$C_{1-4}$ alkyl, $C_{3-6}$ monocyclic cycloalkyl, $C_{5-12}$ bicyclic cycloalkyl, 5- or 6-membered monocyclic heteroaryl, 4-7 membered monocyclic heterocyclyl, 8-11 membered fused-heteroaryl, 8-11 membered fused-heterocyclyl and -R$^{y2}$; wherein the monocyclic heteroaryl, the bicyclic heteroaryl the monocyclic heterocyclyl and the bicyclic heterocyclyl contain at least one heteroatom independently selected from the group consisting of O (oxygen), S (sulfur), C(=O), S(=O), S(=O)$_2$ and N (nitrogen); wherein the —$C_{1-4}$ alkyl is optionally substituted with one or two or three substituents independently selected from halogen, cyano, -hydroxy, —$C_{1-4}$ alkoxy, —$C_{1-4}$ haloalkyl, —$C_{1-4}$ haloalkoxy, —C(=O)OR$^{W1}$, —C(=O)NHS(=O)$_2$R$^{W3}$, —C(=O)N(R$^{W1}$)R$^{W2}$, —S(=O)$_2$R$^{W3}$, —S(=O)N(R$^{W1}$)R$^{W2}$, —N(R$^{W1}$)C(=O)R$^{W3}$, —N(R$^{W1}$)S(=O)R$^{W3}$, —N(R$^{W1}$)C(=O)N(R$^{W2}$)R$^{W3}$ and —N(R$^{W1}$)S(=O)N(R$^{W2}$)R$^{W3}$; wherein the C$_{3-6}$ monocyclic cycloalkyl, the C$_{3-6}$ monocyclic cycloalkyl(C$_{1-4}$ alkyl), the 5- or 6-membered monocyclic heteroaryl, the 4-7 membered monocyclic heterocyclyl, the 8-11 membered fused-heteroaryl, the 8-11 membered fused-heterocyclyl and the 4-7 membered monocyclic heterocyclyl(CH$_2$) are optionally substituted with one or two or three substituents independently selected from halogen, cyano, —$C_{1-4}$ alkyl, hydroxy, —$C_{1-4}$ alkoxy, —$C_{1-4}$ haloalkyl, —$C_{1-4}$ haloalkoxy, —C(=O)OR$^{W1}$, —C(=O)NHS(=O)$_2$R$^{W3}$, —C(=O)N(R$^{W1}$)R$^{W2}$, —S(=O)$_2$R$^{W3}$, —S(=O)N(R$^{W1}$)R$^{W2}$, —N(R$^{W1}$)C(=O)R$^{W3}$, —N(R$^{W1}$)S(=O)R$^{W3}$, —N(R$^{W1}$)C(=O)N(R$^{W2}$)R$^{W3}$ and —N(R$^{W1}$)S(=O)N(R$^{W2}$)R$^{W3}$; and R$^{p1}$ and R$^{q2}$ can be independently hydrogen, —$C_{1-4}$ alkyl, —$C_{1-4}$ halolkyl or C$_{3-6}$ monocyclic cycloalkyl(CH$_2$);

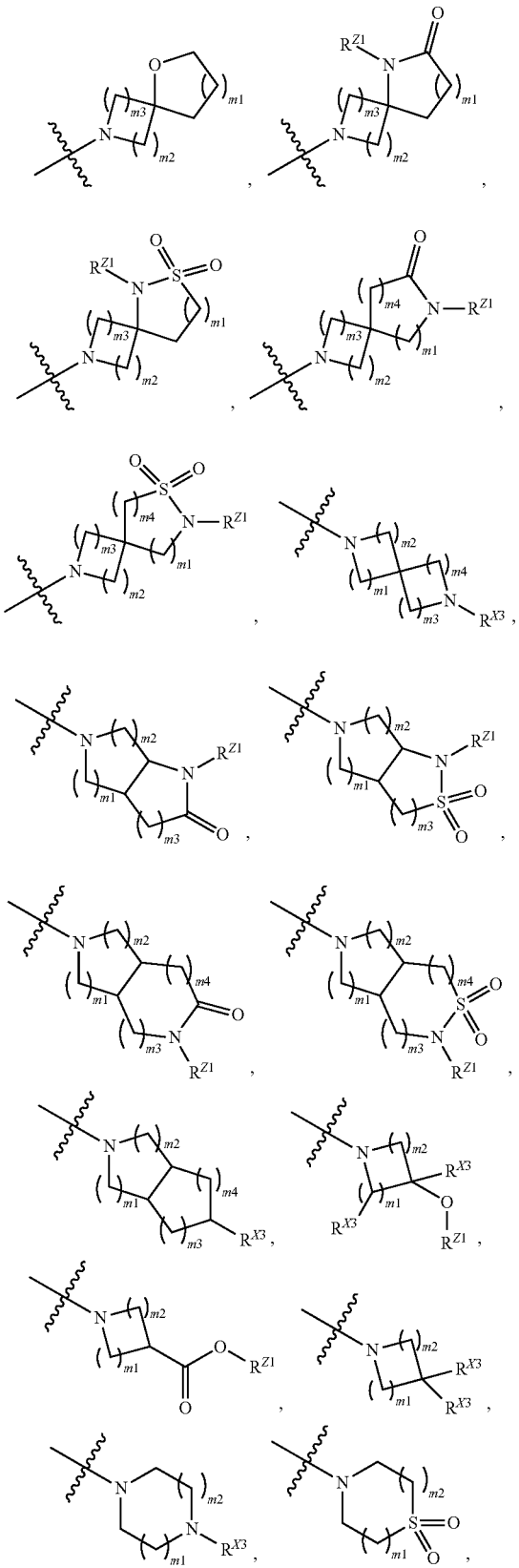

-continued

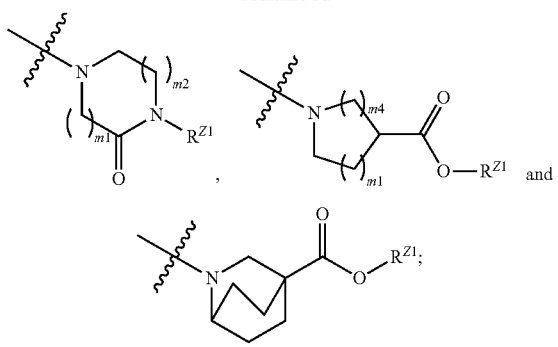

wherein $R^{x1}$ is optionally substituted with one or two substituents independently selected from halogen, cyano, —$C_{1-4}$ alkyl, hydroxy, —$C_{1-4}$ alkoxy, —$C_{1-4}$ haloalkyl, —$C_{1-4}$ haloalkoxy, —C(=O)O$R^{Z1}$, —C(=O)NHS(=O)$_2R^{Z3}$, —C(=O)N($R^{Z1}$)$R^{Z2}$, —S(=O)$_2R^{Z3}$, —S(=O)$_2$N($R^{Z1}$)$R^{Z2}$, —N($R^{Z1}$)C(=O)$R^{Z3}$, —N($R^{Z1}$)S(=O)$R^{Z3}$, —N($R^{Z1}$)C(=O)N($R^{Z1}$)$R^{Z3}$ and —N($R^{Z1}$)S(=O)$_2$N($R^{Z2}$)$R^{Z3}$;

$R^{x2}$ can be selected from:

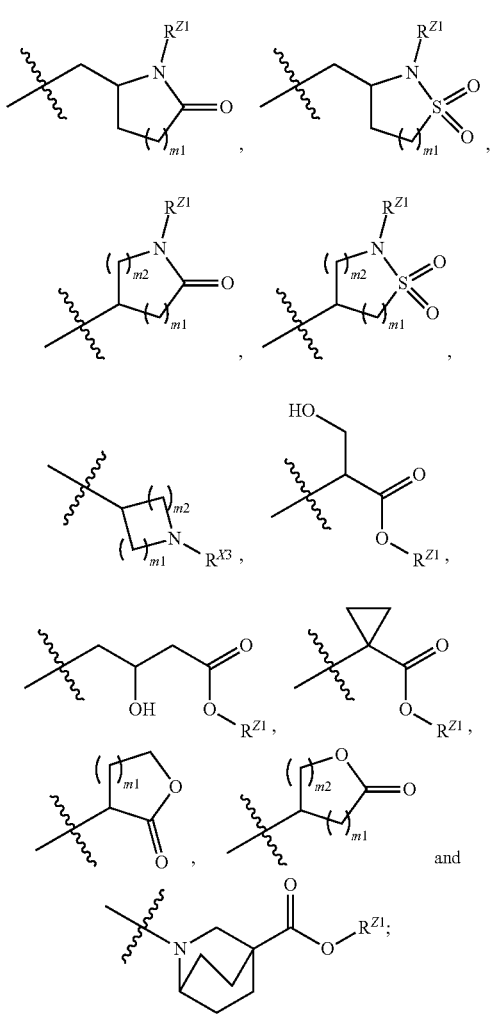

$R^{y1}$ can be selected from:

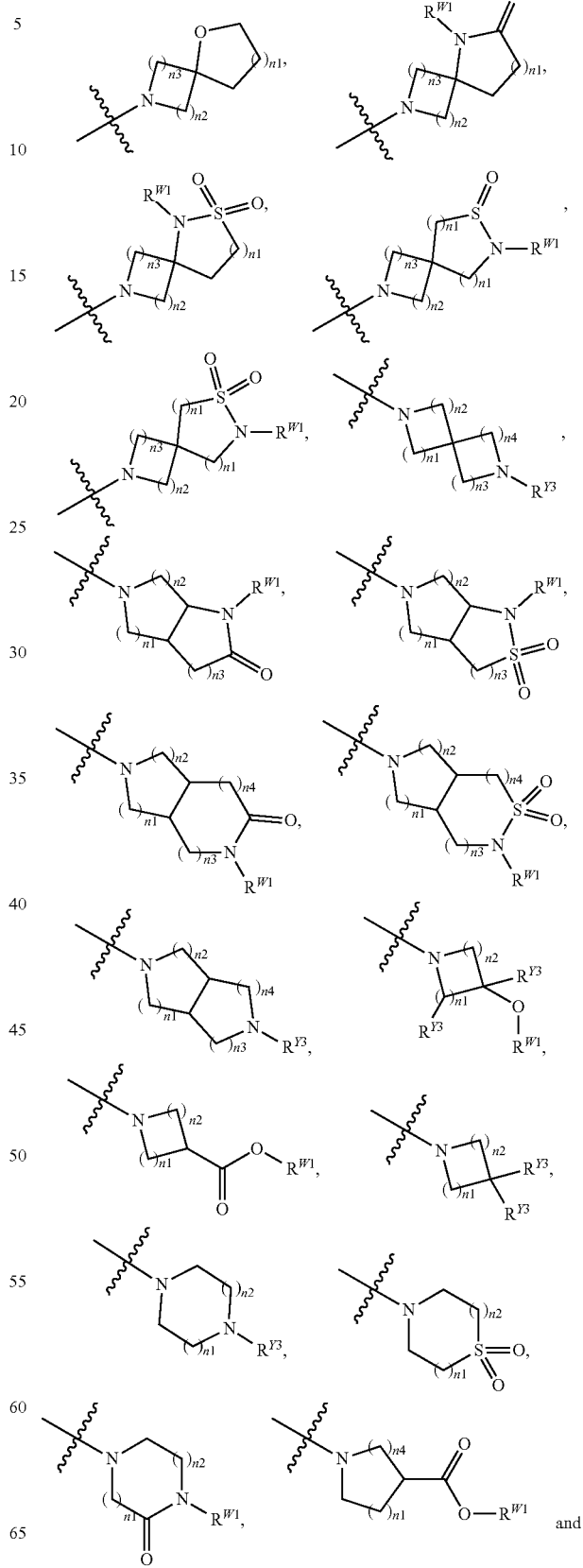

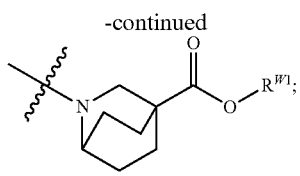

wherein $R^{y1}$ is optionally substituted with one or two substituents independently selected from halogen, cyano, —$C_{1-4}$ alkyl, hydroxy, —$C_{1-4}$ alkoxy, —$C_{1-4}$ haloalkyl, —$C_{1-4}$ haloalkoxy, —$C(=O)OR^{W1}$, —$C(=O)NHS(=O)_2R^{W3}$, —$C(=O)N(R^{W1})R^{W2}$, —$S(=O)_2R^{W3}$, —$S(=O)N(R^{W1})R^{W2}$, —$N(R^{W1})C(=O)R^{W3}$, —$N(R^{W1})S(=O)R^{W3}$, —$N(R^{W1})C(=O)N(R^{W2})R^{W3}$ and —$N(R^{W1})S(=O)N(R^{W2})R^{W3}$;

$R^{y2}$ can be selected from:

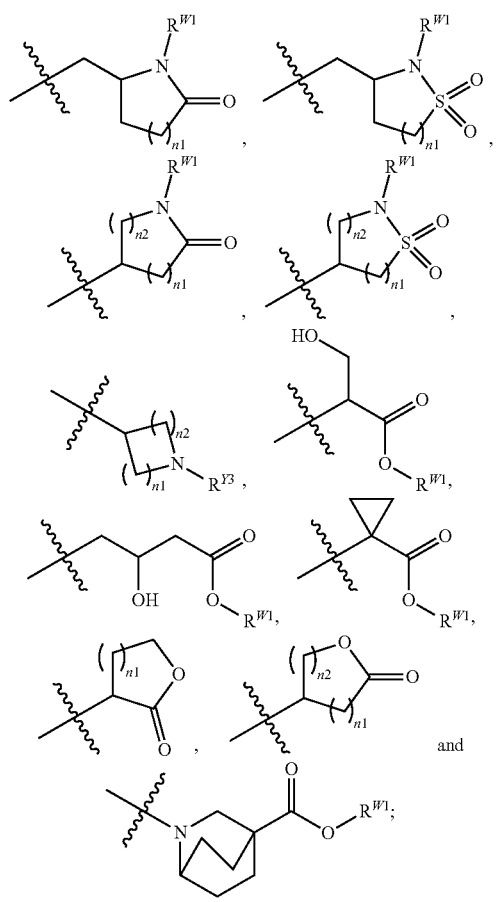

$R^{5a1}$ and $R^{5b1}$ can be independently selected from hydrogen, —$C_{1-4}$ alkyl, —$C_{1-4}$ haloalkyl, —$C_{1-4}$ alkoxy and —$C_{1-4}$ haloalkoxy; or $R^{5a1}$ and $R^{5b1}$ can be taken together along with the atom to which $R^{5a1}$ and $R^{5b1}$ are attached to form monocyclic —$C_{3-6}$ cycloalkyl or 4-6 monocyclic heterocyclyl, wherein the —$C_{3-6}$ cycloalkyl or the 4-6 monocyclic heterocyclyl can be optionally further substituted;

$R^{5a2}$ and $R^{5b2}$ can be independently selected from hydrogen, —$C_{1-4}$ alkyl, —$C_{1-4}$ haloalkyl, —$C_{1-4}$ alkoxy and —$C_{1-4}$ haloalkoxy; or $R^{5a2}$ and $R^{5b2}$ can be taken together along with the atom to which $R^{5a2}$ and $R^{5b2}$ are attached to form monocyclic —$C_{3-6}$ cycloalkyl or 4-6 monocyclic heterocyclyl, wherein the —$C_{3-6}$ cycloalkyl or the 4-6 monocyclic heterocyclyl can be optionally further substituted;

$R^{5a3}$ and $R^{5b3}$ can be independently selected from hydrogen, —$C_{1-4}$ alkyl, —$C_{1-4}$ haloalkyl, —$C_{1-4}$ alkoxy and —$C_{1-4}$ haloalkoxy; or $R^{5a3}$ and $R^{5b3}$ can be taken together along with the atom to which $R^{5a3}$ and $R^{5b3}$ are attached to form monocyclic —$C_{3-6}$ cycloalkyl or 4-6 monocyclic heterocyclyl, wherein the —$C_{3-6}$ cycloalkyl or the 4-6 monocyclic heterocyclyl can be optionally further substituted;

$R^{7a2}$ and $R^{7a3}$ can be independently selected from hydrogen, halogen, cyano, —$C_{1-4}$ alkyl, —$C_{1-4}$ haloalkyl, —$C_{1-4}$ alkoxy and —$C_{1-4}$ haloalkoxy;

$m_1$, $m_2$, $m_3$, $n_1$, $n_2$ and $n_3$ can be independently 1 or 2;

$m_4$ and $n_4$ can be independently 0, 1 or 2;

each $R^{X3}$ can be selected from hydrogen, halogen, —$C_{1-4}$ alkyl, —$C_{1-4}$ haloalkyl, —$C(=O)R^{Z3}$, —$C(=O)OR^{Z1}$, —$S(=O)_2R^{Z1}$, —$C(=O)N(R^{Z1})R^{Z2}$ and —$S(=O)N(R^{Z1})R^{Z2}$;

each $R^{Y3}$ can be selected from hydrogen, halogen, —$C_{1-4}$ alkyl, —$C_{1-4}$ haloalkyl, —$C(=O)R^{Z3}$, —$C(=O)OR^{Z3}$, —$S(=O)_2R^{W3}$, —$C(=O)N(R^{W1})R^{W2}$ and —$S(=O)N(R^{W1})R^{W2}$;

$R^{Z1}$, $R^{Z2}$, $R^{W1}$ and $R^{W2}$ can be independently selected from hydrogen, —$C_{1-4}$ alkyl, and —$C_{1-4}$ haloalkyl; and $R^{Z3}$ and $R^{W3}$ can be independently selected from hydrogen, —$C_{1-4}$ alkyl and —$C_{1-4}$ haloalkyl.

Embodiment 2

The compound of Embodiment 1, wherein a compound of Formula (II), or a pharmaceutically acceptable salt thereof, having the structure:

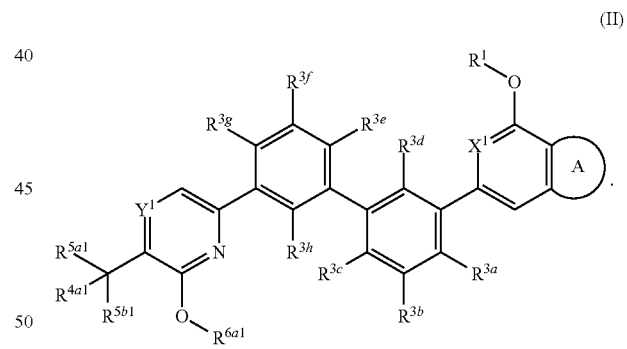

(II)

Embodiment 3

The compound of Embodiment 2, wherein $Y^1$ can be N.

Embodiment 4

The compound of Embodiment 2 or 3; wherein $R^{4a1}$ can be -$R^{y1}$.

Embodiment 5

The compound of Embodiment 2 or 3; wherein $R^{4a1}$ can be —$NR^{p1}R^{q1}$.

Embodiment 6

The compound of any one of Embodiment 2-5, wherein $R^{5a1}$ and $R^{5b1}$ can be each hydrogen.

Embodiment 7

The compound of Embodiment 1, wherein a compound of Formula (III), or a pharmaceutically acceptable salt thereof, having the structure:

(III)

Embodiment 8

The compound of Embodiment 7, wherein $Y^2$ can be N.

Embodiment 9

The compound of Embodiment 7 or 8, wherein $R^{4a2}$ can be -$R^{y1}$.

Embodiment 10

The compound of Embodiment 7 or 8; wherein $R^{4a2}$ can be —$NR^{p1}R^{q1}$.

Embodiment 11

The compound of any one of Embodiment 7-10, wherein $R^{5a2}$ and $R^{5b2}$ can be each hydrogen.

Embodiment 12

The compound of any one of Embodiment 7-11, wherein $R^{7a2}$ can be —$C_{1-4}$ haloalkyl (such as —$CHF_2$ and —$CF_3$).

Embodiment 13

The compound of Embodiment 1, wherein a compound of Formula (IV), or a pharmaceutically acceptable salt thereof, having the structure:

(IV)

Embodiment 14

The compound of Embodiment 13, wherein $Y^3$ can be N.

Embodiment 15

The compound of Embodiment 13 or 14, wherein $R^{4a3}$ can be -$R^{y1}$.

Embodiment 16

The compound of Embodiment 13 or 14; wherein $R^{4a3}$ can be —$NR^{p1}R^{q1}$.

Embodiment 17

The compound of any one of Embodiments 13-16, wherein $R^{5a3}$ and $R^{5b3}$ can be each hydrogen.

Embodiment 18

The compound of any one of Embodiment 7-11, wherein $R^{7a2}$ can be —$C_{1-4}$ haloalkyl (such as —$CHF_2$ and —$CF_3$).

Embodiment 19

The compound of Embodiment 4, 9 or 15, wherein -$R^{y1}$ can be selected from:

Embodiment 20

The compound of Embodiment 19, wherein $n_1$, $n_2$ and $n_3$ can be each 1.

Embodiment 21

The compound of Embodiment 19, wherein $n_1$ can be 1; and $n_2$ can be 2.

Embodiment 22

The compound of Embodiment 5, 10 or 16, wherein —NR$^{p1}$R$^{q1}$; wherein R$^{p1}$ can be -R$^{y2}$; and -R$^{y2}$ can be selected from:

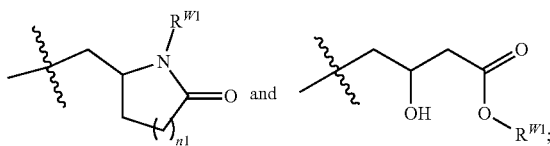

and R$^{q1}$ can be hydrogen.

Embodiment 23

The compound of any one of Embodiments 19-22, wherein R$^{W1}$ can be hydrogen or —C$_{1-4}$ alkyl.

Embodiment 24

The compound of Embodiment 22 or 23, wherein n$_1$ can be 1.

Embodiment 25

The compound of any one of Embodiments 1-24, wherein Ring A can be a monocyclic C$_{5-7}$ cycloalkyl substituted with R$^{2a1}$.

Embodiment 26

The compound of Embodiment 25, wherein the monocyclic C$_{5-7}$ cycloalkyl substituted with R$^{2a1}$ can be selected from:

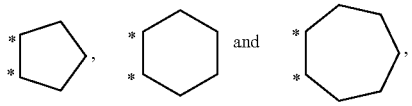 [SMILES: C1CCCC1 ; C1CCCCC1 ; C1CCCCCC1]

wherein asterisks indicate the position of the fused bond.

Embodiment 27

The compound of Embodiment 25 or 26, wherein R$^{2a1}$ can be —N(R$^{m1}$)R$^{n1}$.

Embodiment 28

The compound of Embodiment 27, wherein R$^{2a1}$ can be —N(C$_{1-4}$ alkyl)R$^{n1}$ wherein the C$_{1-4}$ alkyl is optionally substituted with one or two or three substituents independently selected from halogen, cyano, hydroxy, —C$_{1-4}$ alkoxy, —C$_{1-4}$ haloalkyl, —C$_{1-4}$ haloalkoxy, —C(=O)OR$^{Z1}$, —C(=O)NHS(=O)$_2$R$^{Z3}$, —C(=O)N(R$^{Z1}$)R$^{Z2}$, —S(=O)$_2$R$^{Z3}$, —S(=O)$_2$N(R$^{Z1}$)R$^{Z2}$, —N(R$^{Z1}$)C(=O)R$^{Z3}$, —N(R$^{Z1}$)S(=O)$_2$R$^{Z3}$, —N(R$^{Z1}$)C(=O)N(R$^{Z2}$)R$^{Z3}$ and —N(R$^{Z1}$)S(=O)N(R$^{Z2}$)R$^{Z3}$.

Embodiment 29

The compound of Embodiment 27, wherein R$^{m1}$ can be -R$^{x2}$, wherein -R$^{x2}$ can be selected from:

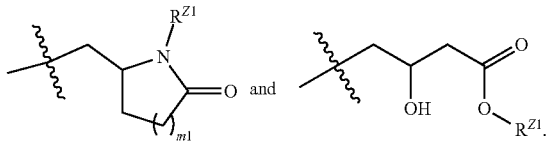

Embodiment 30

The compound of Embodiment 29, wherein m$_1$ can be 1.

Embodiment 31

The compound of Embodiment 25 or 26, wherein R$^{2a1}$ can be -R$^{x1}$.

Embodiment 32

The compound of Embodiment 31, wherein -R$^{x1}$ can be selected from:

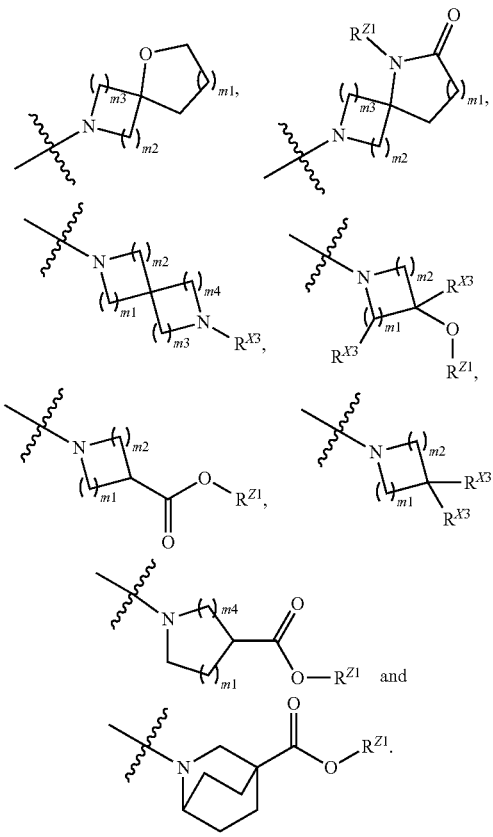

Embodiment 33

The compound of Embodiment 32, wherein m$_1$, m$_2$, m$_3$ and m$_4$ can be each 1.

Embodiment 34

The compound of any one of Embodiments 29, 30, 32 or 33, wherein R$^{Z1}$ can be hydrogen or —C$_{1-4}$ alkyl.

Embodiment 35
The compound of any one of Embodiments 25-34, wherein $R_{n1}$ can be hydrogen.
Embodiment 36
The compound of Embodiment 25 or 26, wherein $R^{2a1}$ can be selected from:
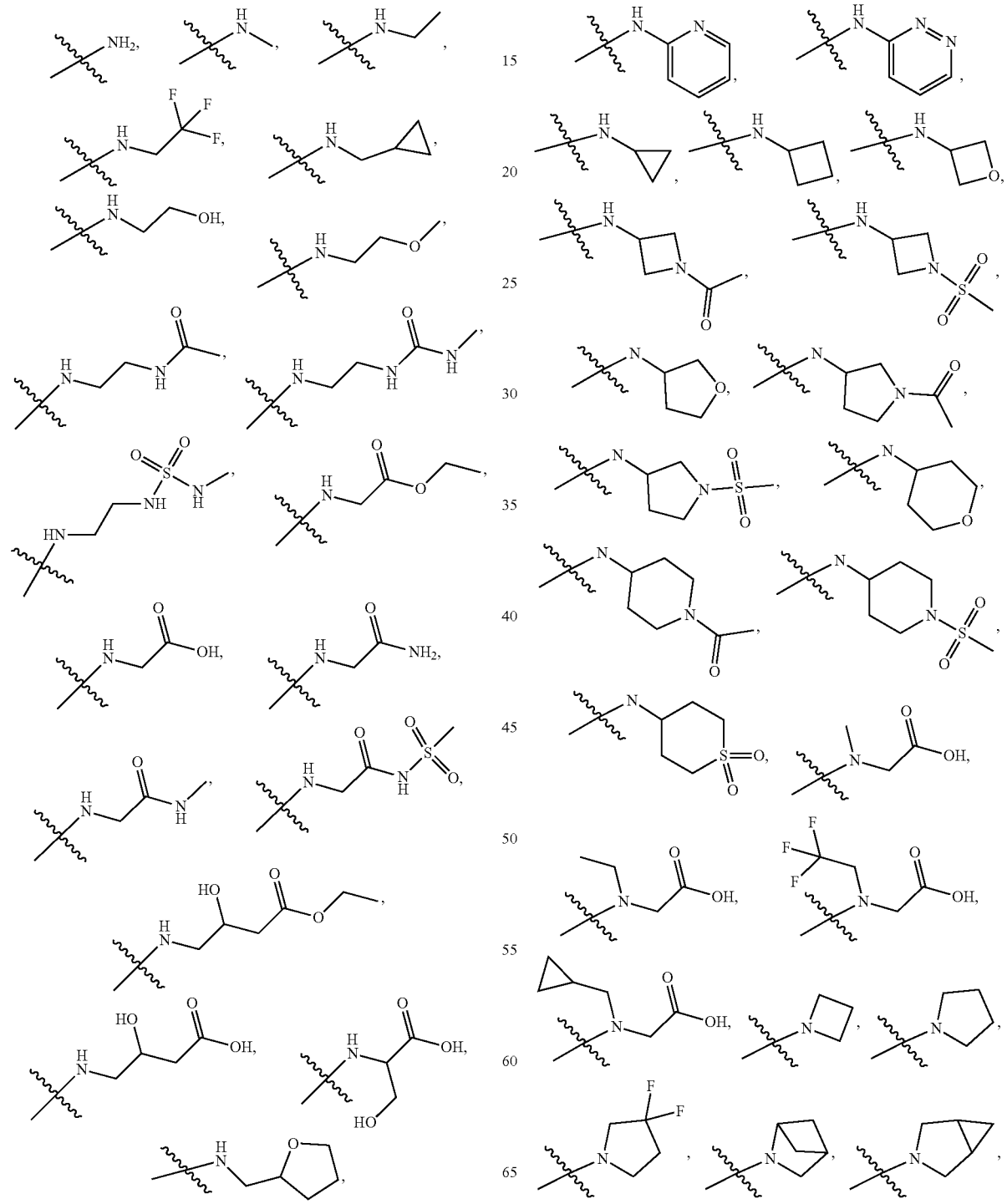

-continued

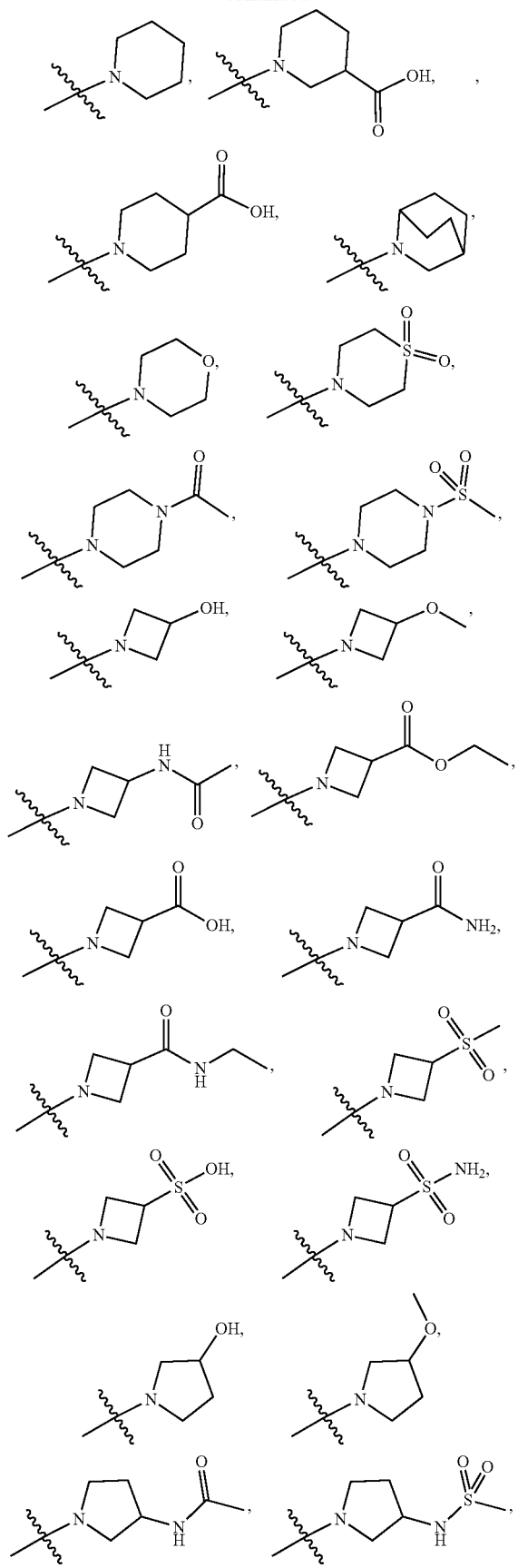

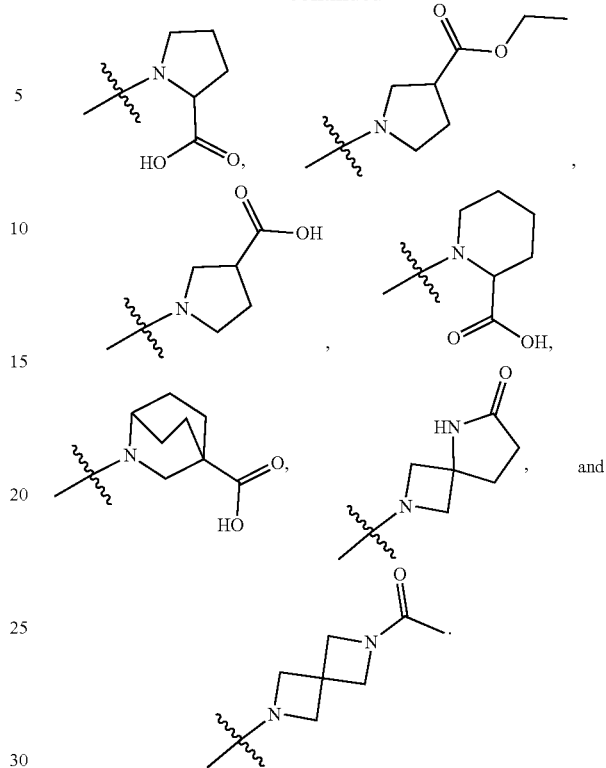

Embodiment 37

The compound of any one of Embodiments 1-24, wherein Ring A can be a bicyclic $C_{6\text{-}12}$ cycloalkyl substituted with $R^{2a2}$.

Embodiment 38

The compound of Embodiment 37, wherein the bicyclic $C_{6\text{-}12}$ cycloalkyl substituted with $R^{2a2}$ can be selected from:

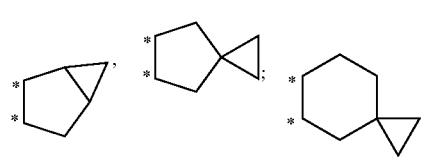

wherein asterisks indicate the position of the fused bond.

Embodiment 39

The compound of Embodiment 37 or 38, wherein $R^{2a2}$ can be $-N(R^{m1})R^{n1}$.

Embodiment 40

The compound of Embodiment 39, wherein $R^{2a2}$ can be $-N(C_{1\text{-}4}\text{ alkyl})R^{n1}$ wherein the $C_{1\text{-}4}$ alkyl is optionally substituted with one or two or three substituents independently selected from halogen, cyano, hydroxy, $C_{1\text{-}4}$ alkoxy, $-C_{1\text{-}4}$ haloalkyl, $-C_{1\text{-}4}$ haloalkoxy, $-C(=O)OR^{Z1}$, $-C(=O)NHS(=O)_2R^{Z3}$, $-C(=O)N(R^{Z1})R^{Z2}$, —S(=O)$_2$R$^{Z3}$, —S(=O)$_2$N(R$^{Z1}$)R$^{Z2}$, —N(R$^{Z1}$)C(=O)R$^{Z3}$, —N(R$^{Z1}$)S(=O)R$^{Z3}$, —N(R$^{Z1}$)C(=O)N(R$^{Z2}$)R$^{Z3}$ and —N(R$^{Z1}$)S(=O)N(R$^{Z2}$)R$^{Z3}$.

Embodiment 41

The compound of Embodiment 39, wherein R$^{m1}$ can be -R$^{x2}$, wherein -R$^{x2}$ can be selected from:

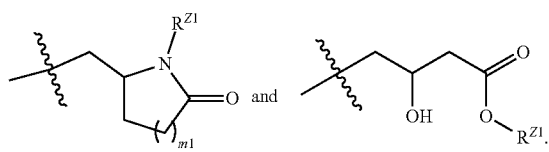

Embodiment 42

The compound of Embodiment 41, wherein m$_1$ can be 1.

Embodiment 43

The compound of Embodiment 37 or 38, wherein R$^{2a2}$ can be -R$^{x1}$.

Embodiment 44

The compound of Embodiment 43, wherein -R$^{x1}$ can be selected from:

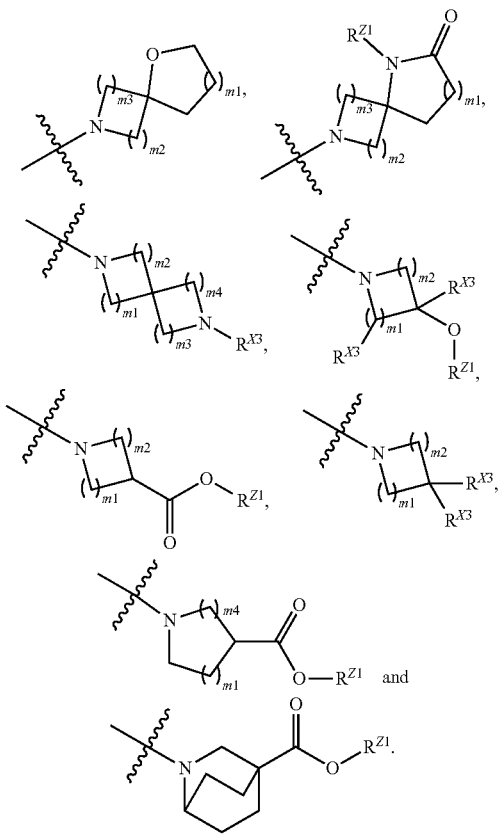

Embodiment 45

The compound of Embodiment 44, wherein m$_1$, m$_2$, m$_3$ and m$_4$ can be each 1.

Embodiment 46

The compound of any one of Embodiments 41, 42, 44 or 45, wherein R$^{Z1}$ can be hydrogen or —C$_{1-4}$ alkyl.

Embodiment 47

The compound of any one of Embodiments 39-42, wherein R$^{m1}$ can be hydrogen.

Embodiment 48

The compound of Embodiment 37 or 38, wherein R$^{2a2}$ can be selected from:

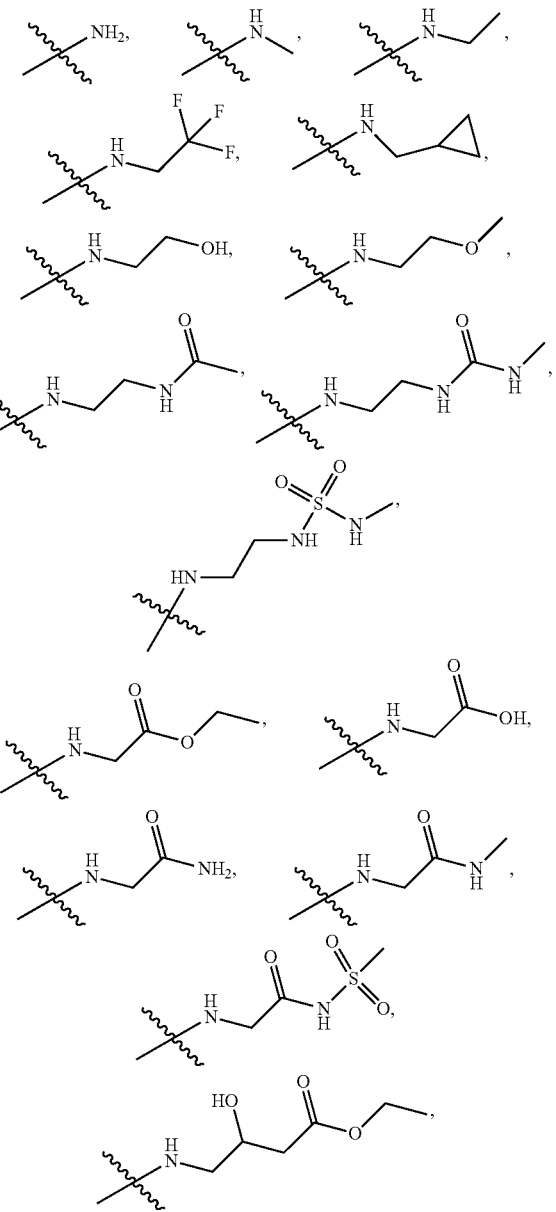

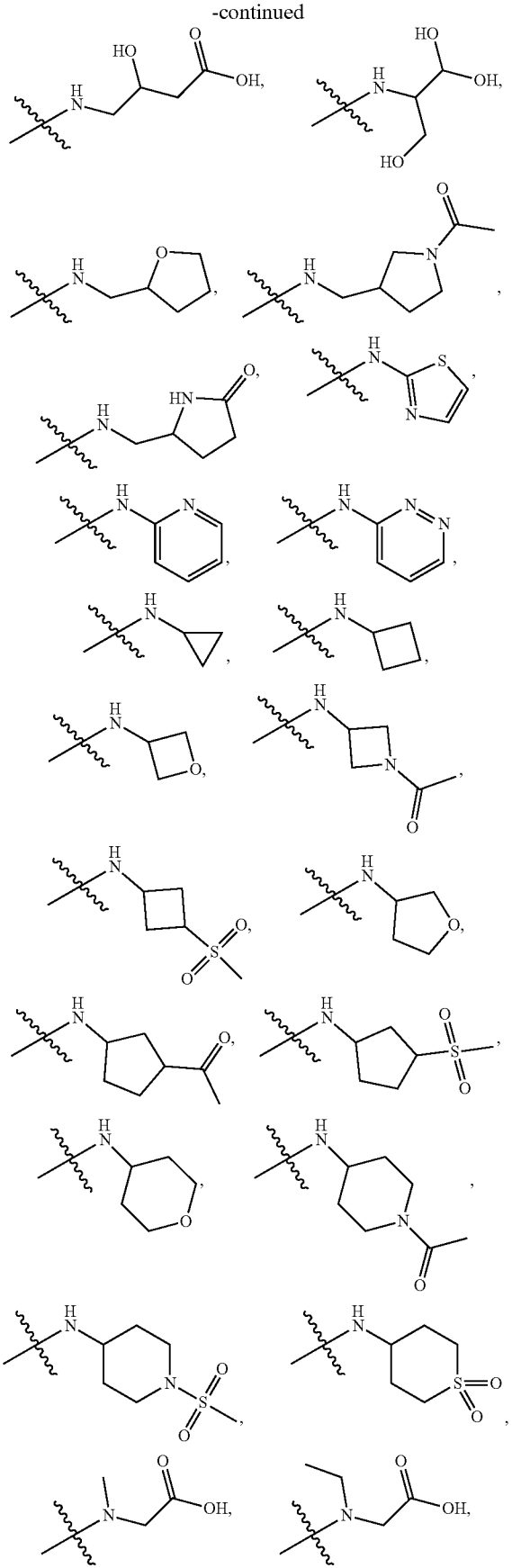
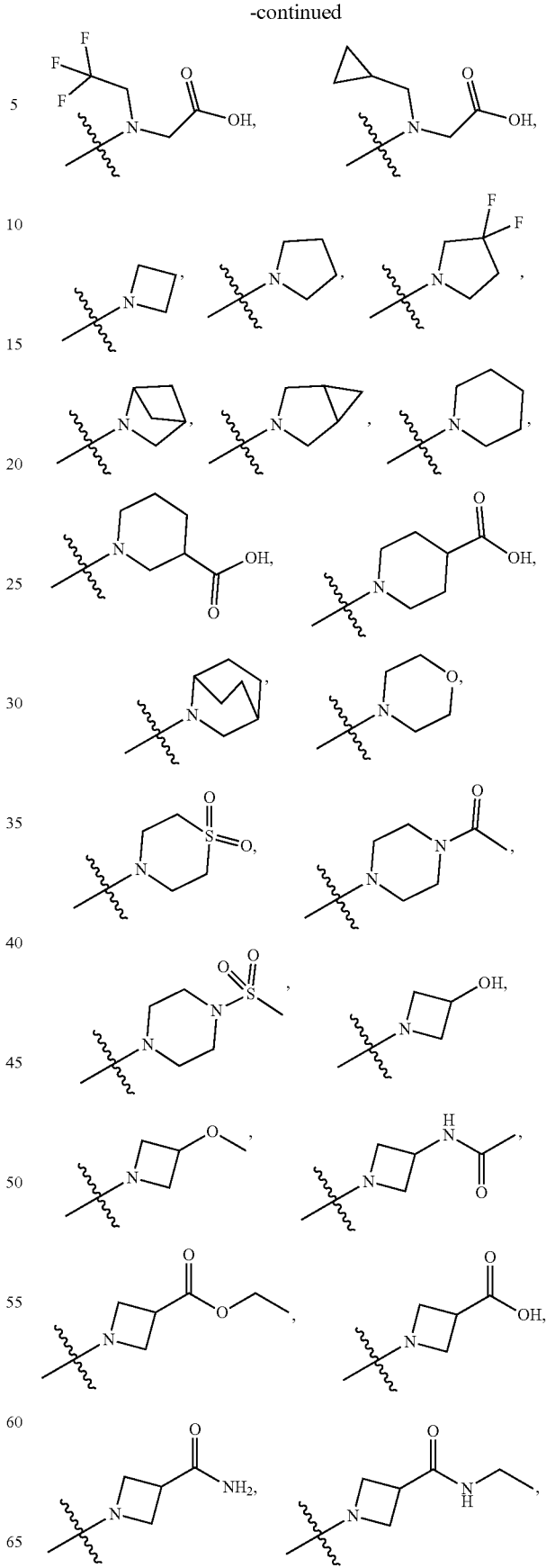

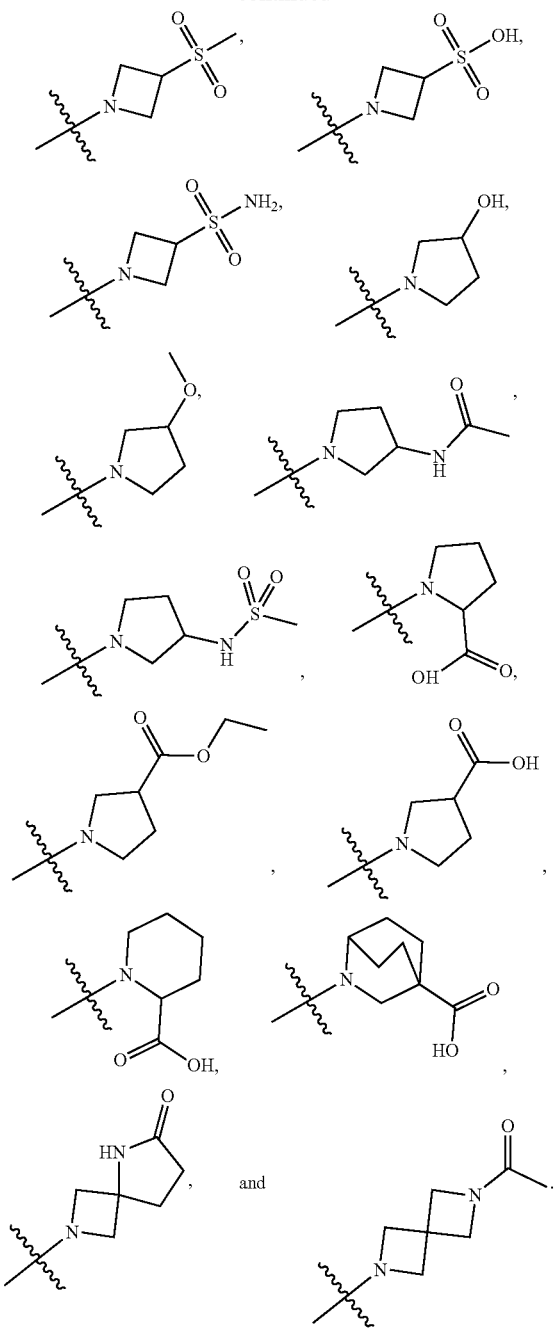

Embodiment 49

The compound of any one of Embodiments 1-24, wherein Ring A can be a 5-7 membered nitrogen-containing monocyclic heterocyclyl, wherein a nitrogen of the 5-7 membered nitrogen-containing monocyclic heterocyclyl is optionally substituted with $R^{2a3}$, wherein a carbon of the 5-7 membered nitrogen-containing monocyclic heterocyclyl is optionally substituted with $R^{2a4}$ or $R^{2a5}$, and wherein when $R^{2a5}$ is present, $R^{2a5}$ is attached at a carbon atom adjacent to a nitrogen of the 5-7 membered nitrogen-containing monocyclic heterocyclyl.

Embodiment 50

The compound of Embodiment 49, wherein the 5-7 membered nitrogen-containing monocyclic heterocyclyl, wherein a nitrogen of the 5-7 membered nitrogen-containing monocyclic heterocyclyl is optionally substituted with $R^{2a3}$, wherein a carbon of the 5-7 membered nitrogen-containing monocyclic heterocyclyl is optionally substituted with $R^{2a4}$ or $R^{2a5}$, and wherein when $R^{2a5}$ is present, $R^{2a5}$ is attached at a carbon atom adjacent to a nitrogen of the 5-7 membered nitrogen-containing monocyclic heterocyclyl is selected from:

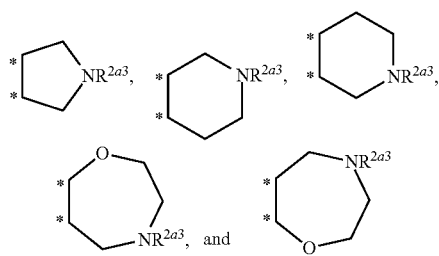

wherein asterisks indicate the position of the fused bond, and $R^{2a4}$ and $R^{2a5}$ are each optionally present.

Embodiment 51

The compound of Embodiment 49 or 50, wherein $R^{2a3}$ can be $-C_{1-4}$ alkyl, wherein the $-C_{1-4}$ alkyl can be optionally substituted with one or two or three substituents independently selected from halogen, cyano, hydroxy, $-C_{1-4}$ alkoxy, $-C_{1-4}$ haloalkoxy, $-C(=O)OR^{Z1}$, $-C(=O)NHS(=O)_2R^{Z3}$, $-C(=O)N(R^{Z1})R^{Z2}$, $-S(=O)_2R^{Z3}$, $-S(=O)_2 N(R^{Z1})R^{Z2}$, $-NHC(=O)R^{Z3}$, $-NHC(=O)N(R^{Z1})R^{Z3}$ and $-N(R^{Z1})S(=O)_2N(R^{Z2})R^{Z3}$.

Embodiment 52

The compound of Embodiment 51, wherein $R^{2a3}$ can be selected from $-(CH_2)_{1-2}-C(=O)OR^{Z1}$, $-(CH_2)_{1-2}-OH$ and $-(CH_2)_{1-2}-C_{1-4}$ alkoxy.

Embodiment 53

The compound of Embodiment 49 or 50, wherein $R^{2a3}$ can be $-R^{x2}$.

Embodiment 54

The compound of Embodiment 53, wherein $-R^{x2}$ can be selected from:

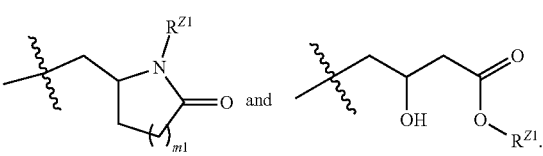

Embodiment 55

The compound of Embodiment 54, wherein $m_1$ can be 1.

Embodiment 55

The compound of any one of Embodiments 54 or 55, wherein $R^{z1}$ can be hydrogen or —$C_{1-4}$ alkyl.

Embodiment 57

The compound of any one of Embodiments 49-55, wherein $R^{2a4}$ can be selected from —$C_{1-4}$ alkyl, —C(=O)OR$^{Z4}$, —OR$^{Z4}$ and —N(R$^{m3}$)R$^{n3}$.

Embodiment 58

The compound of Embodiment 57, wherein the —$C_{1-4}$ alkyl can be substituted with —C(=O)OR$^{z1}$.

Embodiment 59

The compound of Embodiment 57, wherein $R^{Z4}$ can be hydrogen or —$C_{1-4}$ alkyl.

Embodiment 60

The compound of Embodiment 57, wherein $R^{2a4}$ can be —NH(R$^{m3}$), wherein R$^{m3}$ can be selected from —$C_{1-4}$ alkyl and —$C_{3-6}$ monocyclic cycloalkyl.

Embodiment 61

The compound of any one of Embodiments 49-60, wherein $R^{2a5}$ can be —C(=O)OR$^{z5}$.

Embodiment 62

The compound of any one of Embodiments 49-60, wherein $R^{2a5}$ can be —$C_{1-4}$ alkyl optionally substituted with one or two or three substituents independently selected halogen, cyano, hydroxy, —$C_{1-4}$ alkoxy, —$C_{1-4}$ haloalkoxy, —C(=O)OR$^{z1}$, —C(=O)NHS(=O)$_2$R$^{z3}$, —C(=O)N(R$^{z1}$)R$^{z2}$, —S(=O)$_2$R$^{z3}$, —S(O)$_2$N(R$^{z1}$)R$^{z2}$, —NHC(=O)R$^{z3}$, —NHC(=O)N(R$^{z1}$)R$^{z3}$ and —N(R$^{z1}$)S(=O)$_2$N(R$^{z2}$)R$^{z3}$; and wherein $R^{z5}$ can be selected from hydrogen, —$C_{1-4}$ alkyl, —$C_{1-4}$ haloalkyl and —$C_{3-6}$ cycloalkyl.

Embodiment 63

The compound of Embodiment 62, wherein $R^{2a5}$ can be —$C_{1-4}$ alkyl substituted with one or two or three substituents independently selected from hydroxy and —C(=O)OH.

Embodiment 64

The compound of any one of Embodiments 1-24, wherein Ring A can be a 6-12 membered nitrogen-containing bicyclic heterocyclyl, wherein a nitrogen of the 6-12 membered nitrogen-containing bicyclic heterocyclyl is optionally substituted with $R^{2a6}$;

Embodiment 65

The compound of Claim 64, wherein a nitrogen of the 6-12 membered nitrogen-containing bicyclic heterocyclyl is optionally substituted with $R^{2a6}$ can be selected

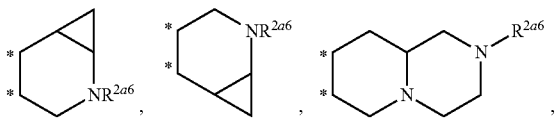

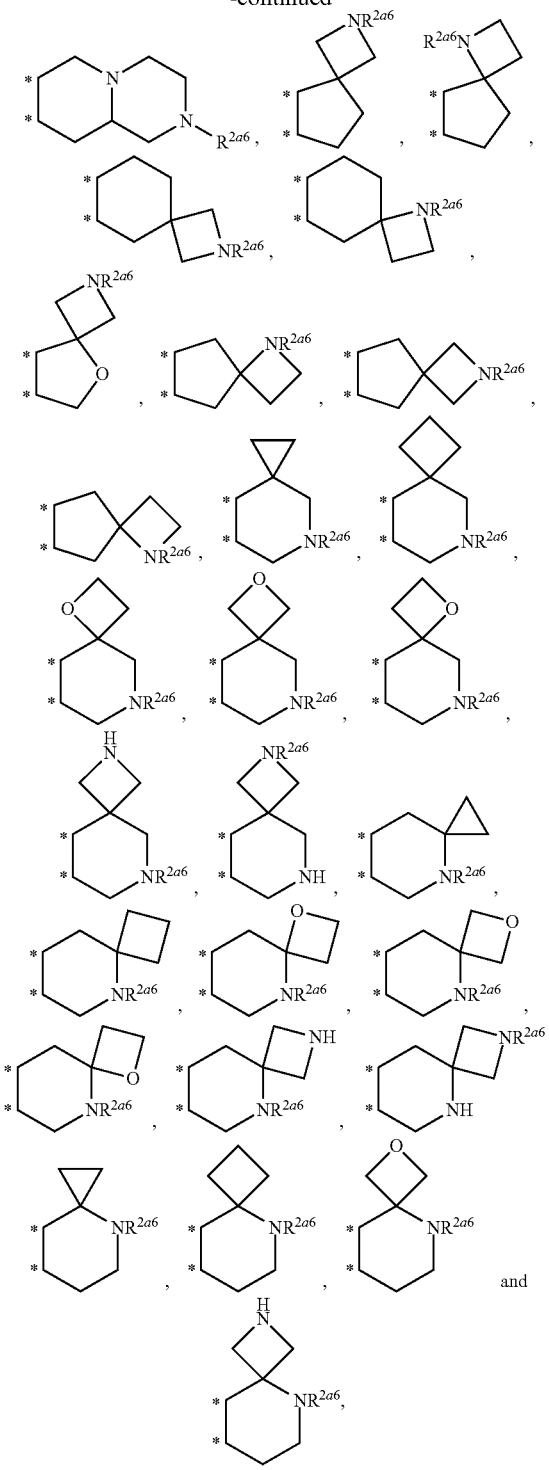

wherein asterisks indicate the position of the fused bond.

Embodiment 66

The compound of any one of Embodiments 1-24, wherein Ring A can be a 5-7 membered oxygen-containing monocyclic heterocyclyl substituted with $R^{2a7}$ or $R^{2a8}$, wherein when $R^{2a8}$ is present, $R^{2a8}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens.

Embodiment 67

The compound of Embodiment 66, wherein the 5-7 membered oxygen-containing monocyclic heterocyclyl substituted with $R^{2a7}$ or $R^{2a8}$; wherein $R^{2a8}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens can be selected from:

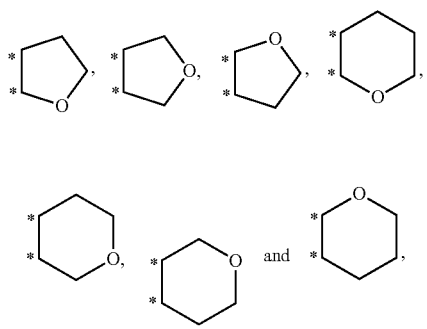

wherein asterisks indicate the position of the fused bond, and $R^{3a7}$ or $R^{3a8}$ is present.

Embodiment 68

The compound of Embodiment 66 or 67, wherein $R^{2a7}$ can be —N($R^{n1}$)$R^{n1}$.

Embodiment 69

The compound of Embodiment 68, wherein $R^{2a7}$ can be —N($C_{1-4}$ alkyl)$R^{n1}$ wherein the $C_{1-4}$ alkyl is optionally substituted with one or two or three substituents independently selected from halogen, cyano, hydroxy, —$C_{1-4}$ alkoxy, —$C_{1-4}$ haloalkyl, —$C_{1-4}$ haloalkoxy, —C(=O)O$R^{Z1}$, —C(=O)NHS(=O)$_2R^{Z3}$, —C(=O)N($R^{Z1}$)$R^{Z2}$, —S(=O)$_2R^{Z3}$, —S(=O)$_2$N($R^{Z1}$)$R^{Z2}$, —N($R^{Z1}$)C(=O)$R^{Z3}$, —N($R^{Z1}$)S(=O)$R^{Z3}$, —N($R^{Z1}$)C(=O)N($R^{Z2}$)$R^{Z3}$ and —N($R^{Z1}$)S(=O)N($R^{Z2}$)$R^{Z3}$.

Embodiment 70

The compound of Embodiment 68, wherein $R^{n1}$ can be -$R^{x2}$, wherein -$R^{x2}$ can be selected from:

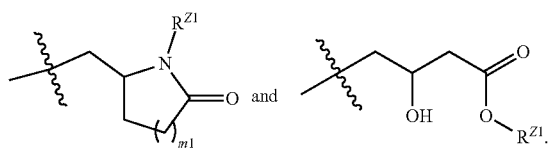

Embodiment 71

The compound of Embodiment 70, wherein $m_1$ can be 1.

Embodiment 72

The compound of Embodiment 69 or 70, wherein $R^{2a7}$ can be -$R^{x1}$.

Embodiment 73

The compound of Embodiment 72, wherein -$R^{x1}$ can be selected from:

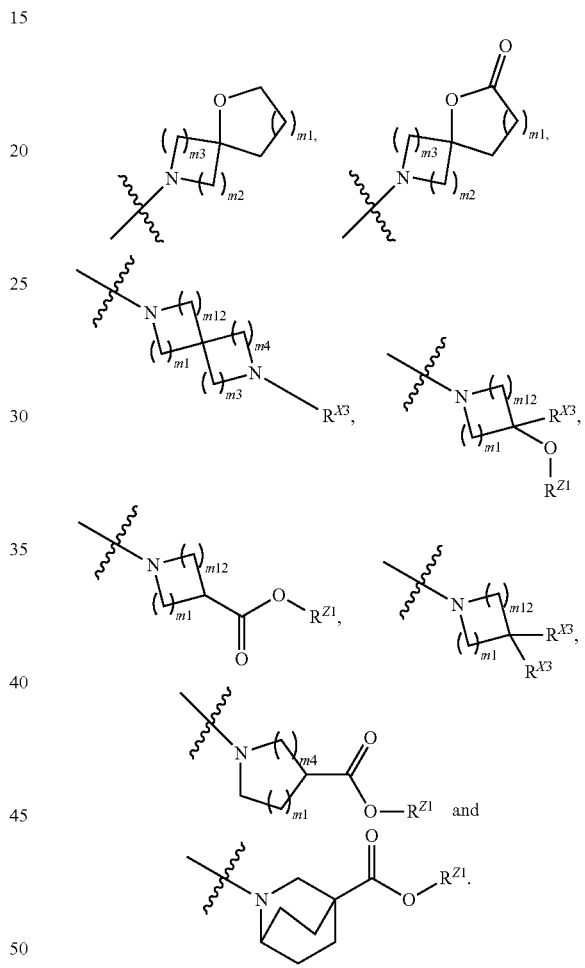

Embodiment 74

The compound of Embodiment 73, wherein $m_1$, $m_2$, $m_3$ and $m_4$ can be each 1.

Embodiment 75

The compound of any one of Embodiments 70, 71, 73 or 74, wherein $R^{Z1}$ can be hydrogen or —$C_{1-4}$ alkyl.

Embodiment 76

The compound of any one of Embodiments 68-71, wherein $R^{n1}$ can be hydrogen.

Embodiment 77
The compound of Embodiment 66 or 67, wherein $R^{2a7}$ can be selected from:
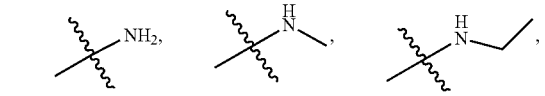
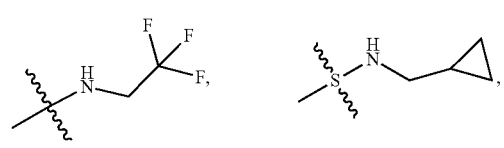
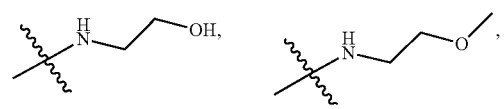
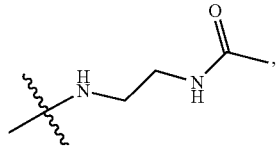
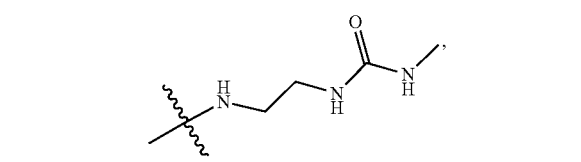
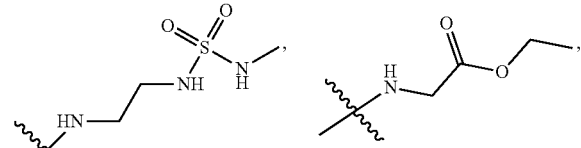
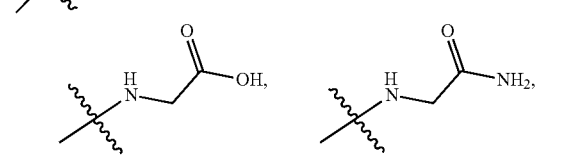
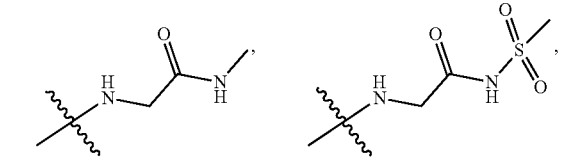
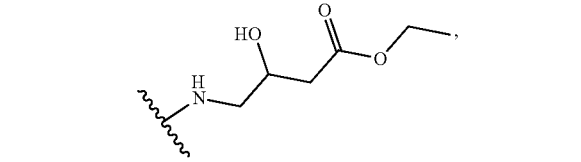
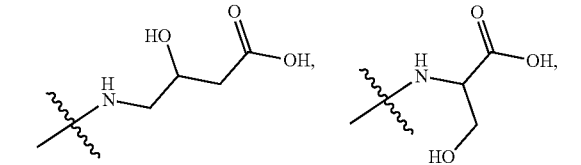
-continued
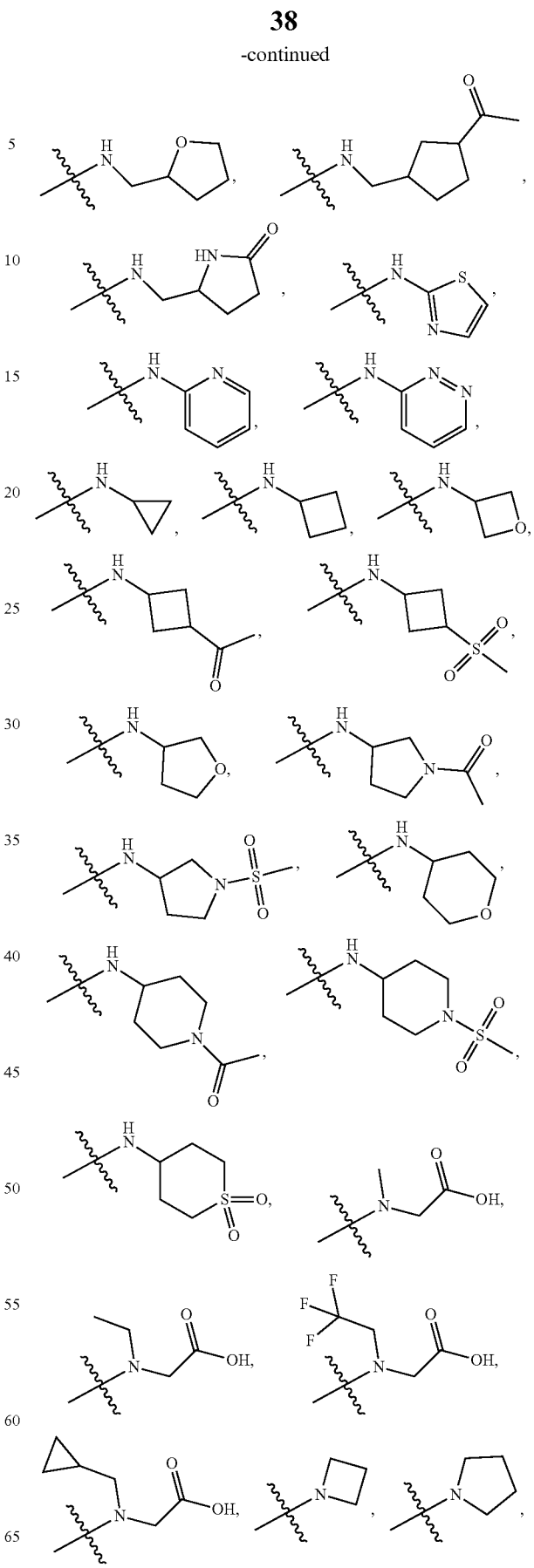

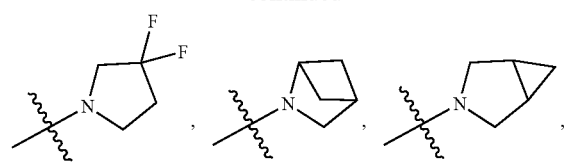
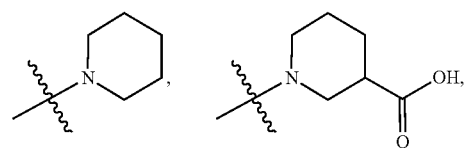
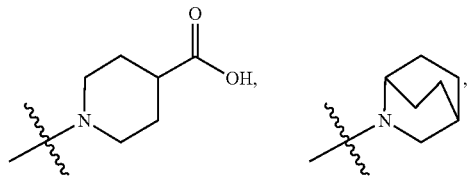
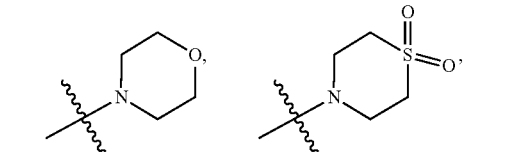
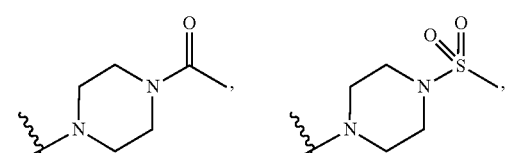
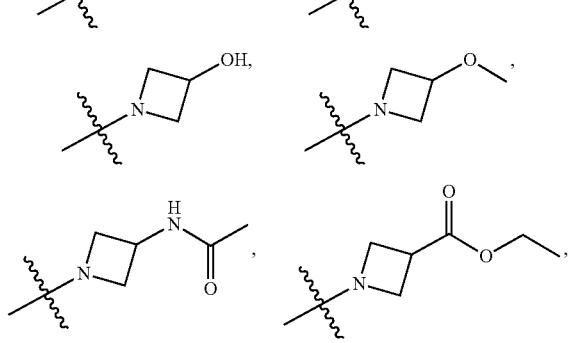
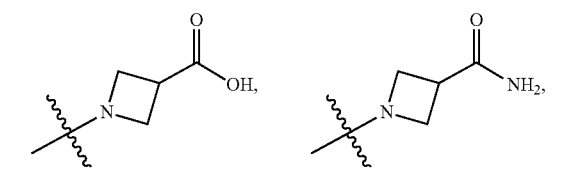
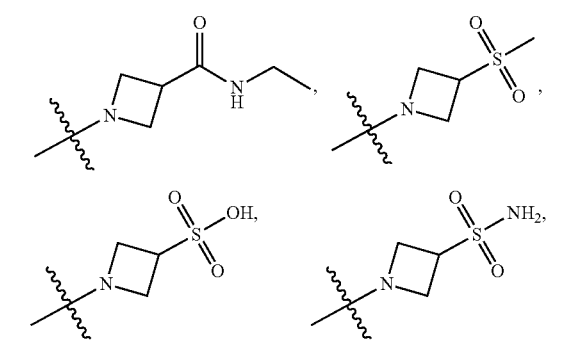
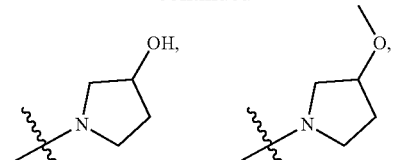
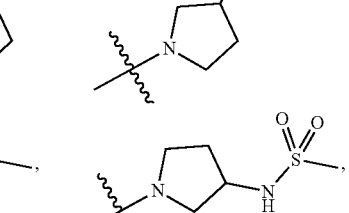
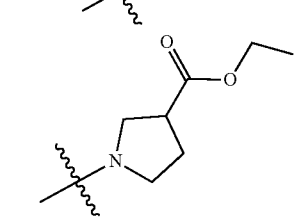
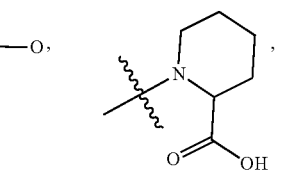
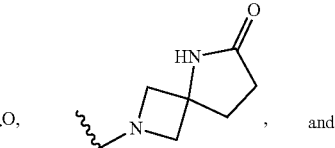
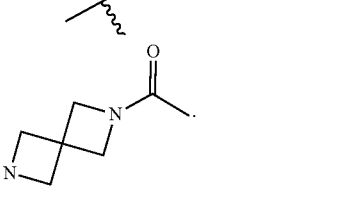
and
Embodiment 78
The compound of any one of Embodiments 66-77, wherein $R^{2a8}$ can be —$(C_{1\text{-}4}$ alkyl$)R^{x1}$.
Embodiment 79
The compound of Claim 78, wherein -$R^{x1}$ is
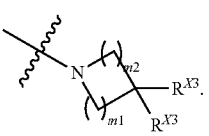
Embodiment 80
The compound of Claim 79, wherein $m_1$ and $m_2$ are each 1.

Embodiment 81

The compound of Claim 79 or 80, wherein $R^{Z1}$ is hydrogen.

Embodiment 82

The compound of Claim 79, wherein $R^{X3}$ is —C(=O)OR$^{Z1}$.

Embodiment 83

The compound of Claim 82, wherein $R^{Z1}$ is hydrogen or —C$_{1-4}$ alkyl.

Embodiment 84

The compound of any one of Claims 66-79, wherein $R^{2a8}$ is selected from the group consisting of:

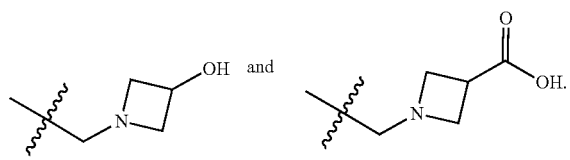 [SMILES: *CN1CC(O)C1 ; *CN1CC(C(=O)O)C1]

Embodiment 85

The compound of any one of Embodiments 1-84, wherein $R^1$ can be —C$_{1-4}$ alkyl.

Embodiment 86

The compound of any one of Embodiments 1-84, wherein $R^1$ can be —C$_{1-4}$ haloalkyl.

Embodiment 87

The compound of any one of Embodiments 1-84, wherein $R^1$ can be -monocyclic C$_{3-6}$cycloalkyl.

Embodiment 88

The compound of any one of Embodiments 1-84, wherein $R^1$ can be —(C$_{1-4}$alkyl)monocyclic C$_{3-6}$cycloalkyl.

Embodiment 89

The compound of any one of Embodiments 1-84, wherein $R^1$ can be 4-6 membered monocyclic heterocyclic ring.

Embodiment 90

The compound of any one of Embodiments 1-84, wherein $R^1$ can be aryl(C$_{1-4}$alkyl). As an example, $R^1$ can be benzyl.

Embodiment 91

The compound of any one of Embodiments 1-84, wherein $R^1$ can be —(C$_{1-4}$alkyl) 5- or 6-membered monocyclic heteroaryl. In some embodiments, $R^1$ can be a nitrogen-containing be —(C$_{1-4}$alkyl) 5- or 6-membered monocyclic heteroaryl, such as —(CH$_2$)pyridine.

Embodiment 92

The compound of any one of Embodiments 1-91, wherein $R^{3a}$, $R^{3b}$, $R^{3c}$, $R^{3e}$, $R^{3f}$ and $R^{3g}$ can be each hydrogen.

Embodiment 93

The compound of any one of Embodiments 1-92, wherein $R^{3d}$ and $R^{3h}$ can be each halogen.

Embodiment 94

The compound of any one of Embodiments 1-92, wherein $R^{3d}$ can be halogen; and $R^{3h}$ can be —CH$_3$.

Embodiment 95

The compound of Embodiment 93 or 94, wherein the halogen can be chloro or fluoro.

Embodiment 96

The compound of Embodiment 1 selected from:

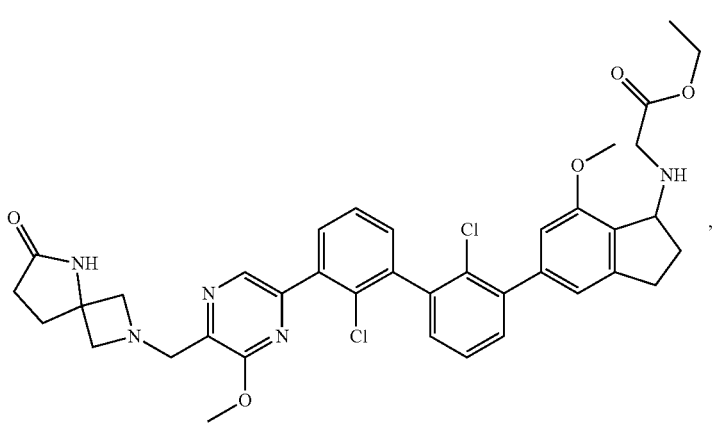

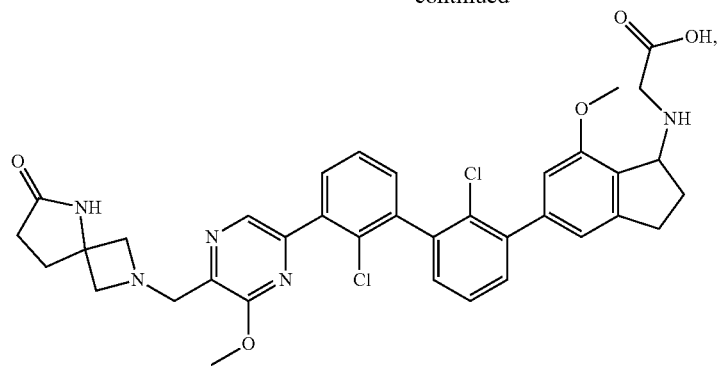
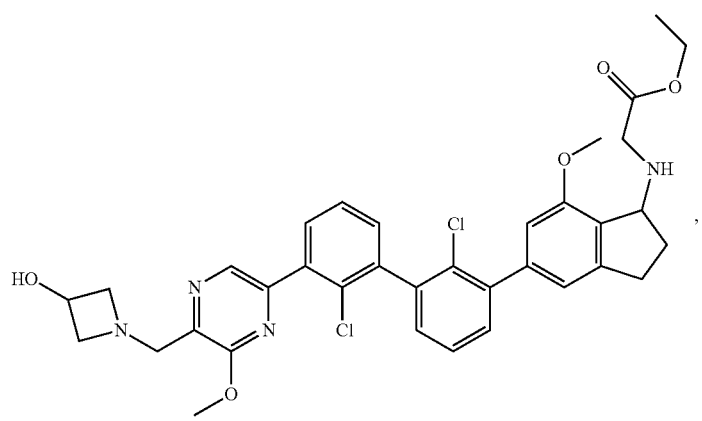
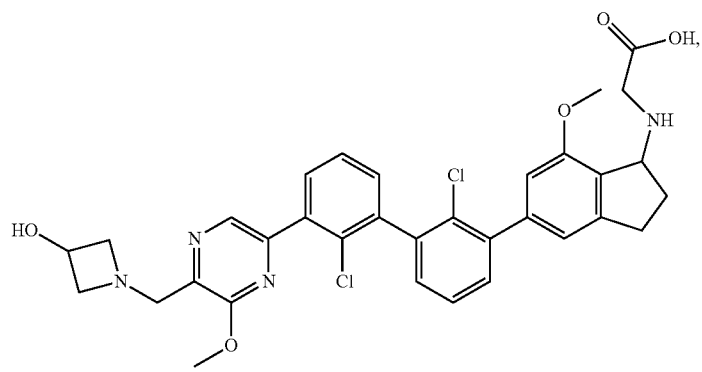
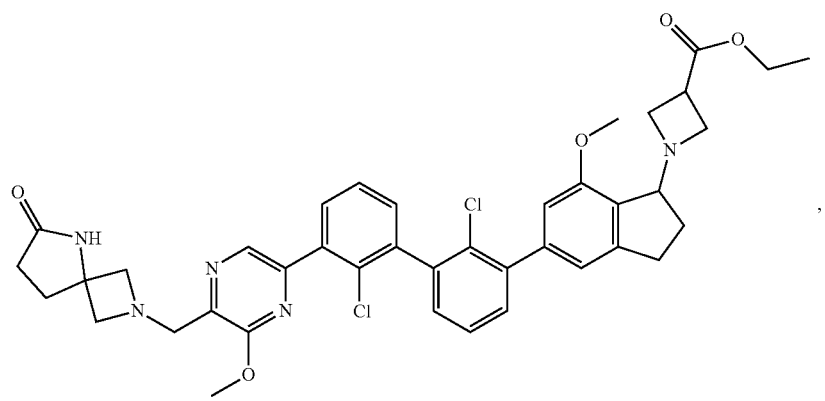

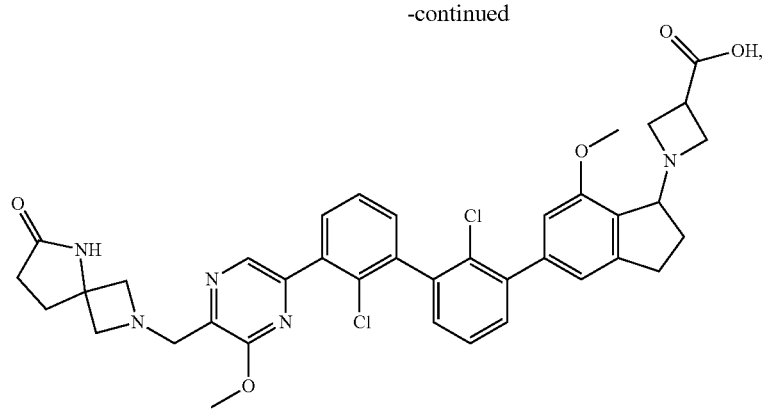
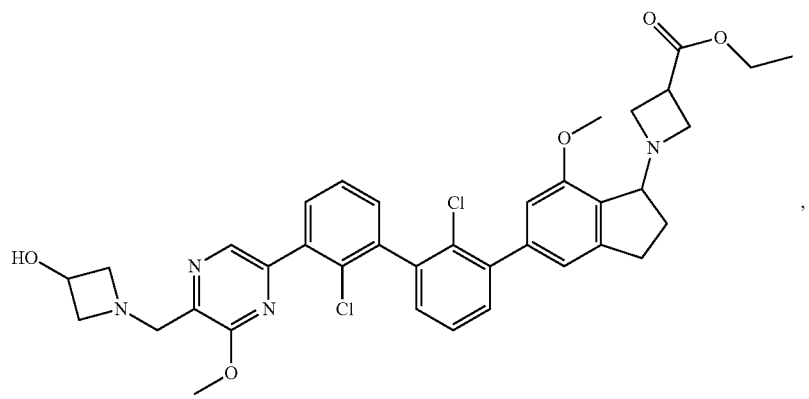
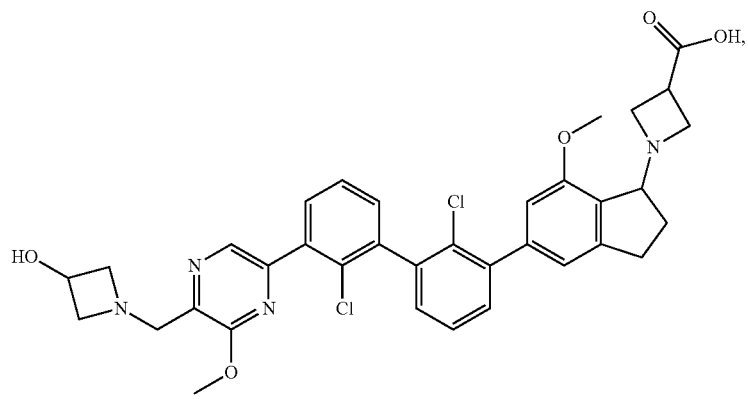
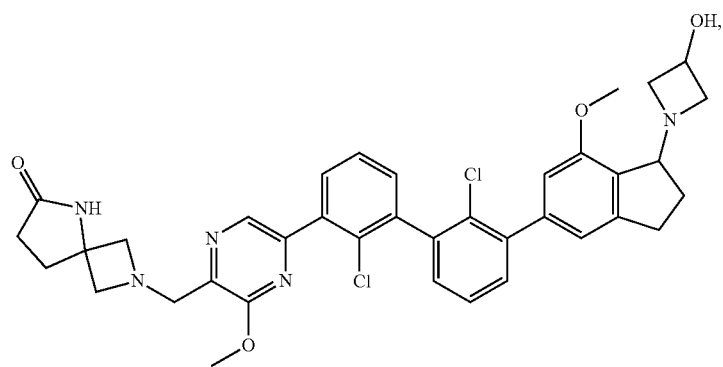

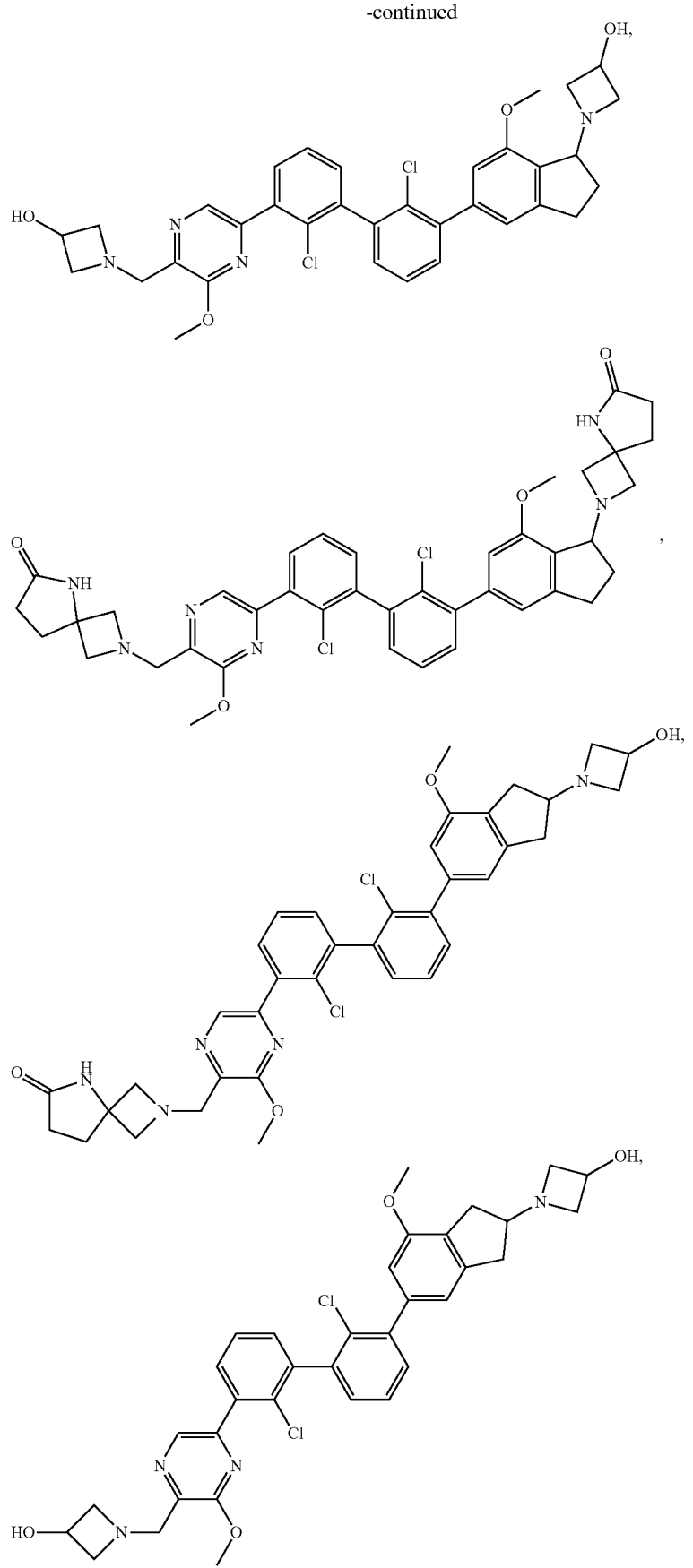

-continued
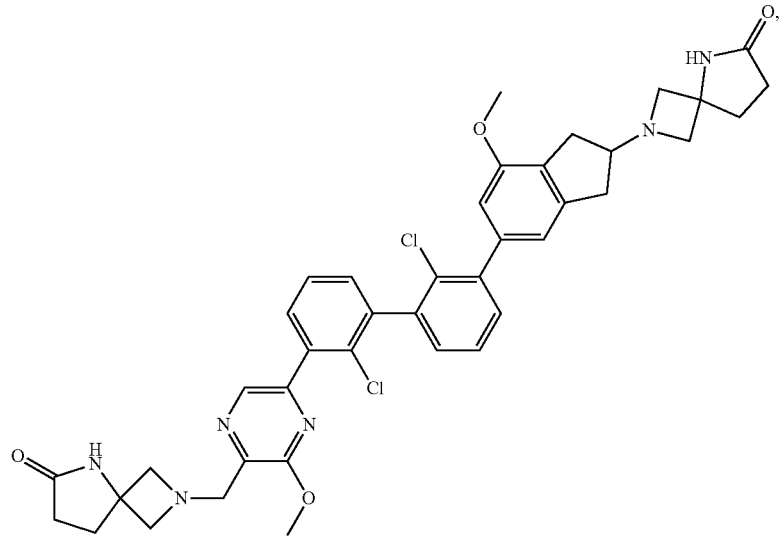
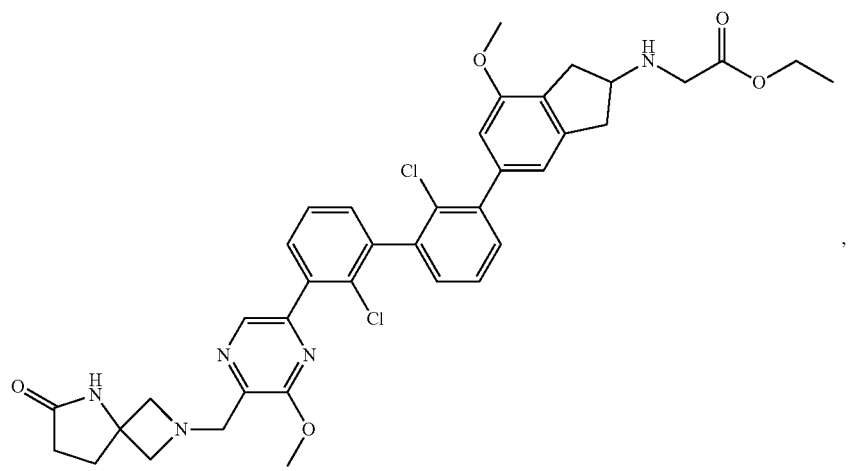
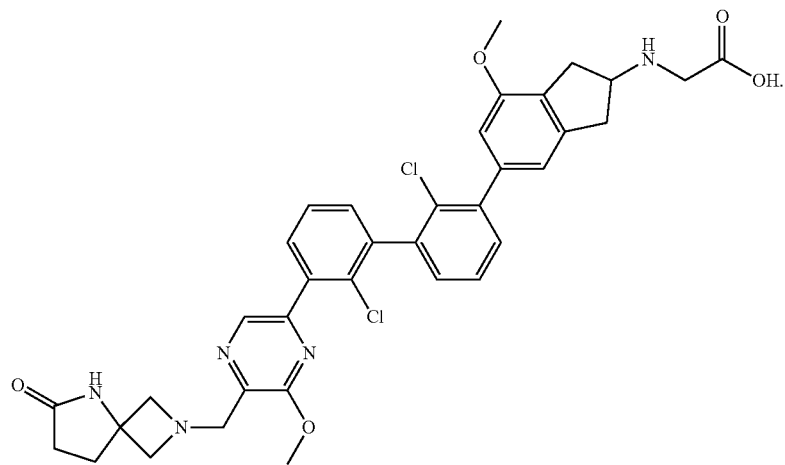

-continued
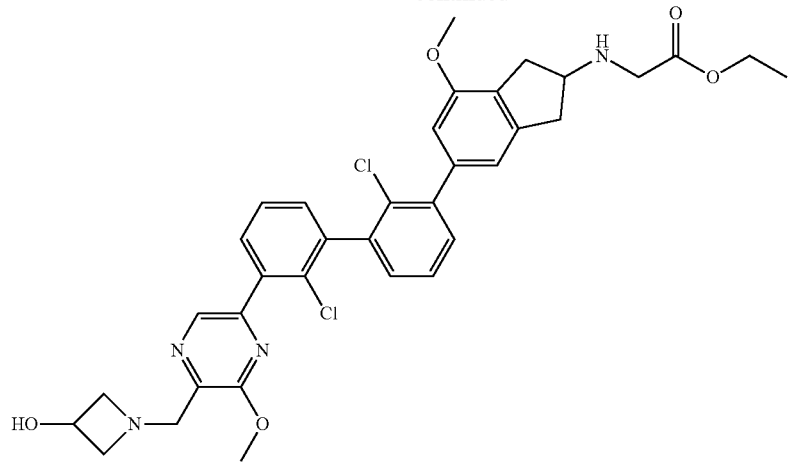
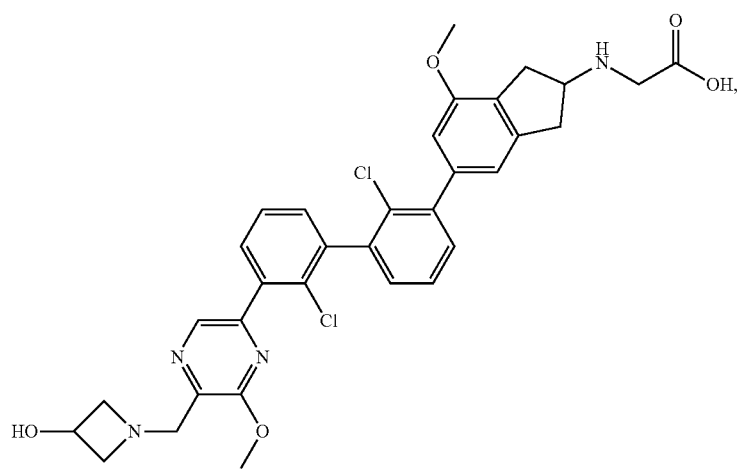
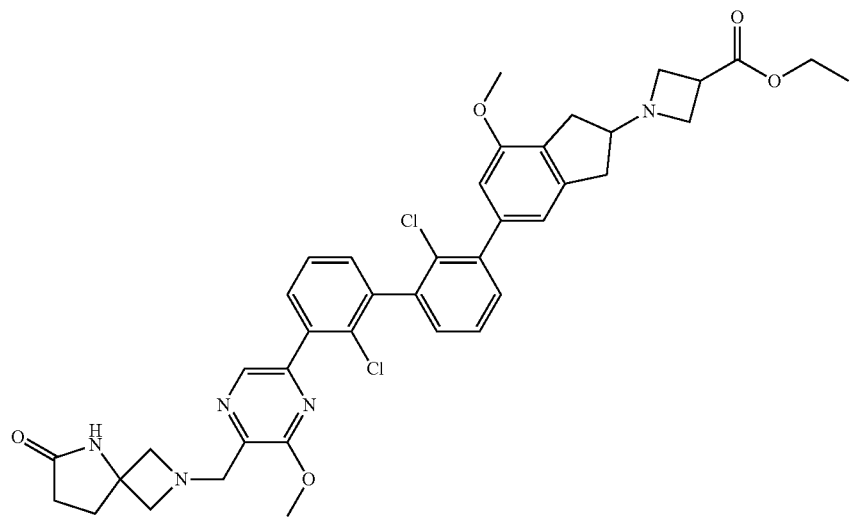

-continued
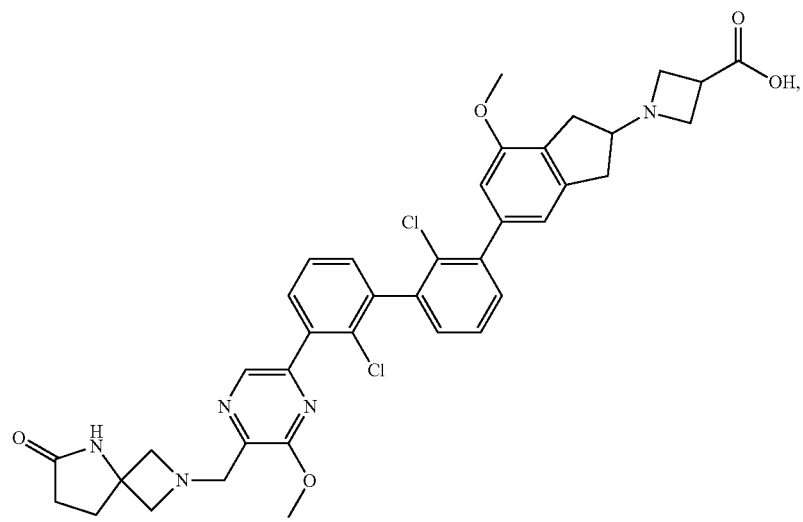
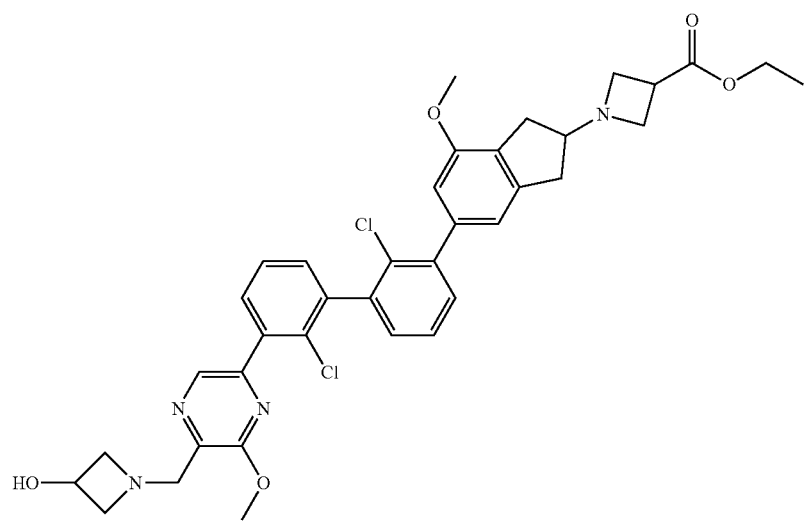
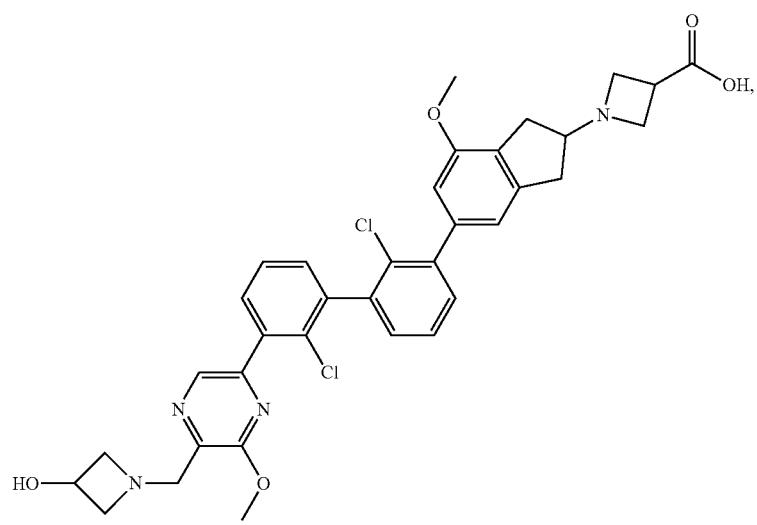

-continued
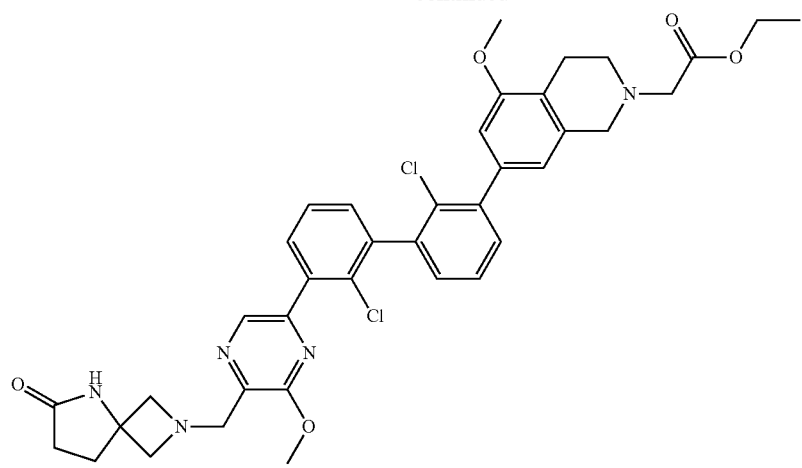
,
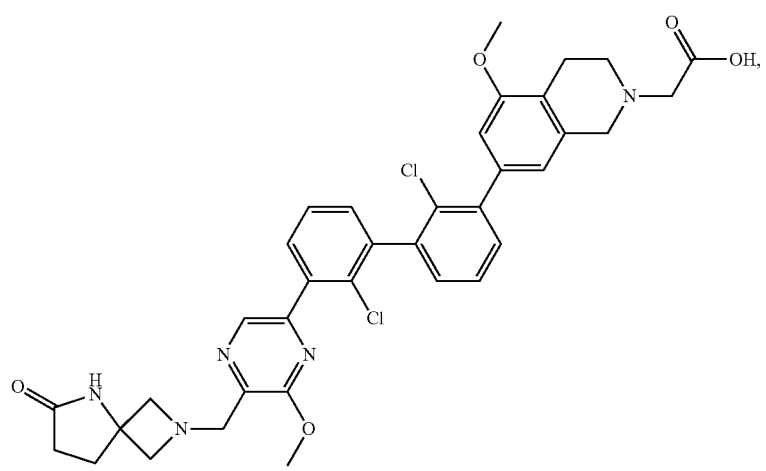
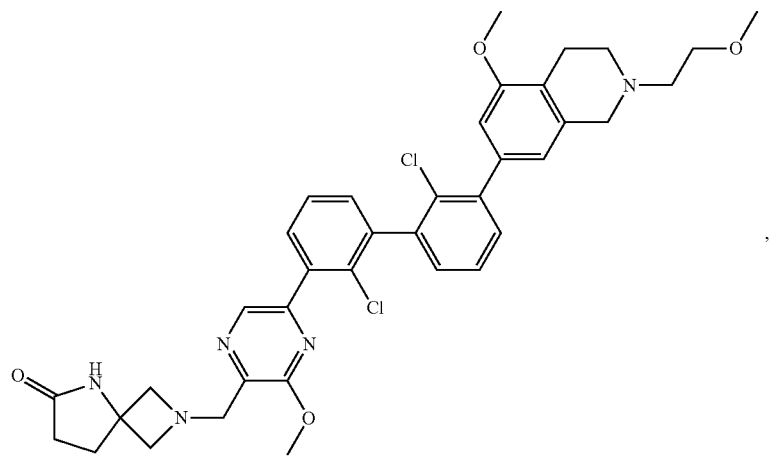
,

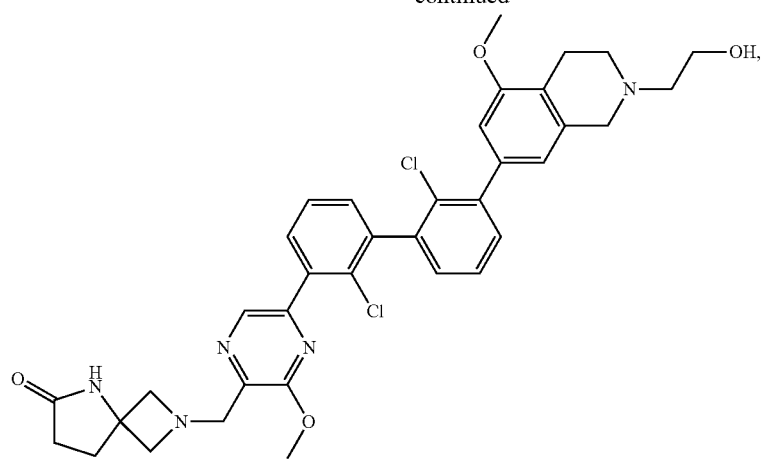
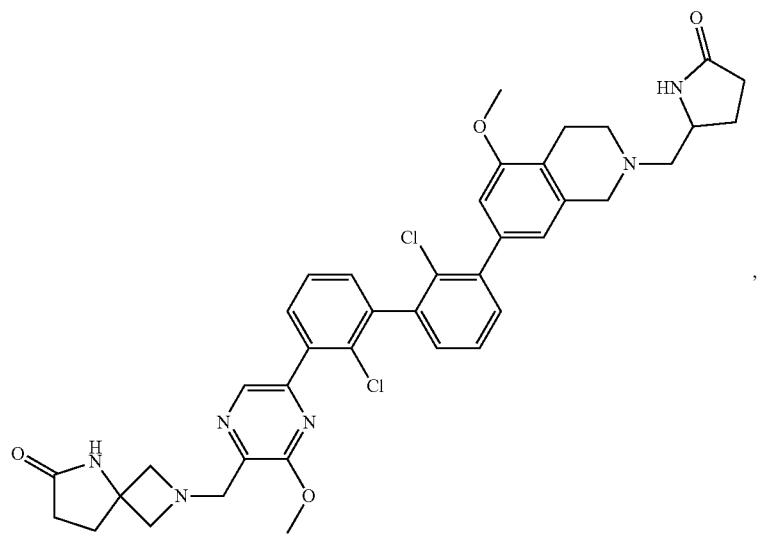
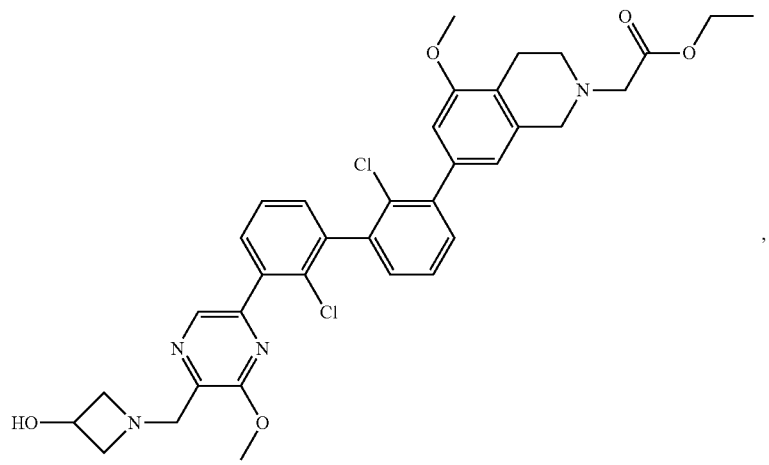

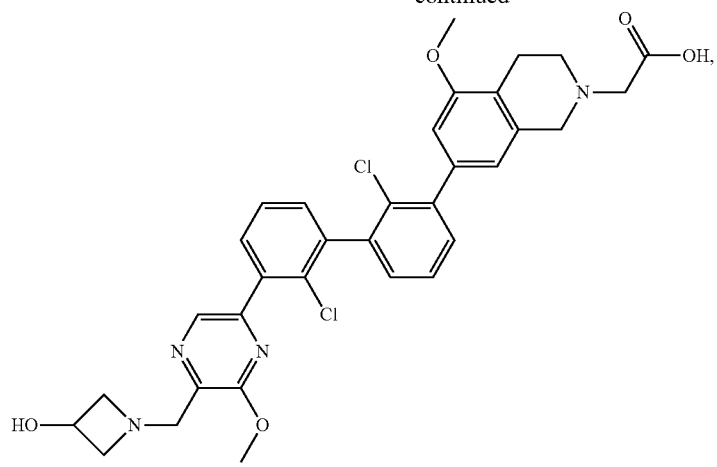
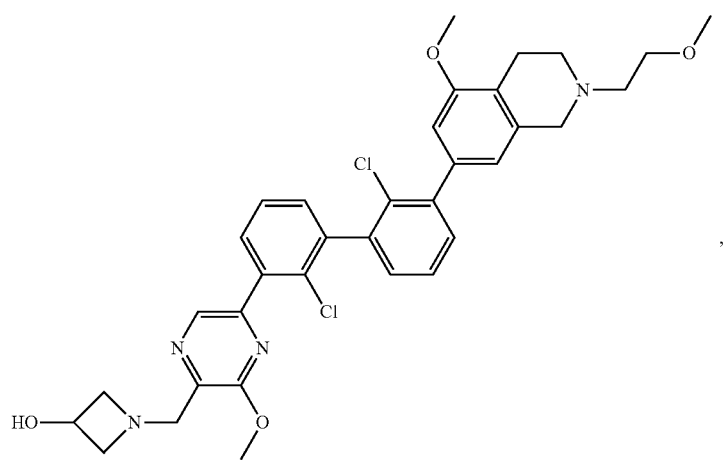
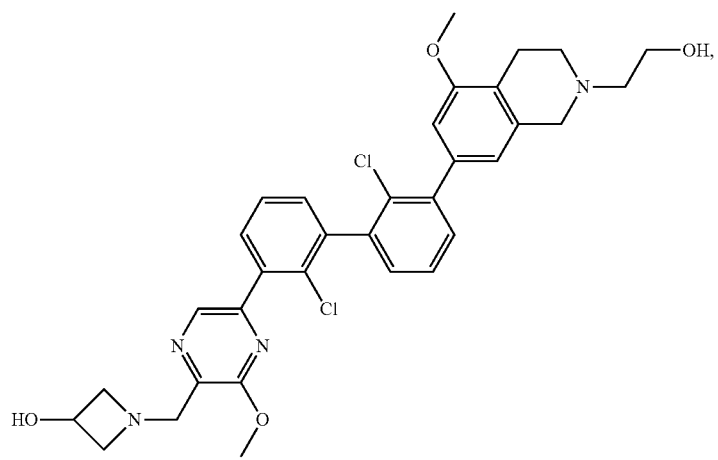

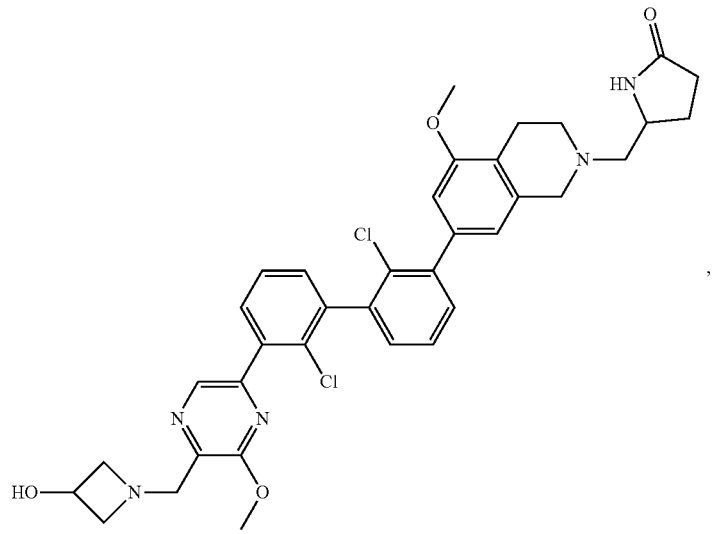
,
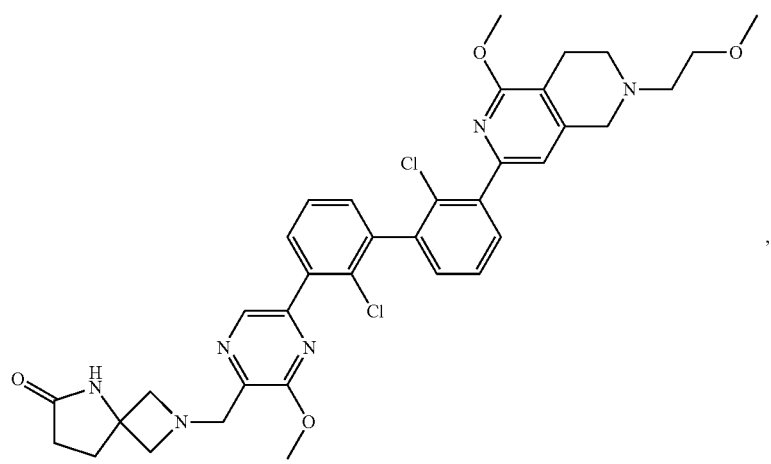
,
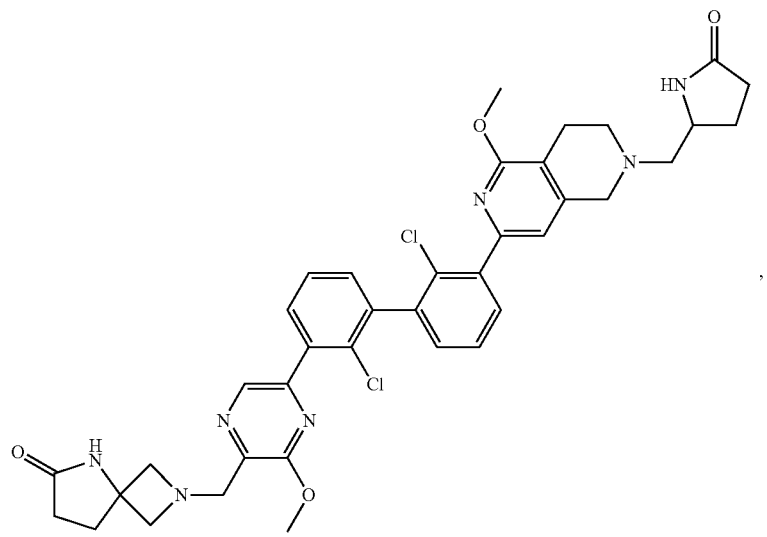
,

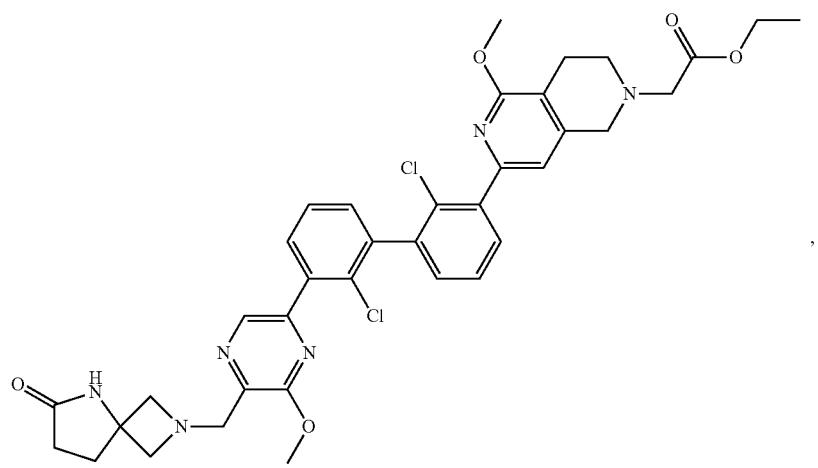
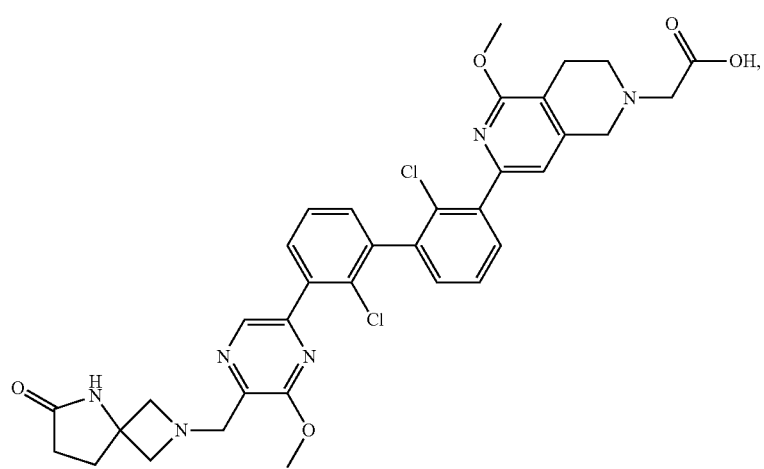
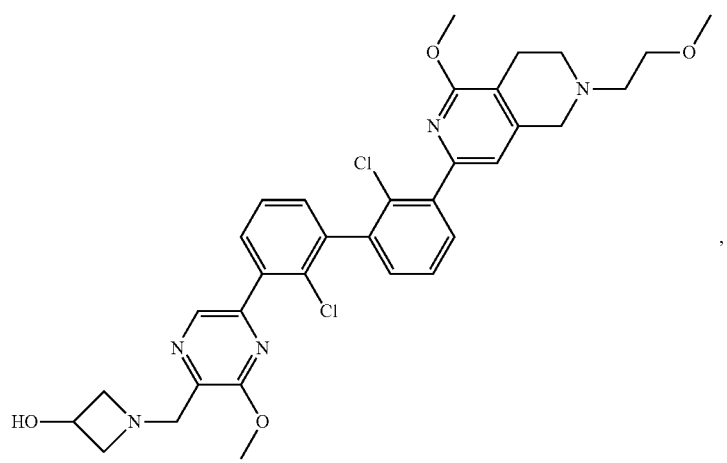

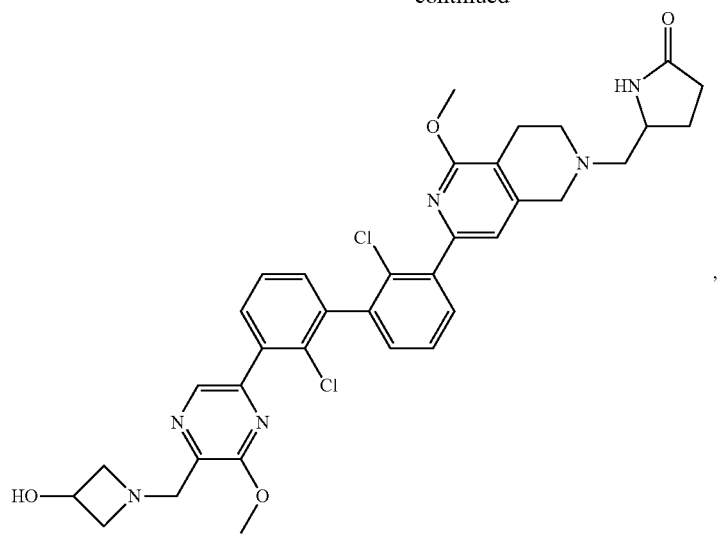
,
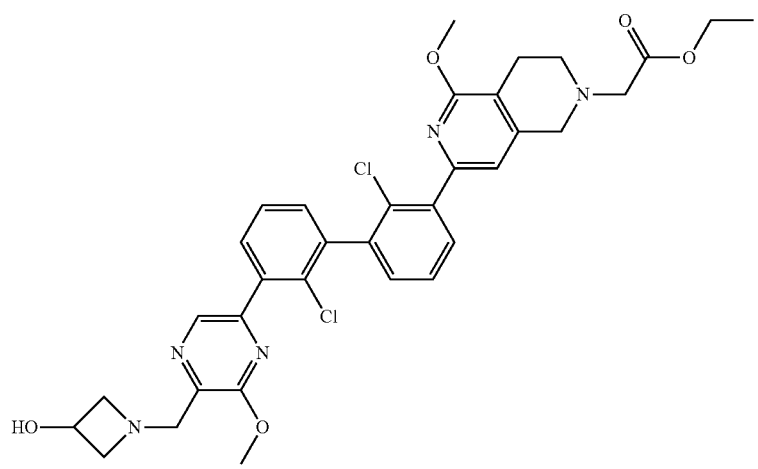
,
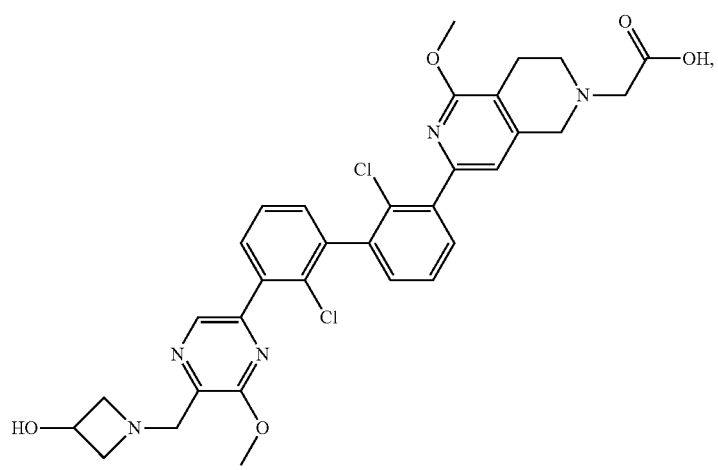

-continued
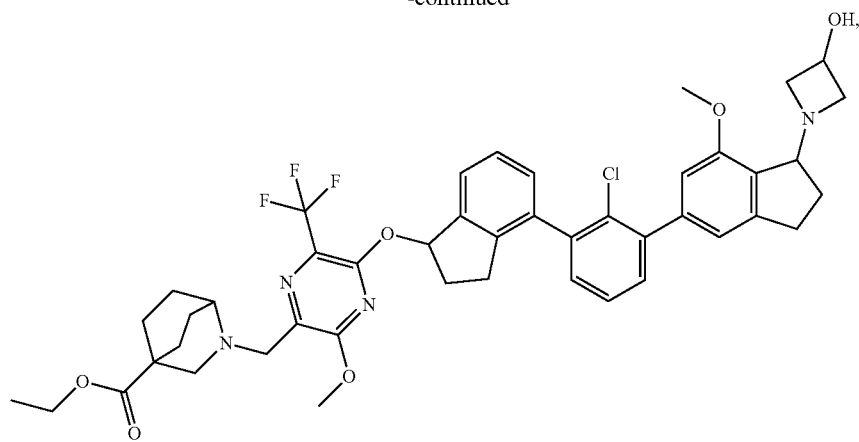
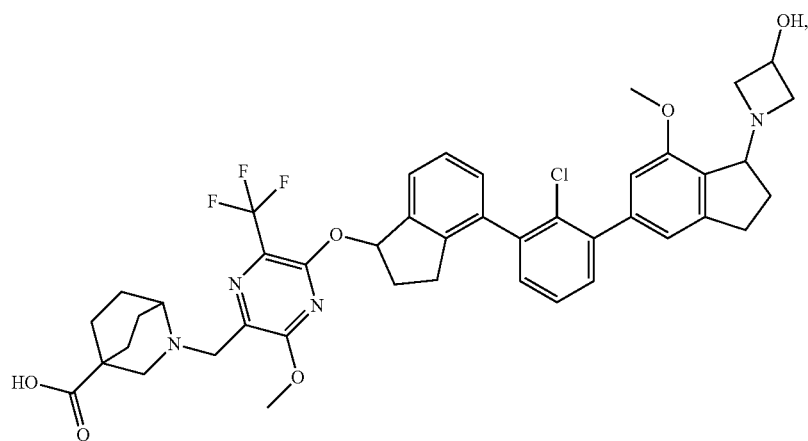
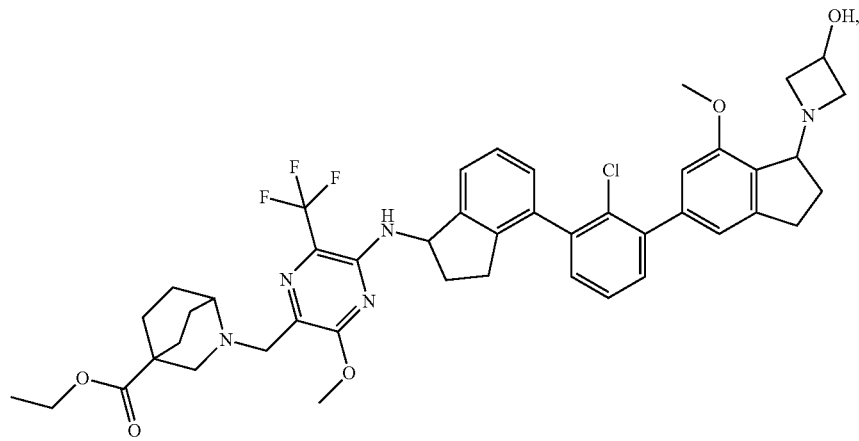

-continued
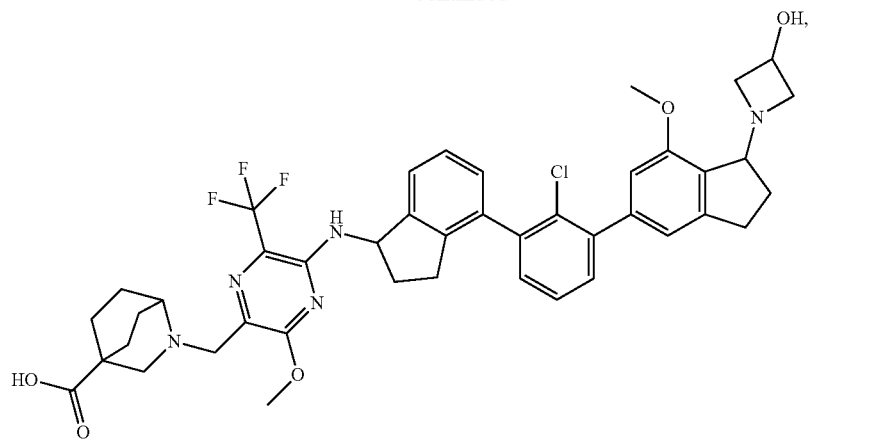
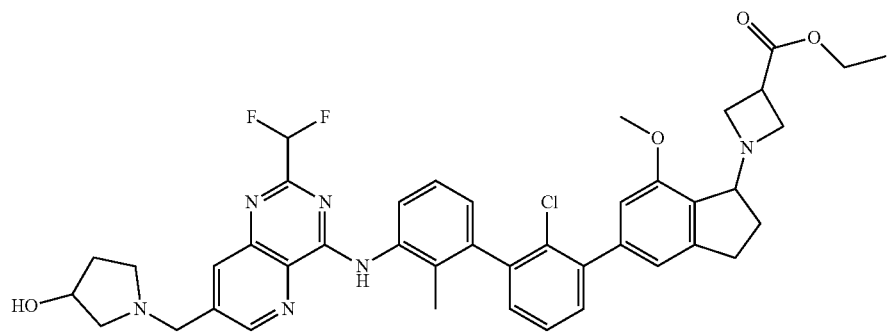
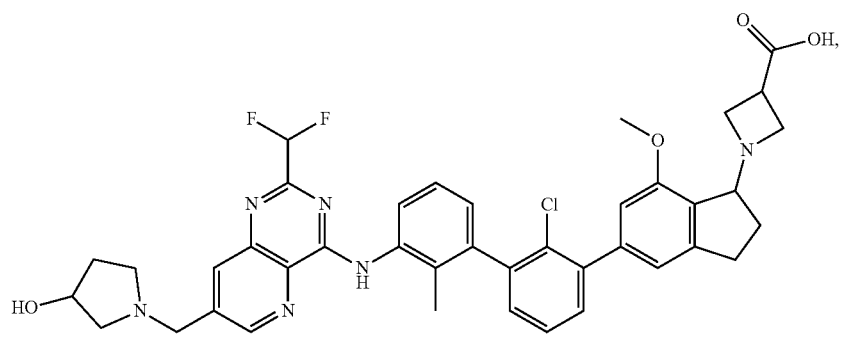
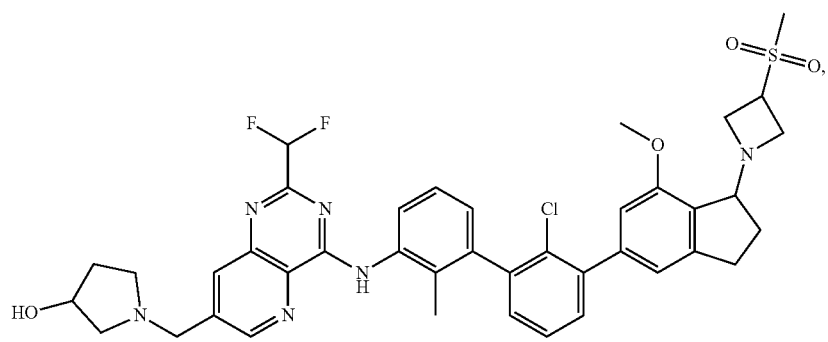

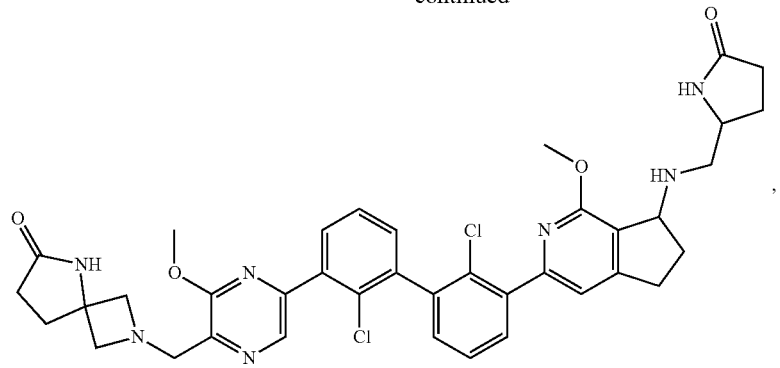
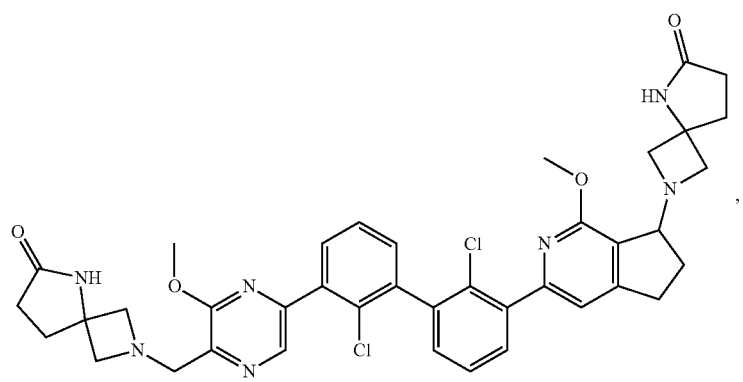
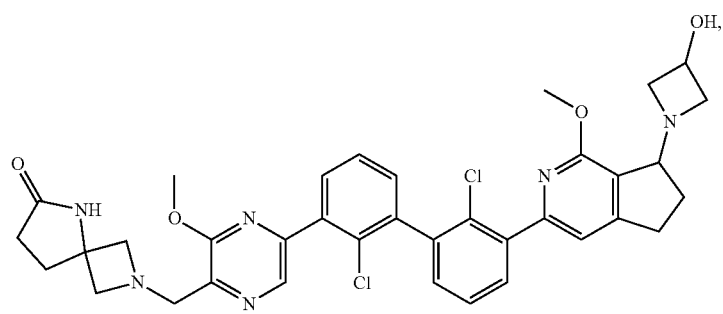
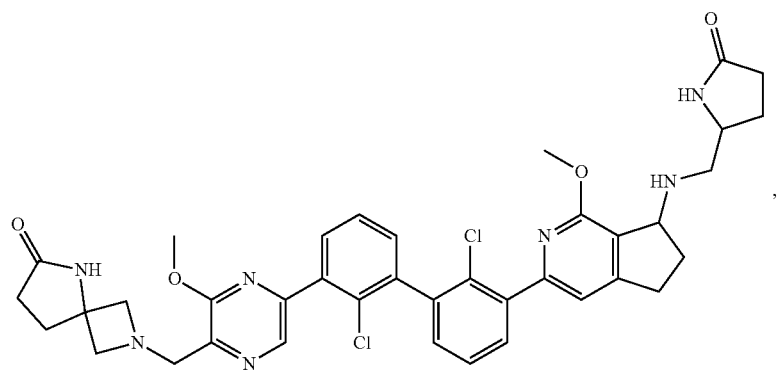

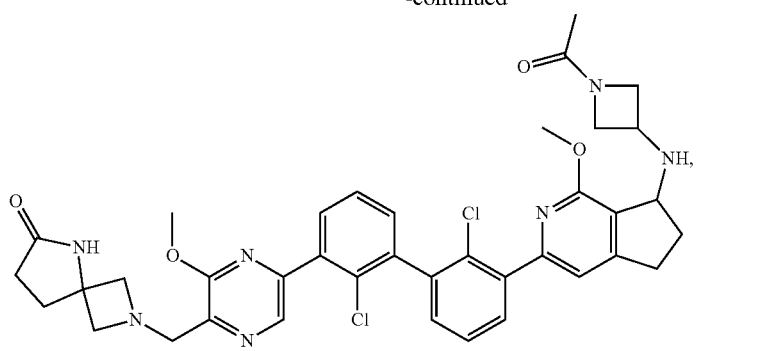
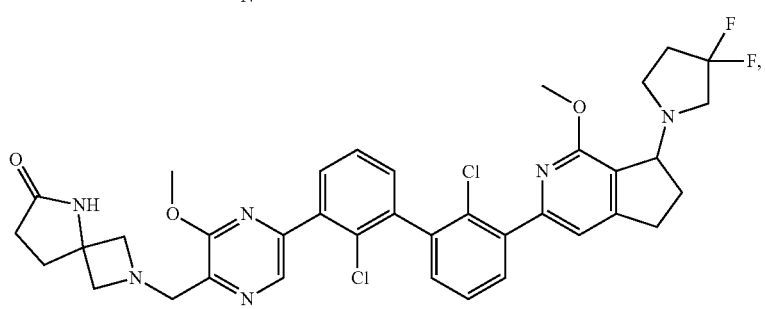
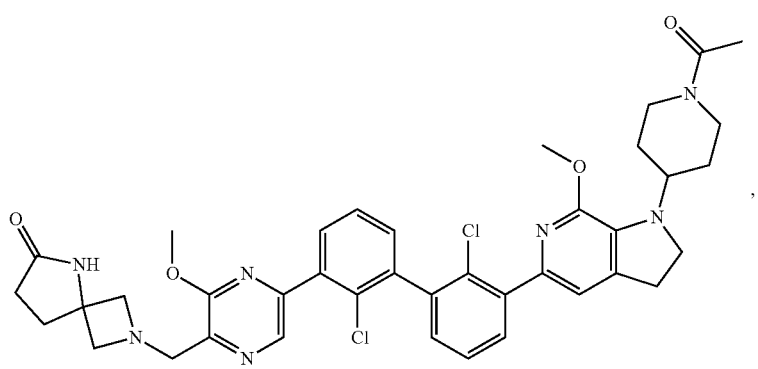
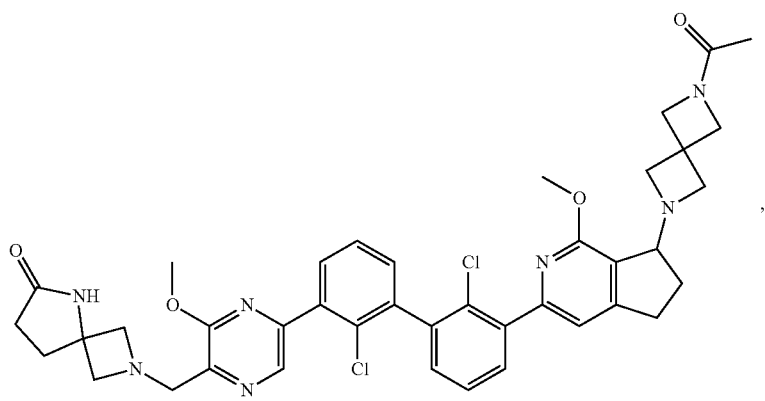

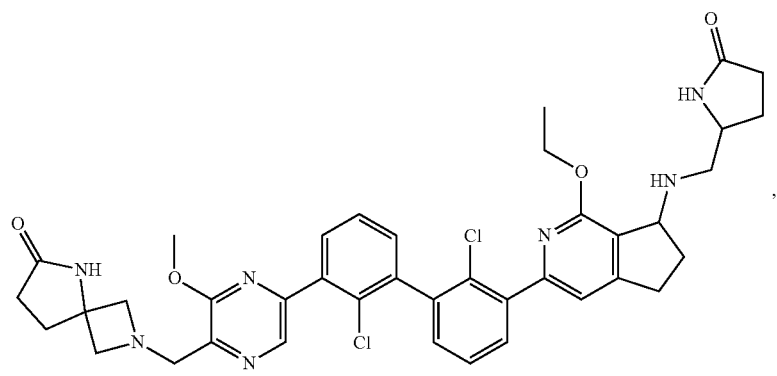
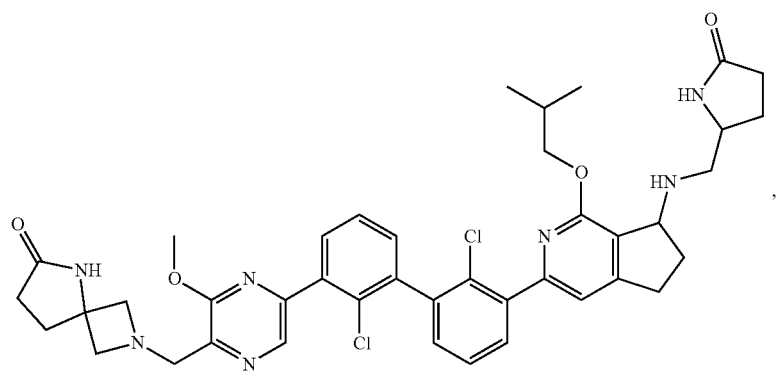
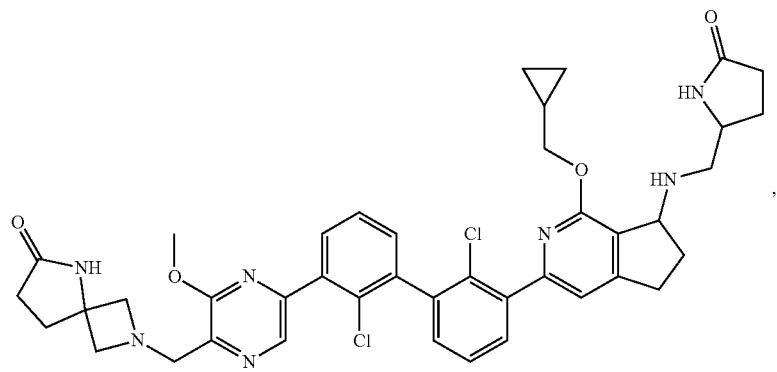
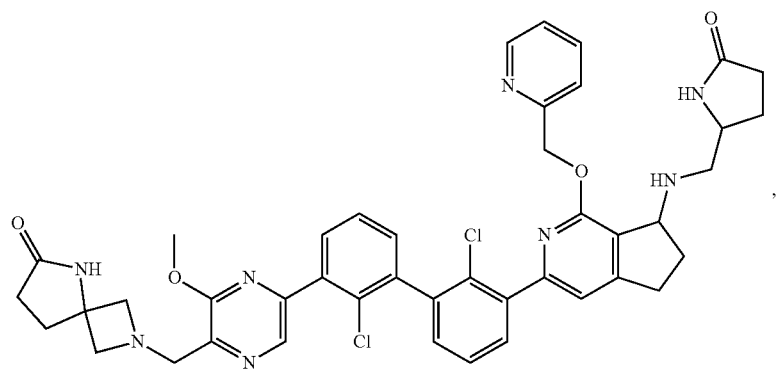

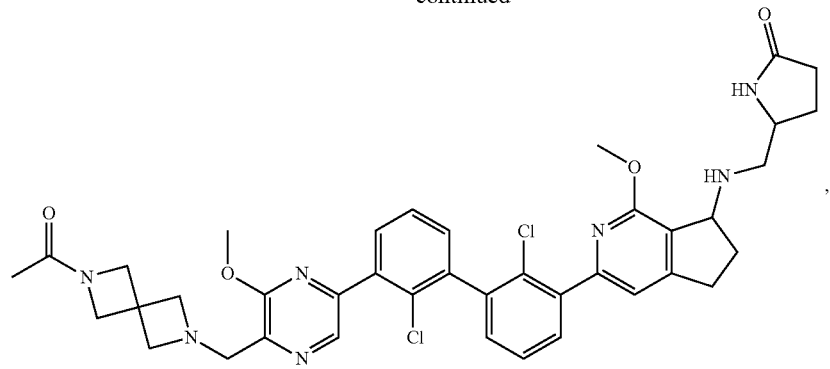
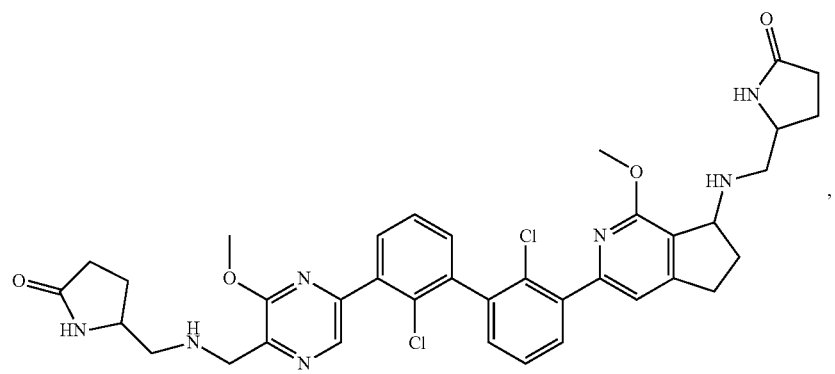
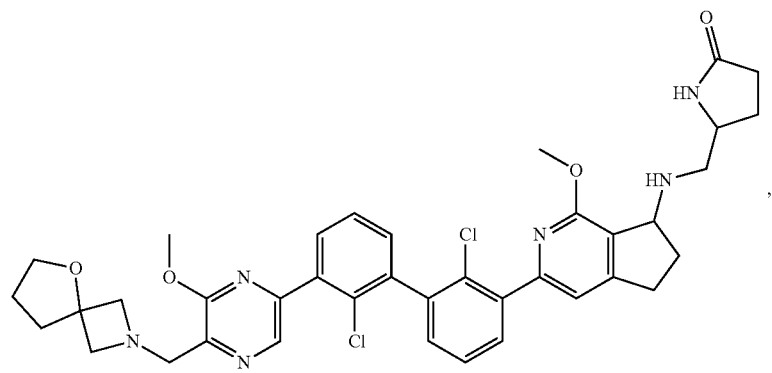
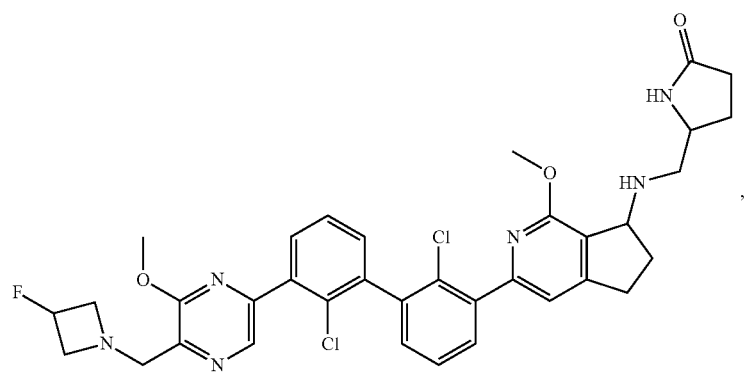

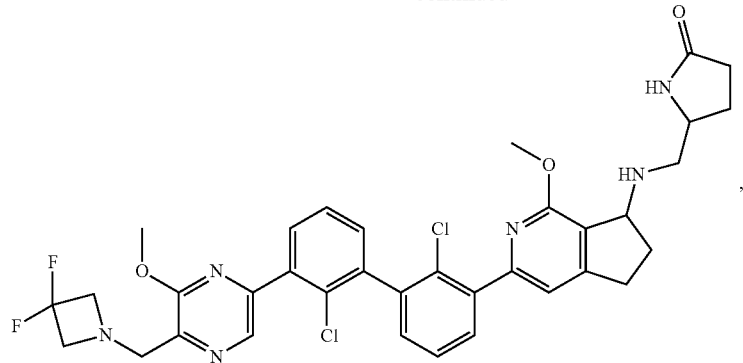
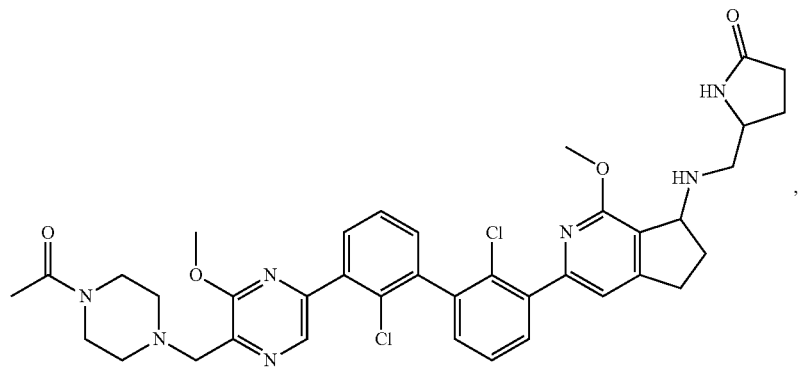
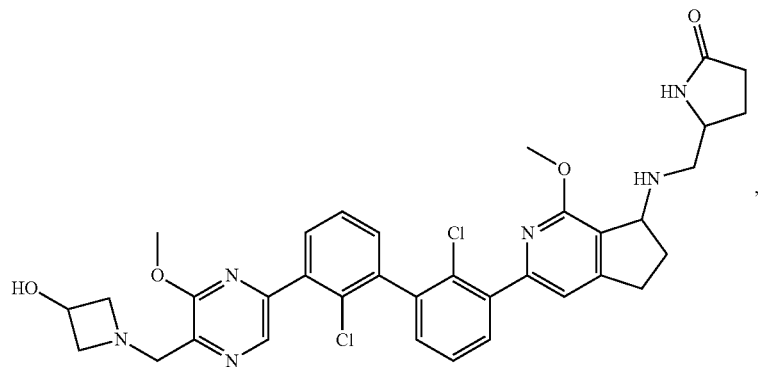
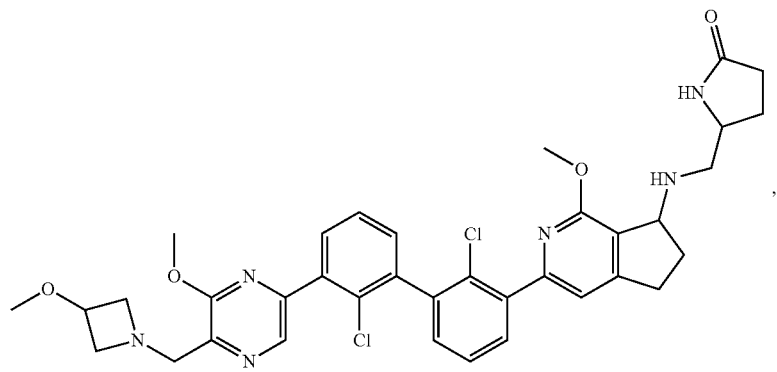

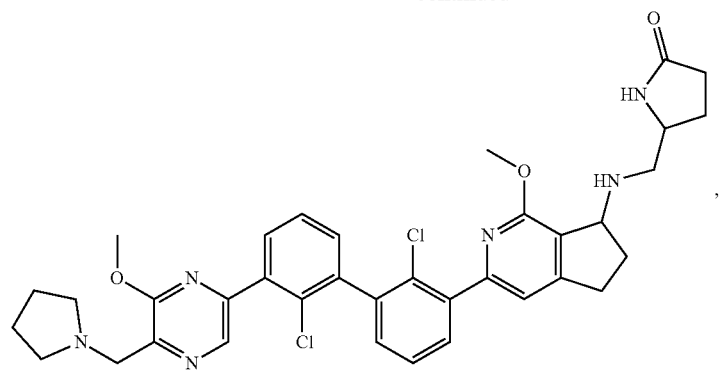
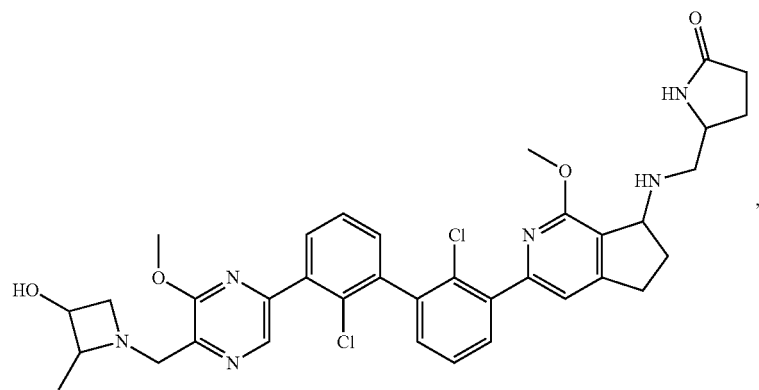
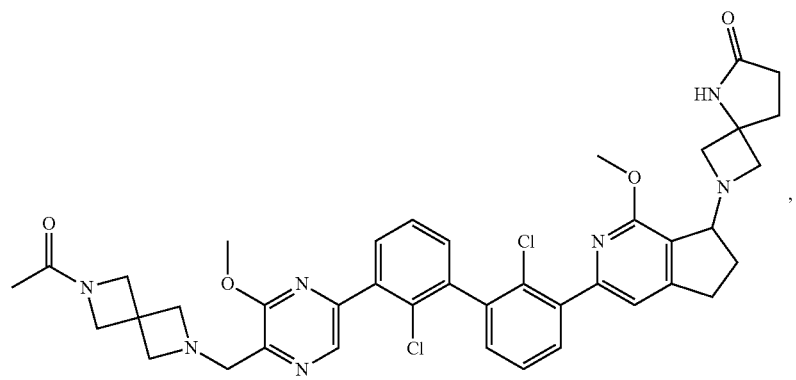
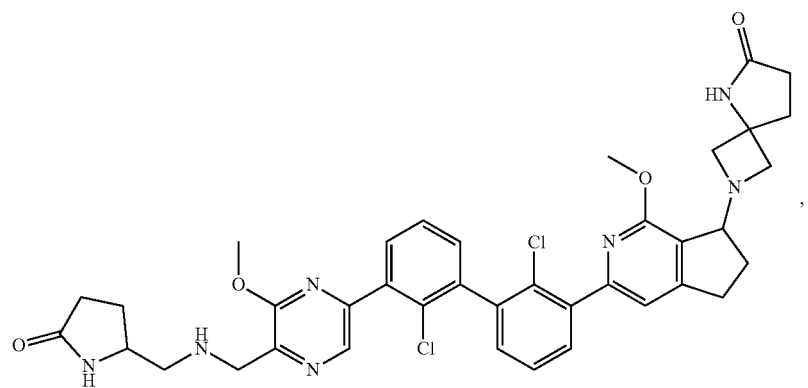

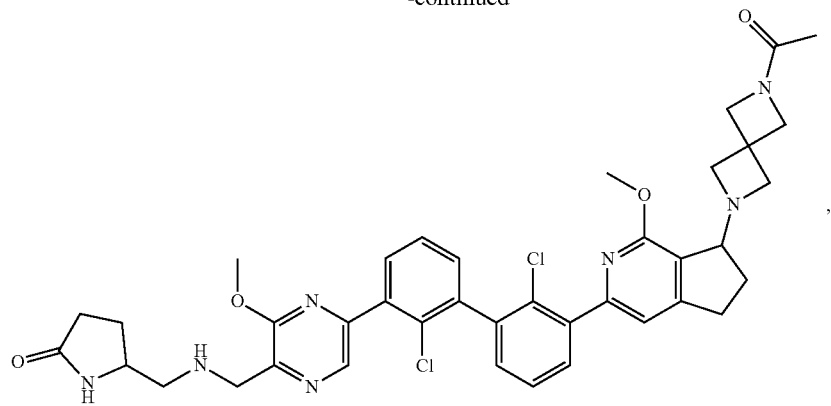
,
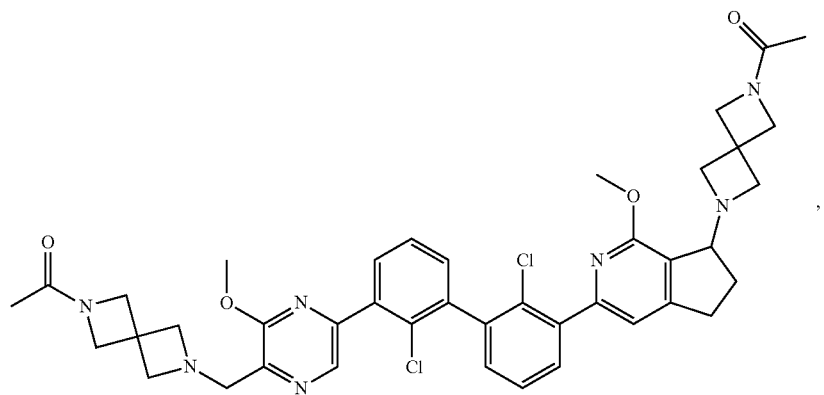
,
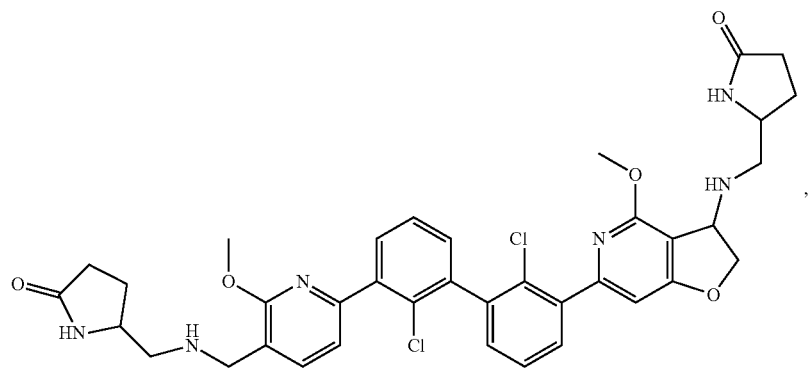
,
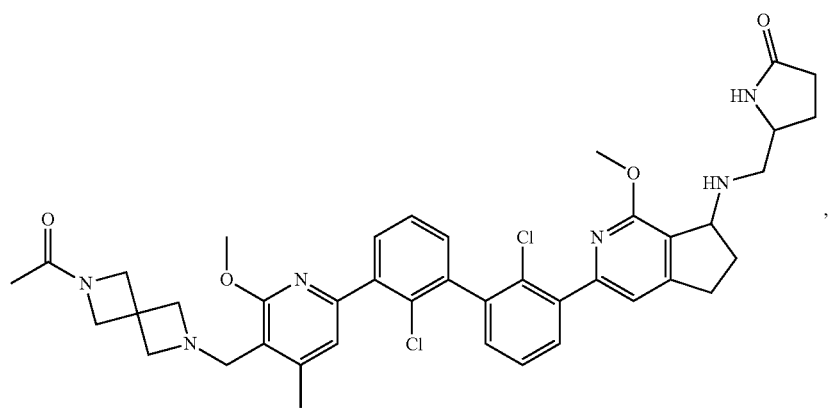
,

-continued
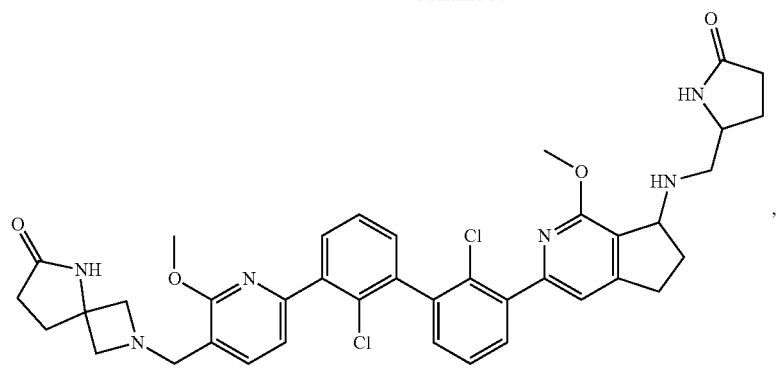
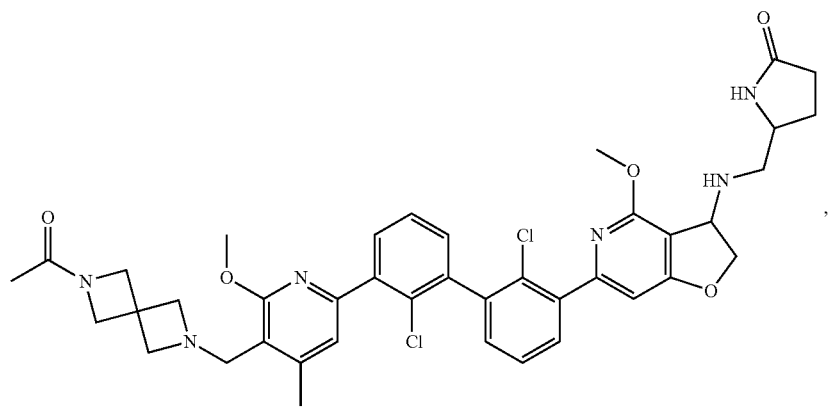
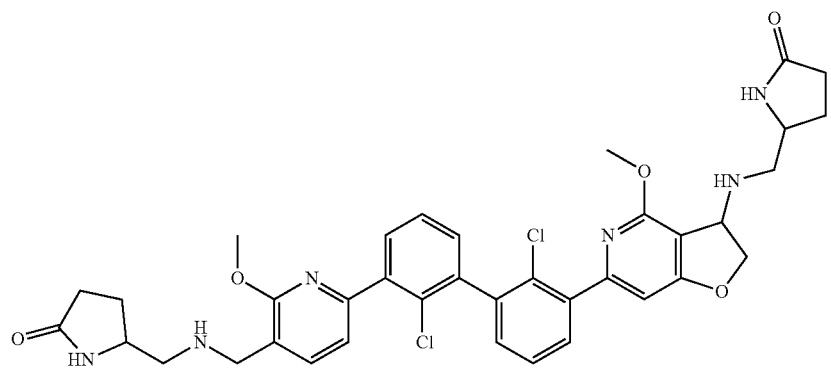
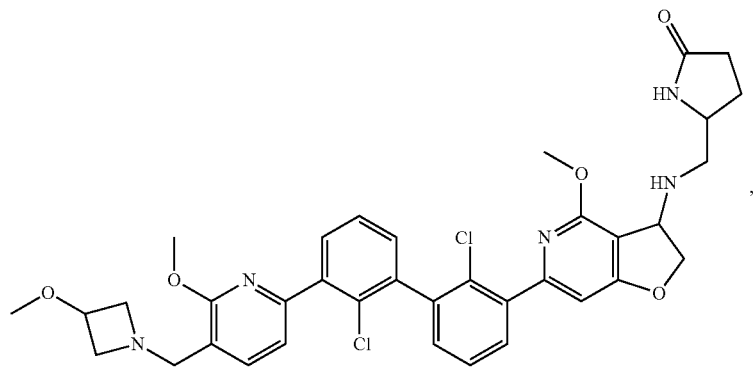

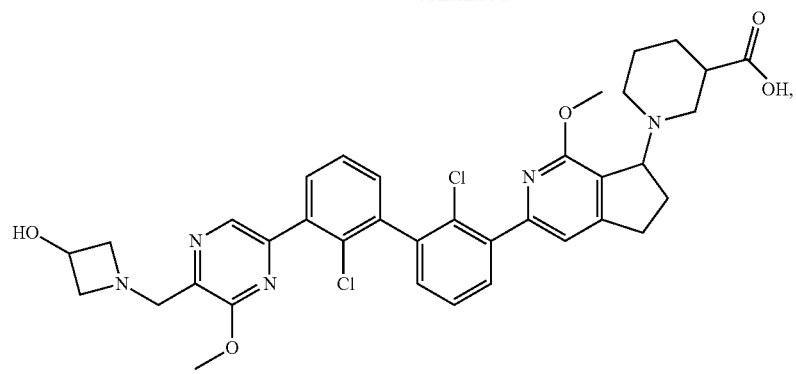
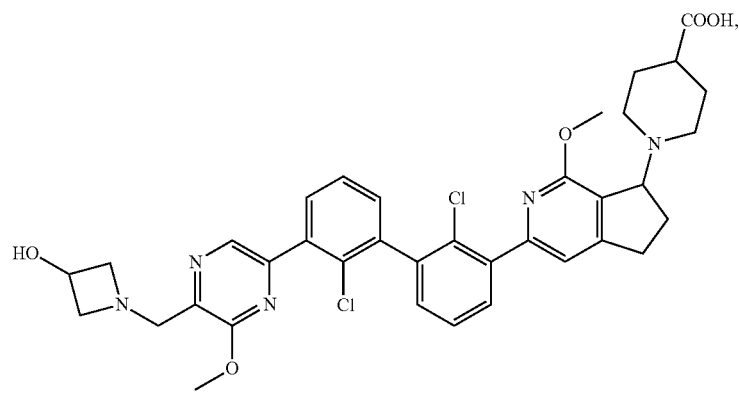
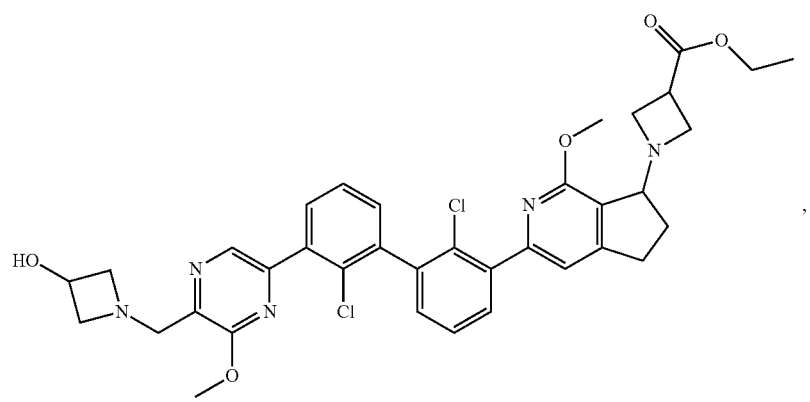
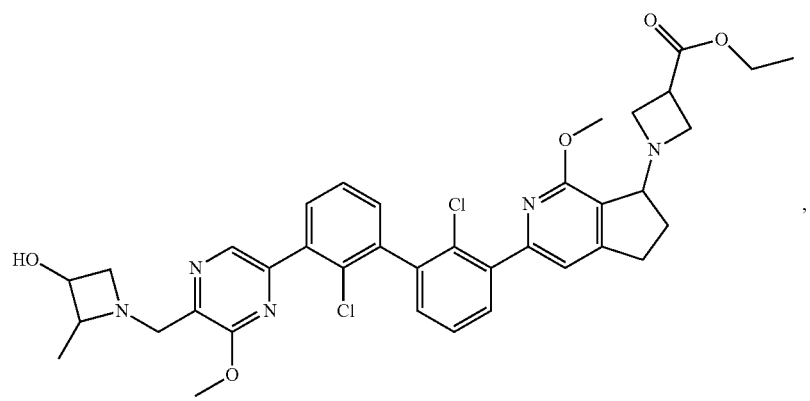

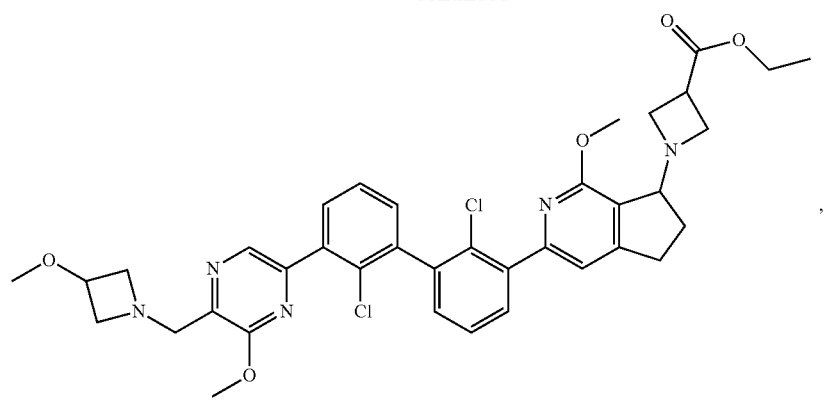
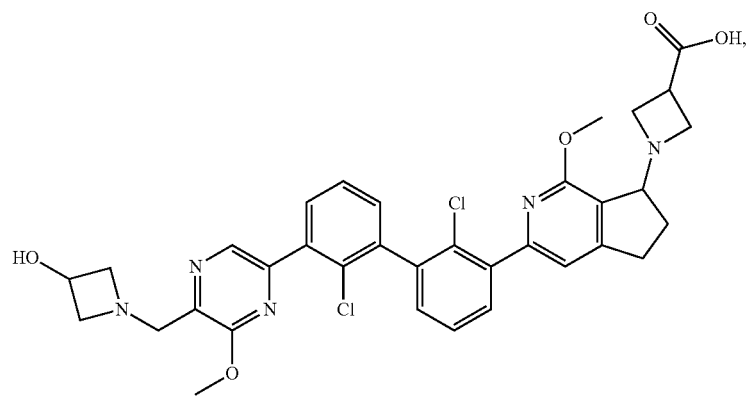
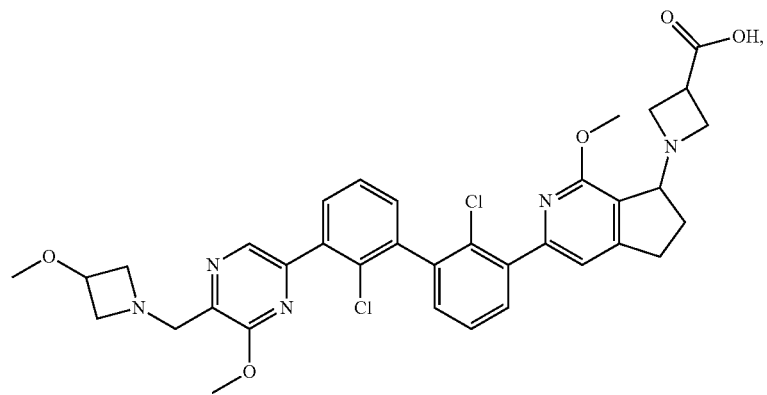
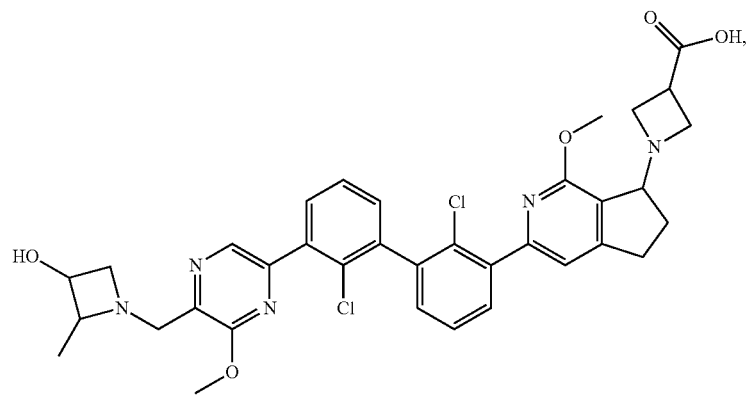

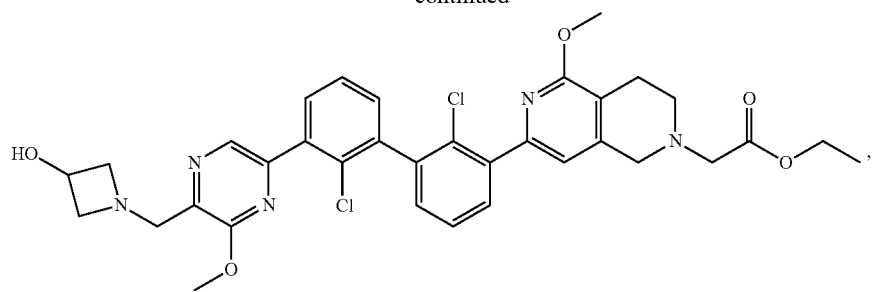
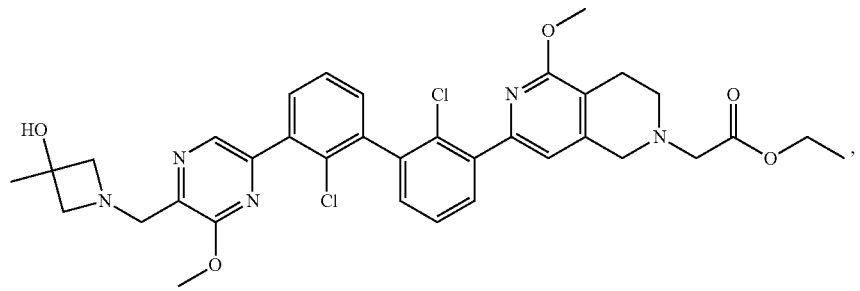
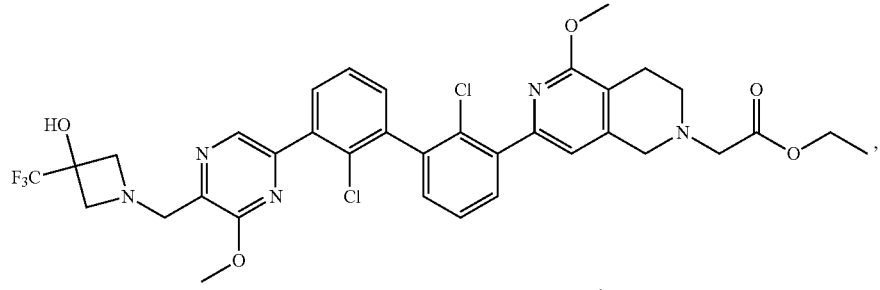
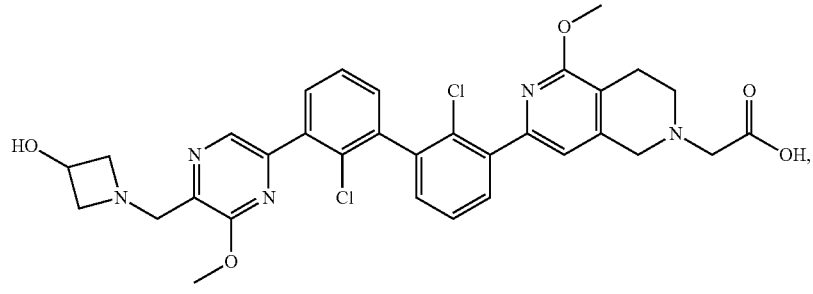
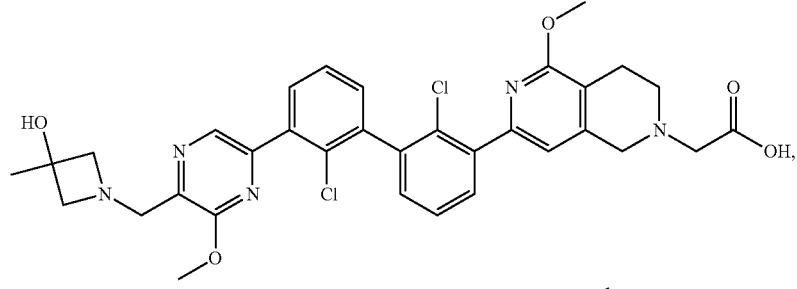
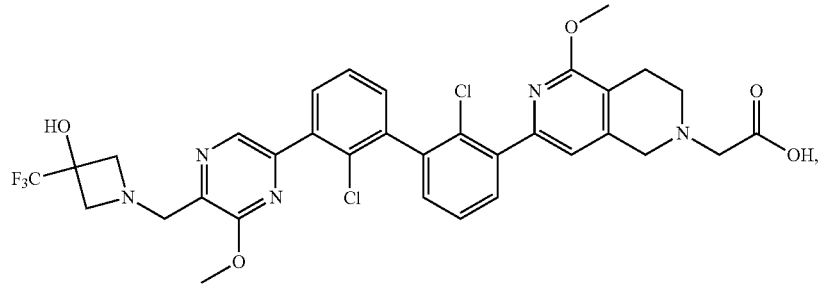

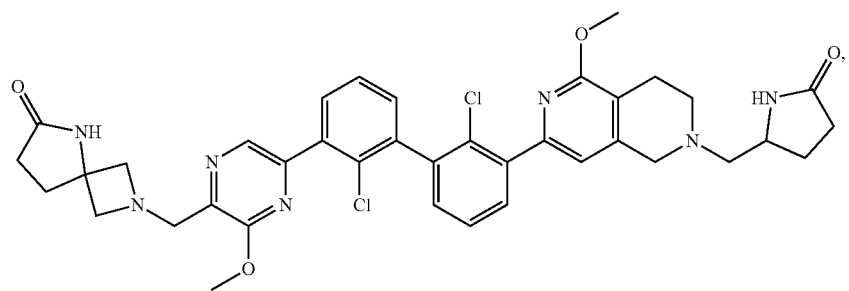
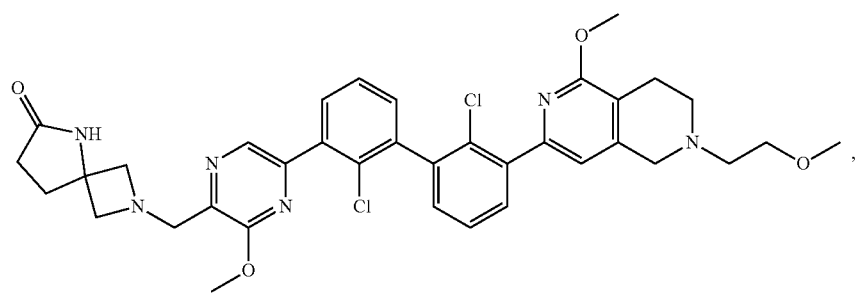
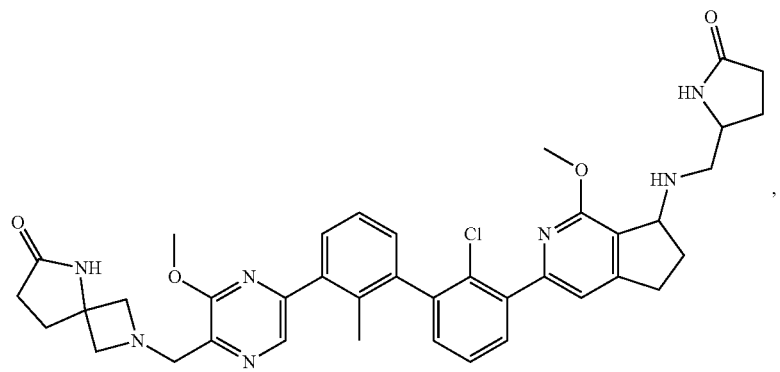
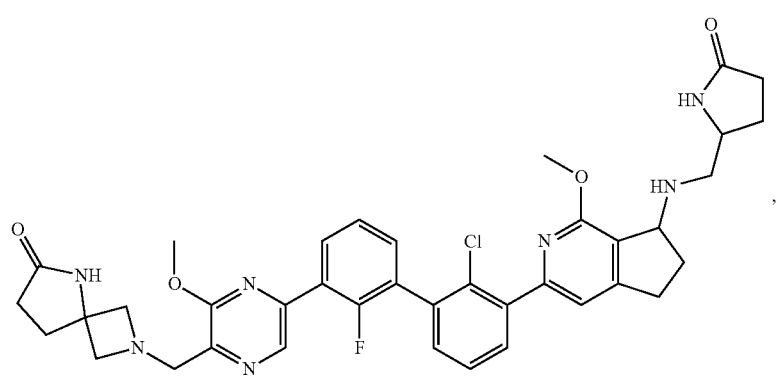

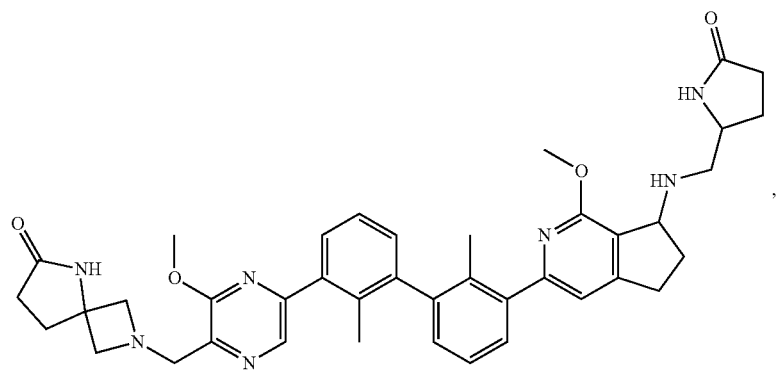

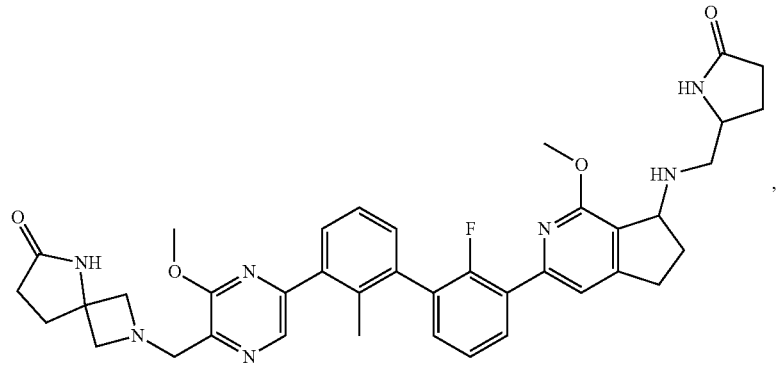

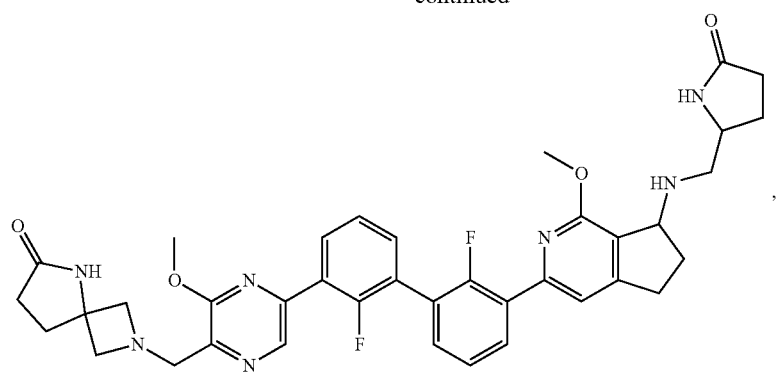
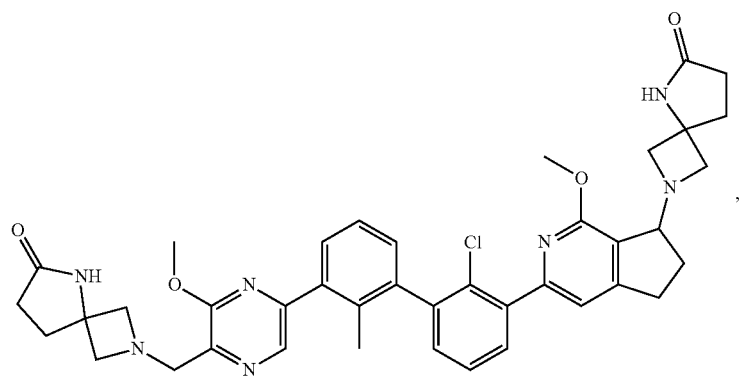
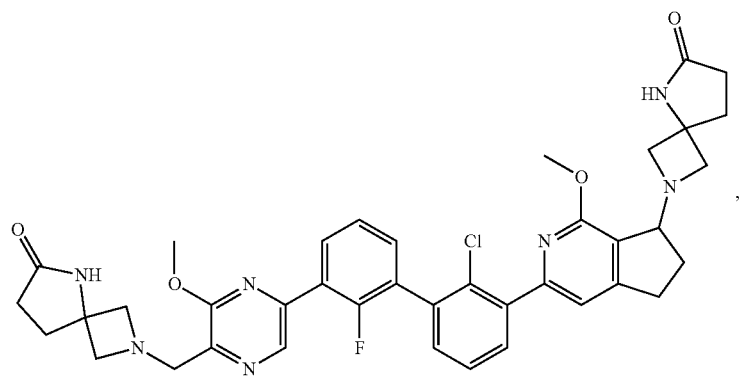
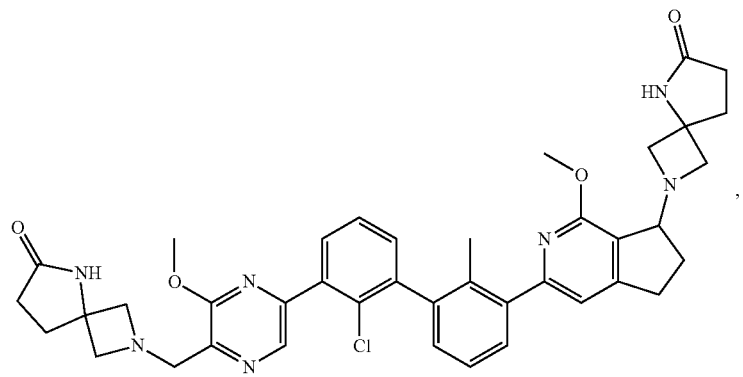

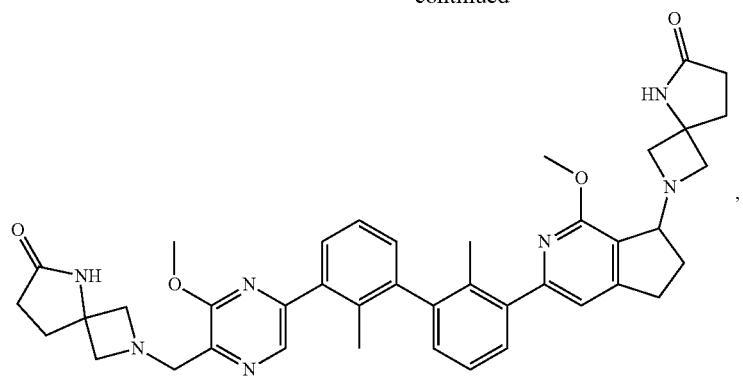
,

,

,
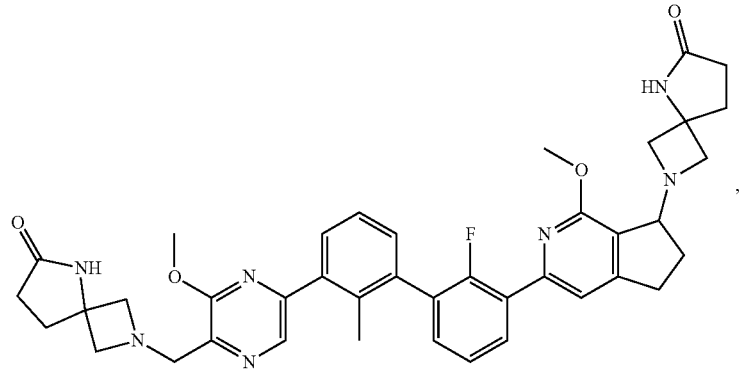
,

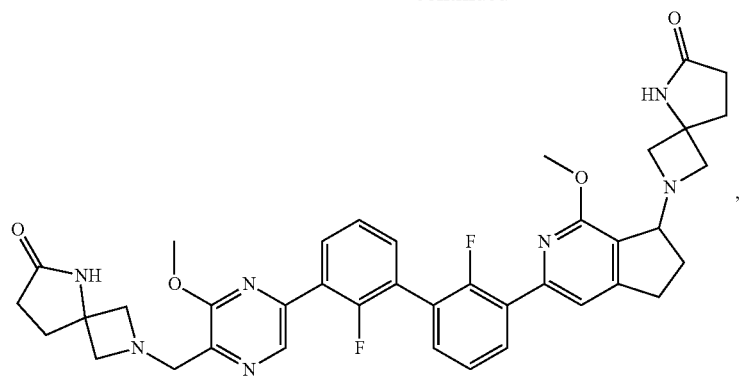
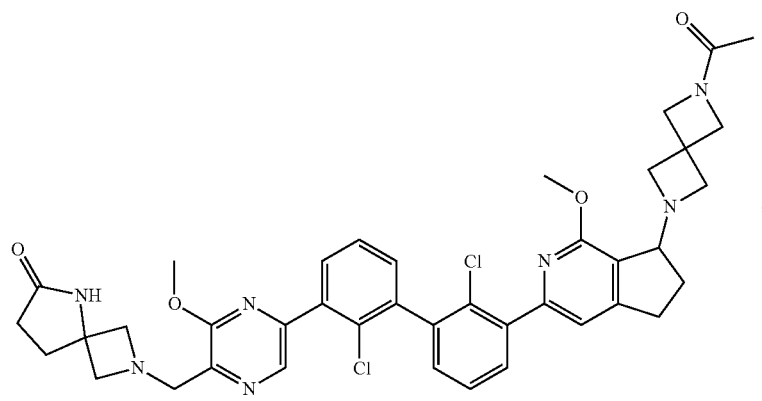
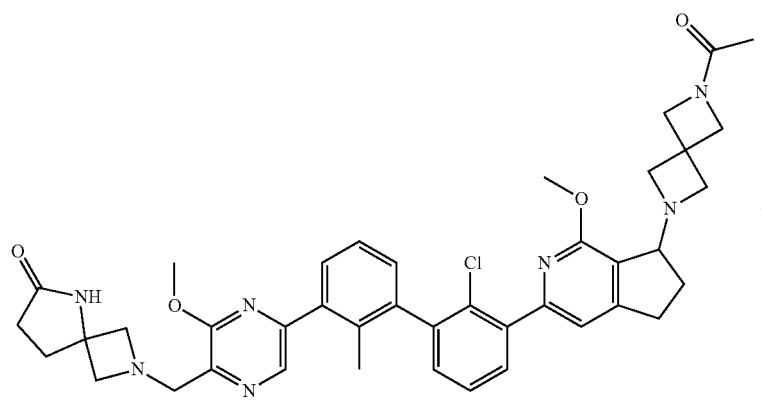
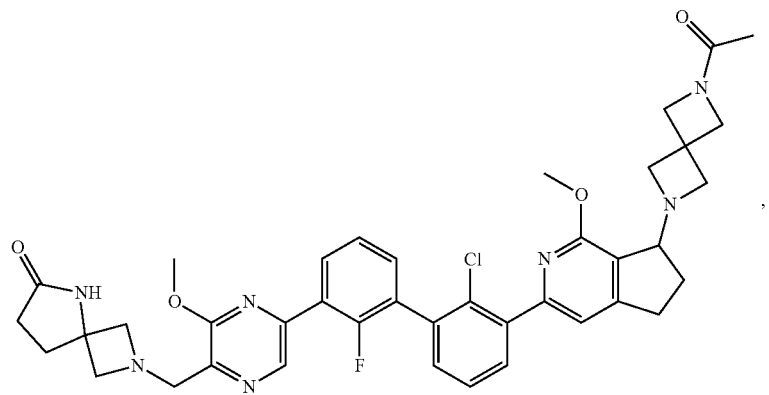

,
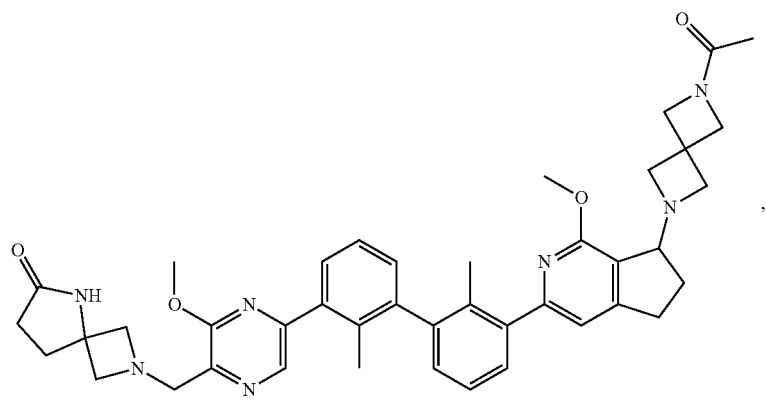,
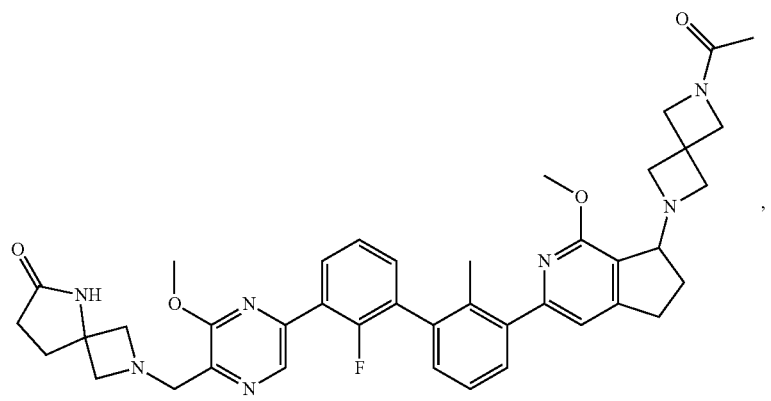,
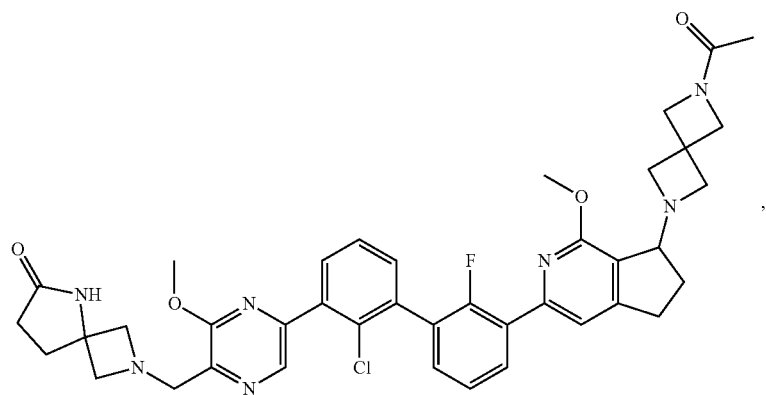,

-continued

,
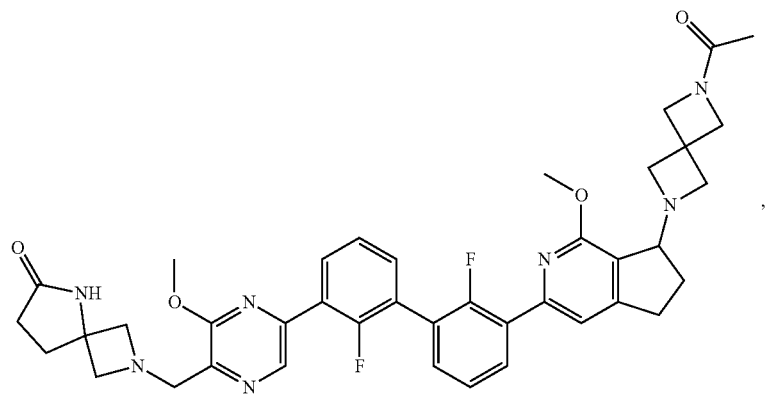
,
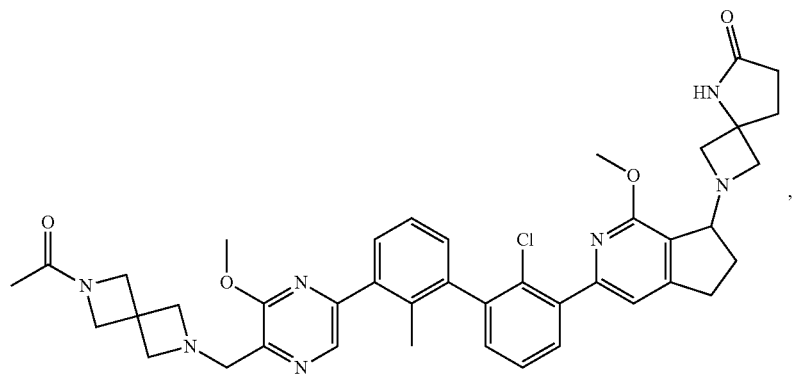
,
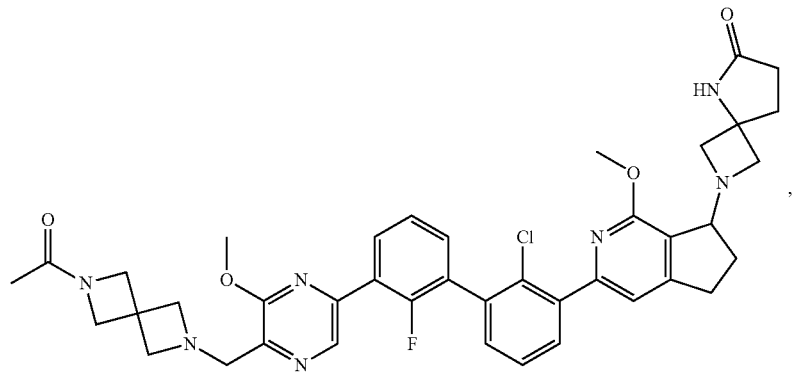
,


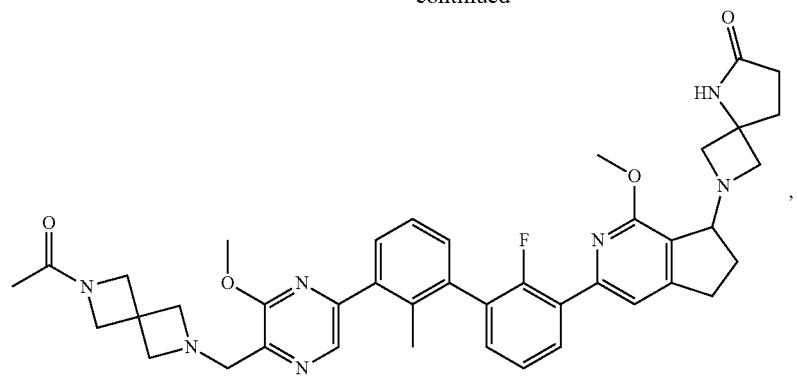
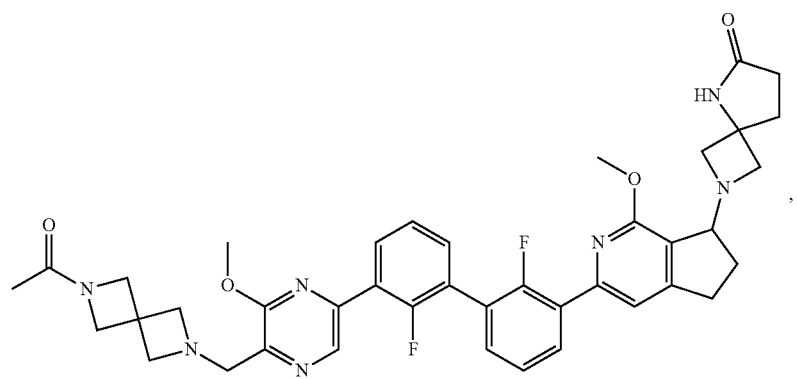
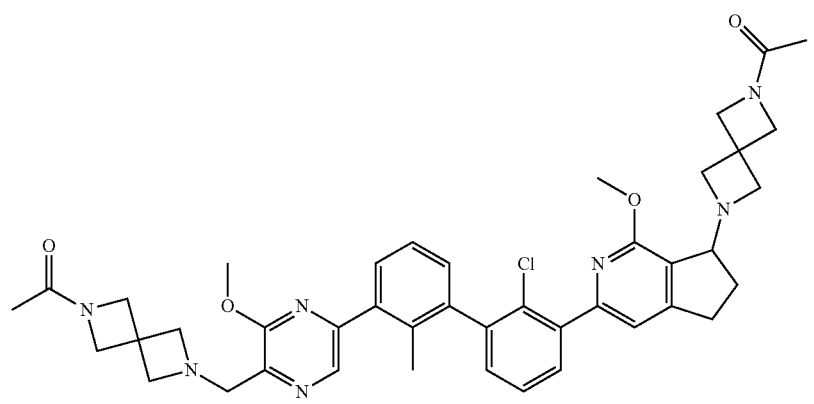
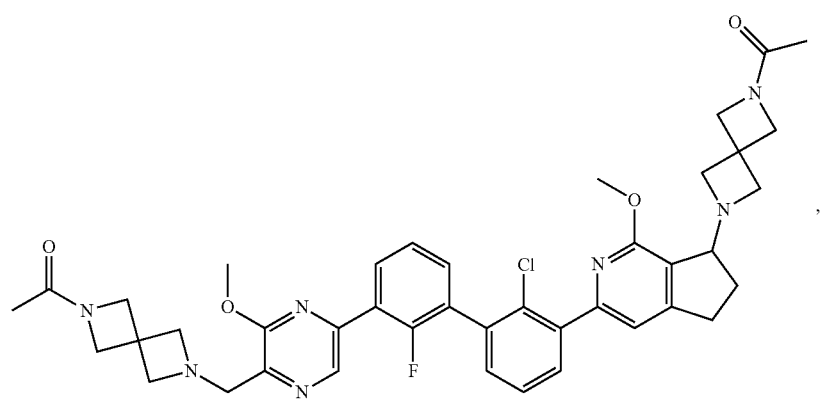

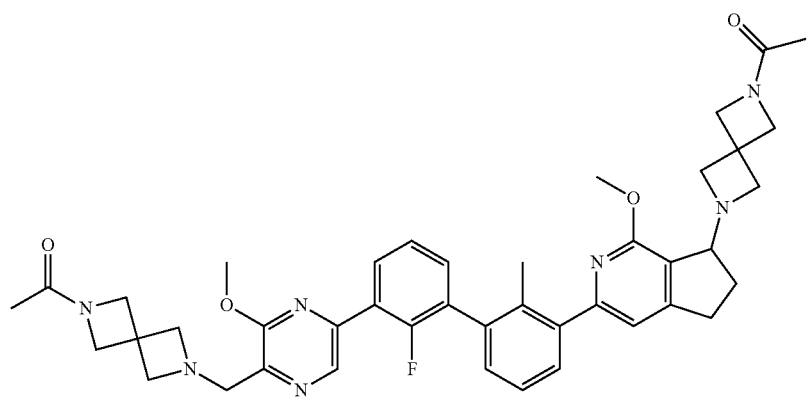
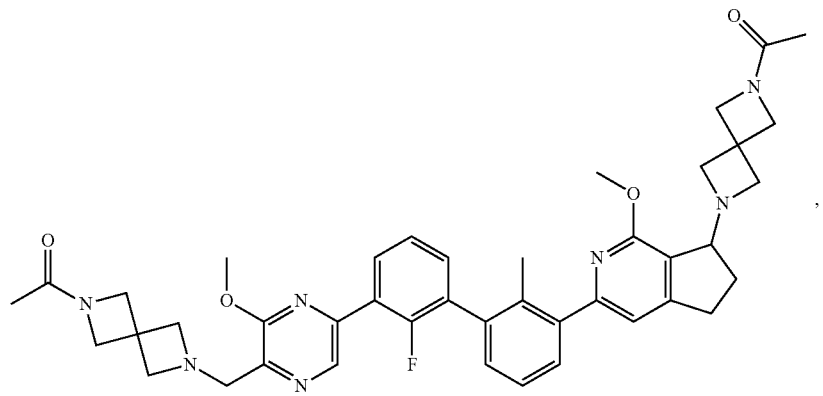
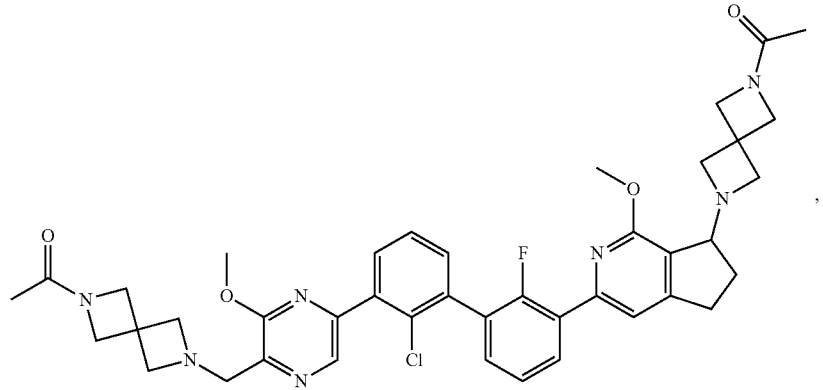

-continued
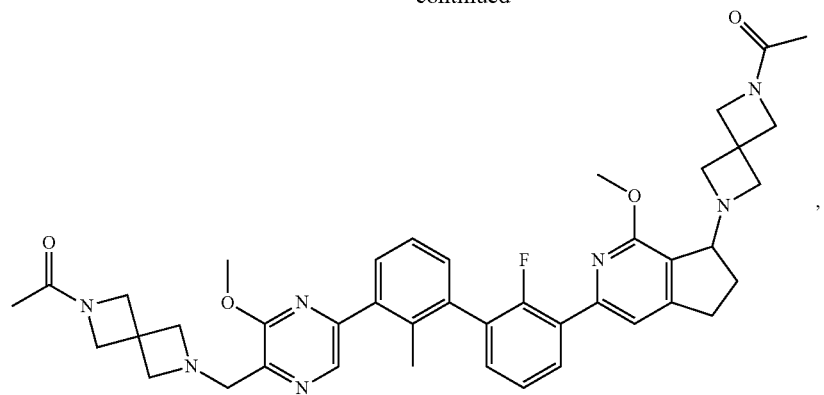
,
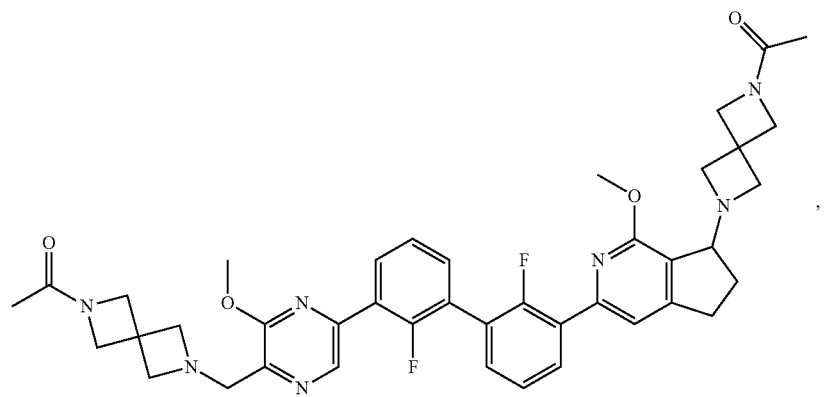
,
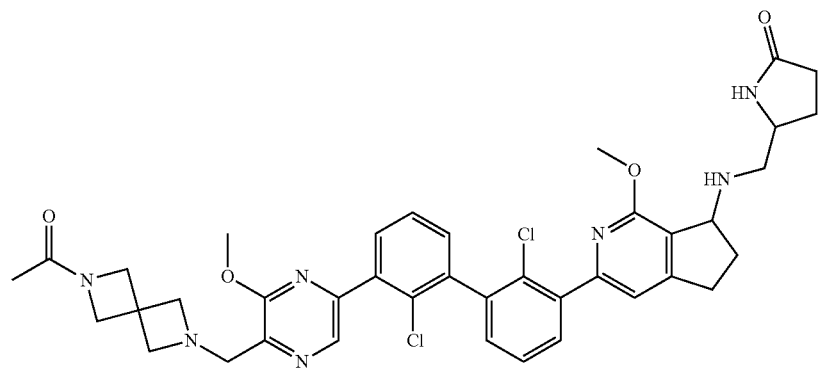
,
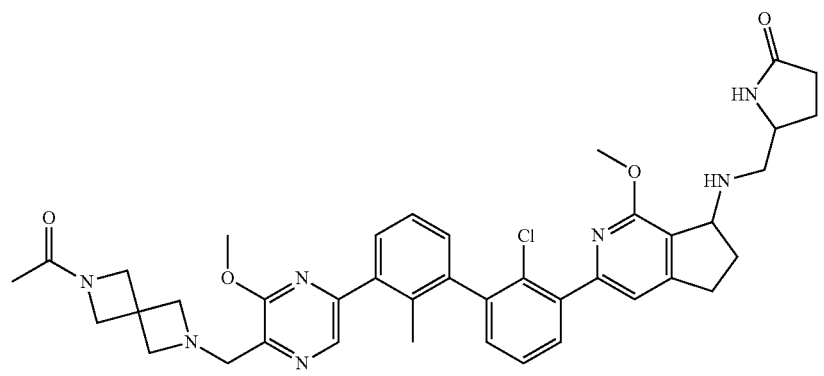
,

-continued
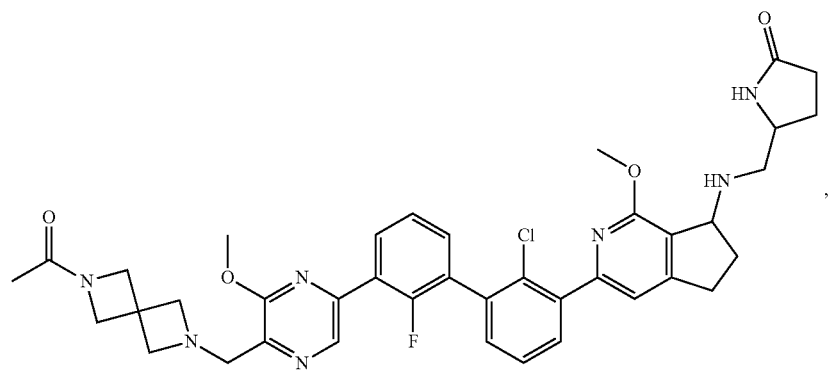
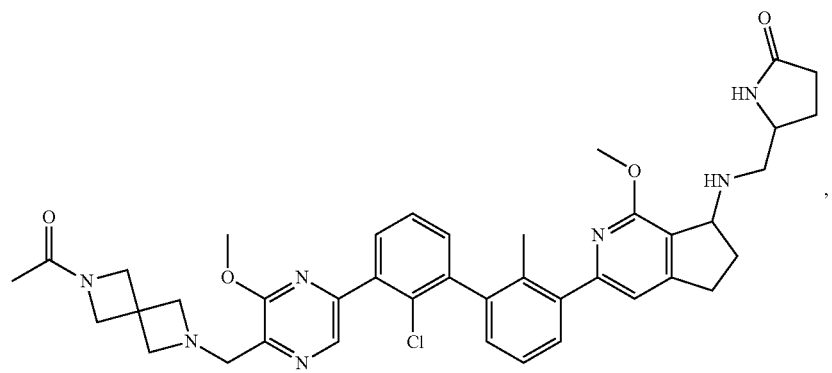
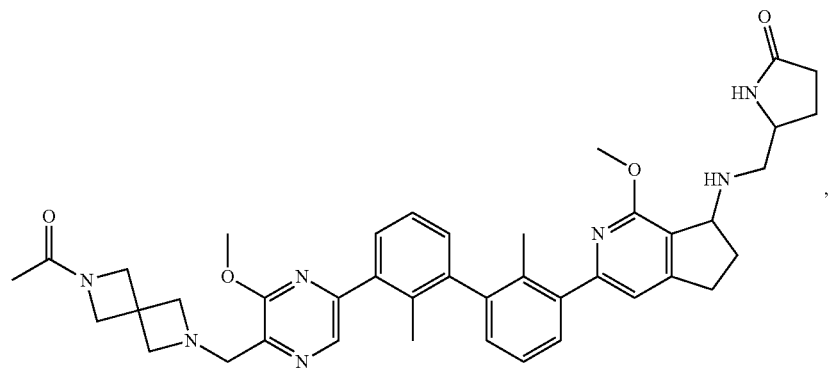
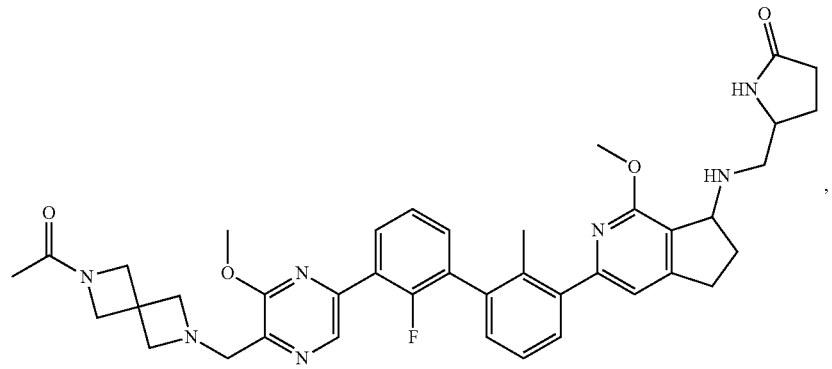

-continued
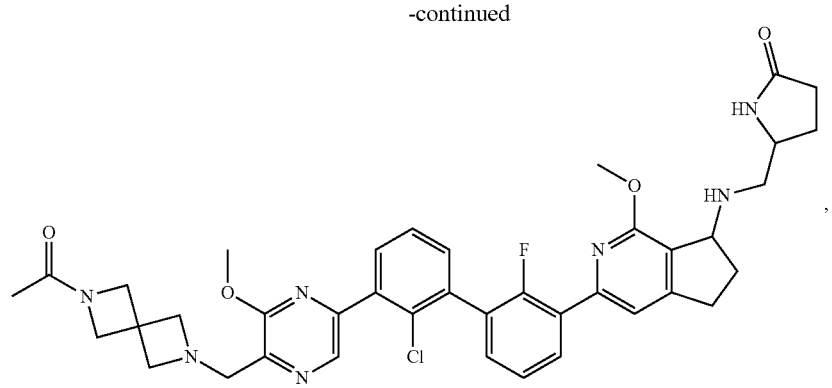
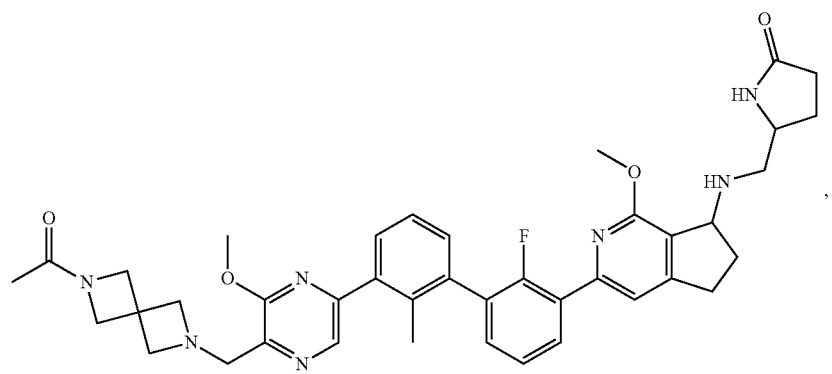
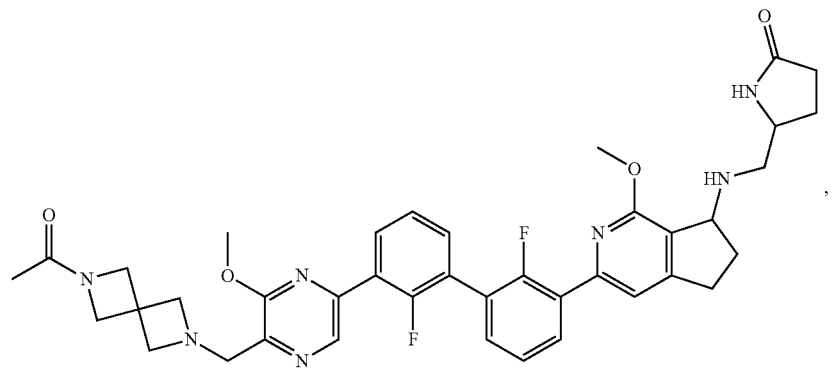
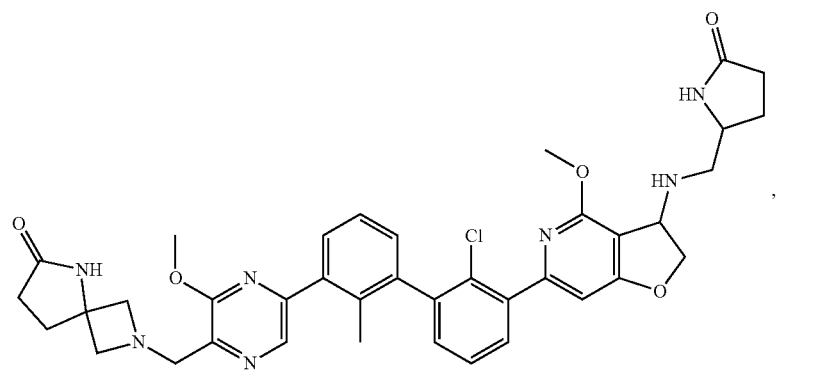

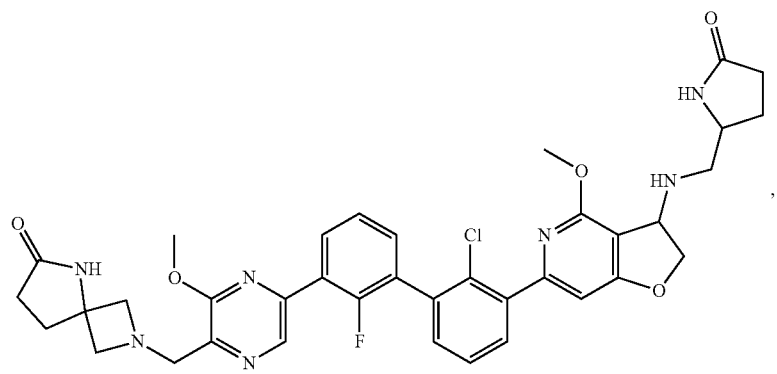
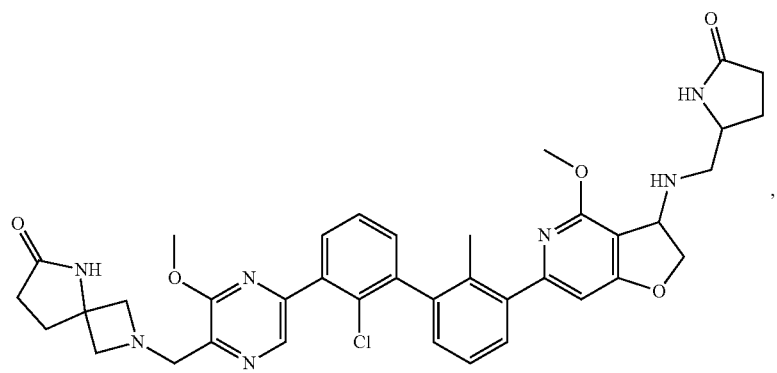
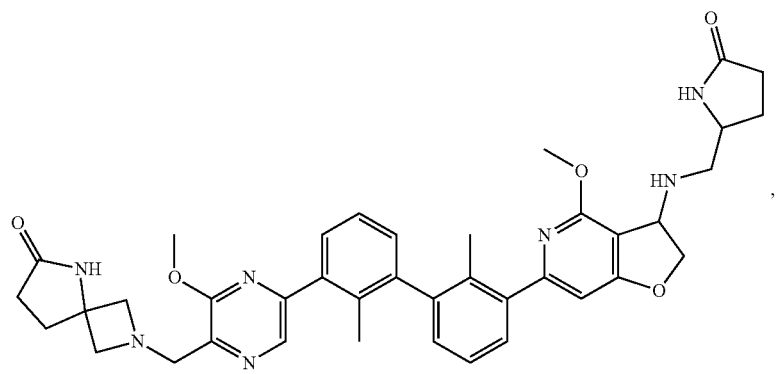
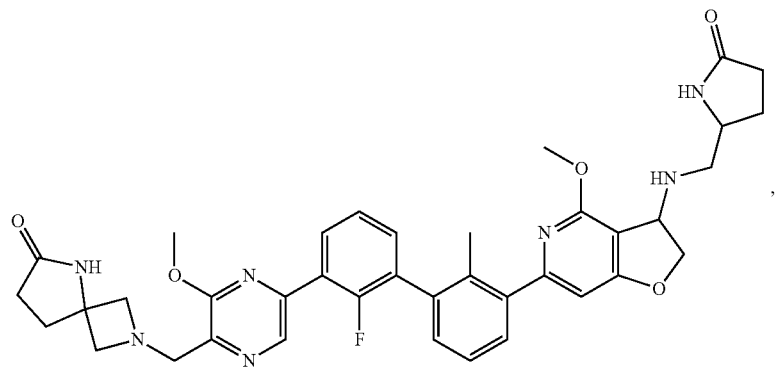

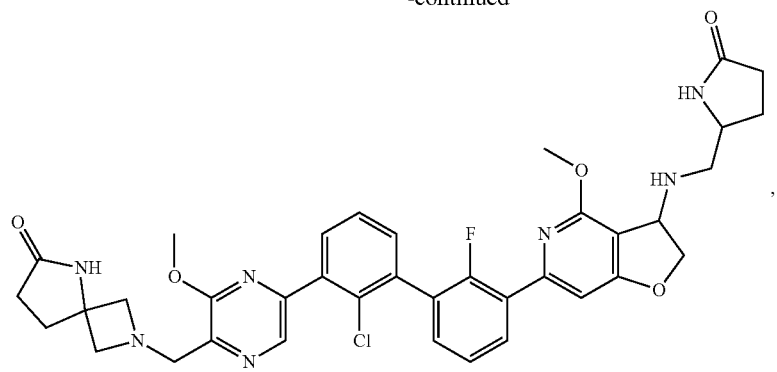
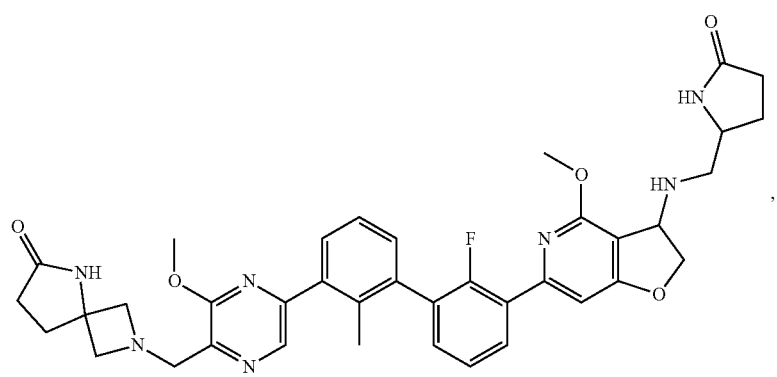
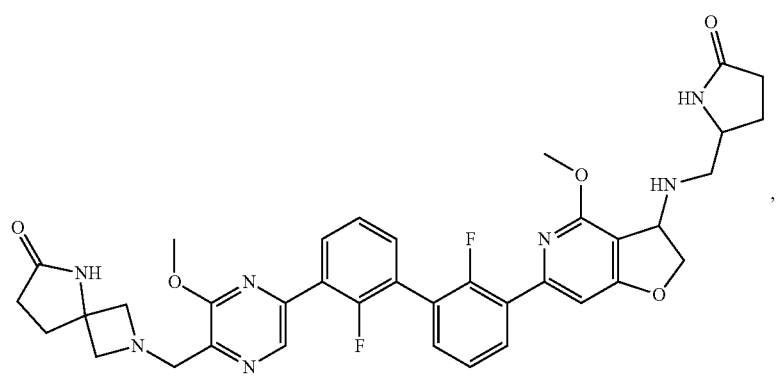

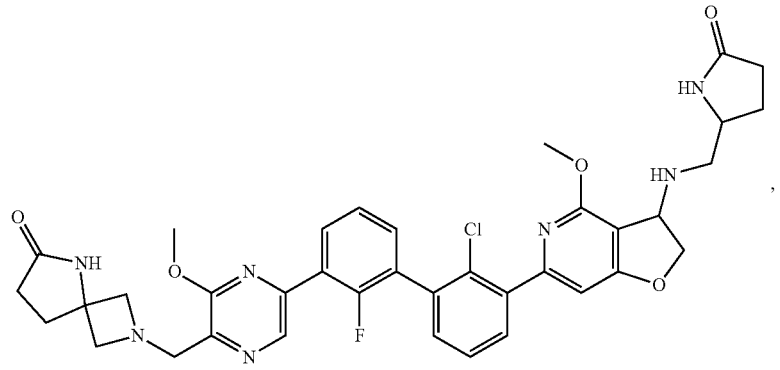
,
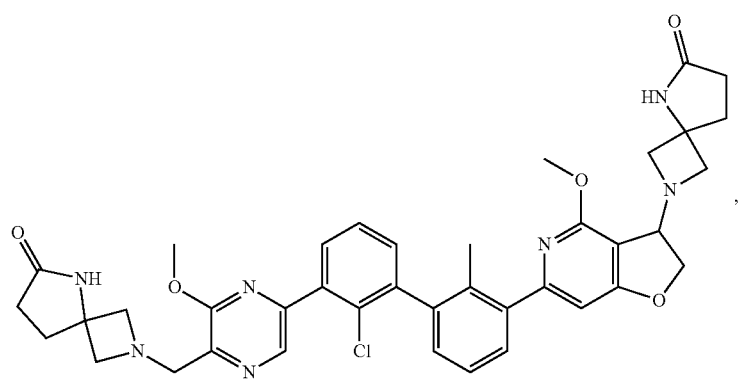
,
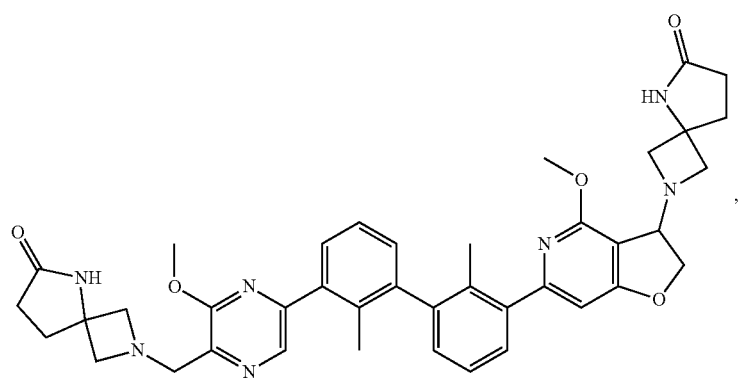
,
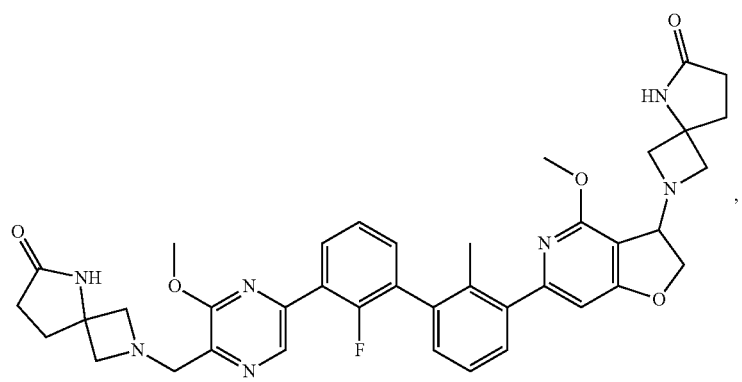
,

-continued
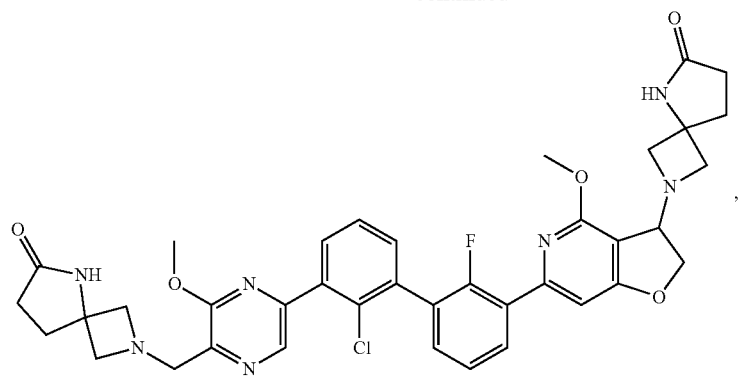
,
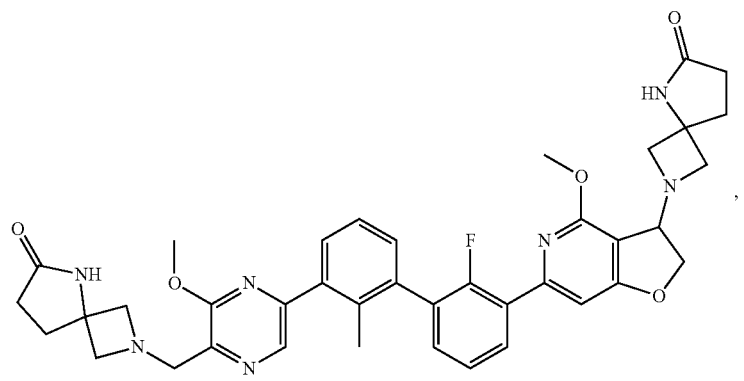
,

,
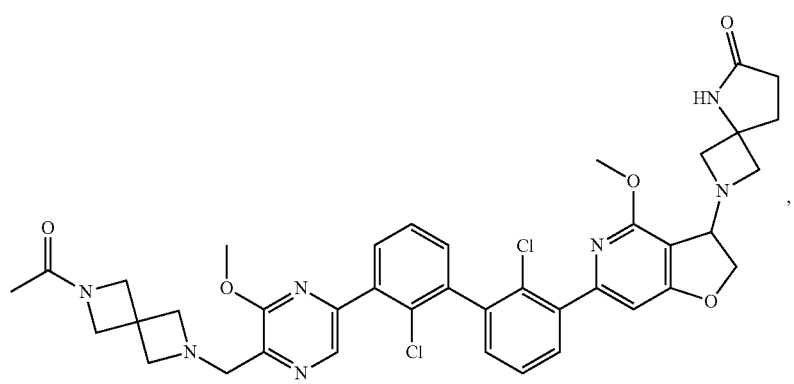
,

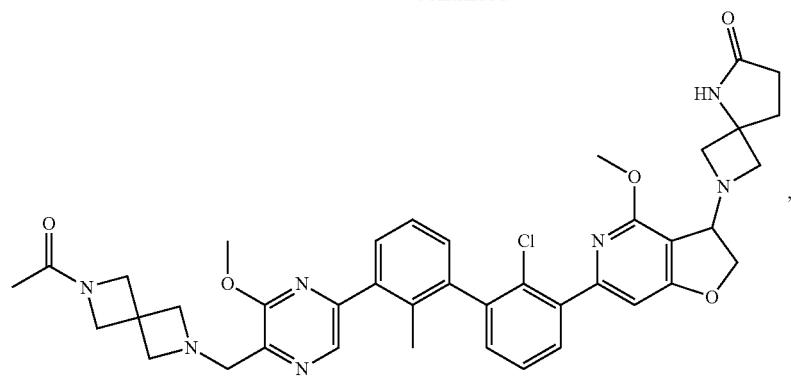
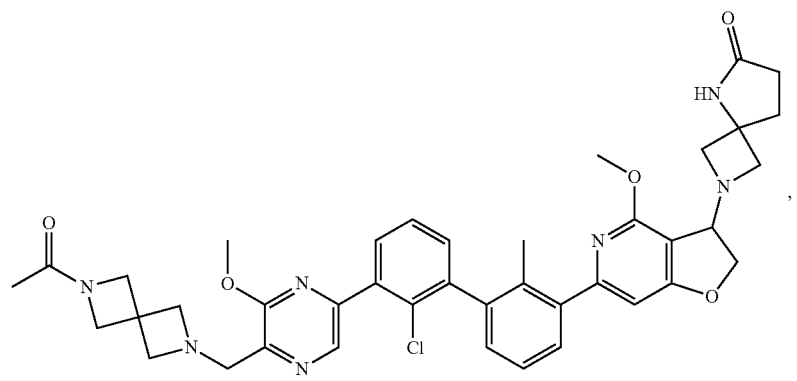
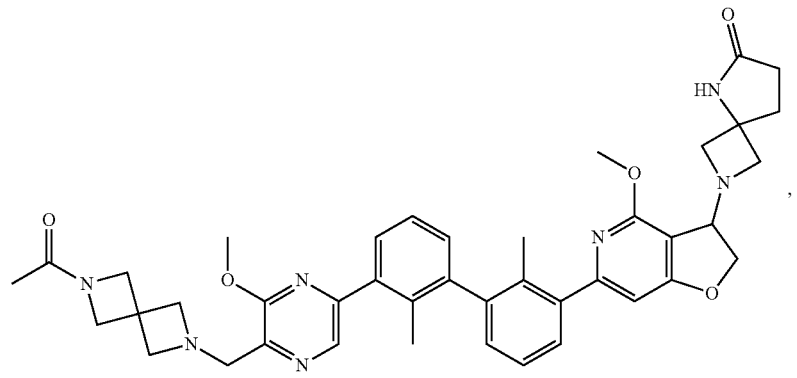

-continued
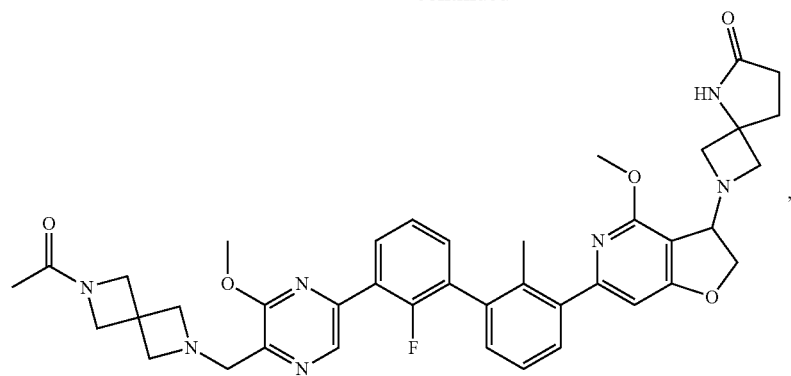
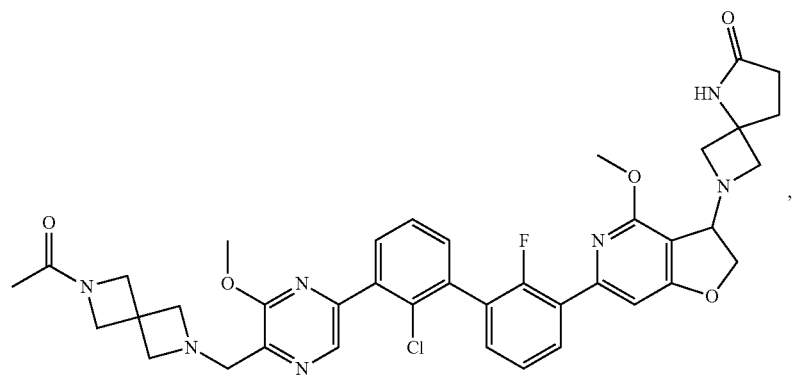
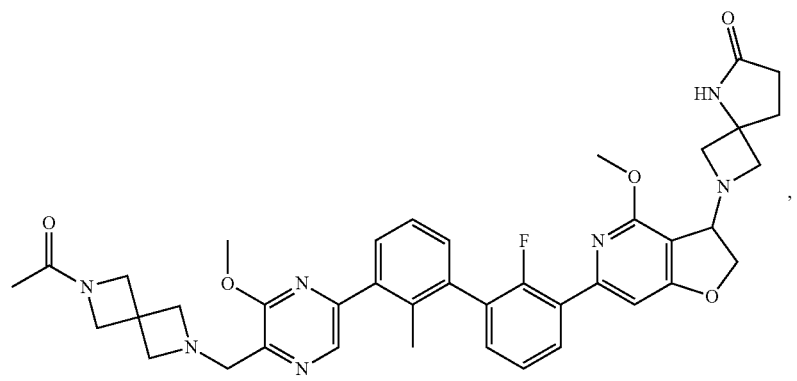
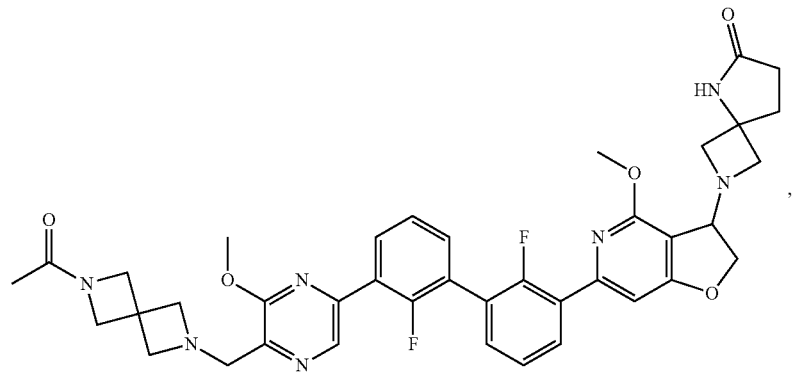

-continued
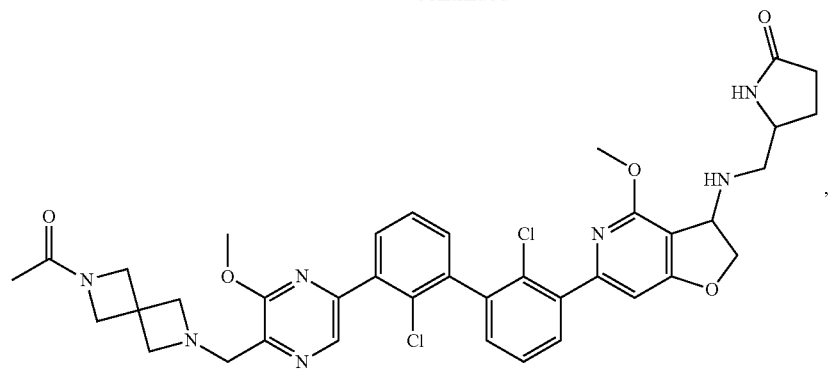
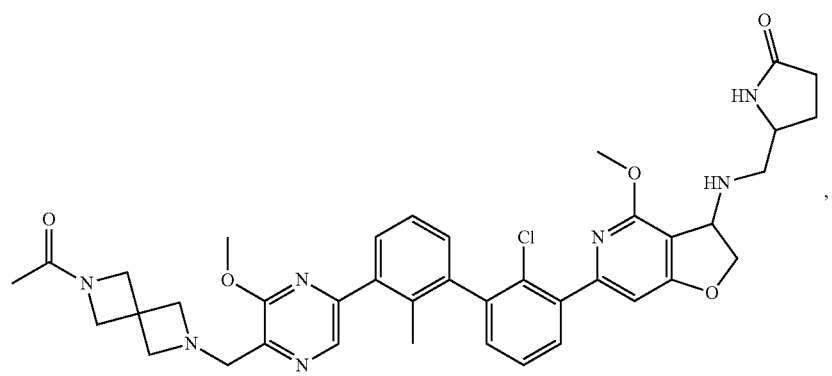
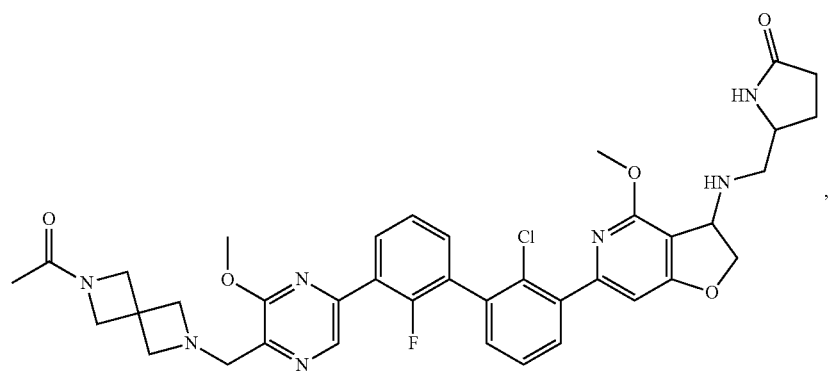
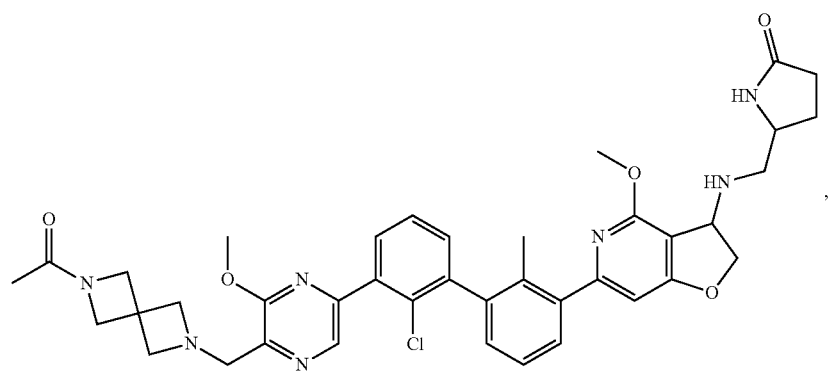

-continued
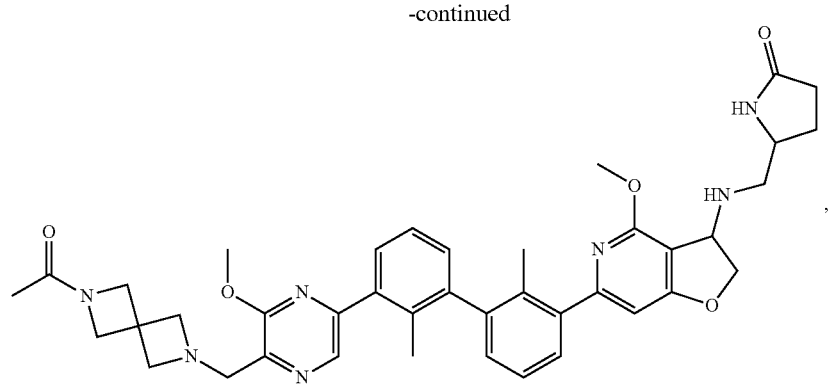
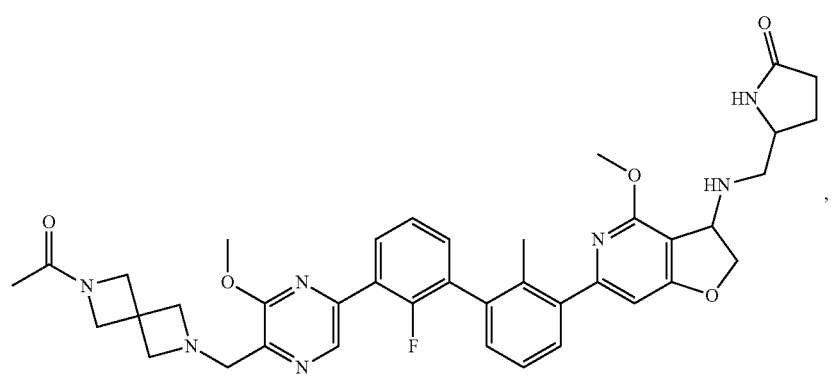
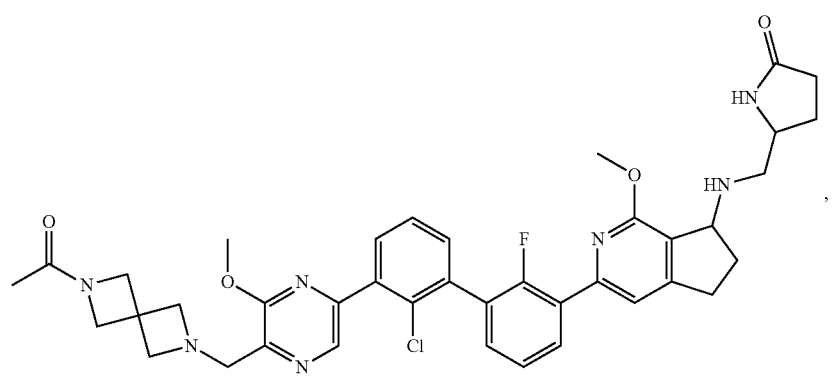
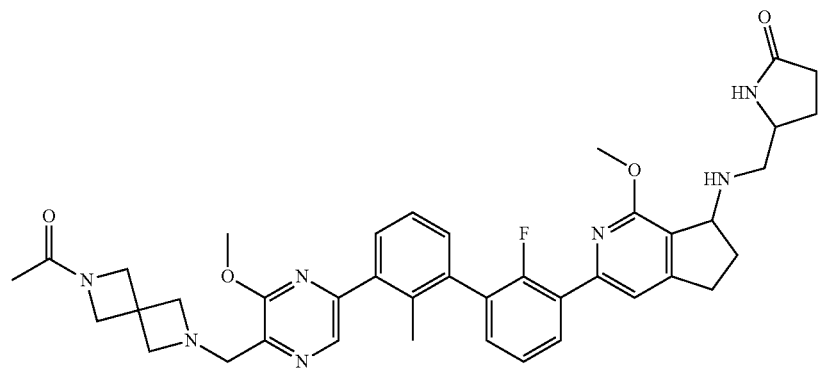
and

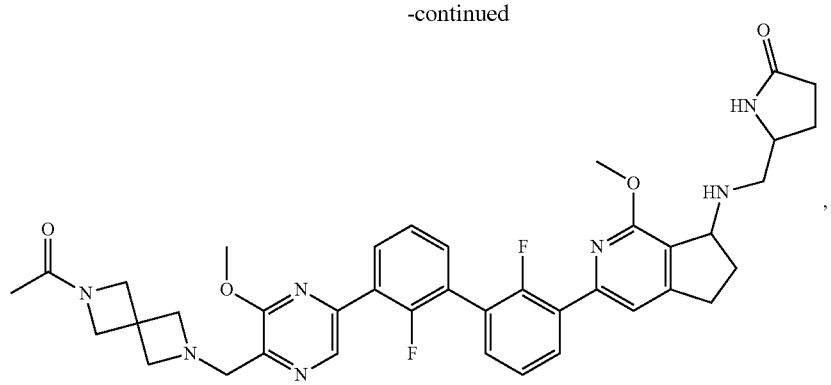
or a pharmaceutically acceptable salt of any of the foregoing.
Embodiment 97
The compound of Embodiment 1 selected from:
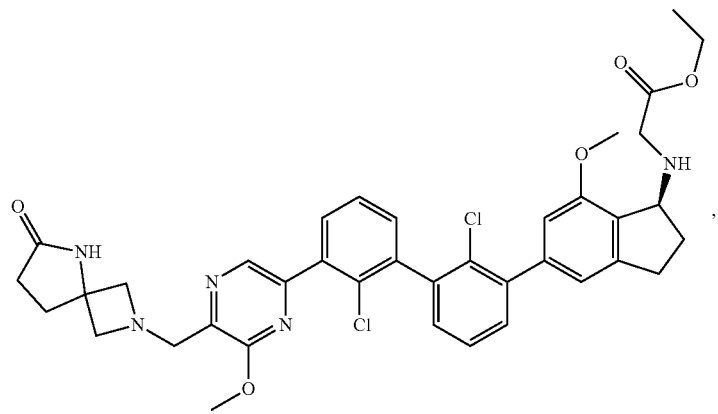
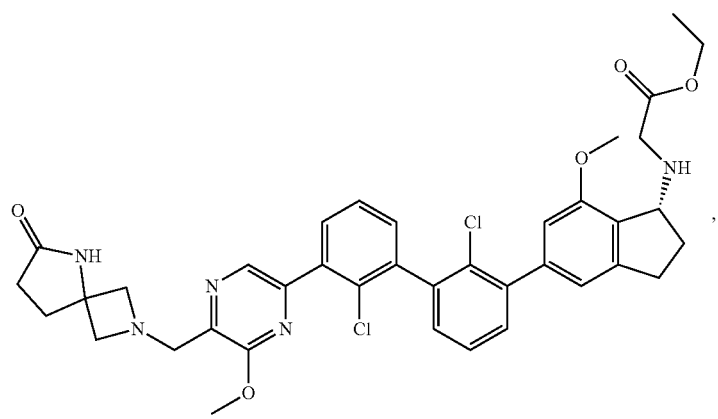

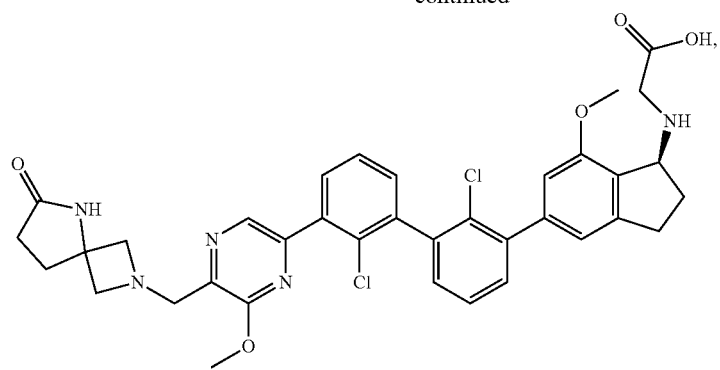
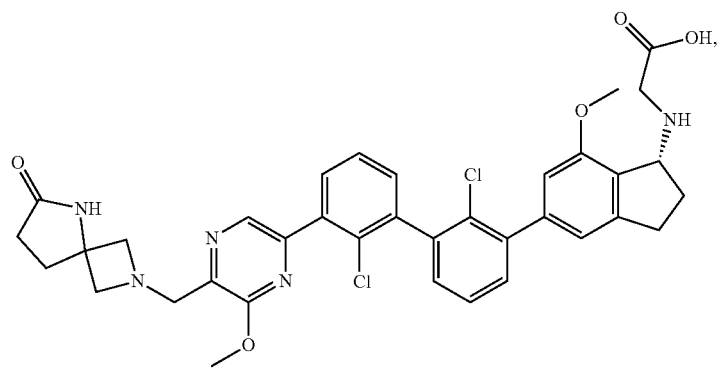
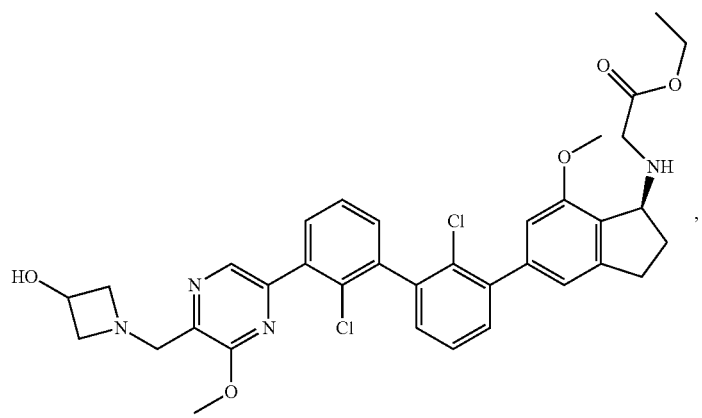
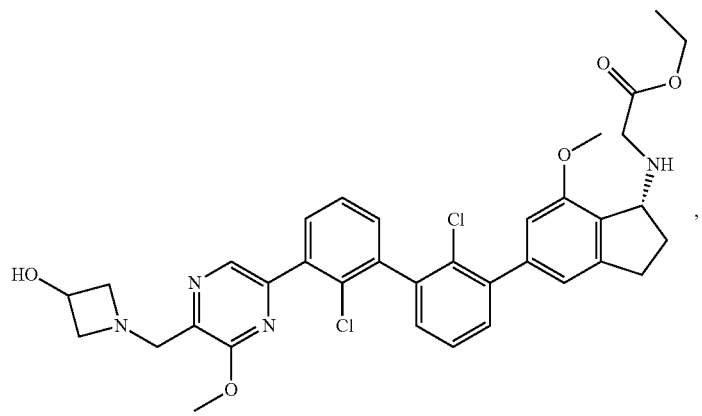

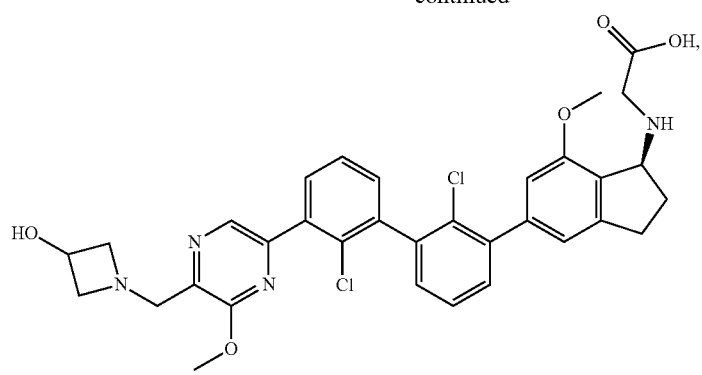
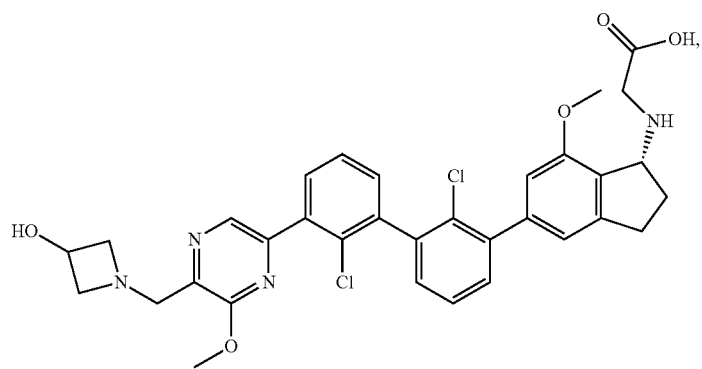
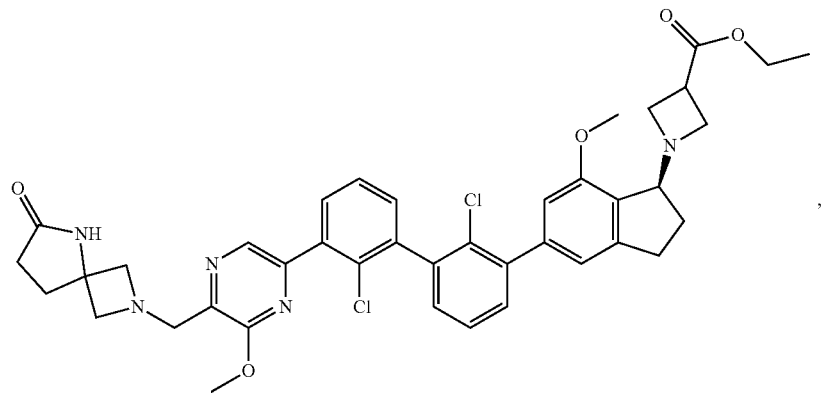
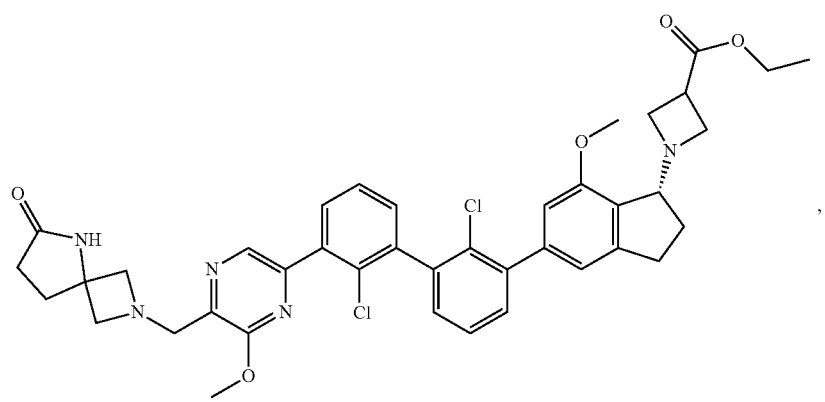

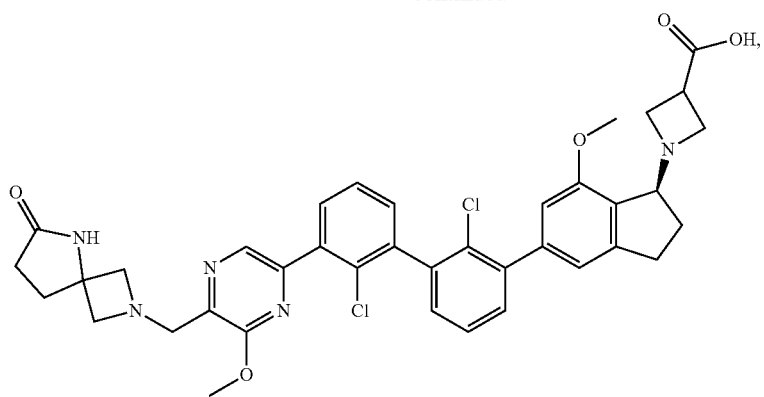
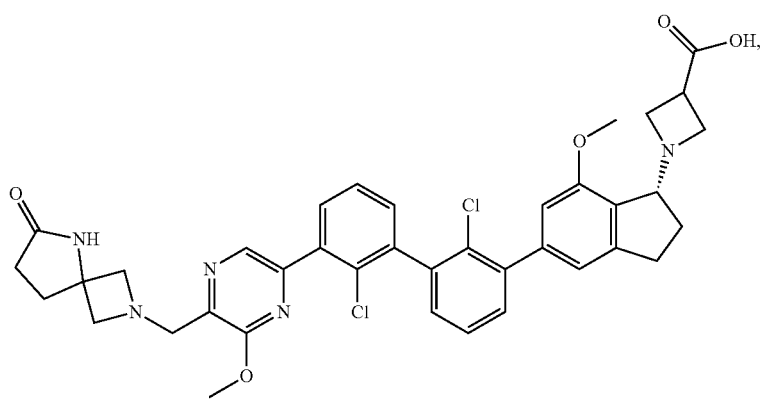

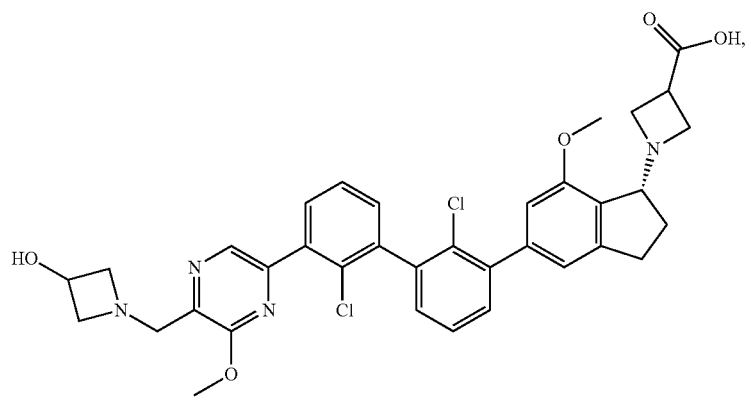

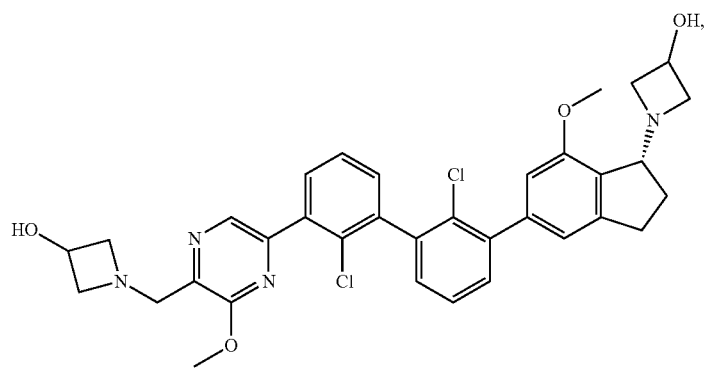
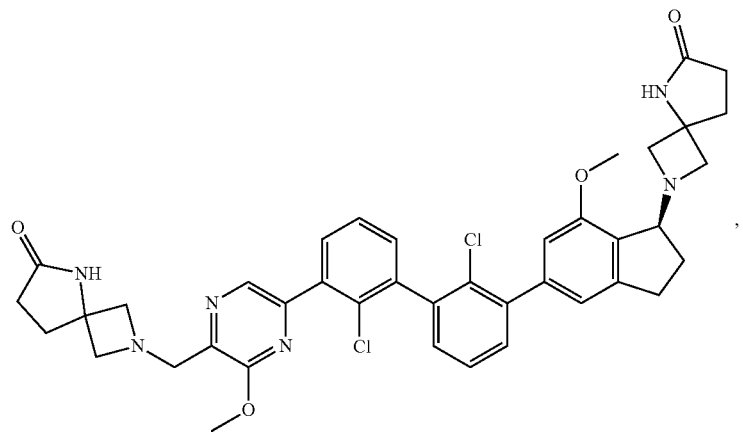
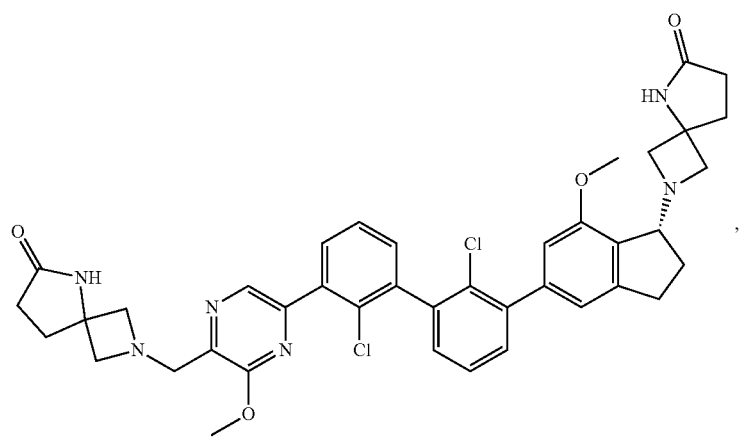

-continued
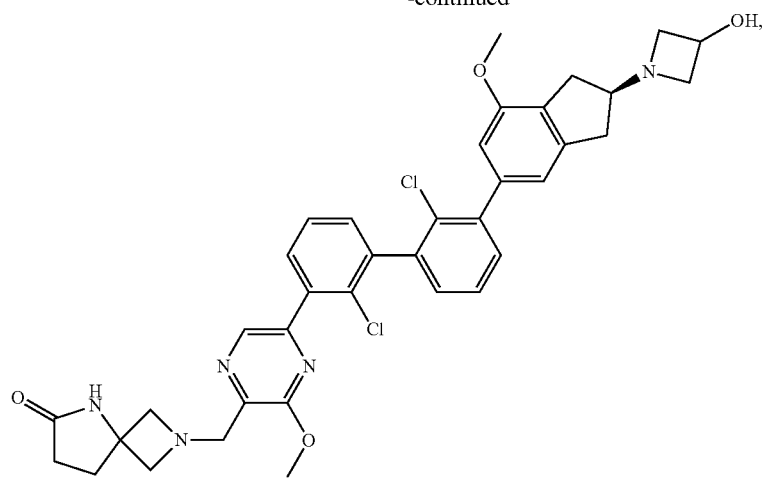
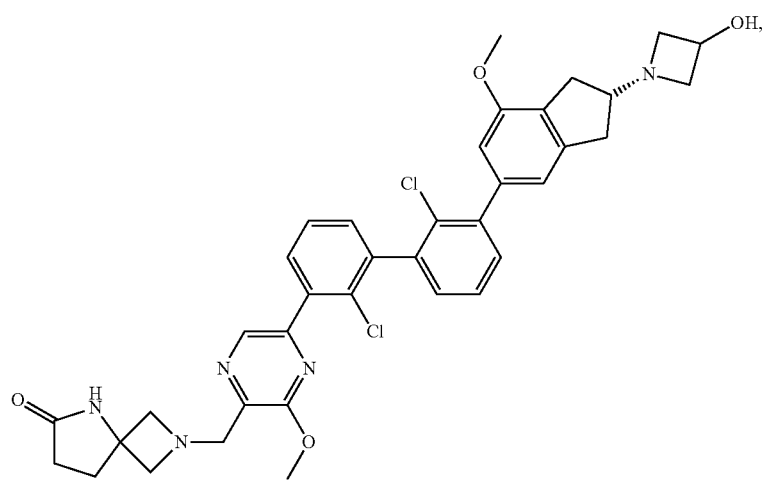
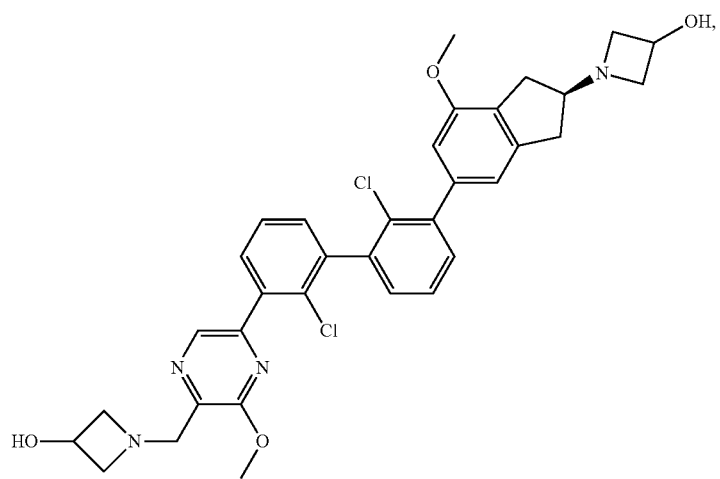

-continued
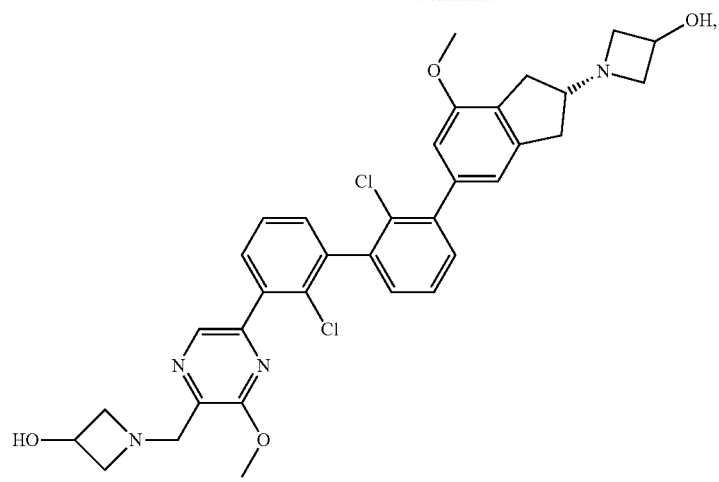
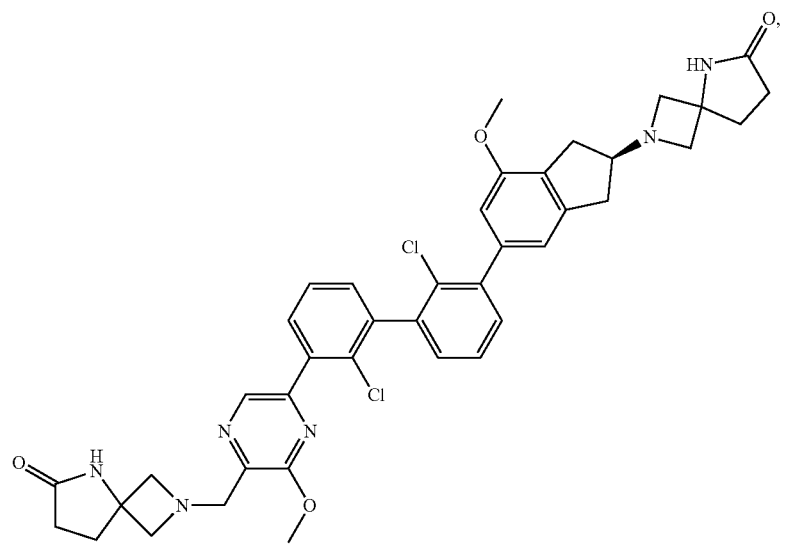
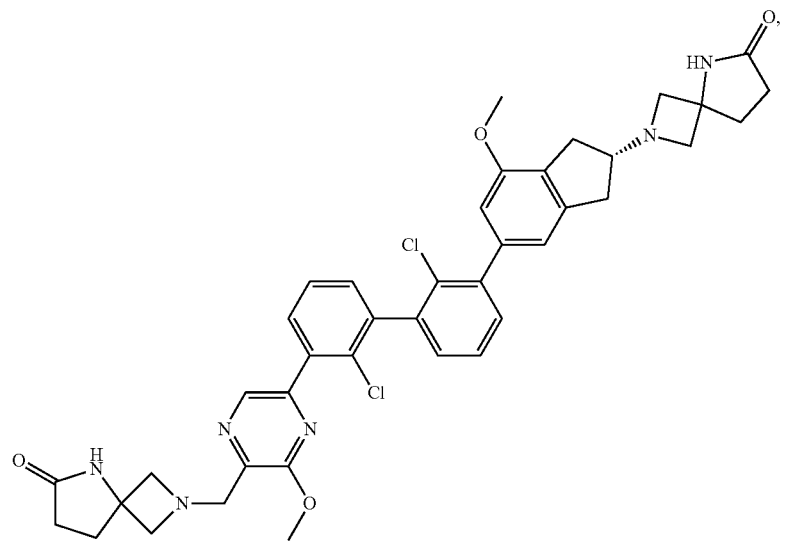

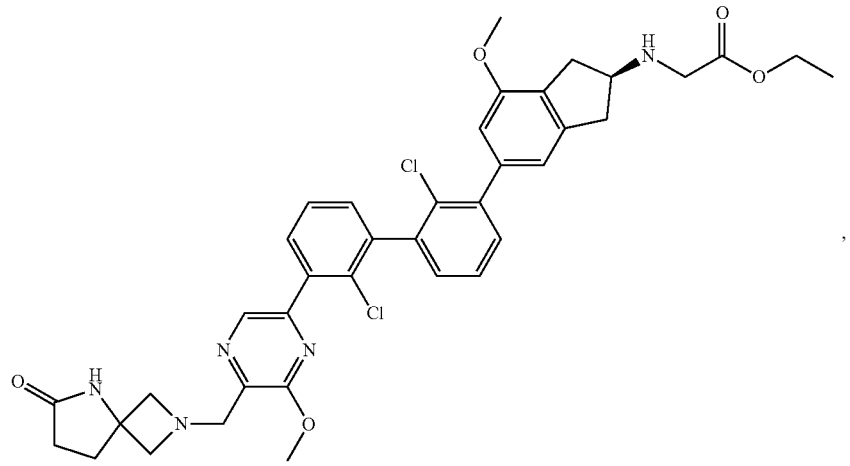
,
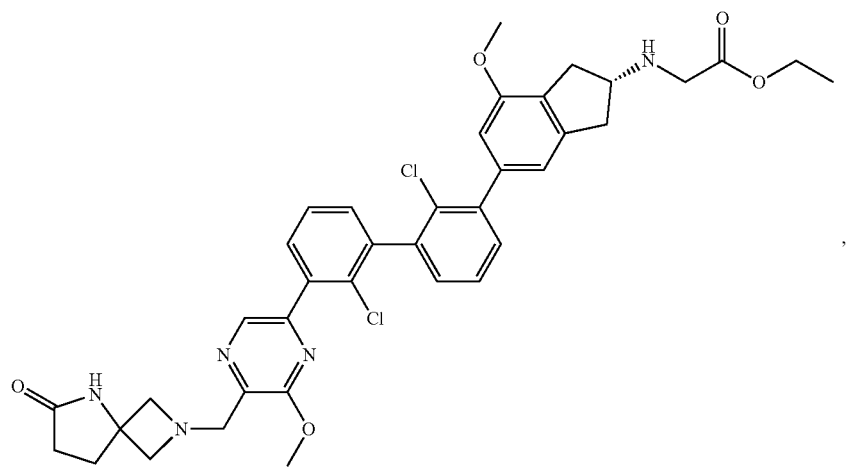
,
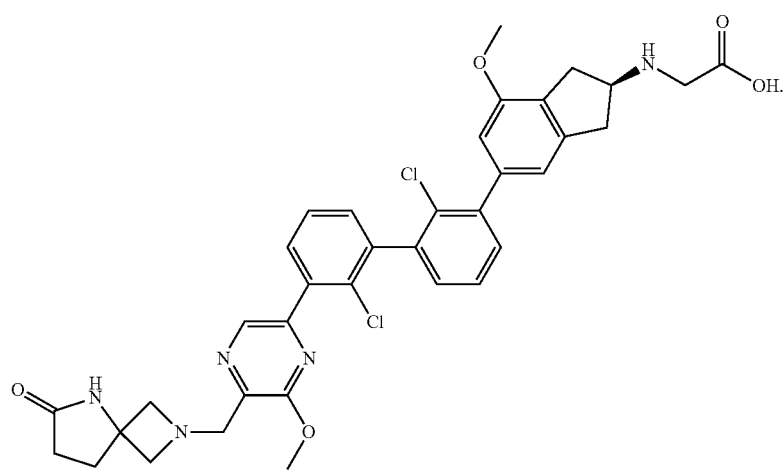

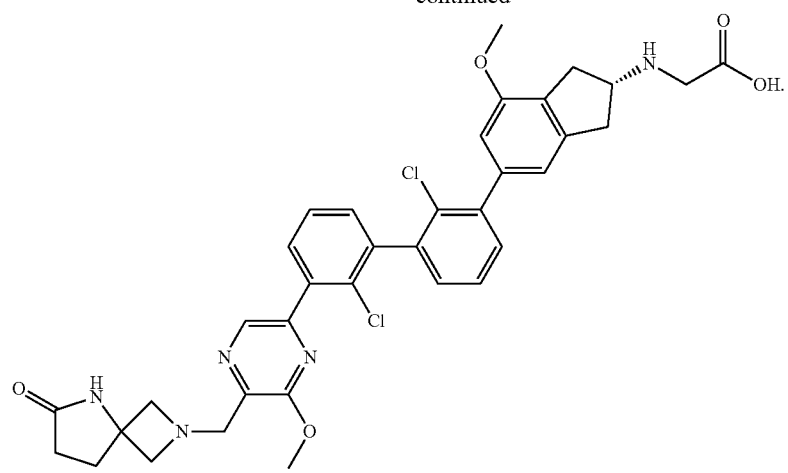

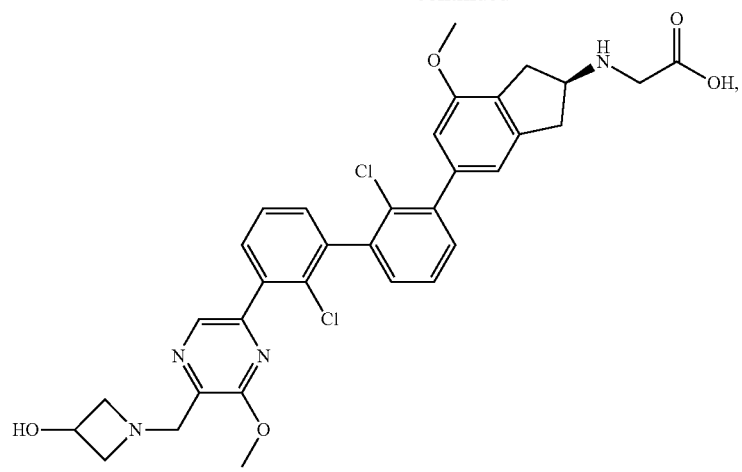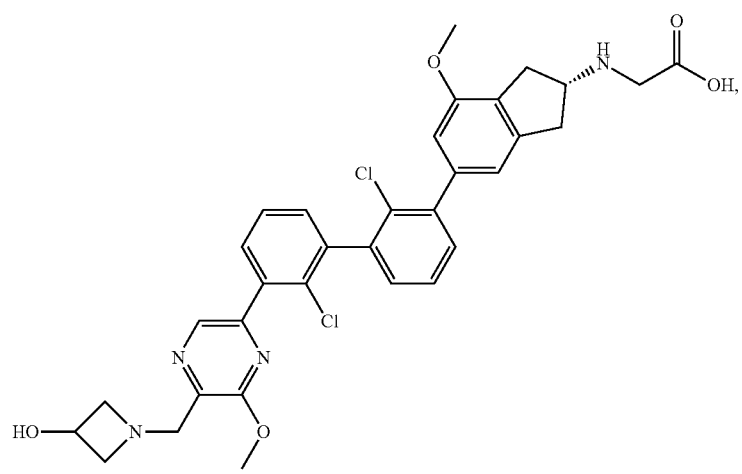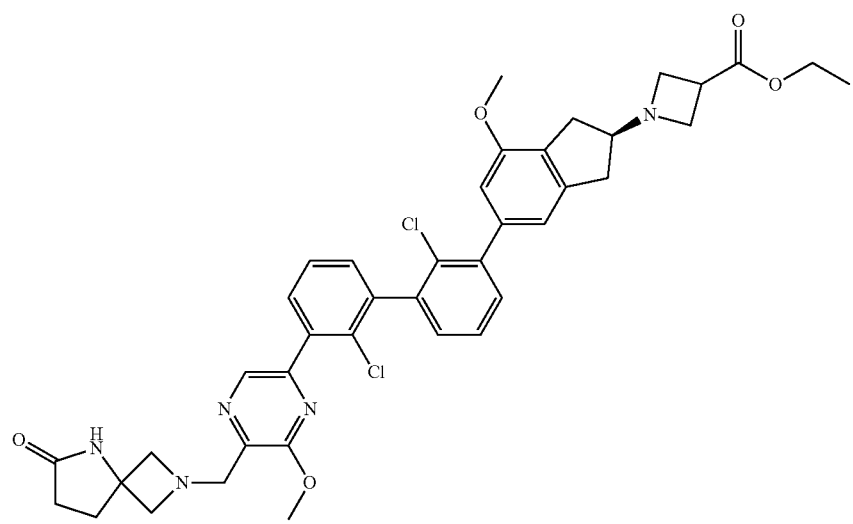

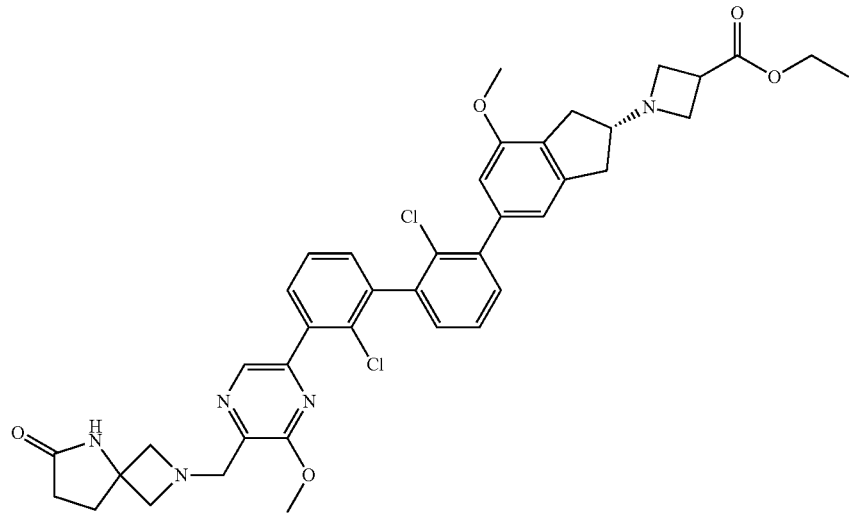
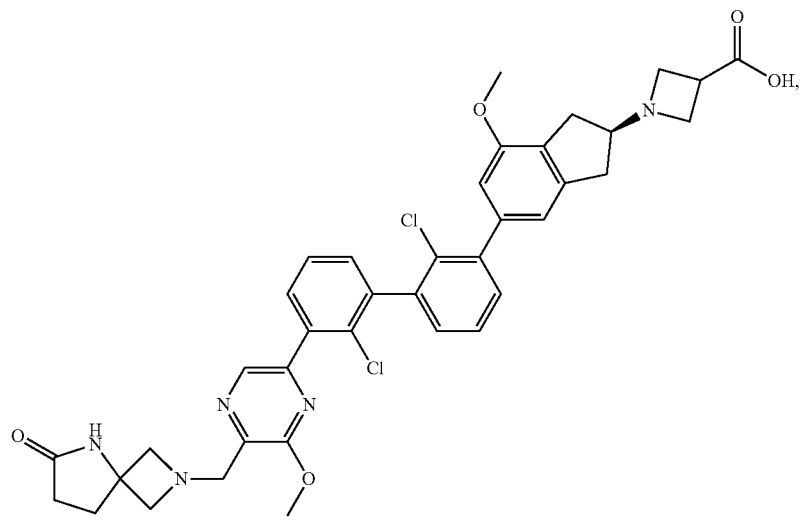
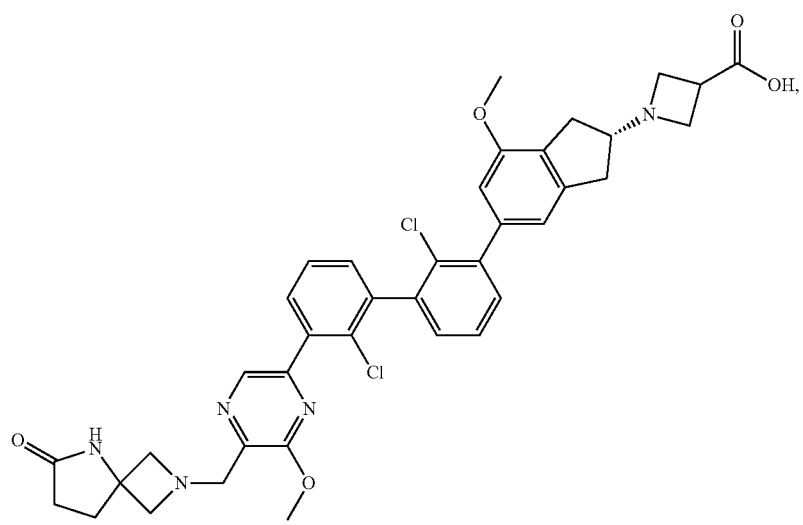

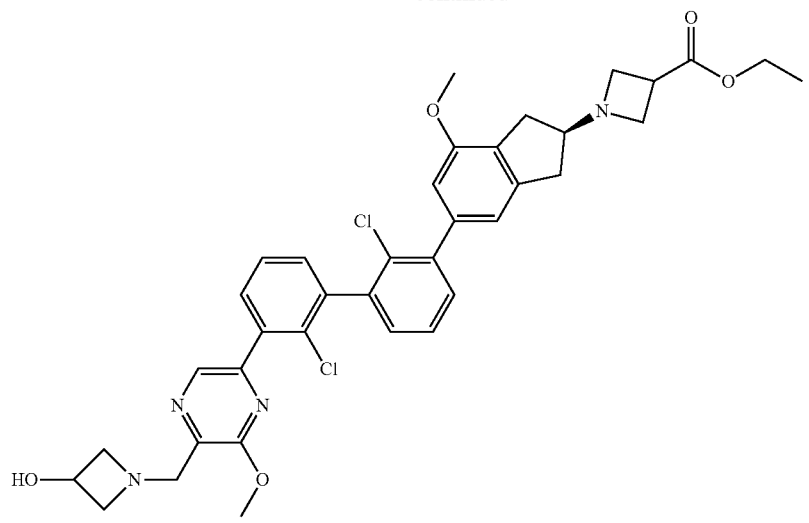
,
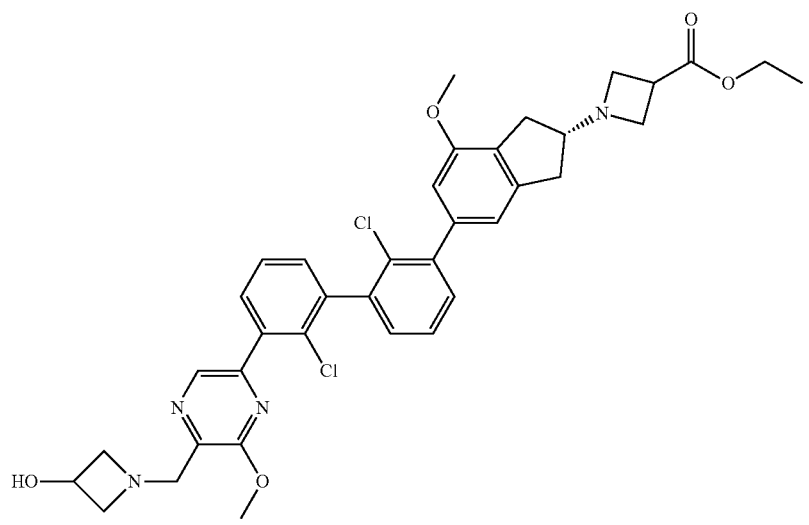
,
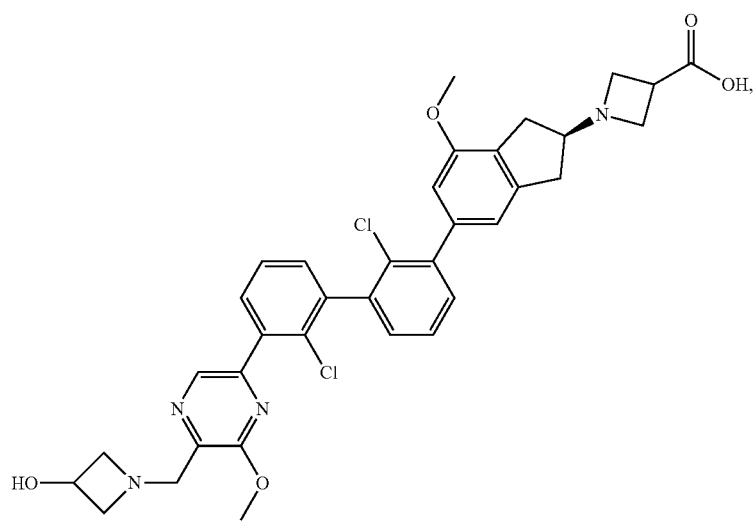

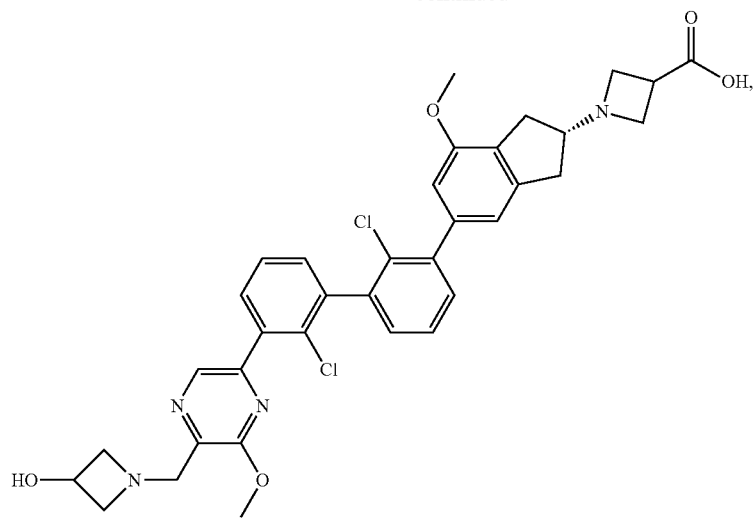
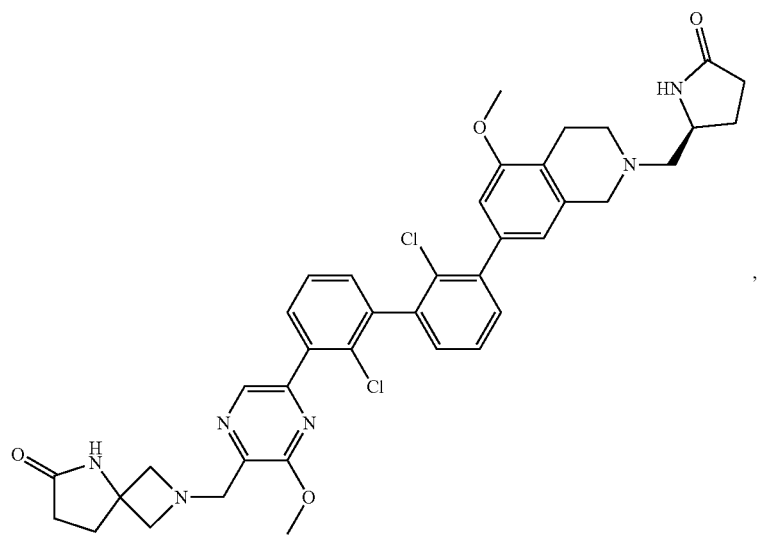
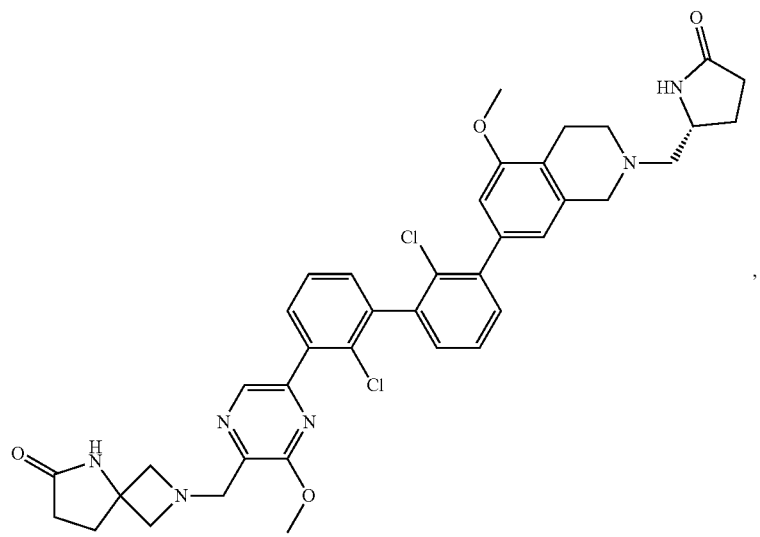

-continued
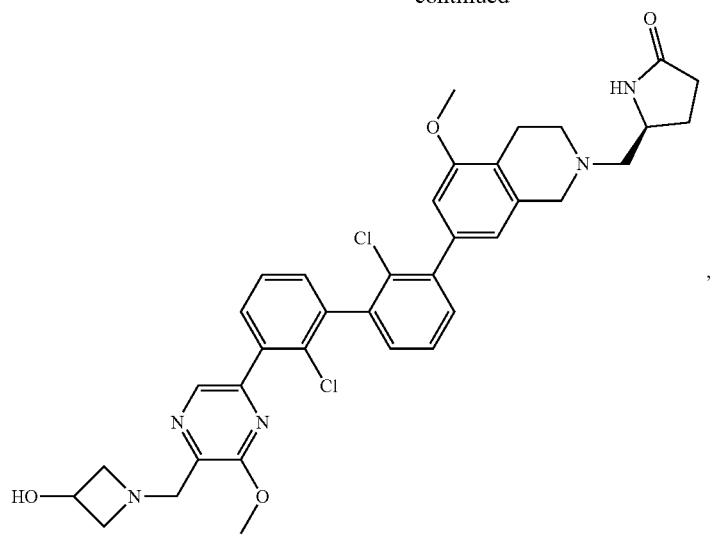
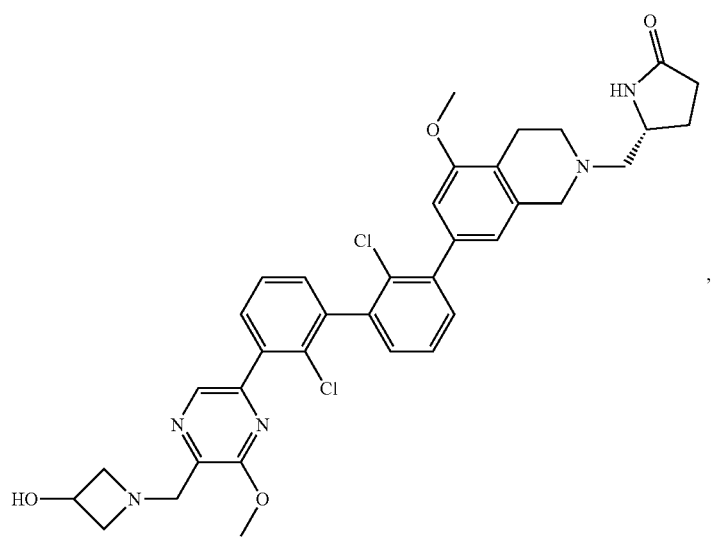
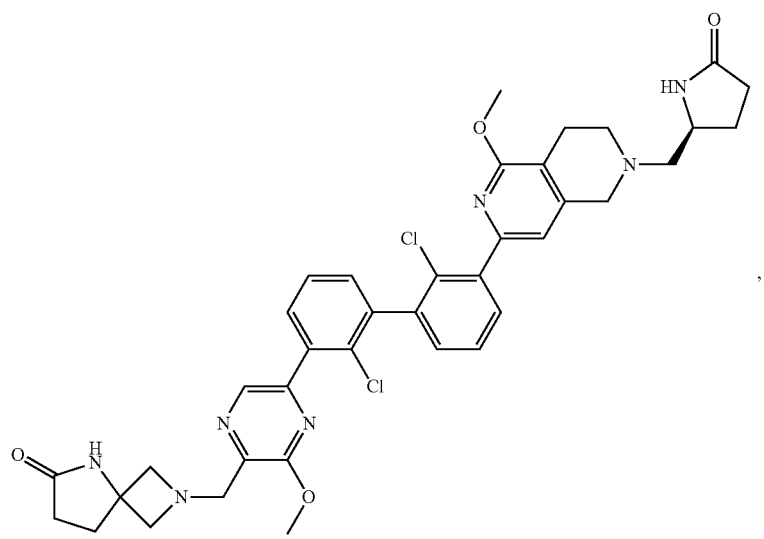

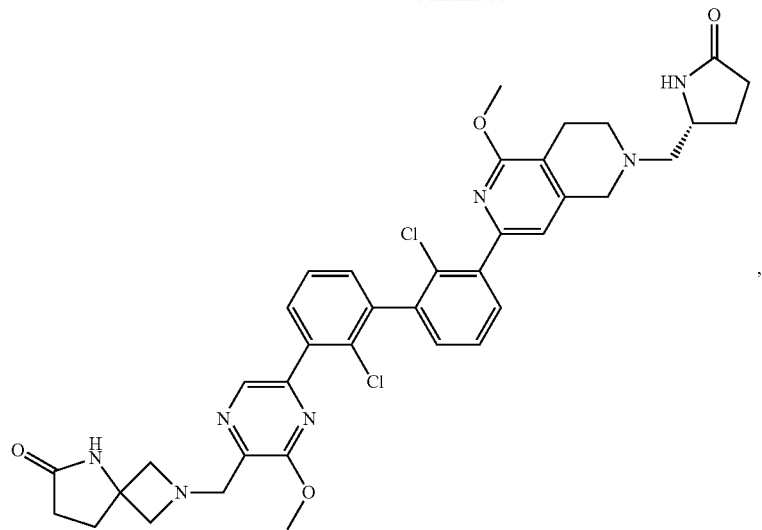


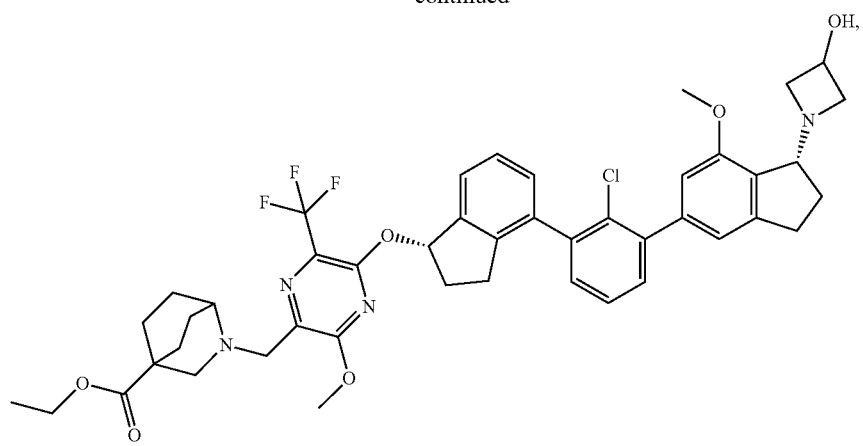
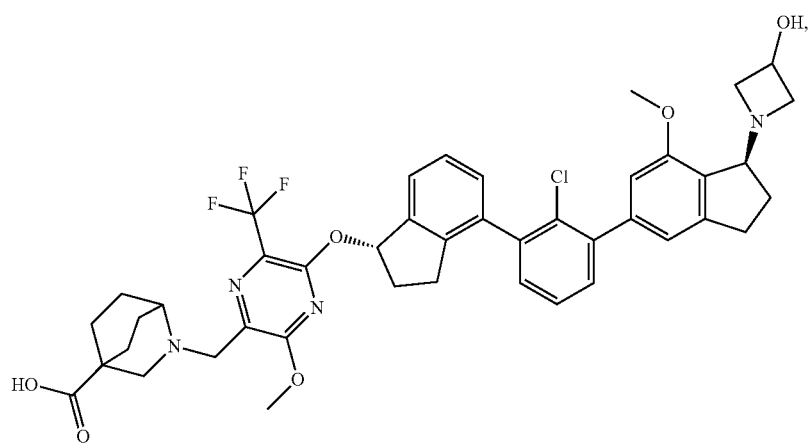
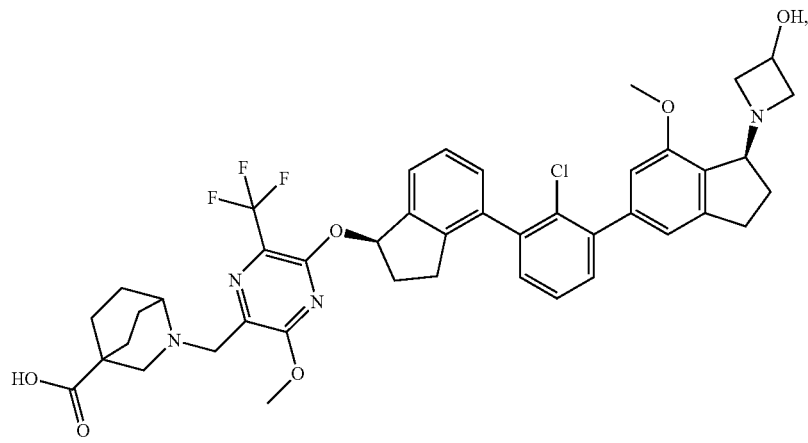

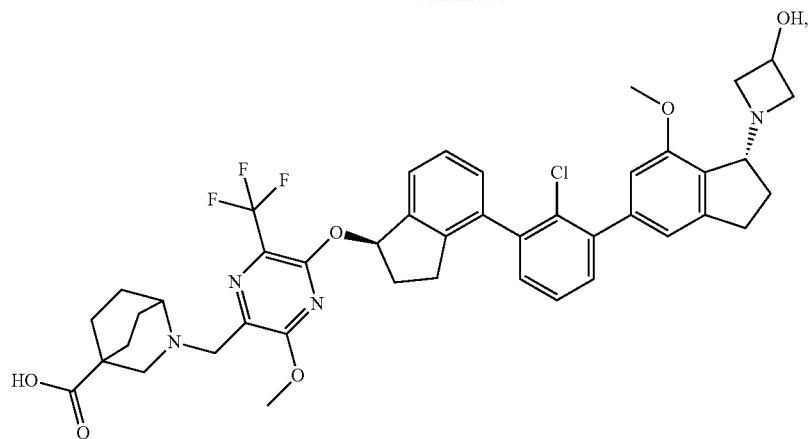
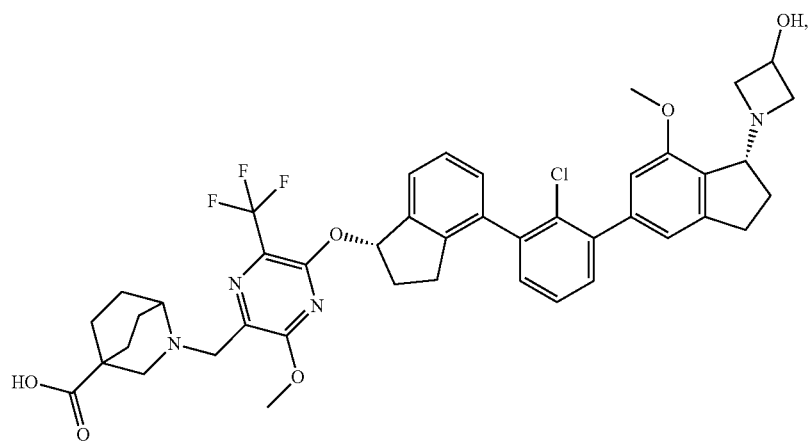
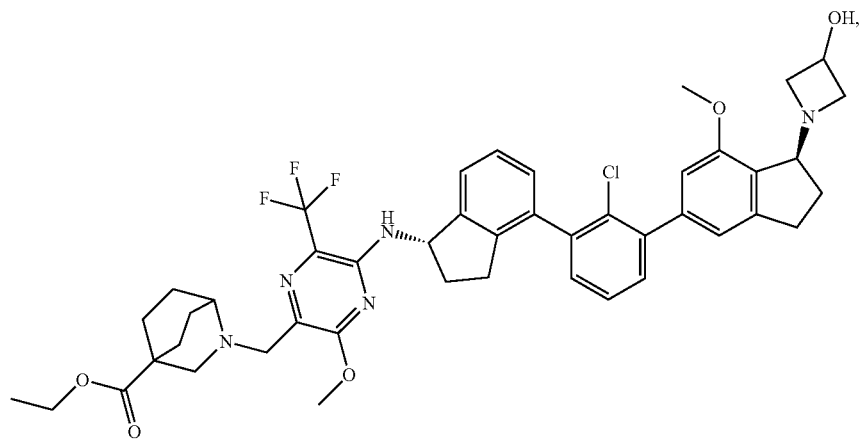

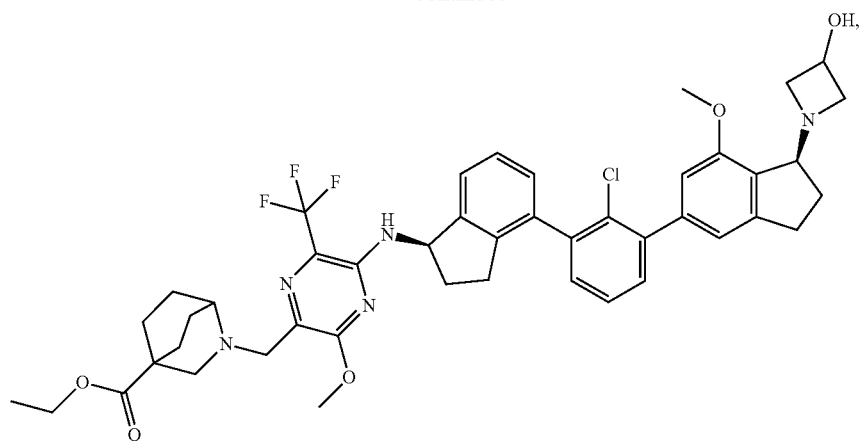
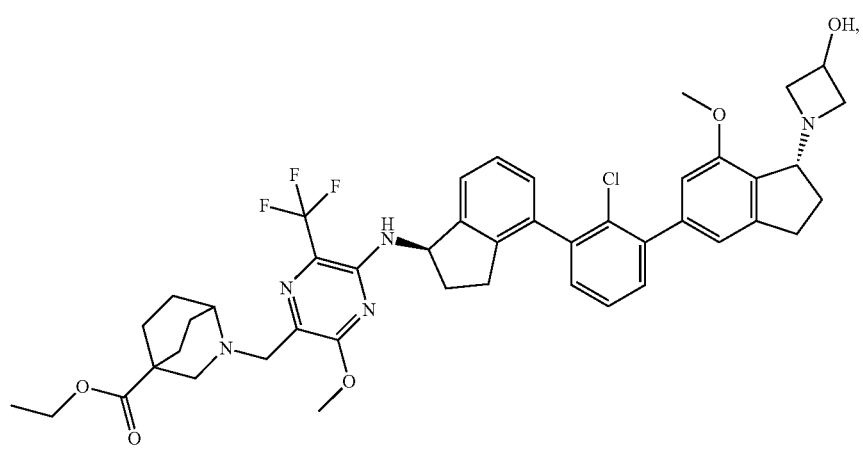
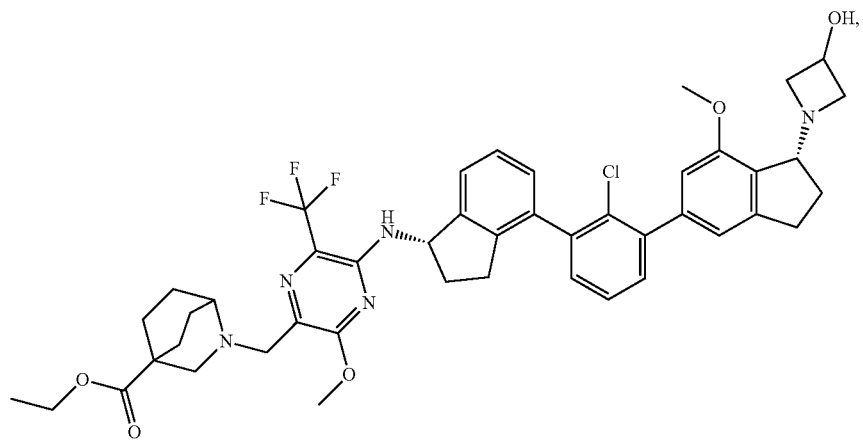

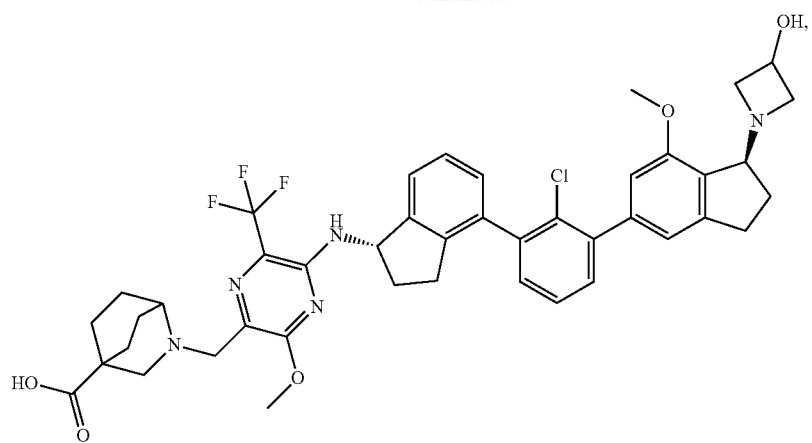
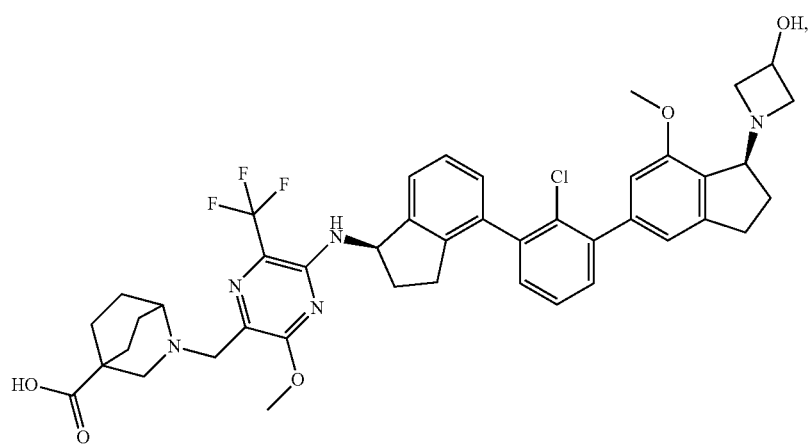
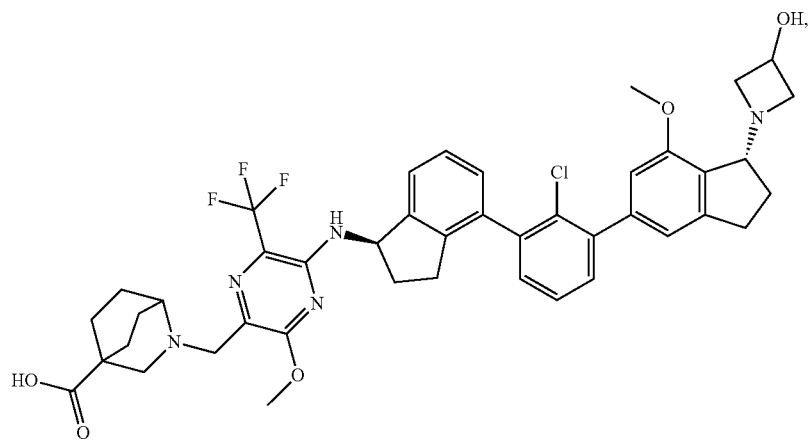

-continued
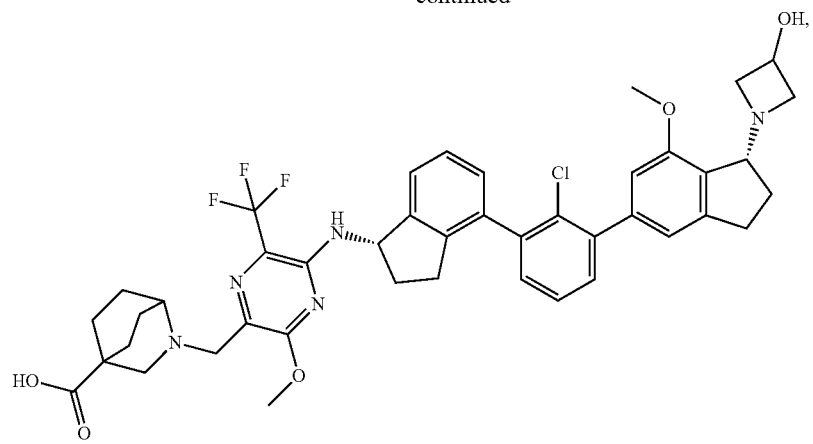
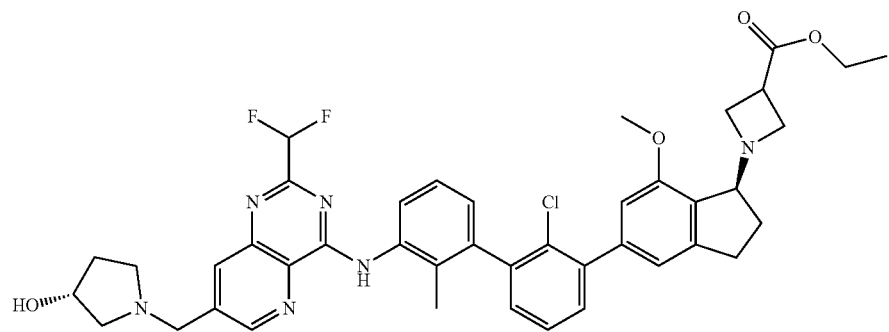
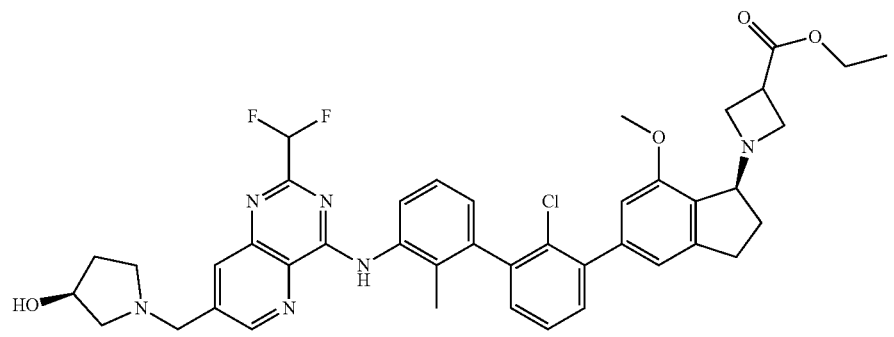

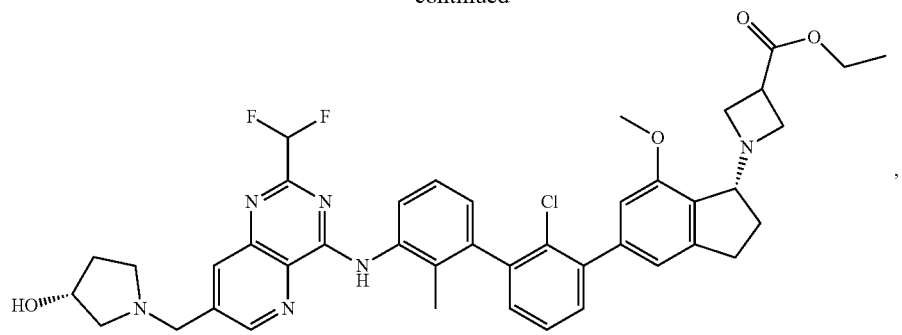
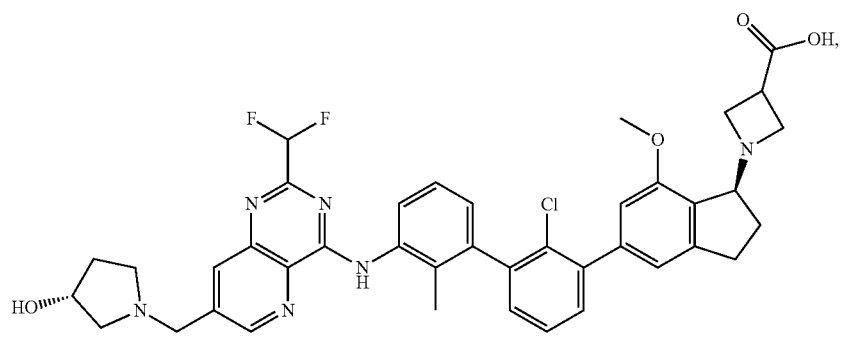
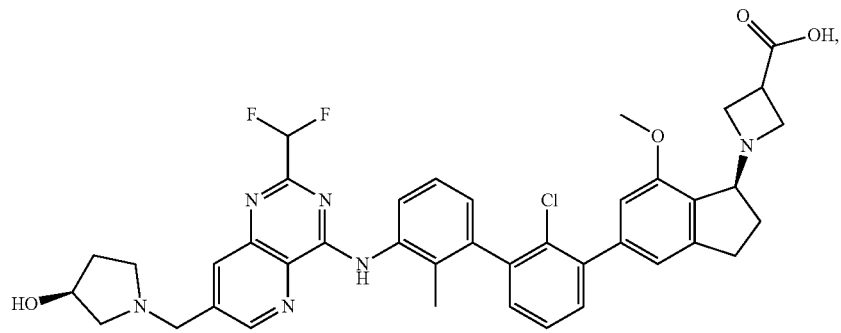
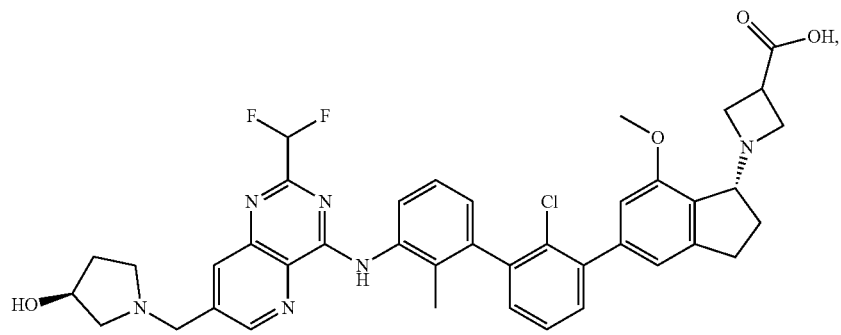
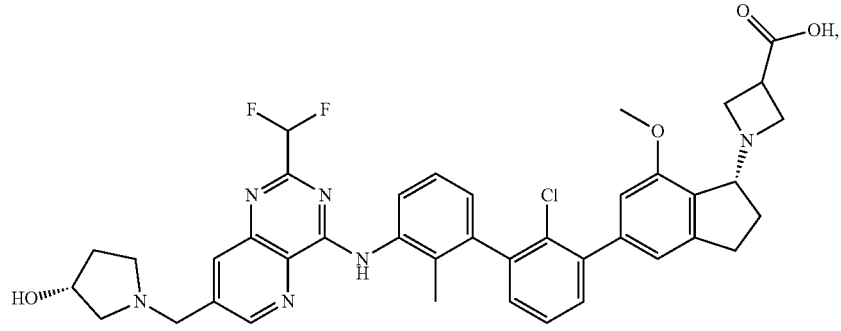

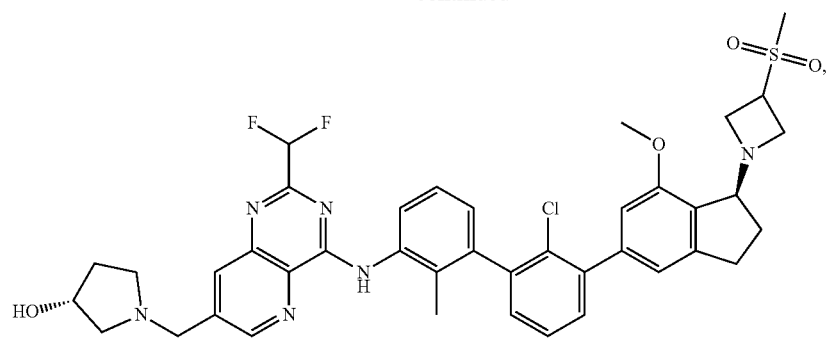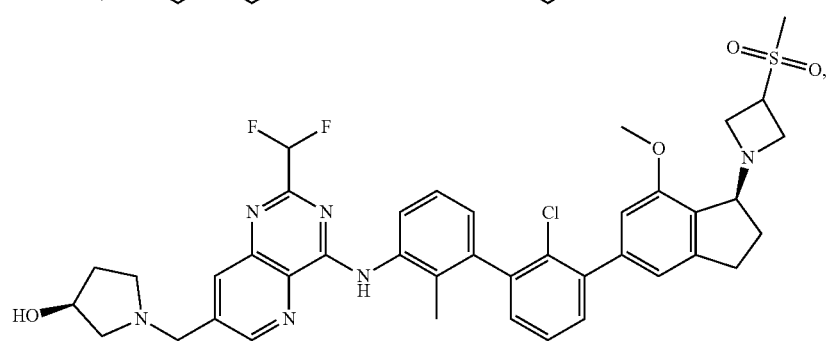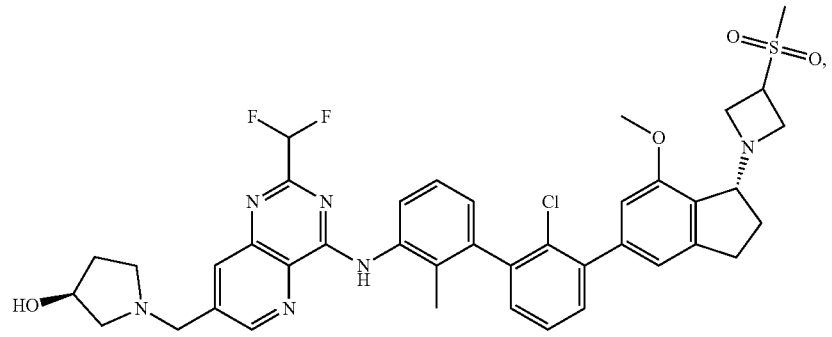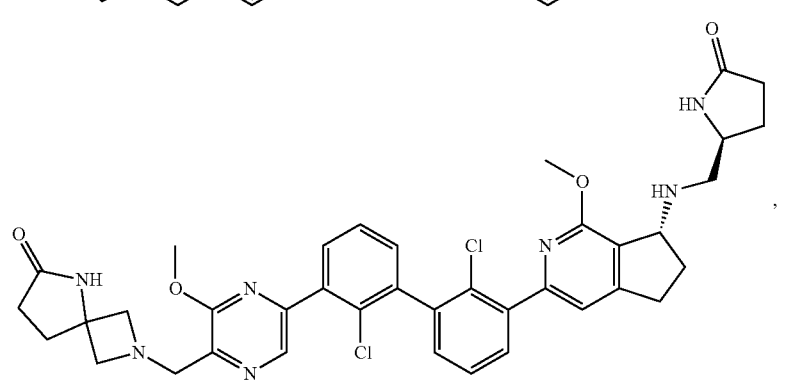

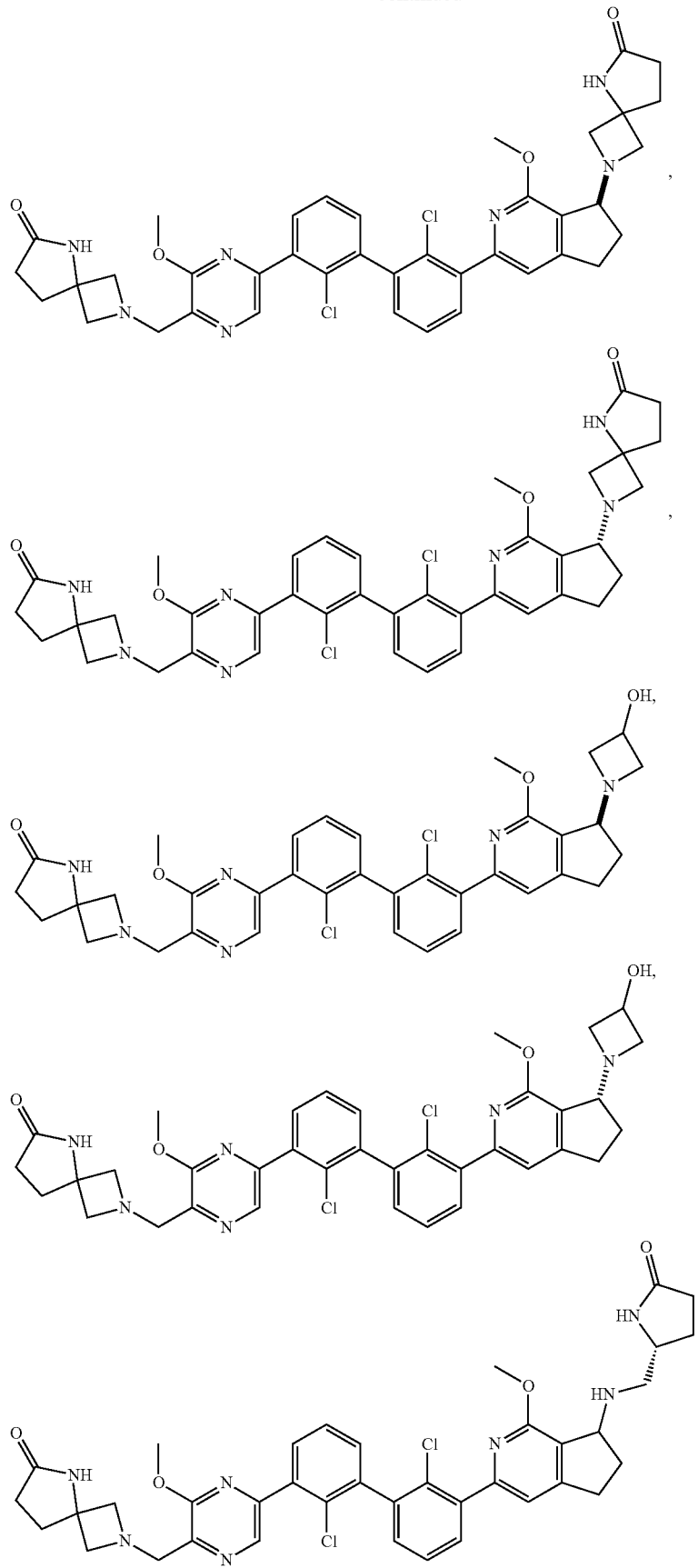

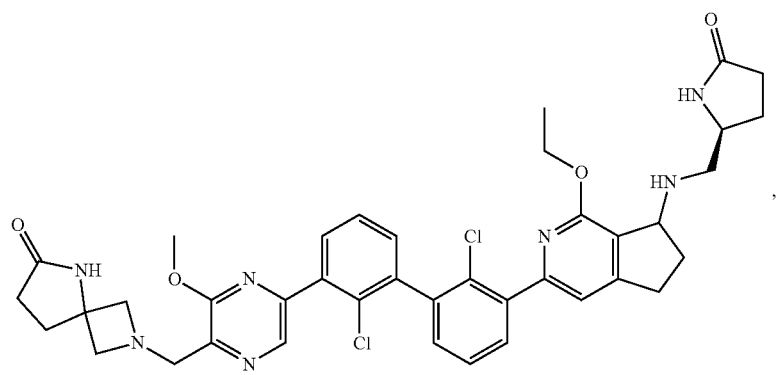
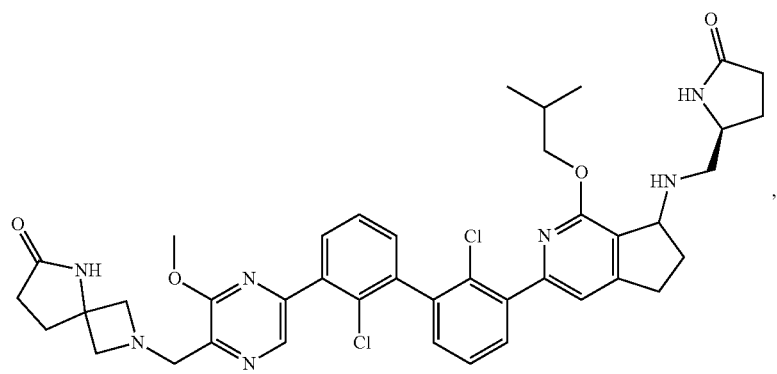
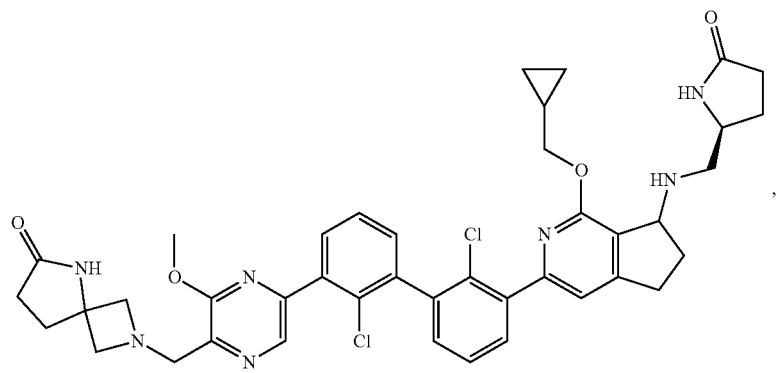
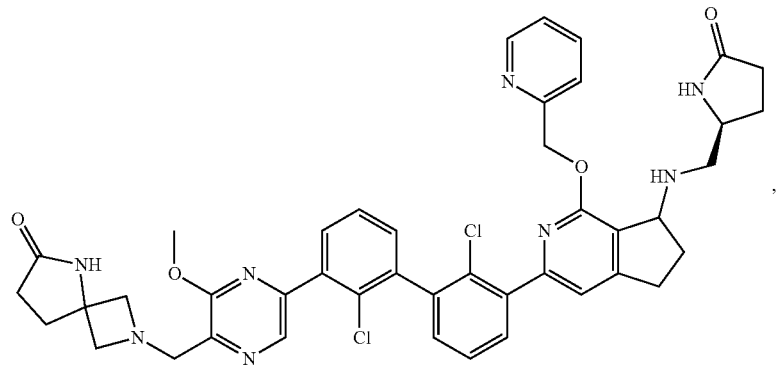

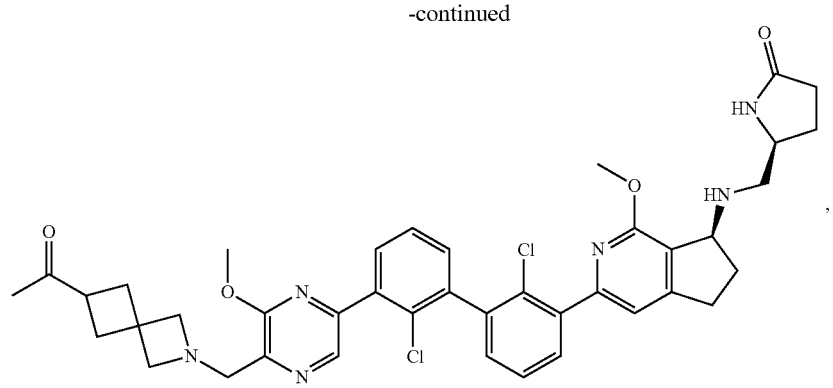
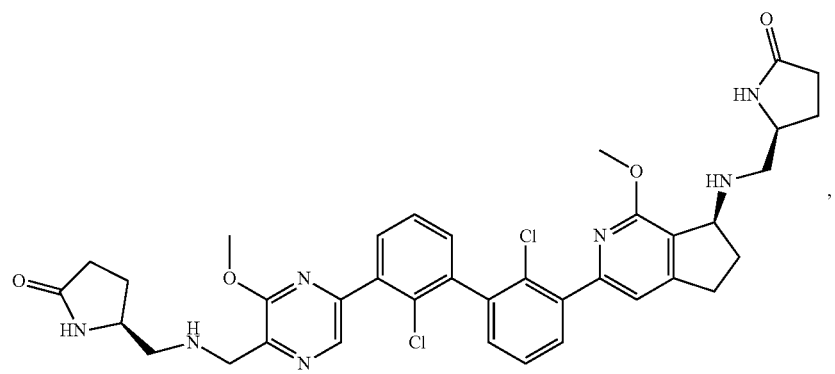
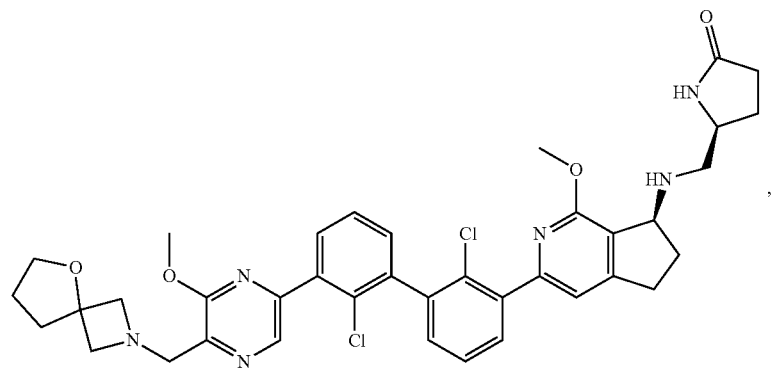
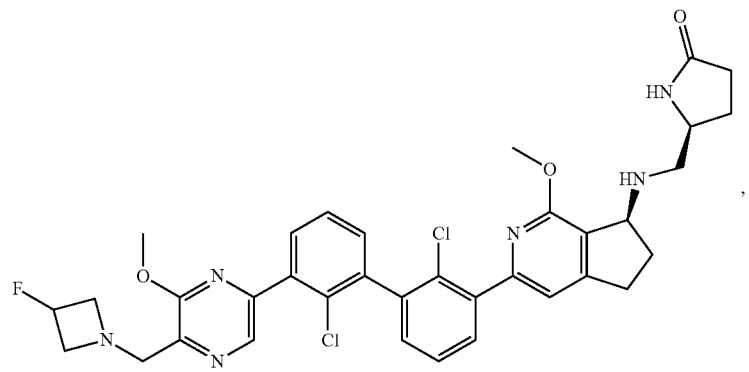

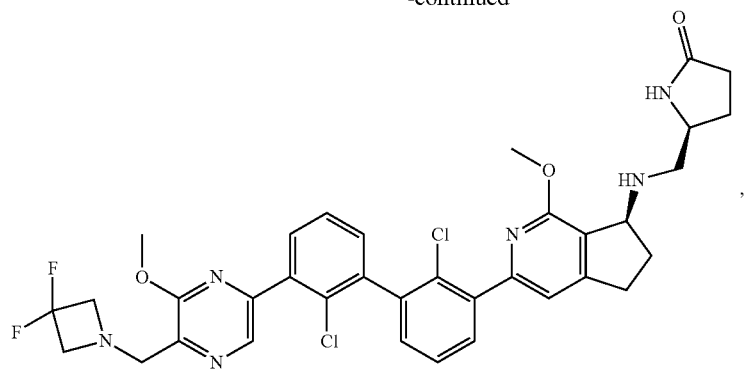
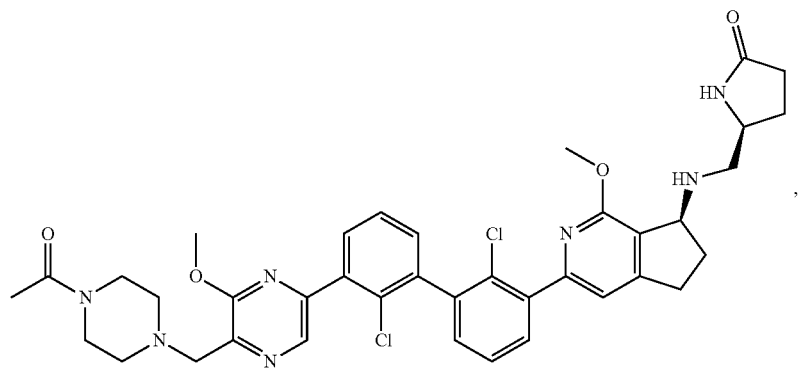
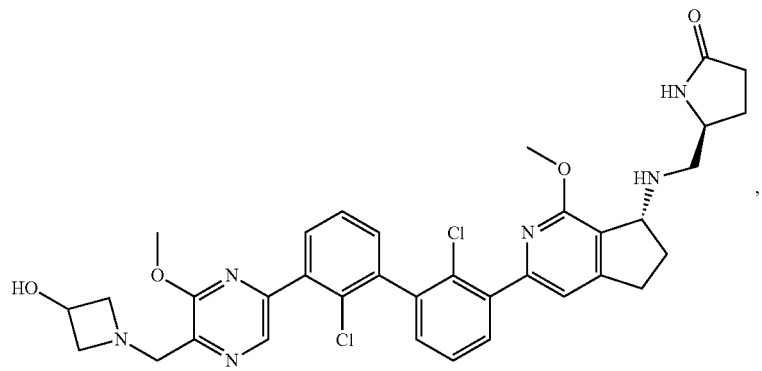
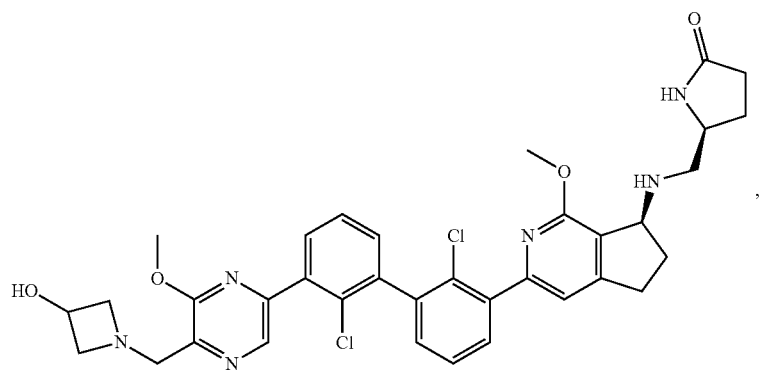

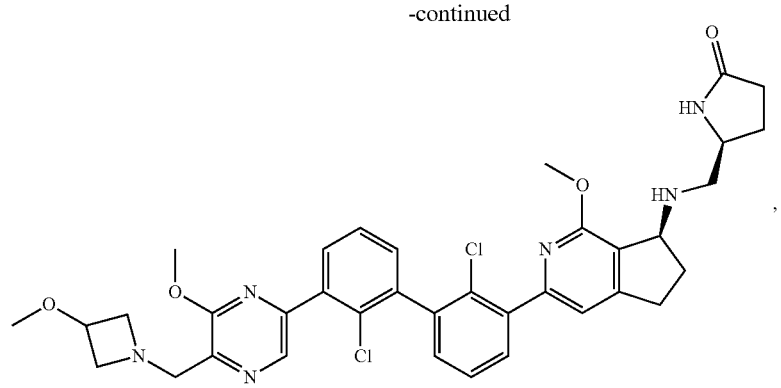
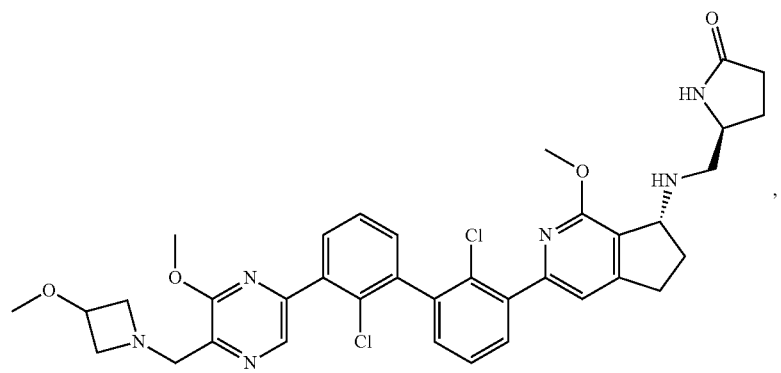
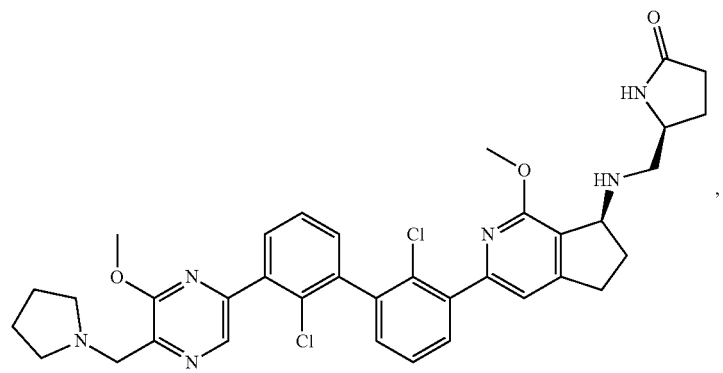
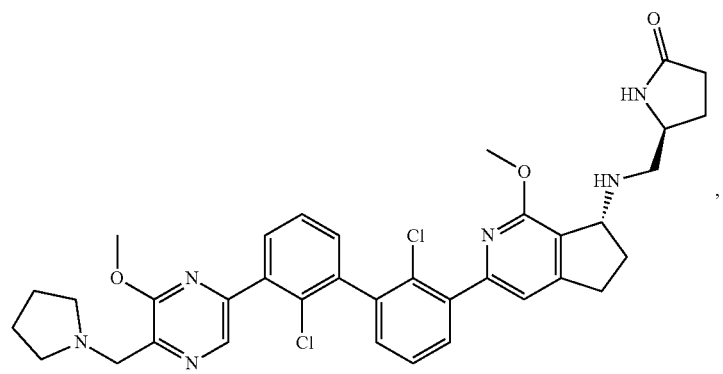

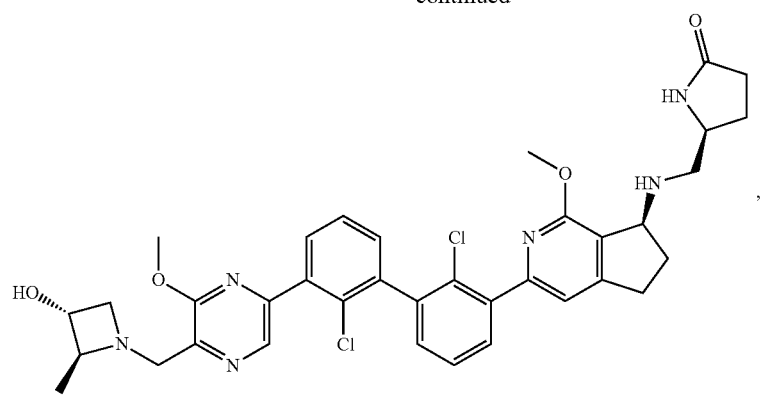
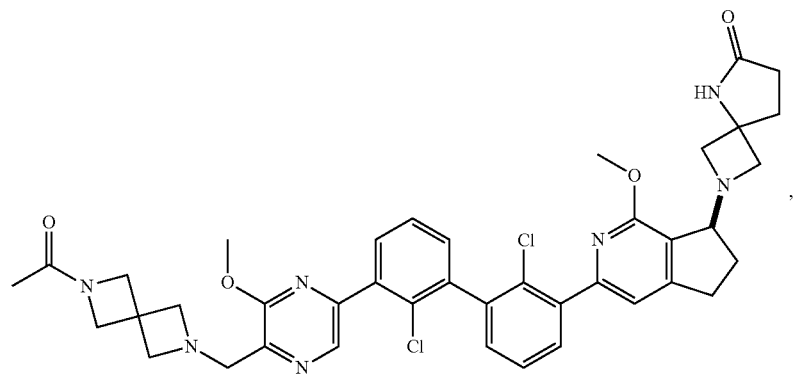
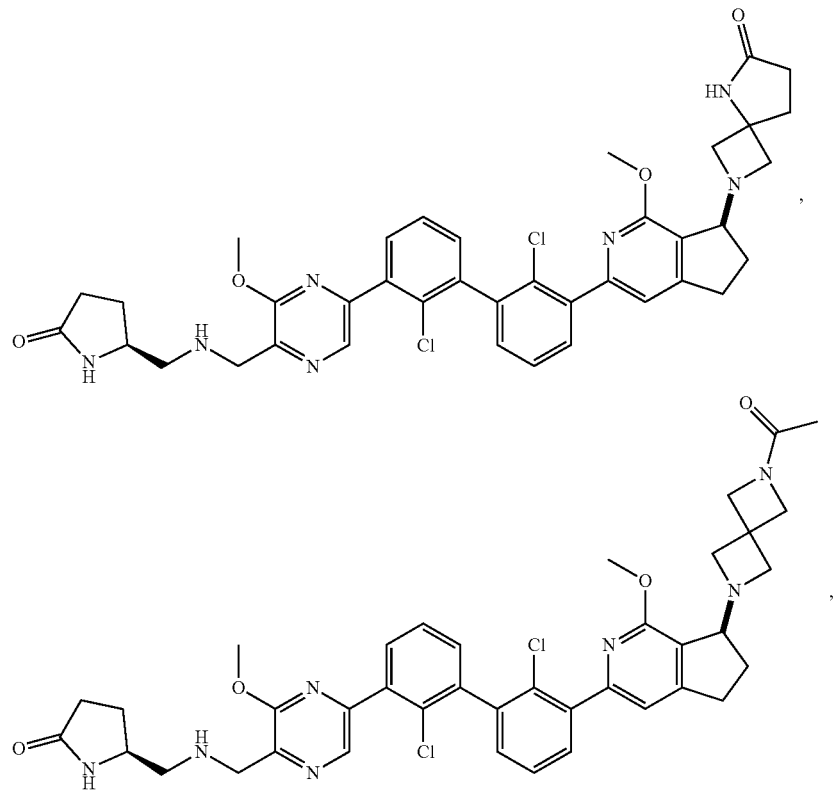

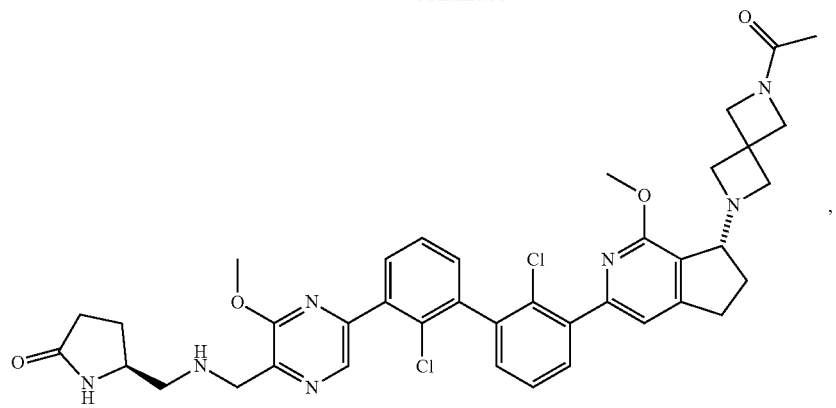
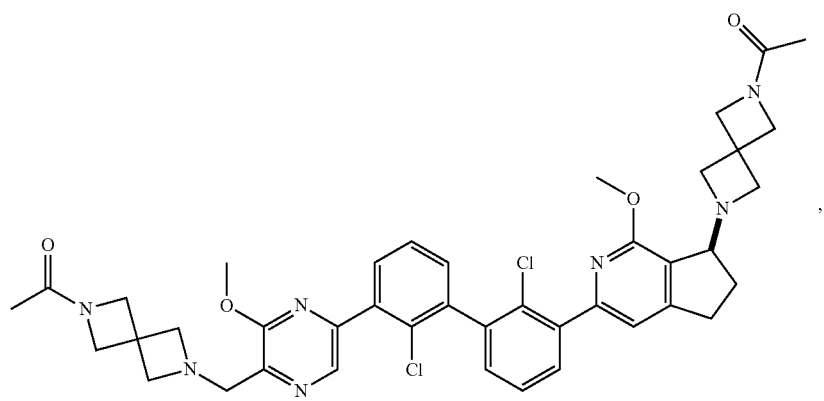
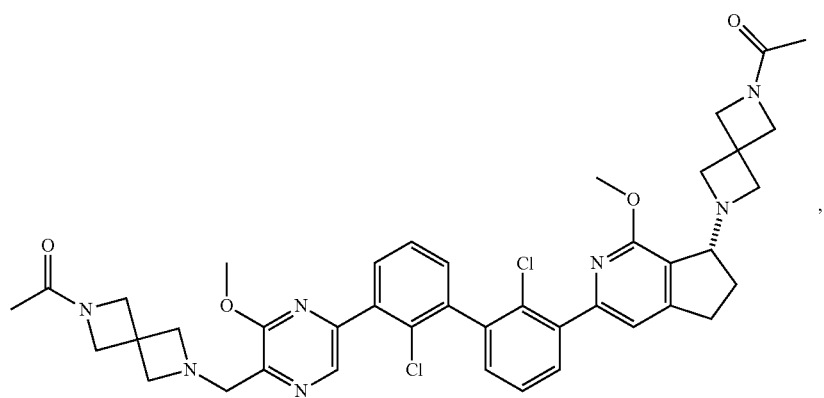
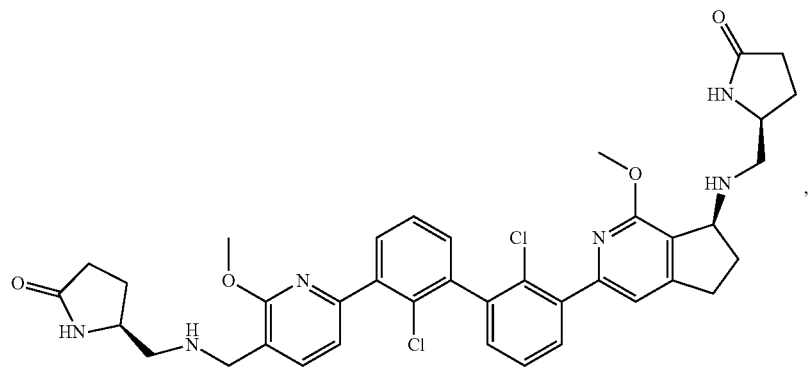

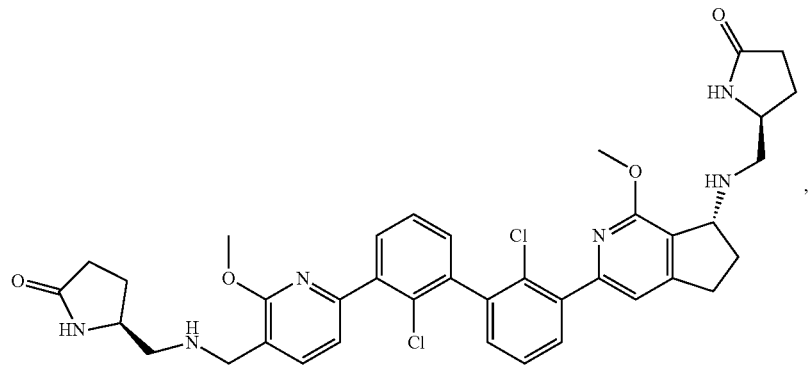
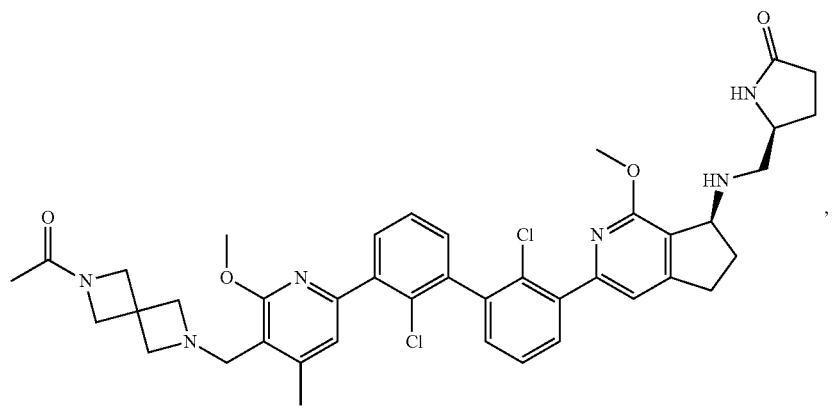
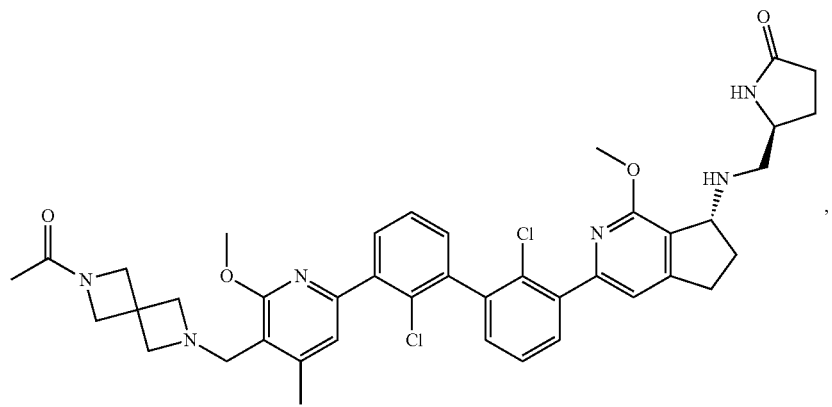
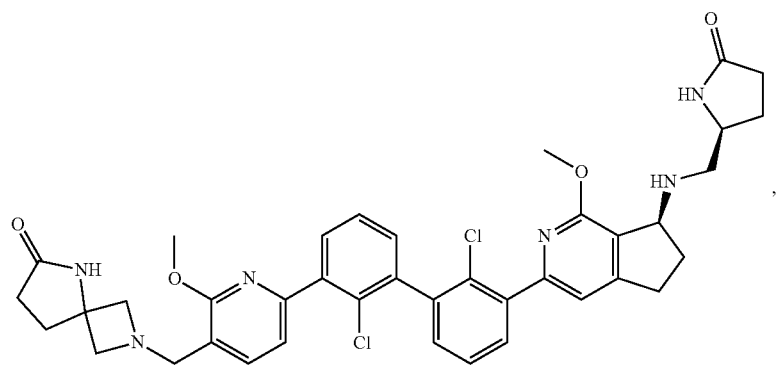

-continued
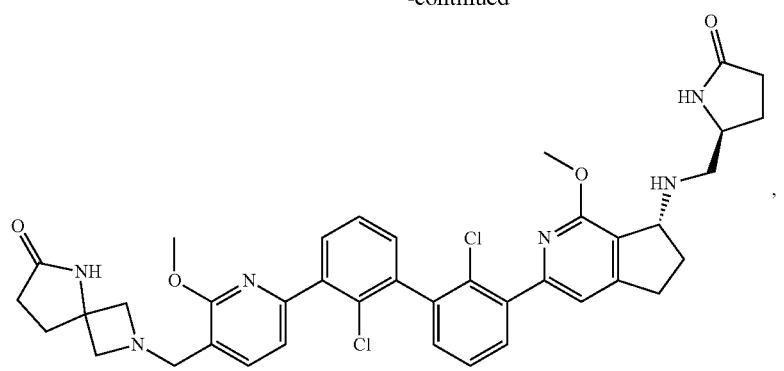
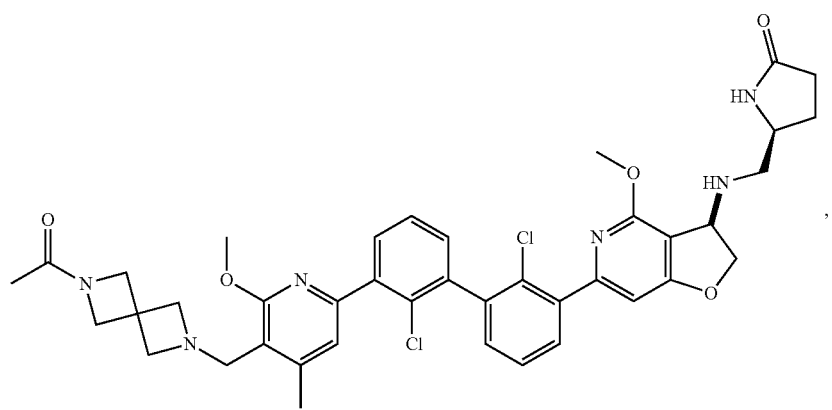
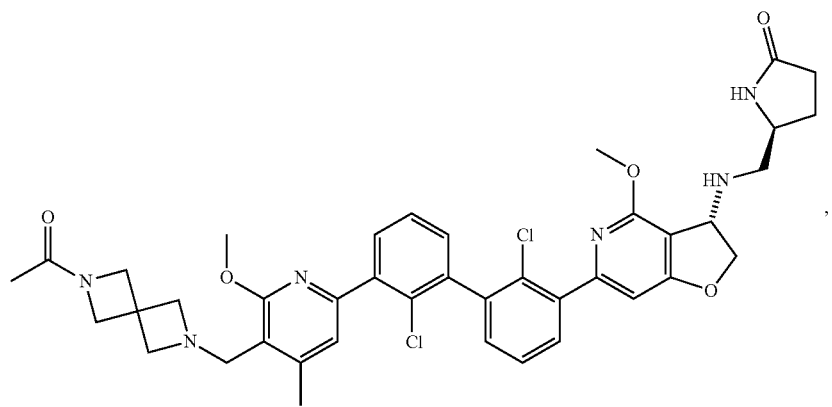
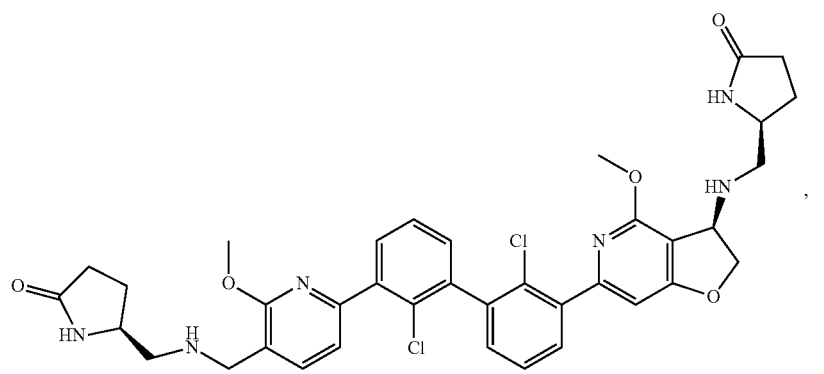

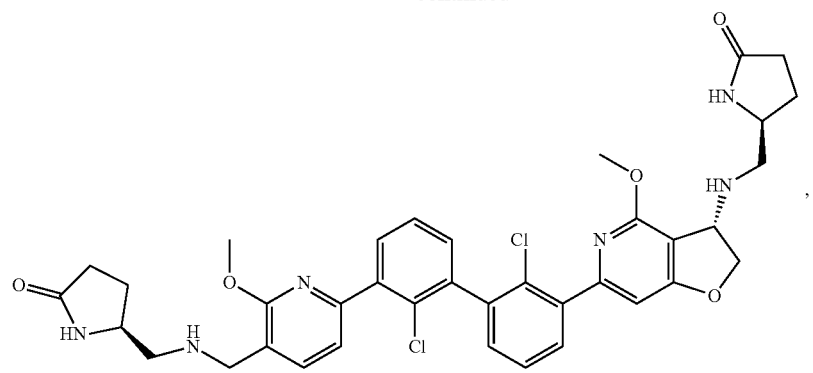
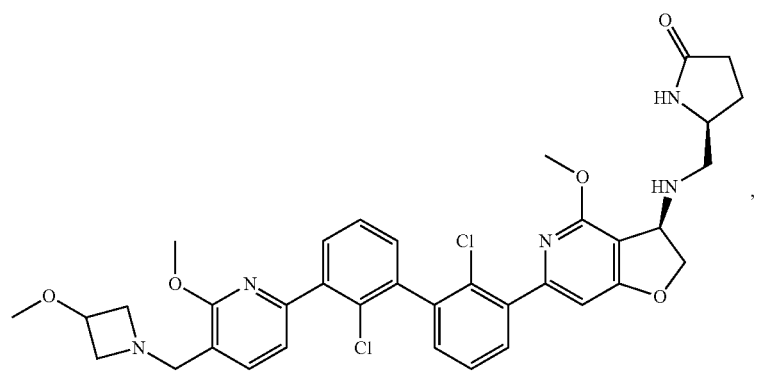
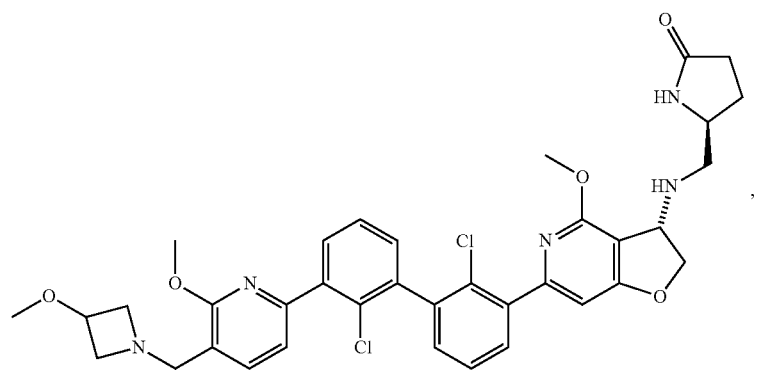
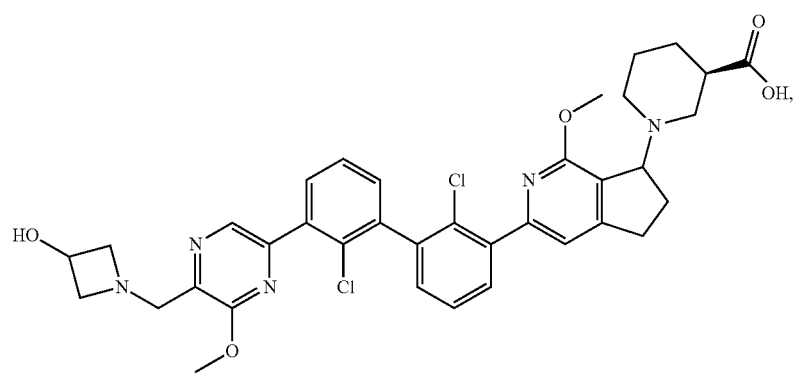

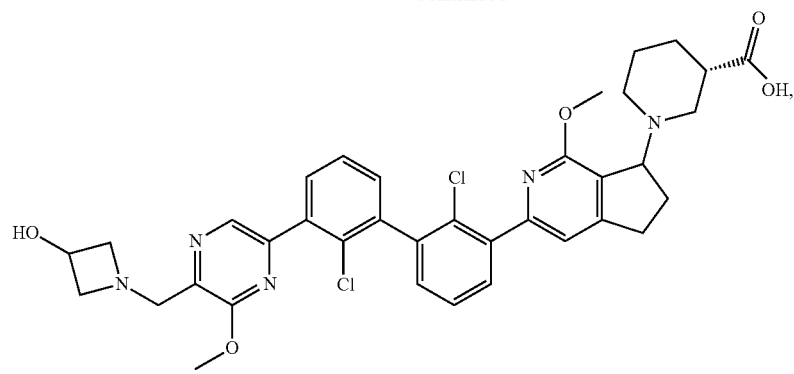
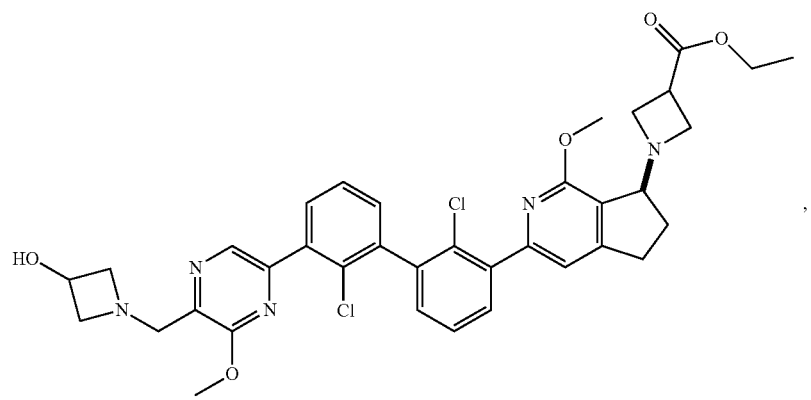
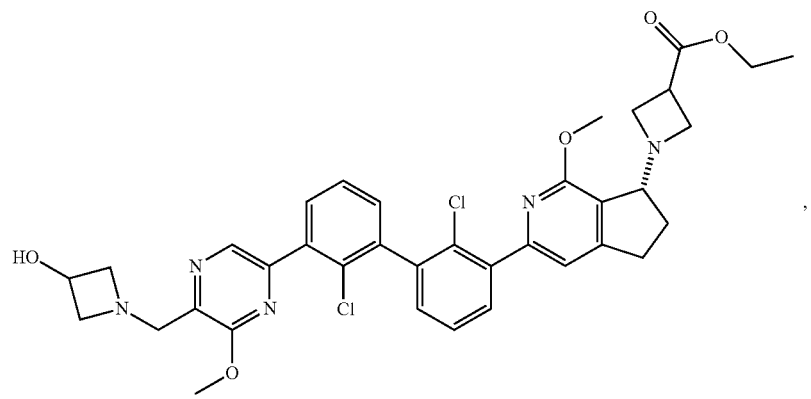
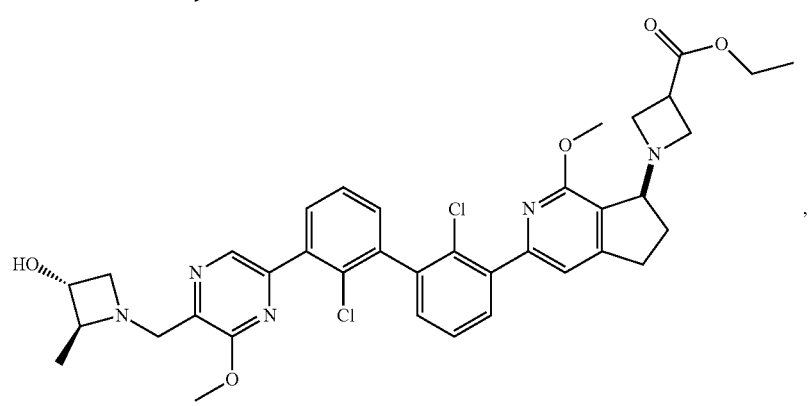

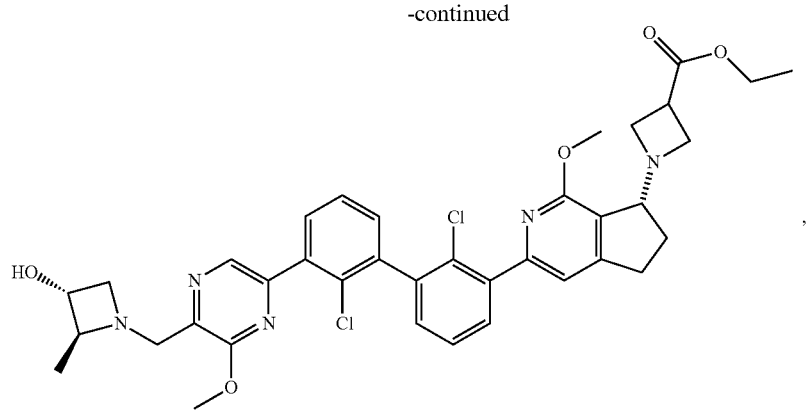

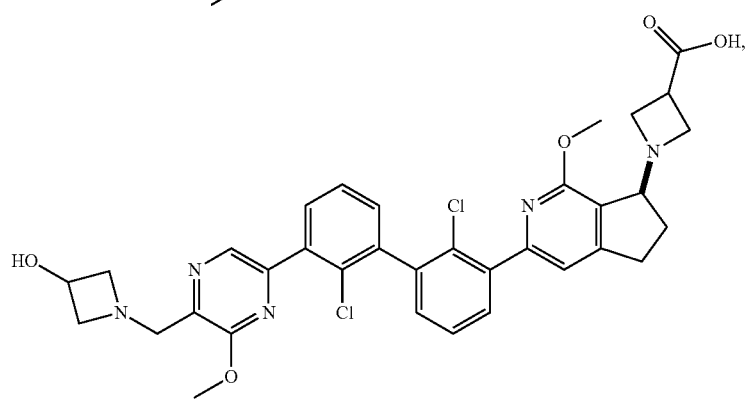

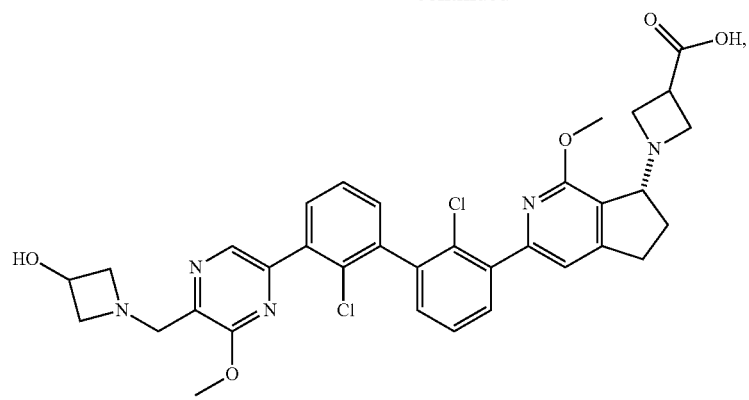
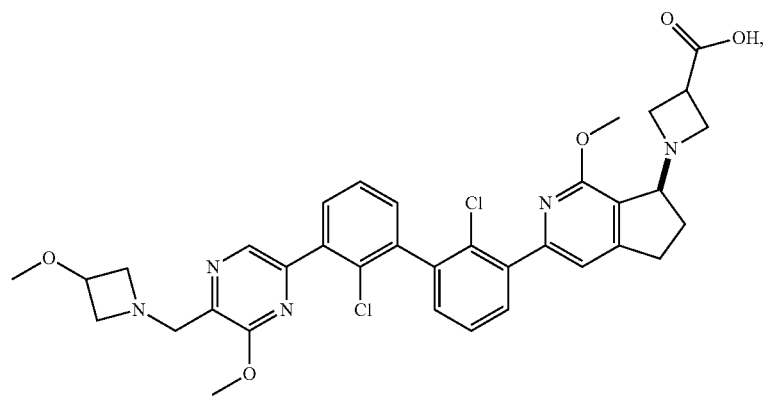
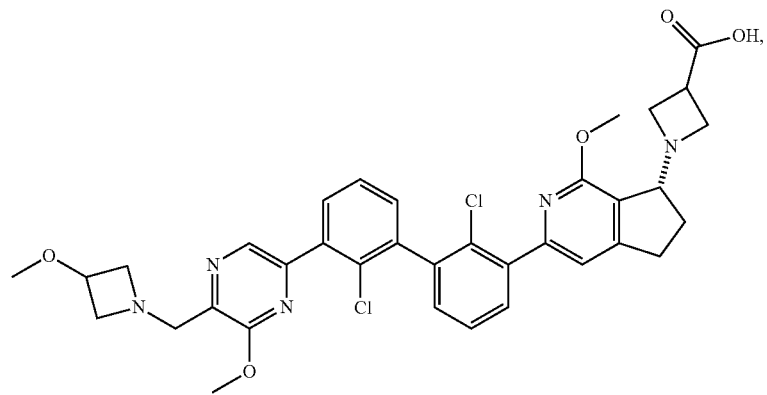
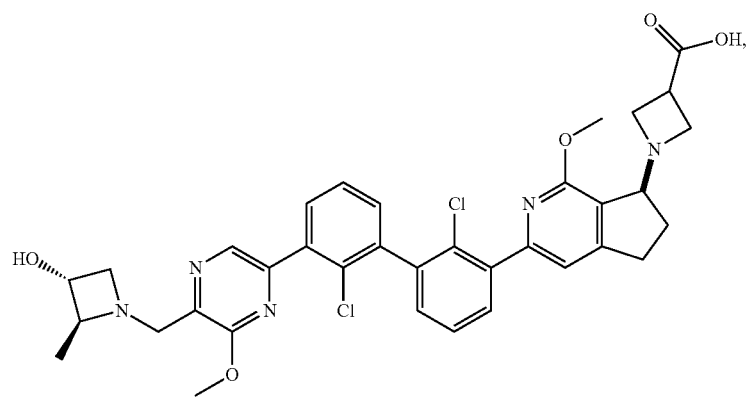

-continued
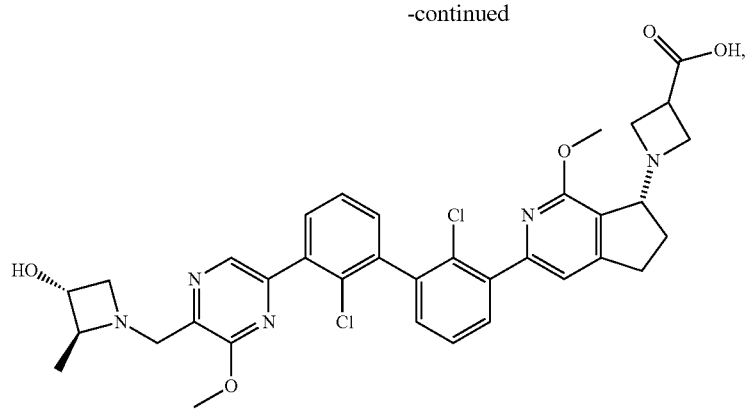
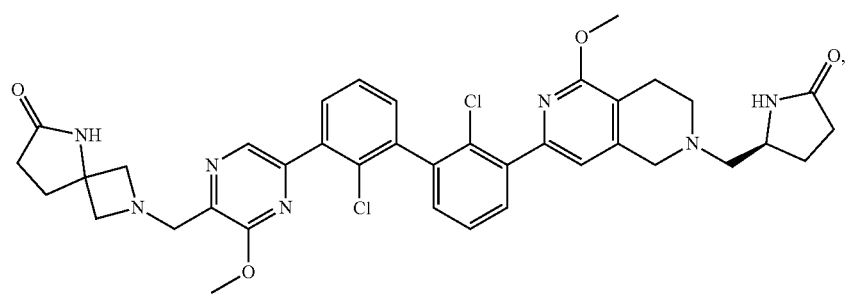
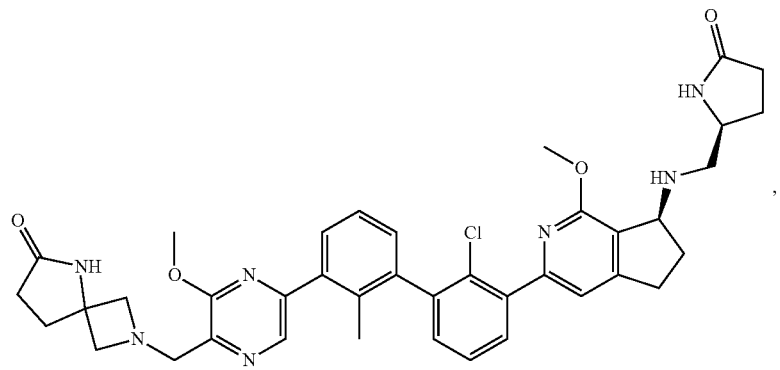
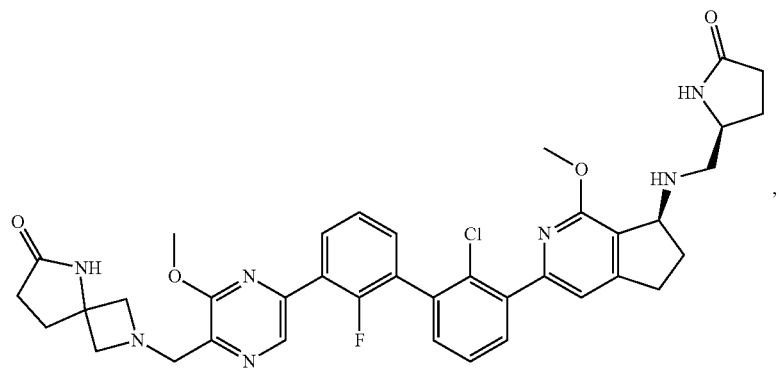

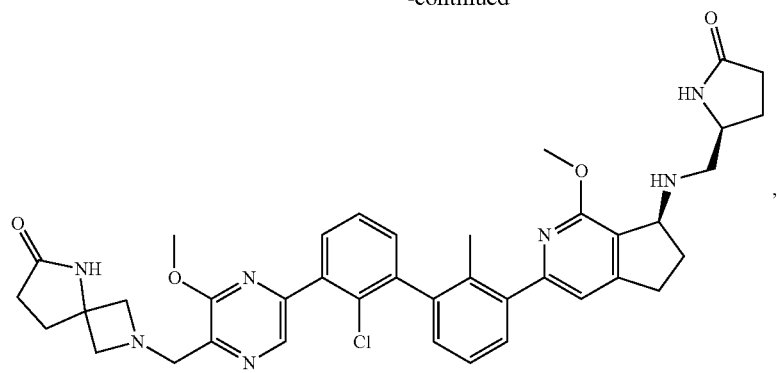
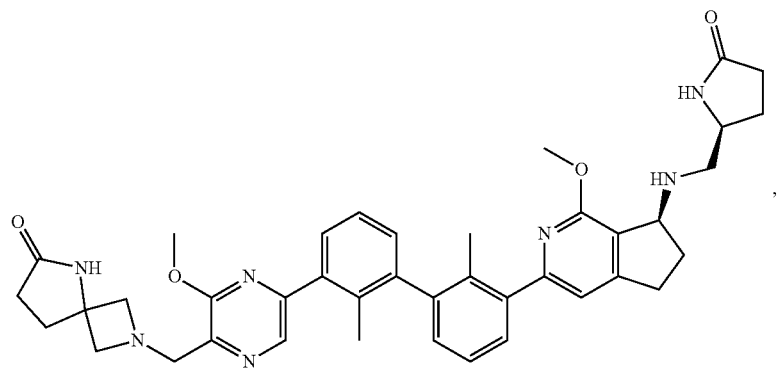

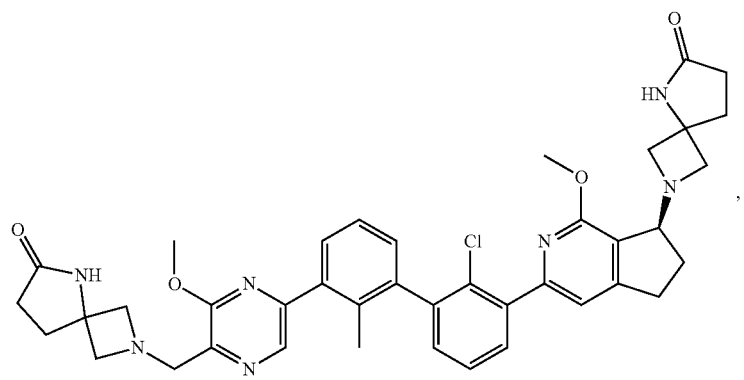
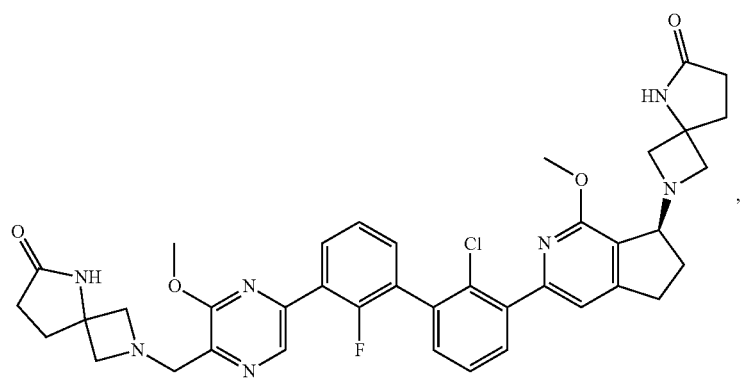

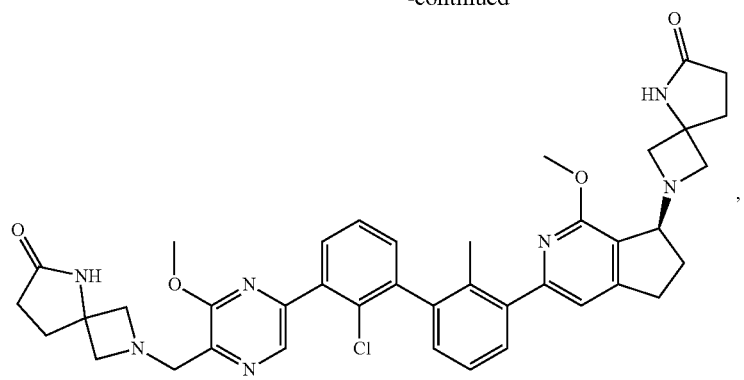
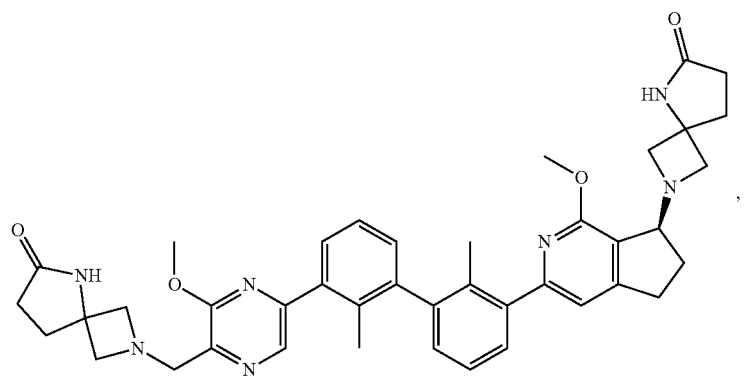

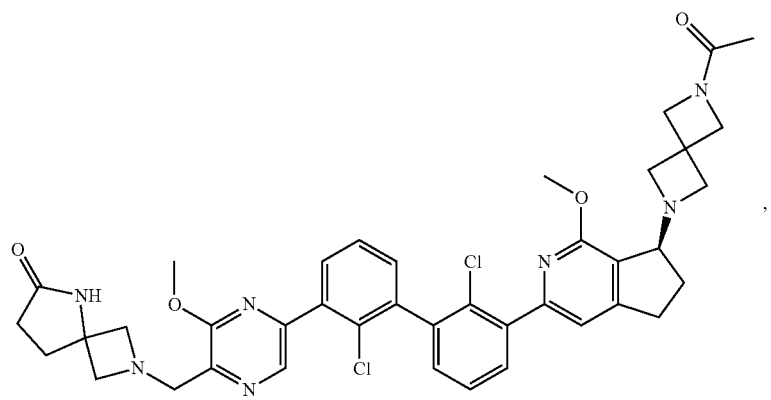
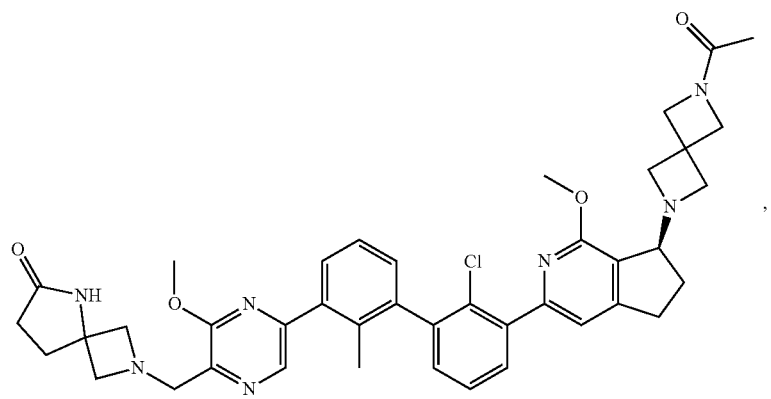

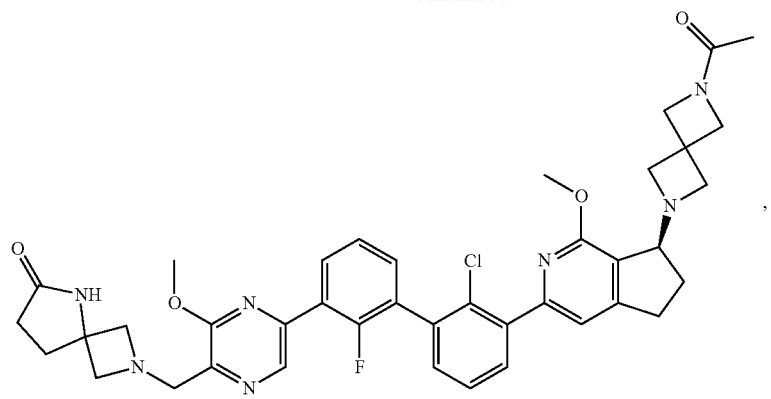

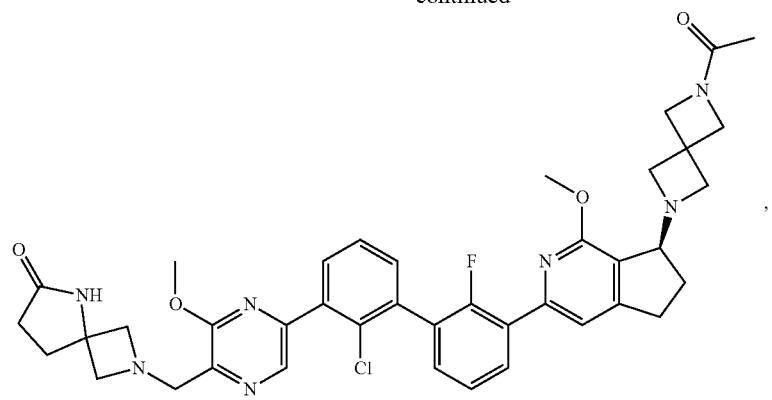
,

,

,
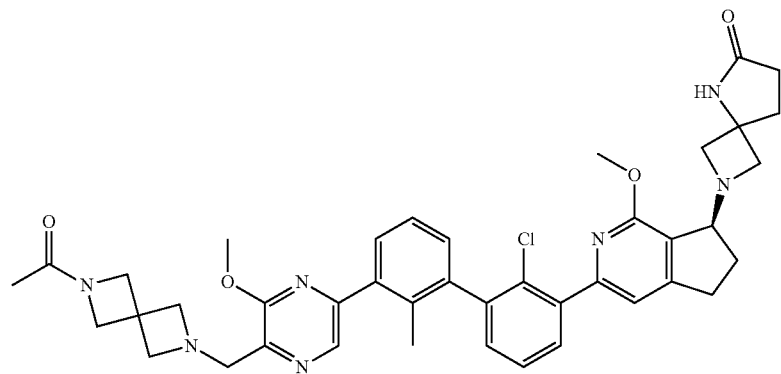
,

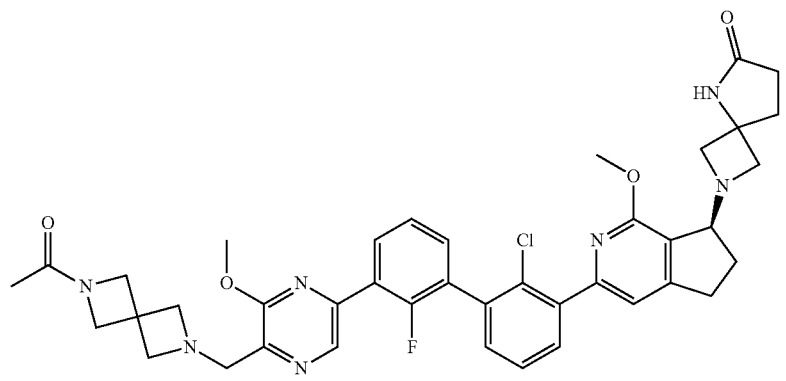
,
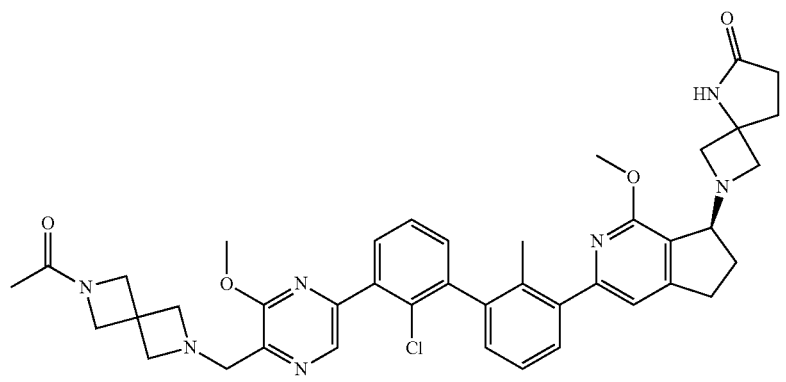
,
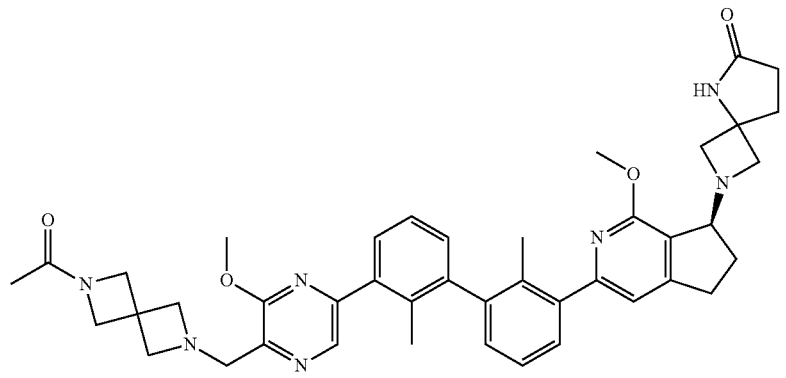
,
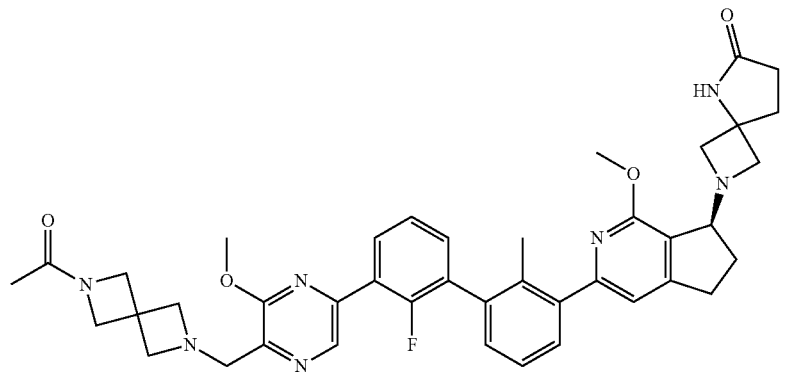
,

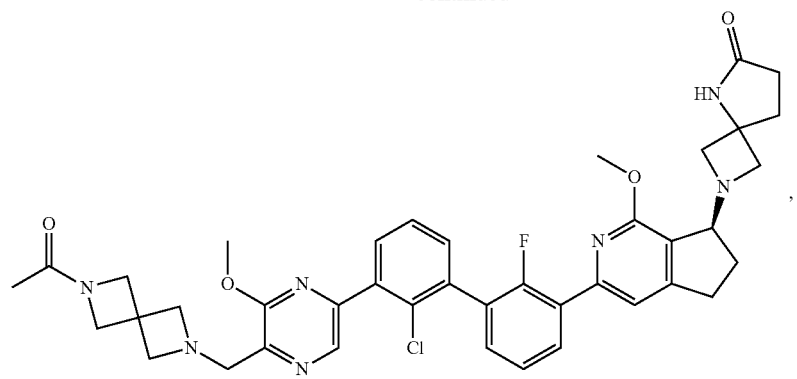

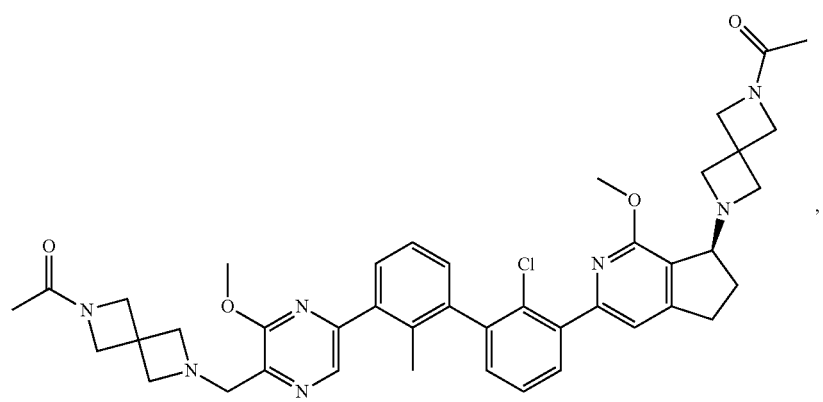

-continued
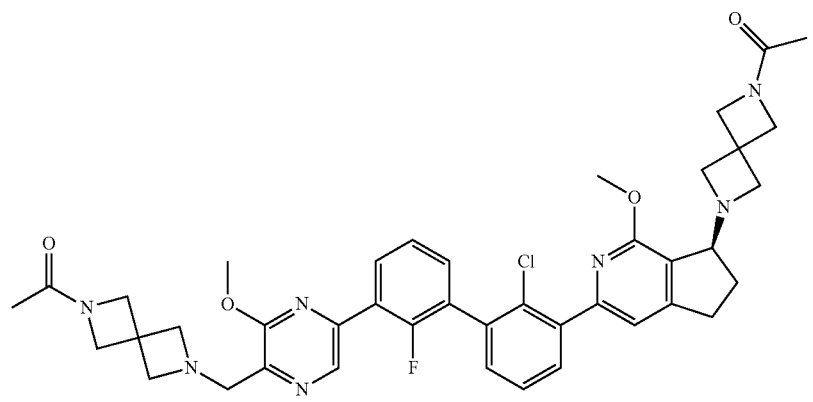
,
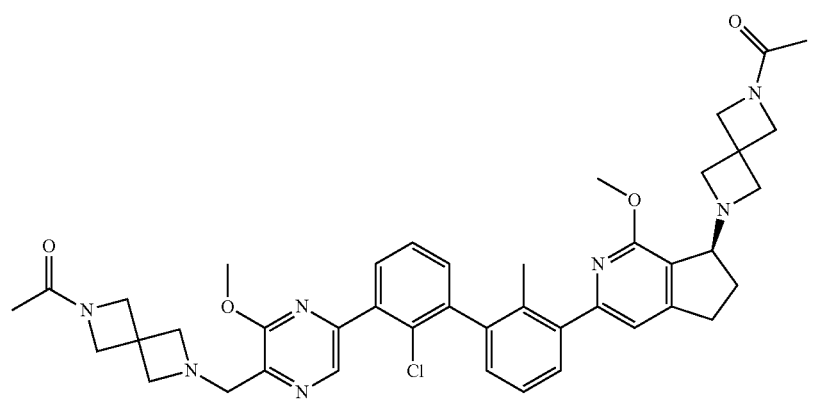
,
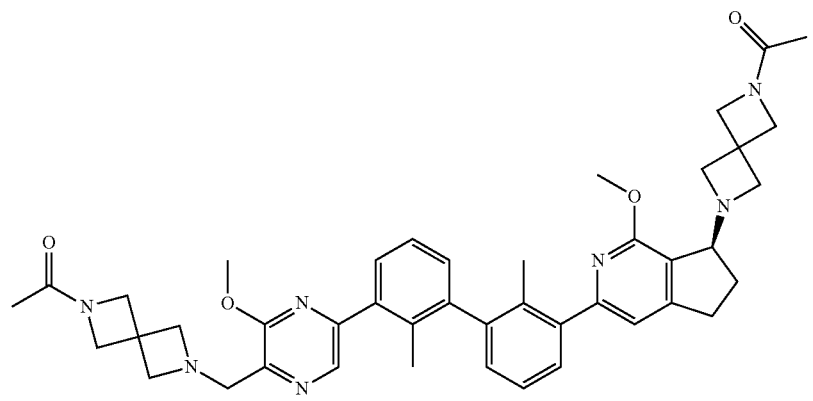
,
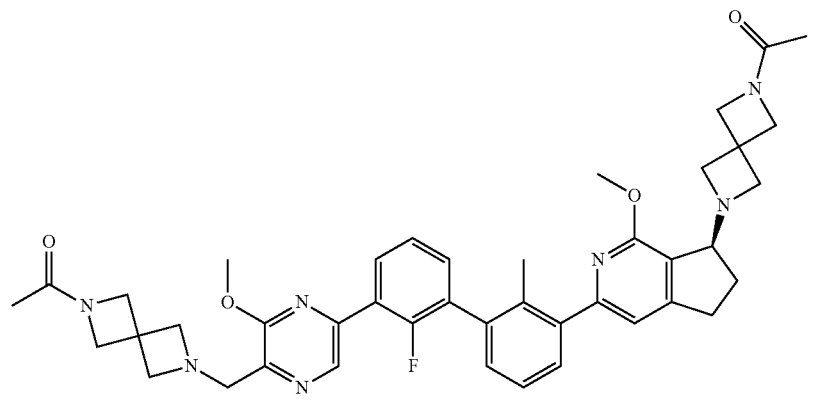
,

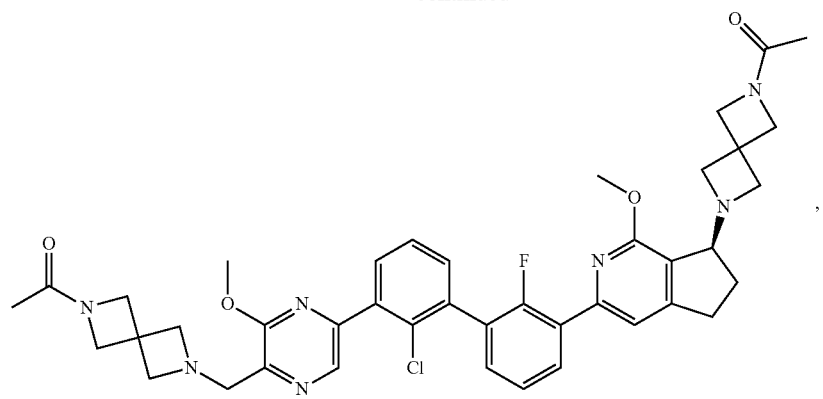,
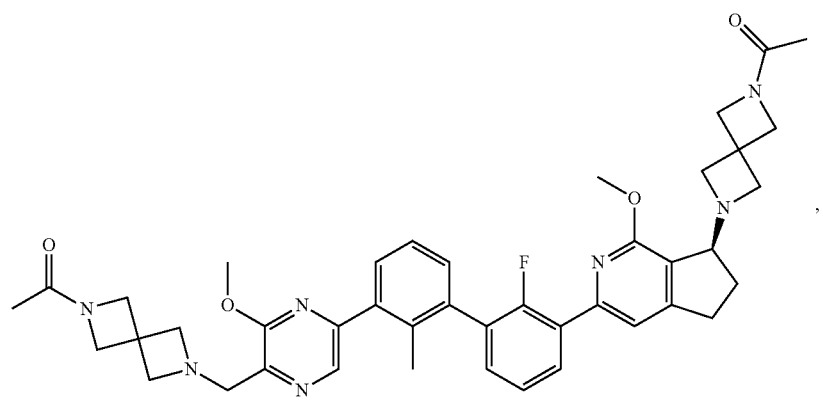,
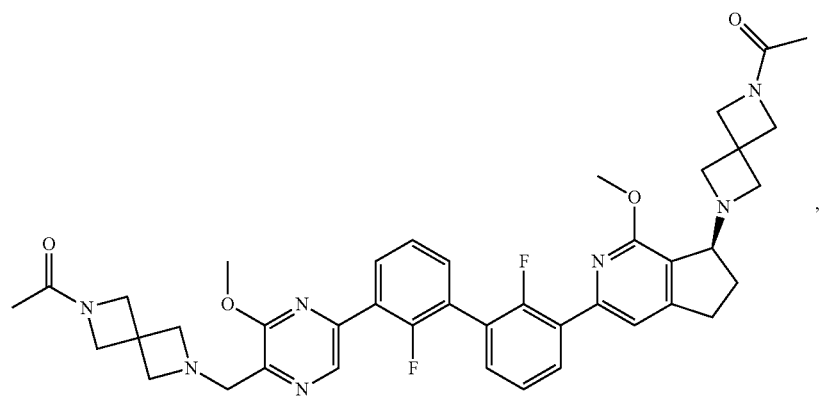,
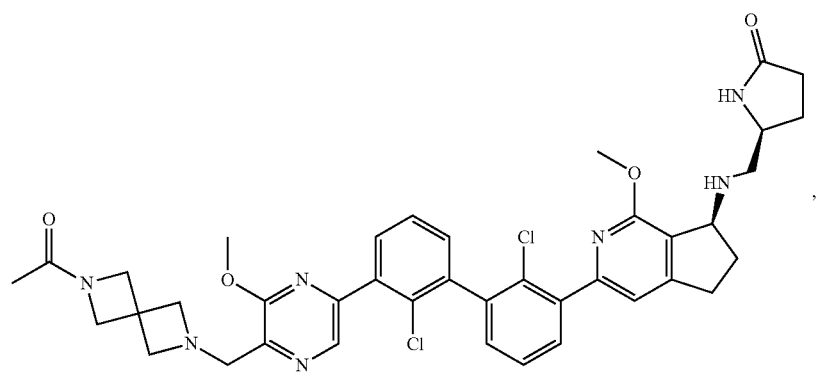,

-continued
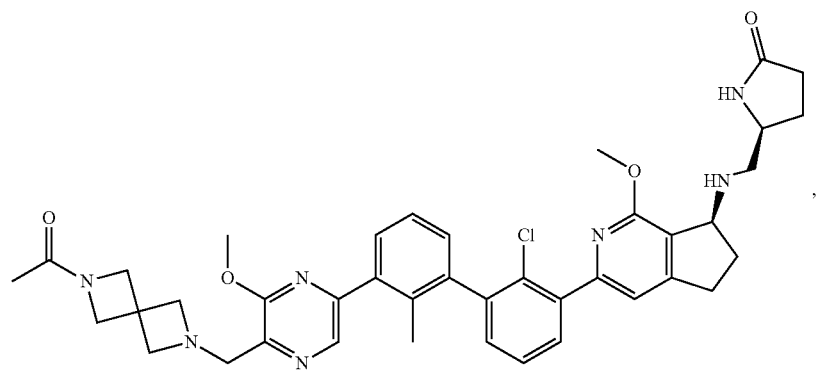
,
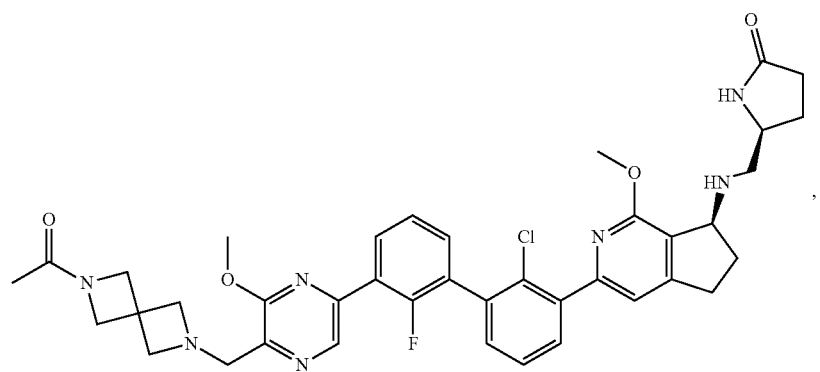
,
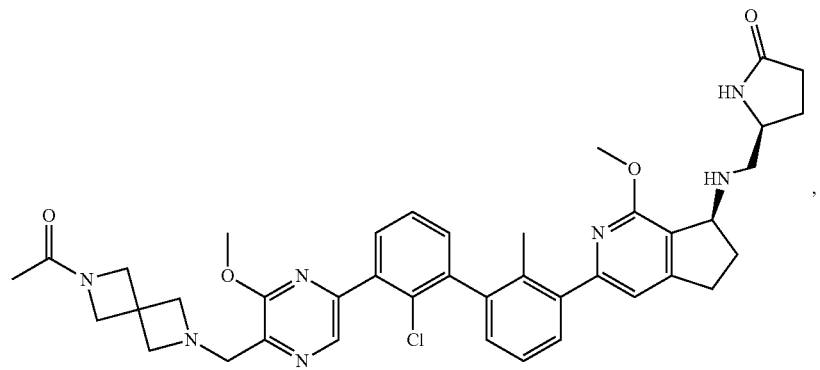
,
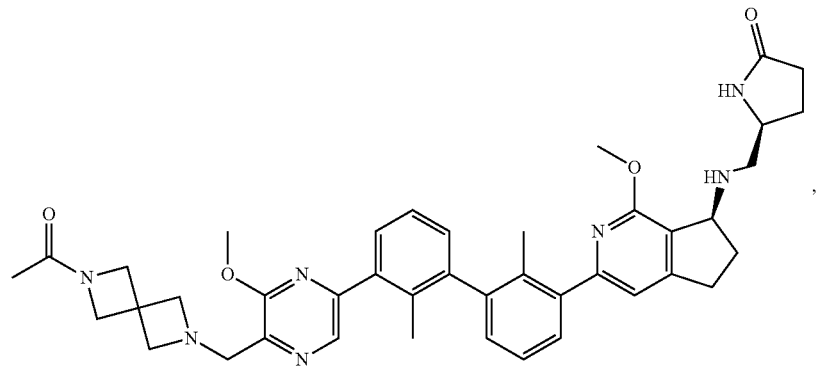
,


,
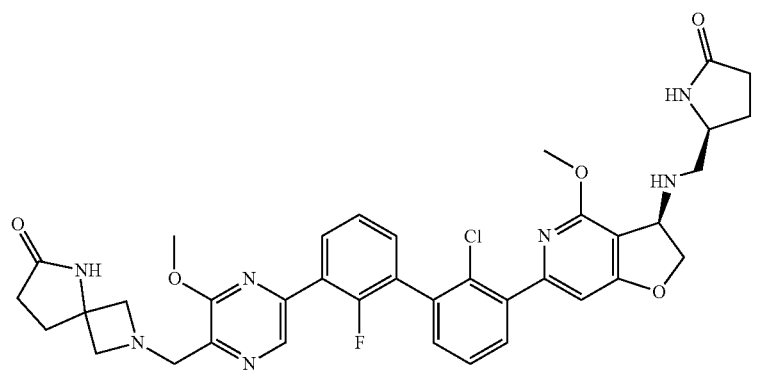,
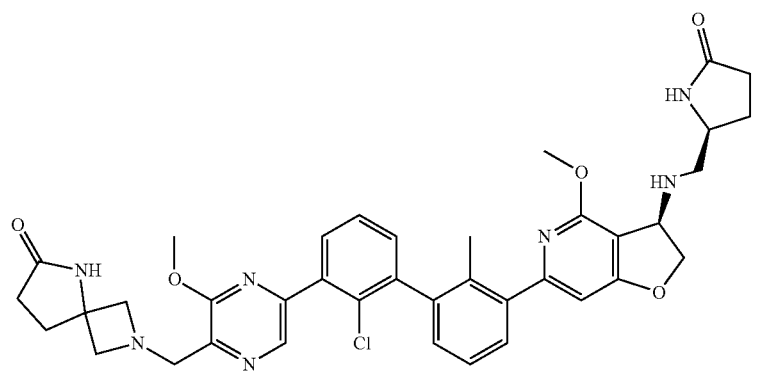,
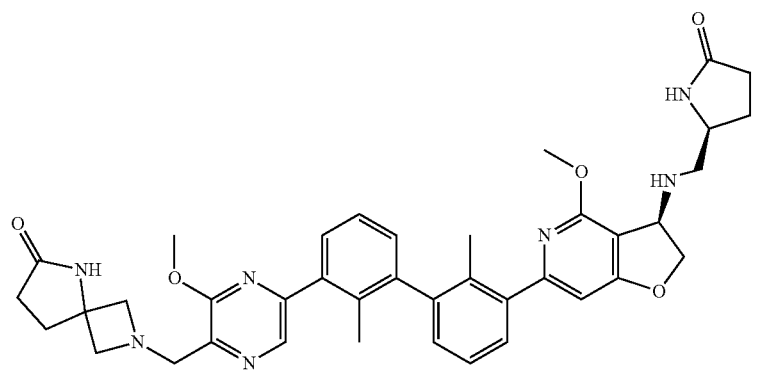,

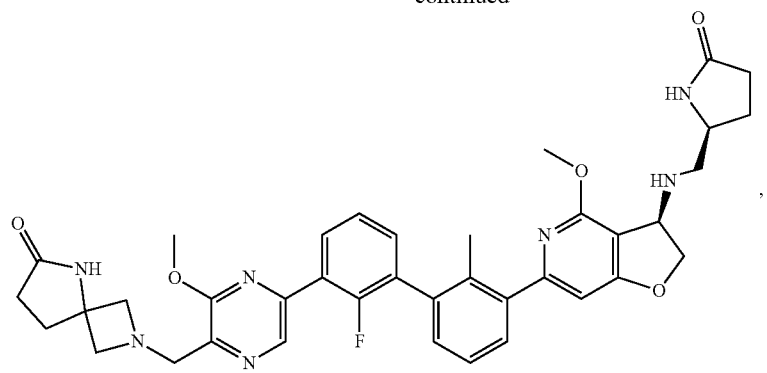,
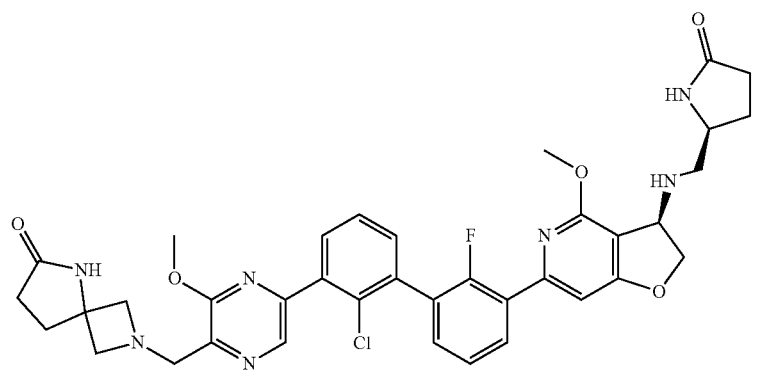,
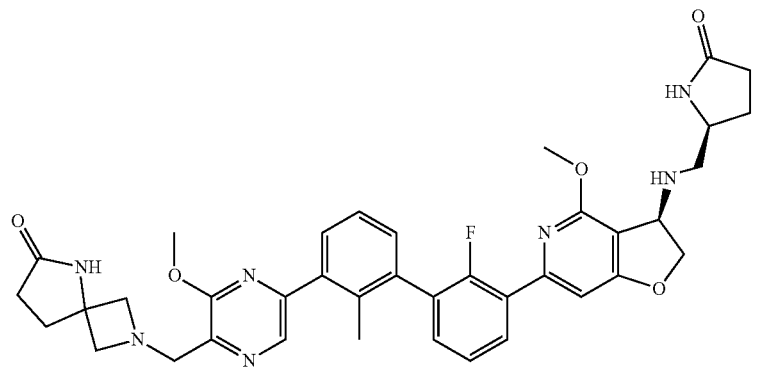,
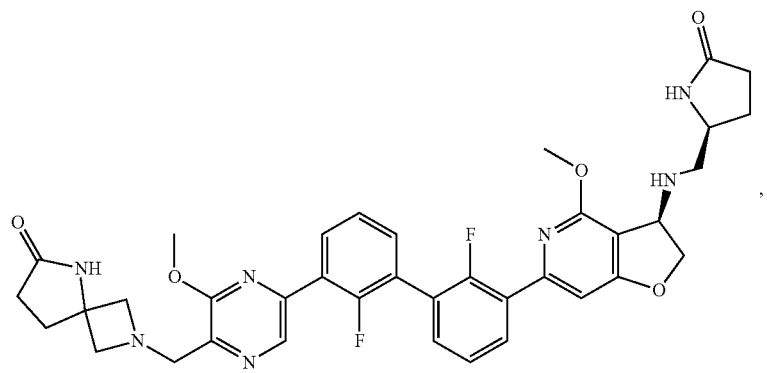,

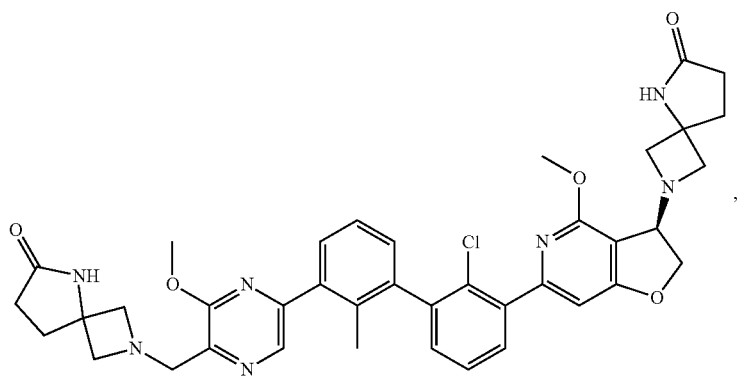
,

,
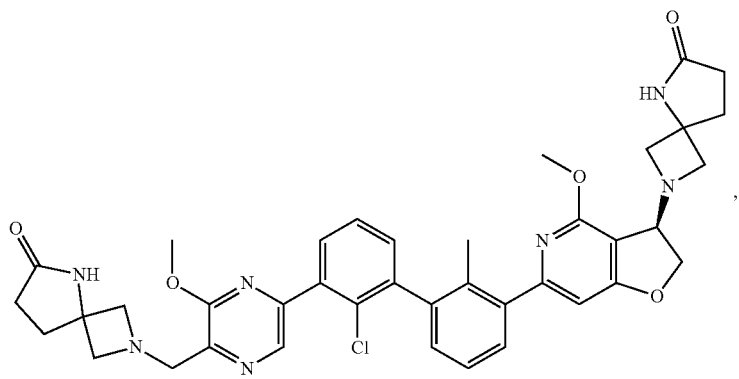
,
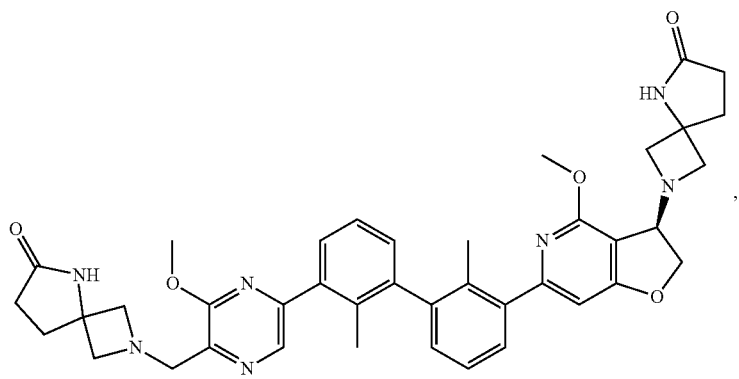
,

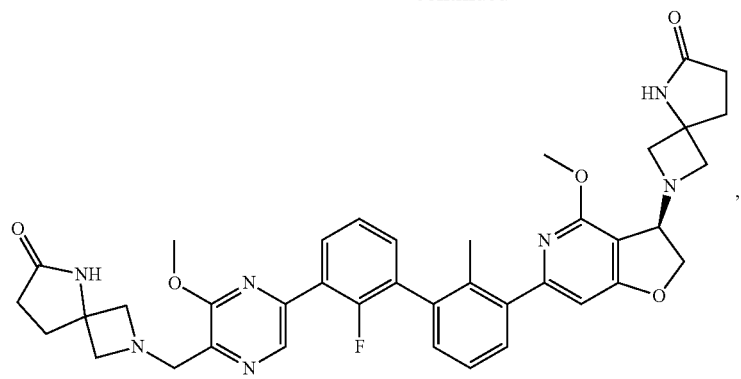
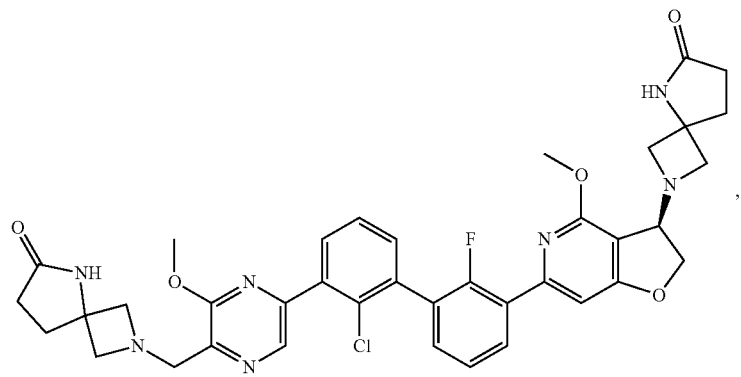
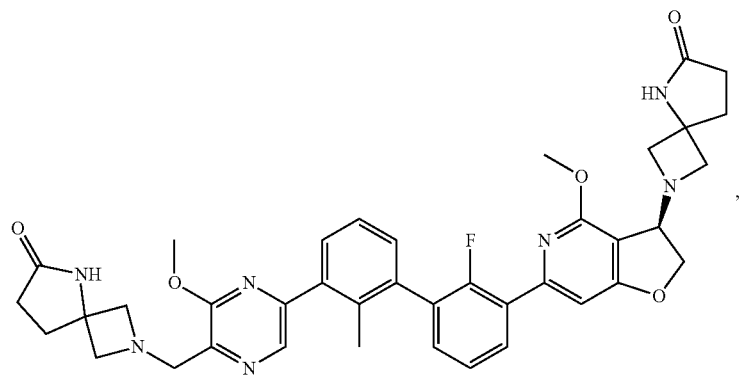
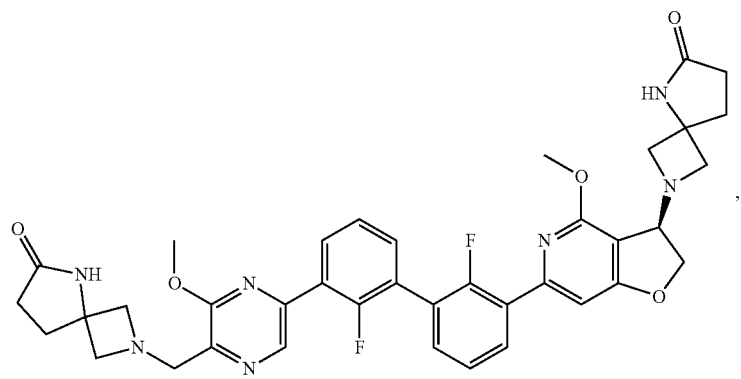

-continued
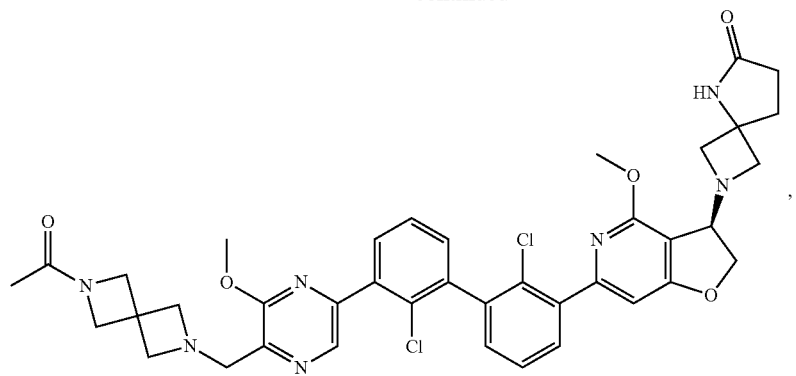
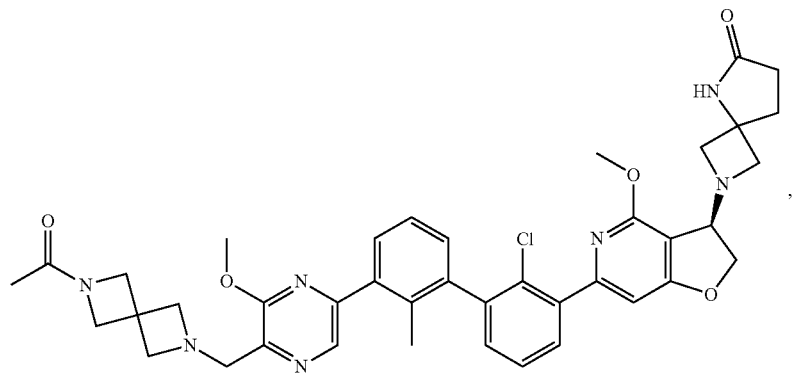
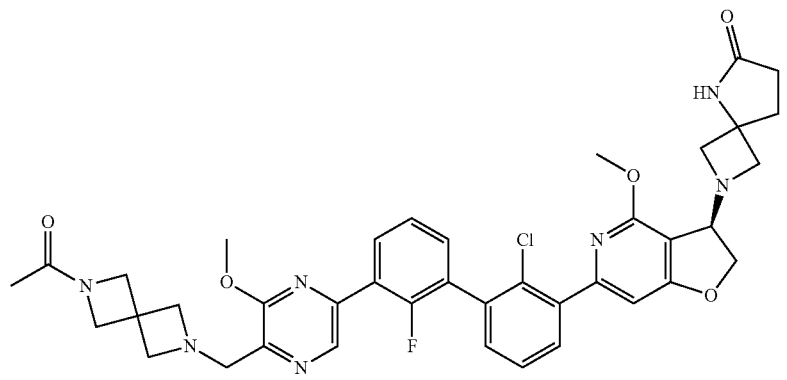

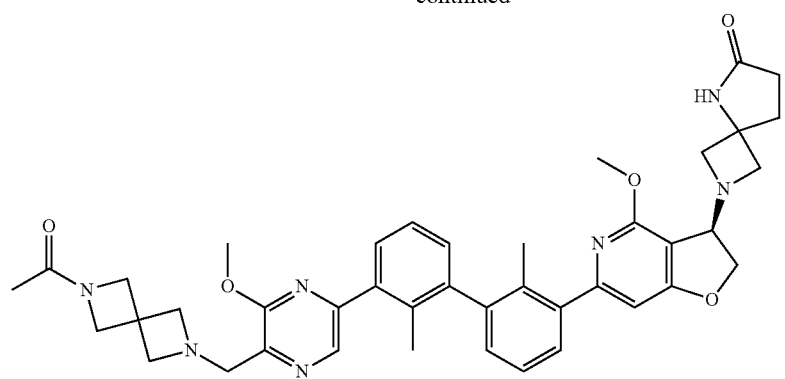
,
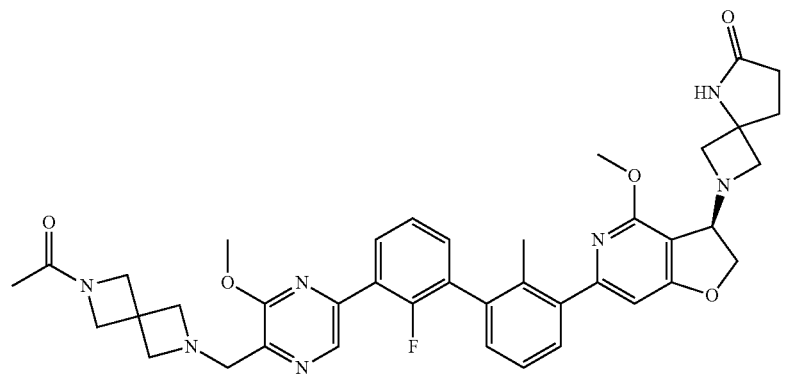
,
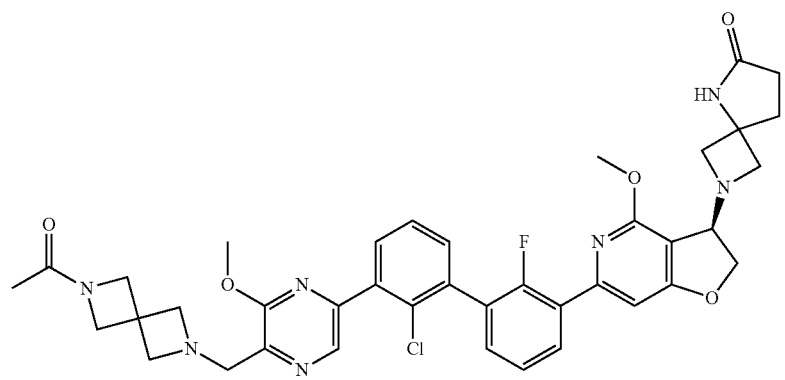
,
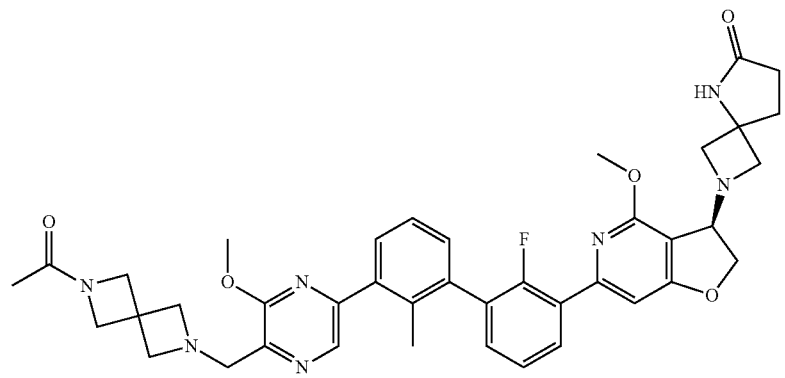
,

-continued
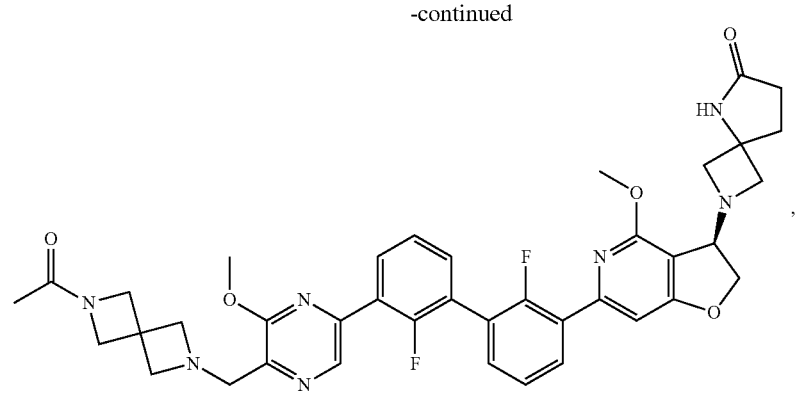
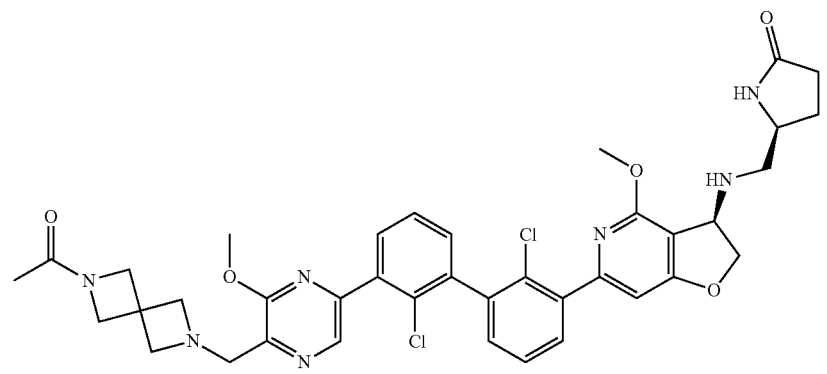
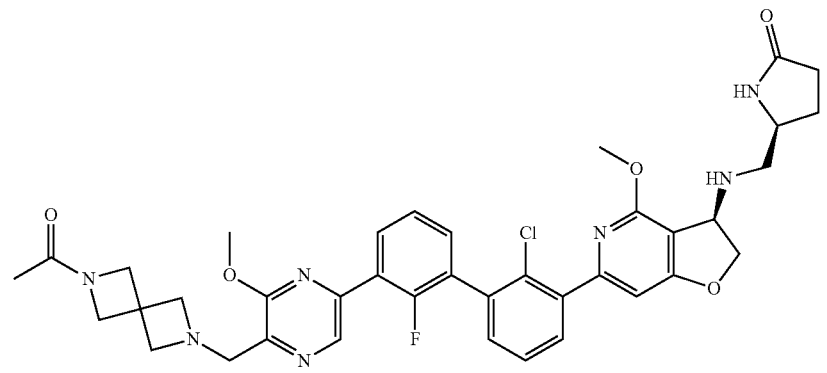

-continued
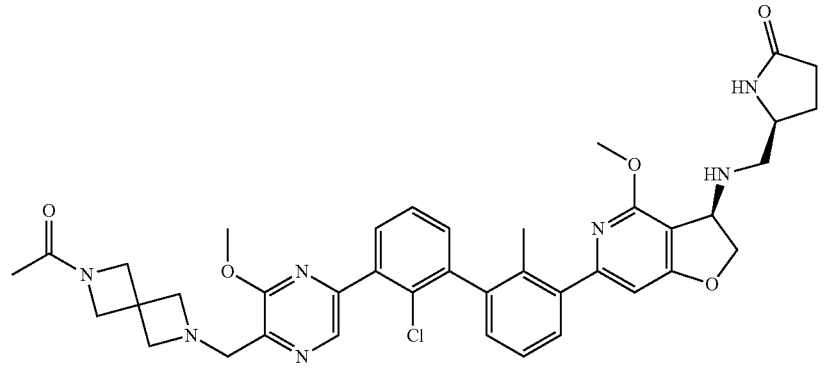
,
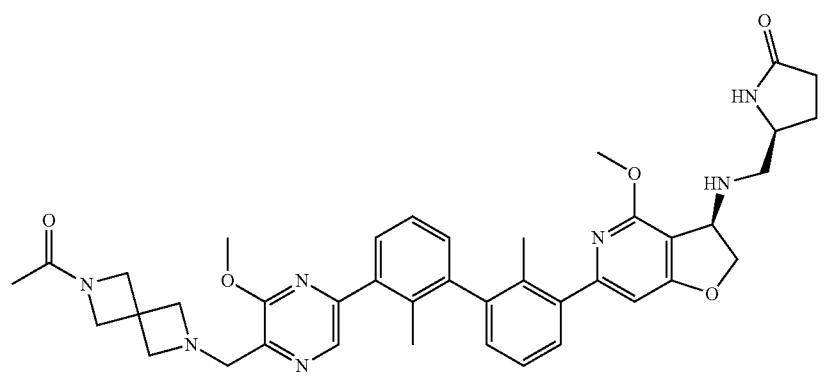
,
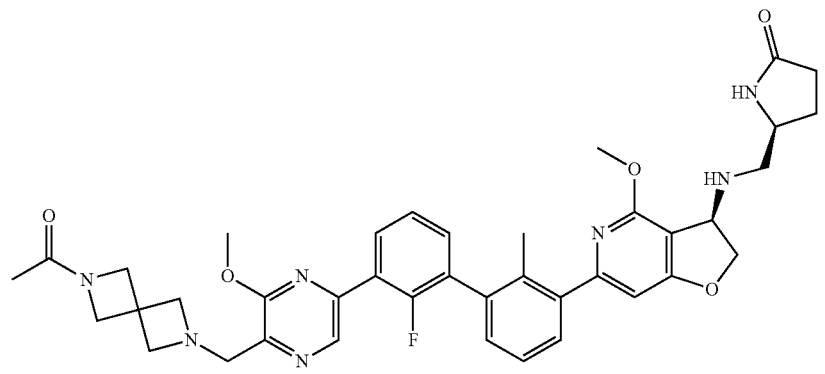
,
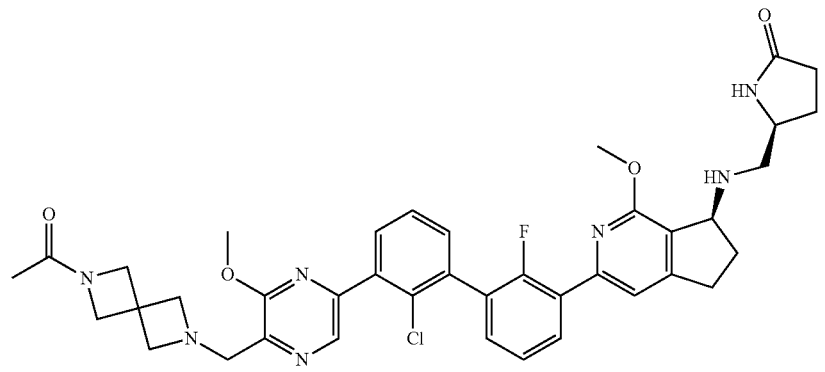
,

-continued

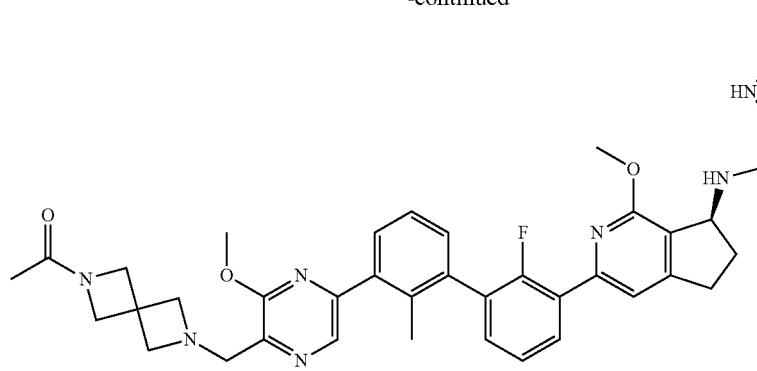

and

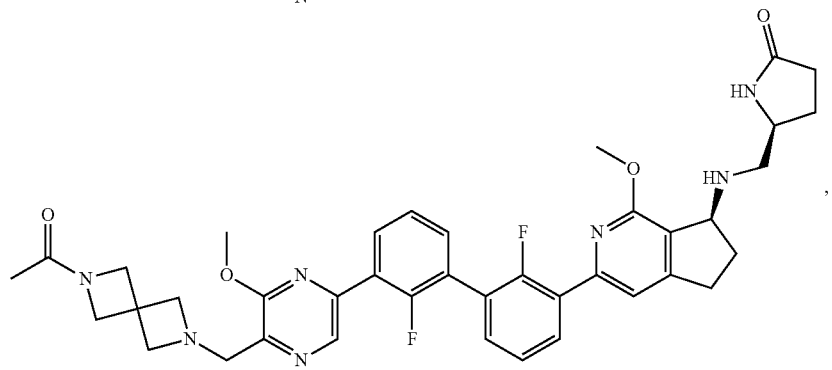

, or a pharmaceutically acceptable salt of any of the foregoing.

Embodiment 98

A pharmaceutical composition that can include an effective amount of a compound of any one of Embodiments 1-97, or a pharmaceutically acceptable salt thereof, and excipient.

Embodiment 99

A method for treating hepatitis B in a subject that can include administering to the subject in need thereof an effective amount of a compound of any one of Embodiments 1-97, or a pharmaceutically acceptable salt thereof.

Embodiment 100

A method for treating hepatocellular carcinoma (HCC) in a subject that can include administering to the subject in need thereof an effective amount of a compound of any one of Embodiments 1-97, or a pharmaceutically acceptable salt thereof.

Embodiment 101

The method of any one of Embodiments 99-100, that can further include administering surgery, radiation therapy, chemotherapy, targeted therapy, immunotherapy, hormonal therapy, or antiviral therapy.

Embodiment 102

A compound of any one of Embodiments 1-97, or a pharmaceutically acceptable salt thereof, for use in treating hepatitis B.

Embodiment 103

A compound of any one of Embodiments 1-97, or a pharmaceutically acceptable salt thereof, for use in treating hepatocellular carcinoma (HCC).

Embodiment 104

The compound of any one of Embodiments 102-103, that can further include administering surgery, radiation therapy, chemotherapy, targeted therapy, immunotherapy, hormonal therapy, or antiviral therapy.

Embodiment 105

Use of a compound of any one of Embodiments 1-97, or a pharmaceutically acceptable salt thereof, in the preparation of a medicament for use in treating hepatitis B.

Embodiment 106

Use of a compound of any one of Embodiments 1-97, or a pharmaceutically acceptable salt thereof, in the preparation of a medicament for use in treating hepatocellular carcinoma (HCC).

Embodiment 107

The use of any one of Embodiments 105-106, that can further include administering surgery, radiation therapy, chemotherapy, targeted therapy, immunotherapy, hormonal therapy, or antiviral therapy.

Methods for the Preparation

In this section, as in all other sections unless the context indicates otherwise, references to Formula (I), along with pharmaceutical acceptable salts thereof, include all other sub-groups and examples thereof as provided herein. The general preparations of some representative examples of compounds of Formula (I) are described herein, and are generally prepared from starting materials which are either commercially available or prepared by standard synthetic processes used by those skilled in the art.

In this section, as in all other sections unless the context indicates otherwise, references to Formula (I), Formula (II), Formula (III) and Formula (IV), along with pharmaceutical acceptable salts thereof, include all other sub-groups and examples thereof as provided herein. The general preparations of some representative examples of compounds of Formula (I), Formula (II), Formula (III), and Formula (IV) are described herein, and are generally prepared from starting materials which are either commercially available or prepared by standard synthetic processes used by those skilled in the art.

The following schemes a represent example preparations compounds of Formula (I), Formula (II), Formula (III) and Formula (IV), along with pharmaceutically acceptable salts thereof. Compounds of Formula (I), Formula (II), Formula (III) and Formula (IV), along with pharmaceutically acceptable salts thereof may also be prepared by analogous reaction protocols as described in the general schemes below, combined with standard synthetic processes used by those skilled in the art.

All variables shown in the schemes are defined as mentioned herein, unless otherwise is indicated or is clear from the context.

Compounds of Formula (II) can be prepared according to General Scheme 1.

General Scheme 1

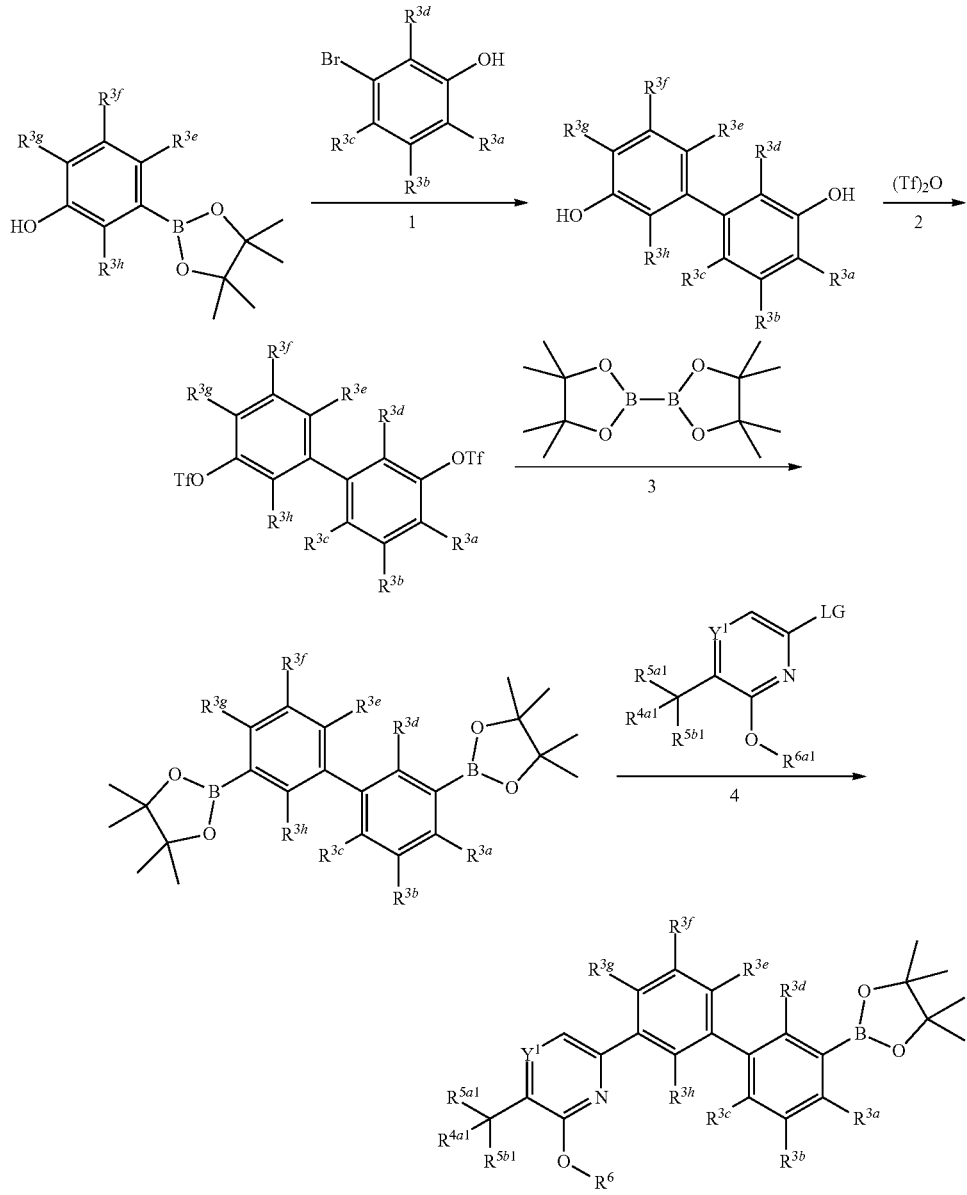

Int-A

-continued

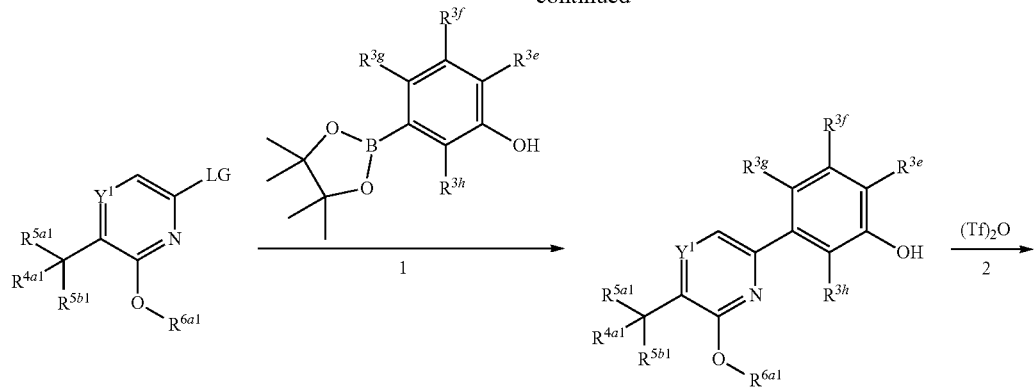

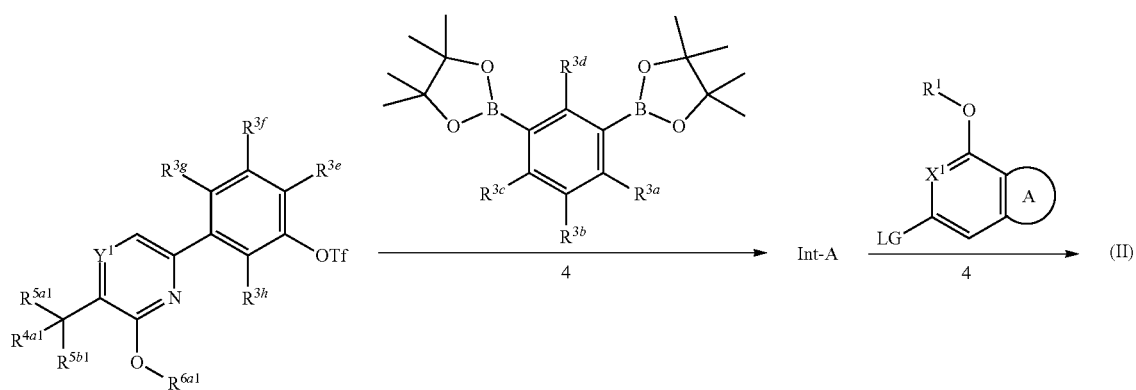

In Scheme 1, LG is defined as Br or Cl. All other variables in Scheme 1 are defined according to descriptions provided herein. In Scheme 1, the following reaction conditions apply: (1) In the presence of suitable catalyst, such as bis(triphenylphosphine)palladium(II) dichloride, in a suitable solvent, such as 1,4-dioxane, with a suitable base, such as for example $K_3PO_4$ at a suitable temperature, such as for example 90° C.; (2) In the presence of suitable base (for example, DIPEA) in a suitable solvent (such as DCM) at a suitable temperature, for example, 20° C.; (3) In the presence of suitable catalyst (for example, bis(triphenylphosphine)palladium(II) dichloride) in a suitable solvent, such as 1,4-dioxane, with a suitable base (for example, KOAc) at a suitable temperature (for example, 90° C.); (4) In the presence of suitable catalyst (for example bis(triphenylphosphine)palladium(II) dichloride) in a suitable solvent, such as 1,4-dioxane, with a suitable base, such as $K_2CO_3$ at a suitable temperature (for example 90° C.).

In general, compounds of Formula (III) can be prepared according to Scheme 2:

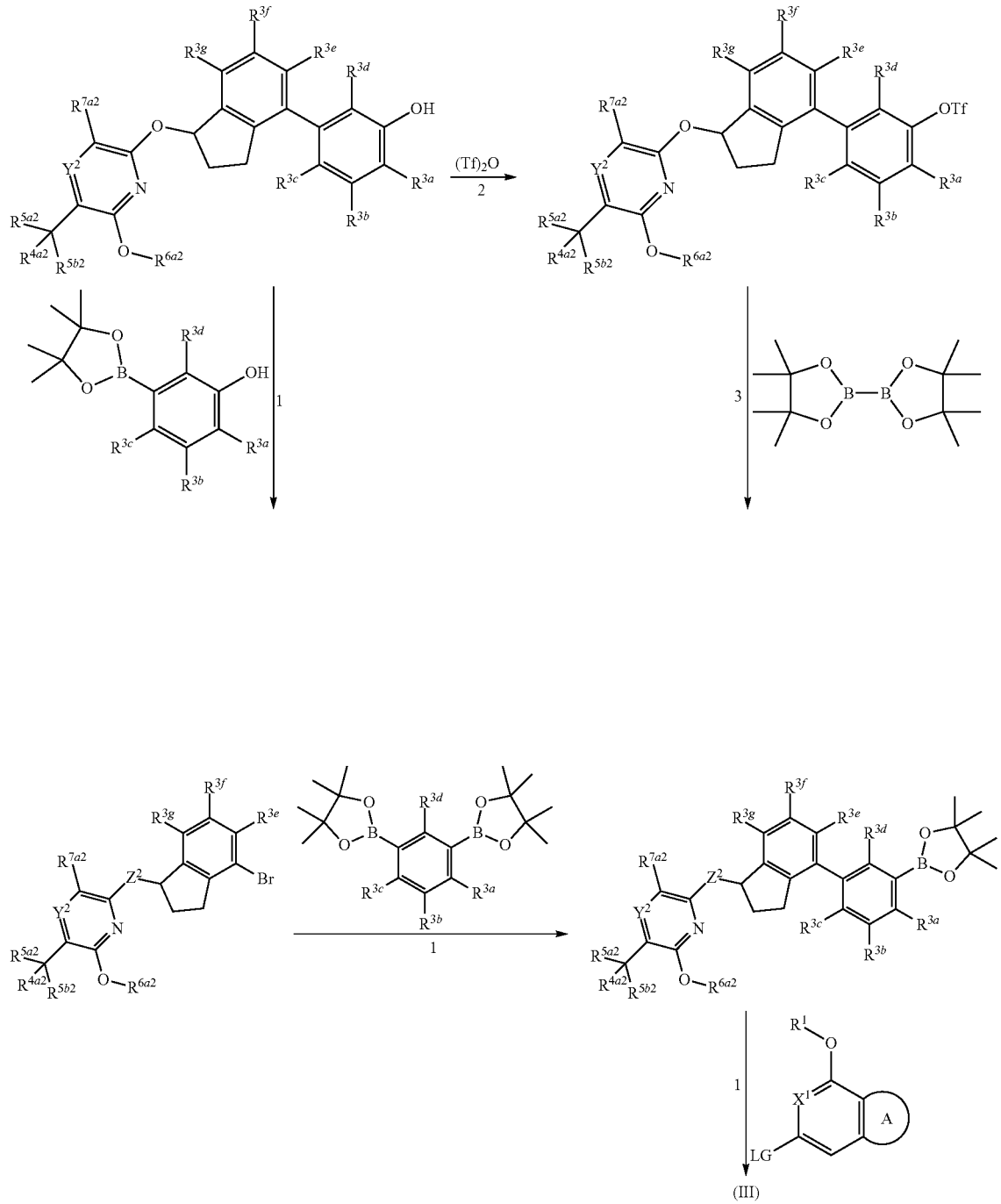

General Scheme 2

In Scheme 2, LG is defined as Br or Cl. All other variables in Scheme 2 are defined according to descriptions provided herein. In Scheme 2, the following reaction conditions typically apply: (1) In the presence of suitable catalyst, such as bis(triphenylphosphine)palladium(II) dichloride, in a suitable solvent (for example, 1,4-dioxane) with a suitable base, such as $K_2CO_3$, at a suitable temperature (for example 90° C.); (2) In the presence of suitable base (for example, DIPEA) in a suitable solvent, such as DCM, at a suitable temperature (for example, 20° C.). (3) In the presence of suitable catalyst, such as bis(triphenyl-phosphine)palladium (II) dichloride, in a suitable solvent (for example, 1,4-dioxane) with a suitable base (for example, KOAc) at a suitable temperature, such as 90° C.

In general, compounds of Formula (IV) can be prepared according to Scheme 3:

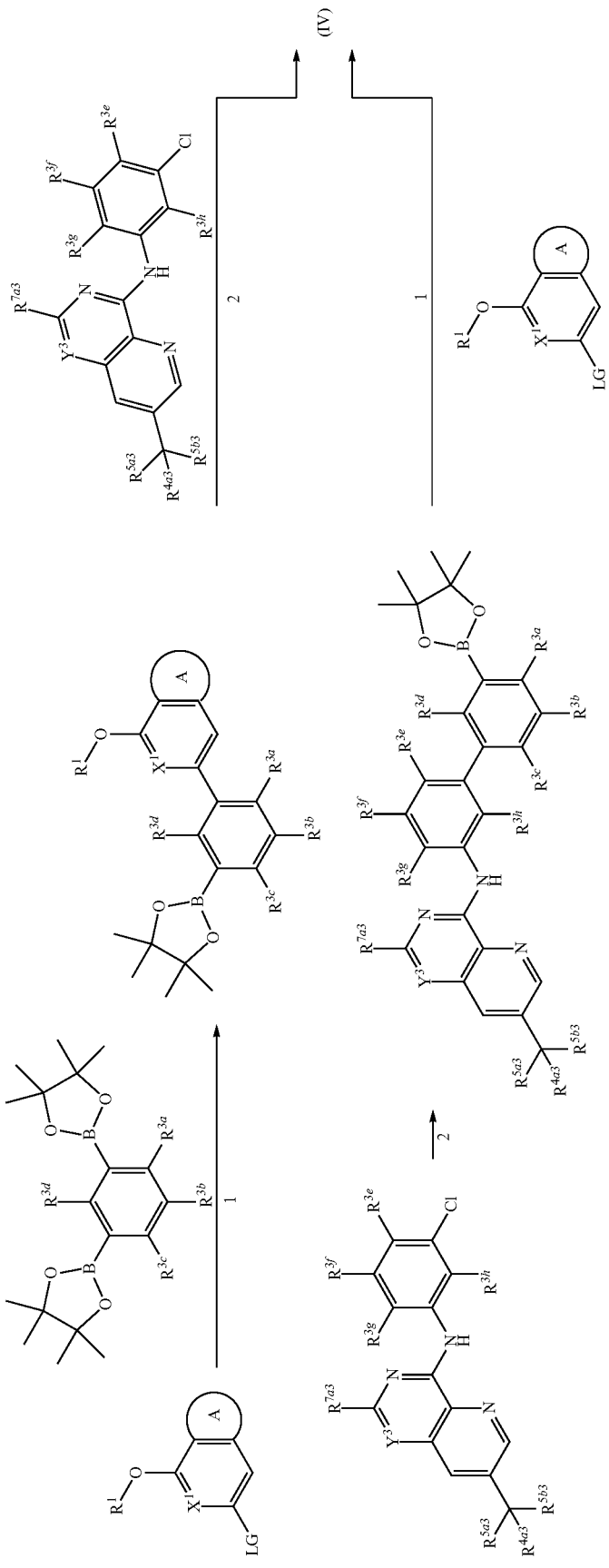

In Scheme 3, LG is defined as Br or Cl. All other variables in Scheme 3 are defined according to descriptions provided herein. In Scheme 3, the following reaction conditions typically apply: (1) In the presence of suitable catalyst (for example, bis(triphenylphosphine)palladium(II) dichloride) in a suitable solvent, such as 1,4-dioxane, with a suitable base (for example, $K_2CO_3$) at a suitable temperature (for example, 90° C.); (2) In the presence of suitable catalyst, such as chloro(2-dicyclohexylphosphino-2',4',6'-triisopropyl-1,1'-biphenyl)[2-(2'-amino-1,1'-biphenyl)]palladium (II), in a suitable solvent, such as a mixture of water and 1,4-dioxane purged with $N_2$, with a suitable base (for example, $K_3PO_4$) at a suitable temperature, such as 100° C.

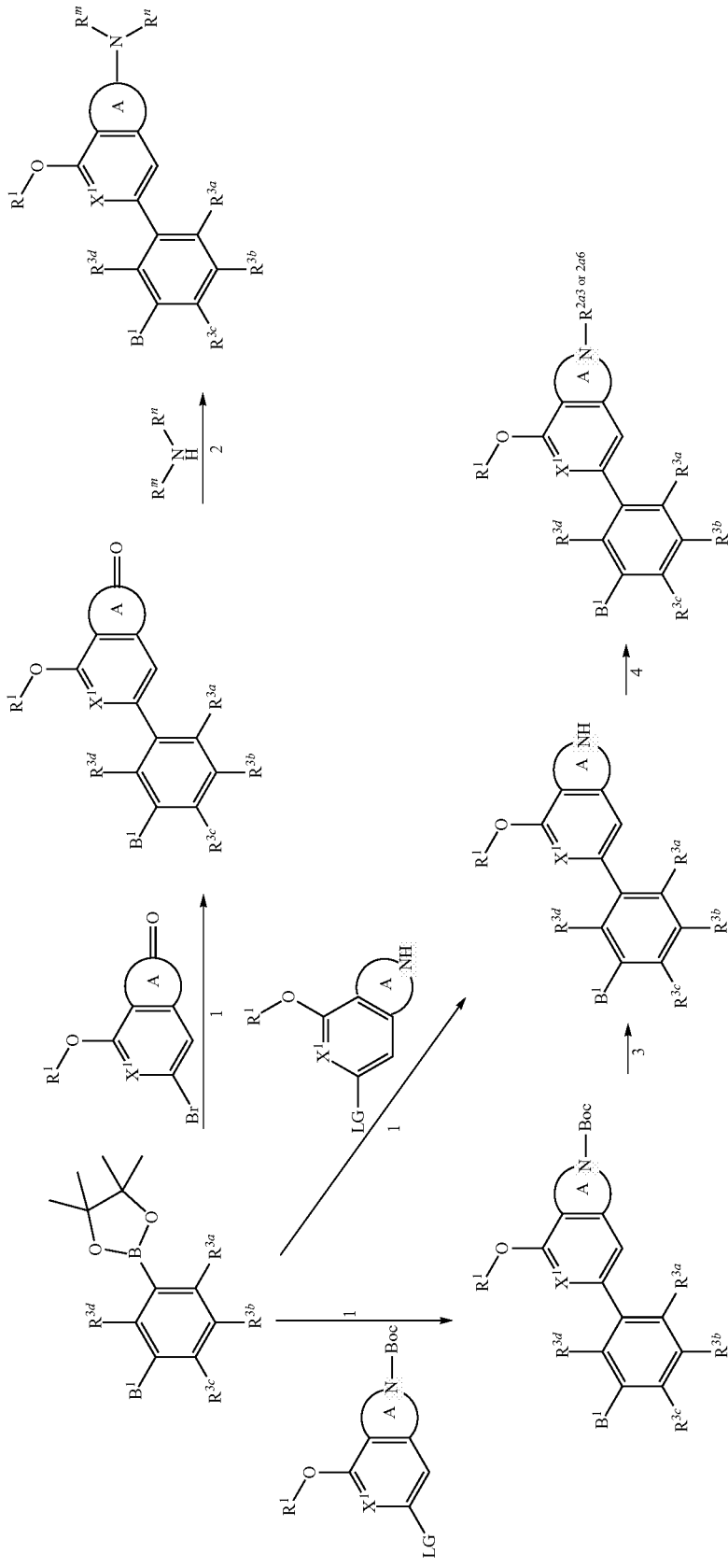
General Scheme 4

In Scheme 4, LG is defined as Br or Cl. All other variables in Scheme 4 are defined according to descriptions provided herein. In Scheme 4, the following reaction conditions typically apply: (1) In the presence of suitable catalyst (for example, bis(triphenylphosphine)palladium(II) dichloride) in a suitable solvent, such as 1,4-dioxane, with a suitable base (for example, K₂CO₃) at a suitable temperature (for example, 90° C.); (2) In the presence of an appropriate reductive reagent, such as sodium cyanoborohydride or sodium triacetoxyborohydride, in a suitable solvent (for example, DCM or MeOH) at a suitable temperature, such as approximately 20° C.; (3) In the presence of suitable acid (for example, TFA or HCl) in a suitable solvent (for example, DCM or dioxane) at a suitable temperature, such as 20° C.; (4) Different sets of reaction conditions dependent on the coupling reagents for introducing $R^{3a3}$ or $R^{3a6}$: (4a) A coupling reagent containing an aldehyde or a ketone as a reactive group, in the presence of appropriate reductive reagent such as sodium cyanoborohydride or sodium triacetoxyborohydride, in a suitable solvent (for example, DCM or MeOH) at a suitable temperature (for example, 20° C.); (4b) A coupling reagent containing halogen as a leaving group connected to an non-aromatic carbon adjacent to nitrogen, in the presence of appropriate base (such as TEA or DIEA) at suitable temperature (for example, 50° C.) with or without a suitable solvent, such as DCM; (4c) A coupling reagent containing a halogen as a leaving group connected to an aromatic carbon adjacent to nitrogen, in the presence of appropriate base (such as TEA or DIEA) at suitable temperature (for example, 150° C.) with or without a suitable solvent, such as NMP; (4d) A coupling reagent containing a halogen as a leaving group connected to a non-aromatic carbon, the coupling reaction can be done with in the presence of an appropriate palladium catalyst (for example, Ruphos-Pd-G3) with a suitable ligand (for example, Ruphos) with a suitable base, such as for example Cs₂CO₃, in a suitable solvent (such as 1,4-dioxane) at suitable temperature (for example, 100° C.); (4e) A coupling reagent containing an epoxide as a reactive group, in the presence of a suitable base (such as TEA) in a suitable solvent, such as EtOH, at a suitable temperature (for example, 80° C.).

General Scheme 5

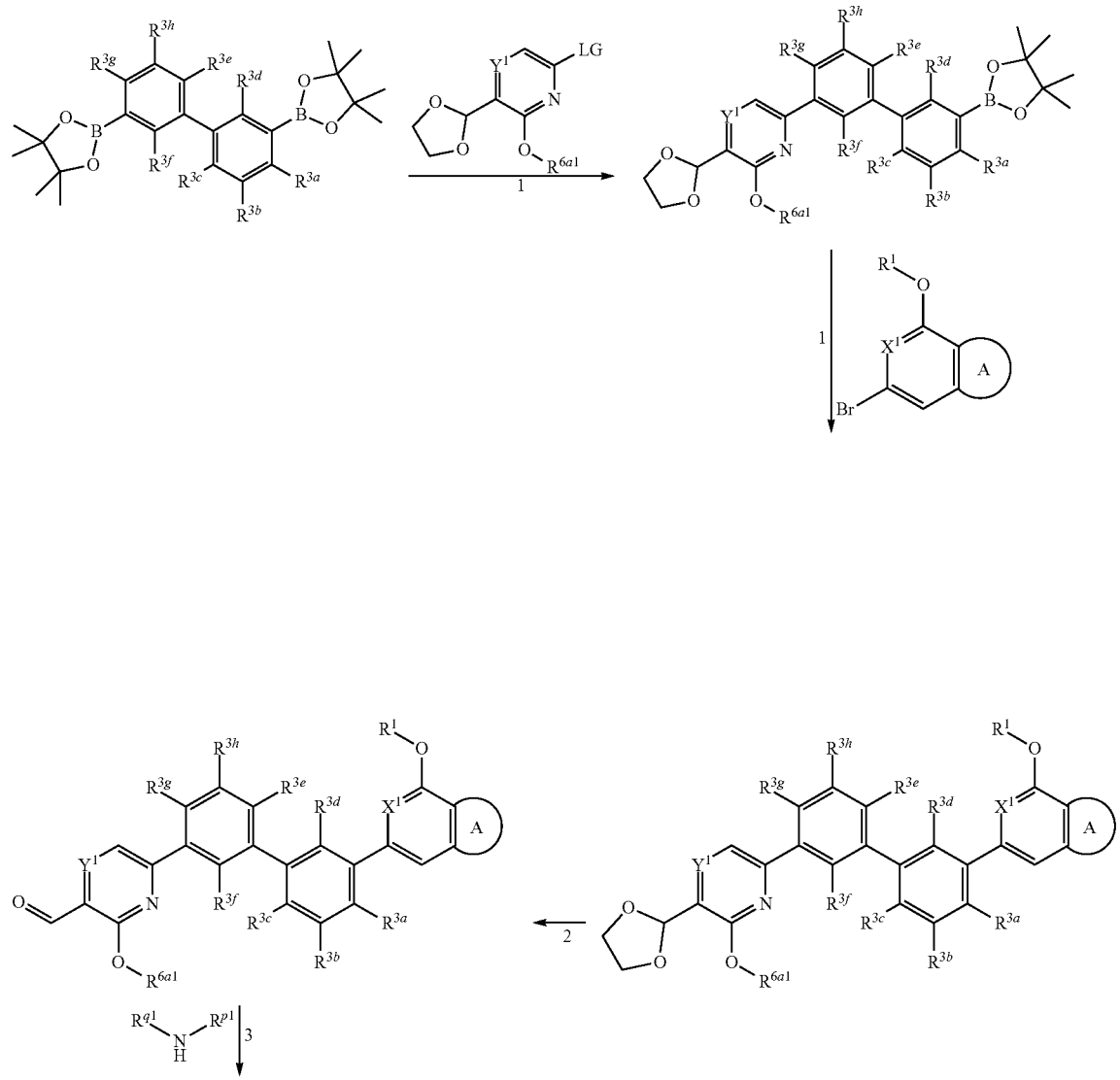

-continued

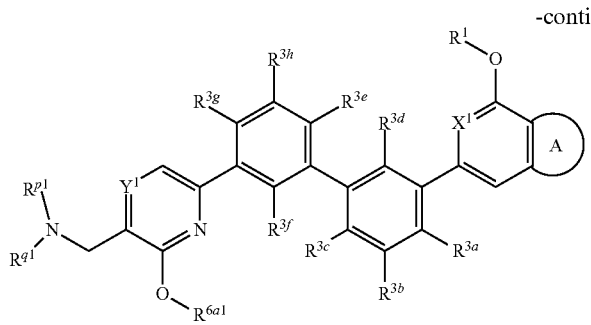

In Scheme 5, LG is defined as Br or Cl. All other variables in Scheme 5 are defined according to descriptions provided herein. In General Scheme 5, the following reaction conditions can be used in each of the indicates reactions: (1) In the presence of a suitable catalyst, such as bis(triphenylphosphine)palladium(II) dichloride, in a suitable solvent (for example, 1,4-dioxane) with a suitable base, such as $K_2CO_3$, at a suitable temperature (for example approximately 90° C.); (2) In the presence of a suitable acid, such as concentric HCl acid, in a suitable solvent (for example the mixture of $H_2O$ and THF), at a suitable temperature (for example approximately 20° C.); (3) In the presence of an appropriate reductive reagent, such as sodium cyanoborohydride or sodium triacetoxyborohydride, in a suitable solvent (for example, DCM or MeOH) at a suitable temperature, such as approximately 20° C.

A skilled person will realize that typically after a column purification, the desired fractions can be collected, and the solvent can be evaporated to obtain the desired compound or intermediate. In addition, a skilled person will realize that in the reactions described in the schemes provided herein, it may be necessary to protect reactive functional groups, for example, hydroxy, amino, or carboxy groups, where these are desired in the final product, to minimize any side reactions. Conventional protecting groups can be used in accordance with standard practice. A skilled person will realize that in the reactions described in schemes herein, it may be advisable or necessary to perform the reaction under an inert atmosphere, for example, under $N_2$-gas atmosphere. It will be apparent to a skilled person that a mixture may be cooled before reaction work-up (refers to the series of manipulations required to isolate and purify the product(s) of a chemical reaction, for example quenching, column chromatography and extraction). A skilled person will realize that heating a reaction mixture under stirring may enhance the reaction outcome. In some reactions, microwave heating may be used instead of conventional heating to shorten the overall reaction time.

A skilled person will realize that another sequence of the chemical reactions shown in the schemes herein, may also provide a compound described herein (such as Formula (I), Formula (II), Formula (III) and Formula (IV), or a pharmaceutically acceptable salt of any of the foregoing). A skilled person will realize that intermediates and final compounds shown in the schemes herein may be further functionalized according to methods known by a person skilled in the art. For example, a primary or secondary amine group may be reductively alkylated by reaction with an aldehyde or a ketone in the presence of a suitable reducing reagent (for example, sodium triacetoxyborohydride ($NaBH(AcO)_3$) together with a suitable solvent (such as, DCM) at a suitable temperature (for example, room temperature); or alternatively, in the presence of $NaBH_3CN$ together with a suitable solvent (for example, MeOH) at a suitable temperature, such as between room temperature and 50° C. In case one of the starting materials is available as a salt form, the skilled person will realize that it may be preferable to first treat the salt with a base, for example, N,N-diisopropylethylamine (DIPEA). A skilled person will realize that additional compounds described herein (for example, Formula (I), Formula (II), Formula (III) and Formula (IV), along with pharmaceutically acceptable salts of any of the foregoing) can be prepared by using similar synthetic protocols as described in the schemes herein.

Pharmaceutical Compositions

Some embodiments described herein relate to pharmaceutical compositions that comprise, consist essentially of, or consist of an effective amount of a compound described herein (such as a compound of Formula (I), or a pharmaceutically acceptable salt thereof) and a pharmaceutically acceptable carrier, excipient, or combination thereof. A pharmaceutical composition described herein is suitable for human and/or veterinary applications.

The terms "function" and "functional" as used herein refer to a biological, enzymatic, or therapeutic function.

The terms "effective amount" or "effective dose" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "pharmaceutically acceptable salts" includes relatively non-toxic, inorganic and organic acid, or base addition salts of compositions, including without limitation, analgesic agents, therapeutic agents, other materials, and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc, and the like. Salts may also be formed with suitable organic bases, including those that are non-toxic and strong enough to form such salts. For example, the class of such organic bases may include but are not limited to mono-, di-, and trialkylamines, including methylamine, dimethylamine, and triethylamine; mono-, di-, or trihydroxyalkylamines including mono-, di-, and triethanolamine; amino acids, including glycine, arginine and lysine; guanidine; N-methylglucosamine; N-methylglucamine; L-glutamine; N-methylpiperazine; morpholine; ethylenediamine; N-benzylphenethylamine; trihydroxymethyl aminoethane.

"Formulation", "pharmaceutical composition", and "composition" as used interchangeably herein are equivalent terms referring to a composition of matter for administration to a subject.

The term "pharmaceutically acceptable" means compatible with the treatment of a subject, and in particular, a human.

The terms "agent" refers to an active agent that has biological activity and may be used in a therapy. Also, an "agent" can be synonymous with "at least one agent," "compound," or "at least one compound," and can refer to any form of the agent, such as a derivative, analog, salt or a prodrug thereof. The agent can be present in various forms, components of molecular complexes, and pharmaceutically acceptable salts (e.g., hydrochlorides, hydrobromides, sulfates, phosphates, nitrates, borates, acetates, maleates, tartrates, and salicylates). The term "agent" can also refer to any pharmaceutical molecules or compounds, therapeutic molecules or compounds, matrix forming molecules or compounds, polymers, synthetic molecules and compounds, natural molecules and compounds, and any combination thereof.

The term "subject" as used herein has its ordinary meaning as understood in light of the specification and refers to an animal that is the object of treatment, inhibition, or amelioration, observation or experiment. "Animal" has its ordinary meaning as understood in light of the specification and includes cold- and warm-blooded vertebrates and/or invertebrates such as fish, shellfish, or reptiles and, in particular, mammals. "Mammal" has its ordinary meaning as understood in light of the specification, and includes but is not limited to mice, rats, rabbits, guinea pigs, dogs, cats, sheep, goats, cows, horses, primates, such as humans, monkeys, chimpanzees, or apes. In some embodiments, the subject is human.

Proper formulation is dependent upon the route of administration chosen. Techniques for formulation and administration of the compounds described herein are known to those skilled in the art. Multiple techniques of administering a compound exist in the art including, but not limited to, enteral, oral, rectal, topical, sublingual, buccal, intraaural, epidural, epicutaneous, aerosol, parenteral delivery, including intramuscular, subcutaneous, intra-arterial, intravenous, intraportal, intra-articular, intradermal, peritoneal, intramedullary injections, intrathecal, direct intraventricular, intraperitoneal, intranasal or intraocular injections. Pharmaceutical compositions will generally be tailored to the specific intended route of administration. Pharmaceutical compositions can also be administered to isolated cells from a patient or individual, such as T cells, Natural Killer cells, B cells, macrophages, lymphocytes, stem cells, bone marrow cells, or hematopoietic stem cells.

The pharmaceutical compound can also be administered in a local rather than systemic manner, for example, via injection of the compound directly into an organ, tissue, cancer, tumor or infected area, often in a depot or sustained release formulation. Furthermore, one may administer the compound in a targeted drug delivery system, for example, in a liposome coated with a tissue specific antibody. The liposomes may be targeted to and taken up selectively by the organ, tissue, cancer, tumor, or infected area.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

As used herein, a "carrier" refers to a compound, particle, solid, semi-solid, liquid, or diluent that facilitates the passage, delivery and/or incorporation of a compound to cells, tissues and/or bodily organs. For example, without limitation, a lipid nanoparticle (LNP) is a type of carrier that can encapsulate a compound, or a pharmaceutically acceptable salt thereof, as described herein to thereby protect the compound, or a pharmaceutically acceptable salt thereof, as described herein from degradation during passage through the bloodstream and/or to facilitate delivery to a desired organ, such as to the liver.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

The term "excipient" has its ordinary meaning as understood in light of the specification, and refers to inert substances, compounds, or materials added to a pharmaceutical composition to provide, without limitation, bulk, consistency, stability, binding ability, lubrication, disintegrating ability etc., to the composition. Excipients with desirable properties include but are not limited to preservatives, adjuvants, stabilizers, solvents, buffers, diluents, solubilizing agents, detergents, surfactants, chelating agents, antioxidants, alcohols, ketones, aldehydes, ethylenediaminetetraacetic acid (EDTA), citric acid, salts, sodium chloride, sodium bicarbonate, sodium phosphate, sodium borate, sodium citrate, potassium chloride, potassium phosphate, magnesium sulfate sugars, dextrose, fructose, mannose, lactose, galactose, sucrose, sorbitol, cellulose, serum, amino acids, polysorbate 20, polysorbate 80, sodium deoxycholate, sodium taurodeoxycholate, magnesium stearate, octylphenol ethoxylate, benzethonium chloride, thimerosal, gelatin, esters, ethers, 2-phenoxyethanol, urea, or vitamins, or any combination thereof. The amount of the excipient may be found in a pharmaceutical composition at a percentage of 0%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 95%, 100% w/w or any percentage by weight in a range defined by any two of the aforementioned numbers.

The term "adjuvant" as used herein refers to a substance, compound, or material that stimulates the immune response and increase the efficacy of protective immunity and is administered in conjunction with an immunogenic antigen, epitope, or composition. Adjuvants serve to improve immune responses by enabling a continual release of antigen, up-regulation of cytokines and chemokines, cellular recruitment at the site of administration, increased antigen uptake and presentation in antigen presenting cells, or activation of antigen presenting cells and inflammasomes. Commonly used adjuvants include but are not limited to alum, aluminum salts, aluminum sulfate, aluminum hydroxide, aluminum phosphate, calcium phosphate hydroxide, potassium aluminum sulfate, oils, mineral oil, paraffin oil, oil-in-water emulsions, detergents, MF59®, squalene, AS03, α-tocopherol, polysorbate 80, AS04, monophosphoryl lipid A, virosomes, nucleic acids, polyinosinic:polycytidylic acid, saponins, QS-21, proteins, flagellin, cytokines, chemokines, IL-1, IL-2, IL-12, IL-15, IL-21, imidazoquinolines, CpG oligonucleotides, lipids, phospholipids, dioleoyl phosphatidylcholine (DOPC), trehalose dimycolate, peptidoglycans, bacterial extracts, lipopolysaccharides, or Freund's Adjuvant, or any combination thereof.

The term "purity" of any given substance, compound, or material as used herein refers to the actual abundance of the substance, compound, or material relative to the expected abundance. For example, the substance, compound, or material may be at least 80, 85, 90, 91, 92, 93, 94, 95, 96, 97, 98, 99, or 100% pure, including all decimals in between. Purity may be affected by unwanted impurities, including but not limited to side products, isomers, enantiomers, degradation products, solvent, carrier, vehicle, or contaminants, or any combination thereof. Purity can be measured technologies including but not limited to chromatography, liquid chromatography, gas chromatography, spectroscopy, UV-visible spectrometry, infrared spectrometry, mass spectrometry, nuclear magnetic resonance, gravimetry, or titration, or any combination thereof.

Methods of Use

Some embodiments disclosed herein related to selecting a subject or patient in need. In some embodiments, a patient is selected who is in need of treatment, inhibition, amelioration, prevention or slowing of diseases or conditions associated with PD-L1 dysregulation. In some embodiments, such diseases or conditions associated with PD-L1 dysregulation may include, for example, cancer, HCC, viral infections, or HBV. In some embodiments, a subject can be selected who has previously been treated for the disease or disorder described herein. In some embodiments, a subject can be selected who has previously been treated for being at risk for the disease or disorder described herein. In some embodiments, a subject can be selected who has developed a recurrence of the disease or disorder described herein. In some embodiments, a subject can be selected who has developed resistance to therapies for the disease or disorder described herein. In some embodiments, a subject can be selected who may have any combination of the aforementioned selection criteria.

Compounds, and pharmaceutically acceptable salts thereof, disclosed herein can be evaluated for efficacy and toxicity using known methods. A non-limiting list of potential advantages of a compound, or a pharmaceutically acceptable salt thereof, described herein include improved stability, increased safety profile, increased efficacy, increased binding to the target, increased specificity for the target (for example, a cancer cell or virally infected cell).

The terms "treating," "treatment," "therapeutic," or "therapy" as used herein has its ordinary meaning as understood in light of the specification, and do not necessarily mean total cure or abolition of the disease or condition. The term "treating" or "treatment" as used herein (and as well understood in the art) also means an approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable. "Treating" and "treatment" as used herein also include prophylactic treatment. Treatment methods comprise administering to a subject a therapeutically effective amount of an active agent. The administering step may consist of a single administration or may comprise a series of administrations. The compositions are administered to the subject in an amount and for a duration sufficient to treat the subject. The length of the treatment period depends on a variety of factors, such as the severity of the condition, the age and genetic profile of the subject, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required.

Some embodiments described herein relate to a method of treating, inhibiting, ameliorating, preventing, or slowing the disease or disorder described herein. In some embodiments, the methods include administering to a subject identified as suffering from the disease or disorder described herein an effective amount of a compound, or a pharmaceutically acceptable salt thereof, described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating, inhibiting ameliorating, preventing, or slowing the disease or disorder described herein. Still other embodiments described herein relate to the use of a compound, or a pharmaceutically acceptable salt thereof, as described herein or a pharmaceutical composition that includes an effective amount of a compound, or a pharmaceutically acceptable salt thereof, as described herein for treating, inhibiting ameliorating, preventing, or slowing the disease or disorder described herein.

Some embodiments described herein relate to a method for inhibiting replication of a cancer cell or a virus that can include contacting the cell or virus or administering to a subject identified as suffering from a cancer or a viral infection with an effective amount of a compound, or a pharmaceutically acceptable salt thereof, described herein, or a pharmaceutical composition that includes an effective amount of a compound, or a pharmaceutically acceptable salt thereof, described herein. Other embodiments described herein relate to the use of an effective amount of a compound, or a pharmaceutically acceptable salt thereof, described herein, or a pharmaceutical composition that includes an effective amount of a compound, or a pharmaceutically acceptable salt thereof, described herein in the manufacture of a medicament for inhibiting replication of a cancer cell or virus. Still other embodiments described herein relate to an effective amount of a compound, or a pharmaceutically acceptable salt thereof, described herein, or a pharmaceutical composition that includes an effective amount of a compound, or a pharmaceutically acceptable salt thereof, described herein for inhibiting replication of a cancer cell or virus. In some embodiments, the cancer cell is an HCC cell. In some embodiments, the virus is hepatitis B.

Some embodiments described herein relate to a method for inhibiting cell proliferation, such as inhibiting cell proliferation of a cancer cell or cell infected with a virus, that can include administering to a subject identified as suffering from a disease wherein inhibiting cell proliferation is desirable with an effective amount of a compound, or a pharmaceutically acceptable salt thereof, described herein, or a pharmaceutical composition that includes effective amount of a compound, or a pharmaceutically acceptable salt thereof, described herein. Other embodiments described herein relate to the use of an effective amount of a compound, or a pharmaceutically acceptable salt thereof, described herein, or a pharmaceutical composition that includes an effective amount of a compound, or a pharmaceutically acceptable salt thereof, described herein in the manufacture of a medicament for inhibiting cell proliferation, such as inhibiting cell proliferation of a cancer cell or cell infected with a virus. Still other embodiments described herein relate to an effective amount of a compound, or a pharmaceutically acceptable salt thereof, described herein, or a pharmaceutical composition that includes an effective amount of a compound, or a pharmaceutically acceptable salt thereof, described herein for inhibiting cell proliferation, such as inhibiting cell proliferation of a cancer cell or cell infected with a virus. In some embodiments, the cancer cell is an HCC cell. In some embodiments, the cell infected with a virus is infected with hepatitis B virus.

Some embodiments described herein relate to a method of inducing apoptosis of a cell (for example, a cancer cell or cell infected with a virus) that can include contacting the cell with an effective amount of a compound, or a pharmaceutically acceptable salt thereof, described herein, or a pharmaceutical composition that includes an effective amount of a compound of Formula (I), or a pharmaceutically acceptable salt thereof, as described herein. Other embodiments described herein relate to using an effective amount of a compound, or a pharmaceutically acceptable salt thereof, as described herein or a pharmaceutical composition that includes an effective amount of a compound, or a pharmaceutically acceptable salt thereof, described herein in the manufacture of a medicament for inducing apoptosis of a cell, such as a cancer cell or cell infected with a virus. Still other embodiments described herein relate to the use of an effective amount of a compound, or a pharmaceutically acceptable salt thereof, as described herein or a pharmaceutical composition that includes an effective amount of a compound, or a pharmaceutically acceptable salt thereof, as described herein for inducing apoptosis of a cell, such as a cancer cell or cell infected with a virus. In some embodiments, the cancer cell is an HCC cell. In some embodiments, the cell infected with a virus is infected with hepatitis B virus.

Some embodiments described herein relate to a method of decreasing the viability of a cell (for example, a cancer cell or cell infected with a virus) that can include contacting the cell with an effective amount of a compound, or a pharmaceutically acceptable salt thereof, described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for decreasing the viability of a cell, such as a cancer cell or cell infected with a virus. Still other embodiments described herein relate to the use of an effective amount of a compound, or a pharmaceutically acceptable salt thereof, as described herein or a pharmaceutical composition that includes an effective amount of a compound, or a pharmaceutically acceptable salt thereof, as described herein for decreasing the viability of a cell, such as a cancer cell or cell infected with a virus. In some embodiments, the cancer cell is an HCC cell. In some embodiments, the cell infected with a virus is infected with hepatitis B virus.

Those of skill in the treatment of such diseases could determine the effective therapeutic daily amount from test results. An effective therapeutic daily amount would be from about 0.005 mg/kg to 50 mg/kg. in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight.

In some embodiments, the effective amount of a compound, or a pharmaceutically acceptable salt thereof, described herein is dosed more than one time. In some embodiments, the compound, or a pharmaceutically acceptable salt thereof, described herein can be administered every 1, 2, 3, 4, 5, 6, 7 days, or 1, 2, 3, 4 weeks, or 1, 2, 3, 4, 5, 6, 7, 8, 9, 10, 11, 12 months, or 1, 2, 3, 4, 5 years, or any period or combination thereof within the range defined by any two aforementioned times. In some embodiments, at least one loading dose and at least one maintenance dose is administered to the subject, where the at least one loading dose is a higher dose of a compound, or a pharmaceutically acceptable salt thereof, described herein than the at least one maintenance dose.

As used herein, the term "combination therapy" is intended to define therapies which comprise the use of a combination of two or more pharmaceutical compounds/agents or therapies. Thus, references to "combination therapy", "combinations" and the use of compounds/agents "in combination" in this application may refer to compounds/agents that are administered as part of the same overall treatment regimen. As such, the dosage or timing of each of the two or more compounds/agents may differ: each may be administered at the same time or at different times. Accordingly, the compounds/agents of the combination may be administered sequentially (e.g. before or after) or simultaneously, either in the same pharmaceutical formulation (i.e. together), or in different pharmaceutical formulations (i.e. separately). Each of the two or more compounds/agents in a combination therapy may also differ with respect to the route of administration.

The term "inhibitor", as used herein, refers to an enzyme inhibitor or receptor inhibitor which is a molecule that binds to an enzyme or receptor, and decreases and/or blocks its activity. The term may relate to a reversible or an irreversible inhibitor.

Cancer may be treated with surgery, radiation therapy, chemotherapy, targeted therapies, immunotherapy or hormonal therapies. Any of these mentioned therapies may be used in conjunction with another therapy as a combination therapy. Chemotherapeutic compounds include but are not limited to alemtuzumab, altretamine, azacitidine, bendamustine, bleomycin, bortezomib, busulfan, cabazitaxel, capecitabine, carboplatin, carmofur, carmustine, chlorambucil, chlormethine, cisplatin, cladribine, clofarabine, cyclophosphamide, cytarabine, dacarbazine, dactinomycin, daunorubicin, decitabine, denosumab, docetaxel, doxorubicin, epirubicin, estramustine, etoposide, everolimus, floxuridine, fludarabine, fluorouracil, fotemustine, gemcitabine, gemtuzumab, hydroxycarbamide, ibritumomab, idarubicin, ifosfamide, irinotecan, ixabepilone, lomustine, melphalan, mercaptopurine, methotrexate, mitomycin, mitoxantrone, nedaplatin, nelarabine, ofatumumab, oxaliplatin, paclitaxel, pemetrexed, pentostatin, pertuzumab, procarbazine, raltitrexed, streptozotocin, tegafur, temozolomide, temsirolimus, teniposide, tioguanine, topotecan, tositumomab, valrubicin, vinblastine, vincristine, vindesine, vinflunine, or vinorelbine, or any combination thereof.

As used herein, the term "protein kinase inhibitor" refers to inhibitors of protein kinases, serine/threonine kinases, tyrosine kinases, or dual-specificity kinases for the treatment of cancer or other illness. In some embodiments, the protein kinase inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the protein kinase inhibitor includes but is not limited to acalabrutinib, adavosertib, afatinib, alectinib, axitinib, binimetinib, bosutinib, brigatinib, cediranib, ceritinib, cetuximab, cobimetinib, crizotinib, cabozantinib, dacomitinib, dasatinib, entrectinib, erdafitinib, erlotinib, fostamatinib, gefitinib, ibrutinib, imatinib, lapatinib, lenvatinib, lestaurtinib, lortatinib, masitinib, momelotinib, mubritinib, neratinib, nilotinib, nintedanib, olmutinib, osimertinib, pacritinib, panitumumab, pazopanib, pegaptanib, ponatinib, radotinib, regorafenib, rociletinib, ruxolitinib, selumetinib, semaxanib, sorafenib, sunitinib, SU6656, tivozanib, toceranib, trametinib, trastuzumab, vandetanib, or vemurafenib, or any combination thereof.

As used herein, the term "checkpoint inhibitor" refers to an immunotherapy that targets immune checkpoints to stimulate immune function. In some embodiments, the checkpoint inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the immune checkpoint is the PD-1/PD-L1 checkpoint. In some embodiments, the PD-1 checkpoint includes but is not limited to nivolumab, pembrolizumab, spartalizumab, cemiplimab, camrelizumab, sintilimab, tislelizumab, toripalimab, AMP-224 or AMP-514, or any combination thereof. In some embodiments, the PD-L1 checkpoint inhibitor includes but is not limited to atezolizumab, avelumab, durvalumab, KN035, AUNP12, CA-170, or BMS-986189, or any combination thereof. In some embodiments, the immune checkpoint is the CTLA-4 checkpoint. In some embodiments, the CTLA-4 checkpoint inhibitor includes but is not limited to ipilimumab or tremilimumab, or any combination thereof.

As used herein, the term "VEGF inhibitor" refers to inhibitors of vascular endothelial growth factor (VEGF) or a VEGF receptor (VEGFR). In some embodiments, the VEGF inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the VEGF inhibitor includes but is not limited to aflibercept, axitinib, bevacizumab, brivanib, cabozantinib, cediranib, lenvatinib, linifinib, nintedanib, pazopanib, ponatinib, ramucirumab, regorafenib, semaxanib, sorafenib, sunitinib, tivozanib, toceranib, or vandetanib, or any combination thereof.

As used herein, the term "antiviral medication" refers to a pharmaceutical composition administered to treat a viral infection. In some embodiments, the viral infection is caused by adenovirus, Ebola virus, coronavirus, Epstein-Barr virus (EBV), Friend virus, hantavirus, hepatitis B virus (HBV), hepatitis C virus (HCV), herpes simplex virus, human immunodeficiency virus (HIV), human metapneumovirus, human papillomavirus (HPV), influenza virus, Japanese encephalitis virus, Kaposi's sarcoma-associated herpesvirus, lymphocytic choriomeningitis virus, parainfluenza virus, rabies virus, respiratory syncytial virus, rhinovirus, varicella zoster virus. In some embodiments, the antiviral medication is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the antiviral medication is an interferon, a capsid assembly modulator, a sequence specific oligonucleotide, an entry inhibitor, or a small molecule immunomodulatory. In some embodiments, the antiviral medication includes but is not limited to AB-423, AB-506, ABI-H2158, ABI-HO731, acyclovir, adapromine, adefovir, alafenamide, amantadine, asunaprevir, baloxavir marboxil, beclabuvir, boceprevir, brivudine, cidofovir, ciluprevir, clevudine, cytarabine, daclatasvir, danoprevir, dasabuvir, deleobuvir, dipivoxil, edoxudine, elbasvir, entecavir, faldaprevir, famciclovir, favipiravir, filibuvir, fomivirsen, foscarnet, galidesivir, ganciclovir, glecaprevir, GLS4, grazoprevir, idoxuridine, imiquimod, IFN-α, interferon alfa 2b, JNJ-440, JNJ-6379, lamivudine, laninamivir, ledipasvir, mericitabine, methisazone, MK-608, moroxydine, narlaprevir, NITD008, NZ-4, odalasvir, ombitasvir, oseltamivir, paritaprevir, peginterferon alfa-2a, penciclovir, peramivir, pibrentasvir, pimodivir, pleconaril, podophyllotoxin, presatovir, radalbuvir, ravidasvir, remdesivir, REP 2139, REP 2165, resiquimod, RG7907, ribavirin, rifampicin, rimantadine, ruzasvir, samatasvir, setrobuvir, simeprevir, sofosbuvir, sorivudine, sovaprevir, taribavirin, telaprevir, telbivudine, tenofovir, tenofovir disoproxil, triazavirin, trifluridine, tromantadine, umifenovir, uprifosbuvir, valaciclovir, valgancicovir, vaniprevir, vedroprevir, velpatasvir, vidarabine, voxilaprevir, or zanamivir, or any combination thereof.

The term "% w/w" or "% wt/wt" as used herein has its ordinary meaning as understood in light of the specification and refers to a percentage expressed in terms of the weight of the ingredient or agent over the total weight of the composition multiplied by 100. The term "% v/v" or "% vol/vol" as used herein has its ordinary meaning as understood in the light of the specification and refers to a percentage expressed in terms of the liquid volume of the compound, substance, ingredient, or agent over the total liquid volume of the composition multiplied by 100.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

Hereinafter, the term "rt", "r.t." or "RT" means room temperature; "Me" means methyl; "MeOH" means methanol; "Et" means ethyl; "EtOH" means ethanol; "NaH" means sodium hydride; "NaBH(AcO)$_3$" or "NaBH(OAc)$_3$" means sodium triacetoxyborohydride; "EtOAc" means ethyl acetate; "TEA" or "Et$_3$N" means triethylamine; "DCM"

means dichloromethane; "MeCN" or "ACN" means acetonitrile; "DMF" means -dimethyl formamide; "DMA" means dimethyl acetamide; "Pd(dppf)Cl$_2$." means [1.1'-Bis(diphenylphosphino)ferrocene]-dichloropalladium(II); "THF" means tetrahydrofuran; "i-PrOH" or "iPrOH" means 2-propanol; "LC" means liquid chromatography; "LCMS" means Liquid Chromatography/Mass spectrometry; "HPLC" means high-performance liquid chromatography; "prep-HPLC" means preparative high-performance liquid chromatography; "TFA" means trifluoroacetic acid; "RP" means reversed phase; "min" means minute(s); "h" means hour(s); "PE" means petroleum ether; "v/v" means volume per volume; "Celite®" means diatomaceous earth; "DMSO" means dimethyl sulfoxide; "SFC" means Supercritical Fluid Chromatography; "DIPE" means diisopropyl ether; "DIPEA" or "DIEA" means N,N-diisopropylethylamine; "Pd$_2$(dba)$_3$" means Tris(dibenzylideneacetone)-dipalladium; "Pd(OAc)$_2$" means palladium(II) acetate; "AcOH" means acetic acid; "DMAP" means 4-(dimethylamino)pyridine; "t-BuOK", "BuO" or "KOtBu" means potassium tert-butoxide; "TLC" means thin layer chromatography; "prep-TLC" means preparative TLC; "KOAc" means potassium acetate.

For intermediates that were used in a next reaction step as a crude or as a partially purified intermediate, estimated mol amounts (in some cases indicated by ~) are indicated in the reaction protocols described below, or alternatively theoretical mol amounts are indicated.

The meanings of the abbreviations in the nuclear magnetic resonance spectra are provided as follows: s=singlet, d=doublet, dd=double doublet, dt=double triplet, ddd=double doublet, Sept=septet, t=triplet, m=multiplet, br=broad, brs=broad singlet, q=quartet.

Preparation of Intermediates

Example A1

Preparation of Intermediate 4

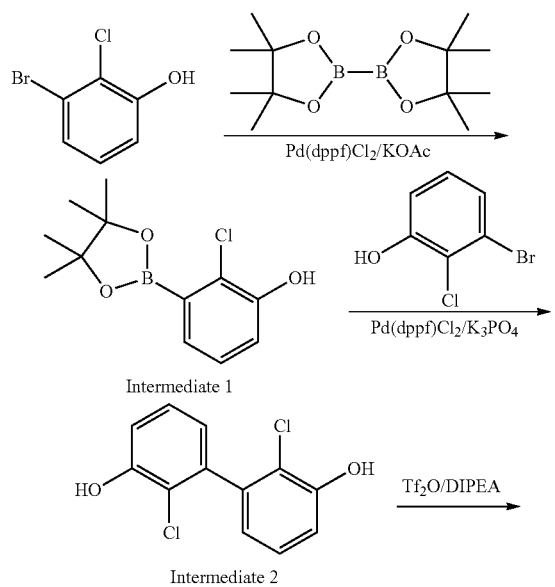

Intermediate 1

Intermediate 2

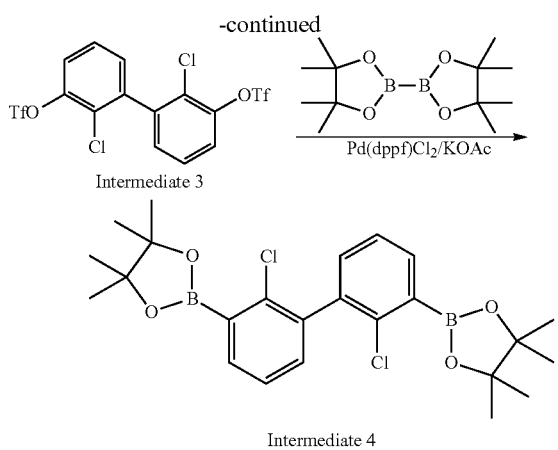

Intermediate 3

Intermediate 4

Step 1: A mixture of 3-Bromo-2-chlorophenol (110 g, 530 mmol), Pd(dppf)Cl$_2$ (38.8 g, 53.0 mmol), KOAc (146 g, 1.48 mol) and Bis(pinacolato)diboron (148 g, 583 mmol) in dioxane (1220 mL) was degassed and purged with N$_2$ (3×). The mixture was stirred at 90° C. for 16 h. The two batches of the same reaction were combined to work up. The reaction was cooled to 20° C. and then filtered. The filter cake was washed with DCM (2×1000 mL). The filtrate was concentrated to give the crude product, which was purified by column chromatography (100-200 mesh silica gel) eluted with PE:EtOAc (1:0~20:1) to give a residue (240 g), which was triturated with PE (500 mL) for 2 h and then filtered. The filter cake was dried in vacuum to give Intermediate 1 (172 g) as a white solid. $^1$H NMR: (400 MHz, DMSO-d$_6$) δ 10.02 (s, 1H), 7.17-7.08 (m, 1H), 7.08-6.98 (m, 2H), 1.30 (s, 12H).

Step 2: A mixture of Intermediate 1 (81.0 g, 318 mmol), 3-Bromo-2-chlorophenol (72.6 g, 350 mmol), K$_3$PO$_4$ (203 g, 955 mmol), Pd(dppf)Cl$_2$ (11.6 g, 15.9 mmol) in a solution of dioxane (1620 mL) and H$_2$O (540 mL) was degassed and purged with N$_2$ (3×). The mixture was stirred at 90° C. for 16 h. The reaction was cooled to 20° C. and concentrated to give a residue. The residue was dissolved in EtOAc (1000 mL) and H$_2$O (500 mL), and then the mixture was filtered. The filter cake was washed with EtOAc (2×100 mL) and then separated. The aqueous phase was adjusted to pH=3 with 6 N HCl and extracted with DCM (2×500 mL). The combined organic layers were concentrated to give Intermediate 2 (91.0 g, crude) as a brown solid. $^1$H NMR: (400 MHz, DMSO-d$_6$) δ 10.22 (br s, 2H), 7.21-7.15 (m, 2H), 7.02-6.97 (m, 2H), 6.69 (dd, J=1.4, 7.5 Hz, 2H).

Step 3: To a solution of Intermediate 2 (91.0 g, 357 mmol) and DIPEA (173 g, 1.34 mol, 234 mL) in DCM (2200 mL) was slowly added Tf$_2$O (237 g, 838 mmol, 138 mL) at 0° C.-5° C. The reaction was warmed up to 20° C. and stirred for 2 h. TLC (PE:EtOAc=5:1, R$_f$=0.64) showed the starting material was consumed completely. The reaction was washed with aqueous sat. NaHCO$_3$ (1000 mL), brine (500 mL), dried over MgSO$_4$ and concentrated to give the crude product. The crude product was purified by column chromatography (100-200 mesh silica gel) eluted with THF:PE (0:1-1:9) to give Intermediate 3 (100.3 g) as a yellow solid. $^1$H NMR: (400 MHz, DMSO-d$_6$) δ 7.86 (dd, J=1.3, 8.3 Hz, 2H), 7.74 (t, J=8.0 Hz, 2H), 7.66 (dd, J=1.4, 7.7 Hz, 2H).

Step 4: A mixture of Intermediate 3 (95.3 g, 184 mmol), KOAc (90.1 g, 918 mmol), Pd(dppf)Cl$_2$ (20.2 g, 27.5 mmol) and Bis(pinacolato)diboron (117 g, 459 mmol) in dioxane (1300 mL) was degassed and purged with N$_2$ (3×). The mixture was stirred at 90° C. for 16 h. TLC (PE:EtOAc=5:1, $R_f$=0.60) showed the starting material was consumed completely. The mixture was cooled to 20° C., and then the mixture was filtered. The filter cake was washed with DCM (2×100 mL). The filtrate was concentrated to give the crude product. The crude product was purified by column chromatography (100-200 mesh silica gel) eluted with THF:PE (0:1-1:20) to give a residue (110 g), which was triturated with PE (500 mL) for 16 h, and then filtered. The filter cake was dried in vacuum to give Intermediate 4 (55.0 g, 62% yield) as a white solid. $^1$H NMR: (400 MHz, DMSO-$d_6$) δ 7.65 (dd, J=1.8, 7.2 Hz, 2H), 7.51-7.27 (m, 4H), 1.32 (s, 24H).

Example A2

Preparation of Intermediate 6

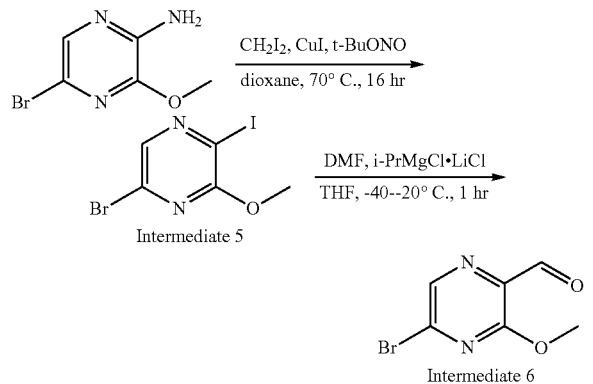

Step 1: A mixture of compound 2-Amino-3,5-dibromopyrazine (150 g, 0.73 mol), CH$_2$I$_2$ (118 g, 0.36 mol, 35.6 mL), CuI (28.0 g, 0.15 mol) and dioxane (700 mL) was stirred at 70° C. for 0.5 h. t-BuONO (113 g, 1.10 mol, 131 mL) was then added into the mixture dropwise at 70° C. The brown mixture was stirred at 70° C. for 15.5 h. The reaction was run in parallel 2 times. TLC (PE:EtOAc=10:1, $R_f$=0.8) showed that the reaction was complete. The mixture was cooled to 25° C. The mixture was filtered through a celite pad, and the filtrate was concentrated under reduced pressure to give a residue. The crude product was triturated with methanol (500 mL) at 0-5° C. for 3 h. The precipitate was filtered and dried in vacuum to give Intermediate 5 (251 g, crude) as a yellow solid. $^1$H NMR: (400 MHz, CDCl$_3$) δ 8.26 (s, 1H), 4.03-3.92 (m, 3H).

Step 2: To a solution of Intermediate 5 (60 g, 0.19 mol) in THF (480 mL) was added i-PrMgCl—LiCl (168 mL, 0.23 mol) at −40° C. The mixture was stirred at −40° C. for 0.5 h. To the resulting solution was added DMF (55.7 g, 0.76 mol) dropwise at −40° C. The mixture was stirred at −20° C. for 0.5 h. TLC (PE:EtOAc=5:1, $R_f$=0.3) showed that the reaction was complete. The reaction was quenched by the addition of aqueous citric acid solution (5%, 500 mL), stirred at 20° C. for 10 mins and extracted with EtOAc (2×500 mL). The combined organic layers were washed with brine (500 mL), dried over Na$_2$SO$_4$, filtered and concentrated in vacuum to give a residue. The residue was purified by flash silica gel chromatography (ISCO® 330 g SepaFlash® Silica Flash Column, Eluent of 0~6% EtOAc:PE gradient @ 100 mL/min) to give Intermediate 6 (116 g, 56% yield) as a yellow solid. $^1$H NMR: (400 MHz, DMSO-$d_6$) δ 10.15-10.00 (m, 1H), 8.64 (s, 1H), 4.04 (s, 3H).

Example A3

Preparation of Intermediate 9

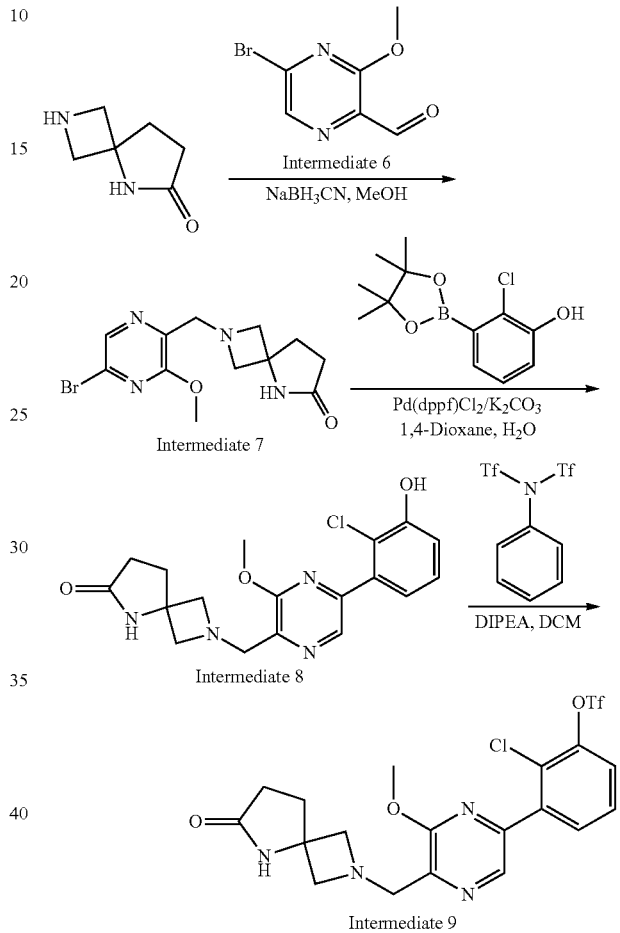

Step 1: To a solution of Intermediate 6 (55.0 g, 0.25 mol) and 2,5-Diazaspiro[3.4] octan-6-one TFA salt (89.2 g, 0.28 mol) in DCM (800 mL) was added MgSO$_4$ (122 g, 1.01 mol) and Et$_3$N (51.3 g, 0.51 mol, 70.5 mL). The mixture was stirred at 15° C. for 30 mins, and then NaBH(OAc)$_3$ (161 g, 0.76 mol) was added at 0° C. The mixture was stirred at 15° C. for 1 h. The reaction was run in parallel 2 times. TLC (DCM:MeOH=10:1, $R_f$=0.4) showed that the reaction was complete. The mixture was diluted with DCM (800 mL) and sat. NaHCO$_3$ solution (800 mL). The aqueous phase was separated and extracted with (CHCl$_3$:i-PrOH=3:1). The combined organic layers were washed with brine (1000 mL), dried over Na$_2$SO$_4$, filtered and concentrated in vacuum to give a residue. The crude product was purified by recrystallization from EtOAc (300 mL) at 25° C. to give Intermediate 7 (120 g, 69% yield) as white solid. $^1$H NMR: (400 MHz, CDCl$_3$) δ 8.24-8.17 (m, 1H), 6.52 (br s, 1H), 4.06-3.97 (m, 3H), 3.81-3.71 (m, 2H), 3.58 (d, J=8.6 Hz, 2H), 3.39 (d, J=8.6 Hz, 2H), 2.47-2.32 (m, 4H).

Step 2: To a mixture of compound 2-chloro-3-(4,4,5,5-tetramethyl-1,3,2-dioxaborolan-2-yl)phenol (94.1 g, 370 mmol), Intermediate 7 (110 g, 336 mmol) and K$_2$CO$_3$ (139 g, 1.01 mol) in dioxane (1100 mL) and H$_2$O (220 mL) was added Pd(dppf)Cl$_2$ (24.6 g, 33.6 mmol). The brown mixture was purged with N$_2$ for 3 times and stirred at 100° C. for 1 h. The mixture was poured into H$_2$O (1000 mL) and extracted with EtOAc (3×1000 mL). The combined organic layers were washed with brine (1000 mL), dried over Na$_2$SO$_4$, filtered and concentrated in vacuum to give a residue. The residue was purified by flash silica gel chromatography (ISCO®; 330 g SepaFlash® Silica Flash Column, Eluent of 0~5% MeOH/DCM@100 mL/min) to give Intermediate 8 (123 g, 97% yield) as brown solid. $^1$H NMR: (400 MHz, DMSO-d$_6$) δ 10.38 (br s, 1H), 8.33 (s, 1H), 8.14 (s, 1H), 7.39-7.17 (m, 1H), 7.06 (br dd, J=7.8, 13.7 Hz, 2H), 3.94 (s, 3H), 3.72 (s, 2H), 3.44 (br d, J=7.1 Hz, 2H), 3.25 (br d, J=7.1 Hz, 2H), 2.28-2.07 (m, 4H).

Step 2: To a mixture of Intermediate 8 (123 g, 328 mmol) and N-Phenyl-bis(trifluoromethane sulfonimide) (123 g, 344 mmol) in DCM (2260 mL) was added DIEA (127 g, 984 mmol, 171 mL) dropwise at 15° C. The brown mixture was stirred at 15° C. for 16 h. The residue was diluted with ice water (2000 mL) and extracted with DCM (2×1000 mL). The combined organic layers were washed with brine (2×1000 mL), dried over MgSO$_4$, filtered and concentrated under reduced pressure to give a residue. The crude product was triturated with EtOAc (600 mL) for 2 h and filtered to give Intermediate 9 (136 g, 81% yield) as a yellow solid. $^1$H NMR: (400 MHz, DMSO-d$_6$) δ 8.54-8.39 (m, 1H), 8.15 (s, 1H), 7.90-7.60 (m, 3H), 3.96 (s, 3H), 3.75 (s, 2H), 3.45 (d, J=8.1 Hz, 2H), 3.25 (d, J=8.0 Hz, 2H), 2.30-2.06 (m, 4H).

Example A4

Preparation of Intermediate 10

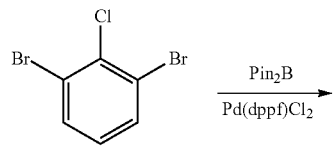

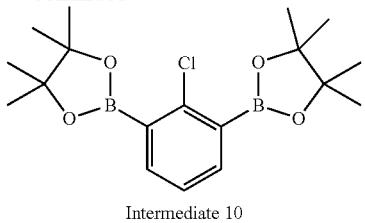

Intermediate 10

To a mixture of 1,3-dibromo-2-chloro-benzene (50 g, 184.95 mmol, 1 eq.) and 4,4,5,5-tetramethyl-2-(4,4,5,5-tetramethyl-1,3,2-dioxaborolan-2-yl)-1,3,2-dioxaborolane (93.93 g, 369.89 mmol, 2 eq.) in dioxane (400 mL) were added KOAc (90.76 g, 924.73 mmol, 5 eq.) and Pd(dppf)Cl$_2$ (13.53 g, 18.49 mmol, 0.1 eq.) at 25° C. under N$_2$. The reaction was stirred at 110° C. for 12 h. The reaction was evaporated and diluted with water (500 mL). The mixture was extracted with MTBE (2×500 mL). The organic layer was evaporated to give the crude product. The crude product was triturated with MeOH (150 mL) to give the Intermediate 10 (41.31 g, 61% yield) as white solid. $^1$H NMR: (400 MHz, CDCl$_3$) δ 7.59 (d, J=7.2 Hz, 2H), 7.13 (t, J=7.2 Hz, 1H), 1.29 (s, 24H).

Example A5

Preparation of Intermediate 11

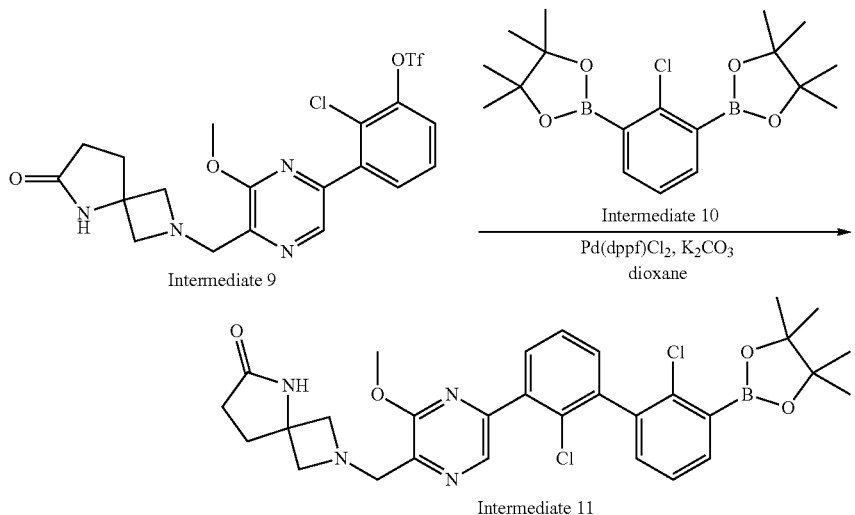

A mixture of Intermediate 9 (4.0 g, 7.89 mmol) and Intermediate 10 (8.63 g, 23.7 mmol), Pd(dppf)Cl$_2$ (577 mg, 789 μmol), KBr (939 mg, 7.89 mmol) and K$_2$CO$_3$ (4.36 g, 31.6 mmol) in dioxane (40 mL) was degassed and purged with N$_2$ for 3 times. The mixture was stirred at 100° C. for 18 h under N$_2$ atmosphere. The mixture was diluted with H$_2$O (200 mL) and extracted with EtOAc (3×200 mL). The combined organic layers were washed with brine (300 mL), dried over anhydrous Na$_2$SO$_4$, filtered and concentrated to give a residue, which was purified by flash silica gel chromatography (ISCO®; 120 g SepaFlash® Silica Flash Column, 0-5% MeOH/DCM) to give crude Intermediate 11 (~80% purity based on LCMS) as a brown solid. LCMS (C$_{30}$H$_{34}$BCl$_2$N$_4$O$_4$$^+$) (ES, m/z): 595.1 [M+H]$^+$.

Example A6

Preparation of Intermediate 13

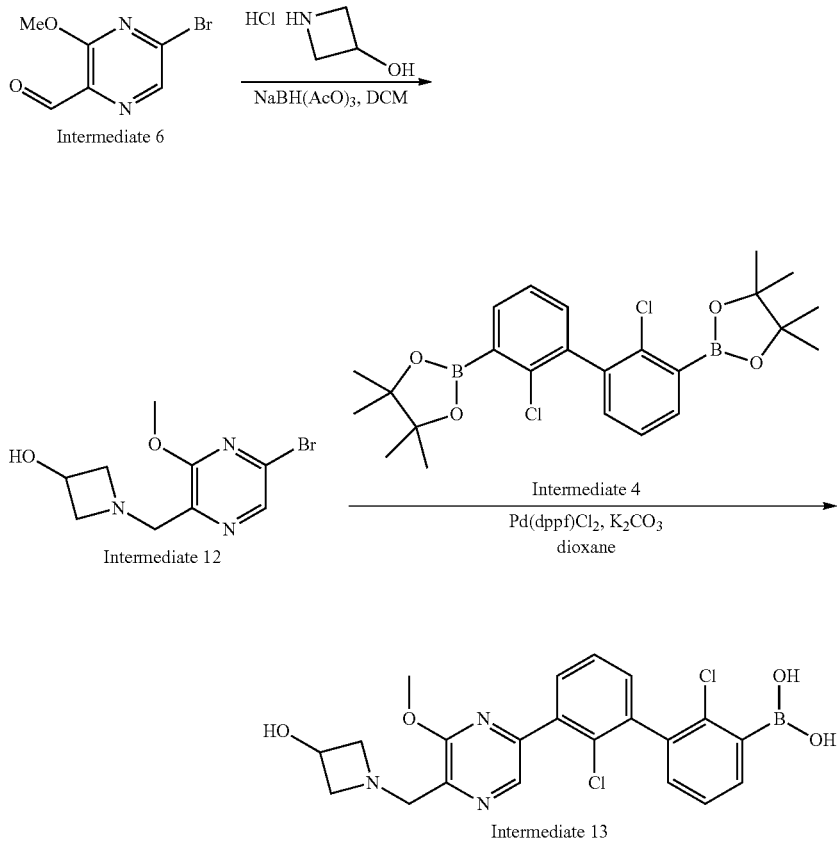

Step 1: A mixture of compound Intermediate 6 (2 g, 9.22 mmol) and 3-hydroxyazetidine hydrochloride (1.51 g, 13.82 mmol) in DCM (20 mL) was stirred at 20° C. for 15 h, and then was added NaBH(OAc)$_3$ (5.86 g, 27.65 mmol). The mixture was stirred at 20° C. for another 1 h. The mixture was partitioned between water (50 mL) and EtOAc (100 mL). The organic phase was separated, washed with brine (20 mL), dried over Na$_2$SO$_4$, filtered and concentrated to give a residue, which was purified by prep-HPLC (Column: Phenomenex luna C18 250*80 mm*10 um; Condition: water (0.225% FA)-ACN; Begin B: 0; End B: 30; Gradient Time (min): 10; 100% B Hold Time (min): 3; Flow Rate (mL/min): 250; Injections: 1) to give Intermediate 12 (800 mg, 32% yield) as a yellow oil. LCMS (C$_9$H$_{13}$BrN$_3$O$_2$$^+$) (ES, m/z): 273.8 [M+H]$^+$.

Step 2: A mixture of Intermediate 12 (400 mg, 1.46 mmol), Intermediate 4 (1.04 g, 2.19 mmol), Pd(dppf)Cl$_2$ (107 mg, 146 μmol), K$_2$CO$_3$ (605 mg, 4.38 mmol) in dioxane (20 mL) was degassed and purged with N$_2$ for 3 times, and then the mixture was stirred at 95° C. for 16 h under N$_2$ atmosphere. The mixture was filtered and concentrated to give a residue, which was purified by flash silica gel chromatography (ISCO®; 4 g SepaFlash® Silica Flash Column, 0~100% EtOAc:PE) and prep-HPLC (Column: Xtimate C18 150*40 mm*10 um; Condition: water (0.225% FA)-ACN; Begin B: 15; End B: 45; Gradient Time (min): 10; 100% B Hold Time (min): 2; Flow Rate (mL/min): 90; Injections: 5) to give Intermediate 13 (70 mg) as a yellow solid. $^1$H NMR (400 MHz, CD$_3$OD) δ 8.46 (s, 1H), 7.67 (dd, J=1.3, 7.7 Hz, 1H), 7.54 (t, J=7.6 Hz, 1H), 7.41 (br d, J=4.5 Hz, 3H), 7.36-7.28 (m, 1H), 5.49 (s, 1H), 4.53 (s, 2H), 4.44-4.35 (m, 2H), 4.10 (s, 3H), 3.92 (br dd, J=5.6, 10.9 Hz, 2H), 3.73 (br t, J=6.6 Hz, 1H), 3.35 (s, 1H), 2.66 (s, 1H). LCMS (C$_{21}$H$_{21}$BCl$_2$N$_3$O$_4$$^+$) (ES, m/z): 460.3 [M+H]$^+$.

Example A7

Preparation of Intermediate 15

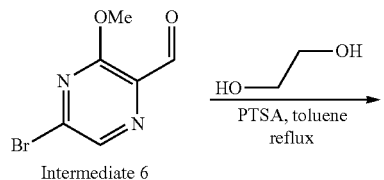

Intermediate 6

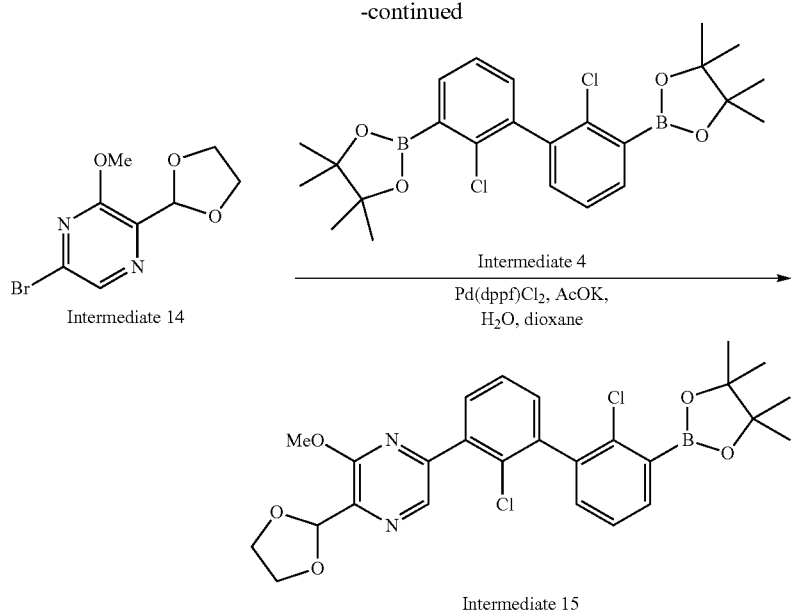

Intermediate 15

Step 1: A mixture of compound Intermediate 6 (5 g, 23.04 mmol), ethylene glycol (2.58 mL, 46.08 mmol) and PTSA (397 mg, 2.30 mmol) in toluene (50 mL) was stirred at 100° C. for 12 h under N₂ atmosphere. The reaction was quenched by sat. NaHCO₃ (400 mL), and then extracted with EtOAc (2×300 mL). The combined organic layers were dried over Na₂SO₄, filtered and concentrated to give a residue, which was purified by flash silica gel chromatography (ISCO®; 80 g SepaFlash® Silica Flash Column, 0~30% EtOAc:PE) to give Intermediate 14 (5.91 g) as a yellow oil. ¹H NMR (400 MHz, CDCl₃) δ 8.24 (s, 1H), 6.16 (s, 1H), 4.27-4.18 (m, 2H), 4.14-4.06 (m, 2H), 4.04 (s, 3H).

Step 2: To a solution of Intermediate 14 (2 g, 4.21 mmol, 1 eq.) and Intermediate 4 (1.10 g, 4.21 mmol) in dioxane (30 mL) and H₂O (2 mL) were added Pd(dppf)Cl₂ (308.08 mg, 421.04 µmol) and AcOK (1.24 g, 12.63 mmol, 3 eq.) at 25° C. The mixture was stirred at 110° C. for 2 h under N₂. The resulting mixture was filtered and concentrated. The residue was diluted with H₂O (150 mL) and extracted with EtOAc (3×150 mL). The combined organic layers were washed with brine (100 mL), dried over anhydrous Na₂SO₄, filtered and concentrated to give a residue, which was purified by flash silica gel chromatography (ISCO®; 20 g SepaFlash® Silica Flash Column, 0~40% EtOAc:PE) to give Intermediate 15 (820 mg, 37% yield) as a yellow oil. ¹H NMR (400 MHz, CDCl₃) δ 8.54 (s, 1H), 7.76-7.33 (m, 6H), 6.28 (s, 1H), 4.35-4.27 (m, 2H), 4.18-4.11 (m, 2H), 4.09 (s, 3H), 3.75 (t, J=6.5 Hz, 1H), 2.05 (s, 1H), 1.86 (td, J=3.2, 6.6 Hz, 2H), 1.44-1.13 (m, 11H).

Example A8

Preparation of Intermediate 17

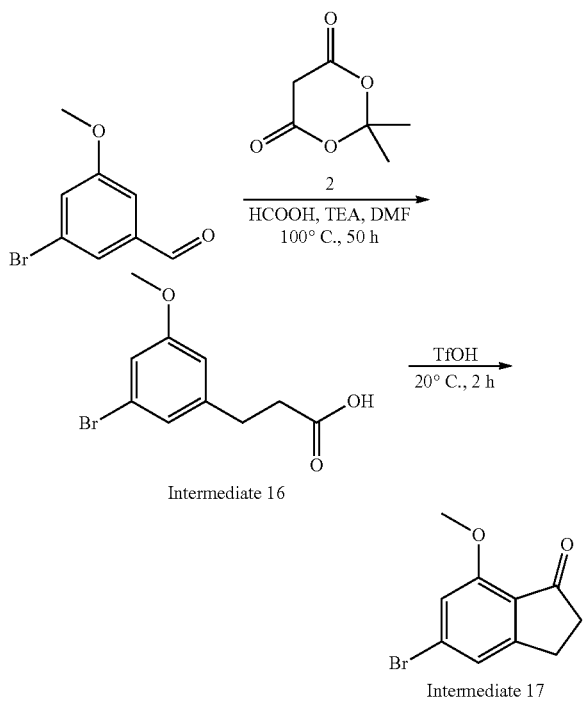

Step 1: To HCOOH (16.5 mL, 419 mmol,) at 0° C. was added TEA (23.3 mL, 167.41 mmol) dropwise at 0° C. The mixture was stirred at 0° C. for 30 min. To the mixture were added 3-Bromo-5-methoxybenzaldehyde (30 g, 140 mmol) and isopropylidene malonate (20.1 g, 140 mmol,) in DMF (180 mL) dropwise at 25° C. The mixture was stirred at 100° C. for 50 hours. The reaction was cooled to 0° C., quenched with conc. HCl (120 mL) and diluted with water (800 mL). The mixture was extracted with DCM (2×400 mL). The combined organic layers were washed with NaOH (1N, 2×800 mL). The combined aqueous phases were acidified to pH~2 with conc. HCl, and then extracted with EtOAc (2×300 mL). The combined organic layers were washed with brine (2×300 mL), dried over $Na_2SO_4$, filtered and concentrated to give Intermediate 16 (70 g, 97% yield) as a pink solid, which was used into the next step without further purification. $^1$H NMR (400 MHz, CDCl$_3$) δ 6.96 (s, 1H), 6.91 (t, J=1.9 Hz, 1H), 6.69 (s, 1H), 3.78 (s, 3H), 2.95-2.88 (m, 2H), 2.70-2.62 (m, 2H).

Step 2: A solution of Intermediate 16 (70 g, 270 mmol) in TfOH (150 mL) was stirred at 25° C. for 2 h. The reaction was quenched by the addition of ice water (1500 mL) at 0° C., and then extracted with DCM (3×600 mL). The combined organic layers were washed with NaHCO$_3$ (2×800 mL), dried over anhydrous $Na_2SO_4$ and concentrated to give a residue, which was purified by flash silica gel chromatography (ISCO®; 220 g SepaFlash® Silica Flash Column, 0~15% DCM:PE) to give Intermediate 17 (12.6 g, 19% yield) as a yellow solid. $^1$H NMR (400 MHz, CDCl$_3$) δ 7.19 (d, J=0.9 Hz, 1H), 6.93 (s, 1H), 3.94 (s, 3H), 3.11-2.97 (m, 2H), 2.73-2.59 (m, 2H).

Example A9

Preparation of Intermediate 19

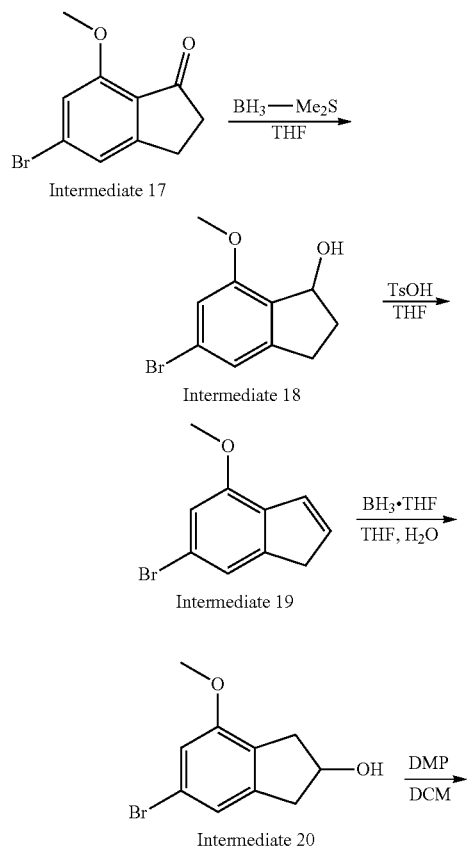

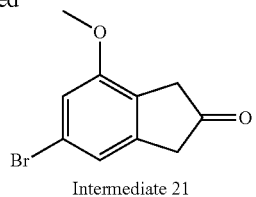

Intermediate 21

Step 1: To a solution of compound Intermediate 17 (3.7 g, 15.4 mmol) in THF (120 mL) was added BH$_3$-Me$_2$S (10 M, 2.61 mL) at −10° C. The mixture was stirred at 25° C. for 2 h. The reaction was quenched by the addition of ice water (200 mL) at 0° C., and extracted with EtOAc (3×200 mL). The combined organic layers were washed with NaHCO$_3$ (2×150 mL), dried over anhydrous $Na_2SO_4$ and concentrated to give a residue, which was purified by flash silica gel chromatography (ISCO®; 20 g SepaFlash® Silica Flash Column, 0~10% EtOAc:PE) to give Intermediate 18 (3.68 g) as a white solid. $^1$H NMR (400 MHz, CDCl$_3$) δ 7.02 (s, 1H), 6.85 (s, 1H), 5.41 (dd, J=4.4, 7.1 Hz, 1H), 3.86 (s, 3H), 3.17-2.98 (m, 1H), 2.93-2.72 (m, 1H), 2.56-2.35 (m, 2H), 2.15-1.93 (m, 1H).

Step 2: To a solution of Intermediate 18 (3.68 g, 15.1 mmol) in THF (350 mL) was added TsOH (782 mg, 4.54 mmol) at 25° C. The mixture was stirred at 60° C. for 16 h. The mixture was diluted with H$_2$O (200 mL) and extracted with EtOAc (3×150 mL). The combined organic layers were wished with brine (200 mL), dried over $Na_2SO_4$, filtered and concentrated to give a residue, which was purified by flash silica gel chromatography (ISCO®; 40 g SepaFlash® Silica Flash Column, 0~5% EtOAc:PE) to give Intermediate 19 (3.16 g, 93% yield) as a white solid. $^1$H NMR (400 MHz, CDCl$_3$) δ 7.26 (s, 1H), 7.01-6.90 (m, 2H), 6.45 (td, J=1.9, 5.6 Hz, 1H), 3.88 (s, 3H), 3.40 (s, 2H);

Step 3: To a solution of Intermediate 19 (3.16 g, 14.0 mmol) in THF (60 mL) was added BH$_3$·THF (1 M, 42.12 mL) at 0° C. The mixture was stirred at 25° C. for 2 h. The reaction was quenched by the addition of ice water (100 mL) at 0° C. and extracted with EtOAc (3×100 mL). The combined organic layers were washed with NaHCO$_3$ (2×80 mL), dried over anhydrous $Na_2SO_4$ and concentrated to give a residue, which was purified by flash silica gel chromatography (ISCO®; 40 g SepaFlash® Silica Flash Column, 0~10% EtOAc:PE) to give Intermediate 20 (2.86 g, 84% yield) as a yellow oil.

Step 4: To a solution of Intermediate 20 in DCM (40 mL) was added Dess-Martin periodinane (7.48 g, 17.7 mmol) at 25° C. The mixture was stirred at 25° C. for 1 h. The mixture was diluted with Na$_2$SO$_3$ (100 mL) and extracted with DCM (3×80 mL). The combined organic layer were wished with brine (100 mL), dried over $Na_2SO_4$, filtered and concentrated to give a residue, which was purified by flash silica gel chromatography (ISCO®; 12 g SepaFlash® Silica Flash Column, 0~10% EtOAc:PE) to give Intermediate 21 (1.4 g, 49% yield) as a white solid. $^1$H NMR (400 MHz, CDCl$_3$) δ 7.08 (s, 1H), 6.93 (s, 1H), 3.85 (s, 3H), 3.53 (s, 2H), 3.40 (s, 2H).

Example A10

Preparation of Intermediate 22-A and Intermediate 22-B

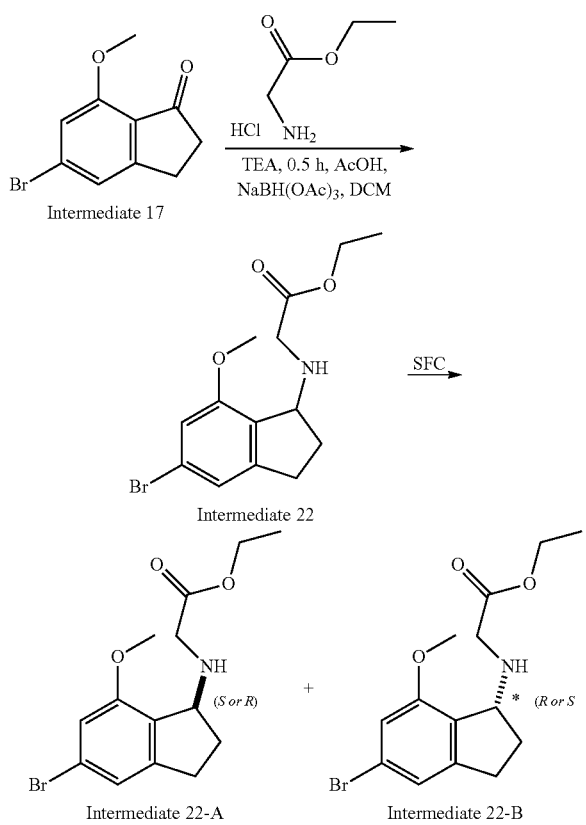

Step 1: To a solution of glycine ethyl ester hydrochloride (637 mg, 4.56 mmol) in DCM (5 mL) was added TEA (721 μL, 5.18 mmol). The mixture was stirred at 40° C. for 0.5 h. Intermediate 17 (500 mg, 2.07 mmol) and AcOH (119 μL, 2.07 mmol) were added into the mixture. The mixture was stirred at 40° C. for 1.5 h. NaBH(OAc)$_3$ (1.32 g, 6.22 mmol) was added into the mixture. The mixture was stirred at 40° C. for 12 h. The mixture was diluted with H$_2$O (20 mL) and extracted with DCM (2×25 mL). The combined organic layers were dried over Na$_2$SO$_4$, filtered and concentrated to give a residue, which was purified by flash silica gel chromatography (ISCO®; 12 g SepaFlash® Silica Flash Column, 0~30% EtOAc:PE) to give Intermediate 22 (600 mg, 87% yield) as a green oil.

Step 2: A mixture of Intermediate 22 (600.00 mg) was purified by SFC (Column: DAICEL CHIRALPAK AD (250 mm*30 mm, 10 μm), Mobile phase: A: CO2; B: Ethanol (0.1% NH$_3$H$_2$O); Gradient: 20% B; Flow Rate (mL/min): 80; Injections: 230 min (2.5 ml per injection, Cycle time: ~5.1 min); Column temperature: 40° C.) to give 230 mg of enantiomer pure Intermediate 22-A (Analytical SFC method A r.t=1.98 minute) as a brown oil and 270 mg of enantiomer pure compound Intermediate 22-B (Analytical SFC method A: r.t=2.76) as a brown oil.

The intermediates shown in Table 1 were prepared by an analogous reaction protocol as was used for the preparation of Intermediate 22-A and Intermediate 22-B using the appropriate starting materials.

Below analytical SFC methods are used to characterize the corresponding intermediates:

SFC method A: Column: Chiral NY 100×4.6 mm I.D., 3 μm; Mobile phase: A: CO$_2$; B: Ethanol (0.05% DEA); Gradient: from 5% to 40% of B in 4.5 min and hold 40% for 2.5 min, then 5% of B for 1 min; Flow rate: 2.8 mL/min; Column temperature: 40° C.

SFC method B: Column: Chiralpak ND-3 100×4.6 mm I.D., 3 μm; Mobile phase: A: CO$_2$; B: Ethanol (0.05% DEA); Gradient: from 5% to 40% of B in 4 min and hold 40% for 2.5 min, then 5% of B for 1.5 min; Flow rate: 2.8 mL/min; Column temp.: 35° C.; ABPR: 1500 psi.

SFC method C: Column: Chiralpak ND-3 100×4.6 mm I.D., 3 um; Mobile phase: A: CO$_2$; B: Ethanol (0.05% DEA); Gradient: from 5% to 40% of B in 4.5 min and hold 40% for 0.5 min, then 5% of B for 1 min; Flow rate: 2.8 mL/min; Column temp.: 35° C.; ABPR: 1500 psi.

SFC method D: Column: Chiralpak ND-3 100×4.6 mm I.D., 3 um; Mobile phase: A: CO$_2$; B: Iso-propanol (0.05% DEA); Gradient: from 5% to 40% of B in 4.5 min and hold 40% for 2.5 min, then 5% of B for 1 min; Flow rate: 2.8 mL/min; Column temp.: 35° C.; ABPR: 1500 psi.

TABLE 1

| Intermediate No. | Structure | SFC Method | Retention time (minute) | Starting materials |
|---|---|---|---|---|
| 23-A | 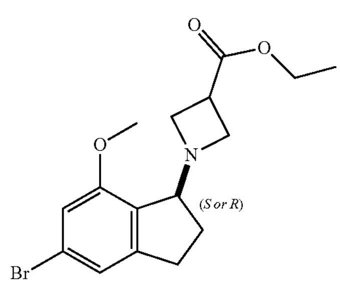 [SMILES: CCOC(=O)C1CN([C@H]2CCc3cc(Br)cc(OC)c32)C1] | A | 1.96 | Intermediate -17 Ethyl azetidine-3-carboxylate hydrochloride |

TABLE 1-continued

| Intermediate No. | Structure | SFC Method | Retention time (minute) | Starting materials |
|---|---|---|---|---|
| 23-B | 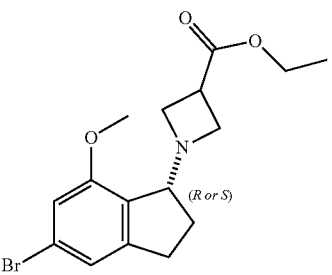 [SMILES: CCOC(=O)C1CN([C@@H]2CCc3cc(Br)cc(OC)c32)C1] | B | 2.51 | Intermediate -17 Ethyl azetidine-3-carboxylate hydrochloride |
| 24-A | 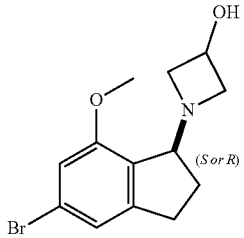 | B | 2.14 | Intermediate -17 3-Hydroxyazetidine-Hydrochloride |
| 24-B | 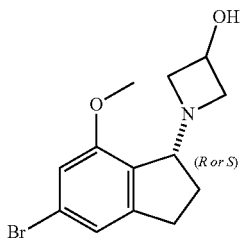 [SMILES: COc1cc(Br)cc2c1[C@H](N1CC(O)C1)CC2] | B | 2.34 | Intermediate -17 3-Hydroxyazetidine-Hydrochloride |
| 25-A | 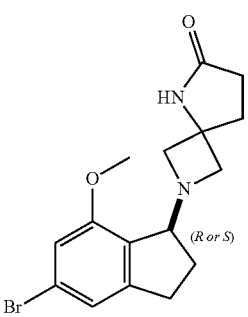 [SMILES: COc1nc(Cl)cc2c1[C@@H](N1CC3(CCC(=O)N3)C1)CC2] | B | 3.52 | Intermediate -17 2,5-Diazaspiro-[3.4]octan-6-one Hydrochloride |
| 25-B | 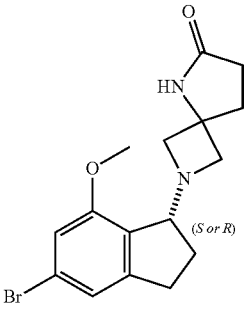 [SMILES: COc1nc(Cl)cc2c1[C@H](N1CC3(CCC(=O)N3)C1)CC2] | B | 4.16 | Intermediate -17 2,5-Diazaspiro-[3.4]octan-6-one Hydrochloride |

TABLE 1-continued

| Intermediate No. | Structure | SFC Method | Retention time (minute) | Starting materials |
|---|---|---|---|---|
| 26-A | ![structure with (S or R)] methoxy-bromo-indanyl-azetidine-OH | C | 2.18 | Intermediate -21 3-Hydroxyazetidine Hydrochloride |
| 26-B | ![structure with (R or S)] methoxy-bromo-indanyl-azetidine-OH | C | 2.39 | Intermediate -21 3-Hydroxyazetidine Hydrochloride |
| 27-A | ![structure with (S or R)] methoxy-bromo-indanyl-diazaspiro octanone | D | 2.90 | Intermediate -21 2,5-Diazaspiro-[3.4]octan-6-one Hydrochloride |
| 27-B | ![structure with (R or S)] methoxy-bromo-indanyl-diazaspiro octanone | D | 4.45 | Intermediate -21 2,5-Diazaspiro-[3.4]octan-6-one Hydrochloride |

Example A11

Preparation of Intermediate 28

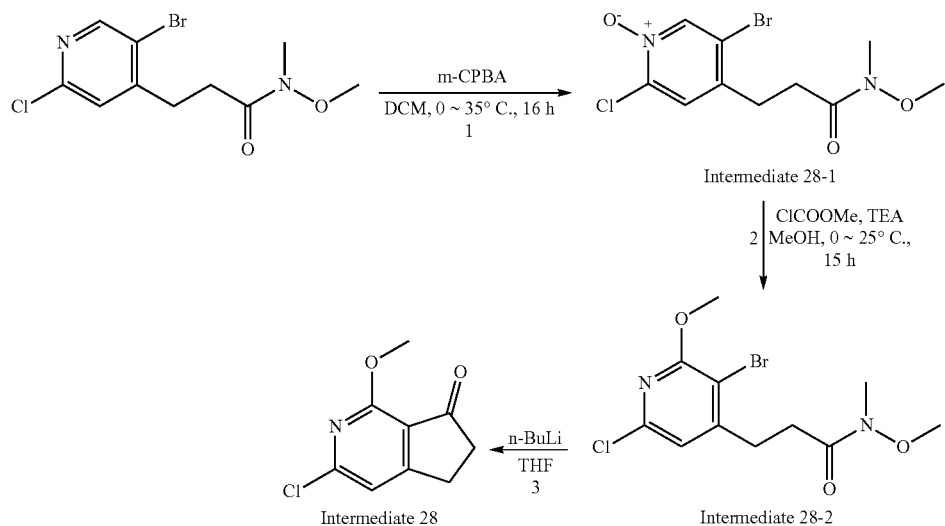

To a solution of 3-(5-bromo-2-chloro-4-pyridyl)-N-methoxy-N-methyl-propanamide (27.5 g, 89.4 mmol) in DCM (400 mL) was added m-CPBA (46.3 g, 268 mmol) at 0° C. The mixture was stirred at 55° C. for 16 hours, poured into sat. aq. Na$_2$S$_2$O$_4$ (300 mL) and extracted with DCM (2×100 mL). The combined organic phases were concentrated in vacuo. The residue was purified by flash silica gel chromatography to provide Intermediate 28-1 as a yellow solid. $^1$H NMR (400 MHz, CDCl$_3$) δ 8.50 (s, 1H), 7.48 (s, 1H), 3.67 (s, 3H), 3.18 (s, 3H), 3.06-2.99 (m, 2H), 2.81-2.75 (m, 2H).

To a solution of Intermediate 28-1 (26.8 g, 82.8 mmol) and methyl carbonochloridate (26.9 g, 285 mmol) in MeOH (150 mL) was added dropwise TEA (41.91 g, 414 mmol) at 0° C., and the mixture was stirred at 0° C. for 1.5 h. Additional methyl carbonochloridate (26.9 g, 285 mmol) was added, followed by TEA (41.91 g, 414 mmol) dropwise at 0° C. The mixture was stirred at 30° C. for 15 h and then concentrated under reduced pressure. The mixture was diluted with 1M aq. NaOH (300 mL) and extracted with EtOAc (2×200 mL). The combined organic layers were wished with brine (2×100 mL), dried over anhydrous $Na_2SO_4$, filtered and concentrated under reduced pressure to give a residue. The residue was purified by flash silica gel chromatography to provide Intermediate 28-2 as a white solid (17 g, 61% yield). $^1$H NMR (400 MHz, $CDCl_3$) δ 6.87 (s, 1H), 4.00 (s, 3H), 3.66 (s, 3H), 3.19 (s, 3H), 3.06-3.01 (m, 2H), 2.74 (br t, 2H).

To a solution of Intermediate 28-2 (3.4 g, 10.1 mmol) in THF (40 mL) was added n-BuLi (2.5 M, 6.04 mL) at −70° C. The mixture was stirred at −70° C. for 0.5 h, poured into sat.aq. $NH_4C_1$ (80 mL) and extracted with EtOAc (2×100 mL). The combined organic layers were washed with brine (2×80 mL), dried over anhydrous $Na_2SO_4$, filtered and concentrated under reduced pressure to give a residue. The residue was purified by flash silica gel chromatography to provide Intermediate 28 as a white solid (1.45 g, 73% yield). $^1$H NMR (400 MHz, $CDCl_3$) δ 7.03 (s, 1H), 4.11 (s, 3H), 3.20-2.97 (m, 2H), 2.79-2.52 (m, 2H).

Example A12

Preparation of Intermediate 29

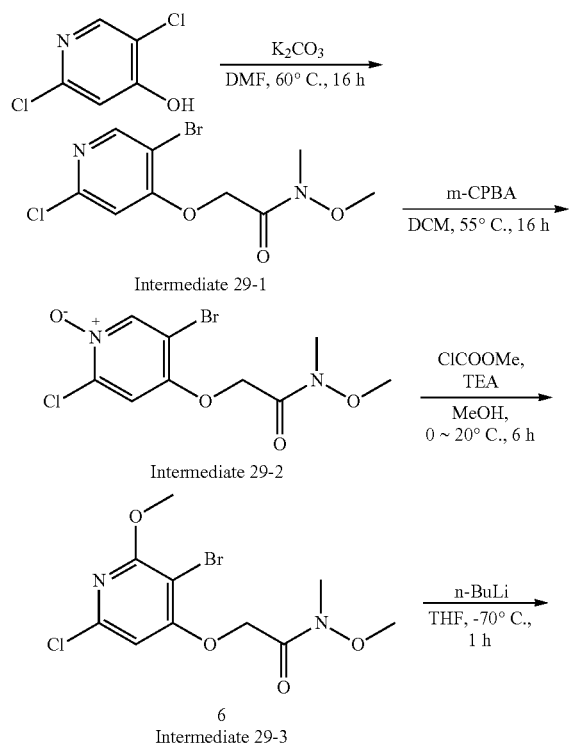

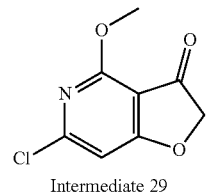

Intermediate 29

A mixture of 5-Bromo-2-chloro-pyridin-4-ol (3 g, 14.4 mmol), 2-bromo-N-methoxy-N-methyl-acetamide (3.93 g, 21.6 mmol), $K_2CO_3$ (5.97 g, 43.2 mmol) in DMF (30 mL) was stirred at 60° C. for 16 h. The mixture was filtered and concentrated under reduced pressure to give a residue, which was purified by flash silica gel chromatography to give Intermediate 29-1 (3.5 g, 78% yield) as a white solid. $^1$H NMR (400 MHz, $CDCl_3$) δ 8.38 (s, 1H), 6.73 (s, 1H), 4.99 (s, 2H), 3.80 (s, 3H), 3.26 (s, 3H).

A mixture of Intermediate 29-1 (2 g, 6.46 mmol), m-CPBA (6.69 g, 38.8 mmol) in DCM (50 mL) was stirred at 55° C. for 16 h. The crude mixture was poured into sat. aq. $Na_2S_2O_3$ (100 mL), extracted with DCM (2×50 mL), washed with brine (50 mL), dried over anhydrous $Na_2SO_4$, filtered and concentrated under reduced pressure to give a residue, which was purified by flash silica gel chromatography to give Intermediate 29-2 (1 g, 48% yield). $^1$H NMR (400 MHz, $CDCl_3$) δ 8.50 (s, 1H), 6.93 (s, 1H), 4.99 (s, 2H), 3.80 (s, 3H), 3.25 (s, 3H).

To a solution of Intermediate 29-2 (1.7 g, 5.22 mmol) and methyl carbonochloridate (1.21 mL, 15.67 mmol) in MeOH (20 mL) was added dropwise TEA (1.59 g, 15.7 mmol, 2.18 mL) at 0° C. After addition, the mixture was stirred at 20° C. for 1 h. Additional methyl carbonochloridate (1.21 mL, 15.67 mmol) was added at 20° C., then TEA (2.18 mL, 15.67 mmol) was added dropwise at 0° C. The mixture was stirred at 20° C. for 3 h and then concentrated under reduced pressure. The residue was diluted with $H_2O$ (40 mL) and extracted with EtOAc (2×50 mL). The combined organic layers were washed with brine (30 mL×2), dried over anhydrous $Na_2SO_4$, filtered and concentrated under reduced pressure to give a residue, which was purified by flash silica gel chromatography to give Intermediate 29-3 (1.3 g, 73% yield) as a white solid. $^1$H NMR (400 MHz, $CDCl_3$) δ 6.44 (s, 1H), 4.96 (s, 2H), 4.01 (s, 3H), 3.79 (s, 3H), 3.25 (s, 3H).

To a solution of Intermediate 29-3 (1.3 g, 3.83 mmol) in THF (15 mL) was added n-BuLi (2.5 M, 2.30 mL) at −70° C. under $N_2$. The mixture was stirred at −70° C. for 1 h. The reaction was quenched by then addition sat. aq. $NH_4C_1$ (10 mL) at 0° C., and then extracted with EtOAc (3×20 mL). The combined organic layers were washed with brine (20 mL), dried over anhydrous $Na_2SO_4$, filtered and concentrated under reduced pressure to give a residue, which was purified by flash silica gel chromatography to give Intermediate 29 (534 mg, 70% yield) as a yellow solid. $^1$H NMR (400 MHz, $CDCl_3$) δ 6.75 (s, 1H), 4.72 (s, 2H), 4.12 (s, 3H).

Example A13

Preparation of Intermediates 31-a and 31-b

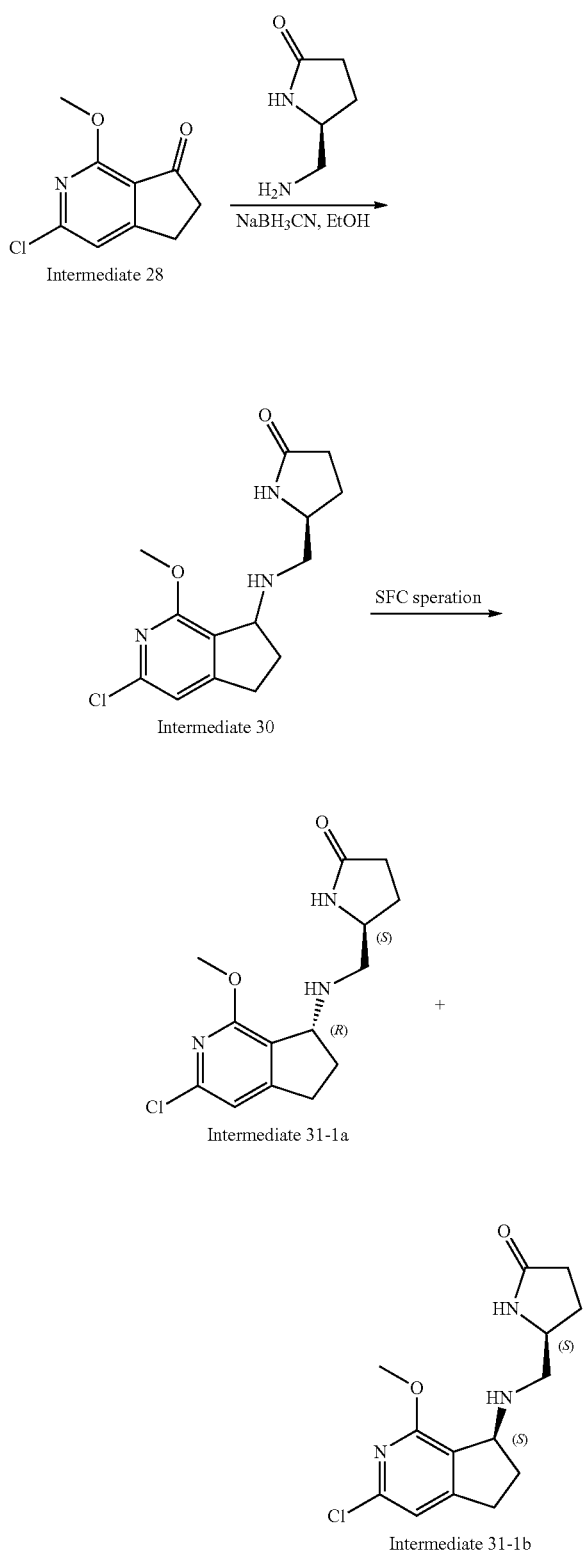

The mixture of Intermediate 28 (1.45 g, 7.34 mmol) and (5S)-5-(aminomethyl)pyrrolidin-2-one HCl salt (2.21 g, 14.7 mmol) in EtOH (20 mL) was stirred at 20-45° C. for 1 h. NaBH$_3$CN (1.38 g, 22 mmol) was added at 20° C. The mixture was stirred at 20-45° C. for 15 h, filtered and concentrated under reduced pressure to give a residue. The residue was diluted with H$_2$O (80 mL) and extracted with EtOAc (2×100 mL). The combined organic layers were washed with brine (2×80 mL), dried over anhydrous Na$_2$SO$_4$, filtered and concentrated under reduced pressure to give a residue. The residue was purified by flash silica gel chromatography to give Intermediate 30 (2.2 g, 92% purity) as a yellow oil.

Intermediate 30 was further separated by SFC (Column: DAICEL CHIRALPAK IC (250 mm*50 mm, 10 um), Mobile phase: A: CO$_2$; B: IPA (0.1% NH$_3$H$_2$O); Gradient: 55% B; Flow Rate (mL/min): 140; Injections: 300 min (3 mL per injection, Cycle time: ~6.8 min); Column temperature: 40° C.) to give pure enantiomers Intermediate 31-1a and Intermediate 31-b. The absolute chiral centers of the intermediates are assigned based on a single crystal structure of Intermediate 31-1b.

Intermediate 31-1a (800 mg) was obtained as a yellow oil with SFC. Rt=3.44 minutes (SFC analytical Instrument: CAS-QD-ANA-SFC-SD (Agilent 1260 with DAD detector); Method: Column: Chrialpak IC-3 100×4.6 mm I.D., 3 μm; Mobile phase: 40% of IPA (0.05%) in CO$_2$; Flow rate: 2.8 mL/min Column temperature: 40° C.). $^1$H NMR (400 MHz, CD$_3$OD) δ 6.96 (s, 1H), 4.51 (dd, J=3.9, 7.7 Hz, 1H), 3.98 (s, 3H), 3.91-3.80 (m, 1H), 3.61 (q, J=7.1 Hz, 1H), 3.18-3.02 (m, 1H), 2.95-2.74 (m, 3H), 2.52-2.40 (m, 1H), 2.39-2.25 (m, 3H), 2.08 (tdd, J=4.4, 8.9, 13.4 Hz, 1H), 1.92-1.76 (m, 1H).

Intermediate 31-1b (1.14 g) was obtained as a yellow solid with SFC. Rt=4.74 minutes (SFC analytical Instrument: CAS-QD-ANA-SFC-SD (Agilent 1260 with DAD detector) Method: Column: Chrialpak IC-3 100×4.6 mm I.D., 3 μm Mobile phase: 40% of IPA (0.05%) in CO$_2$; Flow rate: 2.8 mL/min Column temperature: 40° C.). $^1$H NMR (400 MHz, CD$_3$OD) δ 6.91 (s, 1H), 4.37 (dd, J=4.8, 7.5 Hz, 1H), 3.96 (s, 3H), 3.86-3.74 (m, 1H), 3.05 (ddd, J=5.9, 8.8, 17.1 Hz, 1H), 2.89-2.68 (m, 2H), 2.59 (dd, J=7.1, 11.9 Hz, 1H), 2.46-2.19 (m, 4H), 1.97 (tdd, J=5.3, 8.4, 13.5 Hz, 1H), 1.89-1.72 (m, 1H). The single crystal of intermediate 31-b's formate salt was obtained. The crystal was a colorless needle with the following dimensions: 0.30×0.04×0.04 mm$^3$. The symmetry of the crystal structure was assigned the monoclinic space group P2$_1$ with the following parameters: a=20.8793(7) Å, b=5.8084(2) Å, c=28.1836(9) Å, α=90°, β=102.238(3°), γ=90°, V=3340.3(2) Å3, Z=8, Dc=1.359 g/cm3, F(000)=1440.0, μ(CuKα)=2.236 mm-1, and T=149.99(10) K.

The intermediates shown in Table 2 were prepared by an analogous reaction protocol as was used for the preparation of Intermediates 31-1b using the appropriate starting materials.

TABLE 2

| Intermediate No. | Structure | SFC Method | Retention time (minute) | Starting Materials |
|---|---|---|---|---|
| 31-2a | (structure, S or R) | E | 3.33 | Intermediate 28<br>2,5-Diazaspiro[3.4]octan-6-one hydrochloride |
| 31-2b | (structure, R or S) | E | 4.00 | Intermediate 28<br>2,5-Diazaspiro[3.4]octan-6-one hydrochloride |
| 31-3a | (structure, S or R) | F | 1.19 | Intermediate 28<br>1-(2,6-diazaspiro[3.3]heptan-2-yl)ethan-1-one |
| 31-3b | (structure, R or S) | F | 1.34 | Intermediate 28<br>1-(2,6-diazaspiro[3.3]heptan-2-yl)ethan-1-one |
| 31-4a | (structure, S or R) | H | 3.23 | Intermediate 28<br>azetidin-3-ol hydrochloride |

TABLE 2-continued

| Intermediate No. | Structure | SFC Method | Retention time (minute) | Starting Materials |
|---|---|---|---|---|
| 31-4b | (structure) | H | 3.54 | Intermediate 28 azetidin-3-ol hydrochloride |
| 31-5a | (structure) | E | 1.59 | Intermediate 28 ethyl azetidine-3-carboxylate hydrochloride |
| 31-5b | (structure) | E | 1.90 | Intermediate 28 ethyl azetidine-3-carboxylate hydrochloride |
| 32-1a | (structure) | I | 1.36 | Intermediate 29 (5S)-5-(aminomethyl)pyrrolidin-2-one HCl |
| 32-1b | (structure) | I | 1.67 | Intermediate 29 (5S)-5-(aminomethyl)pyrrolidin-2-one HCl |

TABLE 2-continued

| Intermediate No. | Structure | SFC Method | Retention time (minute) | Starting Materials |
|---|---|---|---|---|
| 32-2a | (S or R) | G | 1.51 | Intermediate 29 2,5-Diazaspiro[3.4]octan-6-one hydrochloride |
| 32-2b | (R or S) | G | 2.10 | Intermediate 29 2,5-Diazaspiro[3.4]octan-6-one hydrochloride |

SFC Method E: Column: UniChiral ND 100×4.6 mm I.D., 5 μm; Mobile phase: A: CO$_2$; B: iso-propanol (0.05% DEA); Gradient: from 5% to 40% of B in 4.5 min and hold 40% for 0.5 min, then 5% of B for 1 min; Flow rate: 2.8 mL/min Column temperature: 40° C.

SFC Method F: Column: Chiralpak AD-3 100×4.6 mm I.D., 3 μm; Mobile phase: A: CO$_2$, B: Ethanol (0.05% DEA); Gradient: from 5% to 40% of B in 4.5 min and hold 40% for 2.5 min, then 5% of B for 1 min; Flow rate: 2.8 mL/min Column temperature: 40° C.

SFC Method G: Column: Chiralpak AD-3 50×4.6 mm I.D., 3 μm; Mobile phase: A: CO$_2$, B: Ethanol (0.05% DEA); Gradient: from 5% to 40% of B in 2.5 min and hold 40% for 0.5 min, then 5% of B for 1 min; Flow rate: 4 mL/min Column temperature: 35° C.

SFC Method H: Column: Lux Cellulose-2 100×4.6 mm I.D., 3 μm; Mobile phase: A: CO$_2$; B: IPA (0.05% DEA); Gradient: from 5% to 40% of B in 4.5 min and hold 40% for 2.5 min, then 5% of B for 1 min; Flow rate: 2.5 mL/min Column temperature: 40° C.

SFC Method I: Column: Chiralpak AY-3 50×4.6 mm I.D., 3 μm; Mobile phase: A: CO$_2$; B: IPA (0.05% DEA); Gradient: from 5% to 40% of B in 2.5 min and hold 40% for 0.5 min, then 5% of B for 1 min; Flow rate: 4 mL/min Column temperature: 35° C.

Example 14

Preparation of Intermediate 33-1

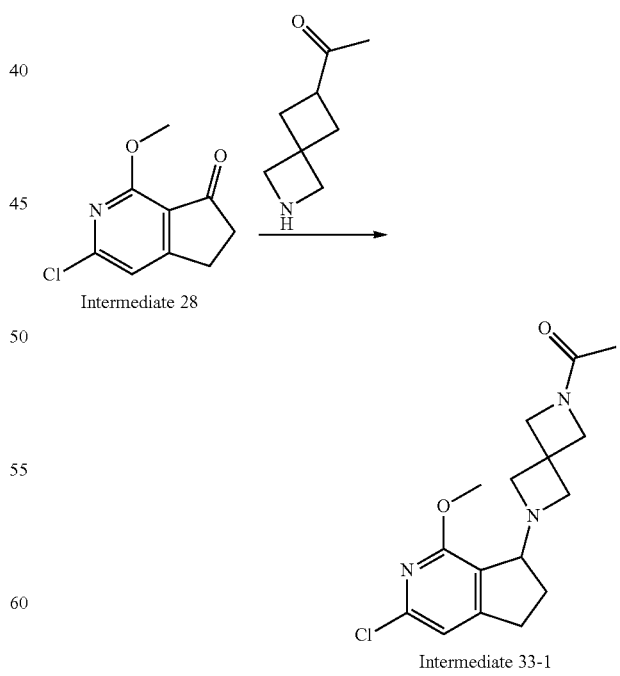

The solution of Intermediate 28 (570 mg, 2.88 mmol), 1-(2,6-diazaspiro [3.3] heptan-2-yl) ethenone TFA salt (3.79 g) and TEA (1.46 g, 14.4 mmol) in EtOH (10 mL) was stirred at 45° C. for 2 h. NaBH₃CN (544 mg, 8.65 mmol) was added into the mixture at 20° C. The mixture was stirred at 45° C. for 14 h. The mixture was concentrated under reduced pressure to give a residue. The residue was diluted with H₂O (80 mL) and extracted with EtOAc (3×80 mL). The combine organic layers were washed with brine (2×80 mL), dried over anhydrous Na₂SO₄, filtered and concentrated under reduced pressure to give a residue. The residue was purified by flash silica gel chromatography to provide Intermediate 33-1 as a pink solid (900 mg). LCMS ($C_{16}H_{21}ClN_3O_2^+$) (ES, m/z): 322.1 [M+H]⁺.

The intermediates shown in Table 3 were prepared by an analogous reaction protocol as was used for the preparation of Intermediates 33-1 using the appropriate starting materials.

TABLE 3

| Intermediate No. | Structure | Starting Materials |
| --- | --- | --- |
| 33-2 | 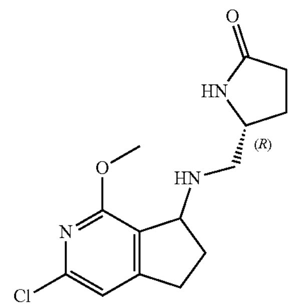 | Intermediate 28<br>(5R)-5-(aminomethyl)pyrrolidin-2-one HCl salt |
| 33-3 | 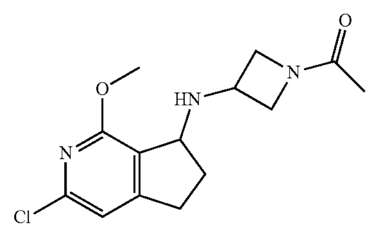 [SMILES: COc1nc(Cl)cc2c1C(NC1CN(C(C)=O)C1)CC2] | Intermediate 28<br>1-(3-aminoazetidin-1-yl)ethanone hydrochloride |
| 33-4 | 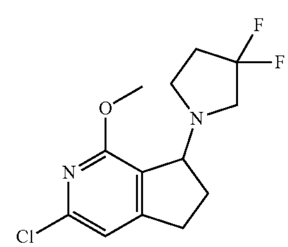 [SMILES: COc1nc(Cl)cc2c1C(N1CCC(F)(F)C1)CC2] | Intermediate 28<br>3,3-difluoropyrrolidine |
| 33-5 | 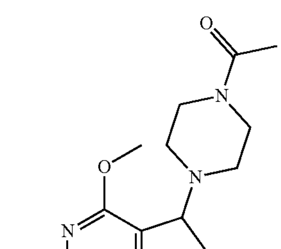 | Intermediate 28<br>1-(piperazin-1-yl)ethanone |
| 33-6 | 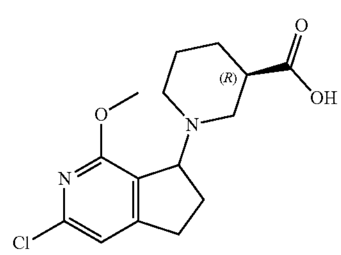 | Intermediate 28<br>(R)-piperidine-3-carboxylic acid |

TABLE 3-continued

| Intermediate No. | Structure | Starting Materials |
| --- | --- | --- |
| 33-7 | 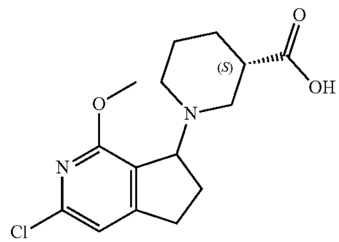 | Intermediate 28<br>(S)-piperidine-3-carboxylic acid |
| 33-8 | 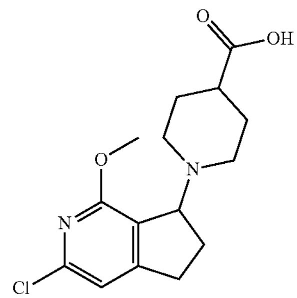 [SMILES: COc1nc(Cl)cc2c1C(N1CCC(C(=O)O)CC1)CC2] | Intermediate 28<br>piperidine-4-carboxylic acid |

Example 15

Preparation of Intermediate 34

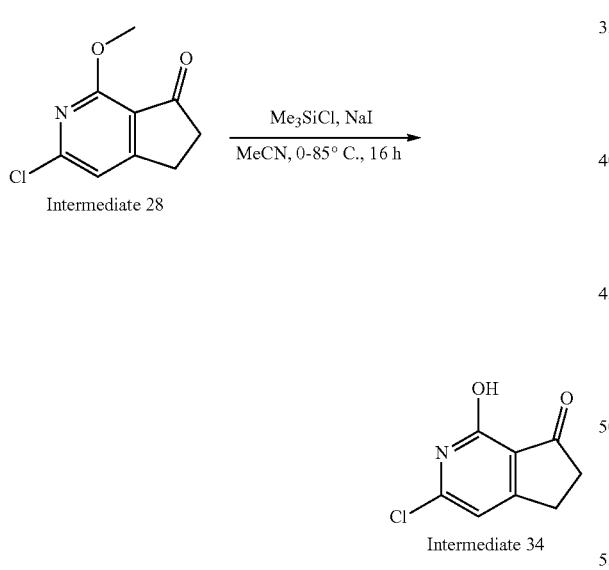

To a solution of Intermediate 28 (4.00 g, 20.2 mmol) and NaI (9.10 g, 60.7 mmol,) in MeCN (150 mL) was added chloro(trimethyl)silane (6.60 g, 60.7 mmol, 7.71 mL) dropwise at 0° C. The mixture was stirred at 85° C. for 16 h. The mixture was filtered and concentrated to give a residue, which was purified by prep-HPLC to give Intermediate 34 (2.8 g, 95% purity) as a yellow solid. LCMS ($C_8H_7ClNO_2$) (ES, m/z): 184.1 [M+H]$^+$.

Example 16

Preparation of Intermediate 35-1

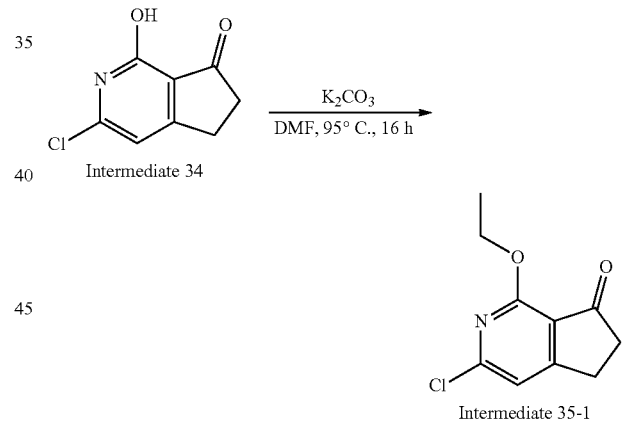

To a solution of Intermediate 34 (150 mg, 817 μmol) and iodoethane (153 mg, 980 μmol) in DMF (3 mL) was added $K_2CO_3$ (169 mg, 1.63 mmol). The mixture was stirred at 95° C. for 16 h, filtered and concentrated under reduced pressure to give a residue, which was purified by flash silica gel chromatography to give Intermediate 35-1 (70 mg, 38% yield) as a yellow solid. LCMS ($C_{10}H_{11}ClNO_2{}^+$) (ES, m/z): 212.1 [M+H]$^+$.

The intermediates shown in Table 4 were prepared by an analogous reaction protocol as was used for the preparation of Intermediates 35-1 using the appropriate starting materials.

TABLE 4

| Intermediate No. | Structure | Starting Materials |
|---|---|---|
| 35-2 | 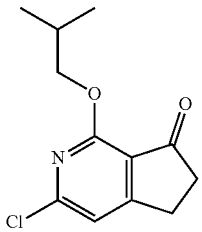 [SMILES: CC(C)COc1nc(Cl)cc2c1C(=O)CC2] | Intermediate 34 1-iodo-2-methyl-propane |
| 35-3 | 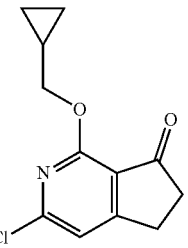 | Intermediate 34 (bromomethyl)cyclopropane |
| 35-4 | 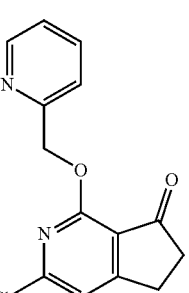 | Intermediate 34 2-(chloromethyl)pyridine-hydrochloride |

Example 17

Preparation of Intermediate 36-1

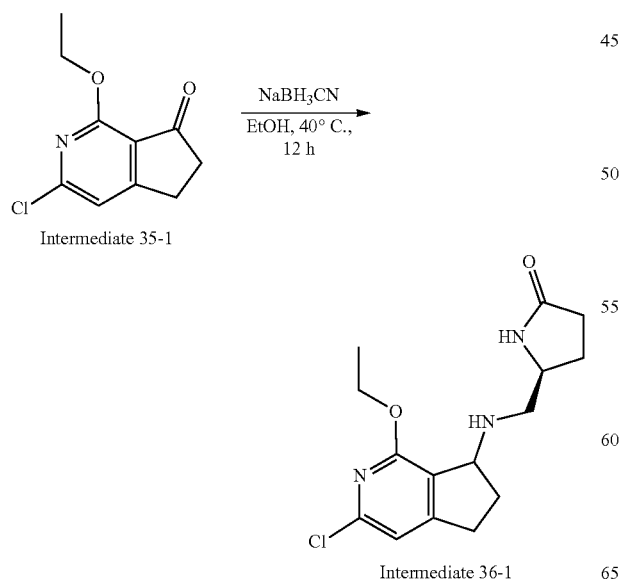

Intermediate 36-1

A solution of Intermediates 35-1 (25 mg, 118 μmol) and (5S)-5-(aminomethyl)pyrrolidin-2-one (27 mg, 179 μmol) in MeOH (0.5 mL) was stirred at 40° C. for 1 h. NaBH$_3$CN (22 mg, 354 μmol) was added into the mixture. The mixture was stirred at 40° C. for 15 h, filtered and concentrated under reduced pressure to give Intermediate 36-1 (38 mg, crude) as a yellow liquid.

The intermediates shown in Table 5 were prepared by an analogous reaction protocol as was used for the preparation of Intermediates 36-1 using the appropriate starting materials.

TABLE 5

| Intermediate No. | Structure | Starting Materials |
|---|---|---|
| 36-2 | 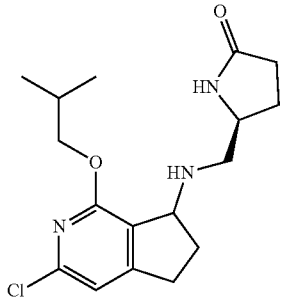 [SMILES: CC(C)COc1nc(Cl)cc2c1C(NC[C@@H]1CCC(=O)N1)CC2] | Intermediate 35-2 (5S)-5-(aminomethyl)pyrrolidin-2-one HCl salt |
| 36-3 | 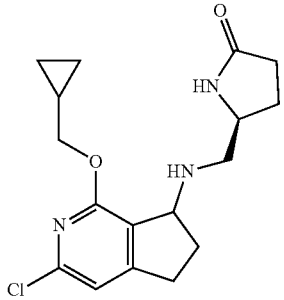 [SMILES: O=C1CC[C@@H](CNC2CCc3cc(Cl)nc(OCC4CC4)c32)N1] | Intermediate 35-3 (5S)-5-(aminomethyl)pyrrolidin-2-one HCl salt |
| 36-4 | 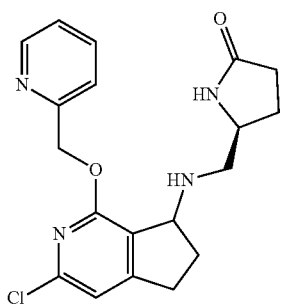 [SMILES: O=C1CC[C@@H](CNC2CCc3cc(Cl)nc(OCc4ccccn4)c32)N1] | Intermediate 35-4 (5S)-5-(aminomethyl)pyrrolidin-2-one HCl salt |

Example 18

Preparation of Intermediate 37-1

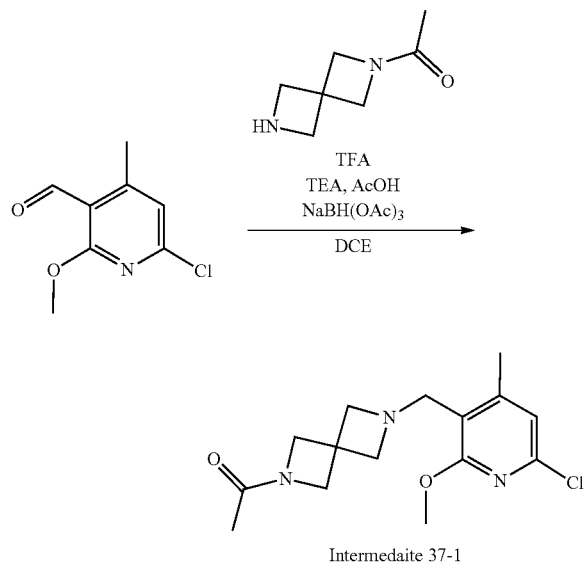

Intermedaite 37-1

To a solution of 1-(2,6-Diazaspiro[3.3]hept-2-yl)ethanone trifluoroacetate (1:1) (85.0 g) in DCE (1000 mL) was added TEA (34.0 g, 335 mmol), and then the mixture was stirred at 15° C. for 30 minutes. (6-Chloro-2-methoxy-4-methylnicotinaldehyde (21.5 g, 116 mmol) was added into the mixture, followed by the addition of AcOH (6.72 g, 112 mmol). The mixture was stirred at 15° C. for 3 h. NaBH(OAc)$_3$ (71.1 g, 335 mmol) was added into the mixture at 0° C. The mixture was stirred at 15° C. for 16 h. The reaction was quenched with MeOH (50 mL), diluted with saturated NaHCO$_3$ (1000 mL), and extracted with DCM (3×1000 mL). The combined organic layers were dried with Na$_2$SO$_4$ and filtered. The filtrate was concentrated under reduced pressure to give a residue. The residue was purified by flash silica gel chromatography to provide Intermediate 37-1 (22.4 g, 98% purity) as a white solid. $^1$H NMR: (400 MHz, MeOD) δ 6.88 (s, 1H), 4.28 (s, 2H), 4.03 (s, 2H), 3.94 (s, 3H), 3.80 (br s, 2H), 3.65 (br s, 4H), 2.36 (s, 3H), 1.83 (s, 3H).

The intermediates shown in Table 6 were prepared by an analogous reaction protocol as was used for the preparation of Intermediates 37-1 using the appropriate starting materials.

TABLE 6

| Intermediate No. | Structure | Starting Materials |
|---|---|---|
| 37-2 | (structure shown) | 6-Chloro-2-methoxy-pyridine-3-carbaldehyde (5S)-5-(aminomethyl)pyrrolidin-2-one HCl salt |
| 37-3 | (structure shown) | 6-Chloro-2-methoxy-pyridine-3-carbaldehyde 1-(2,6-diazaspiro[3.3]heptan-2-yl)ethan-1-one |

Example 19

Preparation of Intermediate 37-4

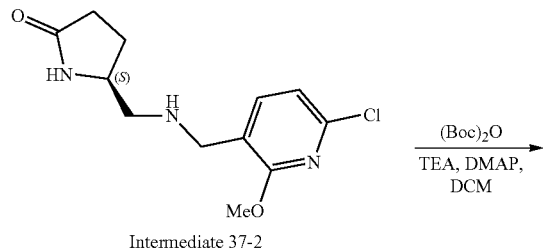

Intermediate 37-2

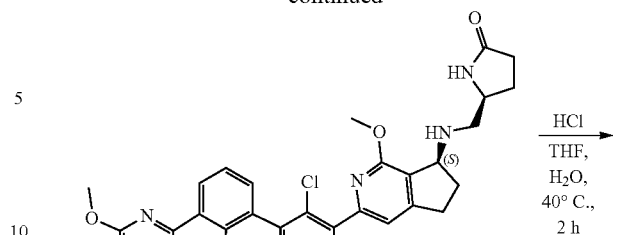

Intermediate 38

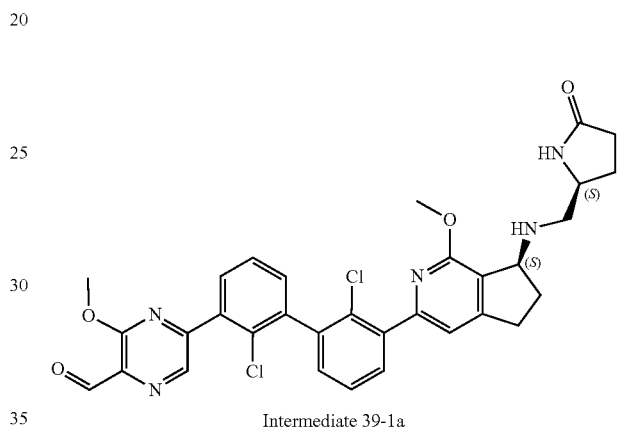

Intermediate 39-1a

Intermediate 37-4

The mixture of Intermediate 37-2 (4.72 g, 17.5 mmol), (Boc)$_2$O (8.44 mL, 36.75 mmol), TEA (7.31 mL, 52.50 mmol) and DMAP (449 mg, 3.67 mmol) in DCM (100 mL) was stirred at 20° C. for 1 h. The mixture was concentrated under reduced pressure to remove the DCM. The residue was diluted with H$_2$O (50 mL) and extracted with EtOAc (3×50 mL). The combined organic layers were washed with brine 50 mL, dried over Na$_2$SO$_4$, filtered and concentrated under reduced pressure to give a residue. The residue was purified by flash silica gel chromatography to provide Intermediate 37-4 (2.55 g, 39% yield) as a colorless oil. $^1$H NMR (400 MHz, DMSO-d$_6$) δ 7.74 (s, 1H), 7.40 (br dd, J=7.6, 13.7 Hz, 1H), 7.10 (br s, 1H), 4.39-4.21 (m, 2H), 3.89 (s, 3H), 3.71 (br d, J=6.1 Hz, 1H), 3.22 (br d, J=19.5 Hz, 2H), 2.20-2.00 (m, 3H), 1.68 (br s, 1H), 1.43-1.26 (m, 9H), 1.47-1.23 (m, 1H).

Example 20

Preparation of Intermediate 39-1a

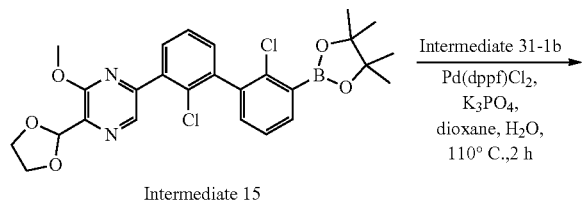

Intermediate 15

A mixture of Intermediate 15 (1.18 g, 2.23 mmol), Intermediate 31-1b (600 mg, 2.03 mmol), Pd(dppf)Cl$_2$ (148 mg, 203 µmol) and K$_2$CO$_3$ (841 mg, 6.09 mmol) in dioxane (15 mL) and H$_2$O (1.5 mL) was degassed and purged with N$_2$ (3×). The mixture was stirred at 110° C. for 2 h under N$_2$ atmosphere. The mixture was filtered and concentrated in vacuo. The residue was diluted with H$_2$O (100 mL) and extracted with EtOAc (2×100 mL). The combined organic layers were washed with brine (2×100 mL), dried over Na$_2$SO$_4$, filtered and concentrated under reduced pressure to give a residue. The residue was purified by flash silica gel chromatography to give Intermediate 38 (1.03 g, 54% yield) as a brown solid. LCMS (C$_{34}$H$_{34}$Cl$_2$N$_5$O$_5$$^+$) (ES, m/z): 662.2 [M+H]$^+$.

To a solution of Intermediate 38 (600 mg, 906 µmol) in THF (3.5 mL) was added aqueous hydrochloric Acid (12 M, 1 mL) and H$_2$O (3 mL). The mixture was stirred at 40° C. for 2 h. The solution was poured into sat. aq. NaHCO$_3$ (60 mL) and then extracted with DCM (3×60 mL). The combined organic layers were washed with brine (2×80 mL), dried over anhydrous Na$_2$SO$_4$, filtered and concentrated under reduced pressure to give Intermediate 39-1a (600 mg, crude) as a brown solid. LCMS (C$_{32}$H$_{30}$Cl$_2$N$_5$O$_4$$^+$) (ES, m/z): 618.2 [M+H]$^+$.

The intermediates shown in Table 7 were prepared by an analogous reaction protocol as was used for the preparation of Intermediate 39-1a using the appropriate starting materials.

TABLE 7

| Intermediate No. | Structure | Starting Materials |
|---|---|---|
| 39-1b | 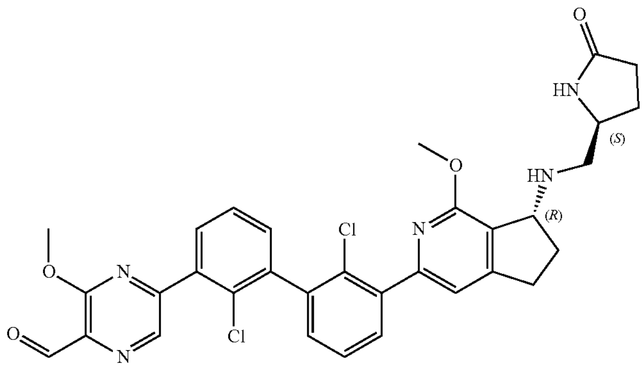 | Intermediate 15<br>Intermediate 31-1a |
| 39-2a | 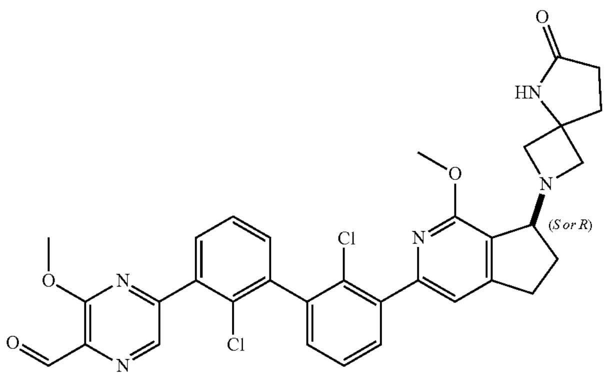 [SMILES: COc1nc(-c2cccc(-c3cccc(-c4cc5c(c(OC)n4)[C@@H](N4CC6(CCC(=O)N6)C4)CC5)c3Cl)c2Cl)cnc1C=O] | Intermediate 15<br>Intermediate 31-2a |
| 39-2b | 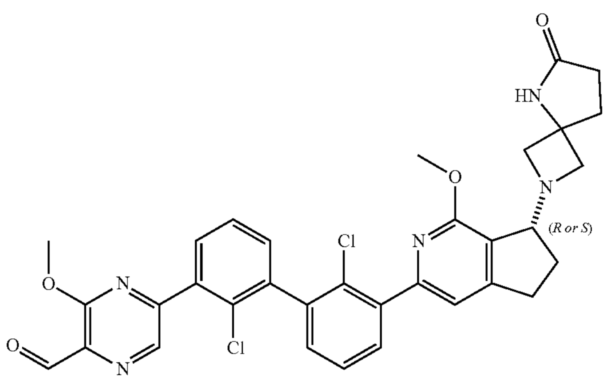 [SMILES: COc1nc(-c2cccc(-c3cccc(-c4cc5c(c(OC)n4)[C@H](N4CC6(CCC(=O)N6)C4)CC5)c3Cl)c2Cl)cnc1C=O] | Intermediate 15<br>Intermediate 31-2b |
| 39-3a | 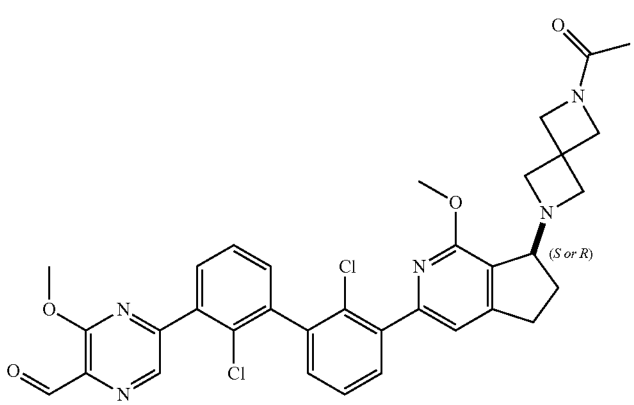 [SMILES: COc1nc(-c2cccc(-c3cccc(-c4cc5c(c(OC)n4)[C@@H](N4CC6(CN(C(C)=O)C6)C4)CC5)c3Cl)c2Cl)cnc1C=O] | Intermediate 15<br>Intermediate 31-3a |

TABLE 7-continued

| Intermediate No. | Structure | Starting Materials |
| --- | --- | --- |
| 39-3b | 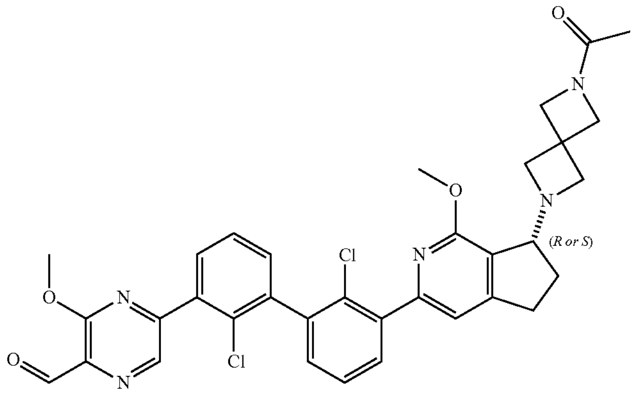 [SMILES: COc1nc(-c2cccc(-c3cccc(-c4cc5c(c(OC)n4)[C@H](N4CC6(CN(C(C)=O)C6)C4)CC5)c3Cl)c2Cl)cnc1C=O] | Intermediate 15<br>Intermediate 31-3b |

Example 21

Preparation of Intermediate 40-1a

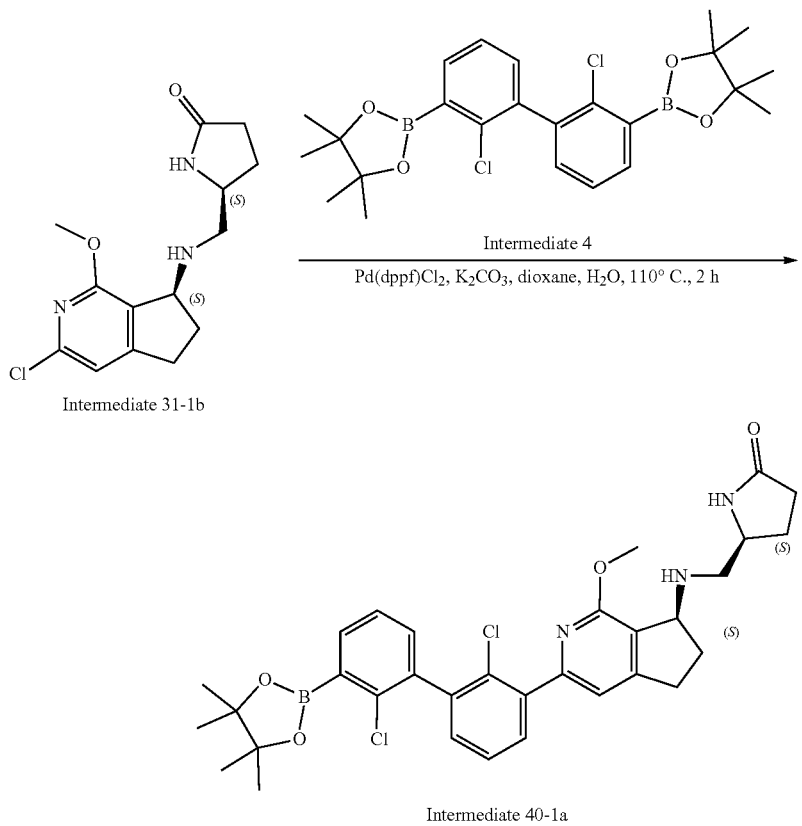

A mixture of Intermediate 31-1b (778 mg, 2.63 mmol), Intermediate 4 (500 mg, 1.05 mmol), Pd(dppf)Cl$_2$ (77 mg, 105 μmol) and K$_2$CO$_3$ (436 mg, 3.16 mmol) in dioxane (6 mL) and H$_2$O (0.6 mL) was degassed and purged with N$_2$ (3×). The mixture was stirred at 110° C. for 2 h under N$_2$ atmosphere. The mixture was filtered and concentrated in vacuo. The residue was diluted with H$_2$O (100 mL) and was extracted with EtOAc (3×80 mL). The combined organic layers were washed with brine (2×100 mL), dried over anhydrous Na$_2$SO$_4$, filtered and concentrated under reduced pressure to give a residue. The residue was purified by prep-HPLC to provide Intermediate 40-1a (270 mg) as a brown solid. LCMS (C$_{40}$H$_{43}$Cl$_2$N$_6$O$_4$$^+$) (ES, m/z): 743.3 [M+H]$^+$.

The intermediates shown in Table 8 were prepared by an analogous reaction protocol as was used for the preparation of Intermediate 40-1a using the appropriate starting materials.

TABLE 8
| Intermediate No. | Structure | Starting Materials |
|---|---|---|
| 40-2a | 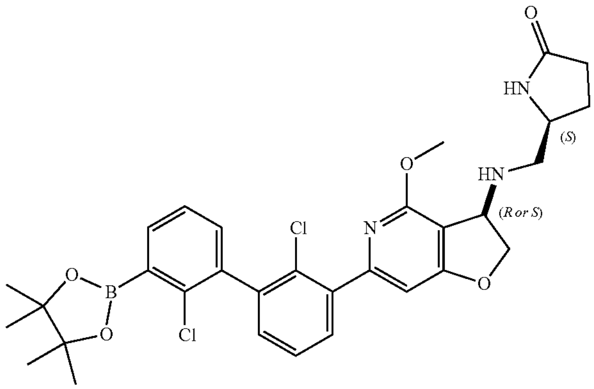 | Intermediate 4<br>Intermediate 32-1a |
| 40-2b | 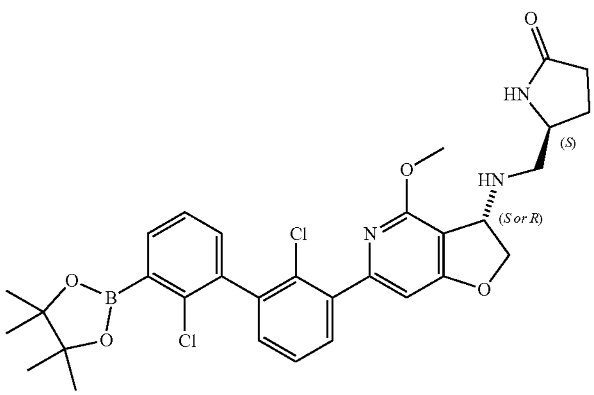 | Intermediate 4<br>Intermediate 32-1b |
Example 22
Preparation of Intermediate 41-1a
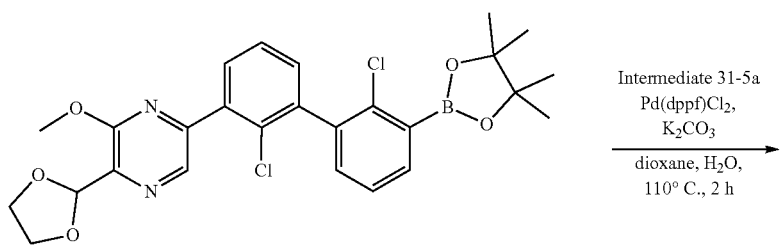

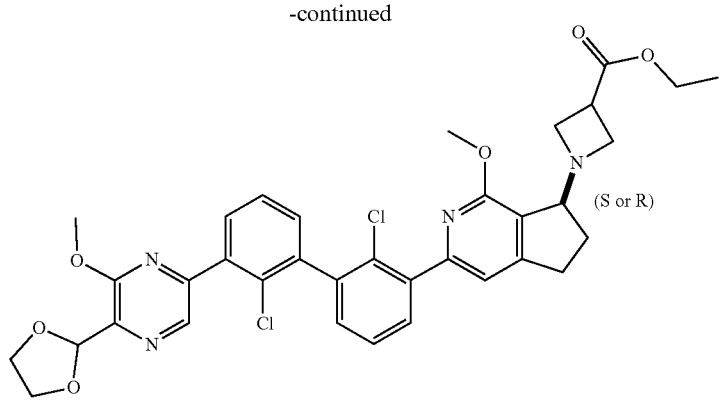

Intermediate 41-1a

To a solution of Intermediate 15 (300 mg, 567 μmol) in dioxane (7 mL) and H₂O (0.5 mL) were added Intermediate 31-5a (160 mg, 515 mol), Pd(dppf)Cl₂ (38 mg, 51.5 μmol) and K₂CO₃ (214 mg, 1.55 mmol). The mixture was degassed and purged with N₂. The mixture was stirred at 110° C. for 2 h under N₂ atmosphere. The mixture was diluted with H₂O (60 mL) and extracted with EtOAc (3×40 mL). The combined organic layers were dried over Na₂SO₄, filtered and concentrated to give a residue, which was purified by flash silica gel chromatography to give Intermediate 41-4a (400 mg, 92% purity) as a brown solid. LCMS ($C_{35}H_{35}Cl_2N_4O_6^+$) (ES, m/z): 677.3 [M+H]⁺.

The intermediates shown in Table 9 were prepared by an analogous reaction protocol as was used for the preparation of Intermediate 41-1a using the appropriate starting materials.

TABLE 9

| Intermediate No. | Structure | Starting Materials |
|---|---|---|
| 41-1b | 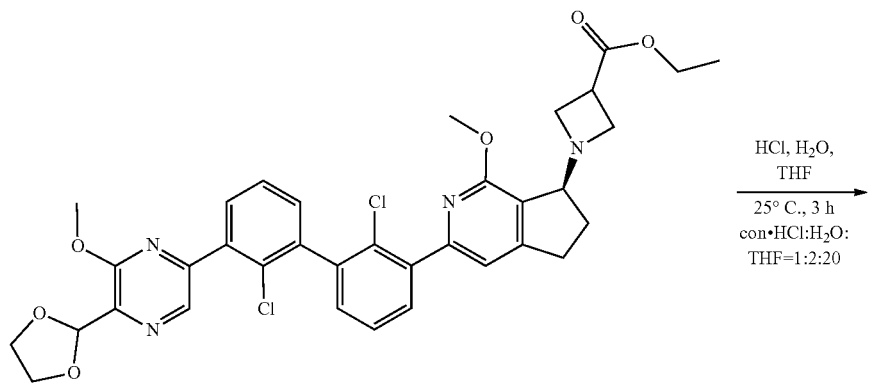 | Intermediate 15<br>Intermediate 31-5b |

Example 23

Preparation of Intermediate 42-1a

Intermediate 41-1a

HCl, H₂O, THF

25° C., 3 h
con·HCl:H₂O:THF=1:2:20

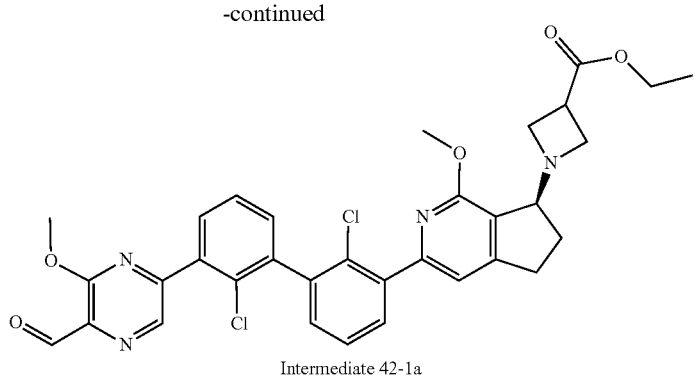

Intermediate 42-1a

To a solution of Intermediate 41-1a (200 mg, 295 μmol) in THF (2 mL) was added a solution of hydrochloric acid (12 M, 0.2 mL) in H$_2$O (0.4 mL). The mixture was stirred at 25° C. for 3 h. The solution was poured into sat. aq. NaHCO$_3$ (20 mL) and then extracted with DCM (3×20 mL). The combined organic layers were washed with brine (2×20 mL), dried over anhydrous Na$_2$SO$_4$, filtered and concentrated under reduced pressure to give Intermediate 42-1a (180 mg, crude) as a yellow solid. LCMS (C$_{33}$H$_{31}$Cl$_2$N$_4$O$_5$$^+$) (ES, m/z): 633.2 [M+H]$^+$.

The intermediates shown in Table 10 were prepared by an analogous reaction protocol as was used for the preparation of Intermediate 42-1a using the appropriate starting materials.

TABLE 10

| Intermediate No. | Structure | Starting Materials |
|---|---|---|
| 42-1b | 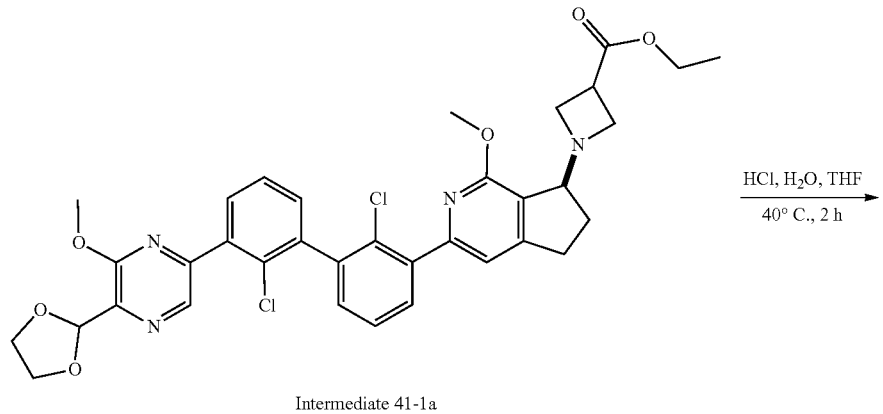 | Intermediate 41-1b |

Example 24

Preparation of Intermediate 43-1a

Intermediate 41-1a

HCl, H$_2$O, THF
40° C., 2 h

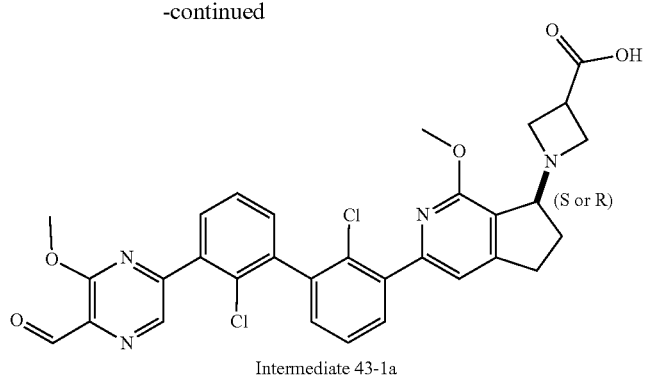

Intermediate 43-1a

To a solution of Intermediate 41-1a (50 mg, 73.8 μmol) in THF (0.7 mL) was added aqueous HCl (12 M, 0.3 mL) and H$_2$O (0.6 mL). After stirring at 40° C. for 2 h, the mixture was poured into sat. aq. NaHCO$_3$ (15 mL) and then extracted with DCM (3×15 mL). The combined organic layers were washed with brine (2×15 mL), dried over anhydrous Na$_2$SO$_4$, filtered and concentrated under reduced pressure to give Intermediate 43-1a (85 mg, crude) as a brown oil. LCMS (C$_{31}$H$_{27}$Cl$_2$N$_4$O$_5{}^+$) (ES, m/z): 605.1 [M+H]$^+$.

The intermediates shown in Table 11 were prepared by an analogous reaction protocol as was used for the preparation of Intermediate 43-1a using the appropriate starting materials.

TABLE 11

| Intermediate No. | Structure | Starting Materials |
|---|---|---|
| 43-1b | (structure shown) | Intermediate 41-1b |

Example 25

Preparation of Intermediate 44

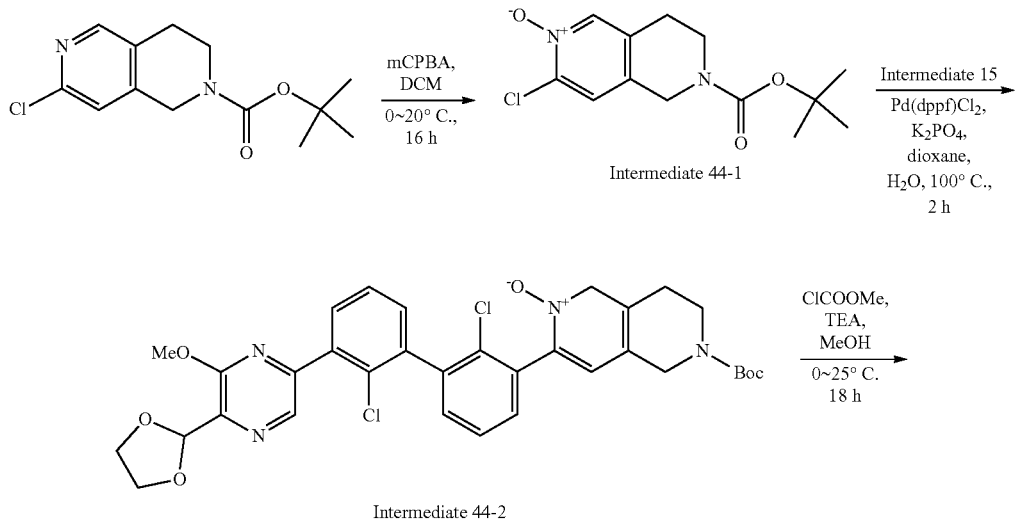

Intermediate 44-2

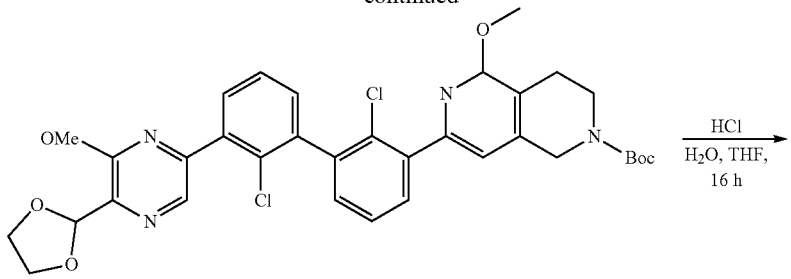

Intermediate 44-3

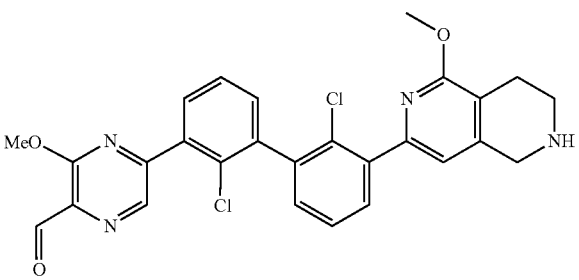

Intermediate 44

To a solution of tert-Butyl-7-chloro-3,4-dihydro-2,6-naphthyridine-2(1h)-carboxylate (10 g, 37.2 mmol) in DCM (200 mL) was added m-CPBA (9.82 g, 48.4 mmol, 85% purity) at 0° C. After stirring at 20° C. for 16 h, the mixture was poured into sat. aq. NaHCO$_3$ (300 mL) and then extracted with DCM (2×200 mL). The combined organic layers were washed with brine (2×200 mL), dried over anhydrous Na$_2$SO$_4$, filtered and concentrated under reduced pressure to give a residue. The residue was purified by flash silica gel chromatography to provide Intermediate 44-1 (8.6 g, 81% yield) as a yellow solid. $^1$H NMR (400 MHz, CDCl$_3$) δ 8.20 (s, 1H), 7.26 (s, 1H), 4.54 (s, 2H), 3.66 (br t, J=5.8 Hz, 2H), 2.77 (br t, J=5.6 Hz, 2H), 1.49 (s, 9H).

A mixture of Intermediate 44-1 (3.92 g, 13.8 mmol), Intermediate 15 (8.01 g, 15.1 mmol), Pd(dppf)Cl$_2$ (1.01 g, 1.38 mmol) and K$_3$PO$_4$ (8.77 g, 41.3 mmol) in dioxane (80 mL) and H$_2$O (4 mL) was degassed and purged with N$_2$ (3×). The mixture was stirred at 100° C. for 2 h under N$_2$ atmosphere, and the mixture was filtered and concentrated in vacuo. The residue was diluted with H$_2$O (350 mL) and extracted with EtOAc (3×300 mL). The combined organic layers were washed with brine (2×200 mL), dried over Na$_2$SO$_4$, filtered and concentrated under reduced pressure to give a residue. The residue was purified by flash silica gel chromatography to provide Intermediate 44-2 (6.3 g, 70% yield) as a brown solid. $^1$H NMR (400 MHz, CDCl$_3$) δ 8.54 (s, 1H), 8.46-8.10 (m, 1H), 7.74-7.36 (m, 7H), 6.28 (s, 1H), 4.83-4.44 (m, 3H), 4.35-4.25 (m, 2H), 4.19-4.13 (m, 2H), 4.08 (s, 3H), 3.86-3.61 (m, 2H), 3.03-2.67 (m, 3H), 1.50 (d, J=4.5 Hz, 9H).

To a solution of Intermediate 44-2 (6.3 g, 9.67 mmol) in MeOH (100 mL) was added methyl carbonochloridate (3.15 mL, 40.7 mmol) and TEA (6.30 mL, 45.26 mmol) at 0° C. The mixture was stirred at 25° C. for 3 h. To the mixture was added additional methyl carbonochloridate (3.15 mL, 40.7 mmol) and TEA (6.30 mL, 45.26 mmol) at 0° C. The mixture was stirred at 25° C. for 15 h and then concentrated under reduced pressure. The residue was diluted with sat. aq. NaOH (200 mL) and extracted with EtOAc (2×300 mL). The combined organic layers were wished with brine (2×200 mL), dried over Na$_2$SO$_4$, filtered and concentrated under reduced pressure to give a residue. The residue was purified by flash silica gel chromatography to provide Intermediate 44-3 (2.3 g, 35.7% yield) as a white solid. $^1$H NMR (400 MHz, CDCl$_3$) δ 8.56 (s, 1H), 7.72-7.57 (m, 2H), 7.52-7.38 (m, 3H), 7.34 (dd, J=1.4, 7.6 Hz, 1H), 7.04 (s, 1H), 6.29 (s, 1H), 4.59 (s, 2H), 4.37-4.27 (m, 2H), 4.18-4.13 (m, 2H), 4.10 (s, 3H), 4.02 (s, 3H), 3.71 (br t, J=5.9 Hz, 2H), 2.81-2.70 (m, 2H), 1.50 (s, 9H).

To a solution of Intermediate 44-3 (1 g, 1.50 mmol) in THF (7 mL) was added a solution H$_2$O (6 mL) and aq. HCl (12M, 3 mL). The mixture was stirred at 25° C. for 16 h. The solution was poured into sat. aq. NaHCO$_3$ (80 mL) and extracted with DCM (3×100 mL). The combined organic layers were washed with brine (2×80 mL), dried over anhydrous Na$_2$SO$_4$, filtered and concentrated under reduced pressure to give Intermediate 44 (830 mg, crude) as a yellow solid.

Example 26

Preparation of Intermediate 45-1

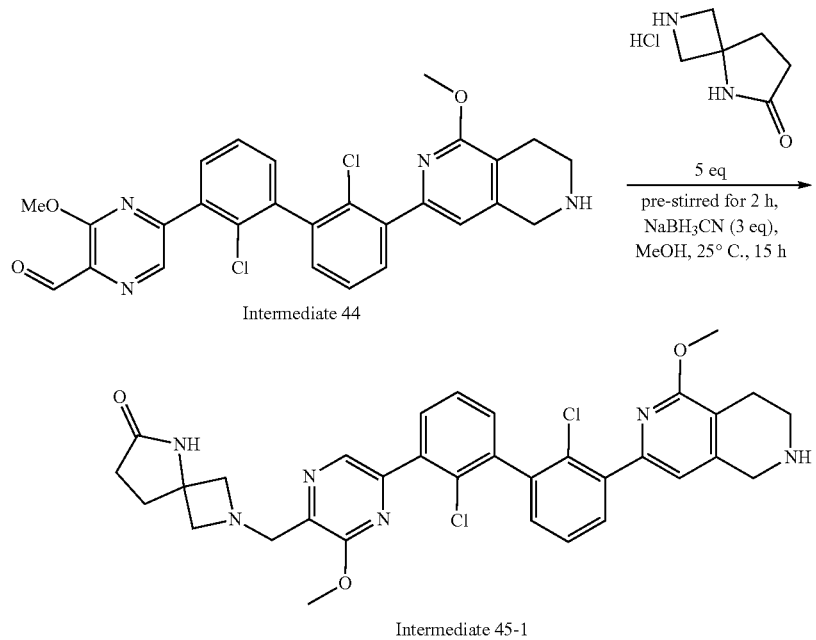

Intermediate 44

Intermediate 45-1

The solution of Intermediate 44 (400 mg, 767 μmol) and 2,5-diazaspiro[3.4]octan-6-one HCl salt (624 mg, 3.84 mmol) in MeOH (10 mL) was stirred at 25° C. for 2 h. To the pre-stirred solution was added NaBH₃CN (241 mg, 3.84 mmol) at 25° C. The mixture was stirred at 25° C. for 15 h, filtered and concentrated under reduced pressure to give a residue. The residue was purified by prep-HPLC to provide Intermediate 45-1 (85 mg, 99% purity) as a yellow solid. LCMS ($C_{33}H_{33}Cl_2N_6O_3^+$) (ES, m/z): 631.2 [M+H]⁺.

The intermediates shown in Table 12 were prepared by an analogous reaction protocol as was used for the preparation of Intermediate 45-1 using the appropriate starting materials.

TABLE 12

| Intermediate No. | Structure | Starting Materials |
|---|---|---|
| 45-2 | 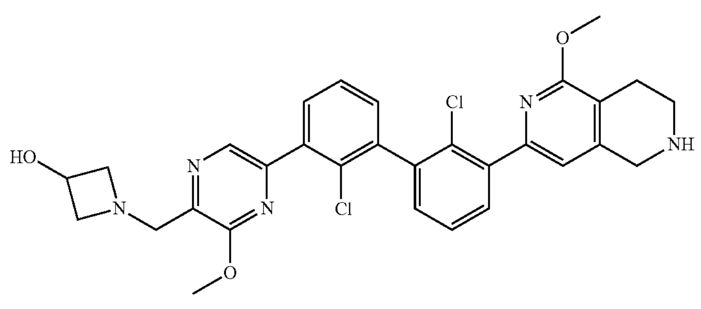 [SMILES: COc1nc(-c2cccc(-c3cccc(-c4cc5c(c(OC)n4)CCNC5)c3Cl)c2Cl)cnc1CN1CC(O)C1] | Intermediate 44<br>Azetidin-3-ol<br>hydrochloride |
| 45-3 | 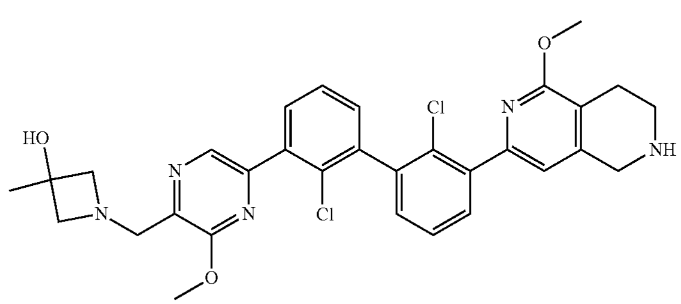 [SMILES: COc1nc(-c2cccc(-c3cccc(-c4cc5c(c(OC)n4)CCNC5)c3Cl)c2Cl)cnc1CN1CC(C)(O)C1] | Intermediate 44<br>3-Methylazetidin-3-ol<br>hydrochloride |

TABLE 12-continued
| Intermediate No. | Structure | Starting Materials |
|---|---|---|
| 45-4 | 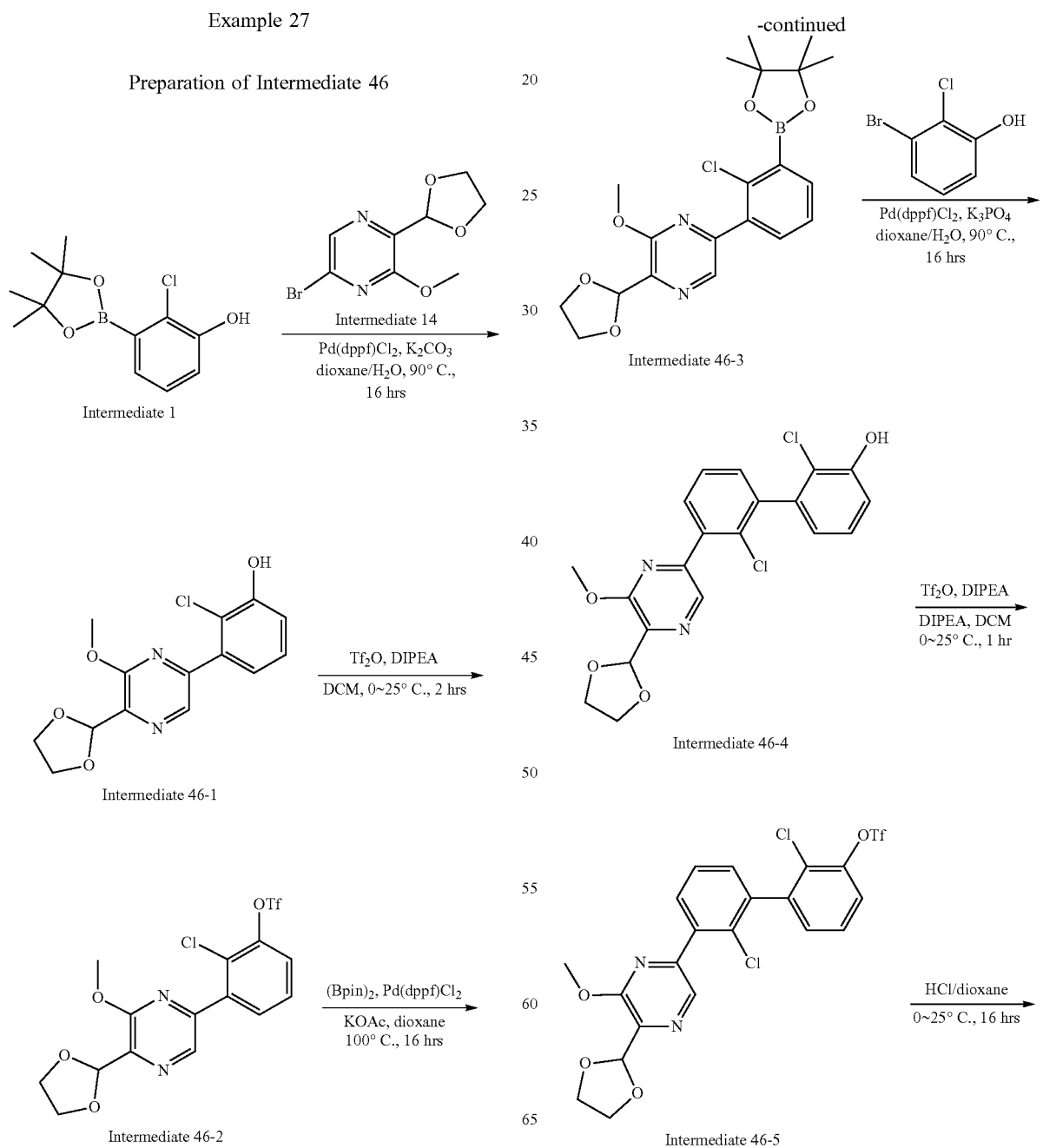 | Intermediate 44<br>3-(trifluoromethyl)azetidin-3-ol hydrochloride |
Example 27
Preparation of Intermediate 46

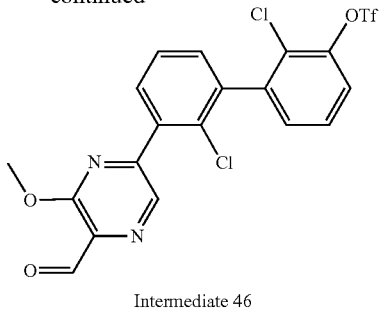

Intermediate 46

To a mixture of Intermediate 1 (128 g, 490 mmol), Intermediate 14 (124.8 g, 490.3 mmol, 1.0 eq.), $K_2CO_3$ (203 g, 1.47 mol) in dioxane (1300 mL) and $H_2O$ (130 mL) was added Pd(dppf)Cl$_2$ (17.9 g, 24.5 mmol). The mixture was degassed and purged with $N_2$ (3×). The mixture was stirred at 90° C. for 1 h, poured into $H_2O$ (1000 mL) and extracted with EtOAc (2×1000 mL). The combined organic layer was washed with brine (1000 mL), dried over MgSO$_4$ and filtered. The filtrate was concentrated to the crude product. The crude product was purified by column chromatography on silica gel to give Intermediate 46-1 as yellow oil. $^1$H NMR: (400 MHz, DMSO-d$_6$) δ 10.44 (s, 1H), 8.41 (s, 1H), 7.28 (s, 1H), 7.16-7.02 (m, 2H), 6.13 (s, 1H), 4.21-4.14 (m, 2H), 4.02 (br d, J=1.0 Hz, 3H), 3.97 (s, 3H).

To a solution of Intermediate 46-1 (150 g, 485.9 mmol, 1.0 eq.), DIPEA (188.4 g, 1.46 mol, 253.9 mL, 3.0 eq.) in DCM (1500 mL) was added Tf$_2$O (157.6 g, 558.8 mmol, 92.2 mL, 1.15 eq.) at 0~5° C. The mixture was stirred at 25° C. for 2 h, and then washed with aq. sat. NaHCO$_3$ (1500 mL). The aqueous layer was extracted with DCM (1000 mL). The combined organic layer was washed with brine (1000 mL), dried over MgSO$_4$ and concentrated to give a crude product. The crude product was purified by silica gel chromatography to give Intermediate 46-2 (150 g) as a brown solid. $^1$H NMR: (400 MHz, DMSO-d$_6$) δ 8.52 (s, 1H), 7.86 (dd, J=1.6, 7.7 Hz, 1H), 7.83-7.78 (m, 1H), 7.75-7.69 (m, 1H), 6.14 (s, 1H), 4.21-4.13 (m, 2H), 4.08-4.01 (m, 2H), 3.99 (s, 3H).

To a solution of Intermediate 46-2 (90 g, 204.2 mmol, 1.0 eq.), (Bpin)$_2$ (77.8 g, 306.3 mmol, 1.5 eq.), KOAc (60.1 g, 612.5 mmol, 3.0 eq.) in dioxane (900 mL) was added Pd(dppf)Cl$_2$ (7.47 g, 10.2 mmol, 0.05 eq.) and then was degassed and purged with $N_2$ (3×). The mixture was stirred at 100° C. for 16 h, filtered and concentrated to give a residue. The crude product was purified by column chromatography on silica gel to give a residue. The residue was triturated with PE (1000 mL) for 1 h and then filtered. The cake was dried under reduced pressure to provide Intermediate 46-3 as a white solid. $^1$H NMR: (400 MHz, DMSO-d$_6$) δ 8.43 (s, 1H), 7.81-7.61 (m, 2H), 7.59-7.35 (m, 1H), 4.20-4.14 (m, 2H), 4.02 (s, 2H), 3.97 (s, 3H), 1.34 (s, 12H).

To a mixture of Intermediate 46-3 (82.0 g, 196 mmol), 3-bromo-2-methylphenol (40.6 g, 195.8 mmol) and K$_3$PO$_4$ (125 g, 588 mmol, 3.0 eq.) in dioxane (820 mL) and H$_2$O (82 mL) was added Pd(dppf)Cl$_2$ (7.17 g, 9.79 mmol). The mixture was degassed and purged with $N_2$ (3×). After stirring at 90° C. for 16 h, the mixture was cooled to 25° C. and filtered. The filtrate was poured into $H_2O$ (500 mL) and extracted with EtOAc (2×1000 mL). The combined organic layer was washed with brine (500 mL), dried over MgSO$_4$ and filtered. The filtrate was concentrated to the crude product. The crude product was purified by silica gel chromatography to provide Intermediate 46-4 as a white solid. $^1$H NMR: (400 MHz, DMSO-d$_6$) δ 10.38-10.29 (m, 1H), 8.47 (s, 1H), 7.71 (dd, J=1.7, 7.7 Hz, 1H), 7.57 (t, J=7.6 Hz, 1H), 7.44 (dd, J=1.6, 7.6 Hz, 1H), 7.29-7.16 (m, 1H), 7.05 (dd, J=1.4, 8.2 Hz, 1H), 6.81 (dd, J=1.4, 7.5 Hz, 1H), 6.14 (s, 1H), 4.20-4.14 (m, 2H), 4.03 (d, J=6.6 Hz, 2H), 3.99 (s, 3H).

To a solution of Intermediate 46-4 (136 g, 324 mmol) and DIPEA (170 mL, 973 mmol) in DCM (1400 mL) was added dropwise Tf$_2$O (64.2 mL, 389 mmol.) at 0-5° C. The mixture was stirred at 25° C. for 1 h, washed with aqueous sat. NaHCO$_3$ (1000 mL) and separated. The aqueous layer was extracted with DCM (500 mL). The combined organic layer was washed with brine (500 mL), dried over MgSO$_4$ and concentrated to give the crude product. The crude product was purified by silica gel chromatography to give Intermediate 46-5 (126 g) as a white solid. $^1$H NMR: (400 MHz, DMSO-d$_6$) δ 8.49 (s, 1H), 7.86-7.73 (m, 2H), 7.72-7.59 (m, 3H), 7.59-7.53 (m, 1H), 6.14 (s, 1H), 4.20-4.14 (m, 2H), 4.06-4.01 (m, 2H), 3.99 (s, 3H).

To a solution of Intermediate 46-5 (25.0 g, 45.3 mmol) in dioxane (260 mL) and $H_2O$ (50 mL) was added dropwise HCl/dioxane (4.0 M, 1000 mL) at 0~10° C. The mixture was stirred at 25° C. for 16 h. The reaction was quenched with $H_2O$ (500 mL), and the mixture extracted with EtOAc (2×500 mL). The combined organic layer was washed with brine (500 mL), dried over MgSO$_4$ and filtered. The filtrate was concentrated to the crude product. The crude product was purified by column chromatography on silica gel to give Intermediate 46 (17.8 g) as a yellow oil. $^1$H NMR: (400 MHz, DMSO-d$_6$) δ 10.18 (s, 1H), 10.25-10.13 (m, 1H), 8.79 (s, 1H), 7.88 (dd, J=1.8, 7.6 Hz, 1H), 7.78 (dd, J=1.5, 8.3 Hz, 1H), 7.72-7.65 (m, 2H), 7.65-7.58 (m, 2H), 4.09 (s, 3H).

Example 28

Preparation of Intermediate 47-1

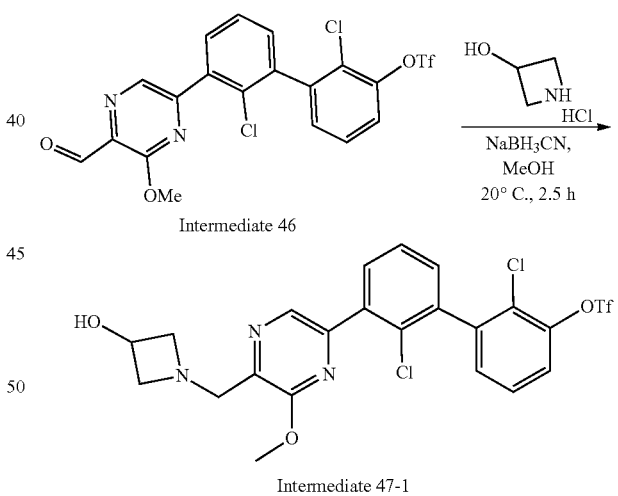

Intermediate 47-1

A mixture of Intermediate 46 (6 g, 11.83 mmol) and 3-Hydroxyazetidine Hydrochloride (2.59 g, 23.7 mmol) in MeOH (60 mL) was stirred at 20° C. for 30 mins. NaBH$_3$CN (2.23 g, 35.5 mmol) was added into the mixture. The mixture was stirred at 20° C. for 2 h, filtered and concentrated to give a residue, which was purified by flash column to give Intermediate 47-1 (6.3 g) as a red solid. LCMS ($C_{22}H_{19}Cl_2F_3N_3O_5S^+$) (ES, m/z): 565.9 [M+H]$^+$. $^1$H NMR (400 MHz, CDCl$_3$) δ 8.47 (s, 1H), 7.69 (dd, J=1.7, 7.7 Hz, 1H), 7.52-7.42 (m, 3H), 7.41-7.32 (m, 2H), 4.40 (dt, J=2.6, 4.6 Hz, 1H), 4.05 (s, 3H), 3.96 (s, 2H), 3.13-3.04 (m, 1H), 2.96-2.82 (m, 2H), 2.69-2.61 (m, 1H), 2.23 (tdd, J=6.7, 8.4, 13.6 Hz, 1H), 1.88-1.77 (m, 1H).

Example 29

Preparation of Intermediate 48-1

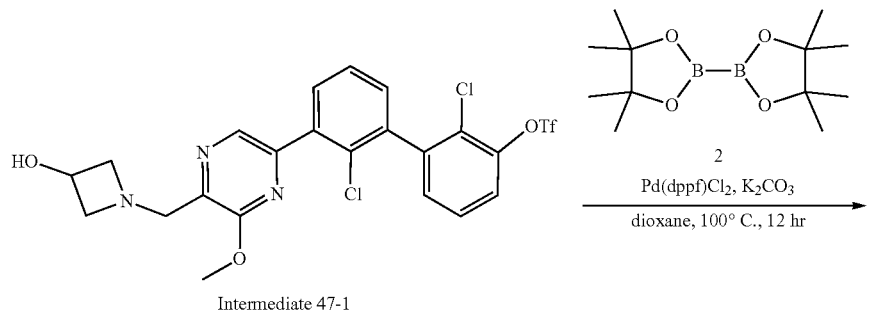

Intermediate 47-1

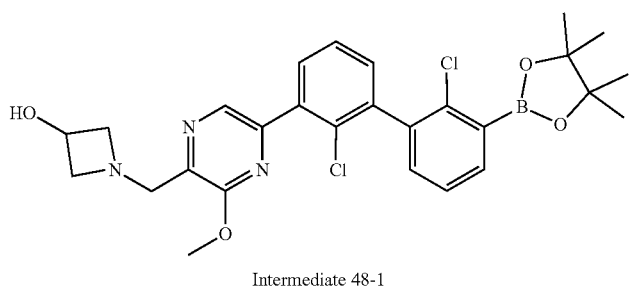

Intermediate 48-1

A mixture of Intermediate 47-1 (360 mg, 638 mol), (Bpin)$_2$ (486 mg, 1.91 mmol), Pd(dppf)Cl$_2$·CH$_2$Cl$_2$ (52.09 mg, 63.79 μmol) and KOAc (250 mg, 2.55 mmol) in dioxane (7.2 mL) was stirred at 80° C. for 12 h under N$_2$ atmosphere. The mixture was filtered and concentrated to give a residue, which was purified by flash column to give Intermediate 48-1 (280 mg) as a black-brown solid. LCMS (C$_{27}$H$_{31}$BCl$_2$N$_3$O$_4^+$) (ES, m/z): 542.3 [M+H]$^+$.

Preparation of Compounds

Example 1

Preparation of Compound A-1

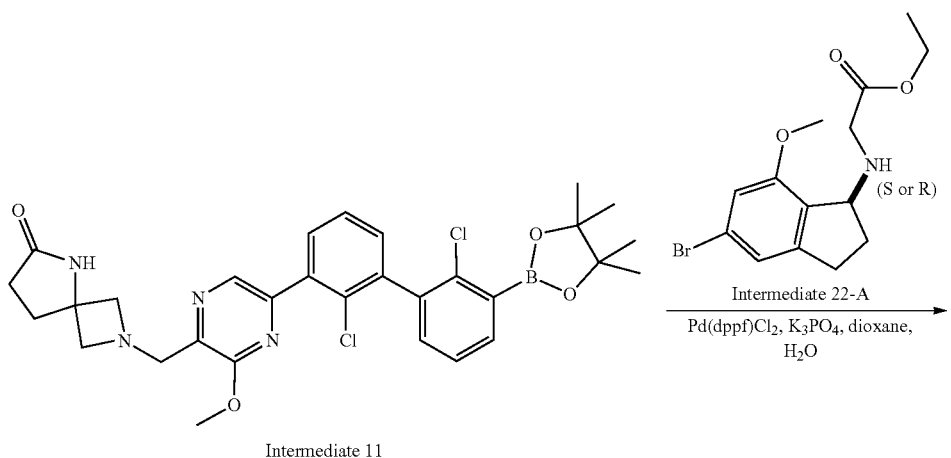

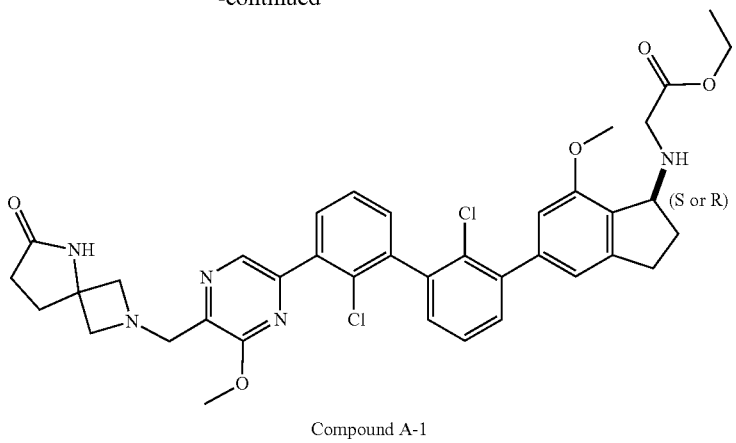

Compound A-1

A mixture of compound Intermediate 22-A (50 mg, 152 mol), Intermediate 11 (119 mg, 80% purity), Pd(dppf)Cl₂ (11.15 mg, 15 μmol) and K₃PO₄ (97 mg, 457 μmol) in dioxane (0.5 mL) and H₂O (0.05 mL) was stirred at 110° C. for 2 h under N₂ atmosphere. The mixture was filtered and concentrated to give a residue, which was purified by prep-HPLC (column: Phenomenex Gemini-NX C18 75*30 mm*3 um; mobile phase: water (10 mM NH₄HCO₃)-ACN; B %: 40%-80%, 14 min; 100% B Hold Time (2 min); Flow Rate (25 mL/min); Injections: 1) to give Compound A-1 (40 mg, 96% purity) as an off-white solid.

The compounds shown below in Table 2 were prepared by an analogous reaction protocol as was used for the preparation of Compound A-1 using the appropriate starting materials.

TABLE 2

| Cmpd No. | Structure | Starting materials |
|---|---|---|
| A-2 | 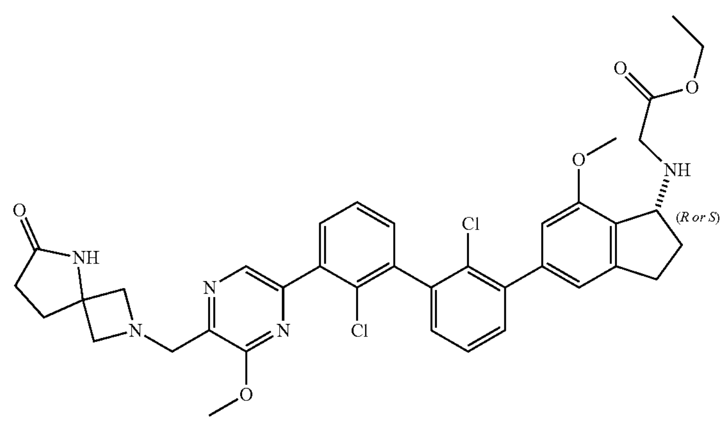 [SMILES: CCOC(=O)CN[C@@H]1CCc2cc(-c3cccc(-c4cccc(-c5cnc(CN6CC7(CCC(=O)N7)C6)c(OC)n5)c4Cl)c3Cl)cc(OC)c21] | Intermediate 11<br>Intermediate 22-B |
| A-3 | 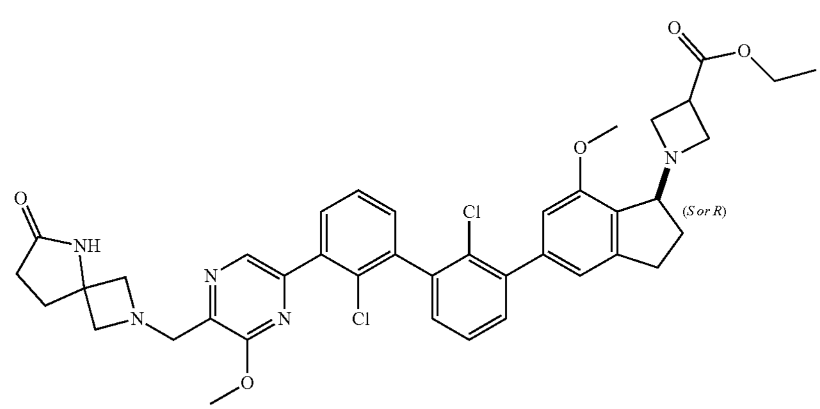 [SMILES: CCOC(=O)C1CN([C@H]2CCc3cc(-c4cccc(-c5cccc(-c6cnc(CN7CC8(CCC(=O)N8)C7)c(OC)n6)c5Cl)c4Cl)cc(OC)c32)C1] | Intermediate 11<br>Intermediate 23-A |

TABLE 2-continued

| Cmpd No. | Structure | Starting materials |
|---|---|---|
| A-4 | 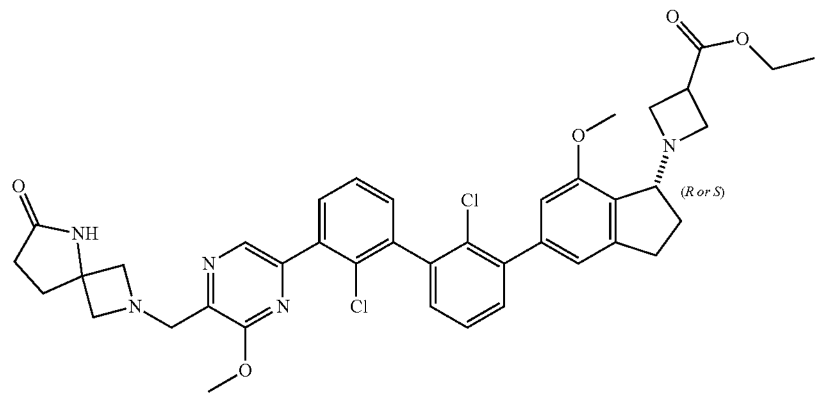 [SMILES: CCOC(=O)C1CN([C@@H]2CCc3cc(-c4cccc(-c5cccc(-c6cnc(CN7CC8(CCC(=O)N8)C7)c(OC)n6)c5Cl)c4Cl)cc(OC)c32)C1] | Intermediate 11<br>Intermediate 23-b |
| A-5 | 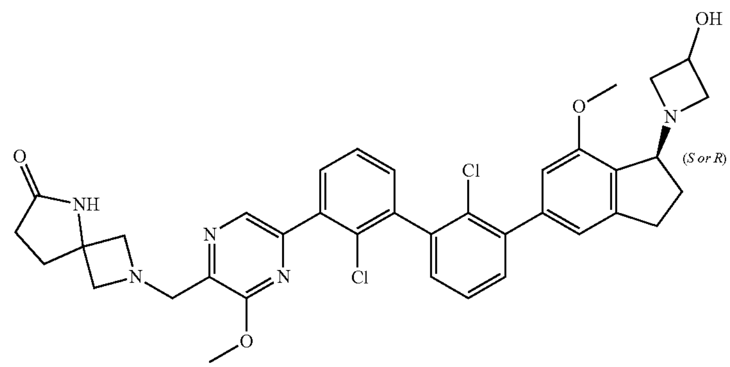 [SMILES: COc1cc(-c2cccc(-c3cccc(-c4cnc(CN5CC6(CCC(=O)N6)C5)c(OC)n4)c3Cl)c2Cl)cc2c1[C@@H](N1CC(O)C1)CC2] | Intermediate 11<br>Intermediate 24-A |
| A-6 | 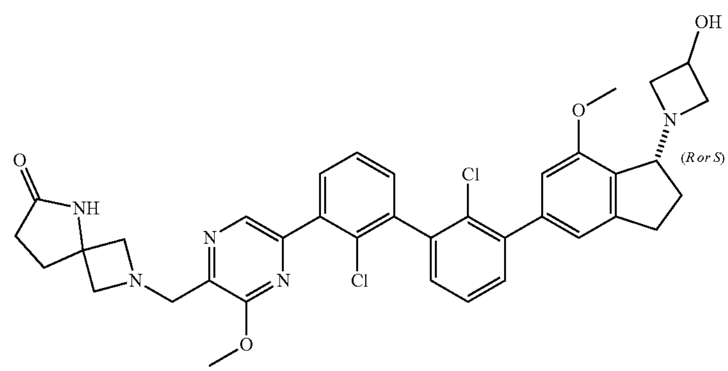 [SMILES: COc1cc(-c2cccc(-c3cccc(-c4cnc(CN5CC6(CCC(=O)N6)C5)c(OC)n4)c3Cl)c2Cl)cc2c1[C@H](N1CC(O)C1)CC2] | Intermediate 11<br>Intermediate 24-B |
| A-7 | 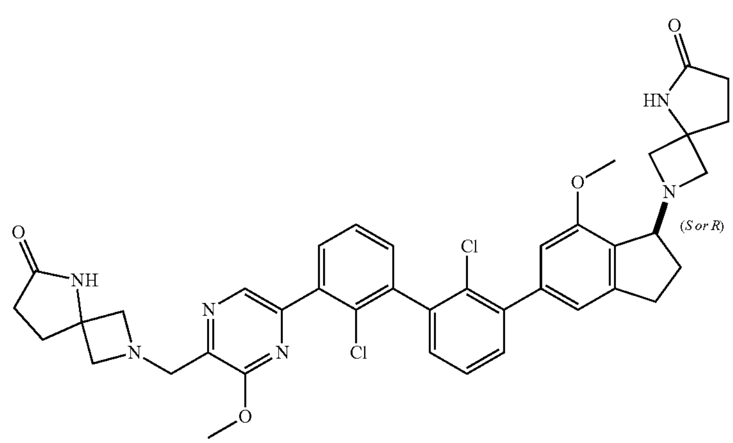 [SMILES: COc1cc(-c2cccc(-c3cccc(-c4cnc(CN5CC6(CCC(=O)N6)C5)c(OC)n4)c3Cl)c2Cl)cc2c1[C@@H](N1CC3(CCC(=O)N3)C1)CC2] | Intermediate 11<br>Intermediate 25-A |

TABLE 2-continued

| Cmpd No. | Structure | Starting materials |
|---|---|---|
| A-8 | 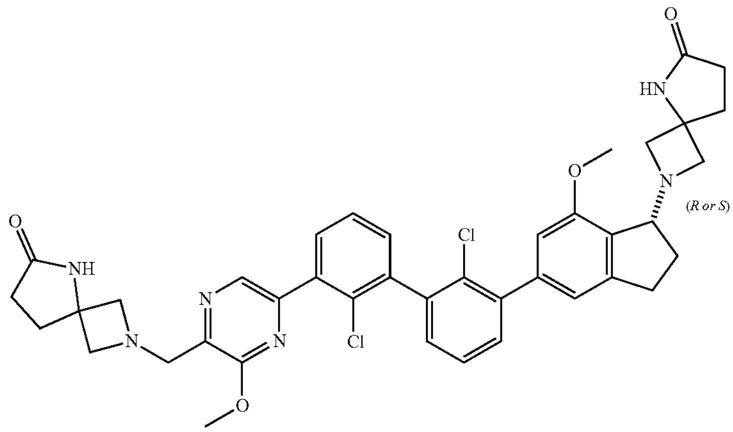 [SMILES: COc1cc(-c2cccc(-c3cccc(-c4cnc(CN5CC6(CCC(=O)N6)C5)c(OC)n4)c3Cl)c2Cl)cc2c1[C@H](N1CC3(CCC(=O)N3)C1)CC2] | Intermediate 11<br>Intermediate 25-B |
| A-9 | 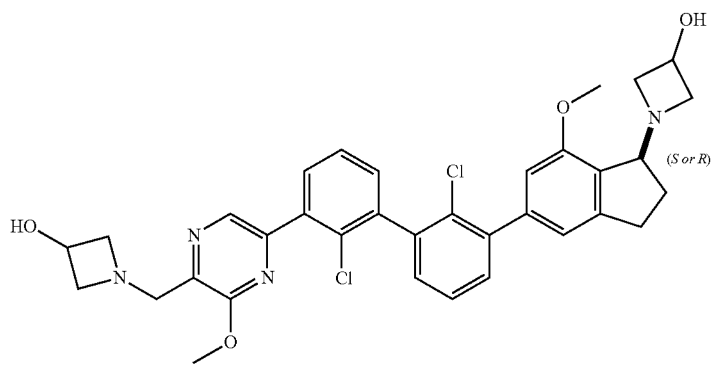 [SMILES: COc1cc(-c2cccc(-c3cccc(-c4cnc(CN5CC(O)C5)c(OC)n4)c3Cl)c2Cl)cc2c1[C@@H](N1CC(O)C1)CC2] | Intermediate 13<br>Intermediate 24-A |
| A-10 | 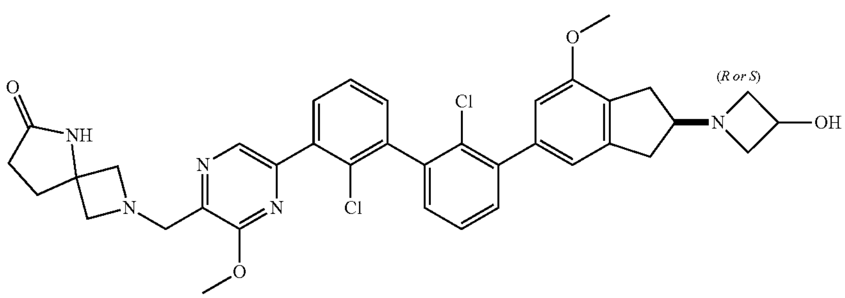 [SMILES: COc1cc(-c2cccc(-c3cccc(-c4cnc(CN5CC6(CCC(=O)N6)C5)c(OC)n4)c3Cl)c2Cl)cc2c1C[C@@H](N1CC(O)C1)C2] | Intermediate 11<br>Intermediate 26-A |
| A-11 | 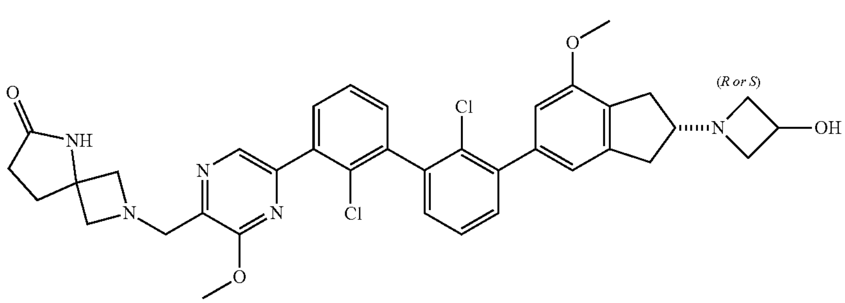 [SMILES: COc1cc(-c2cccc(-c3cccc(-c4cnc(CN5CC6(CCC(=O)N6)C5)c(OC)n4)c3Cl)c2Cl)cc2c1C[C@H](N1CC(O)C1)C2] | Intermediate 11<br>Intermediate 26-B |

TABLE 2-continued
| Cmpd No. | Structure | Starting materials |
|---|---|---|
| A-12 | 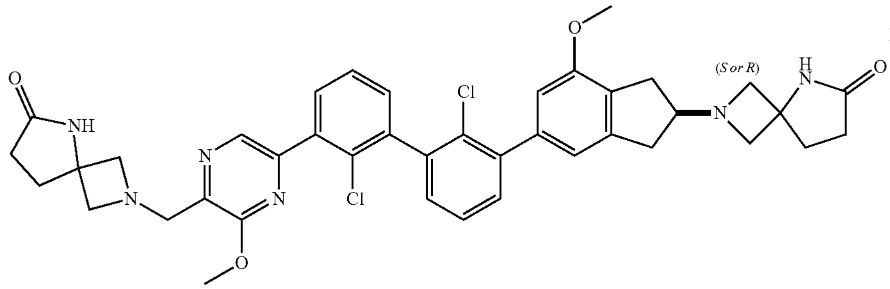 | Intermediate 11<br>Intermediate 27-A |
| A-13 | 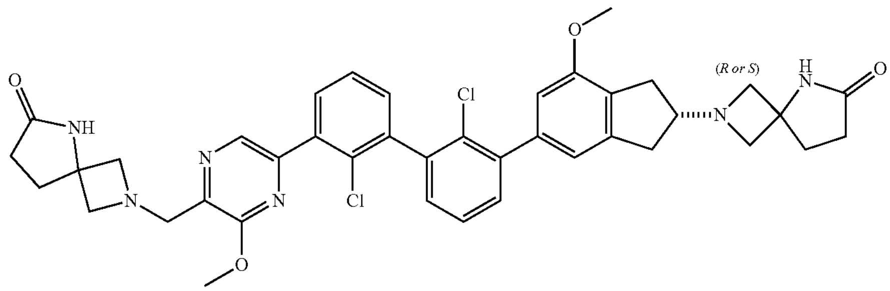 [SMILES: COc1cc(-c2cccc(-c3cccc(-c4cnc(CN5CC6(CCC(=O)N6)C5)c(OC)n4)c3Cl)c2Cl)cc2c1C[C@H](N1CC3(CCC(=O)N3)C1)C2] | Intermediate 11<br>Intermediate 27-B |
Example 2
Preparation of Compound B-1
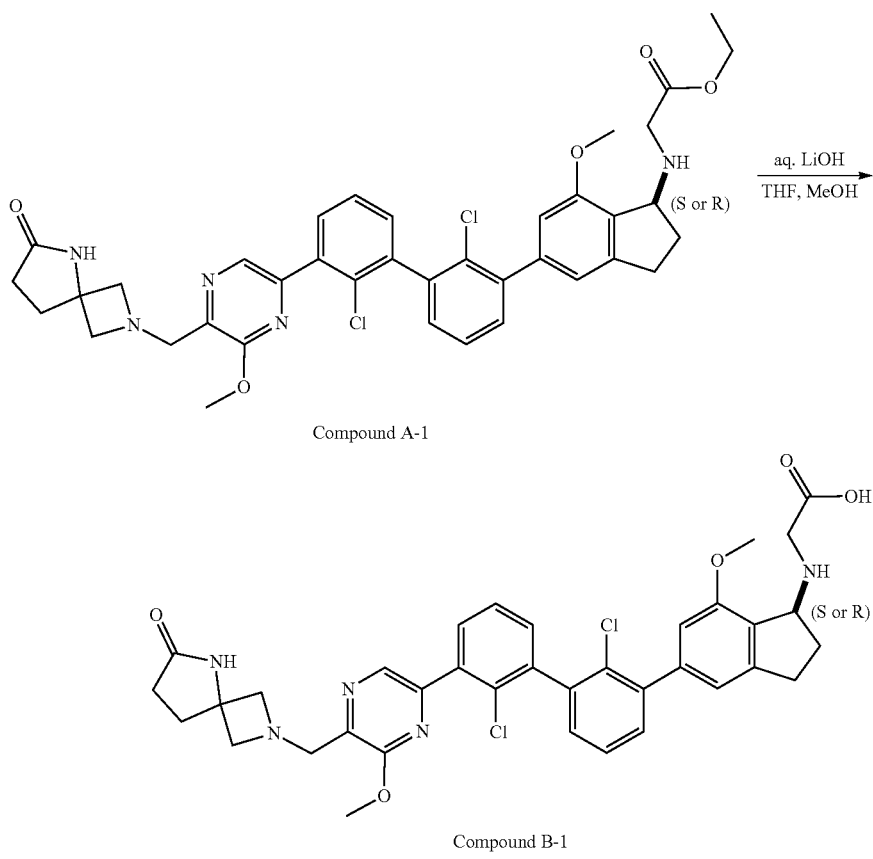
Compound A-1
Compound B-1

A mixture of Compound A-1 (20 mg, 27.9 μmol) and LiOH·H₂O (5 mg, 112 μmol) in H₂O (0.5 mL), MeOH (1.5 mL) and THF (1 mL) was stirred at 40° C. for 2 H. The mixture was concentrated. The residue was adjusted to pH 5~6 with 1N aq. HCl, and then purified by prep-HPLC (column: Phenomenex Gemini-NX C18 75*30 mm*3 um; mobile phase: water (10 mM NH₄HCO₃)-ACN; B %: 13%-53%, 14 min; 100% B Hold Time (2 min); Flow Rate (25 mL/min); Injections: 1) to give compound B-1 (18 mg, 93% yield, 99% purity) as a white solid.

The compounds shown below in Table 3 were prepared by an analogous reaction protocol as was used for the preparation of Compound B-1 using the appropriate starting materials.

TABLE 3

| Cmpd No. | Structure | Starting materials |
|---|---|---|
| B-2 | 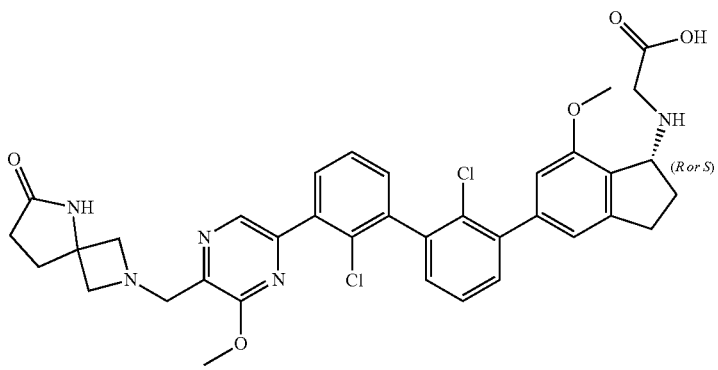 [SMILES: COc1cc(-c2cccc(-c3cccc(-c4cnc(CN5CC6(CCC(=O)N6)C5)c(OC)n4)c3Cl)c2Cl)cc2c1[C@H](NCC(=O)O)CC2] | Compound A-2 |
| B-3 | 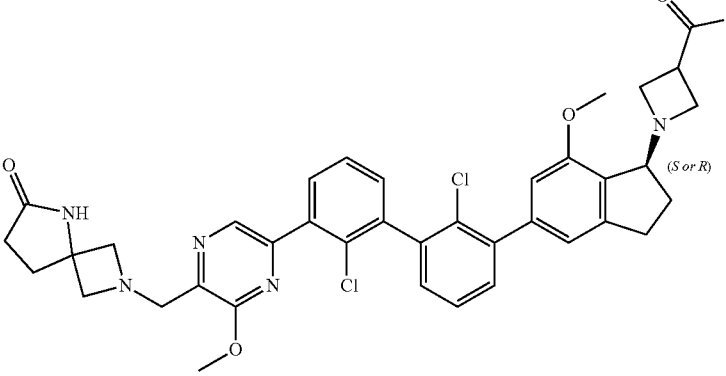 | Compound A-3 |
| B-4 | 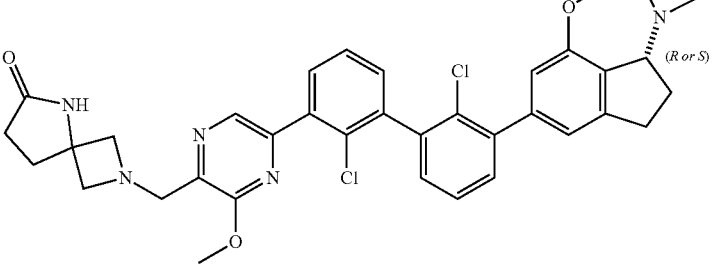 | Compound A-4 |

Example 3

Preparation of Compound C-1

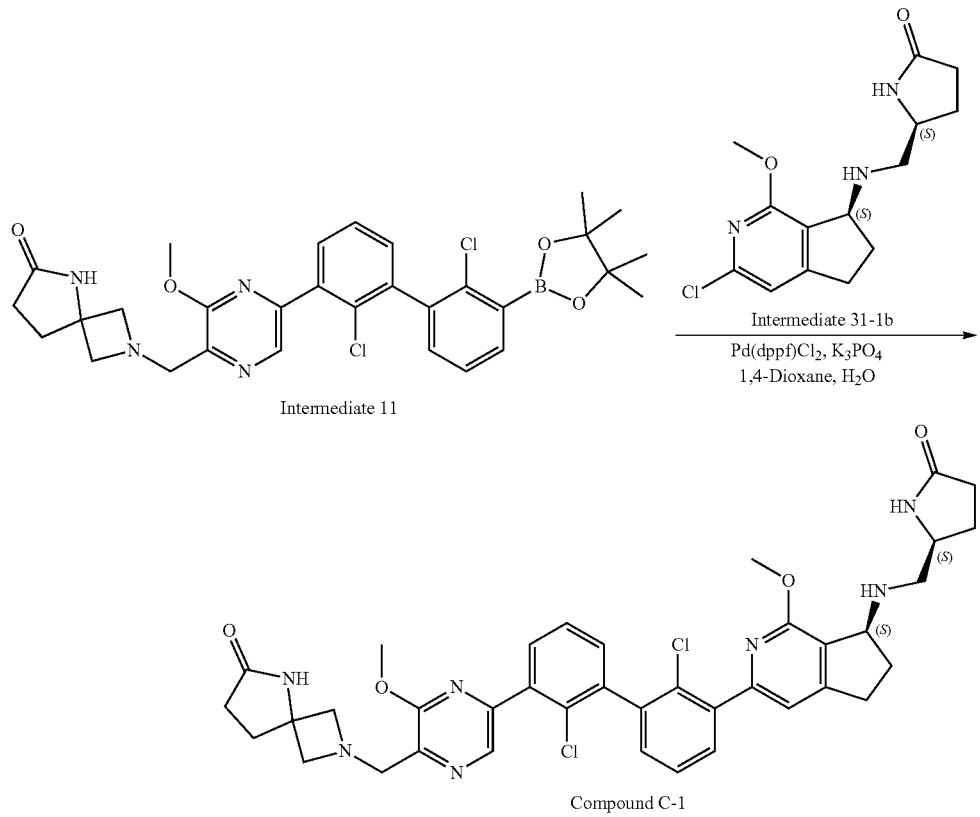

A mixture of Intermediate 31-1b (1.0 g, 3.38 mmol), Intermediate 11 (2.3 g, 3.86 mmol), Pd(dppf)Cl$_2$ (247 mg, 338 μmol) and K$_3$PO$_4$ (2.15 g, 10 mmol) in 1,4-dioxane (35 mL) and H$_2$O (3.5 mL) was degassed and purged with N$_2$ (3×). After stirring at 110° C. for 2 h under N$_2$ atmosphere, the mixture was filtered and concentrated in vacuo to give a residue. The residue was diluted with H$_2$O (150 mL) and extracted with EtOAc (3×120 mL). The combined organic layers were washed with brine (100 mL), dried over anhydrous Na$_2$SO$_4$, filtered and concentrated under reduced pressure to give a residue, which was purified by prep-HPLC to provide Compound C-1 as a white solid formate salt. LCMS (C$_{38}$H$_{40}$Cl$_2$N$_7$O$_4{}^+$) (ES, m/z): 728.5 [M+H]$^+$.

The compounds shown in Table 13 were prepared by an analogous reaction protocol as was used for the preparation of Compound C-1 using the appropriate starting materials.

TABLE 13

| Cmpd No. | Structure | Salt | Starting Materials |
|---|---|---|---|
| C-2 | (structure shown) | | Intermediate 11 Intermediate 31-1a |

TABLE 13-continued

| Cmpd No. | Structure | Salt | Starting Materials |
|---|---|---|---|
| C-3 | 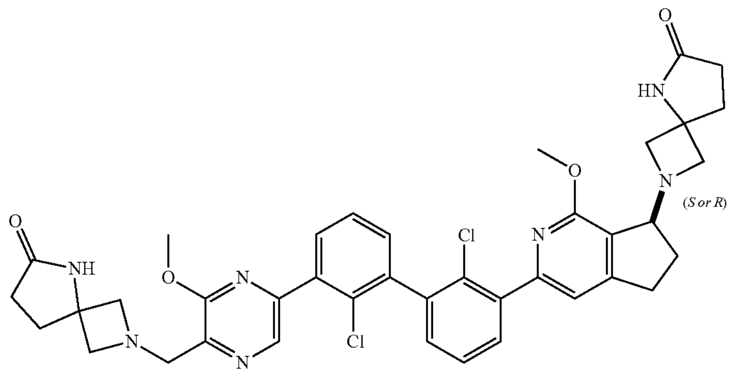 [SMILES: COc1nc(-c2cccc(-c3cccc(-c4cc5c(c(OC)n4)[C@@H](N4CC6(CCC(=O)N6)C4)CC5)c3Cl)c2Cl)cnc1CN1CC2(CCC(=O)N2)C1] | | Intermediate 11<br>Intermediate 31-2a |
| C-4 | 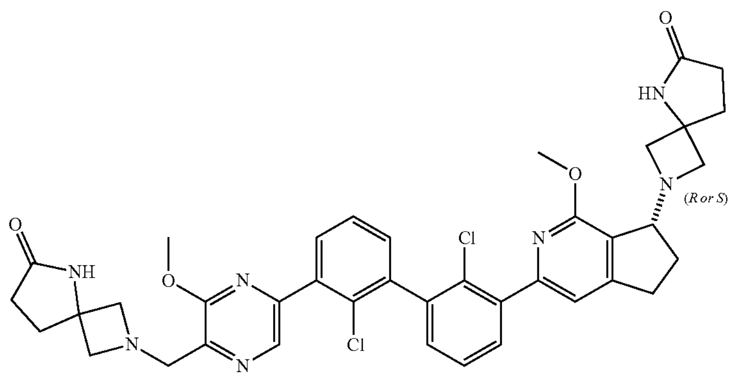 [SMILES: COc1nc(-c2cccc(-c3cccc(-c4cc5c(c(OC)n4)[C@H](N4CC6(CCC(=O)N6)C4)CC5)c3Cl)c2Cl)cnc1CN1CC2(CCC(=O)N2)C1] | | Intermediate 11<br>Intermediate 31-2b |
| C-5 | 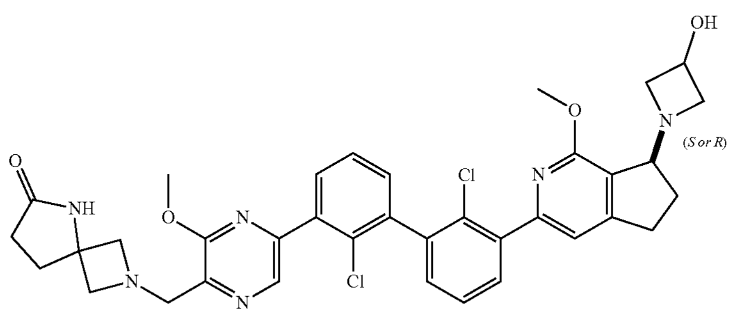 [SMILES: COc1nc(-c2cccc(-c3cccc(-c4cc5c(c(OC)n4)[C@@H](N4CC(O)C4)CC5)c3Cl)c2Cl)cnc1CN1CC2(CCC(=O)N2)C1] | | Intermediate 11<br>Intermediate 31-4a |
| C-6 | 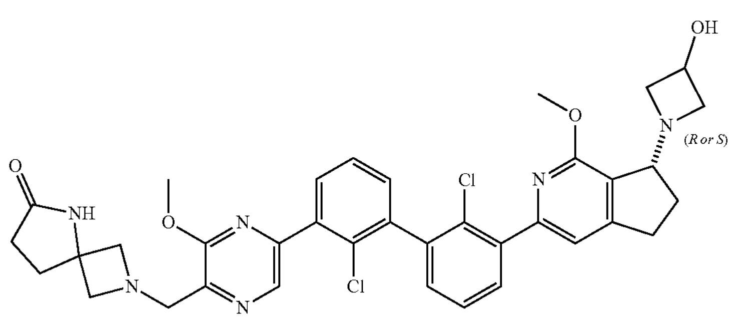 [SMILES: COc1nc(-c2cccc(-c3cccc(-c4cc5c(c(OC)n4)[C@H](N4CC(O)C4)CC5)c3Cl)c2Cl)cnc1CN1CC2(CCC(=O)N2)C1] | | Intermediate 11<br>Intermediate 31-4b |

TABLE 13-continued

| Cmpd No. | Structure | Salt | Starting Materials |
|---|---|---|---|
| C-7 | 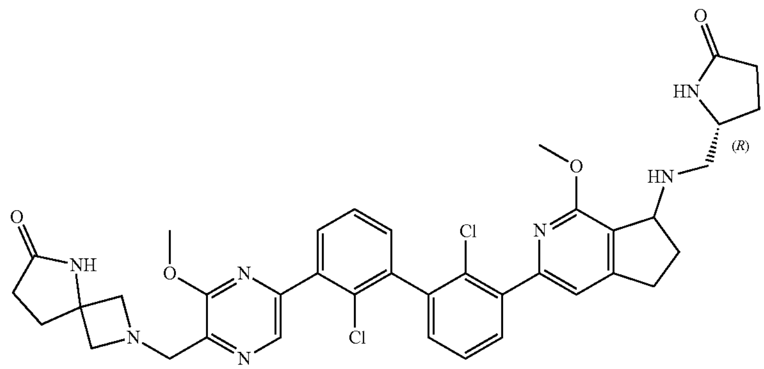 | | Intermediate 11<br>Intermediate 33-2 |
| C-8 | 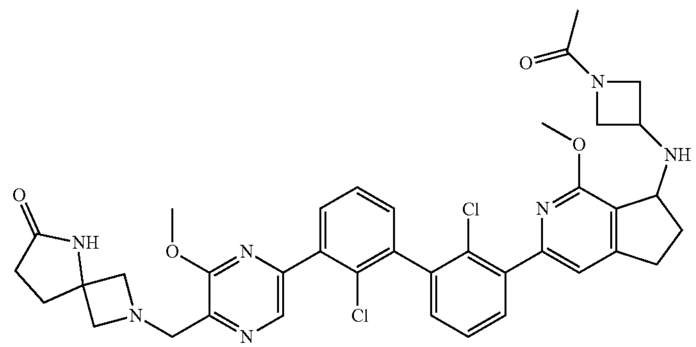 [SMILES: COc1nc(-c2cccc(-c3cccc(-c4cc5c(c(OC)n4)C(NC4CN(C(C)=O)C4)CC5)c3Cl)c2Cl)cnc1CN1CC2(CCC(=O)N2)C1] | | Intermediate 11<br>Intermediate 33-3 |
| C-9 | 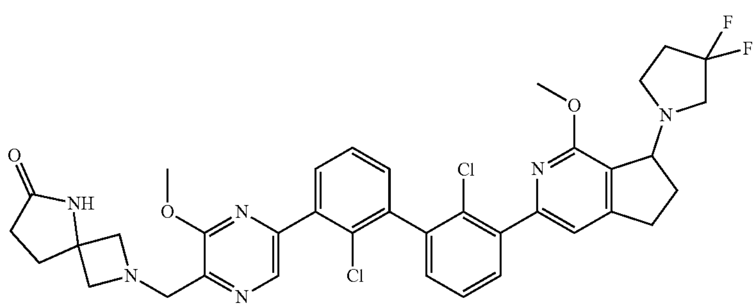 [SMILES: COc1nc(-c2cccc(-c3cccc(-c4cc5c(c(OC)n4)C(N4CCC(F)(F)C4)CC5)c3Cl)c2Cl)cnc1CN1CC2(CCC(=O)N2)C1] | | Intermediate 11<br>Intermediate 33-4 |
| C-10 | 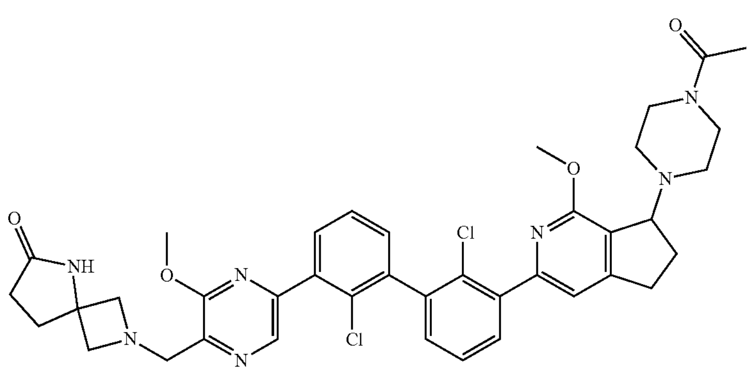 [SMILES: COc1nc(-c2cccc(-c3cccc(-c4cc5c(c(OC)n4)C(N4CCN(C(C)=O)CC4)CC5)c3Cl)c2Cl)cnc1CN1CC2(CCC(=O)N2)C1] | | Intermediate 11<br>Intermediate 33-5 |

TABLE 13-continued

| Cmpd No. | Structure | Salt | Starting Materials |
|---|---|---|---|
| C-11 | 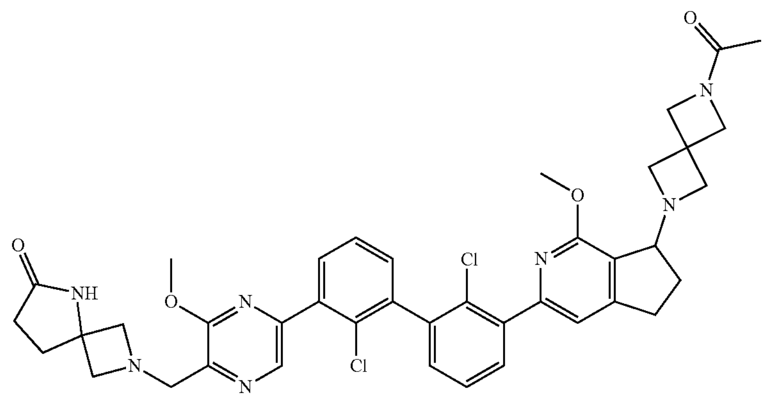 [SMILES: COc1nc(-c2cccc(-c3cccc(-c4cc5c(c(OC)n4)C(N4CC6(CN(C(C)=O)C6)C4)CC5)c3Cl)c2Cl)cnc1CN1CC2(CCC(=O)N2)C1] | 1 eq. of formate | Intermediate 11 Intermediate 33-1 |
| C-12 | 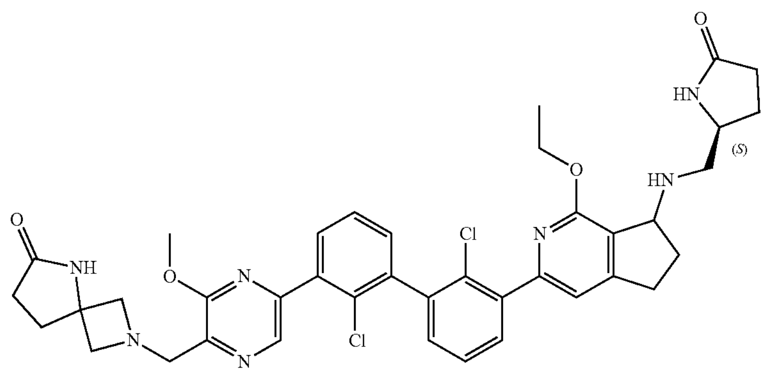 | 1 eq. of formate | Intermediate 11 Intermediate 36-1 |
| C-13 | 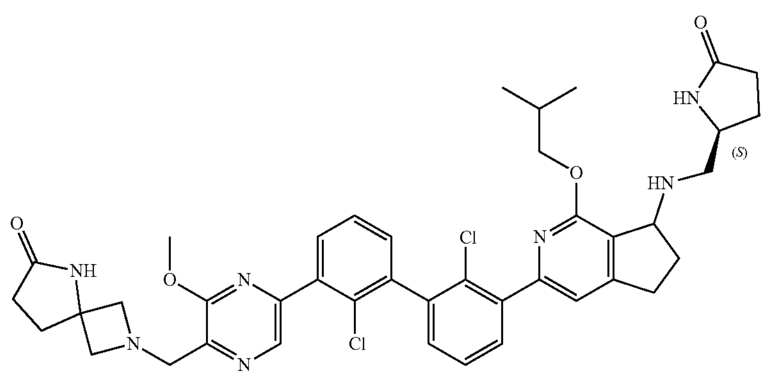 | 1 eq. of formate | Intermediate 11 Intermediate 36-2 |
| C-14 | 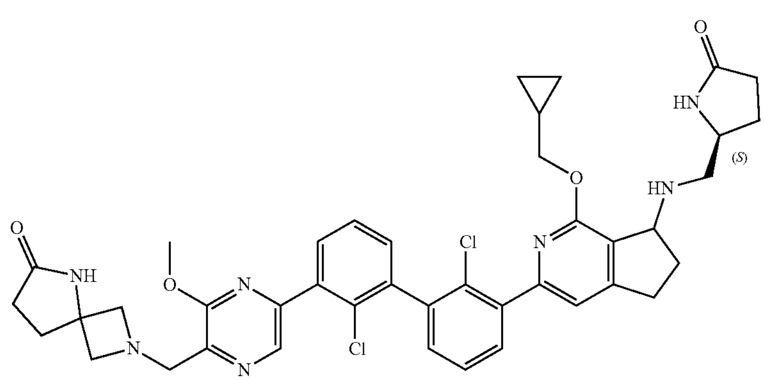 | 1 eq. of formate | Intermediate 11 Intermediate 36-3 |

TABLE 13-continued

| Cmpd No. | Structure | Salt | Starting Materials |
|---|---|---|---|
| C-15 | 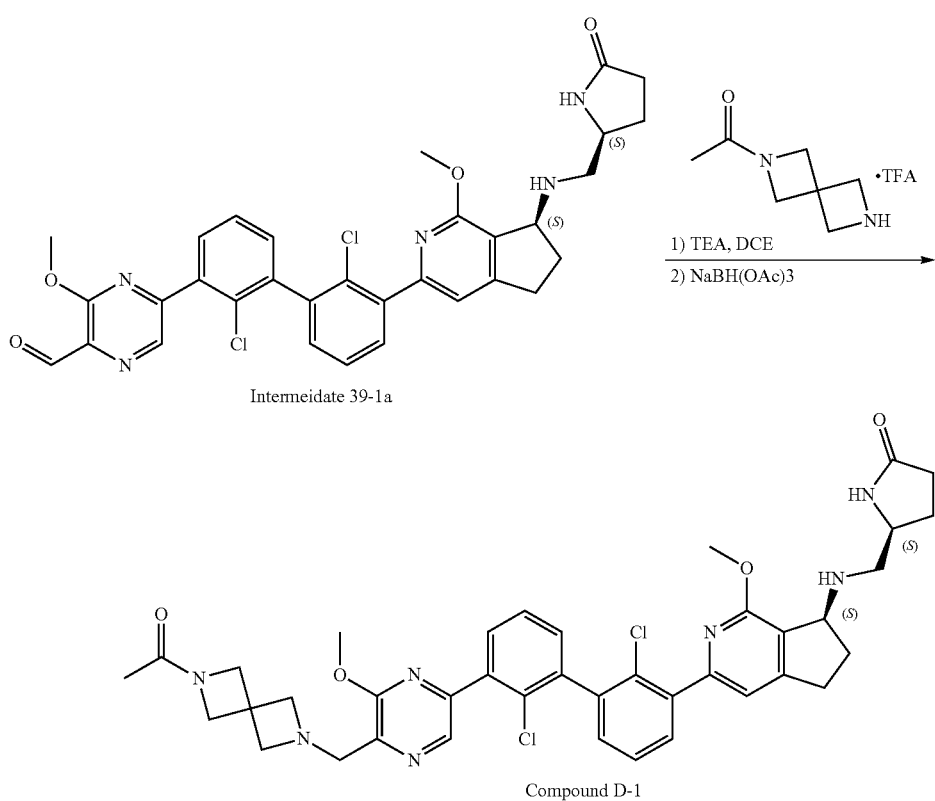 | 1 eq. of formate | Intermediate 11 Intermediate 36-4 |

Example 4

Preparation of Compound D-1 mg) as a white solid. LCMS ($C_{39}H_{42}Cl_2N_7O_4^+$) (ES, m/z): 742.6 [M+H]$^+$. $^1$H NMR (400 MHz, CDCl$_3$) δ 8.49 (s, 1H), 7.63 (dd, J=1.0, 7.6 Hz, 2H), 7.50-7.37 (m, 3H), 7.33 (dd, J=1.7, 7.6 Hz, 1H), 7.20 (d, J=3.3 Hz, 1H), 6.09 (br s, 1H), 4.42 (dd, J=4.9, 6.9 Hz, 1H), 4.24 (s, 2H), 4.08 (s, 2H), 4.04 (d, J=0.8 Hz, 6H), 3.83 (s, 3H), 3.67-3.60 (m, 2H), 3.59-3.52 (m, 2H), 3.15-3.04 (m, 1H), 2.97-2.81 (m, 2H), 2.58 (dd, J=8.9, 11.8 Hz, 1H), 2.44-2.21 (m, 4H), 1.97 (ddd, J=4.7, 8.7, 13.5 Hz, 2H), 1.85 (s, 3H), 1.82-1.74 (m, 2H).

A mixture of Intermediate 39-1a (90 mg, 146 mol), 1-(2,6-diazaspiro[3.3]heptan-2-yl)ethenone TFA salt (111 mg, 437 mol), TEA (61 uL, 437 μmol) in DCE (1 mL) was stirred at 25° C. for 1 h. NaBH(OAc)$_3$ (93 mg, 437 μmol) was added into the mixture. After stirring at 25° C. for 3 h, the reaction was quenched H$_2$O (5 mL) and extracted with DCM (3×6 mL). The combined organic layers were washed with brine (2×5 mL), dried over Na$_2$SO$_4$, filtered and concentrated under reduced pressure to give a residue, which was purified by prep-HPLC to give Compound D-1 (3.40

The compounds shown in Table 14 were prepared by an analogous reaction protocol as was used for the preparation of Compound D-1 using the appropriate starting materials.

TABLE 14
| Cmpd No. | Structure | Salt | Starting Materials |
|---|---|---|---|
| D-2 | 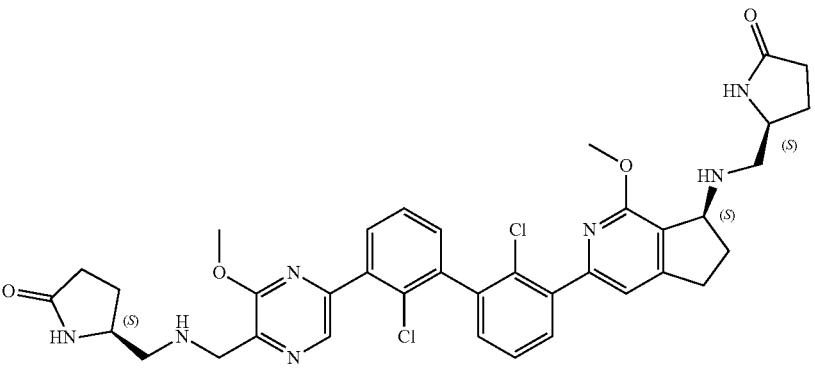 | 1 eq. of formate | Intermediate 39-1a (5)S-5-(aminomethyl)pyrrolidin-2-on HCl salt |
| D-3 | 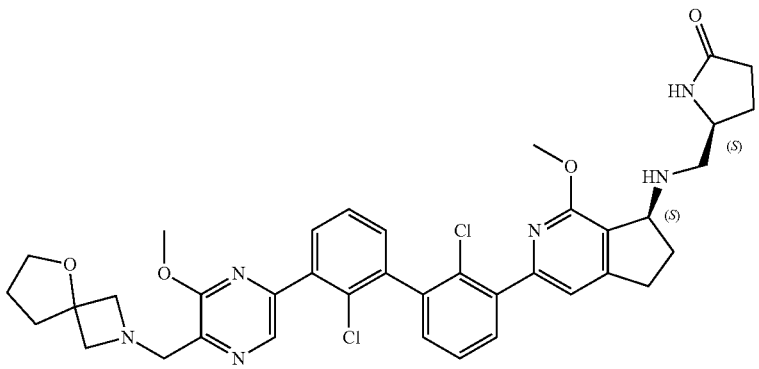 | 1 eq. of formate | Intermediate 39-1a 5-oxa-2-azaspiro[3.4]octane hydrochloride |
| D-4 | 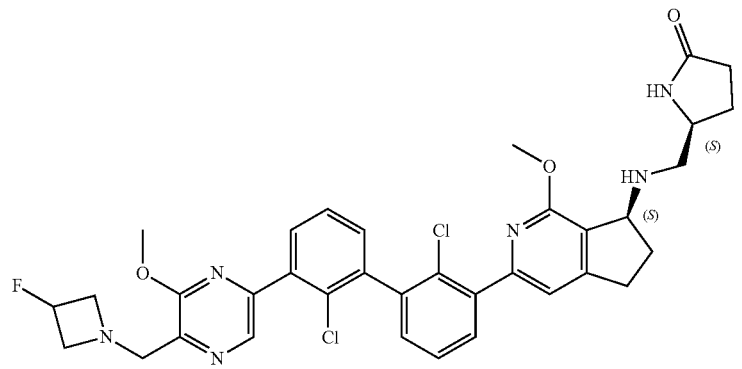 | 1 eq. of formate | Intermediate 39-1a 3-Fluoroazetidine-hydrochloride |
| D-5 | 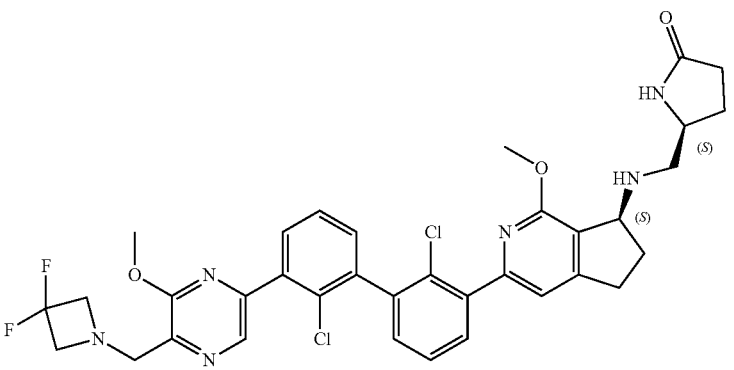 | | Intermediate 39-1a 3,3-difluoroazetidine-hydrochloride |

TABLE 14-continued

| Cmpd No. | Structure | Salt | Starting Materials |
|---|---|---|---|
| D-6 | 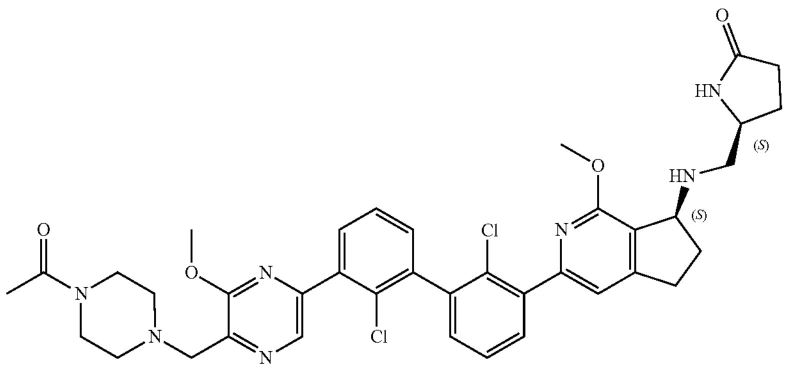 | | Intermediate 39-1a<br>1-Acetylpiperazine |
| D-7 | 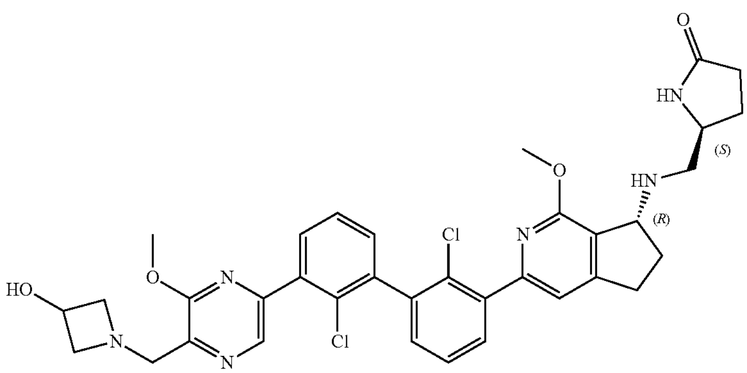 | 1 eq. of formate | Intermediate 39-1b<br>3-Hydroxyazetidine Hydrochloride |
| D-8 | 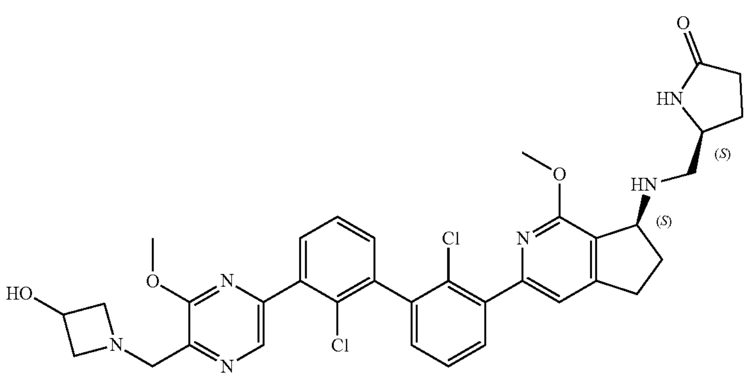 | 1 eq. of formate | Intermediate 39-1a<br>3-Hydroxyazetidine Hydrochloride |
| D-9 | 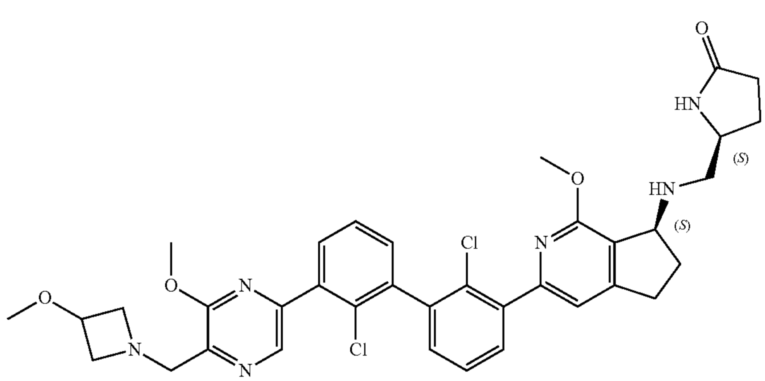 | 1 eq. of formate | Intermediate 39-1a<br>3-methoxyazetidine-hydrochloride |

TABLE 14-continued

| Cmpd No. | Structure | Salt | Starting Materials |
|---|---|---|---|
| D-10 | 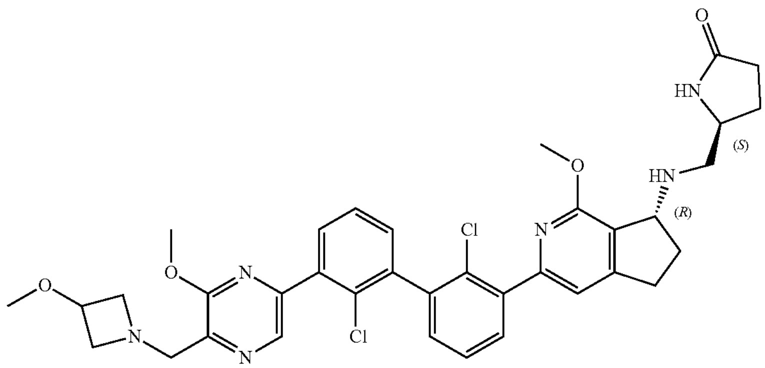 | 1 eq. of formate | Intermediate 39-1b 3-methoxyazetidine hydrochloride |
| D-11 | 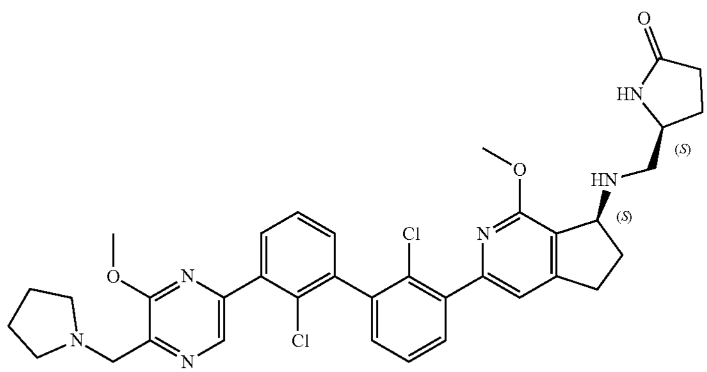 | 1 eq. of formate | Intermediate 39-1a Pyrrolidine |
| D-12 | 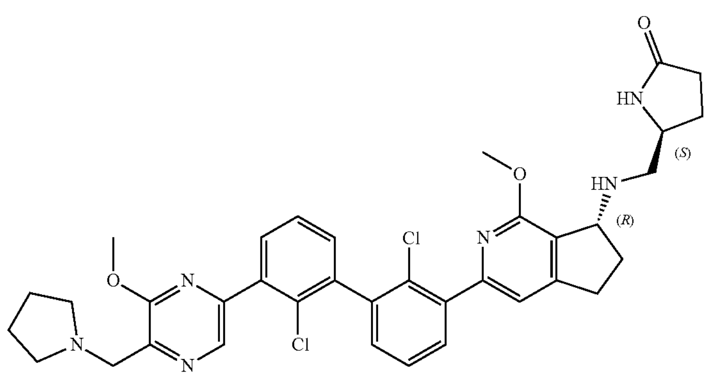 | 1 eq. of formate | Intermediate 39-1b Pyrrolidine |
| D-13 | 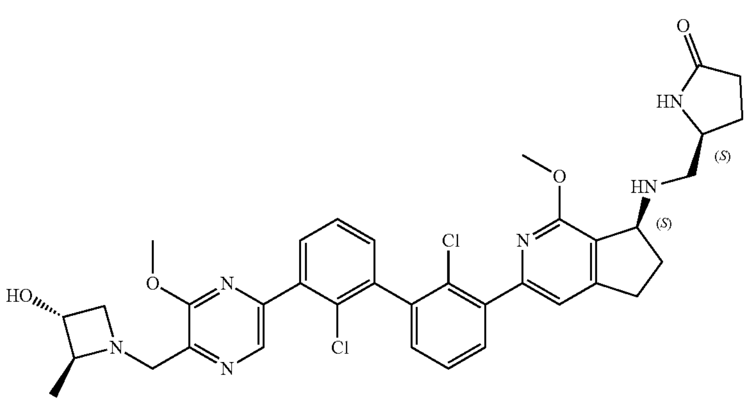 | 1 eq. of formate | Intermediate 39-1a (2S,3R)-2-methylazetidin-3-ol |

TABLE 14-continued

| Cmpd No. | Structure | Salt | Starting Materials |
|---|---|---|---|
| D-14 | 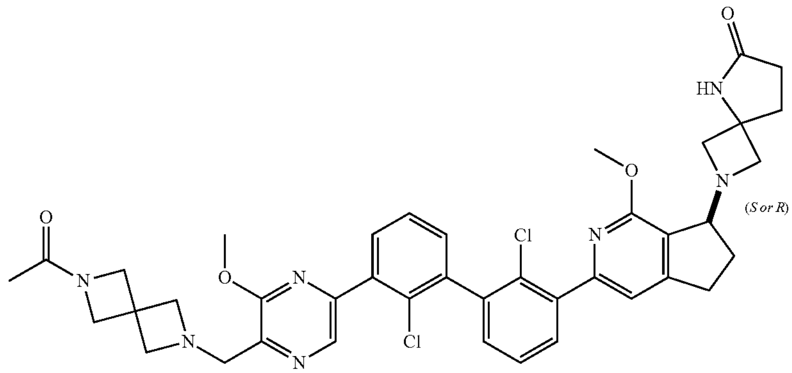 [SMILES: COc1nc(-c2cccc(-c3cccc(-c4cc5c(c(OC)n4)[C@@H](N4CC6(CCC(=O)N6)C4)CC5)c3Cl)c2Cl)cnc1CN1CC2(C1)CN(C(C)=O)C2] | | Intermediate 39-2a<br>1-(2,6-Diazaspiro[3.3]heptan-2-yl)ethan-1-one trifluoroacetic acid |
| D-15 | 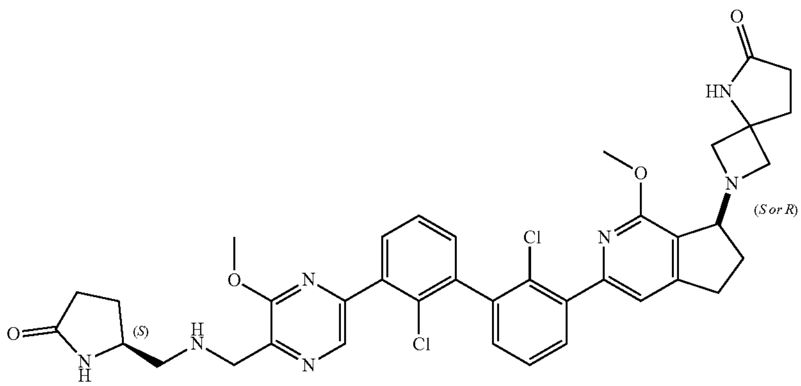 | | Intermediate 39-2a<br>(5S)-5-(aminomethyl)pyrrolidin-2-one HCl salt |
| D-16 | 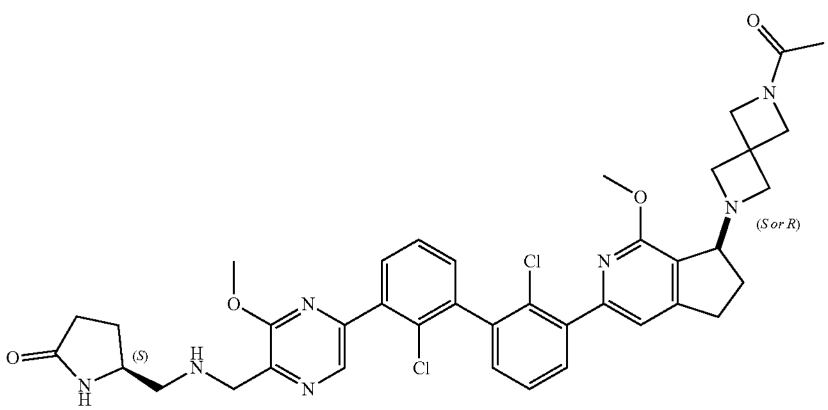 | | Intermediate 39-3a<br>(5S)-5-(aminomethyl)pyrrolidin-2-one HCl salt |
| D-17 | 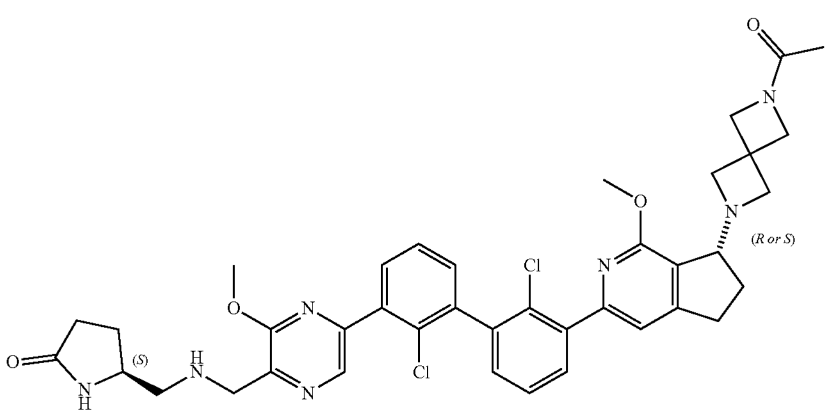 | | Intermediate 39-3b<br>(5S)-5-(aminomethyl)pyrrolidin-2-one HCl salt |

TABLE 14-continued
| Cmpd No. | Structure | Salt | Starting Materials |
|---|---|---|---|
| D-18 | 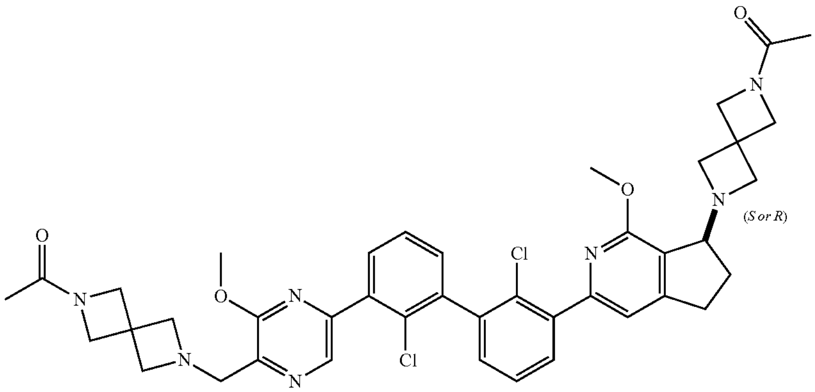 [SMILES: COc1nc(-c2cccc(-c3cccc(-c4cc5c(c(OC)n4)[C@@H](N4CC6(CN(C(C)=O)C6)C4)CC5)c3Cl)c2Cl)cnc1CN1CC2(C1)CN(C(C)=O)C2] | | Intermediate 39-3a<br>1-(2,6-Diazaspiro[3.3]heptan-2-yl)ethan-1-one trifluoroacetic acid |
| D-19 | 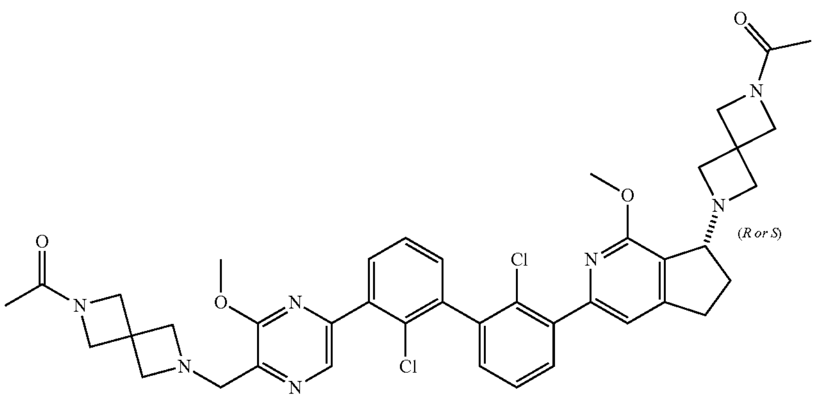 [SMILES: COc1nc(-c2cccc(-c3cccc(-c4cc5c(c(OC)n4)[C@H](N4CC6(CN(C(C)=O)C6)C4)CC5)c3Cl)c2Cl)cnc1CN1CC2(C1)CN(C(C)=O)C2] | | Intermediate 39-3b<br>1-(2,6-Diazaspiro[3.3]heptan-2-yl)ethan-1-one trifluoroacetic acid |
Example 5
Preparation of Compound E-1
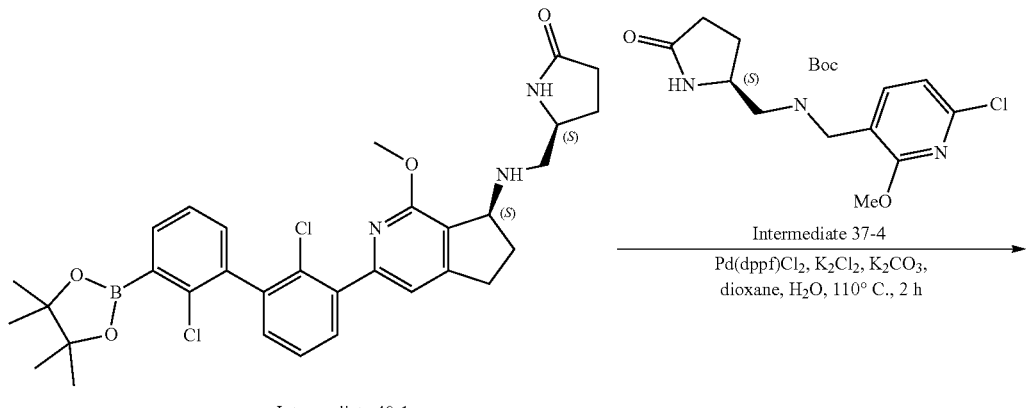
Intermediate 40-1a

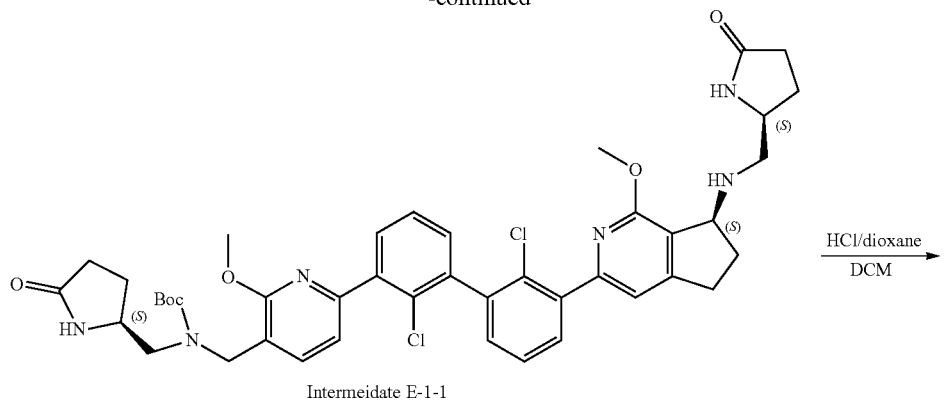

Intermeidate E-1-1

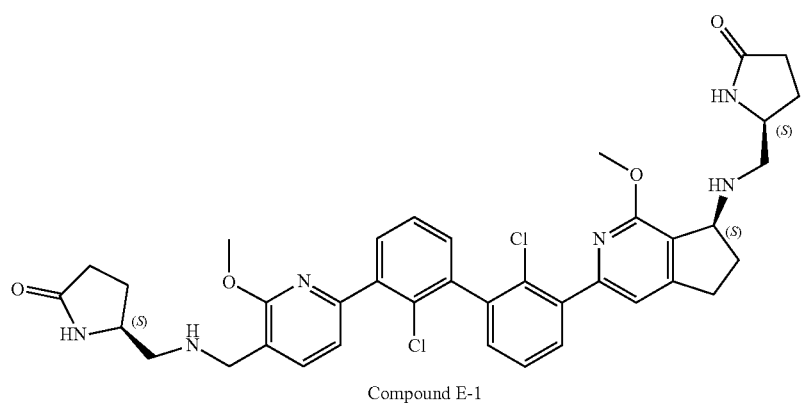

Compound E-1

A mixture of Intermediate 40-1a (50 mg, 82 mol), Intermediate 37-4 (36 mg, 99 mol), Pd(dppf)Cl₂ (6.0 mg, 8.2 μmol) and K₂CO₃ (34 mg, 247 μmol) in dioxane (1 mL) and H₂O (0.1 mL) was stirred at 110° C. for 2 h under N₂ atmosphere. The mixture was filtered and concentrated to give a residue, which was purified by prep-HPLC to give Intermeidate E-1-1 (15 mg) as an off-white solid. LCMS ($C_{43}H_{49}Cl_2N_6O_6^+$) (ES, m/z): 817.5 [M+H]⁺.

To the mixture of Intermediate E-1-1 (15 mg, 18.4 μmol) in DCM (2 mL) was added a solution of HCl in dioxane (6 M, 1.0 mL). After stirring the mixture at 25° C. for 2 h, the mixture was filtered and concentrated to give a residue, which was purified by prep-HPLC to give Compound E-1 (1.12 mg) as an off-white solid formate salt. LCMS ($C_{38}H_{41}Cl_2N_6O_4^+$) (ES, m/z): 716.9 [M+H]⁺. ¹H NMR (400 MHz, CD₃OD) δ 8.54 (s, 1H), 7.73 (d, J=7.4 Hz, 1H), 7.66-7.57 (m, 2H), 7.48 (dt, J=3.7, 7.6 Hz, 2H), 7.36 (d, J=7.5 Hz, 2H), 7.25 (d, J=7.4 Hz, 1H), 7.17 (s, 1H), 4.61 (s, 4H), 4.49 (dd, J=4.9, 7.5 Hz, 1H), 4.02 (s, 6H), 3.89-3.81 (m, 4H), 3.16-3.10 (m, 1H), 2.97-2.85 (m, 1H), 2.80 (dd, J=4.7, 11.9 Hz, 1H), 2.74-2.62 (m, 3H), 2.48-2.39 (m, 1H), 2.38-2.31 (m, 4H), 2.31-2.22 (m, 2H), 2.09-1.96 (m, 1H), 1.90-1.75 (m, 2H).

Example 6A

Preparation of Compound E-2

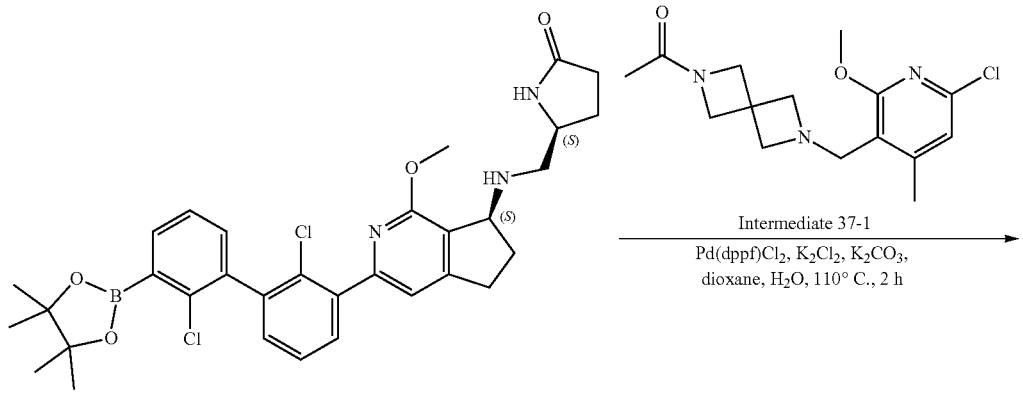

Intermediate 40-1a

-continued

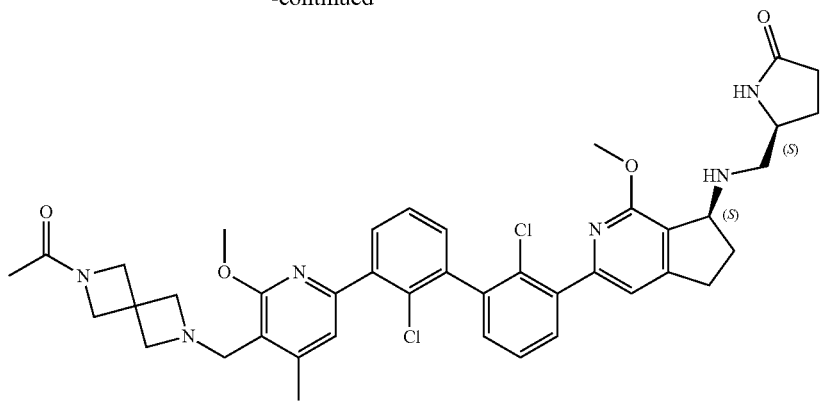

Compound E-2

To the reaction mixture of Intermediate 40-1a (50 mg, 82 μmol) and Intermediate 37-1 (31 mg, 99 μmol) in dioxane (1 mL) were added H$_2$O (0.1 mL), Pd(dppf)Cl$_2$ (6.0 mg, 8.2 μmol) and K$_2$CO$_3$ (34 mg, 247 mol). The mixture was stirred at 110° C. for 2 h under N$_2$ atmosphere. The mixture was filtered and concentrated to give a residue. The residue was purified by prep-HPLC to give compound E-2 (2.33 mg) as an off-white solid. LCMS (C$_{41}$H$_{45}$Cl$_2$N$_6$O$_4$$^+$) (ES, m/z): 757.0 [M+H]$^+$. $^1$H NMR (400 MHz, CDCl$_3$) δ 7.63 (tt, J=1.8, 5.7 Hz, 2H), 7.42 (t, J=7.8 Hz, 2H), 7.36-7.30 (m, 2H), 7.23-7.13 (m, 2H), 6.10-5.98 (m, 1H), 4.47-4.38 (m, 1H), 4.32-4.14 (m, 2H), 4.06 (br s, 2H), 4.05-4.02 (m, 3H), 4.00 (s, 3H), 3.88-3.61 (m, 4H), 3.61-3.37 (m, 3H), 3.16-3.05 (m, 1H), 2.95 (dd, J=3.8, 11.9 Hz, 1H), 2.91-2.82 (m, 1H), 2.64-2.53 (m, 1H), 2.49-2.20 (m, 8H), 2.04-1.92 (m, 1H), 1.85 (s, 3H), 1.82-1.74 (m, 1H).

The compounds shown in Table 15 were prepared by an analogous reaction protocol as was used for the preparation of Compound E-2 using the appropriate starting materials.

TABLE 15

| Cmpd No. | Structure | Salt | Starting Materials |
|---|---|---|---|
| E-3 | ![structure] | 1 eq. of formate | Intermediate 40-1a Intermediate 37-3 |
| E-4 | ![structure] | 1 eq. of formate | Intermediate 40-2a Intermediate 37-1 |

TABLE 15-continued
| Cmpd No. | Structure | Salt | Starting Materials |
|---|---|---|---|
| E-5 | 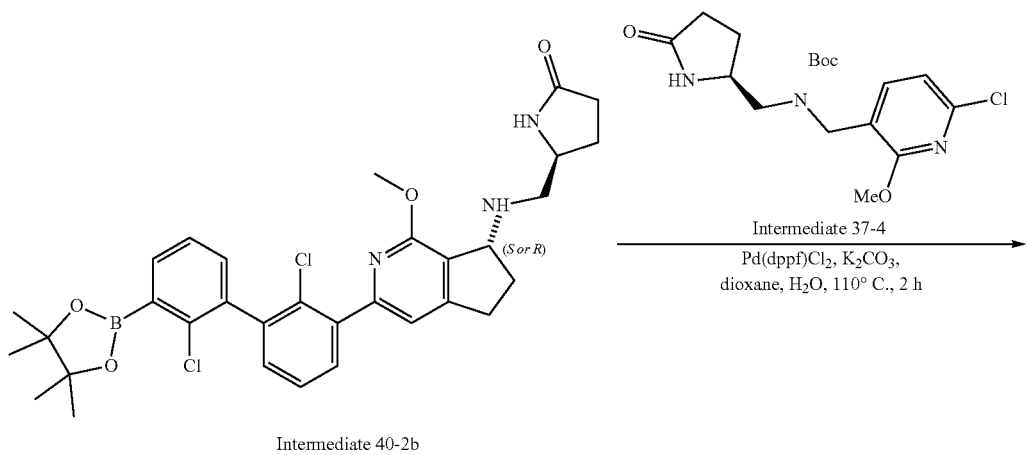 | 1 eq. of formate | Intermediate 40-2b Intermediate 37-1 |
Example 6B
Preparation of Compound E-6
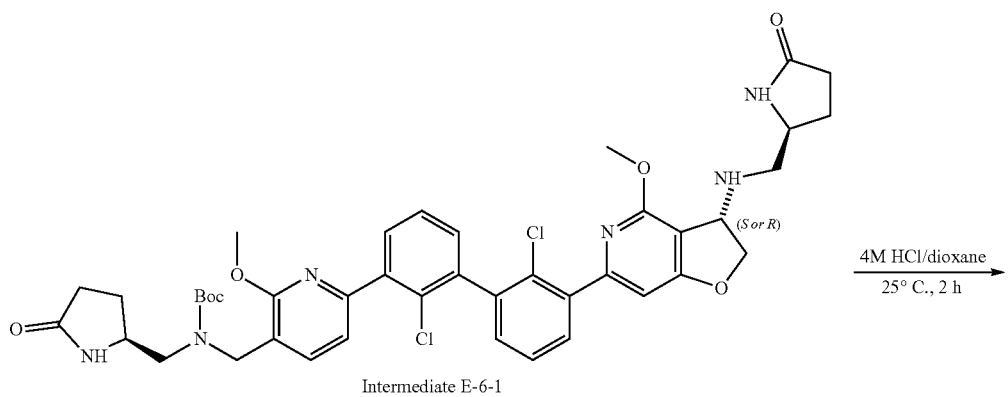

-continued

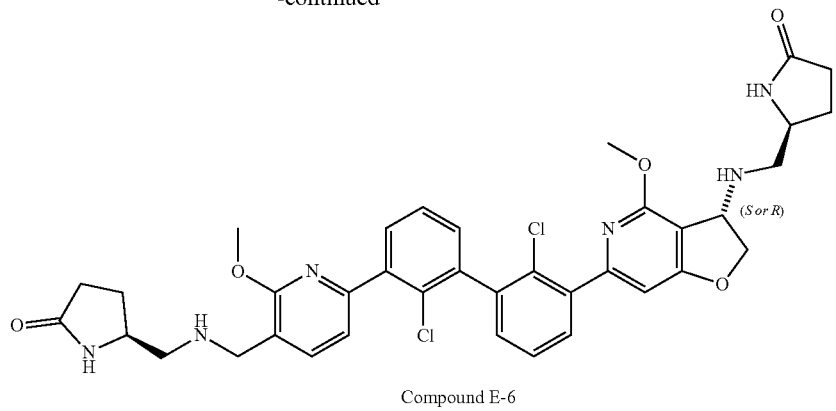

Compound E-6

A mixture of Intermediate 40-2b (40 mg, 66 μmol), Intermediate 37-4 (36 mg, 98 μmol), Pd(dppf)Cl$_2$ (4.8 mg, 6.6 μmol), K$_2$CO$_3$ (27 mg, 197 μmol) in dioxane (1 mL) and H$_2$O (0.1 mL) was degassed and purged with N$_2$ (3×). The mixture was stirred at 110° C. for 2 h under N$_2$ atmosphere. The mixture was filtered and concentrated under reduced pressure to give Intermediate E-6-1 (75 mg, crude) as a black liquid, which was used into the next step without further purification. LCMS (C$_{42}$H$_{47}$Cl$_2$N$_6$O$_7{}^+$) (ES, m/z): 817.2 [M+H]$^+$.

A mixture of Intermediate E-6-1 (75 mg) in HCl/dioxane (4 M, 2 mL) was stirred at 25° C. for 2 h. After adjusting the mixture's pH to be ~8 with sat. aq. NaHCO$_3$, the mixture was concentrated under reduced pressure to give a residue, which was purified by prep-HPLC to give Compound E-6 (1.97 mg) as a white solid. LCMS (C$_{37}$H$_{39}$Cl$_2$N$_6$O$_5{}^+$) (ES, m/z): 717.5 [M+H]$^+$.

Example 6C

Preparation of Compound E-7

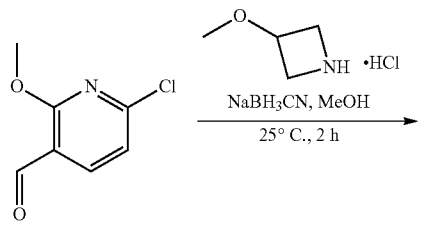

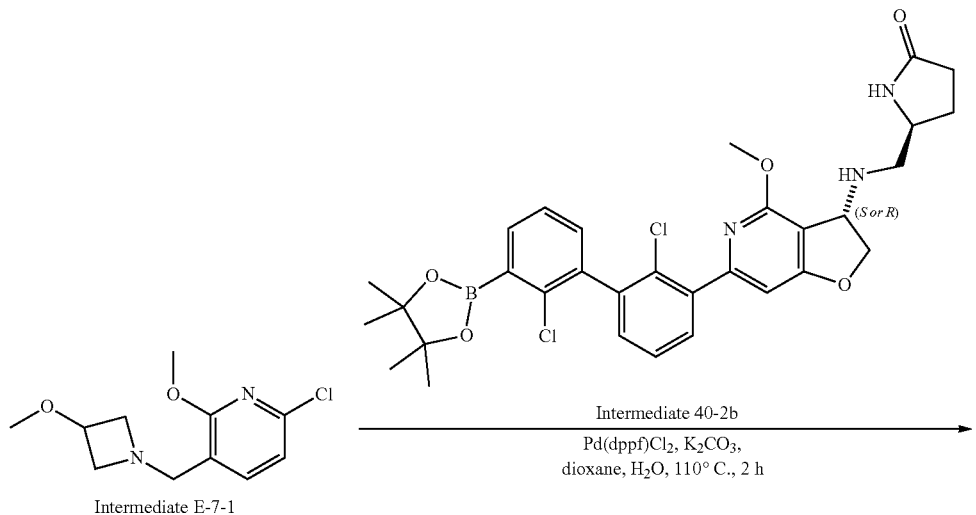

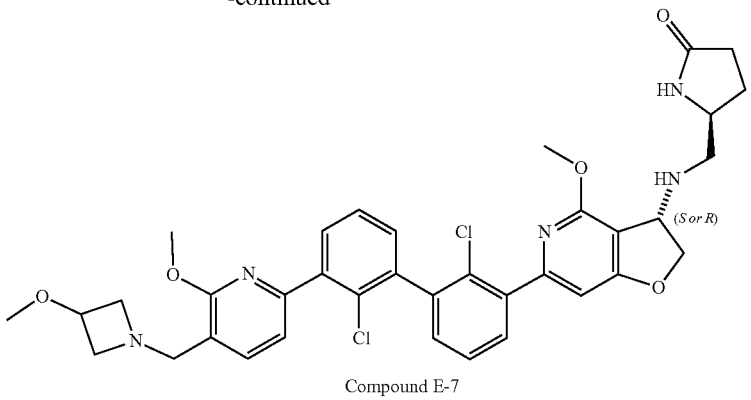

Compound E-7

A mixture of 6-Chloro-2-methoxy-pyridine-3-carbaldehyde (250 mg, 1.46 mmol), 3-methoxyazetidine·HCl salt (270 mg, 2.19 mmol) and NaBH₃CN (275 mg, 4.37 mmol) in MeOH (5 mL) was stirred at 25° C. for 2 h. The reaction was quenched by adding water (20 mL) at 25° C. The mixture was extracted with ethyl acetate (2×20 mL). The combined organic layers were washed with brine (20 mL), dried over anhydrous Na₂SO₄, filtered and concentrated under reduced pressure to give a residue, which was purified by flash silica gel chromatography to give Intermediate E-7-1 (80 mg) as a colorless liquid. LCMS ($C_{11}H_{16}ClN_2O_2^+$) (ES, m/z): 243.2 [M+H]⁺.

A mixture of Intermediate E-7-1 (40 mg, 66 mol), Intermediate 40-2b (28.40 mg, 98 mol), Pd(dppf)Cl₂ (4.8 mg, 6.6 mol), K₂CO₃ (27 mg, 197 μmol) in dioxane (1 mL) and H₂O (0.1 mL) was degassed and purged with N₂ (3×). The mixture was stirred at 110° C. for 2 h under N₂ atmosphere. The mixture was filtered and concentrated under reduced pressure to give a residue, which was purified by prep-HPLC to give Compound E-7 (3.99 mg,) as an off-white solid. LCMS ($C_{36}H_{38}Cl_2N_5O_5^+$) (ES, m/z): 690.5 [M+H]⁺.

Example 7

Preparation of Compound F-1

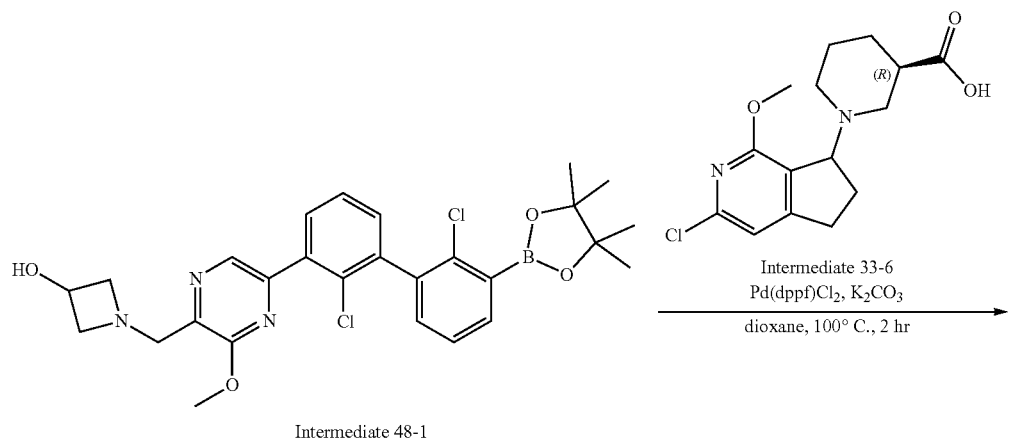

Intermediate 48-1

Pd(dppf)Cl₂, K₂CO₃
dioxane, 100° C., 2 hr

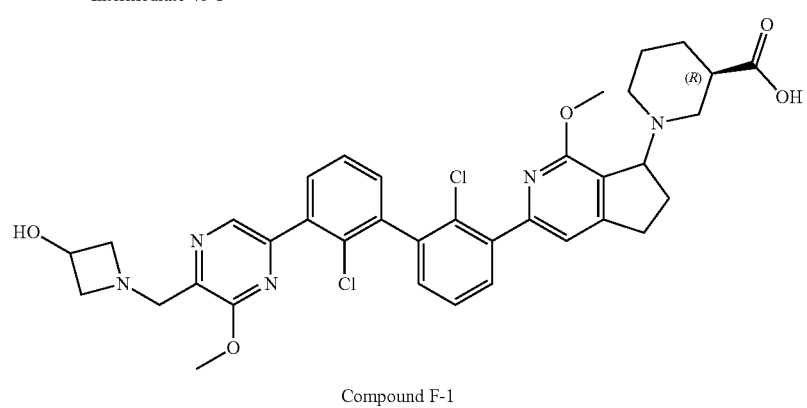

Compound F-1

A mixture of compound Intermediate 33-6 (30 mg, 97 mol), Intermediate 48-1 (55 mg, 101 mol), K$_2$CO$_3$ (40 mg, 290 μmol) and Pd(dppf)Cl$_2$ (7.1 mg, 9.7 μmol) in dioxane (1 mL) and H$_2$O (0.1 mL) was stirred at 110° C. for 2 h under N$_2$ atmosphere. The mixture was filtered and concentrated to give a residue, which was purified by prep-HPLC to give Compound F-1 (3.0 mg) as a white solid. LCMS (C$_{36}$H$_{38}$Cl$_2$N$_5$O$_5^+$) (ES, m/z): 690.4 [M+H]$^+$. $^1$H NMR (400 MHz, CD$_3$OD) δ 8.52 (s, 1H), 8.42 (s, 1H), 7.70-7.62 (m, 2H), 7.57-7.37 (m, 4H), 7.29 (s, 1H), 4.55 (s, 4H), 4.14-4.08 (m, 5H), 4.06 (s, 3H), 4.04-3.97 (m, 2H), 3.44 (br d, J=6.1 Hz, 2H), 3.26-2.92 (m, 6H), 2.79-2.63 (m, 1H), 2.54 (br d, J=9.0 Hz, 2H), 1.85 (br s, 4H).

The compounds shown in Table 16 were prepared by an analogous reaction protocol as was used for the preparation of Compound F-1 using the appropriate starting materials.

TABLE 16

| Cmpd No. | Structure | Salt | Starting Materials |
|---|---|---|---|
| F-2 | 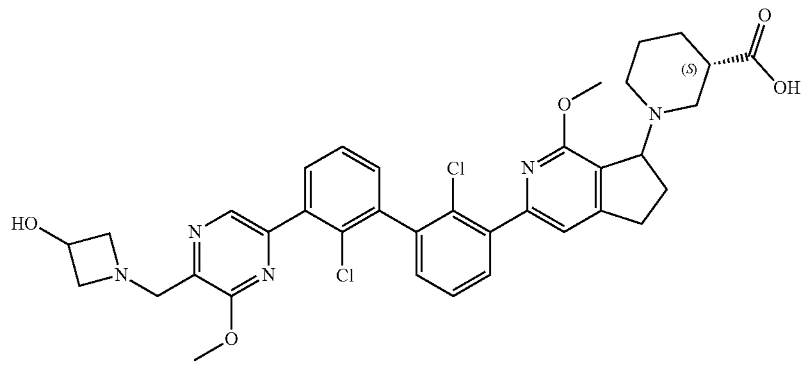 | 1 eq. of formate | Intermediate 48-1 Intermediate 33-7 |
| F-3 | 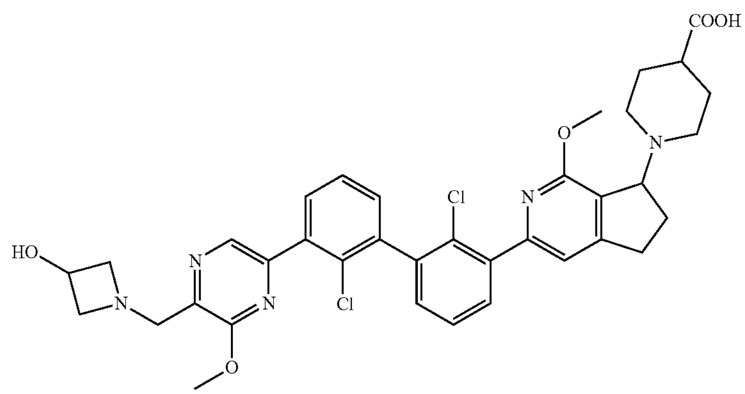 [SMILES: COc1nc(-c2cccc(-c3cccc(-c4cc5c(c(OC)n4)C(N4CCC(C(=O)O)CC4)CC5)c3Cl)c2Cl)cnc1CN1CC(O)C1] | 1 eq. of formate | Intermediate 48-1 Intermediate 33-8 |

Example 8

Preparation of Compound G-1

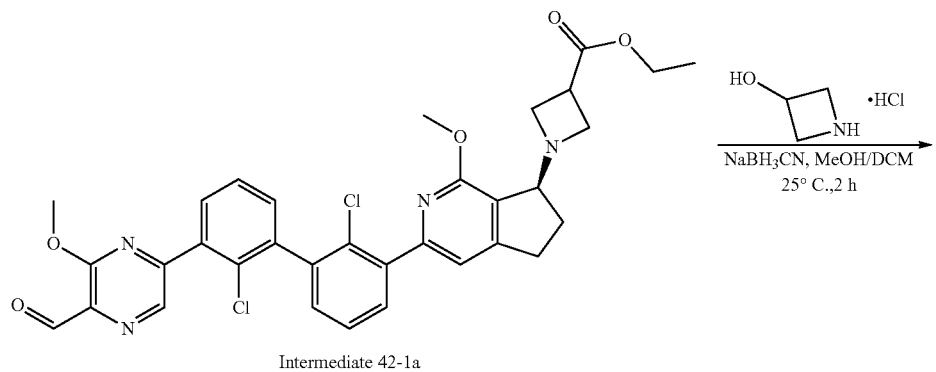

Intermediate 42-1a

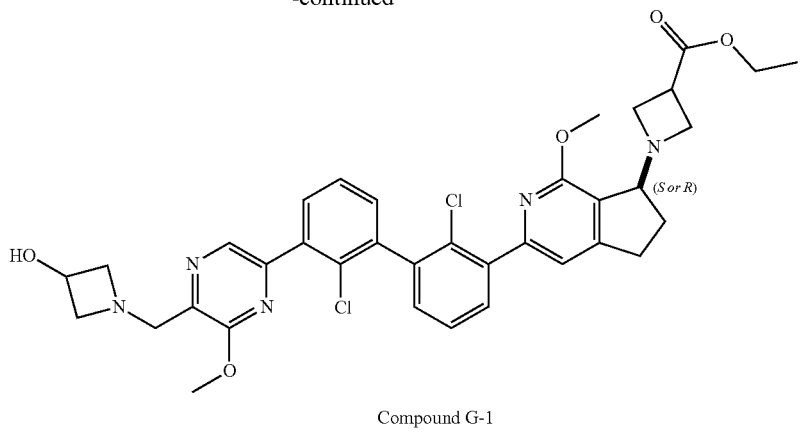

Compound G-1

The mixture of Intermediate 42-1a (90 mg, 142 μmol) and azetidin-3-ol HCl salt (47 mg, 426 μmol) in MeOH (2 mL) and DCM (0.5 mL) was stirred at 25° C. for 0.5 h. After adding NaBH$_3$CN (27 mg, 426 μmol) into the mixture at 25° C., the mixture was stirred at 25° C. for 1.5 h. The mixture was filtered and concentrated under reduced pressure to give a residue. The residue was purified by prep-HPLC to provide Compound G-1 (12.9 mg) as a white solid formate salt. LCMS (C$_{36}$H$_{38}$Cl$_2$N$_5$O$_5{}^+$) (ES, m/z): 690.4 [M+H]$^+$. $^1$H NMR (400 MHz, CDCl$_3$) δ 8.53 (d, J=1.9 Hz, 1H), 8.44 (s, 1H), 7.68-7.59 (m, 2H), 7.51-7.38 (m, 3H), 7.33 (dd, J=1.7, 7.6 Hz, 1H), 7.21 (d, J=6.5 Hz, 1H), 4.63-4.50 (m, 1H), 4.24-4.18 (m, 2H), 4.16 (s, 3H), 4.12-3.98 (m, 9H), 3.97-3.91 (m, 2H), 3.86 (br s, 1H), 3.82-3.76 (m, 1H), 3.70 (br t, J=7.1 Hz, 1H), 3.58 (br t, J=7.6 Hz, 1H), 3.44-3.30 (m, 1H), 3.18 (td, J=8.3, 16.7 Hz, 1H), 2.88-2.74 (m, 1H), 2.25-1.96 (m, 2H), 1.29 (t, J=7.1 Hz, 3H).

The compounds shown in Table 17 were prepared by an analogous reaction protocol as was used for the preparation of Compound G-1 using the appropriate starting materials.

TABLE 17

| Cmpd No. | Structure | Salt | Starting Materials |
|---|---|---|---|
| G-2 | 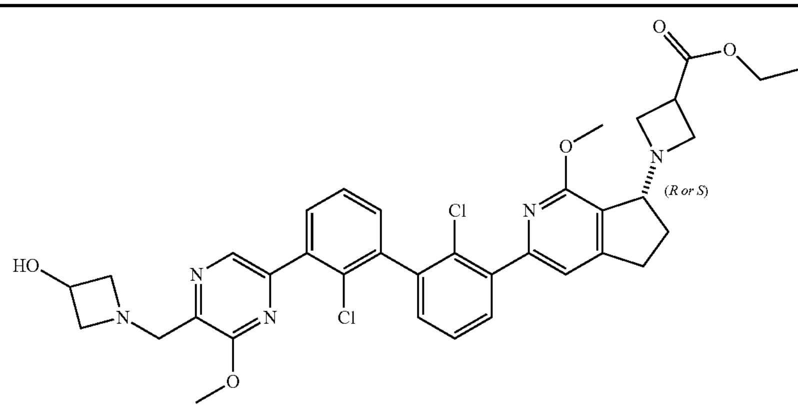 | 1 eq. of formate | Intermediate 42-1b 3-Hydroxyazetidine Hydrochloride |
| G-3 | 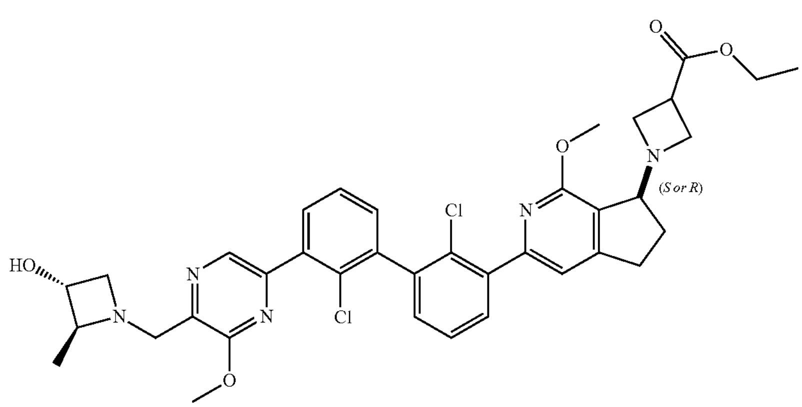 [SMILES: CCOC(=O)C1CN([C@H]2CCc3cc(-c4cccc(-c5cccc(-c6cnc(CN7C[C@@H](O)[C@@H]7C)c(OC)n6)c5Cl)c4Cl)nc(OC)c32)C1] | 1 eq. of formate | Intermediate 42-1a (2S,3R)-2-methylazetidin-3-ol |

TABLE 17-continued

| Cmpd No. | Structure | Salt | Starting Materials |
|---|---|---|---|
| G-4 | 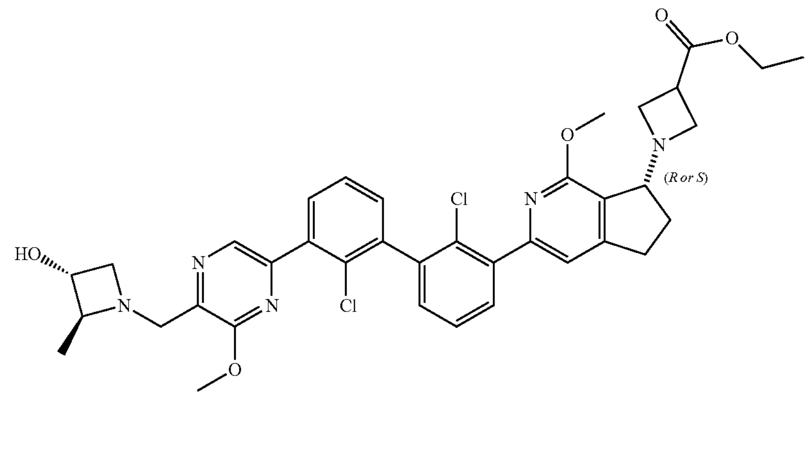 [SMILES: CCOC(=O)C1CN([C@@H]2CCc3cc(-c4cccc(-c5cccc(-c6cnc(CN7C[C@@H](O)[C@@H]7C)c(OC)n6)c5Cl)c4Cl)nc(OC)c32)C1] | 1 eq. of formate | Intermediate 42-1b (2S,3R)-2-methylazetidin-3-ol |
| G-5 | 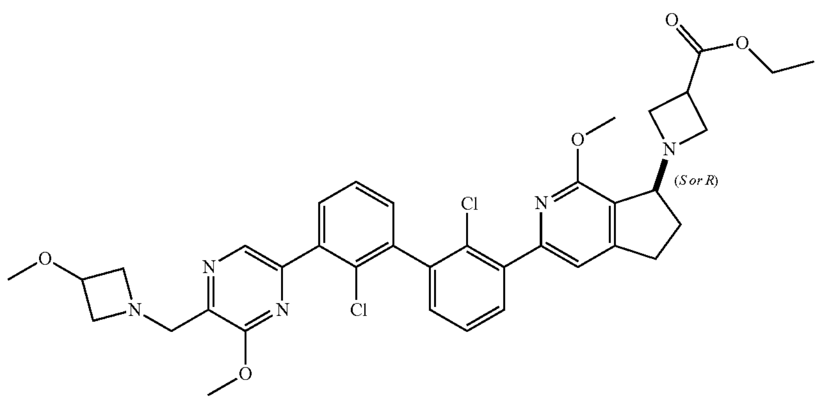 [SMILES: CCOC(=O)C1CN([C@H]2CCc3cc(-c4cccc(-c5cccc(-c6cnc(CN7CC(OC)C7)c(OC)n6)c5Cl)c4Cl)nc(OC)c32)C1] | 1 eq. of formate | Intermediate 42-1a 3-methoxyazetidine hydrochloride |
| G-6 | 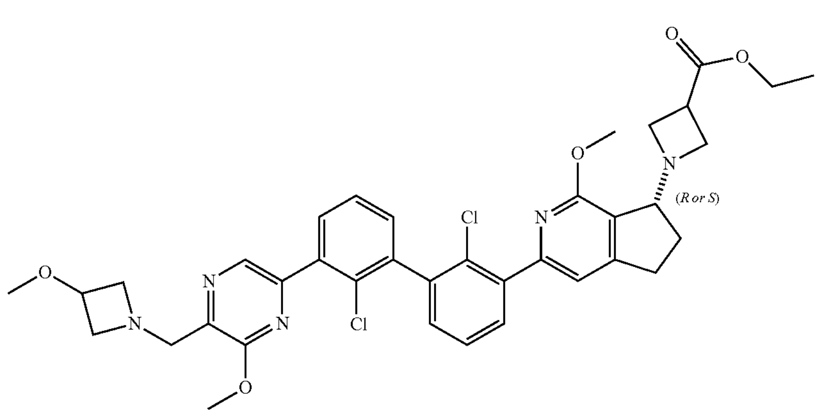 [SMILES: CCOC(=O)C1CN([C@@H]2CCc3cc(-c4cccc(-c5cccc(-c6cnc(CN7CC(OC)C7)c(OC)n6)c5Cl)c4Cl)nc(OC)c32)C1] | 1 eq. of formate | Intermediate 42-1b 3-methoxyazetidine hydrochloride |

Example 9

Preparation of Compound H-1

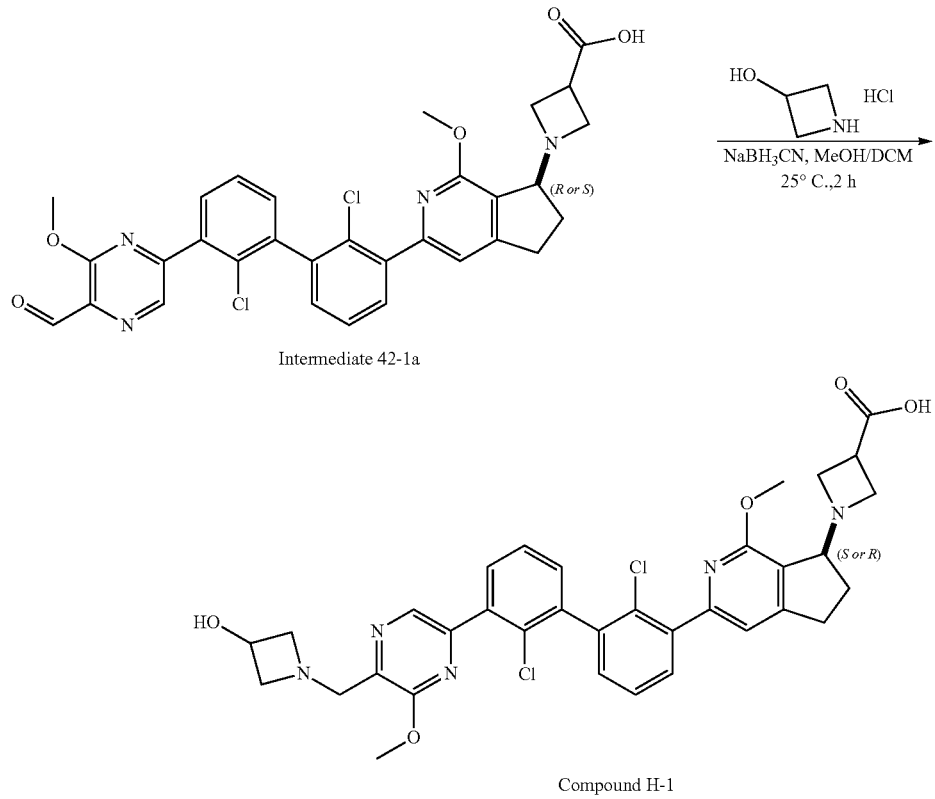

Intermediate 42-1a

Compound H-1

To a solution of Intermediate 42-1a (90 mg, 149 μmol) in MeOH (1.5 mL) and DCM (0.5 mL) was added and azetidin-3-ol HCl salt (49 mg, 446 mol). The mixture was stirred at 25° C. for 0.5 h. After adding NaBH$_3$CN (28 mg, 446 μmol) in the mixture, the mixture was stirred at 25° C. for 1.5 h. The mixture was filtered and concentrated under reduced pressure to give a residue. The residue was purified by prep-HPLC to provide Compound H-1 (19 mg) as a white solid formate salt. LCMS (C$_{34}$H$_{34}$Cl$_2$N$_5$O$_5$$^+$) (ES, m/z): 662.4 [M+H]$^+$. $^1$H NMR (400 MHz, CDCl$_3$) δ 8.51 (s, 1H), 8.44 (s, 1H), 8.37-8.29 (m, 1H), 8.33 (br s, 1H), 7.69-7.58 (m, 2H), 7.49-7.42 (m, 2H), 7.41-7.37 (m, 1H), 7.35-7.30 (m, 1H), 7.20 (br d, J=7.4 Hz, 1H), 4.60-4.54 (m, 1H), 4.44 (br s, 1H), 4.30 (br d, J=2.3 Hz, 1H), 4.12 (br d, J=8.5 Hz, 2H), 4.09 (br s, 2H), 4.07-4.04 (m, 3H), 4.01 (br s, 2H), 3.97 (s, 3H), 3.85 (br s, 2H), 3.74 (br d, J=6.4 Hz, 2H), 3.39-3.18 (m, 2H), 2.82 (br dd, J=8.7, 16.8 Hz, 1H), 2.45-2.15 (m, 2H).

The compounds shown in Table 18 were prepared by an analogous reaction protocol as was used for the preparation of Compound H-1 using the appropriate starting materials.

TABLE 18

| Cmpd No. | Structure | Salt | Starting Materials |
|---|---|---|---|
| H-2 | 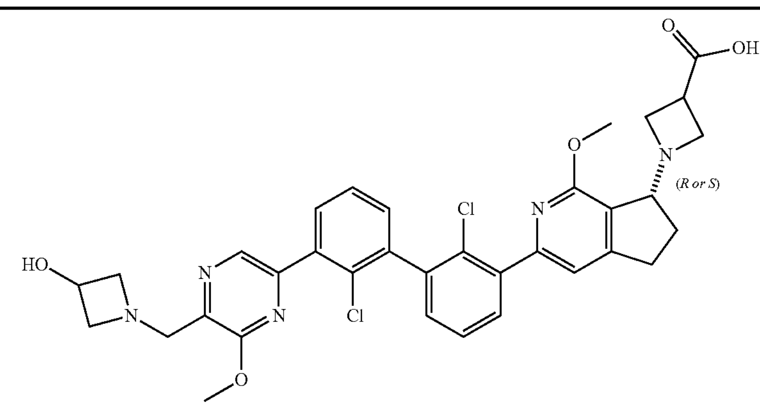 | 1 eq. of formate | Intermediate 42-1b azetidin-3-ol HCl salt |

TABLE 18-continued
| Cmpd No. | Structure | Salt | Starting Materials |
|---|---|---|---|
| H-3 | 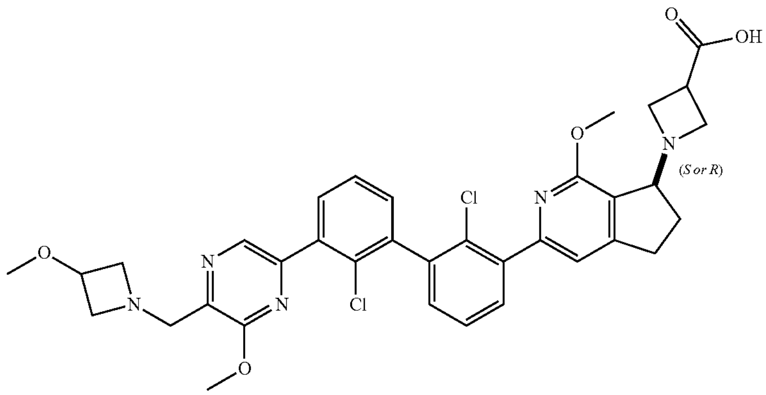 [SMILES: COc1nc(-c2cccc(-c3cccc(-c4cc5c(c(OC)n4)[C@@H](N4CC(C(=O)O)C4)CC5)c3Cl)c2Cl)cnc1CN1CC(OC)C1] | 1 eq. of formate | Intermedate 42-1a 3-methoxyazetidine-hydrochloride |
| H-4 | 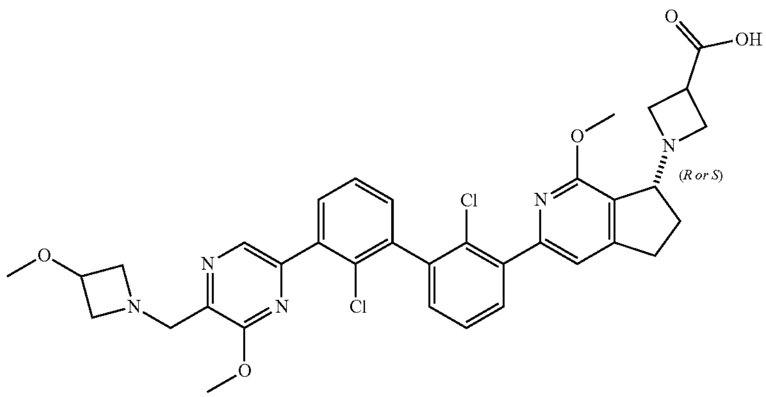 [SMILES: COc1nc(-c2cccc(-c3cccc(-c4cc5c(c(OC)n4)[C@H](N4CC(C(=O)O)C4)CC5)c3Cl)c2Cl)cnc1CN1CC(OC)C1] | 1 eq. of formate | Intermediate 42-1b 3-methoxyazetidine hydrochloride |
Example 10
Preparation of Compound I-1
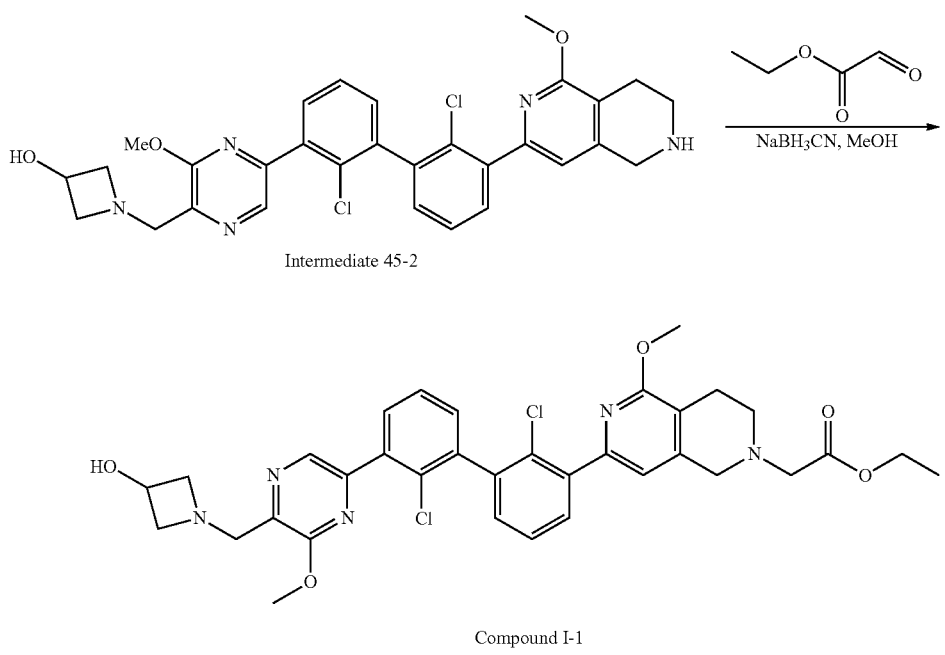
Compound I-1

The mixture of Intermediate 45-2 (10 mg, 17 µmol) and ethyl 2-oxoacetate (18 mg, 172 µmol) in MeOH (1 mL) was stirred at 20° C. for 1 h. After adding NaBH$_3$CN (3.3 mg, 52 µmol) to the mixture at 20° C., the mixture was stirred at 20° C. for 2 h. The mixture was filtered and concentrated under reduced pressure to give a residue. The residue was purified by prep-HPLC to provide Compound I-1 (2.1 mg) as a white solid. LCMS (C$_{34}$H$_{36}$Cl$_2$N$_5$O$_5{}^+$) (ES, m/z): 664.4 [M+H]$^+$.

$^1$H NMR (400 MHz, CD$_3$OD) δ 8.40 (s, 1H), 7.72-7.31 (m, 6H), 6.96 (s, 1H), 4.39 (t, J=6.4 Hz, 1H), 4.21 (q, J=7.2 Hz, 2H), 4.05 (s, 3H), 3.98 (s, 3H), 3.89 (s, 2H), 3.84-3.76 (m, 4H), 3.47 (s, 2H), 3.20-3.11 (m, 2H), 3.00-2.89 (m, 2H), 2.85-2.71 (m, 2H), 1.28 (t, J=7.1 Hz, 3H).

The compounds shown in Table 19 were prepared by an analogous reaction protocol as was used for the preparation of Compound I-1 using the appropriate starting materials.

TABLE 19

| Cmpd No. | Structure | Salt | Starting Materials |
|---|---|---|---|
| I-2 | 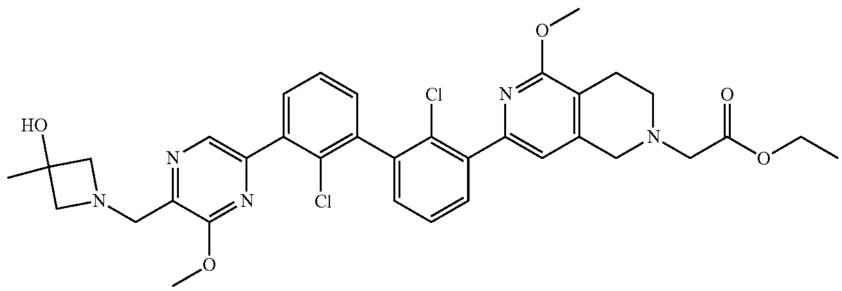 [SMILES: CCOC(=O)CN1CCc2c(cc(-c3cccc(-c4cccc(-c5cnc(CN6CC(C)(O)C6)c(OC)n5)c4Cl)c3Cl)nc2OC)C1] | | Intermediate 45-3<br>3-methylazetidin-3-ol hydrochloride |
| I-3 | 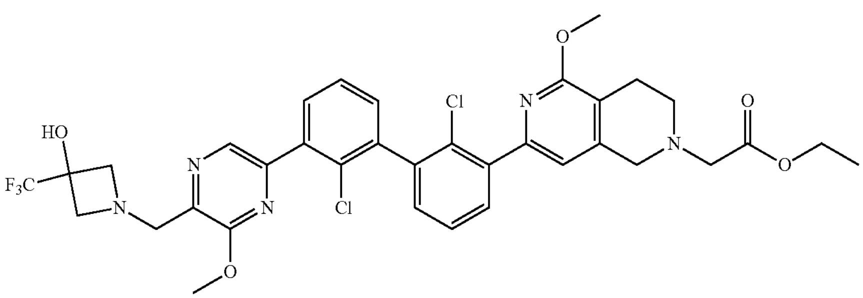 [SMILES: CCOC(=O)CN1CCc2c(cc(-c3cccc(-c4cccc(-c5cnc(CN6CC(O)(C(F)(F)F)C6)c(OC)n5)c4Cl)c3Cl)nc2OC)C1] | | Intermediate 45-4<br>3-(trifluoromethyl)azetidin-3-ol hydrochloride |

Example 11

Preparation of Compound J-1

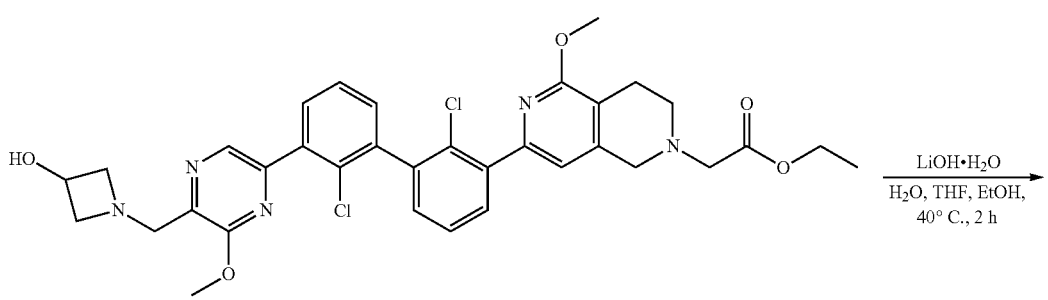

Compound I-1

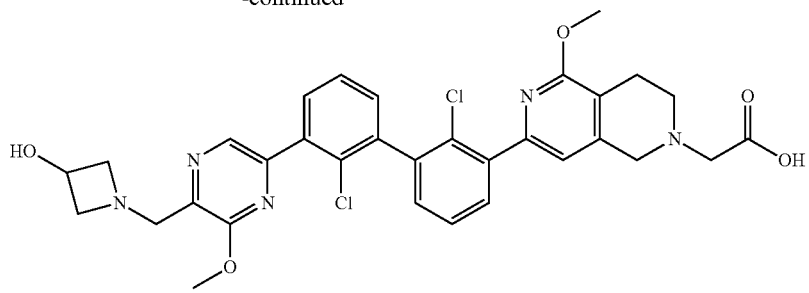

Compound J-1

To a solution of Compound I-1 (10 mg, 15 μmol) in EtOH (0.6 mL) in THF (0.4 mL) and H$_2$O (0.2 mL) was added LiOH·H$_2$O (6.3 mg, 150 μmol) at 25° C. The mixture was stirred at 40° C. for 2 h. The mixture was adjusted to pH-6 with HCl (2M) and filtered to give a residue. The residue was purified by prep-HPLC to provide Compound J-1 (5.7 mg) as a white solid. LCMS (C$_{32}$H$_{32}$Cl$_2$N$_5$O$_5^+$) (ES, m/z): 636.1 [M+H]$^+$. $^1$H NMR (400 MHz, CD$_3$OD) δ 8.53 (s, 1H), 8.43 (s, 1H), 7.65 (ddd, J=1.6, 7.7, 18.0 Hz, 2H), 7.58-7.46 (m, 2H), 7.44 (dd, J=1.8, 7.6 Hz, 1H), 7.37 (dd, J=1.7, 7.6 Hz, 1H), 7.05 (s, 1H), 4.51 (t, J=6.3 Hz, 1H), 4.17 (s, 4H), 4.11-3.94 (m, 7H), 3.58 (s, 2H), 3.53-3.45 (m, 2H), 3.39 (br t, J=6.0 Hz, 2H), 2.96 (br t, J=6.1 Hz, 2H).

The compounds shown in Table 20 were prepared by an analogous reaction protocol as was used for the preparation of Compound J-1 using the appropriate starting materials.

TABLE 20

| Cmpd No. | Structure | Salt | Starting Materials |
|---|---|---|---|
| J-2 | 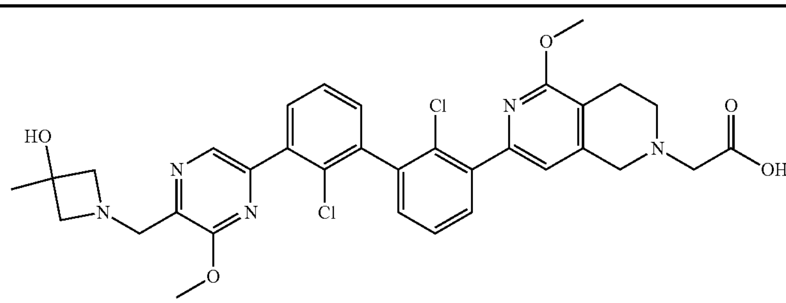 | | Compound I-2 |
| J-3 | 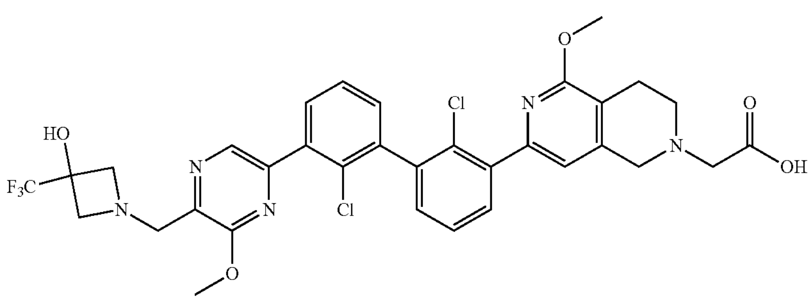 [SMILES: COc1nc(-c2cccc(-c3cccc(-c4cc5c(c(OC)n4)CCN(CC(=O)O)C5)c3Cl)c2Cl)cnc1CN1CC(O)(C(F)(F)F)C1] | | Compound I-3 |
| H-5 | 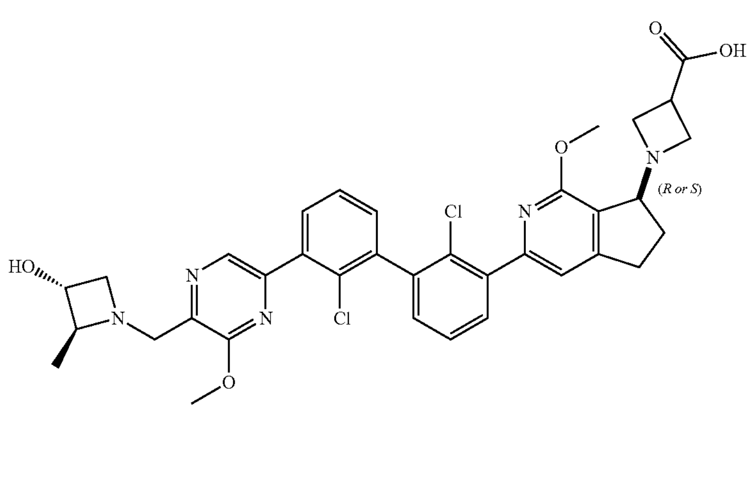 [SMILES: COc1nc(-c2cccc(-c3cccc(-c4cc5c(c(OC)n4)[C@@H](N4CC(C(=O)O)C4)CC5)c3Cl)c2Cl)cnc1CN1C[C@@H](O)[C@@H]1C] | | Compound G-3 |

TABLE 20-continued

| Cmpd No. | Structure | Salt | Starting Materials |
|---|---|---|---|
| H-6 | 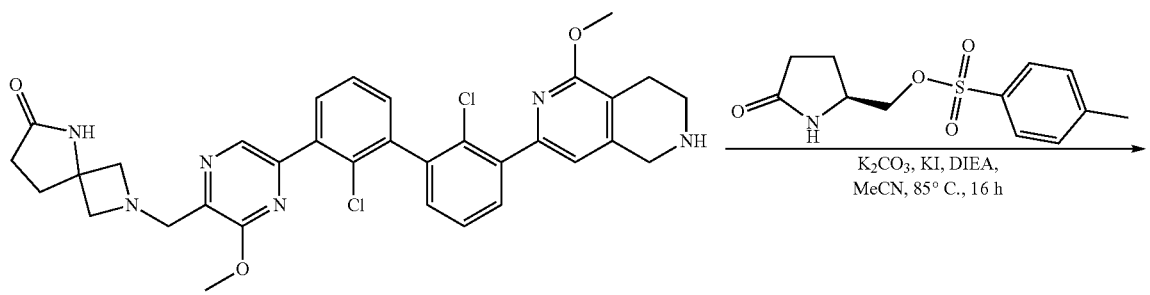 | | Compound G-4 |

Example 12

Preparation of Compound K-1

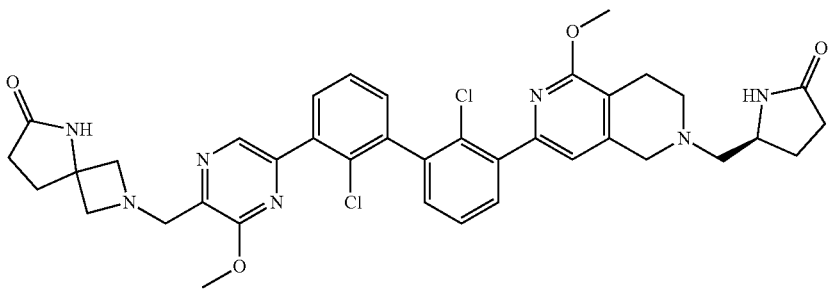

Intermediate 45-1

Compound K-1

A mixture of Intermediate 45-1 (60 mg, 95 mol), [(2S)-5-oxopyrrolidin-2-yl]methyl 4-methylbenzenesulfonate (77 mg, 285 mol), KI (63 mg, 380 μmol) and DIEA (66 μL, 380 μmol) in MeCN (3 mL) was stirred at 85° C. for 16 h. After adding K₂CO₃ (39 mg, 285 μmol) into the mixture at 25° C., the mixture was stirred at 85° C. for 16 h. The mixture was filtered and concentrated under reduced pressure to give a residue. The residue was purified by prep-HPLC to provide Compound K-1 (6.0 mg) as a white solid. LCMS ($C_{38}H_{40}Cl_2N_7O_4^+$) (ES, m/z): 728.2 [M+H]⁺. ¹H NMR (400 MHz, CD₃OD) δ 8.39 (s, 1H), 7.73-7.29 (m, 6H), 6.97 (s, 1H), 4.05 (s, 3H), 4.02-3.93 (m, 4H), 3.90 (s, 2H), 3.81-3.71 (m, 1H), 3.70-3.58 (m, 3H), 3.46 (d, J=9.0 Hz, 2H), 3.00-2.86 (m, 1H), 2.85-2.71 (m, 3H), 2.70-2.52 (m, 2H), 2.47-2.21 (m, 7H), 1.89-1.74 (m, 1H), 1.56-1.54 (m, 1H).

Example 13

Preparation of Compound K-2

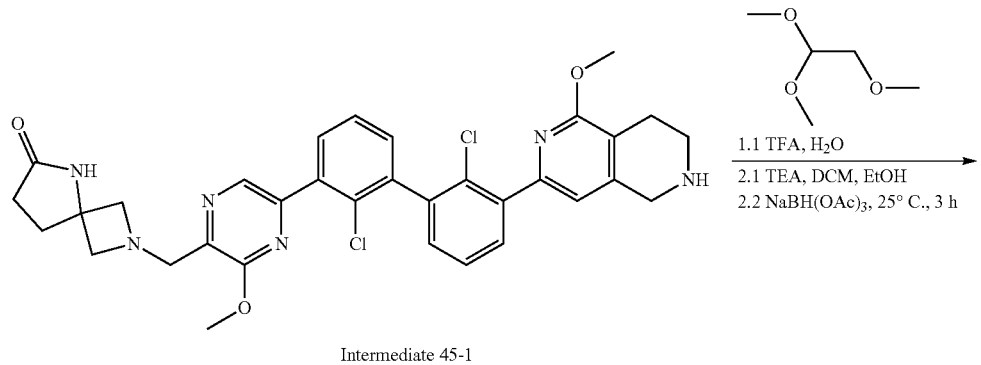

Intermediate 45-1

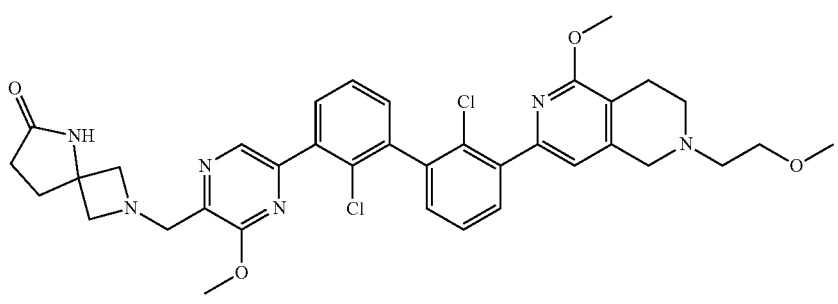

Compound K-2

A mixture of 1,1,2-trimethoxyethane (11 μL, 83 μmol) and TFA (8 μL) in $H_2O$ (8 μL) was stirred at 50° C. for 15 mins. After the mixture was cooled to rt, TEA (15 μL, 111 μmol) and a solution of Intermediate 45-1 (35 mg, 55 μmol) in the mixture of DCM (0.25 mL) and EtOH (0.25 mL) were added into the mixture. After adding $NaBH(OAc)_3$ (47 mg, 222 μmol) into the mixture, the mixture was stirred at 25° C. for 3 h. The mixture was filtered and concentrated under reduced pressure to give a residue. The residue was purified by prep-HPLC to provide Compound K-2 (15 mg) as a yellow solid. LCMS ($C_{36}H_{39}Cl_2N_6O_4^+$) (ES, m/z): 684.4 $[M+H]^+$. $^1H$ NMR (400 MHz, $CD_3OD$) δ 8.40 (s, 1H), 7.70-7.32 (m, 6H), 6.96 (s, 1H), 4.05 (s, 3H), 3.97 (s, 3H), 3.90 (s, 2H), 3.70 (s, 2H), 3.67-3.59 (m, 4H), 3.45 (d, J=9.0 Hz, 2H), 3.36 (s, 3H), 2.92-2.83 (m, 2H), 2.82-2.71 (m, 4H), 2.48-2.30 (m, 4H).

Example 14

Additional Compounds

Other compounds that can be prepared applying similar procedures as those described herein.

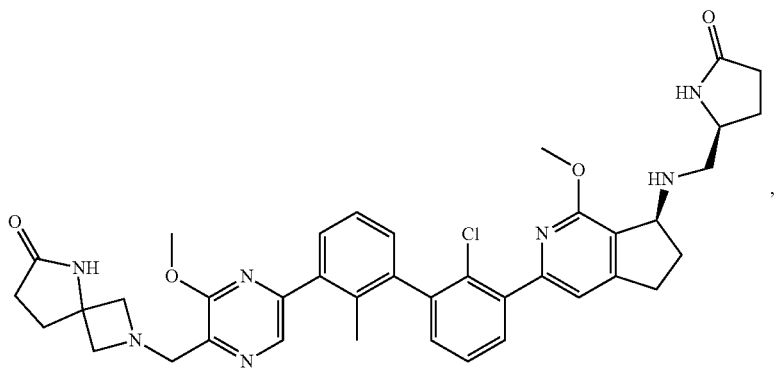

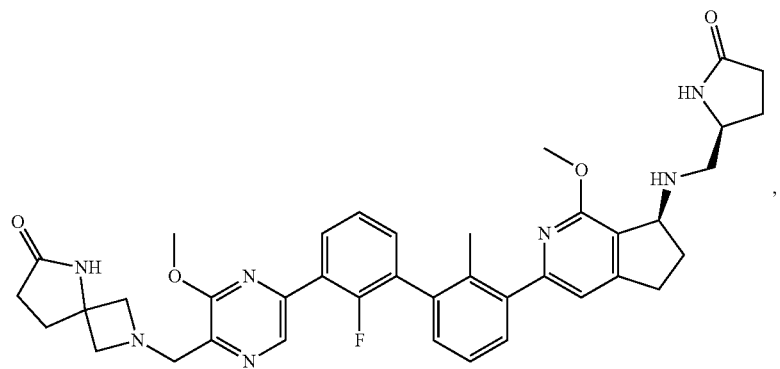

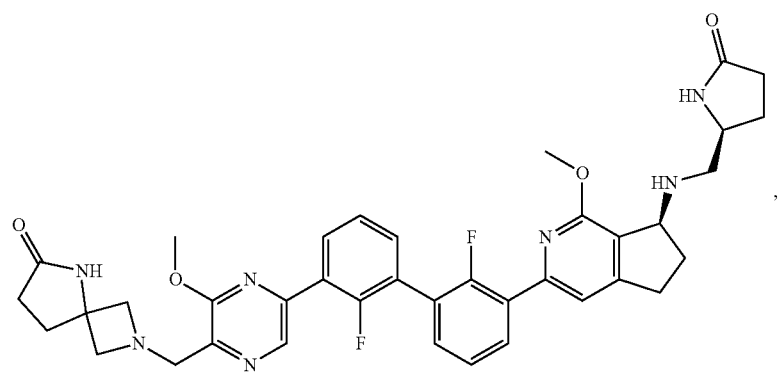
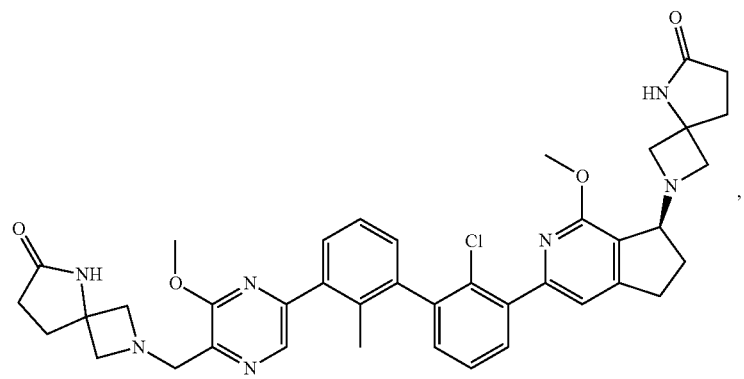

,
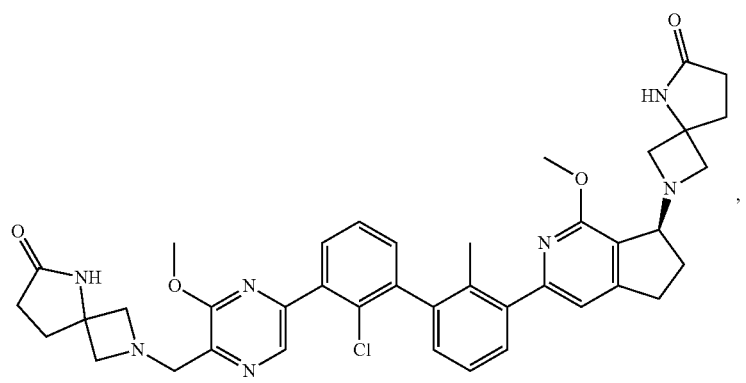
,
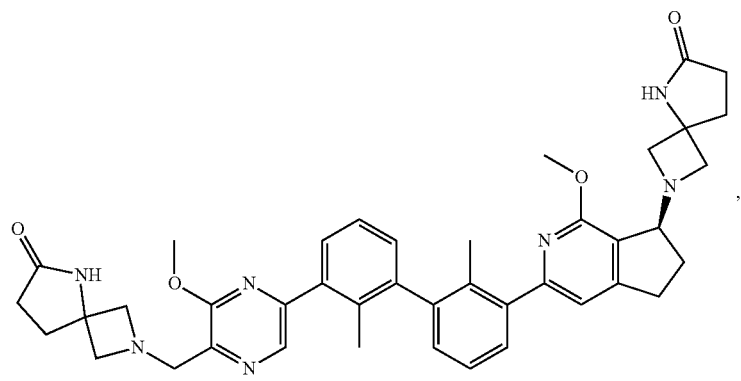
,
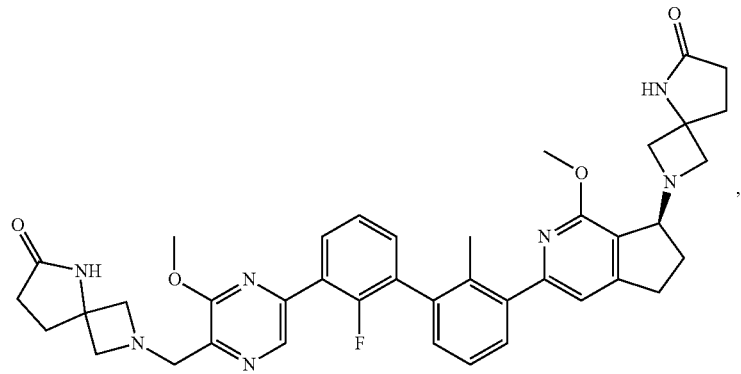
,

-continued
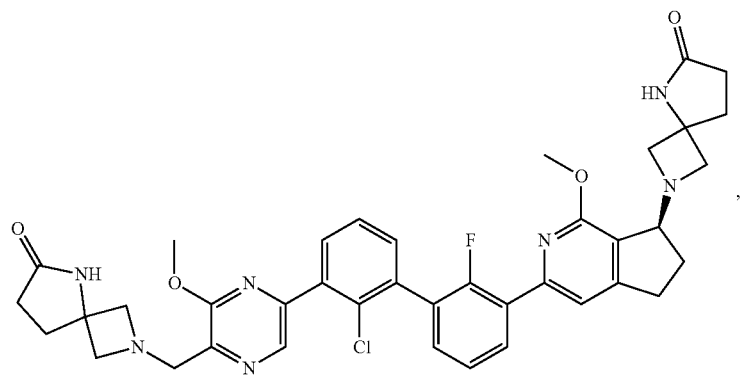
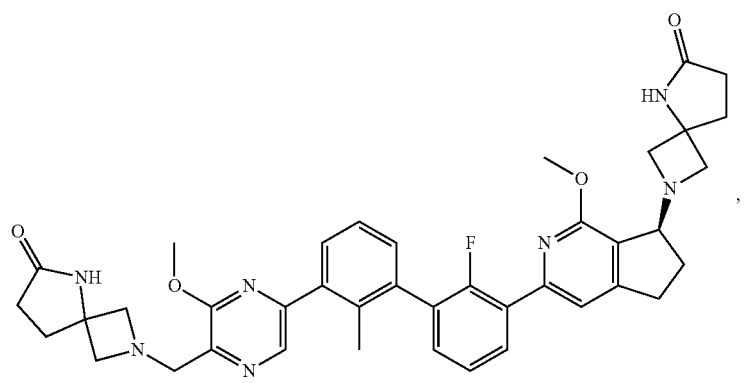
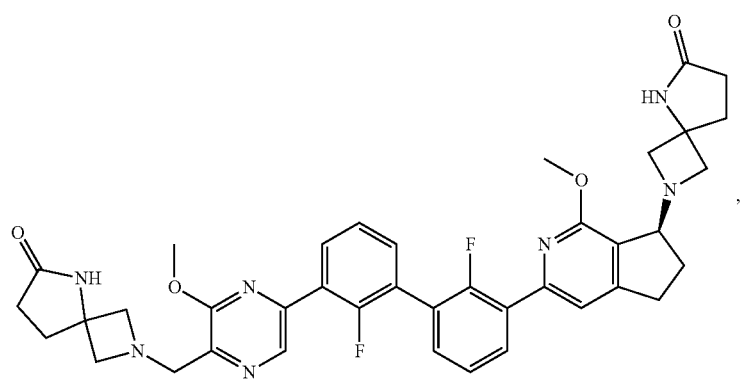
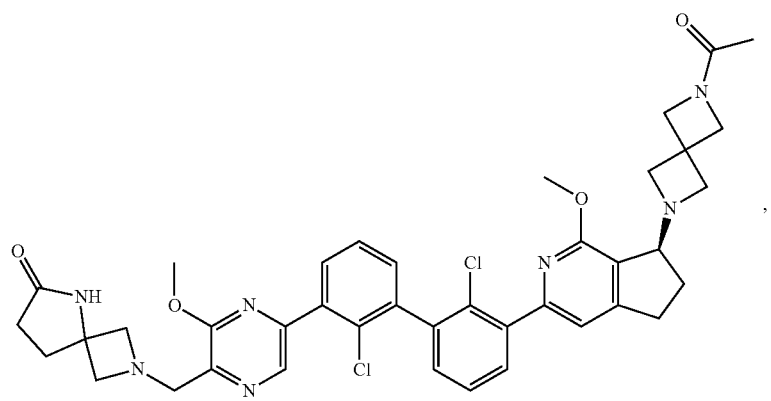

,

,
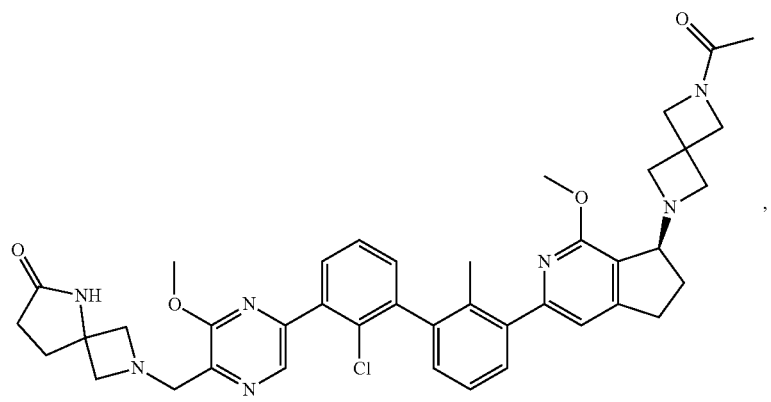
,
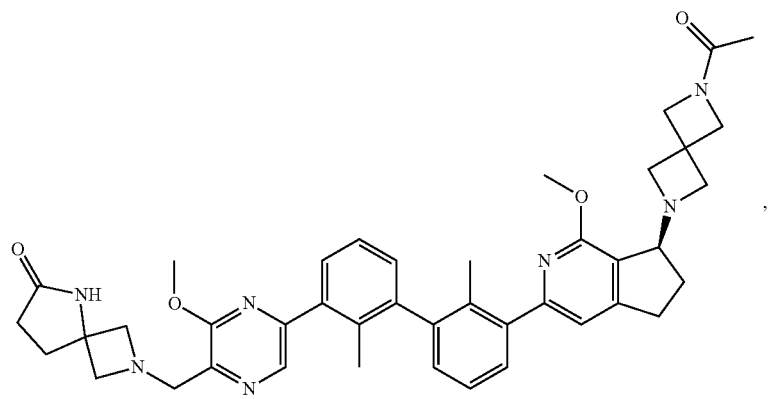
,

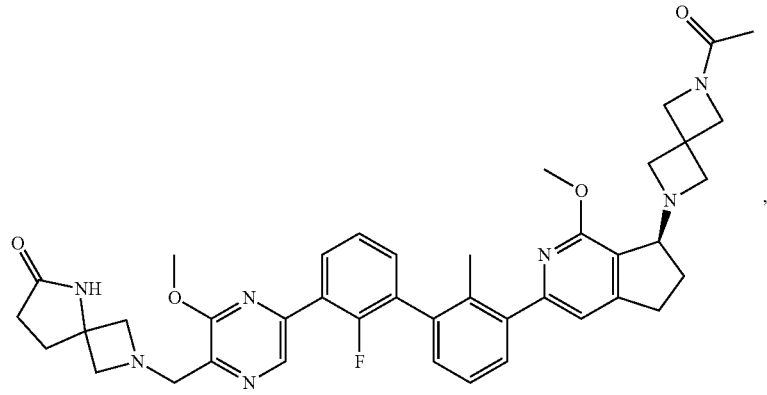
,

,
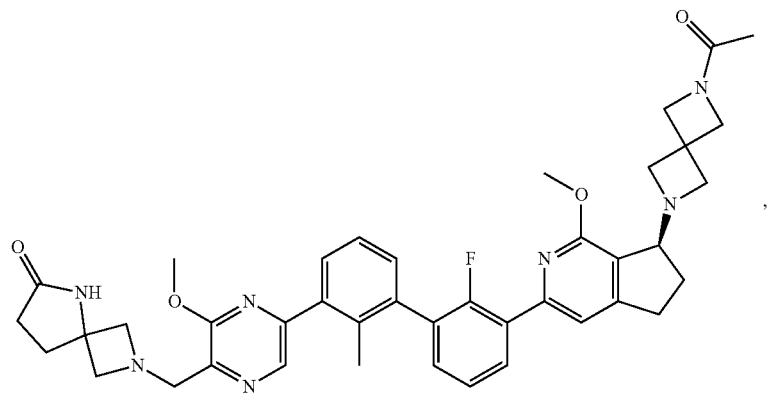
,
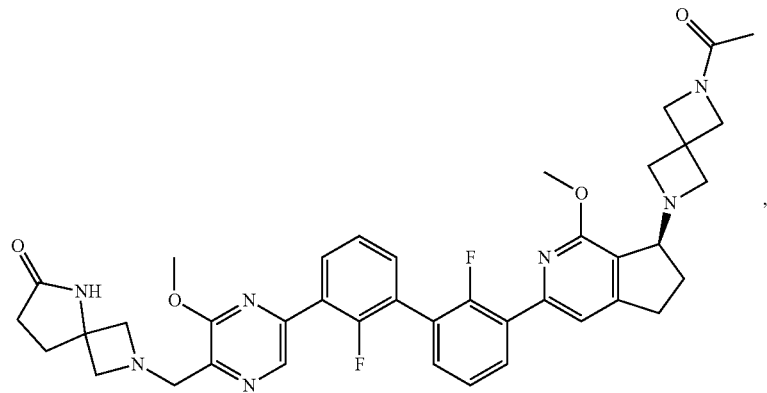
,

-continued
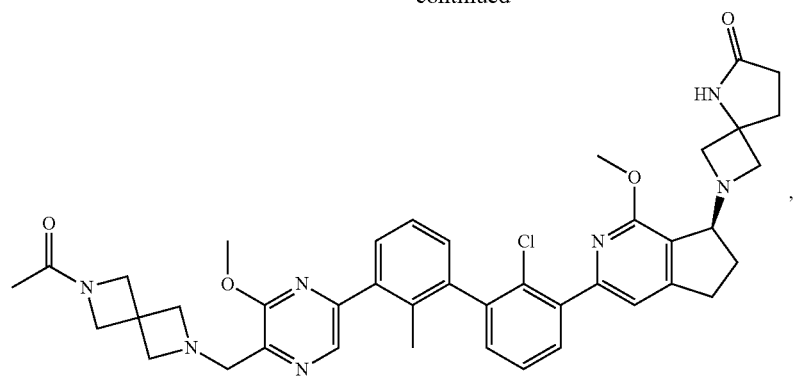
,
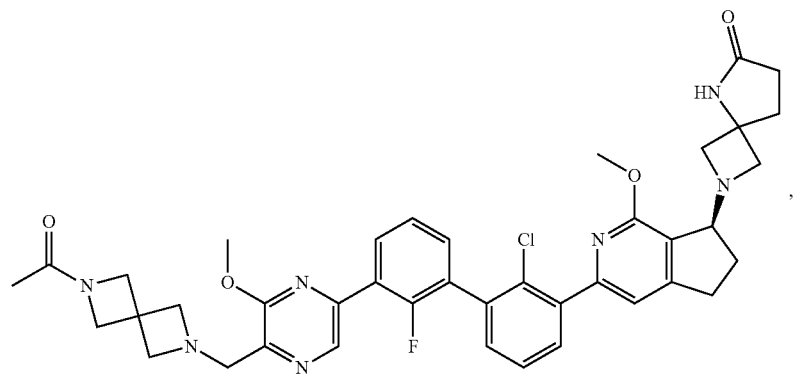
,
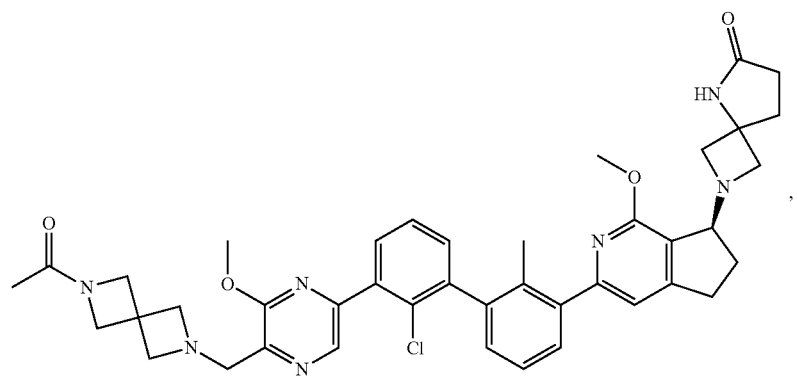
,
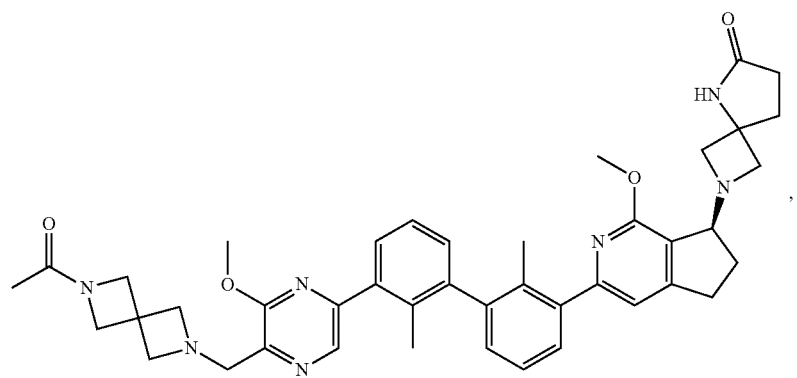
,

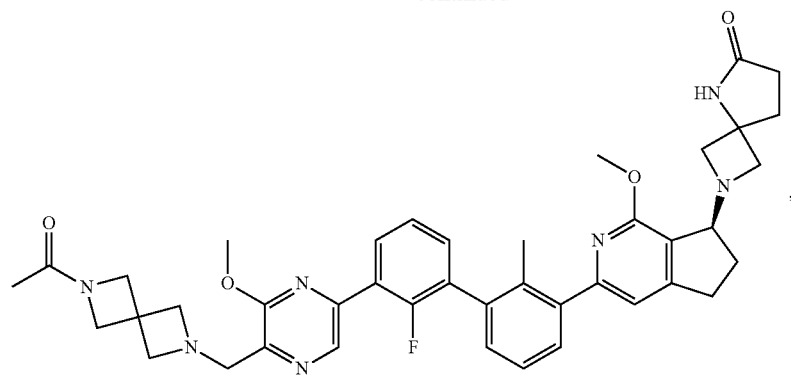,
,
,
,

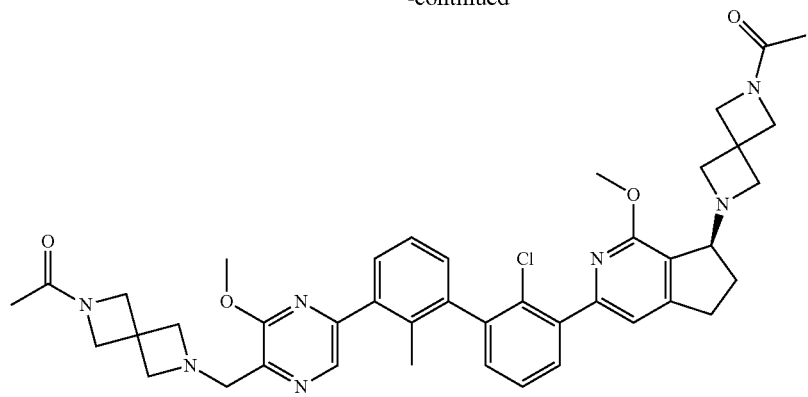,
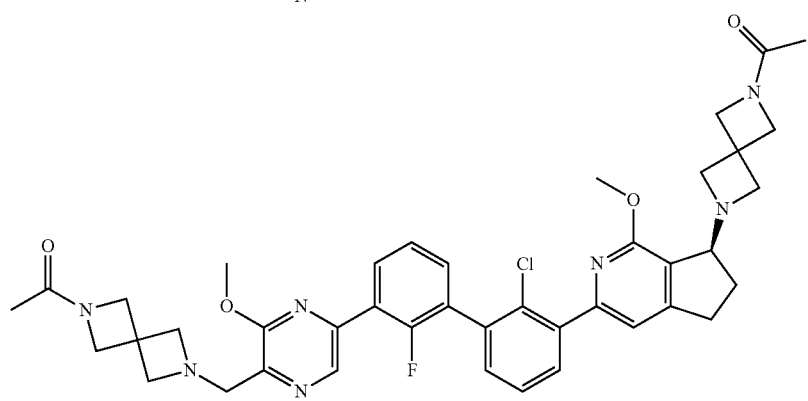,
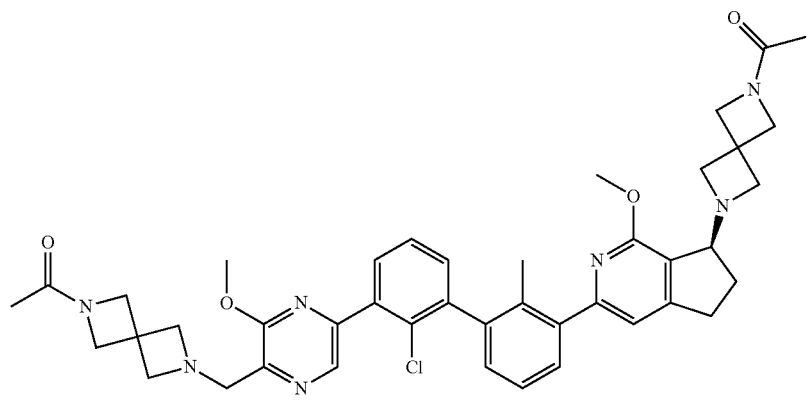,
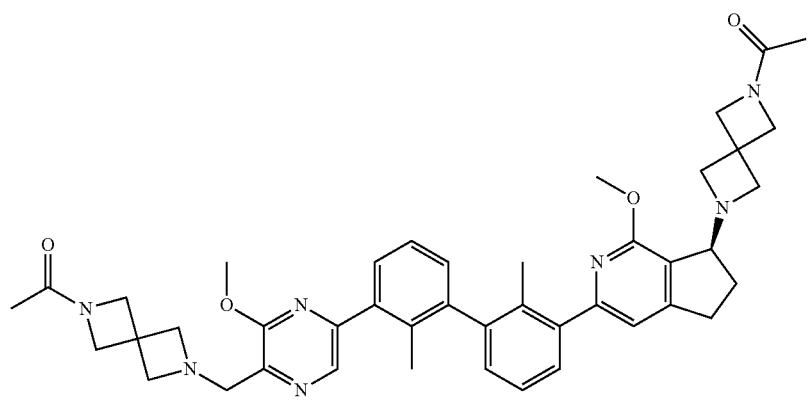,

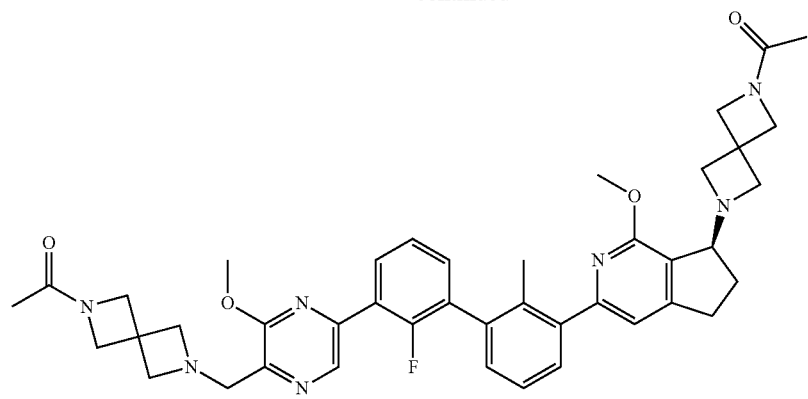
,
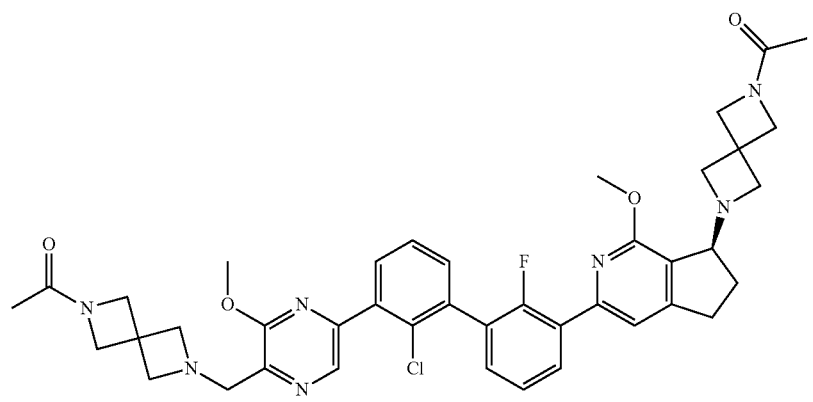
,
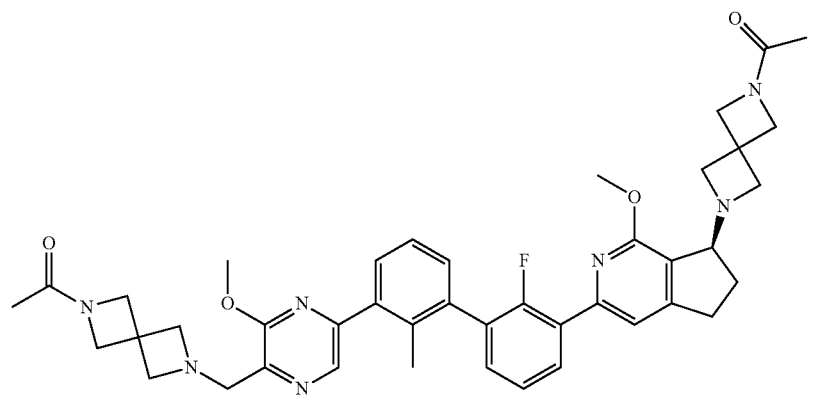
,
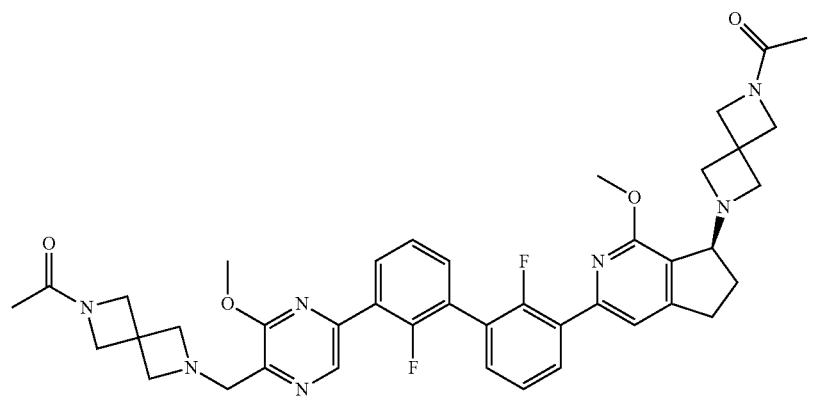
,

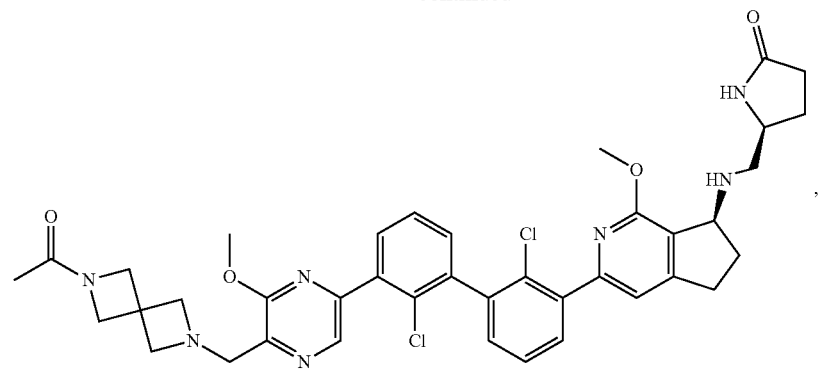
,
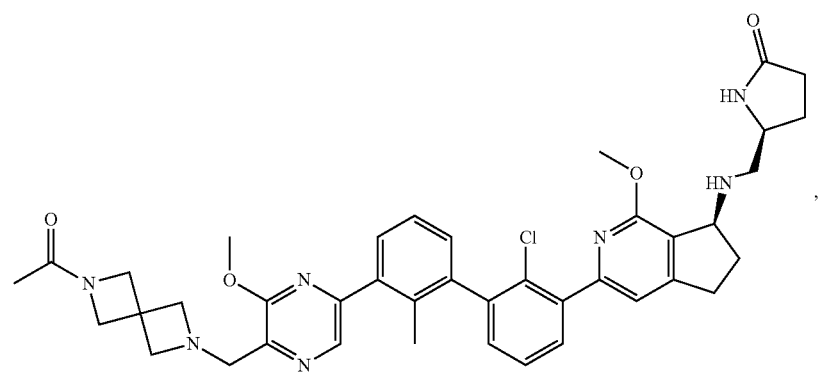
,

,
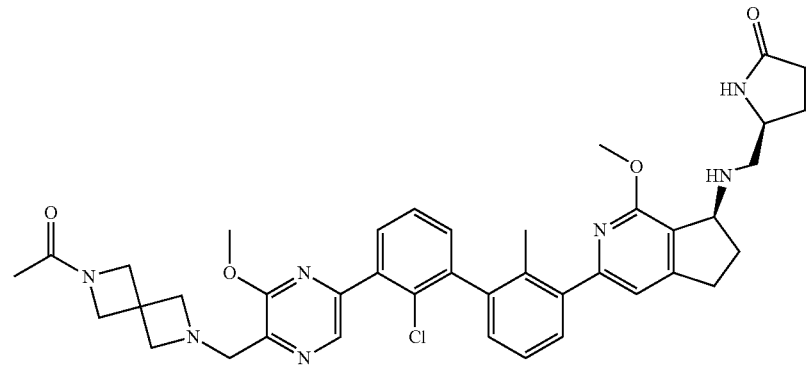
,


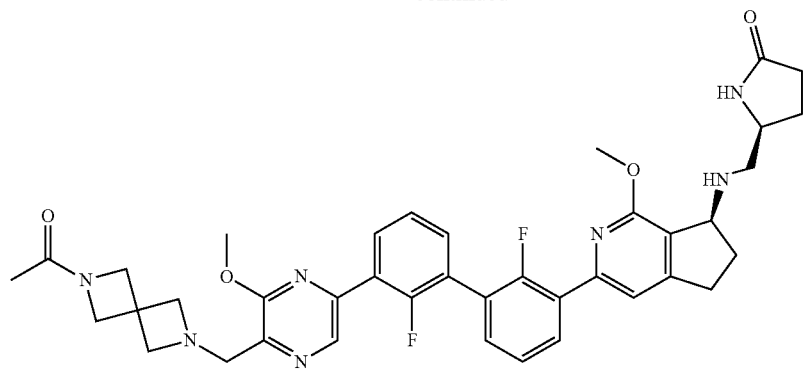
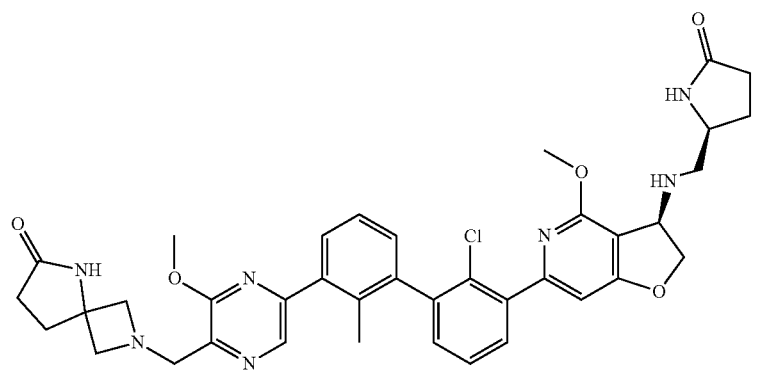
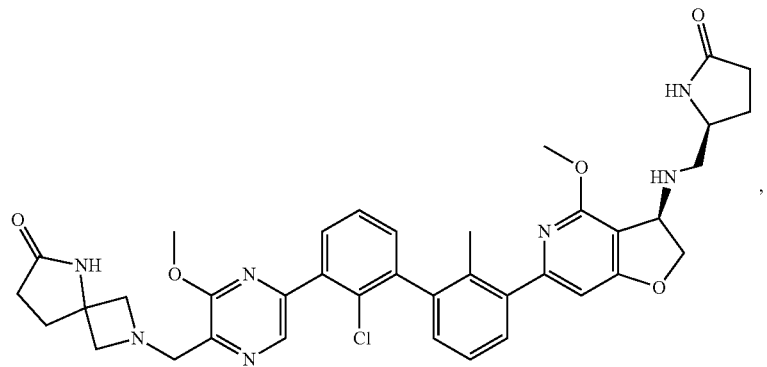

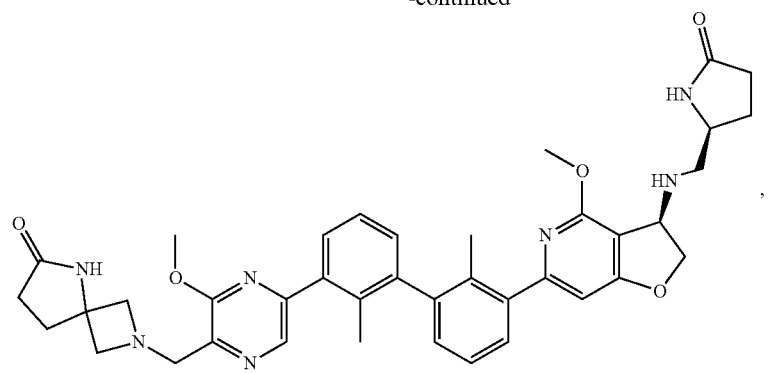
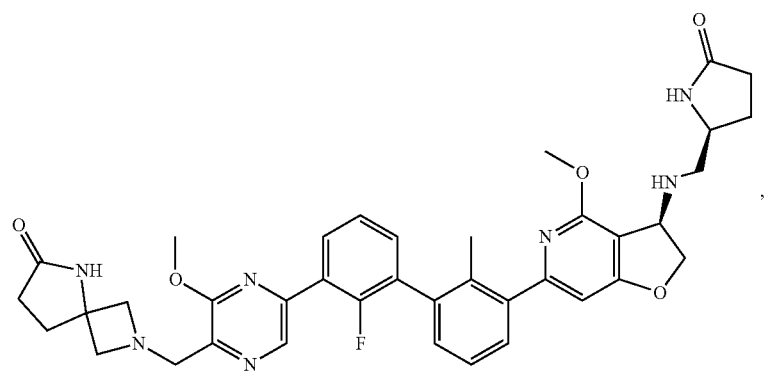
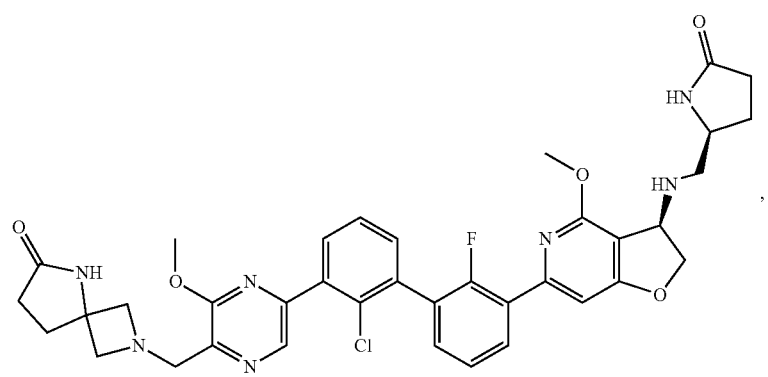
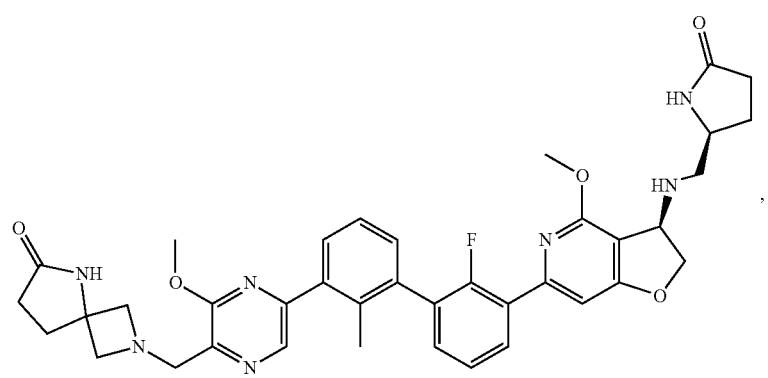

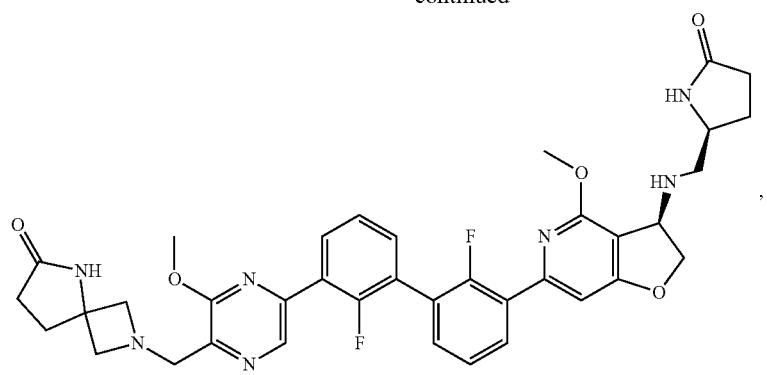
,
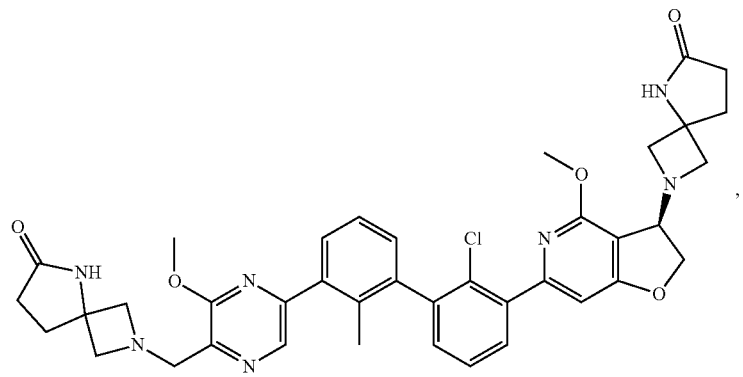
,
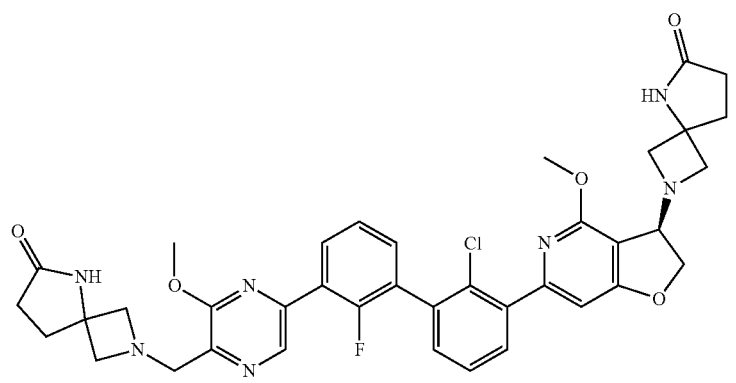
,
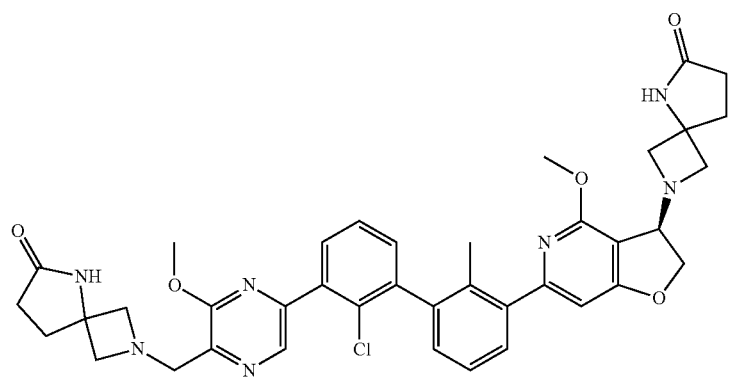
,

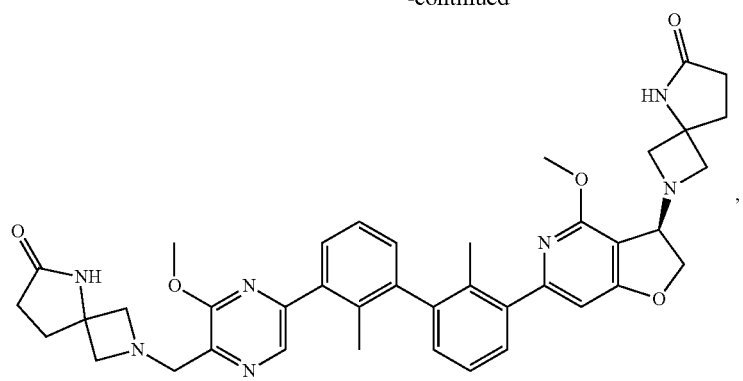,
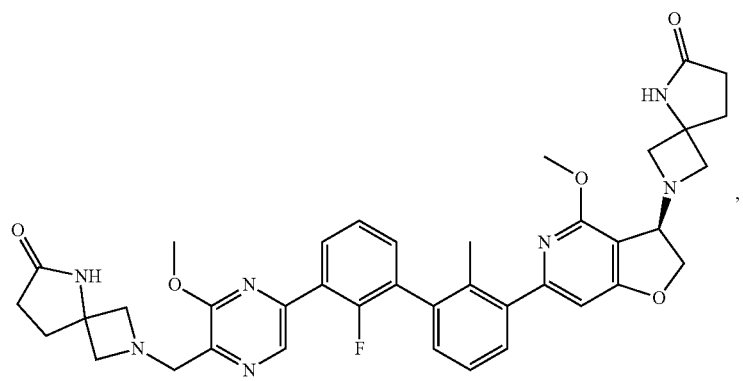,
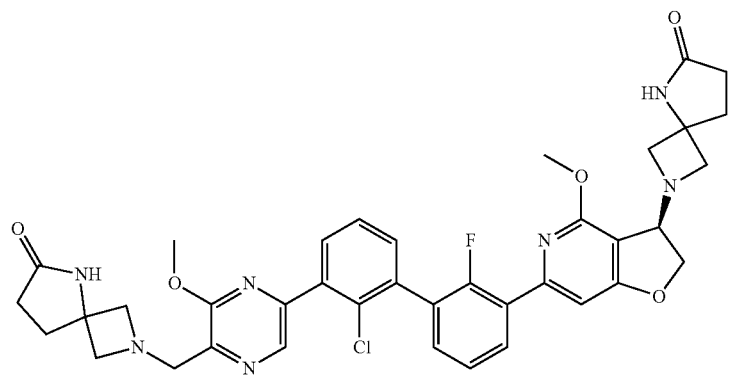,
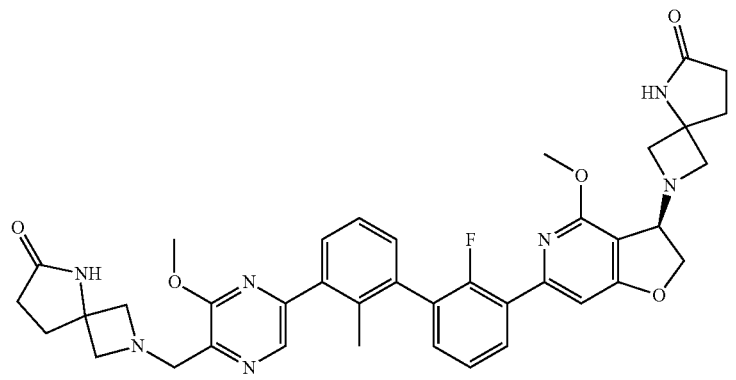,

-continued
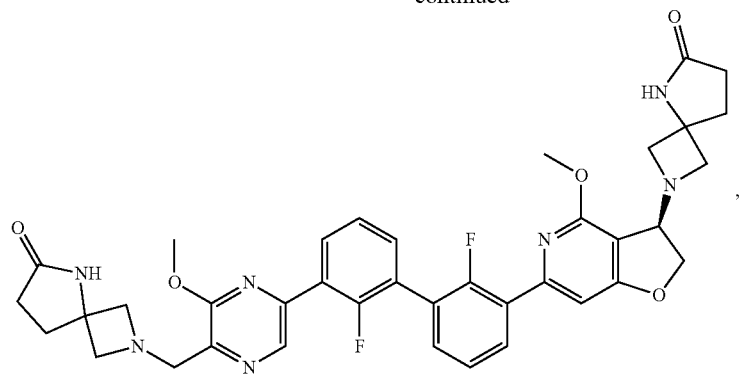
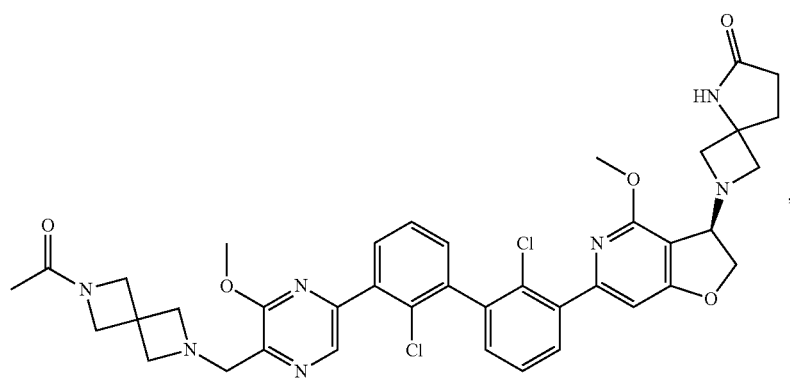

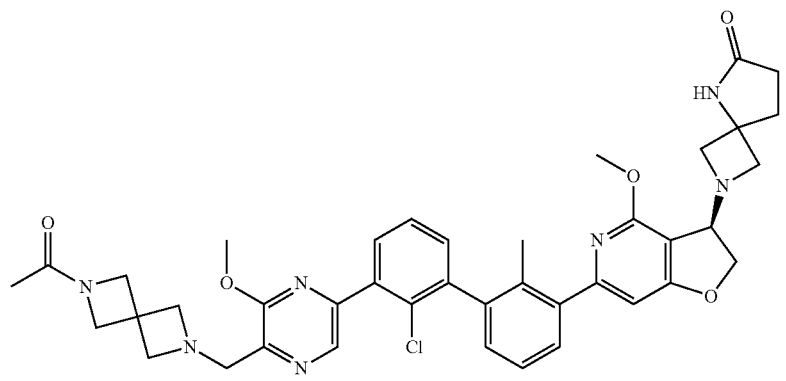,
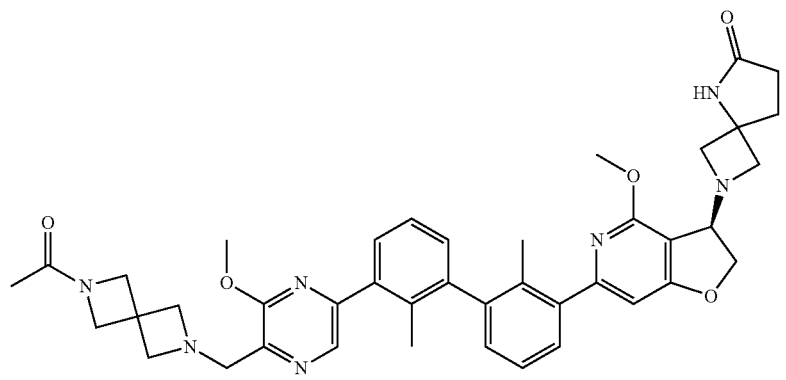,
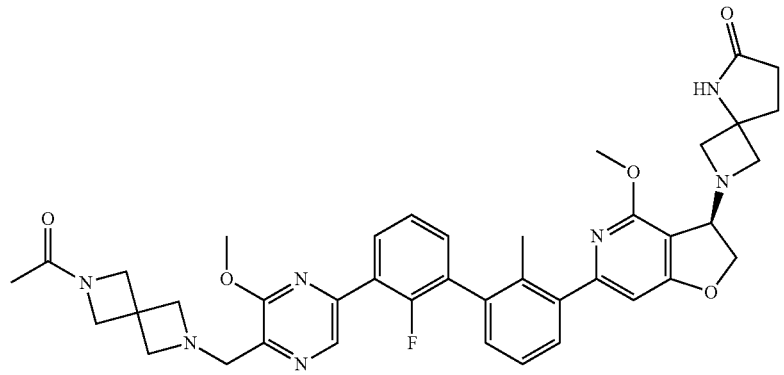,
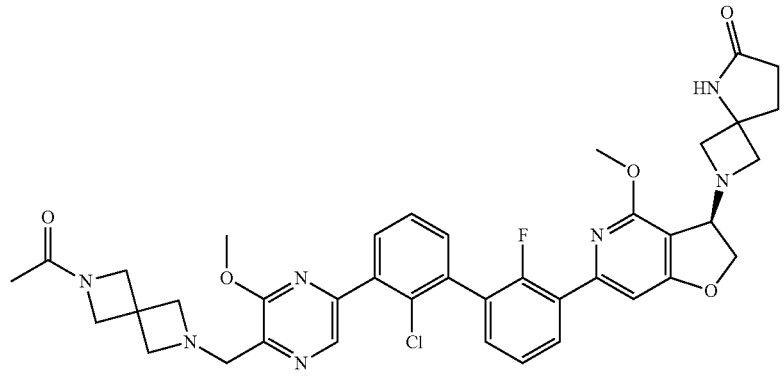,

-continued
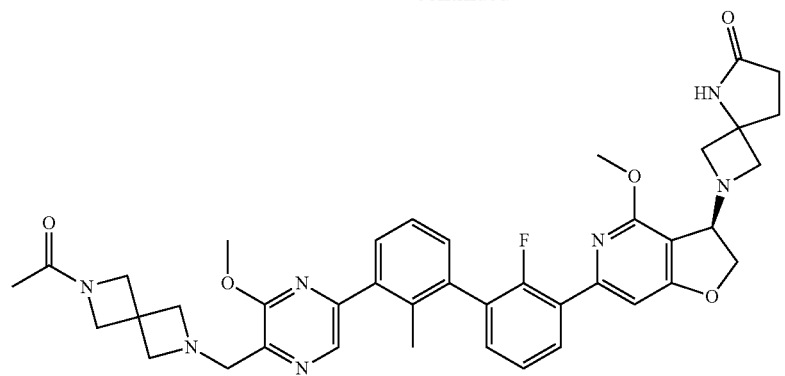
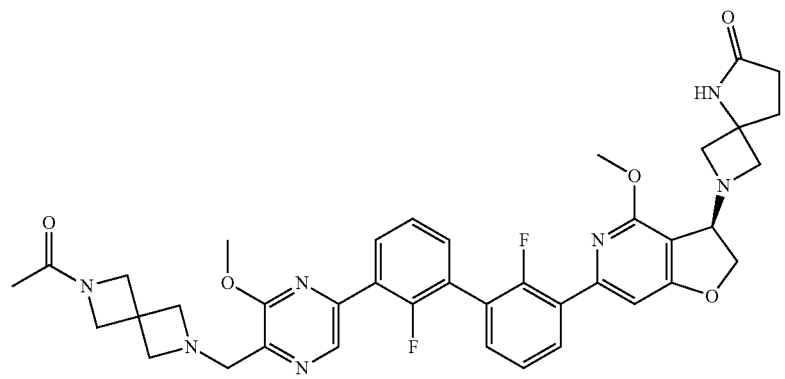

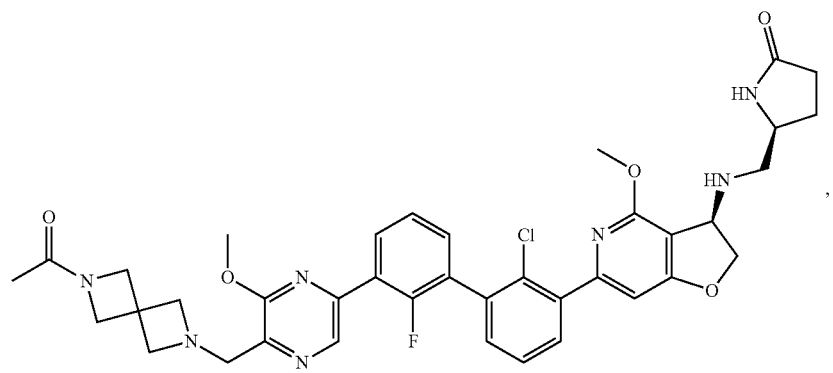

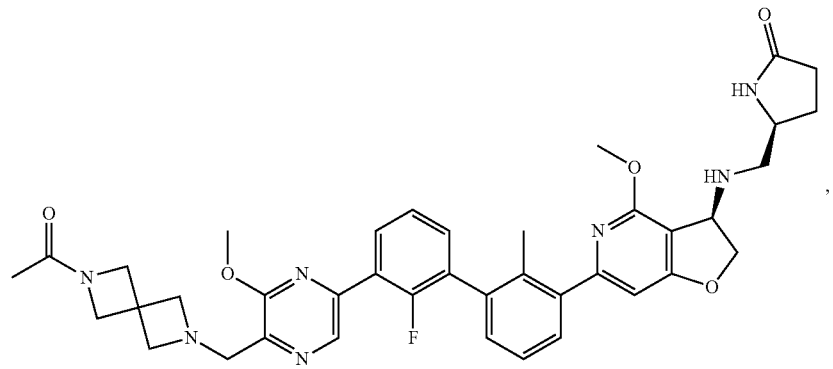

-continued

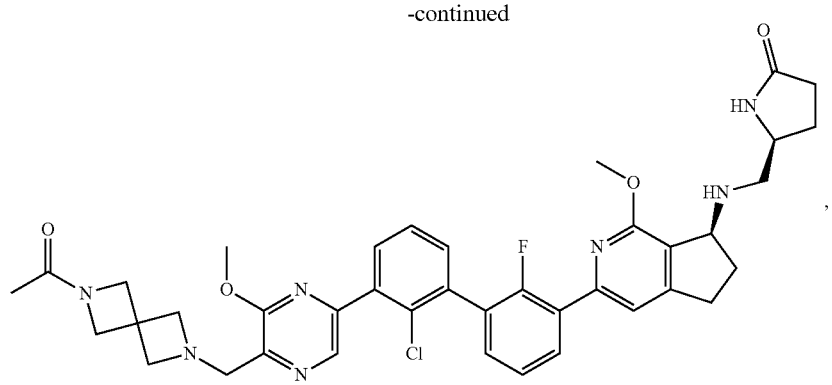

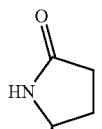

,

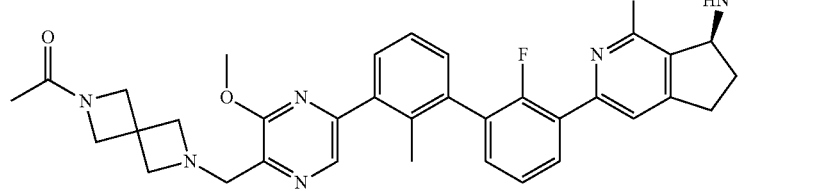

and

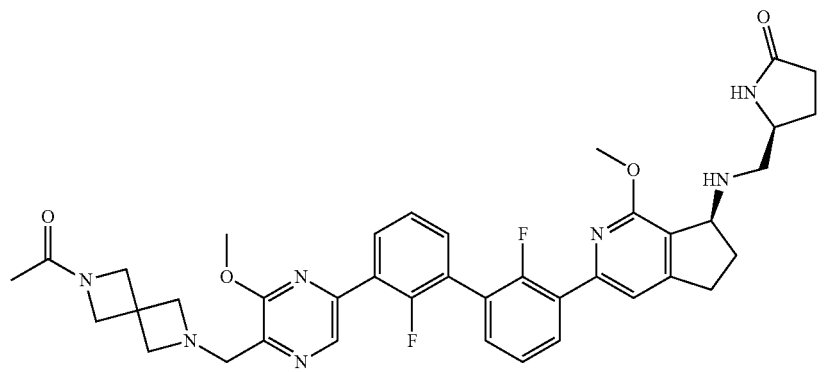

(including pharmaceutically acceptable salts of any of the foregoing).

Example A

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below). Flow from the column was brought to the Mass Spectrometer (MS) which was configured with an atmospheric pressure ion source. It is within the knowledge of the skilled person to set the tune parameters (e.g. scanning range, dwell time) in order to obtain ions allowing the identification of the compound's nominal monoisotopic molecular weight (MW). Data acquisition was performed with appropriate software. Compounds are described by their experimental retention times (Rt) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+Na]$^+$, [M+HCOO]$^-$, etc.). For molecules with multiple isotopic patterns (Br, Cl), the reported value is the one obtained for the lowest isotope mass. All results were obtained with experimental uncertainties that are commonly associated with the method used. Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica, "Q-Tof Quadrupole Time-off light mass spectrometers, "CLND", ChemiLuminescent Nitrogen Detector, "ELSD" Evaporative Light Scanning Detector.

TABLE A

LCMS Method Codes

| Method code | Instrument | Column | Mobile phase | Gradient | Flow | Run Time |
|---|---|---|---|---|---|---|
| 1 | Shimadzu LCMS2020 | Chromolith ® Flash RP-18e 25-3 mm | A: water(4 L) + TFA(1.5 mL) B: acetonitrile (4 L) + TFA (0.75 mL) | from 95% A to 5% A in 0.7 minutes and holding at 5% for 0.4 minutes, to 95% A in 0.01 min held for 0.49 min | 1.5 | 1.5 50 |
| 2 | Shimadzu LC20-MS2020 | Agilent Pursit 5 C18 20*2.0 mm | A: water(4 L) + TFA(1.5 mL) B: acetonitrile (4 L) + TFA (0.75 mL) | from 95% A to 5% A in 0.7 minutes and holding at 5% for 0.4 minutes, to 95% A in 0.01 min held for 0.39 min | 1.5 | 1.5 50 |
| 3 | Shimadzu LCMS2020 | Xbrige Shield RP-18, 5 um, 2.1*50 mm | A: water(4 L) + $NH_3H_2O$ (0.8 mL) B: acetonitrile (4 L) | from 90% A to 20% A in 3 minutes and holding at 20% for 0.5 minutes, to 90% A in 0.01 min held for 0.49 min | 1.0 | 4.0 50 |
| 4 | Shimadzu LCMS2020 | Xtimate ® C18 2.1*30 mm, 3 um | A: water(4 L) + TFA(1.5 mL) B: acetonitrile (4 L) + TFA (0.75 mL) | from 95% A to 5% A in 3 minutes and holding at 5% for 0.5 minutes, to 95% A in 0.01 min held for 0.49 min | 1.0 | 4.0 50 |
| 5 | Shimadzu LCMS2020 | Xtimate ® C18 2.1*30 mm, 3 um | A: water(4 L) + TFA(1.5 mL) B: acetonitrile (4 L) + TFA (0.75 mL) | from 95% A to 5% A in 3 minutes and holding at 5% for 0.5 minutes, to 95% A in 0.01 min held for 0.49 min | 1.2 | 4.0 50 |
| 6 | Shimadzu LCMS2020 | Xtimate C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.0 | 4.0 50 |
| 7 | Shimadzu LCMS2020 | Xtimate ® C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.2 | 4.0 50 |
| 8 | Shimadzu LCMS2020 | Xtimate C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.0 | 4.0 50 |
| 9 | Shimadzu LCMS2020 | Xtimate ® C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.2 | 4.0 50 |
| 10 | Shimadzu LCMS2020 | Xtimate C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.0 | 4.0 50 |
| 11 | Shimadzu LCMS2020 | Xtimate C18 2.1*30 mm, 3 um | A: water(4 L) + TFA(1.5 mL) B: acetonitrile (4 L) + TFA (0.75 mL) | From 100% A to 40% A in 3 minutes, to 10% A in 0.01 min, and holding at 10% for 0.49 min, to 100% A in 0.01 min held for 0.49 min | 1.0 | 4.0 50 |

Flow expressed in mL/min;
column temperature (T) in ° C.;
Run time in minutes

TABLE B

| Cmpd No. | $R_t$ | LC/MS | LCMS Method |
|---|---|---|---|
| A-1 | 1.56 | 716.2 | 7 |
| A-2 | 1.55 | 716.2 | 7 |
| A-3 | 1.59 | 742.3 | 7 |
| A-4 | 1.59 | 742.2 | 7 |
| A-5 | 1.29 | 686.4 | 6 |
| A-6 | 1.30 | 686.4 | 6 |
| A-7 | 1.27 | 739.4 | 6 |
| A-8 | 1.26 | 739.4 | 6 |
| A-9 | 1.31 | 633.4 | 6 |
| A-10 | 1.25 | 686.4 | 6 |
| A-11 | 1.25 | 686.4 | 6 |
| A-12 | 1.24 | 739.5 | 6 |
| A-13 | 1.24 | 739.5 | 6 |
| B-1 | 1.49 | 613.0 | 7 |
| B-2 | 1.49 | 613.0 | 7 |
| B-3 | 1.48 | 714.3 | 7 |
| B-4 | 1.47 | 714.1 | 7 |
| C-1 | 1.25 | 728.5 | 10 |
| C-2 | 1.07 | 728.5 | 10 |
| C-3 | 1.16 | 740.5 | 10 |
| C-4 | 1.13 | 740.5 | 6 |
| C-5 | 1.15 | 687.5 | 6 |
| C-6 | 1.17 | 687.5 | 6 |
| C-7 | 2.04 | 728.3 | 3 |
| C-8 | 2.00 | 728.3 | 3 |
| C-9 | 2.77 | 721.3 | 3 |
| C-10 | 2.19 | 742.4 | 3 |
| C-11 | 1.28 | 754.5 | 6 |
| C-12 | 1.24 | 742.5 | 6 |
| C-13 | 1.53 | 770.6 | 6 |
| C-14 | 1.43 | 768.6 | 6 |
| C-15 | 1.15 | 805.5 | 6 |
| D-1 | 1.27 | 742.6 | 6 |
| D-2 | 1.23 | 716.5 | 6 |
| D-3 | 1.36 | 715.5 | 6 |
| D-4 | 1.16 | 677.1 | 6 |
| D-5 | 1.23 | 695.2 | 6 |
| D-6 | 1.13 | 730.2 | 6 |
| D-7 | 1.09 | 675.4 | 6 |
| D-8 | 1.07 | 675.4 | 6 |
| D-9 | 1.14 | 689.4 | 6 |
| D-10 | 1.15 | 689.5 | 6 |
| D-11 | 1.13 | 673.5 | 6 |
| D-12 | 1.16 | 673.4 | 6 |
| D-13 | 1.09 | 689.4 | 6 |
| D-14 | 1.27 | 754.6 | 6 |
| D-15 | 1.25 | 728.5 | 6 |
| D-16 | 1.27 | 742.6 | 6 |
| D-17 | 1.27 | 742.5 | 6 |
| D-18 | 1.28 | 768.6 | 6 |
| D-19 | 1.28 | 768.6 | 6 |
| E-1 | 1.15 | 715.2 | 6 |
| E-2 | 1.51 | 757.0 | 6 |
| E-3 | 1.85 | 727.6 | 6 |
| E-4 | 1.87 | 757.5 | 11 |
| E-5 | 1.86 | 757.5 | 11 |
| E-6 | 1.25 | 717.5 | 10 |
| E-7 | 1.34 | 690.5 | 10 |
| F-1 | 1.42 | 690.4 | 6 |
| F-2 | 1.23 | 690.4 | 6 |
| F-3 | 1.38 | 690.5 | 6 |
| G-1 | 1.23 | 690.4 | 6 |
| G-2 | 1.22 | 690.4 | 6 |
| G-3 | 1.25 | 704.4 | 6 |
| G-4 | 1.25 | 704.4 | 6 |
| G-5 | 1.28 | 704.5 | 6 |
| G-6 | 1.27 | 704.5 | 6 |
| H-1 | 1.11 | 662.4 | 6 |
| H-2 | 1.23 | 687.4 | 6 |
| H-3 | 1.17 | 676.4 | 6 |
| H-4 | 1.16 | 676.4 | 6 |
| I-1 | 2.65 | 664.4 | 3 |
| I-3 | 2.97 | 732.0 | 3 |
| J-1 | 1.19 | 636.1 | 6 |
| J-2 | 1.27 | 650.0 | 3 |
| J-3 | 1.47 | 704.0 | 3 |
| H-5 | 1.17 | 676.4 | 6 |
| H-6 | 1.15 | 676.4 | 6 |
| K-1 | 2.25 | 728.2 | 3 |
| K-2 | 2.49 | 689.4 | 3 |

Retention time ($R_t$) in min;
LC/MS: without indication the mass is corresponding to $[M + H]^+$

Example B

PDL1/PD1 Binding Assay

Compounds to be tested were serially diluted in DMSO, and further diluted in assay buffer (25 mM Hepes pH 7.4, 150 mM NaCl, 0.005% Tween 20, BSA 0.01%). Diluted compounds were added to the wells with final concentration of DMSO at 1%. PDL1-6×His protein was added to the wells, mixed well with compound. The plates were incubated for 30 min at room temperature. PD1-Fc-Avi-Biotin protein was added to the wells. Final concentration of PDL1 and PD1 protein is 0.3 nM and 2.5 nM, respectively. After a binding time of 30 min at room temperature, Anti-6×His Acceptor beads (final concentration 20 ug/ml) were added to the wells, and the incubation continued for 1 h. Streptavidin Donor beads (final concentration 20 ug/mL) were added at reduced light. The plates were sealed with foil and incubated in the dark for additional 1 h or overnight before reading on an Envision reader. The $IC_{50}$ values were determined by fitting the curves using a four-parameter equation in Graphpad Prism 8.

Example C

PDL1 Dimerization Assay

Serially diluted compounds were added to plate wells with the final concentration of DMASO at 1%. PDL1-6×His and PDL1-strep proteins were diluted in assay buffer (25 mM Hepes pH 7.4, 150 mM NaCl, 0.005% Tween 20, BSA 0.01%), added to the wells, and mixed well with the compounds. The plates were incubated for 2 h at room temperature. Anti-6×His Acceptor beads were added to the wells and the plates were further incubated for 1 h at room temperature. Strep-tactin Donor beads were added to the wells at reduced light. After additional 1 h incubation in the dark, the plates were read on a Envision reader. The final concentrations were 0.5 nM PDL1-6×His, 0.5 nM PDL1-strep, 20 ug/mL Anti-6×His Acceptor beads, 20 ug/mL Strep-tactin Donor beads. The $EC_{50}$ values were determined by fitting the curves using a four-parameter equation in Graphpad Prism 8.

Example D

PD-1/PD-L1 NFAT Reporter Assay

Cellular activity of the compounds was assessed using a co-culture reporter assay in which TCR-mediated NF-AT activity of Jurkat T cells is constitutively inhibited by the engagement of PD-1 by PD-L1 expressing CHO cells.

Blocking the PD-1/PD-L1 interaction will release the inhibitory signal and results in TCR signaling and NFAT-mediated luciferase activity.

CHO cells expressing surface-bound anti-CD3 antibodies and PD-L1 were first seeded overnight and treated with the compounds. Jurkat cells overexpressing PD-1 and a luciferase construct under NF-AT promoter were then immediately seeded on the monolayer of CHO cells. The co-culture was then incubated for 6 hrs at 37° C. Luciferase activity was assessed by adding the ONE-Glo reagent and measuring luminescence with a plate reader. EC50s values were determined from the fit of the dose-response curves Emax (%) corresponds to the maximum NFAT-activation level reached by a given compound relative to the positive control (10 nM Atezolizumab).

Compounds described herein, as exemplified in the Examples, showed $EC_{50}$ or $IC_{50}$ values in the following ranges: A: $IC_{50}$ or $EC_{50} \leq 10$ nM; B: 10 nM $< IC_{50}$ or $EC_{50} \leq 100$ nM; C: 100 nM $< IC_{50}$ or $EC_{50} \leq 1000$ nM; D: 1000 nM $< IC_{50}$ or $EC_{50} \leq 10000$ nM; E: $IC_{50}$ or $EC_{50} > 10000$ nM; n.d.=not determined; n.r.=$EC_{50}$ not reached in the range of tested concentrations starting from 1 nM to 10000 nM.

TABLE C

| Cmpd No. | PD-1/PD-L1 PPI $IC_{50}$ | PD-L1 dimerization $EC_{50}$ | Jurkat NFAT $EC_{50}$ | Jurkat NFAT Emax (%) |
|---|---|---|---|---|
| A-1 | A | F | nd | 33 |
| A-2 | A | F | C | 85 |
| A-3 | A | F | C | 84 |
| A-4 | A |   | nd | 18 |
| A-5 | A |   | C | 102 |
| A-6 | A |   | nd | 32 |
| A-7 | A | F | nd | 24 |
| A-8 | A | D | C | 145 |
| A-9 | A | D | C | 105 |
| A-10 | A |   | B | 172 |
| A-11 | A |   | D | 84 |
| A-12 | A |   | B | 191 |
| A-13 | A |   | D | 58 |
| B-1 | A | D | D | 89 |
| B-2 | A | D | C | 107 |
| B-3 | A |   | C | 112 |
| B-4 | A | F | D | 65 | nd = indicates not determined.

TABLE D

| Cmpd No. | PD-1/PD-L1 PPI $IC_{50}$ | Jurkat NFAT $EC_{50}$ |
|---|---|---|
| C-1 | A | A |
| C-2 | A | C |
| C-3 | A | A |
| C-4 | A | n.r. |
| C-5 | A | A |
| C-6 | A | C |
| C-7 | A | B |
| C-8 | A | B |
| C-9 | A | C |
| C-10 | A | B |
| C-11 | A | B |
| C-12 | A | B |
| C-13 | A | B |
| C-14 | A | B |
| C-15 | A | B |
| D-1 | A | A |
| D-2 | A | A |
| D-3 | A | A |
| D-4 | A | B |
| D-5 | A | B |
| D-6 | A | A |
| D-7 | A | C |
| D-8 | A | A |
| D-9 | A | A |
| D-10 | A | D |
| D-11 | A | A |
| D-12 | A | n.r |
| D-13 | A | A |
| D-14 | A | A |
| D-15 | A | B |
| D-16 | A | n.r |
| D-17 | A | B |
| D-18 | A | n.r. |
| D-19 | A | A |
| E-1 | A | A |
| E-2 | A | A |
| E-3 | A | A |
| E-4 | A | A |
| E-5 | A | n.r |
| E-6 | A | n.r |
| E-7 | A | n.r |
| F-1 | A | B |
| F-2 | A | B |
| F-3 | A | B |
| G-1 | A | B |
| G-2 | A | n.r |
| G-3 |   | n.r. |
| G-4 |   | D |
| G-5 | A | B |
| G-6 | A | D |
| H-1 | A | B |
| H-2 | A | C |
| H-3 | A | B |
| H-4 | A | C |
| I-1 | A | C |
| I-3 |   | D |
| J-1 | A | B |
| J-2 | A | B |
| J-3 | A | D |
| H-5 | A | B |
| H-6 | A | C |
| K-1 | A | B |
| K-2 | A | B |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (II), or a pharmaceutically acceptable salt thereof, having the structure:

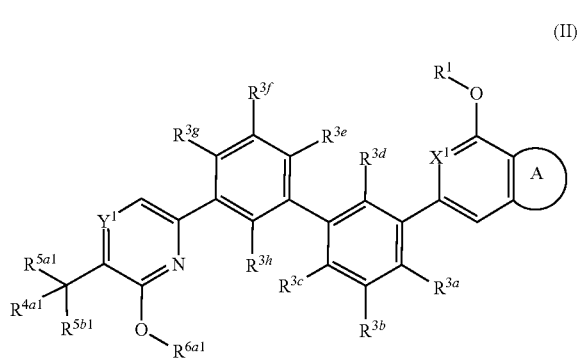

(II)

wherein:

$X^1$ is N or CH;

Ring A is selected from the group consisting of:
- a monocyclic $C_{5-7}$ cycloalkyl substituted with $R^{2a1}$;
- a bicyclic $C_{6-12}$ cycloalkyl substituted with $R^{2a2}$;
- a 5-7 membered nitrogen-containing monocyclic heterocyclyl, wherein a nitrogen of the 5-7 membered nitrogen-containing monocyclic heterocyclyl is optionally substituted with $R^{2a3}$, wherein a carbon of the 5-7 membered nitrogen-containing monocyclic heterocyclyl is optionally substituted with $R^{2a4}$ or $R^{2a5}$, and wherein when $R^{2a5}$ is present, $R^{2a5}$ is attached at a carbon atom adjacent to a nitrogen of the 5-7 membered nitrogen-containing monocyclic heterocyclyl;
- a 6-12 membered nitrogen-containing bicyclic heterocyclyl, wherein a nitrogen of the 6-12 membered nitrogen-containing bicyclic heterocyclyl is optionally substituted with $R^{2a6}$;
- a 5-7 membered oxygen-containing monocyclic heterocyclyl substituted with $R^{2a7}$ or $R^{2a8}$, wherein when $R^{2a8}$ is present, $R^{2a8}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens; and
wherein Ring A is optionally further substituted;

$Y^1$ is N or —$CR^8$, wherein $R^8$ is selected from the group consisting of hydrogen, —$C_{1-4}$ alkyl, and —$C_{1-4}$ haloalkyl;

$R^1$ and $R^{6a1}$ are independently selected from the group consisting of —$C_{1-4}$ alkyl, —$C_{1-4}$ haloalkyl, -monocyclic $C_{3-6}$cycloalkyl, —($C_{1-4}$alkyl)monocyclic $C_{3-6}$cycloalkyl, 4-6 membered monocyclic heterocyclic ring, aryl($C_{1-4}$alkyl) and —($C_{1-4}$alkyl) 5- or 6-membered monocyclic heteroaryl; wherein the —$C_{3-6}$cycloalkyl, the 4-6 membered monocyclic heterocyclyl, the aryl ($C_{1-4}$alkyl) and the -5- or 6-membered monocyclic heteroaryl($C_{1-4}$alkyl) is optionally substituted with one or two or three substituents independently selected from the group consisting of halogen, CN, $C_{1-4}$ alkyl, $C_{3-6}$ monocyclic cycloalkyl and $C_{1-4}$ alkoxy;

$R^{2a1}$, $R^{2a2}$ and $R^{2a7}$ are independently selected from the group consisting of amino, —$N(R^{m1})R^{n1}$, —($C_{3-6}$ monocyclic cycloalkyl)$N(R^{m2})R^{n2}$, -$R^{x1}$ and —($C_{1-4}$ alkyl)$R^{x1}$, $R^{m1}$ and $R^{m2}$ are independently selected from the group consisting of hydrogen, —$C_{1-4}$ alkyl, $C_{3-6}$ monocyclic cycloalkyl, $C_{5-12}$ bicyclic cycloalkyl, 5- or 6-membered monocyclic heteroaryl, 4-7 membered monocyclic heterocyclyl, 8-11 membered fused-heteroaryl, 8-11 membered fused-heterocyclyl and -$R^{x2}$; wherein the monocyclic heteroaryl, the bicyclic heteroaryl the monocyclic heterocyclyl and the bicyclic heterocyclyl contain at least one heteroatom independently selected from the group consisting of O, S, C(=O), S(=O), S(=O)$_2$ and N; wherein the —$C_{1-4}$ alkyl is optionally substituted with one or two or three substituents independently selected from the group consisting of halogen, cyano, hydroxy, —$C_{1-4}$ alkoxy, —$C_{1-4}$ haloalkyl, —$C_{1-4}$ haloalkoxy, —C(=O)O$R^{Z1}$, —C(=O)NHS(=O)$_2R^{Z3}$, —C(=O)N($R^{Z1}$)$R^{Z2}$, —S(=O)$_2R^{Z3}$, —S(=O)$_2$N($R^{Z1}$)$R^{Z2}$, —N($R^{Z1}$)C(=O)$R^{Z3}$, —N($R^{Z1}$)S(=O)$R^{Z3}$, —N($R^{Z1}$)C(=O)N($R^{Z2}$)$R^{Z3}$ and —N($R^{Z1}$)S(=O)N($R^{Z2}$)$R^{Z1}$; wherein the $C_{3-6}$ monocyclic cycloalkyl, the $C_{3-6}$ monocyclic cycloalkyl($C_{1-4}$ alkyl), the 5- or 6-membered monocyclic heteroaryl, the 4-7 membered monocyclic heterocyclyl, the 8-11 membered fused-heteroaryl, the 8-11 membered fused-heterocyclyl and the 4-7 membered monocyclic heterocyclyl(CH$_2$) are optionally substituted with one or two or three substituents independently selected from the group consisting of halogen, cyano, —$C_{1-4}$ alkyl, hydroxy, —$C_{1-4}$ alkoxy, —$C_{1-4}$ haloalkyl, —$C_1$ haloalkoxy, —C(=O)O$R^{Z1}$, —C(=O)NHS(=O)$_2R^{Z3}$, —C(=O)N($R^{Z1}$)$R^{Z2}$, —S(=O)$_2R^{Z3}$, —S(=O)$_2$N($R^{Z1}$)$R^{Z2}$, —N($R^{Z1}$)C(=O)$R^{Z3}$, —N($R^{Z1}$)S(=O)$R^{Z3}$, —N($R^{Z1}$)C(=O)N($R^{Z2}$)$R^{Z3}$ and —N($R^{Z1}$)S(=O)N($R^{Z2}$)$R^{Z3}$; and $R^{n1}$ and $R^{n2}$ is hydrogen, —$C_{1-4}$ alkyl, —$C_{1-4}$ halolkyl or $C_{3-6}$ monocyclic cycloalkyl(CH$_2$);

$R^{2a3}$ and $R^{2a6}$ are independently selected from the group consisting of hydrogen, —$C_4$alkyl, $C_{3-6}$ monocyclic cycloalkyl, $C_{5-12}$ bicyclic cycloalkyl, 5- or 6-membered monocyclic heteroaryl, 4-7 membered monocyclic heterocyclyl, 8-11 membered fused-heteroaryl, 8-11 membered fused-heterocyclyl and -$R^{x2}$; wherein the monocyclic heteroaryl and the monocyclic heterocyclyl contain at least one heteroatom independently selected from the group consisting of O, S, C(=O), S(=O), S(=O)$_2$ and N; wherein the —$C_{1-4}$ alkyl, the —$C_{3-6}$ monocyclic cycloalkyl, the —$C_{3-6}$ monocyclic cycloalkyl($C_{1-4}$ alkyl), the 5- or 6-membered monocyclic heteroaryl, the 4-7 membered monocyclic heterocyclyl and the 4-7 membered monocyclic heterocyclyl(CH$_2$) are optionally substituted with one or two or three substituents independently selected from the group consisting of halogen, cyano, hydroxy, —$C_{1-4}$ alkoxy, —$C_{1-4}$ haloalkoxy, —C(=O)O$R^{Z1}$, —C(=O)NHS(=O)$_2R^{Z3}$, —C(=O)N($R^{Z1}$)$R^{Z2}$, —S(=O)$_2R^{Z3}$, —S(=O)$_2$N($R^{Z1}$)$R^{Z2}$, —NHC(=O)$R^{Z3}$, —NHC(=O)N($R^{Z1}$)$R^{Z3}$ and —N($R^{Z1}$)S(=O)$_2$N($R^{Z2}$)$R^{Z3}$;

$R^{2a4}$ is selected from the group consisting of halogen, —$C_{1-4}$ alkyl, —C(=O)O$R^{Z4}$, —O$R^{Z4}$, —$N(R^{m3})R^{n3}$ and —$C_{3-7}$ cycloalkyl; wherein the —$C_{1-4}$ alkyl and the —$C_{3-7}$ cycloalkyl are optionally substituted with one or two or three substituents independently selected from the group consisting of halogen, cyano, hydroxy, —$C_{1-4}$ alkoxy, —$C_{1-4}$ haloalkoxy, —C(=O)O$R^{Z1}$, —C(=O)NHS(=O)$_2R^{Z3}$, —C(=O)N($R^{Z1}$)$R^{Z2}$, —S(=O)$_2R^{Z3}$, —S(=O)$_2$N($R^{Z1}$)$R^{Z2}$, —NHC(=O)$R^{Z3}$, —NHC(=O)N($R^{Z1}$)$R^{Z3}$ and —N($R^{Z1}$)S(=O)$_2$N($R^{Z2}$)$R^{Z3}$; wherein $R^{m3}$ and $R^{n3}$ are independently selected from the group consisting of hydrogen, —$C_{1-4}$ alkyl and —C$_{3-6}$ monocyclic cycloalkyl; and R$^{Z4}$ is selected from the group consisting of hydrogen, —C$_{1-4}$ alkyl, —C$_{1-4}$ haloalkyl and —C$_{3-6}$ cycloalkyl;

R$^{2a5}$ and R$^{2a8}$ are independently selected from the group consisting of —C$_{1-4}$ alkyl, —C(=O)OR$^{Z5}$, —C$_{3-6}$ monocyclic cycloalkyl and —(C$_{1-4}$ alkyl)R$^{x1}$; wherein the —C$_{1-4}$ alkyl and the —C$_{3-6}$ monocyclic cycloalkyl are optionally substituted with one or two or three substituents independently selected from the group consisting of halogen, cyano, hydroxy, —C$_{1-4}$ alkoxy, —C$_{1-4}$ haloalkoxy, —C(=O)OR$^{Z1}$, —C(=O)NHS(=O)$_2$R$^{Z3}$, —C(=O)N(R$^{Z1}$)R$^{Z2}$, —S(=O)$_2$R$^{Z3}$, —S(=O)$_2$N(R$^{Z1}$)R$^{Z2}$, —NHC(=O)R$^{Z3}$, —NHC(=O)N(R$^{Z1}$)R$^{Z3}$ and —N(R$^{Z1}$)S(=O)$_2$N(R$^{Z2}$)R$^{Z3}$; and wherein R$^{Z5}$ is hydrogen, —C$_{1-4}$ alkyl, —C$_{1-4}$ haloalkyl and —C$_{3-6}$ cycloalkyl;

R$^{3a}$, R$^{3b}$, R$^{3c}$, R$^{3d}$, R$^{3f}$ and R$^{3g}$ are independently selected from the group consisting of hydrogen and halogen;

R$^{3d}$ and R$^{3h}$ are independently selected from the group consisting of hydrogen, halogen, cyano, —CH$_3$, —CH$_2$CH$_3$, —CH$_2$OH, —OCH$_3$ and —SCH$_3$;

R$^{4a1}$ is selected from the group consisting of amino, —NR$^{p1}$R$^{q1}$, —(C$_{3-6}$ monocyclic cycloalkyl)N(R$^{p2}$)R$^{q2}$, -R$^{y1}$ and —(C$_{1-4}$ alkyl)R$^{y1}$;

R$^{p1}$ and R$^{p2}$ are independently selected from the group consisting of hydrogen, —C$_{1-4}$ alkyl, C$_{3-6}$ monocyclic cycloalkyl, C$_{5-12}$ bicyclic cycloalkyl, 5- or 6-membered monocyclic heteroaryl, 4-7 membered monocyclic heterocyclyl, 8-11 membered fused-heteroaryl, 8-11 membered fused-heterocyclyl and -R$^{y2}$; wherein the monocyclic heteroaryl, the bicyclic heteroaryl the monocyclic heterocyclyl and the bicyclic heterocyclyl contain at least one heteroatom independently selected from the group consisting of O, S, C(=O), S(=O), S(=O)$_2$ and N; wherein the —C$_{1-4}$ alkyl is optionally substituted with one or two or three substituents independently selected from the group consisting of halogen, cyano, -hydroxy, —C$_{1-4}$ alkoxy, —C$_{1-4}$ haloalkyl, —C$_{1-4}$ haloalkoxy, —C(=O)OR$^{W1}$, —C(=O)NHS(=O)$_2$R$^{W3}$, —C(=O)N(R$^{W1}$)R$^{W2}$, —S(=O)$_2$R$^{W3}$, —S(=O)N(R$^{W1}$)R$^{W2}$, —N(R$^{W1}$)C(=O)R$^{W3}$, —N(R$^{W1}$)S(=O)R$^{W3}$, —N(R$^{W1}$)C(=O)N(R$^{W2}$)R$^{W3}$ and —N(R$^{W1}$)S(=O)N(R$^{W2}$)R$^{W3}$; wherein the C$_{3-6}$ monocyclic cycloalkyl, the C$_{3-6}$ monocyclic cycloalkyl(C$_{1-4}$ alkyl), the 5- or 6-membered monocyclic heteroaryl, the 4-7 membered monocyclic heterocyclyl, the 8-11 membered fused-heteroaryl, the 8-11 membered fused-heterocyclyl and the 4-7 membered monocyclic heterocyclyl(CH$_2$) are optionally substituted with one or two or three substituents independently selected from the group consisting of halogen, cyano, —C$_{1-4}$ alkyl, hydroxy, —C$_{1-4}$ alkoxy, —C$_{1-4}$ haloalkyl, —C$_{1-4}$ haloalkoxy, —C(=O)OR$^{W1}$, —C(=O)NHS(=O)$_2$R$^{W3}$, —C(=O)N(R$^{W1}$)R$^{W2}$, —S(=O)$_2$R$^{W3}$, —S(=O)N(R$^{W1}$)R$^{W2}$, —N(R$^{W1}$)C(=O)R$^{W3}$, —N(R$^{W1}$)S(=O)R$^{W3}$, —N(R$^{W1}$)C(=O)N(R$^{W2}$)R$^{W3}$ and —N(R$^{W1}$)S(=O)N(R$^{W2}$)R$^{W3}$; and R$^{p1}$ and R$^{q2}$ are independently hydrogen, —C$_{1-4}$ alkyl, —C$_{1-4}$ halolkyl or C$_{3-6}$ monocyclic cycloalkyl(CH$_2$);

R$^{x1}$ is selected from the group consisting of:

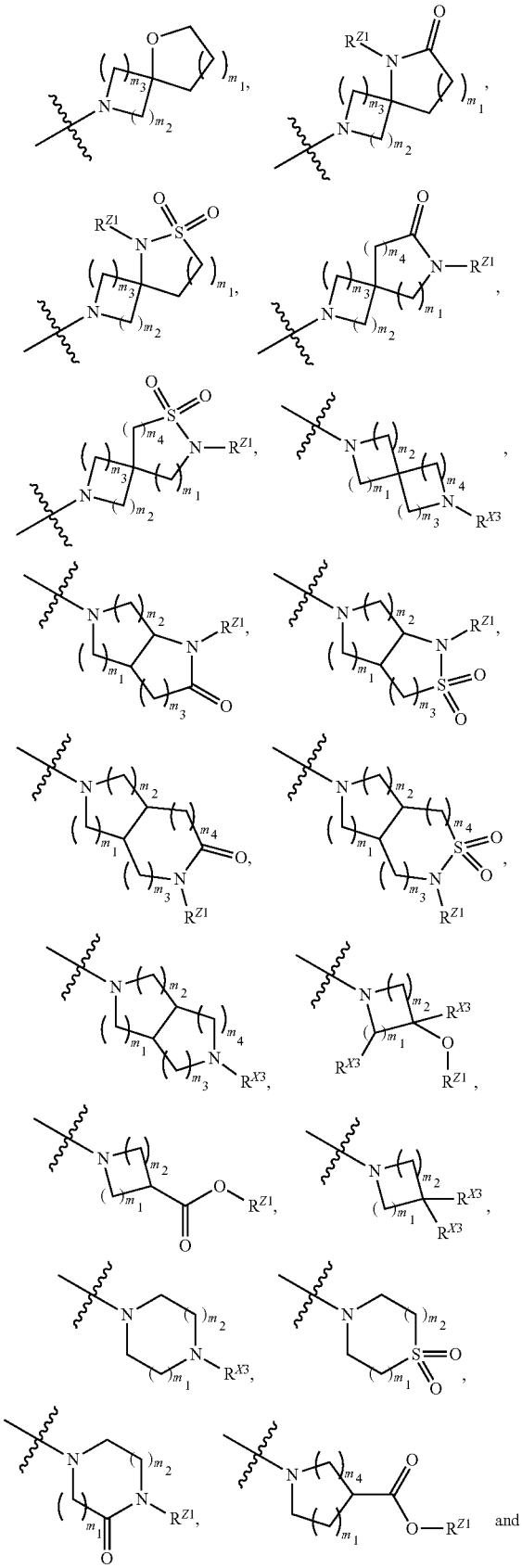

-continued

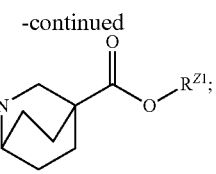

wherein $R^{x1}$ is optionally substituted with one or two substituents independently selected from the group consisting of halogen, cyano, —$C_{1-4}$ alkyl, hydroxy, —$C_4$ alkoxy, —$C_{1-4}$ haloalkyl, —$C_{1-4}$ haloalkoxy, —C(=O)O$R^{Z1}$, —C(=O)NHS(=O)$_2R^{Z3}$, —C(=O)N($R^{Z1}$)$R^{Z2}$, —S(=O)$_2R^{Z3}$, —S(=O)$_2$N($R^{Z1}$)$R^{Z2}$, —N($R^{Z1}$)C(=O)$R^{Z3}$, —N($R^{Z1}$)S(=O)$R^{Z3}$, —N($R^{Z1}$)C(=O)N($R^{Z1}$)$R^{Z3}$ and —N($R^{Z1}$)S(=O)$_2$N($R^{Z2}$)$R^{Z3}$;

$R^{x2}$ is selected from the group consisting of:

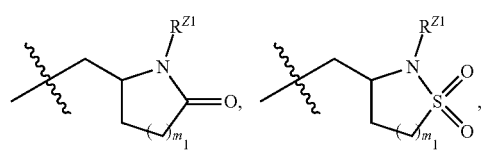

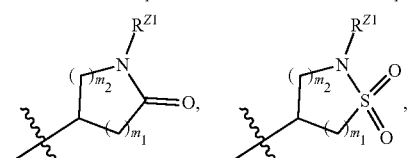

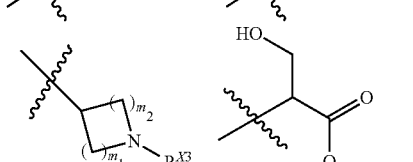

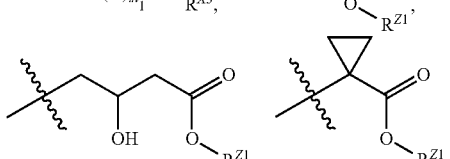

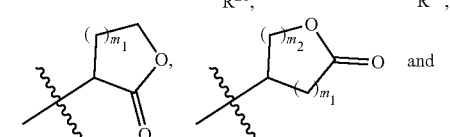 and

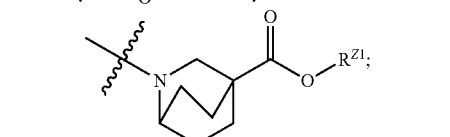

$R^{y1}$ is selected from the group consisting of:

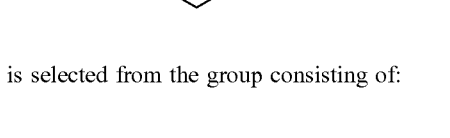

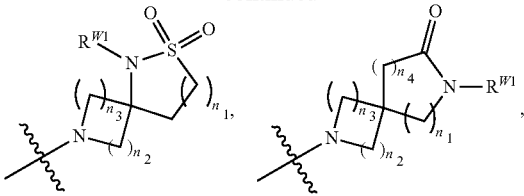

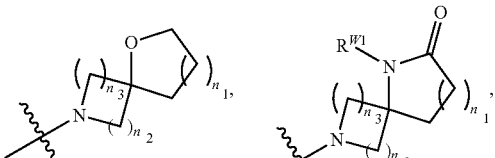

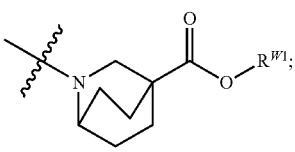

wherein $R^{y1}$ is optionally substituted with one or two substituents independently selected from the group consisting of halogen, cyano, —$C_{1-4}$ alkyl, hydroxy, —C$_{1-4}$ alkoxy, —C$_{1-4}$ haloalkyl, —C$_{1-4}$ haloalkoxy, —C(=O)OR$^{W1}$, —C(=O)NHS(=O)$_2$R$^{W3}$, —C(=O)N(R$^{W1}$)R$^{W2}$, —S(=O)$_2$R$^{W3}$, —S(=O)N(R$^{W1}$)R$^{W2}$, —N(R$^{W1}$)C(=O)R$^{W3}$, —N(R$^{W1}$)S(=O)R$^{W3}$, —N(R$^{W1}$)C(=O)N(R$^{W2}$)R$^{W3}$ and —N(R$^{W1}$)S(=O)N(R$^{W2}$)R$^{W3}$;

R$^{y2}$ is selected from the group consisting of:

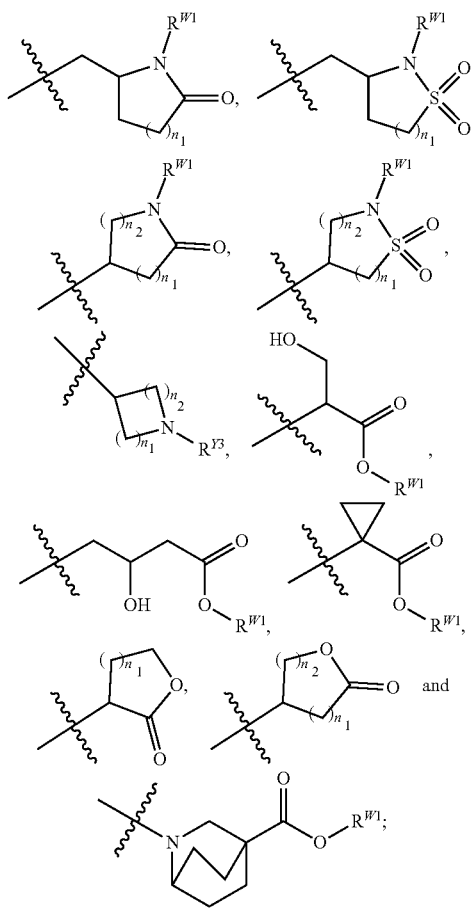

R$^{5a1}$ and R$^{5b1}$ are independently selected from the group consisting of hydrogen, —C$_{1-4}$ alkyl, —C$_{1-4}$ haloalkyl, —C$_{1-4}$ alkoxy and —C$_{1-4}$ haloalkoxy; or R$^{5a1}$ and R$^{5b1}$ are taken together along with the atom to which R$^{5a1}$ and R$^{5b1}$ are attached to form monocyclic —C$_{3-6}$ cycloalkyl or 4-6 monocyclic heterocyclyl, wherein the —C$_{3-6}$ cycloalkyl or the 4-6 monocyclic heterocyclyl can be optionally further substituted;

m$_1$, m$_2$, m$_3$, n$_1$, n$_2$ and n$_3$ are independently 1 or 2;

m$_4$ and n$_4$ are independently 0, 1 or 2;

R$^{X3}$ is selected from the group consisting of hydrogen, halogen, —C$_{1-4}$ alkyl, —C$_{1-4}$ haloalkyl, —C(=O)R$^{Z3}$, —C(=O)OR$^{Z1}$, —S(=O)$_2$R$^{Z1}$, —C(=O)N(R$^{Z1}$)R$^{Z2}$ and —S(=O)N(R$^{Z1}$)R$^{Z2}$;

R$^{Y3}$ is selected from the group consisting of hydrogen, halogen, —C$_{1-4}$ alkyl, —C$_{1-4}$ haloalkyl, —C(=O)R$^{Z3}$, —C(=O)OR$^{Z3}$, —S(=O)$_2$R$^{W3}$, —C(=O)N(R$^{W1}$)R$^{W2}$ and —S(=O)N(R$^{W1}$)R$^{W2}$;

R$^{Z1}$, R$^{Z2}$, R$^{W1}$ and R$^{W2}$ are independently selected from the group consisting of hydrogen, —C$_{1-4}$ alkyl, and —C$_{1-4}$ haloalkyl; and R$^{Z3}$ and R$^{W3}$ are independently selected from the group consisting of hydrogen, —C$_{1-4}$ alkyl and —C$_{1-4}$ haloalkyl.

2. The compound of claim 1; wherein R$^{4a1}$ is -R$^{y1}$; and R$^{5a1}$ and R$^{5b1}$ are each hydrogen.

3. The compound of claim 2, wherein -R$^{y1}$ is selected from the group consisting of:

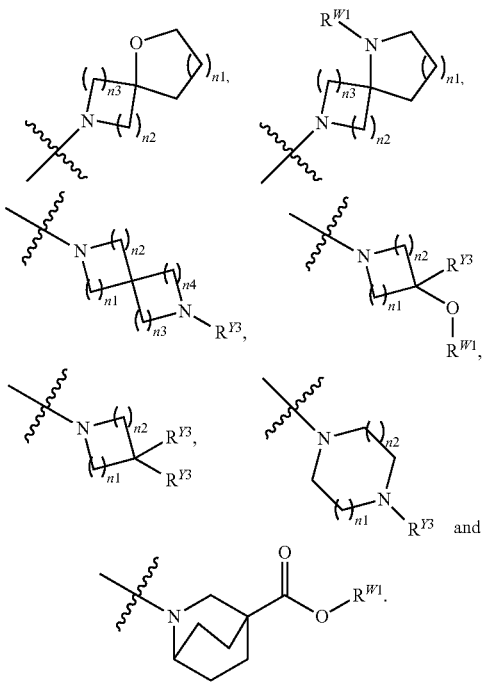

4. The compound of claim 1, wherein Ring A is a monocyclic C$_{5-7}$ cycloalkyl substituted with R$^{2a1}$.

5. The compound of claim 4, wherein R$^{2a1}$ is -R$^{x1}$, wherein -R$^{x1}$ is selected from the group consisting of:

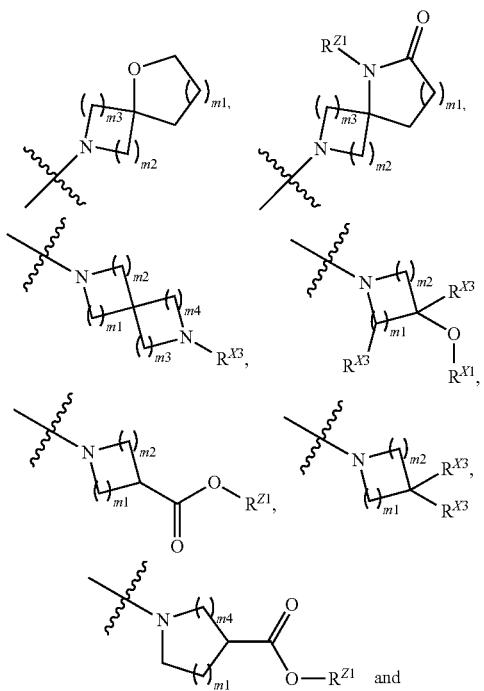

-continued
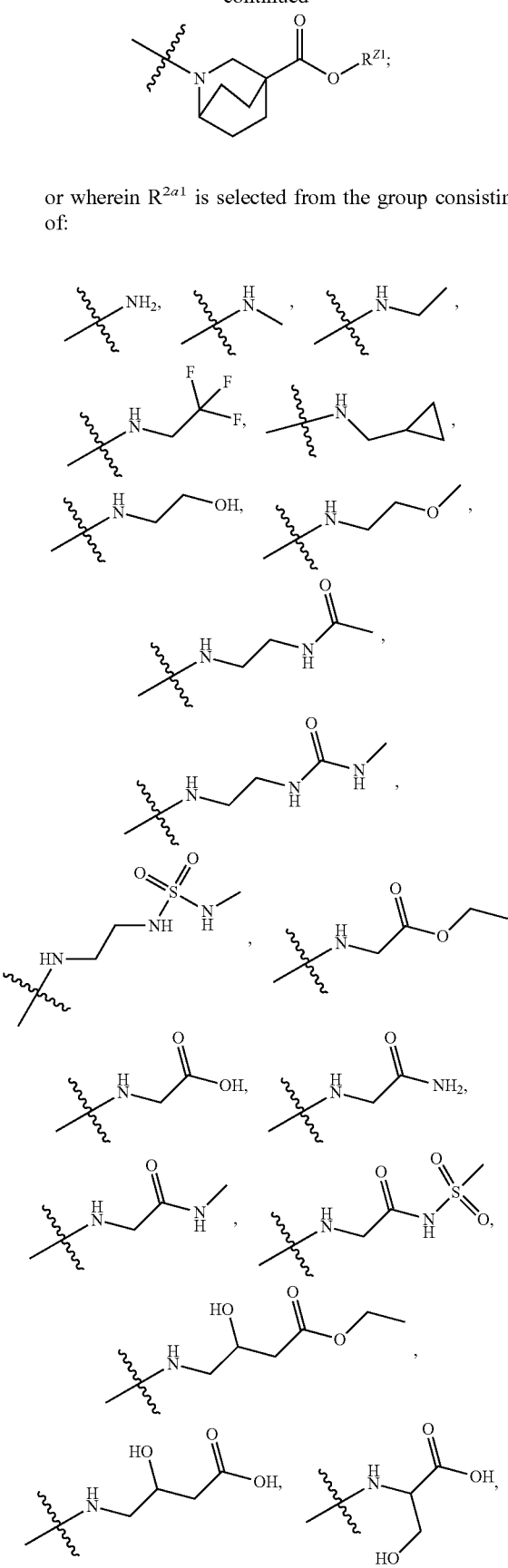
or wherein $R^{2a1}$ is selected from the group consisting of:
-continued
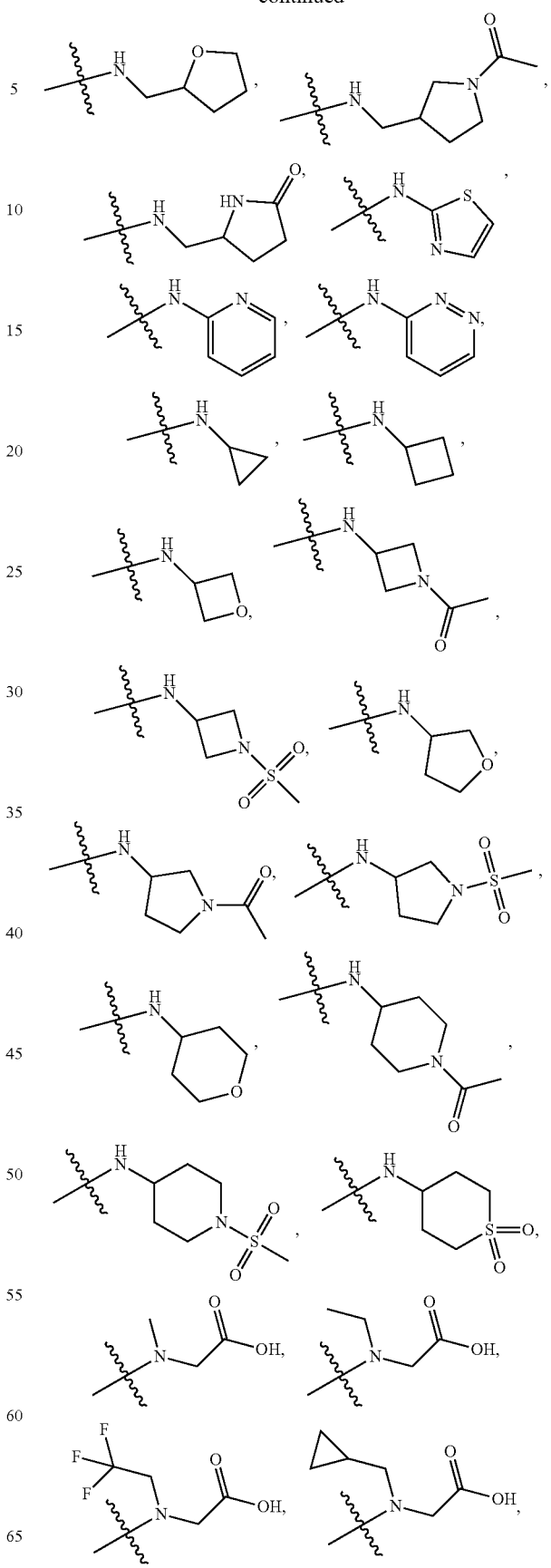

-continued
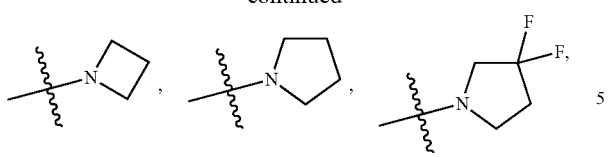
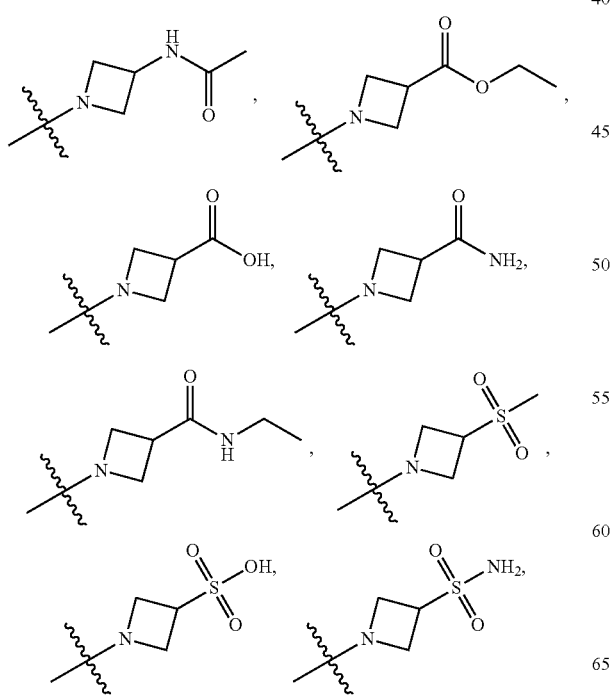
-continued
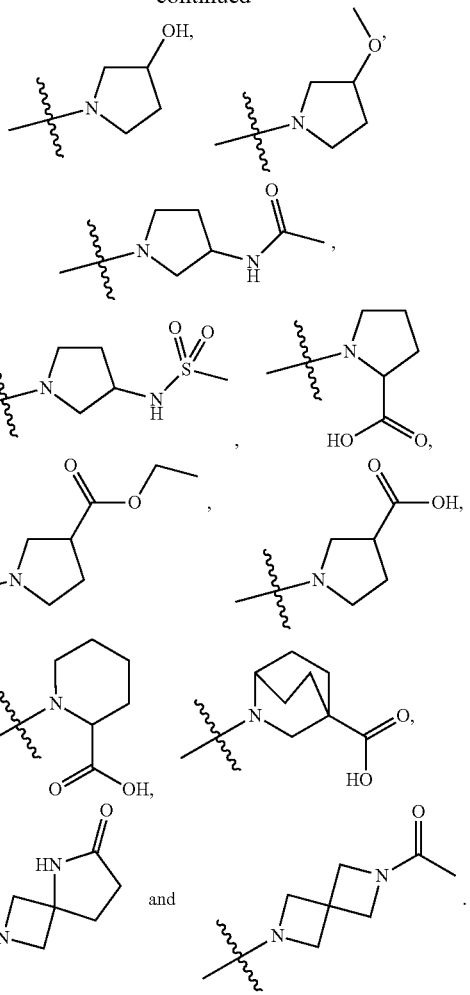
6. The compound of claim 5, wherein $R^{4a1}$ is $-R^{y1}$; and $R^{5a1}$ and $R^{5b1}$ are each hydrogen.
7. The compound of claim 6, wherein $-R^{y1}$ is selected from the group consisting of:
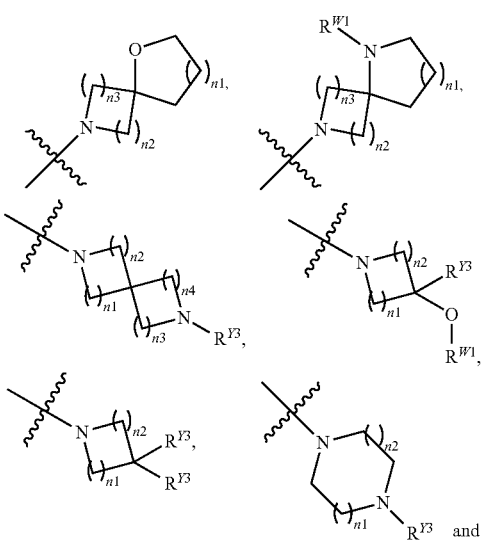

-continued

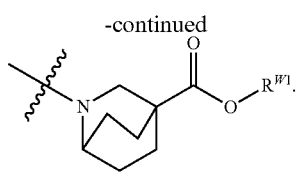

8. The compound of claim 7, wherein $-R^{y1}$ is

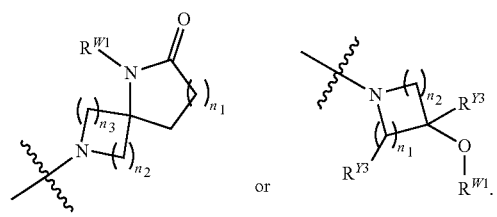

9. The compound of claim 8, wherein $-R^{x1}$ is

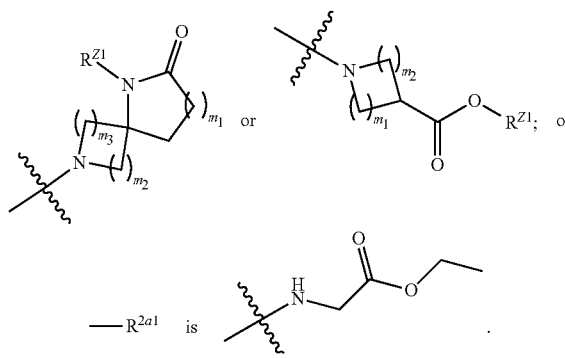

$-R^{2a1}$ is

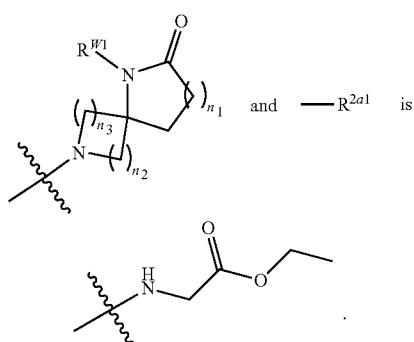

10. The compound of claim 9, wherein $-R^{y1}$ is

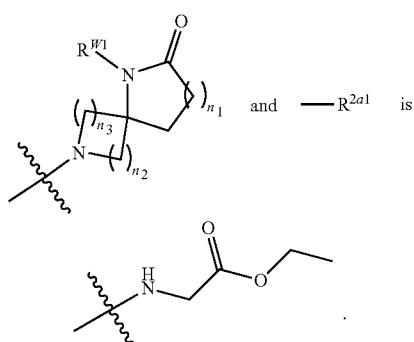

11. The compound of claim 7, wherein $n_1$, $n_2$, $n_3$ and $n_4$ are each 1.

12. The compound of claim 9, wherein $m_1$, $m_2$ and $m_3$ are each 1.

13. The compound of claim 1, wherein Ring A is a 5-7 membered nitrogen-containing monocyclic heterocyclyl, wherein a nitrogen of the 5-7 membered nitrogen-containing monocyclic heterocyclyl is optionally substituted with $R^{2a3}$, wherein a carbon of the 5-7 membered nitrogen-containing monocyclic heterocyclyl is optionally substituted with $R^{2a4}$ or $R^{2a5}$, and wherein when $R^{2a5}$ is present, $R^{2a5}$ is attached at a carbon atom adjacent to a nitrogen of the 5-7 membered nitrogen-containing monocyclic heterocyclyl is selected from the group consisting of:

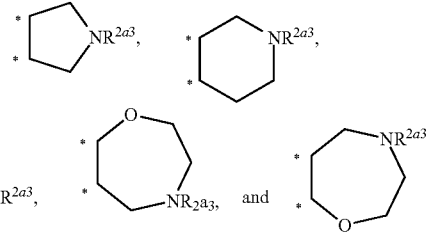

wherein asterisks indicate the position of the fused bond, and $R^{2a4}$ and $R^{2a5}$ are each optionally present; or wherein Ring A is a 5-7 membered oxygen-containing monocyclic heterocyclyl substituted with $R^{2a7}$ or $R^{2a8}$; wherein $R^{2a8}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens is selected from the group consisting of:

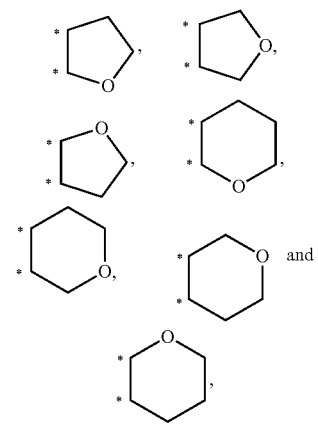

wherein asterisks indicate the position of the fused bond, and $R^{3a7}$ or $R^{3a8}$ is present.

14. The compound of claim 13, wherein Ring A is

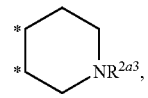

wherein asterisks indicate the position of the fused bond; and $R^{2a3}$ can be selected from the group consisting of $-(CH_2)_{1-2}-C(=O)OR^{Z1}$, $-(CH_2)_{1-2}-OH$ and $-(CH_2)_{1-2}-C_{1-4}$ alkoxy; or Ring A is

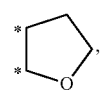

wherein asterisks indicate the position of the fused bond.

15. The compound of claim 6, wherein $R^{2a7}$ is $-R^{x1}$, wherein $-R^{x1}$ is selected from the group consisting of:
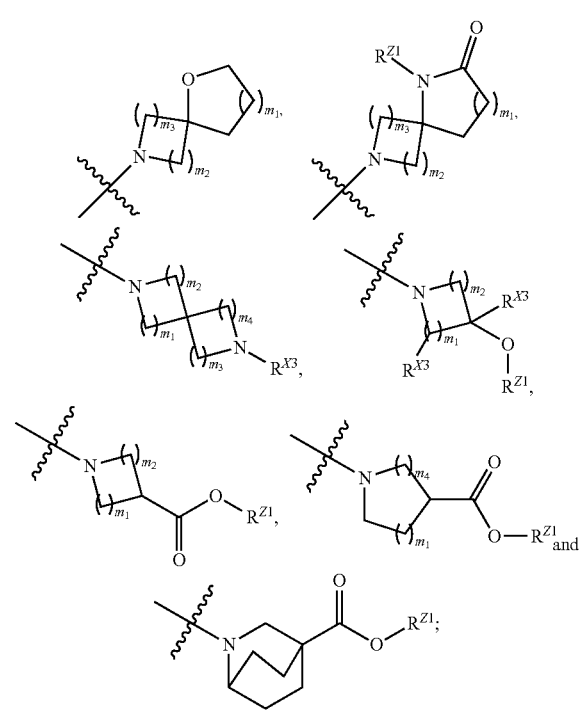
or $R^{2a7}$ is selected from the group consisting of:
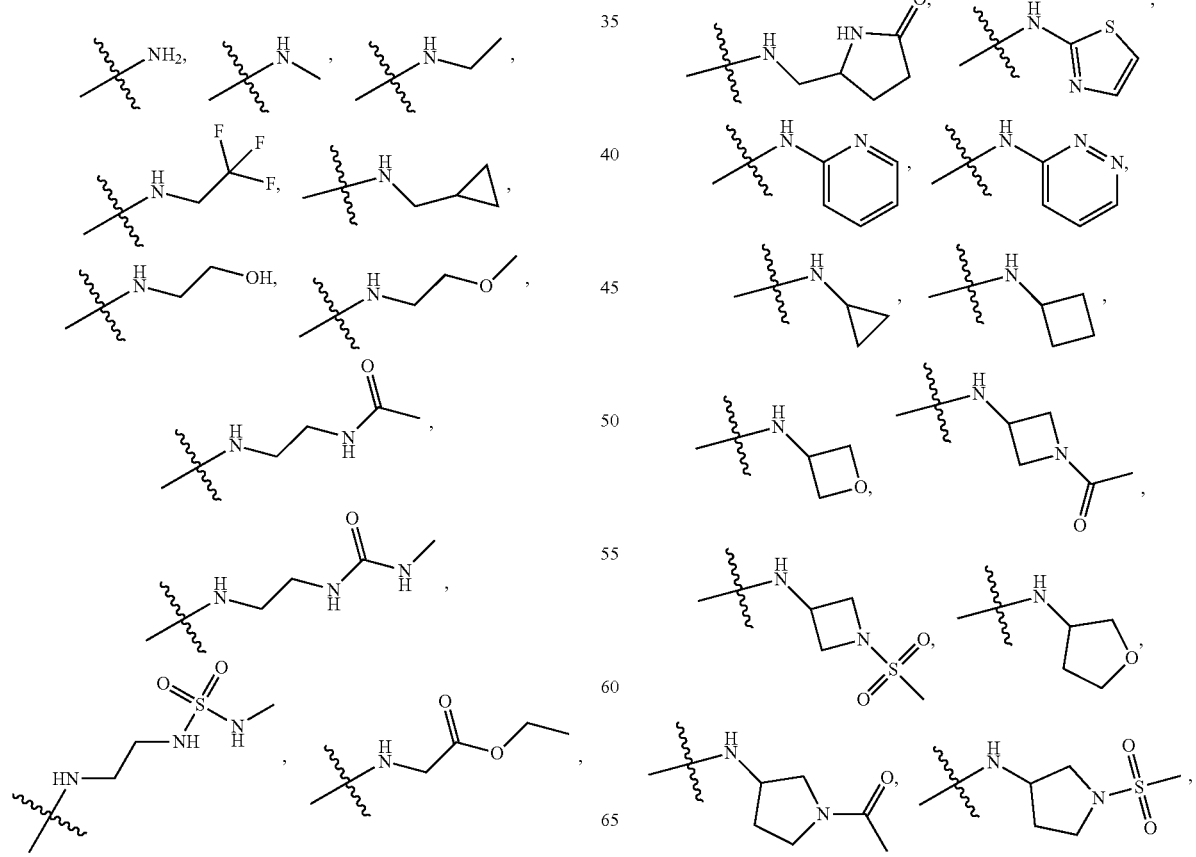

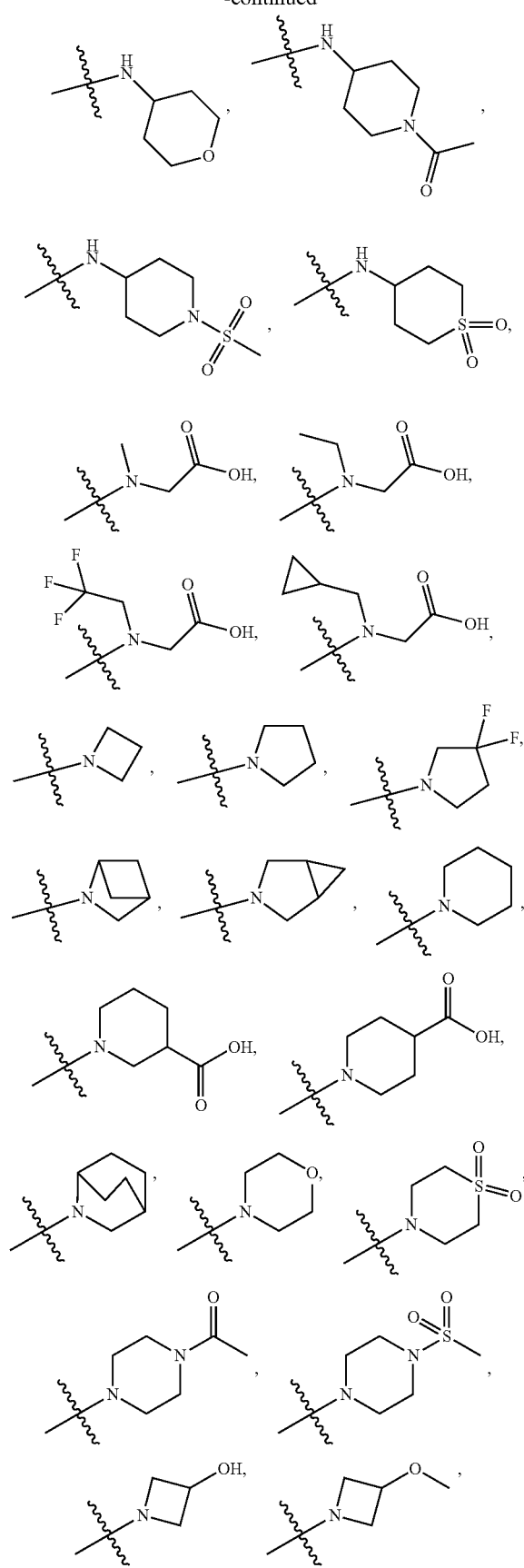
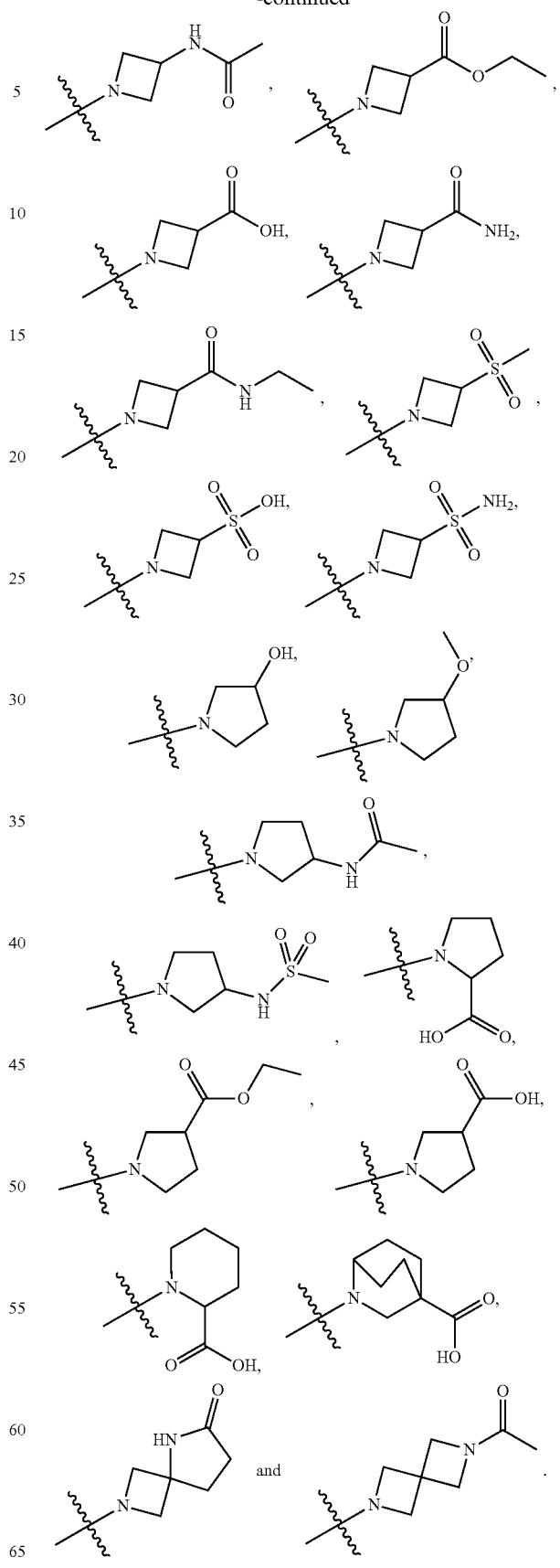

16. The compound of claim 1, wherein $R^1$ is —$C_{1-4}$ alkyl.

17. The compound of claim 1, wherein $R^{3a}$, $R^{3b}$, $R^{3c}$, $R^{3d}$, $R^{3f}$ and $R^{3g}$ are each hydrogen; and $R^{3d}$ and $R^{3h}$ are each halogen; or wherein $R^{3a}$, $R^{3b}$, $R^{3c}$, $R^{3d}$, $R^{3f}$ and $R^{3g}$ are each hydrogen; and $R^{3d}$ is halogen; and $R^{3h}$ is —$CH_3$.

18. The compound of claim 1, wherein $Y^1$ is N.

19. The compound of claim 1, wherein $Y^1$ is —CH or $CH_3$.

20. The compound of claim 4, wherein Ring A is

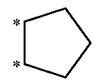

wherein asterisks indicate the position of the fused bond.

21. The compound of claim 1 selected from the group consisting of:

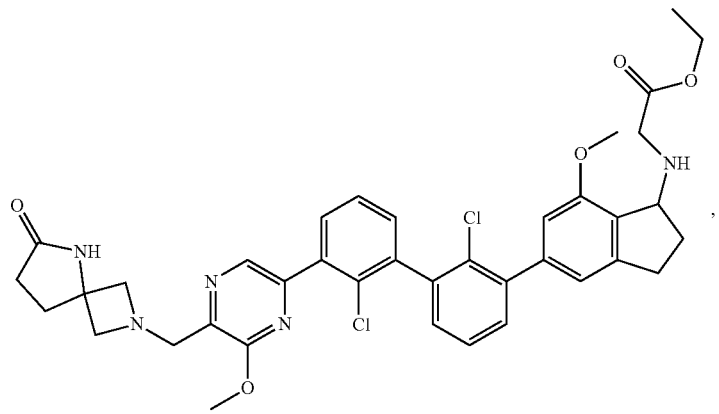 [SMILES: CCOC(=O)CNC1CCc2cc(-c3cccc(-c4cccc(-c5cnc(CN6CC7(CCC(=O)N7)C6)c(OC)n5)c4Cl)c3Cl)nc(OC)c21]

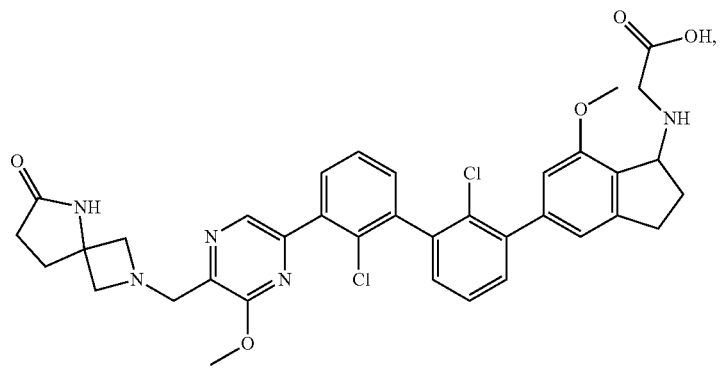

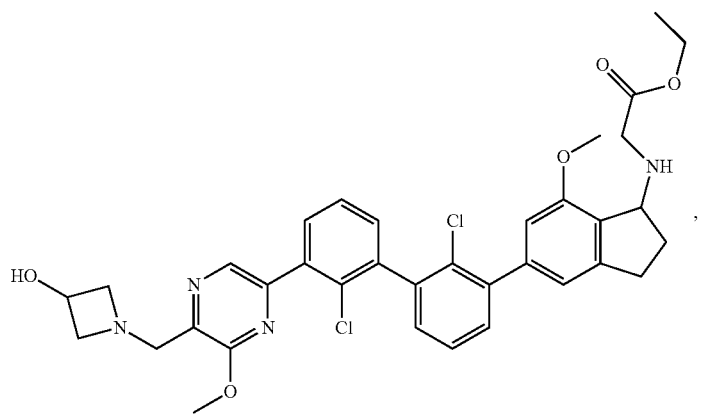

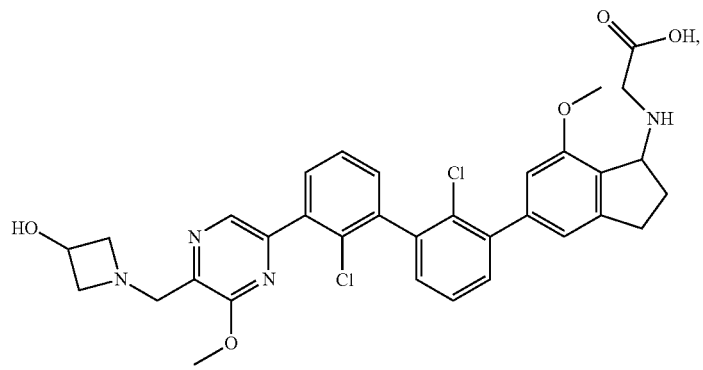
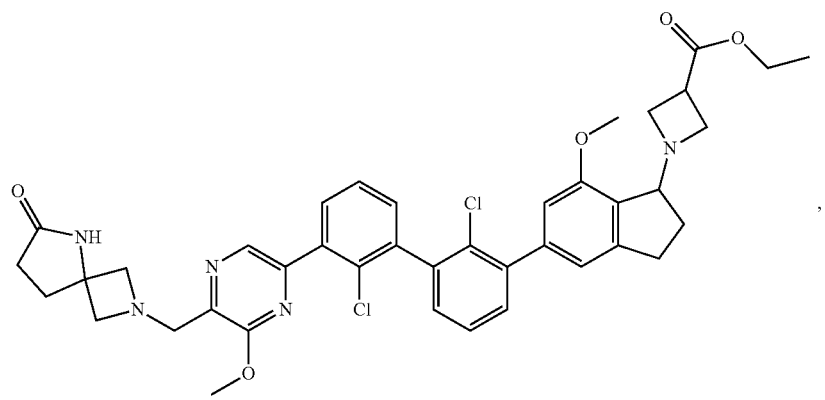
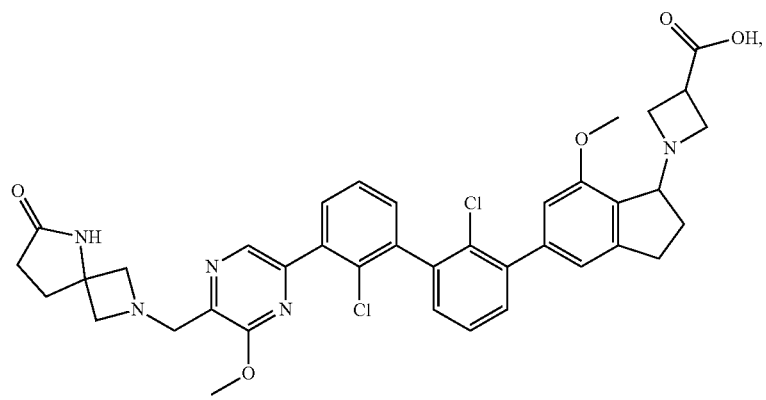
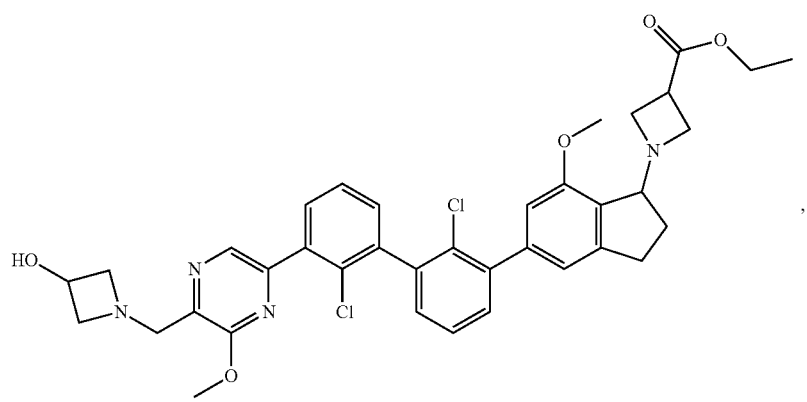

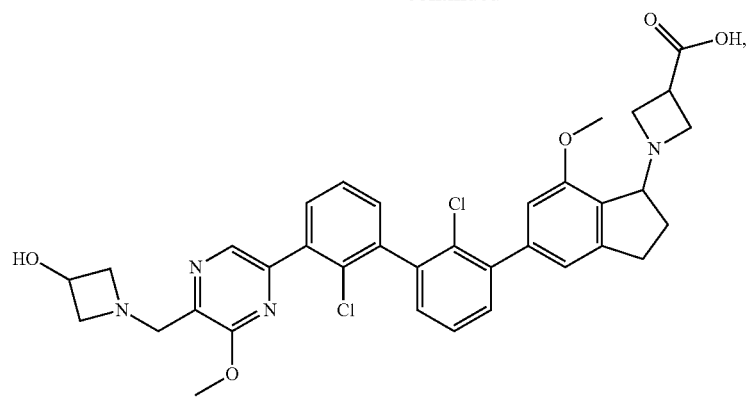
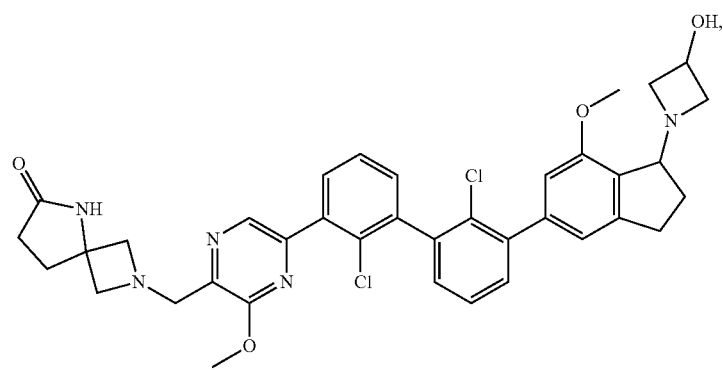
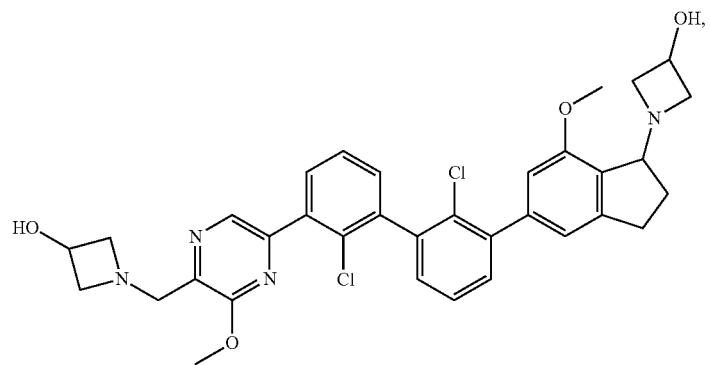
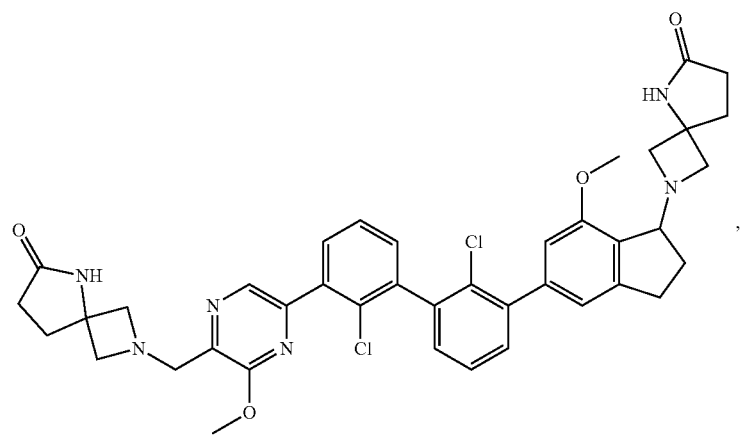

-continued
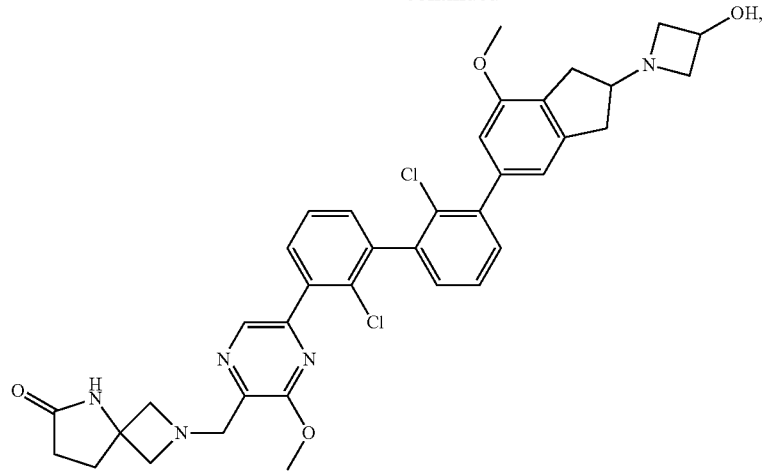
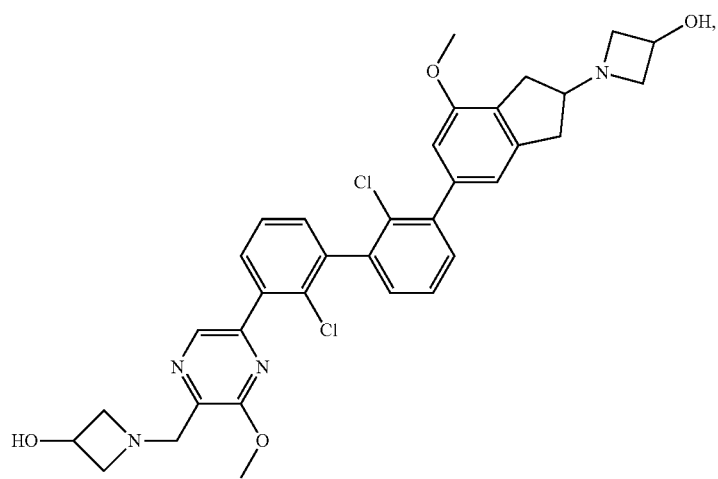
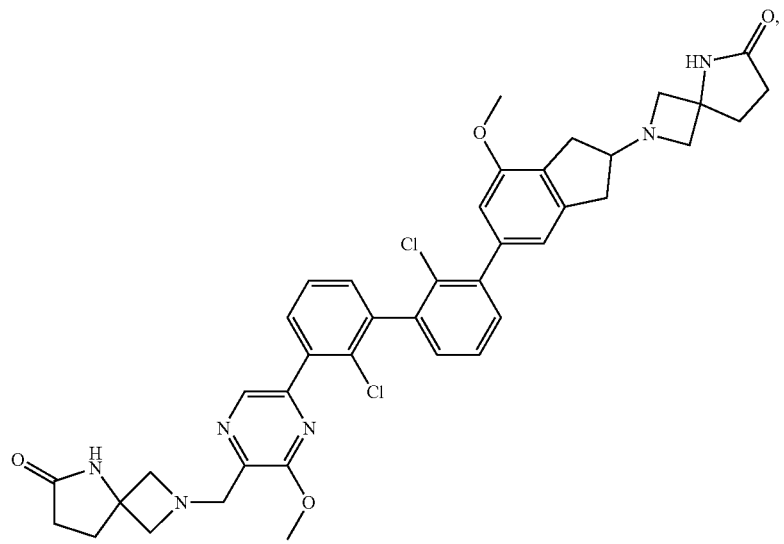

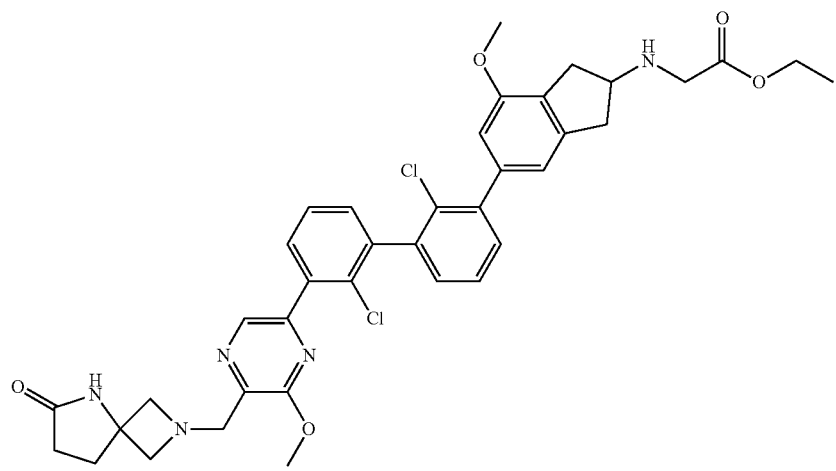

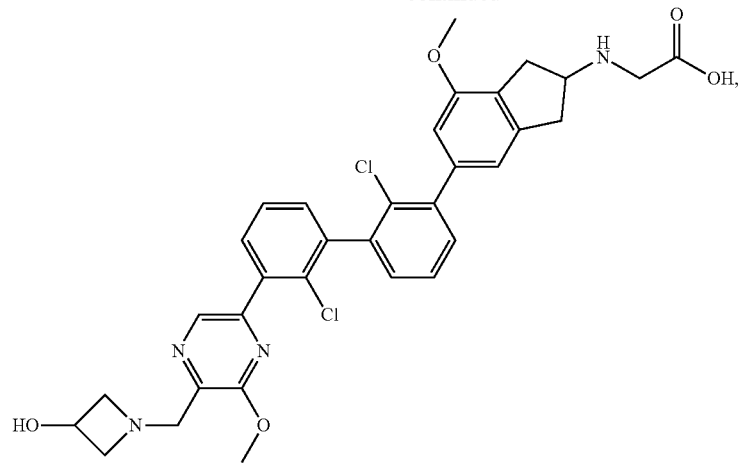
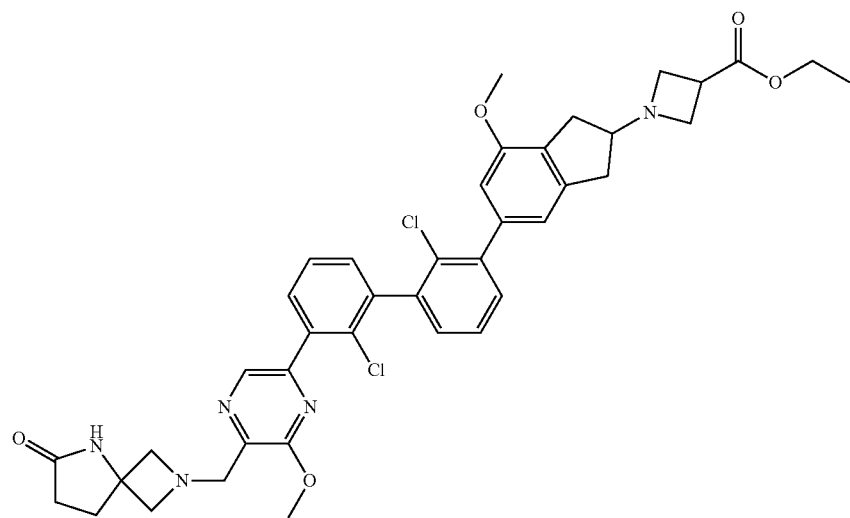
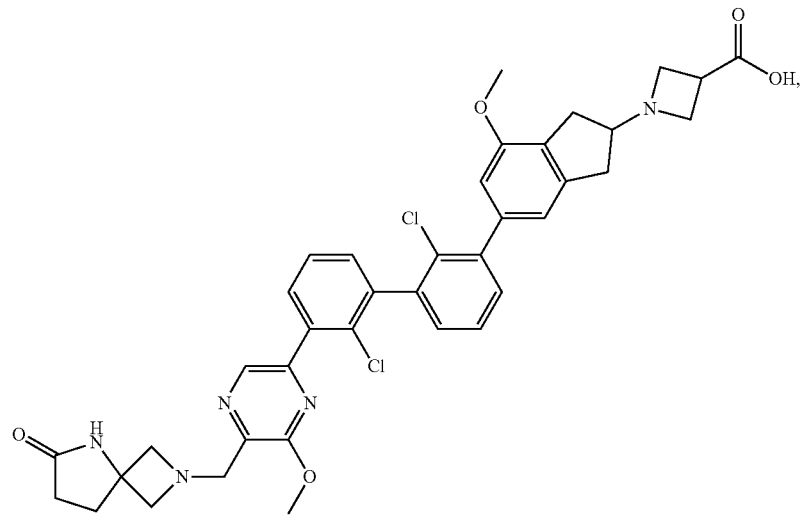

-continued
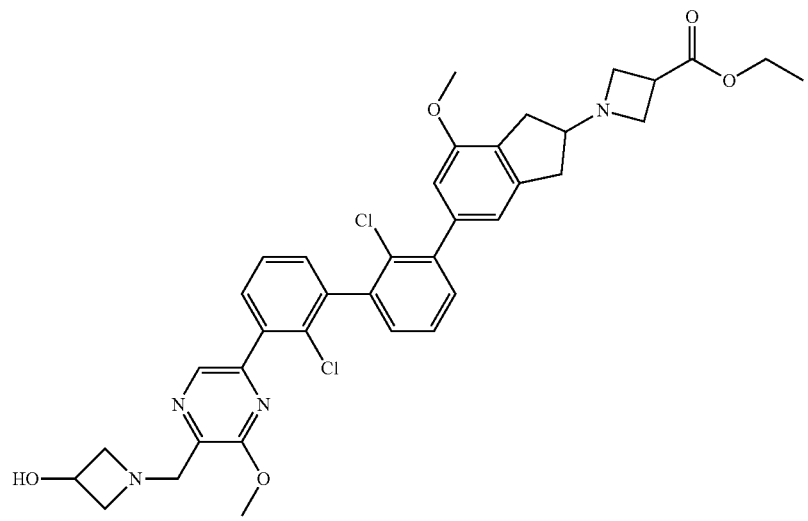
,
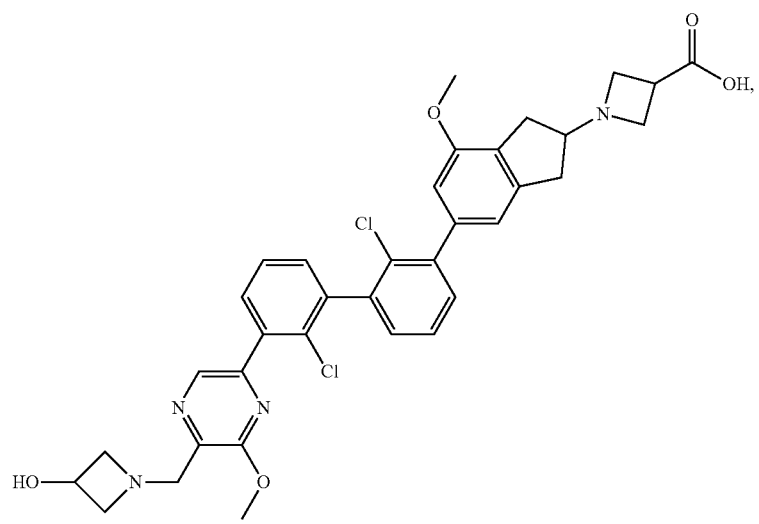
,
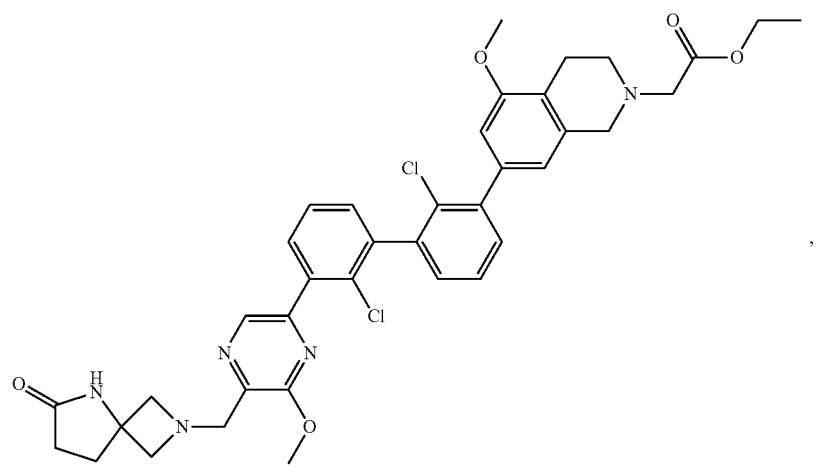
,

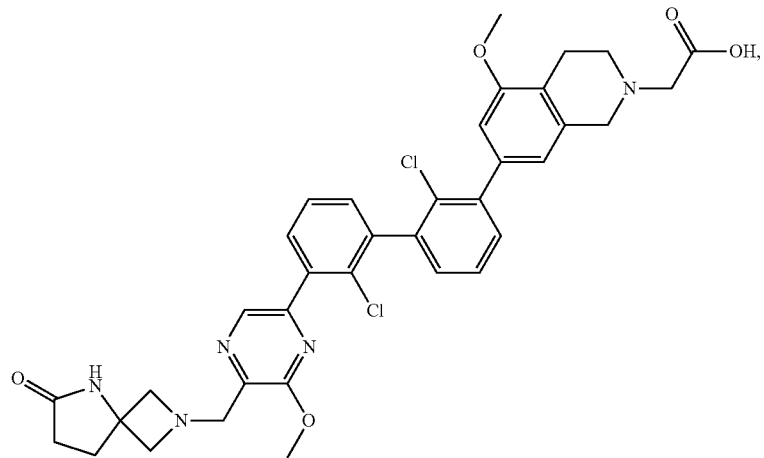
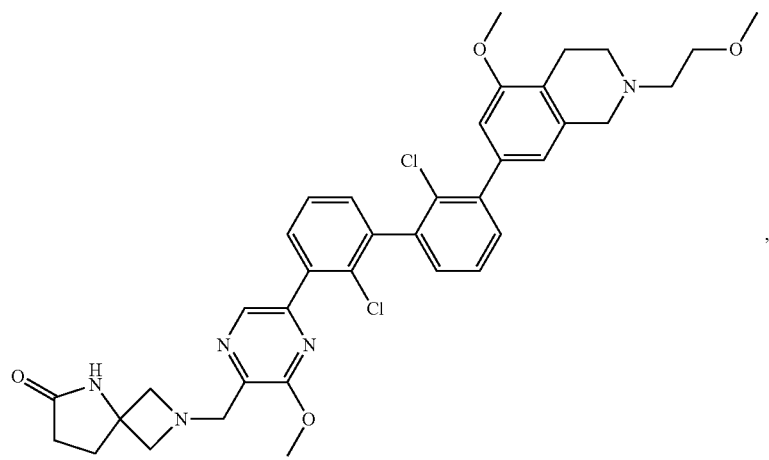
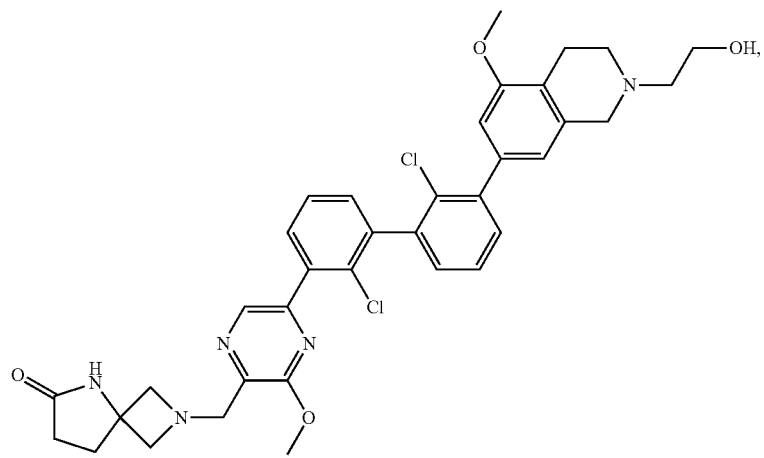

-continued
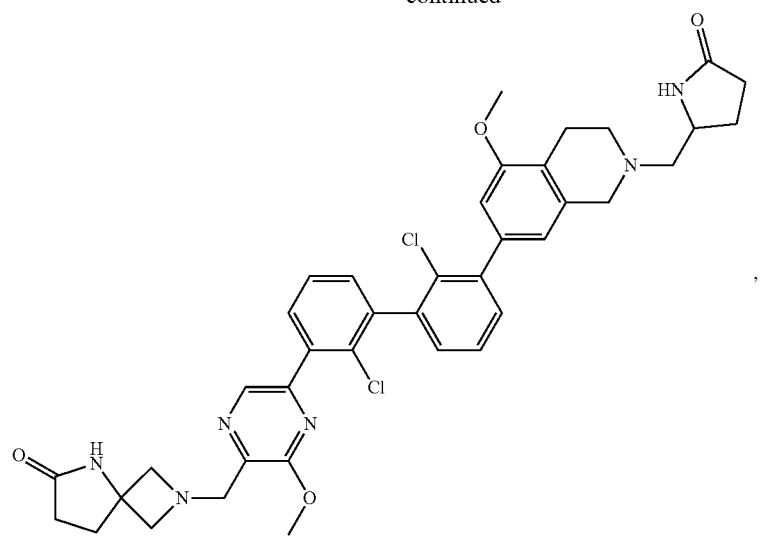
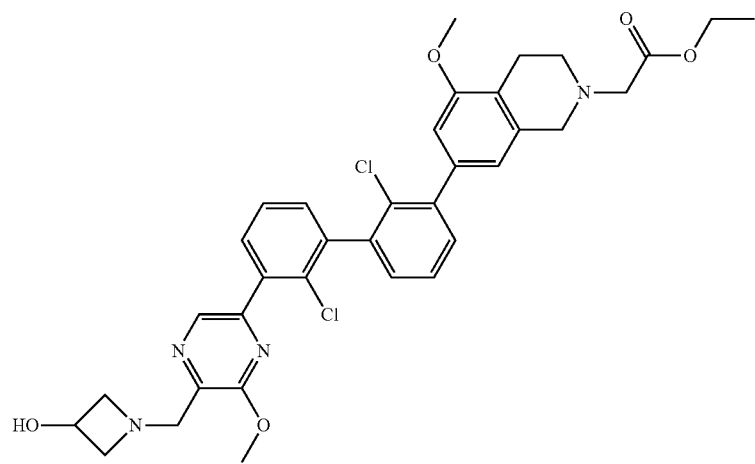
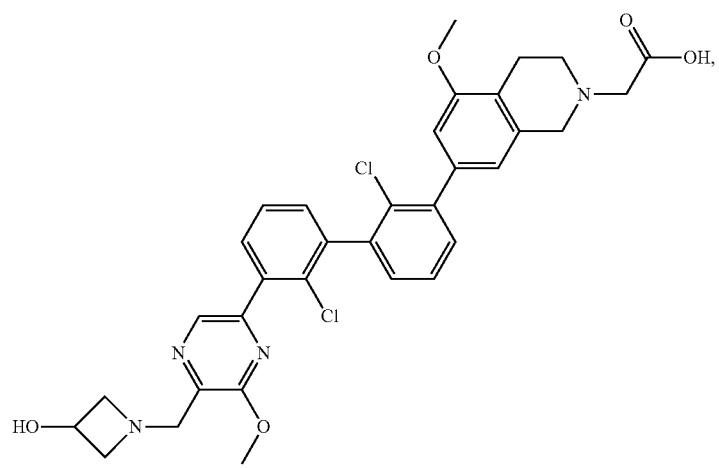

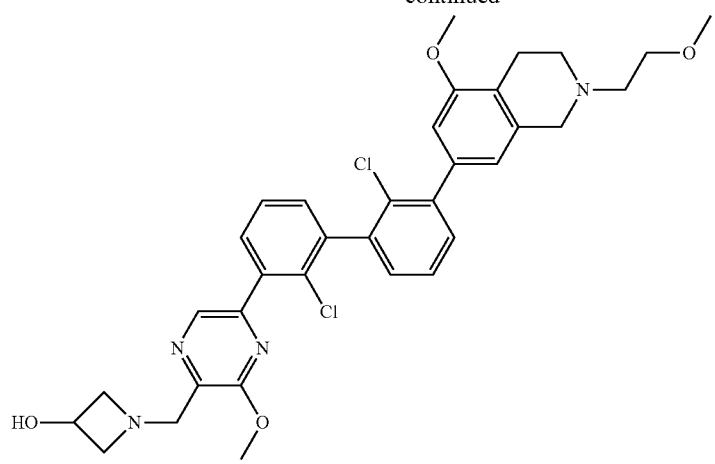
,
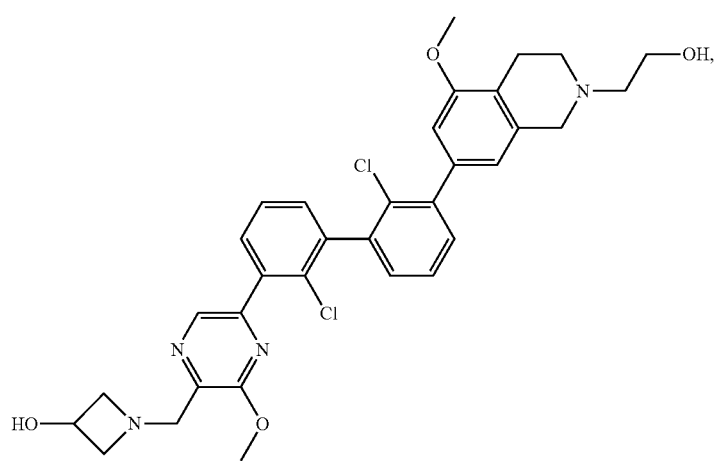
,
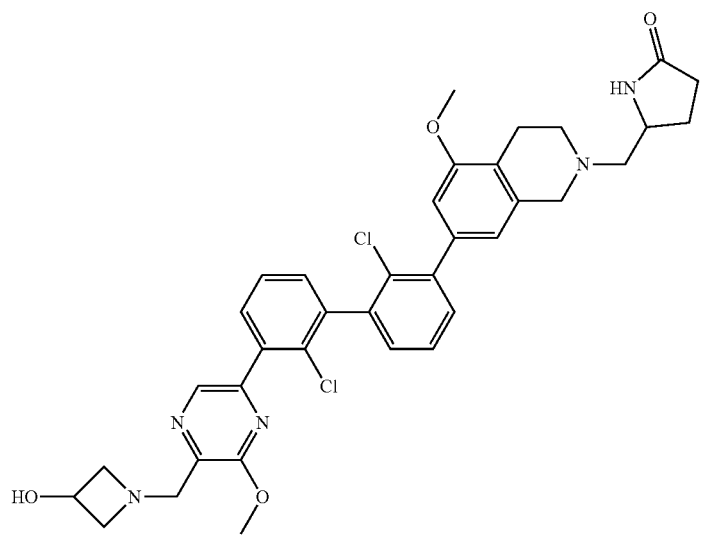
,

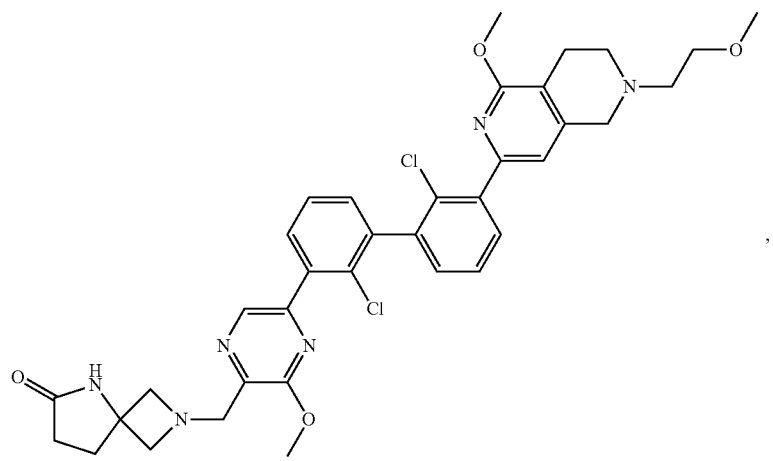
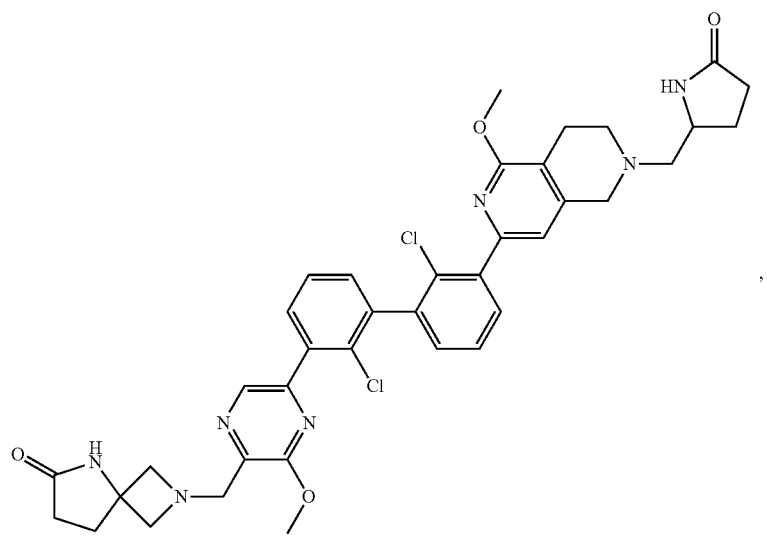
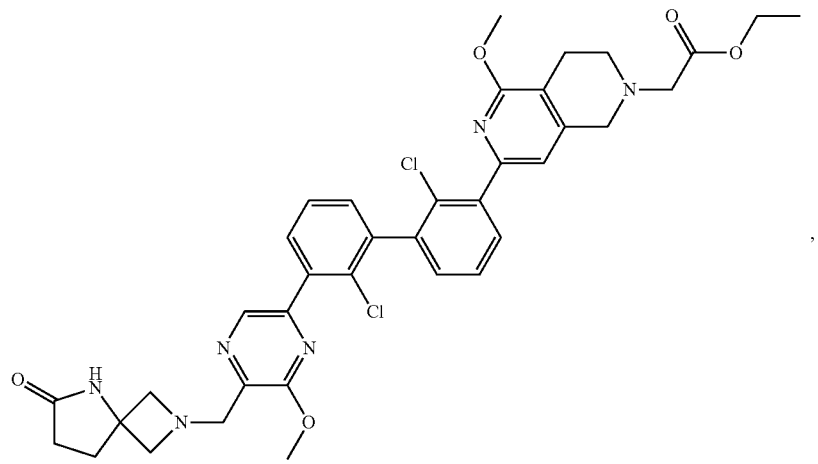

-continued
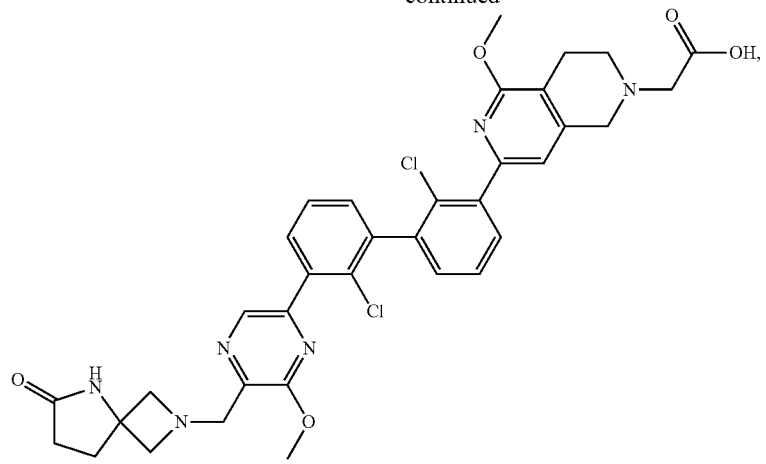
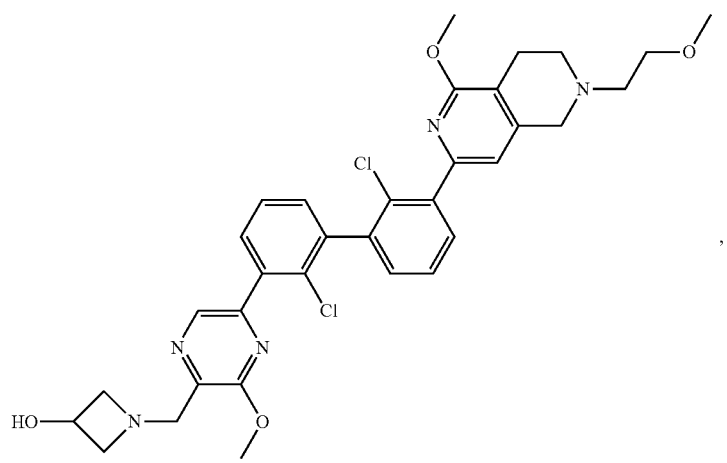
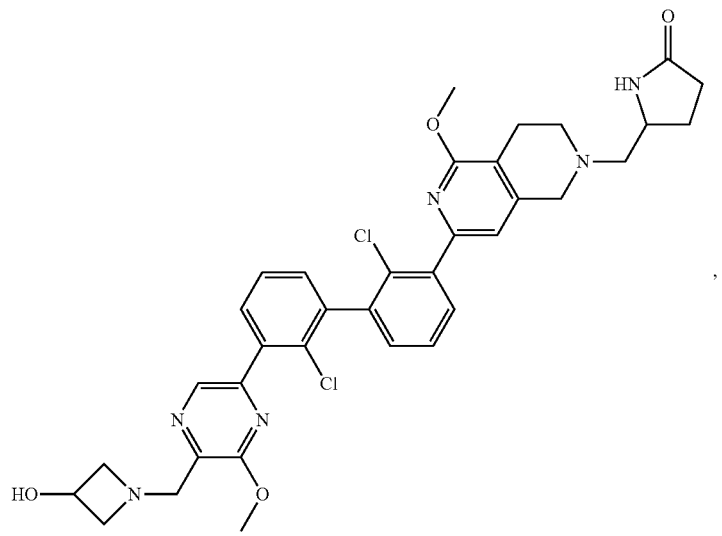

-continued
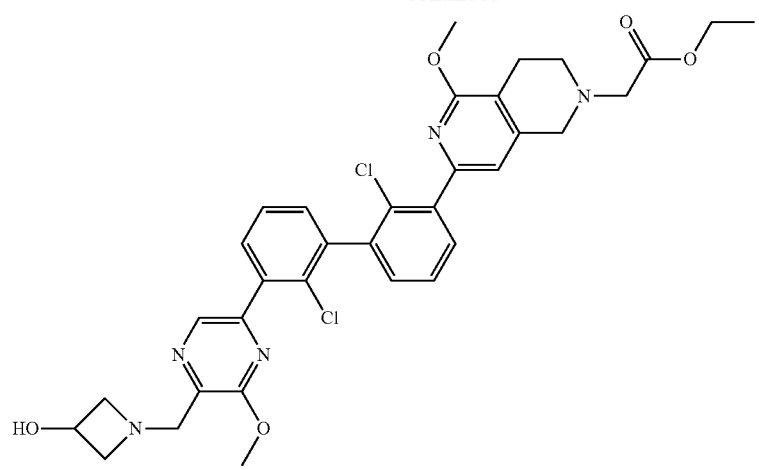
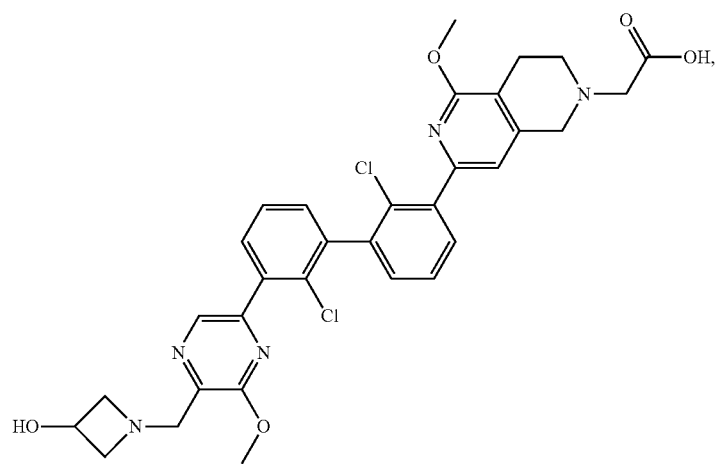
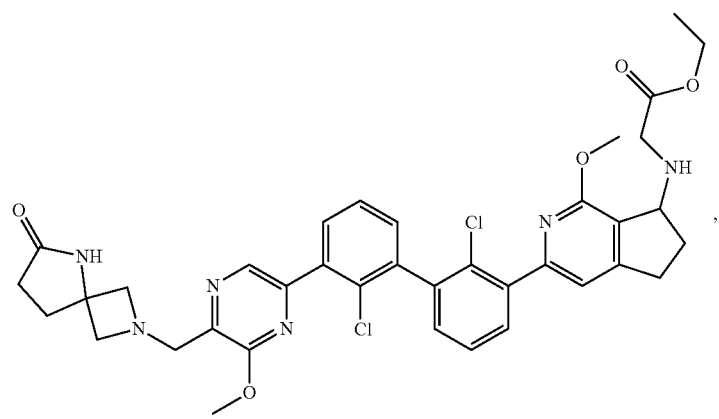
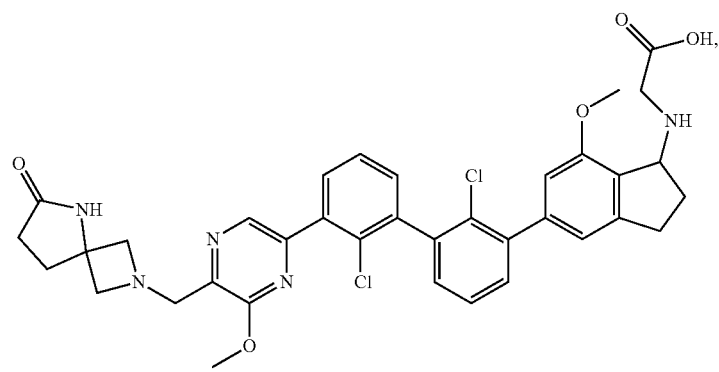

-continued
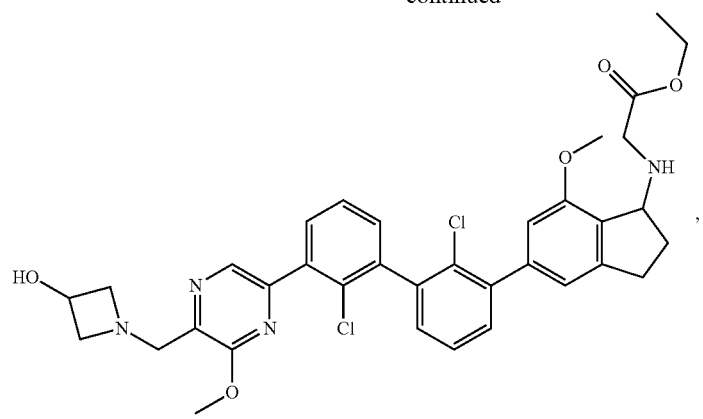
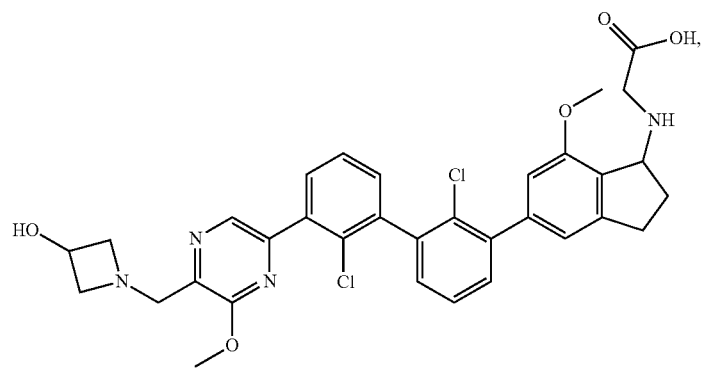
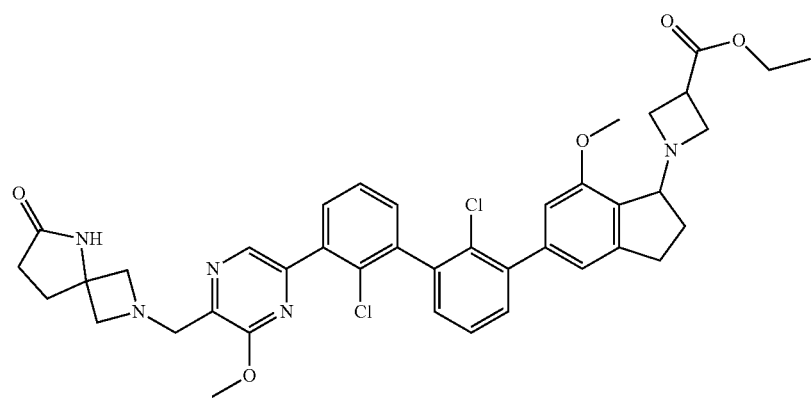
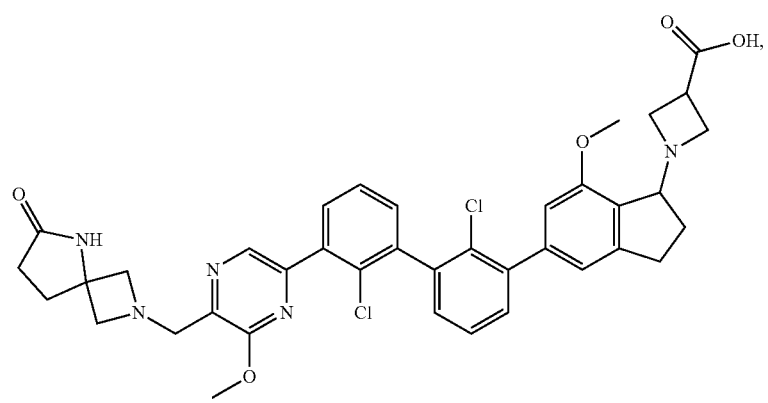

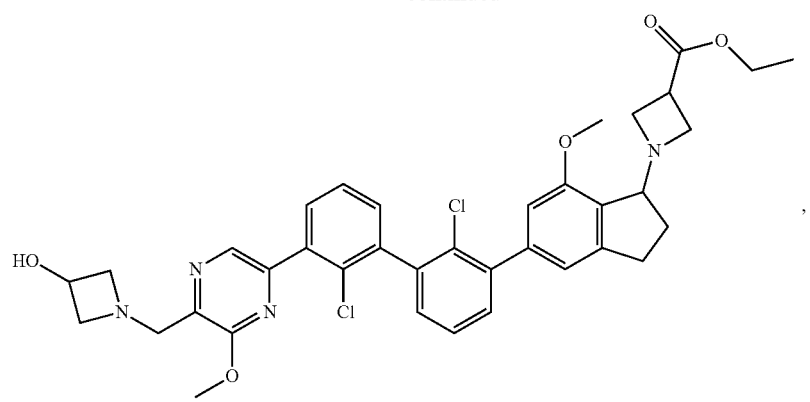
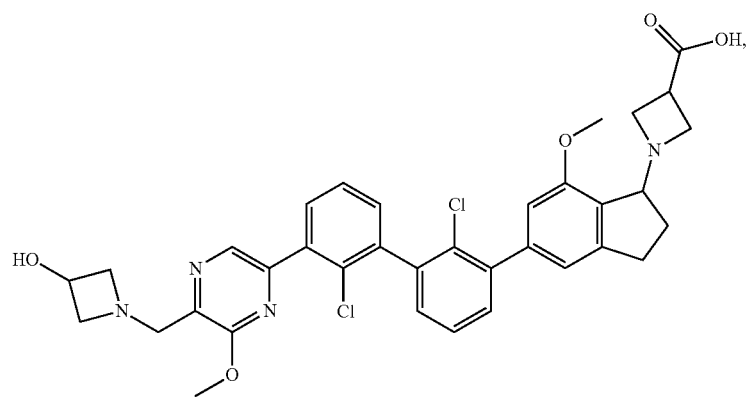
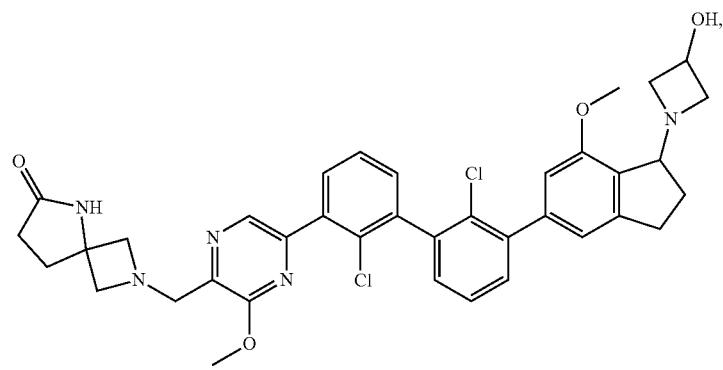
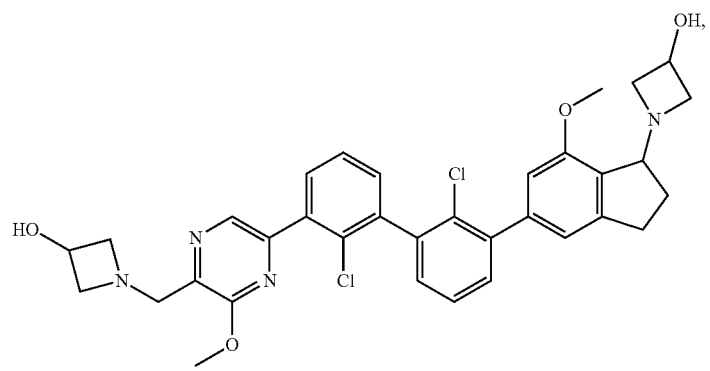

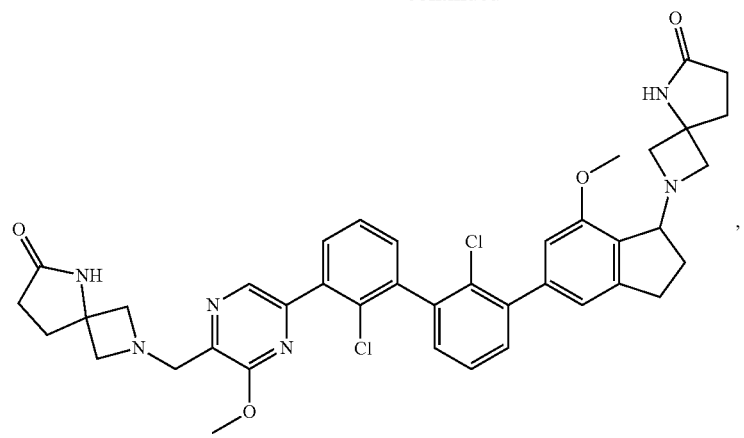
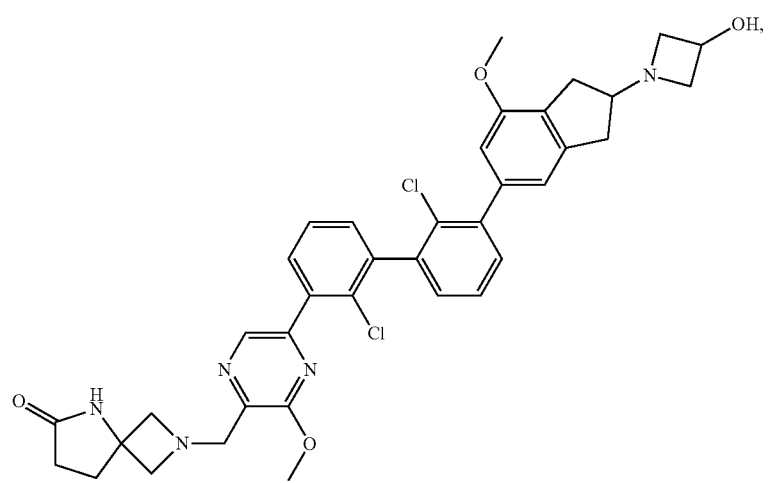
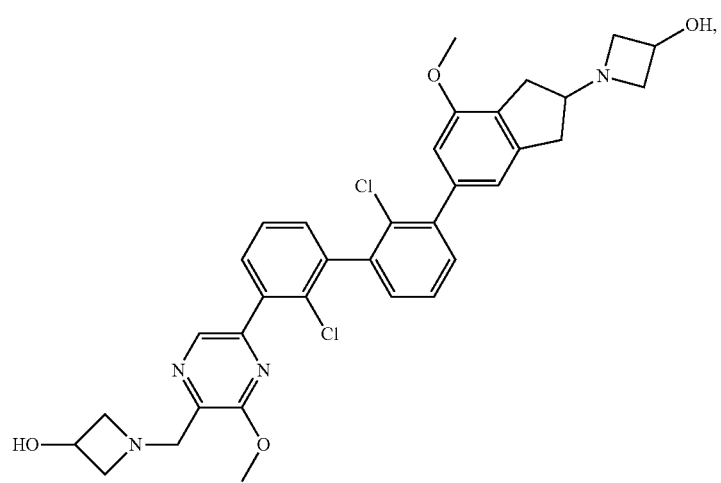

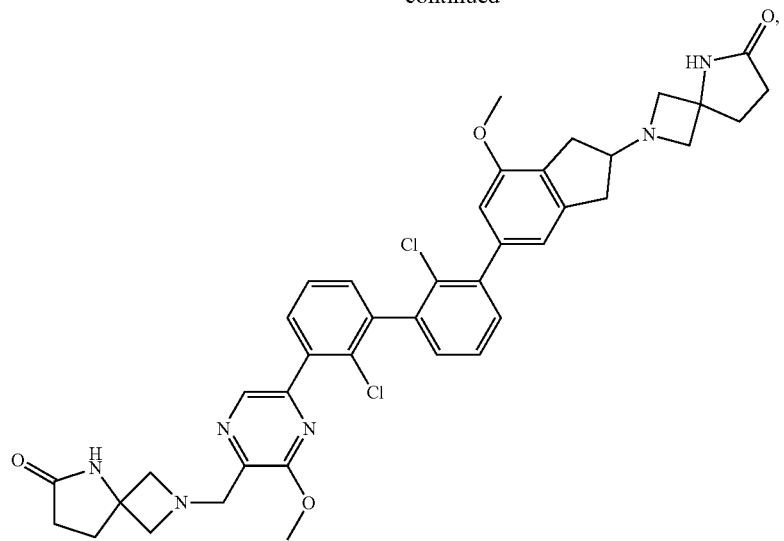
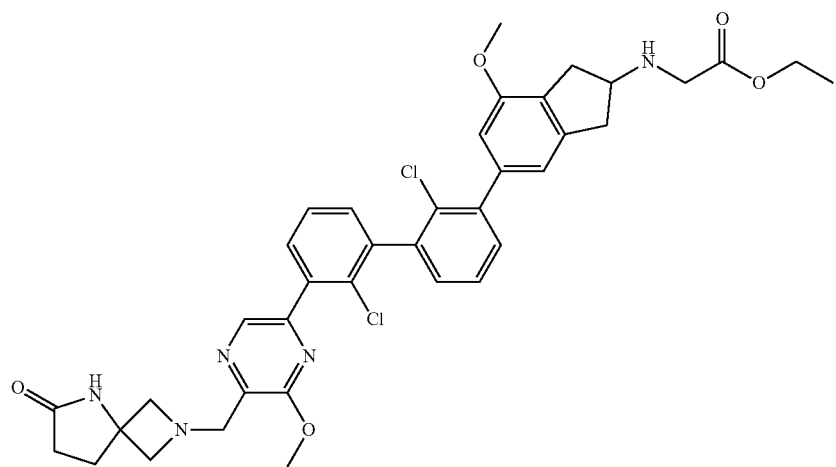
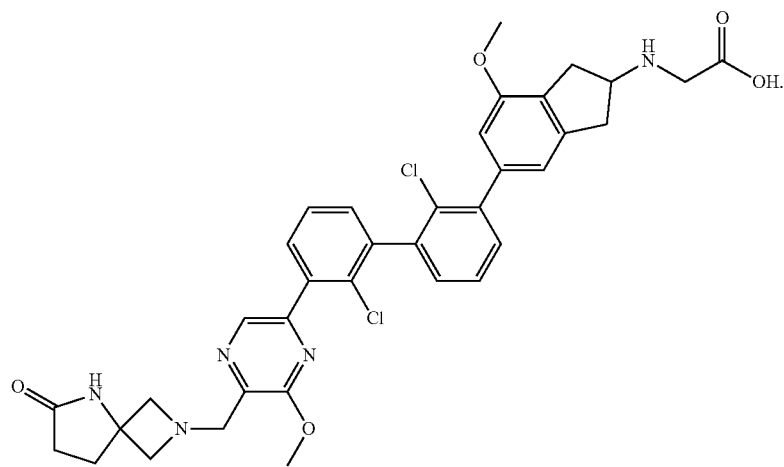

-continued
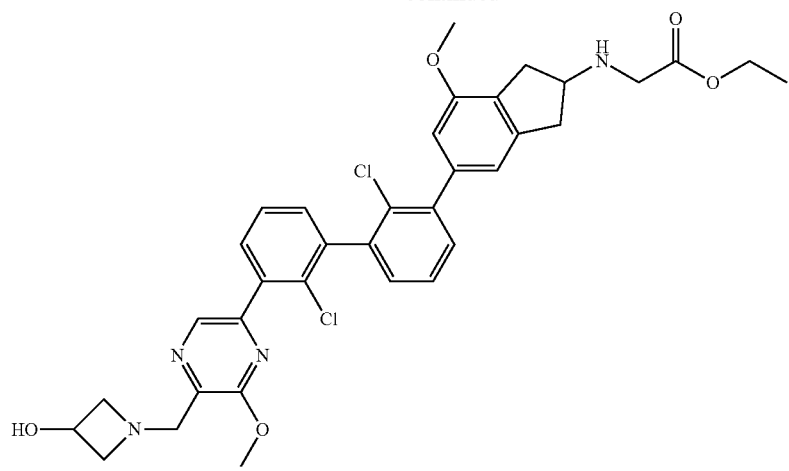
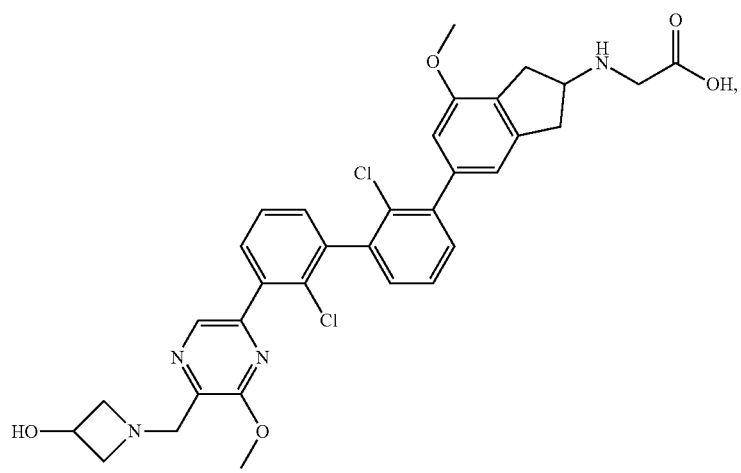
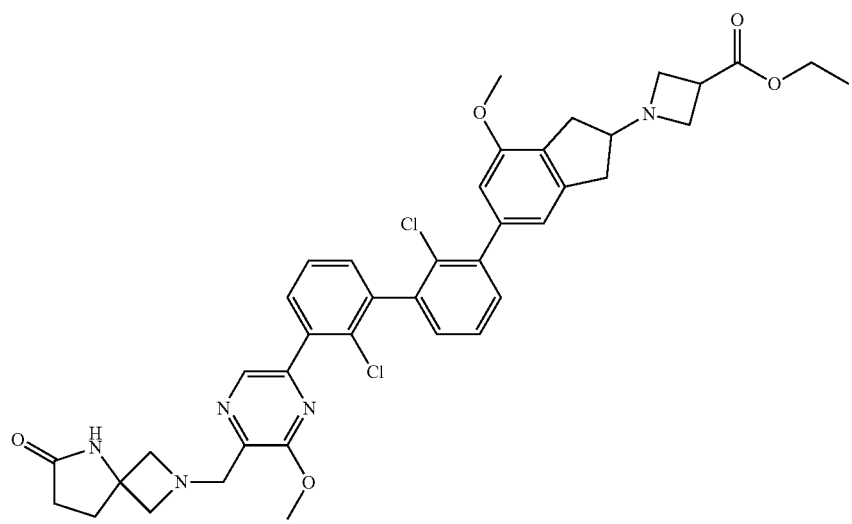

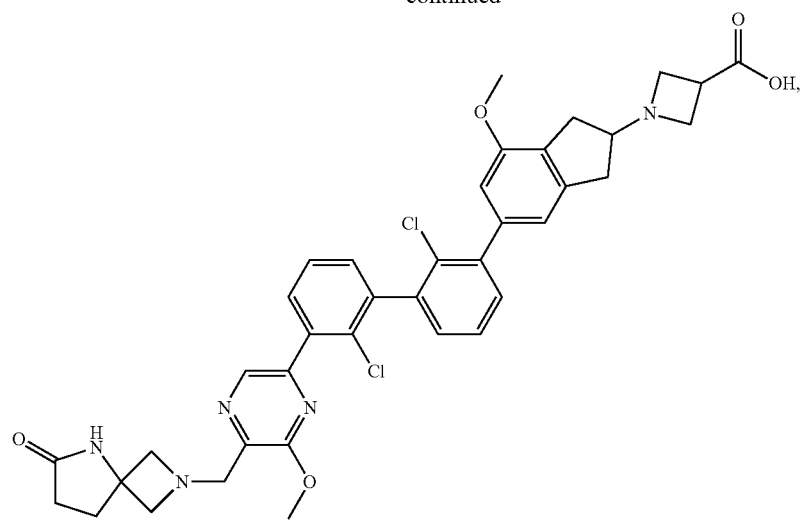
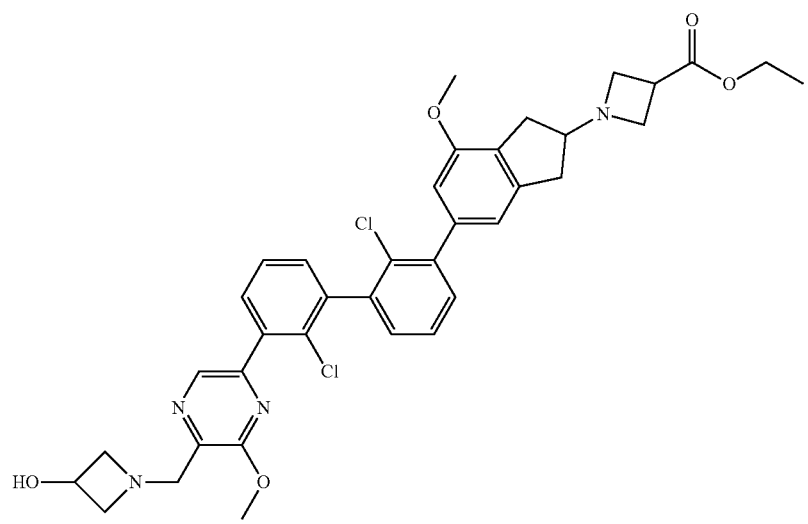
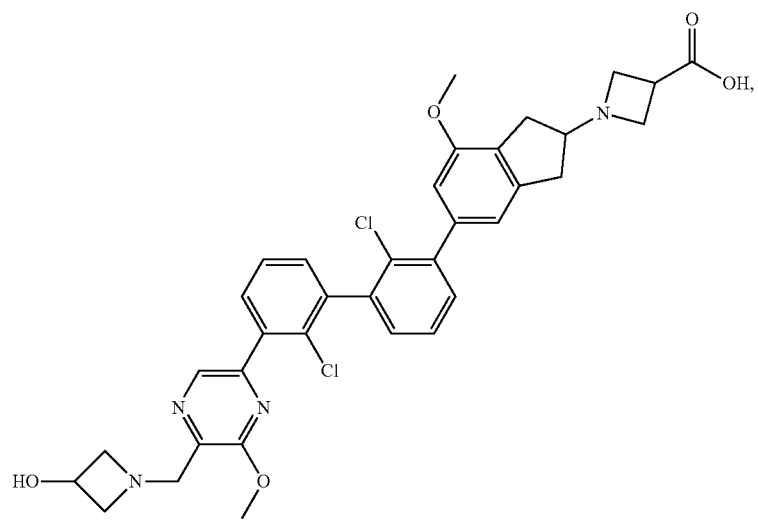

-continued
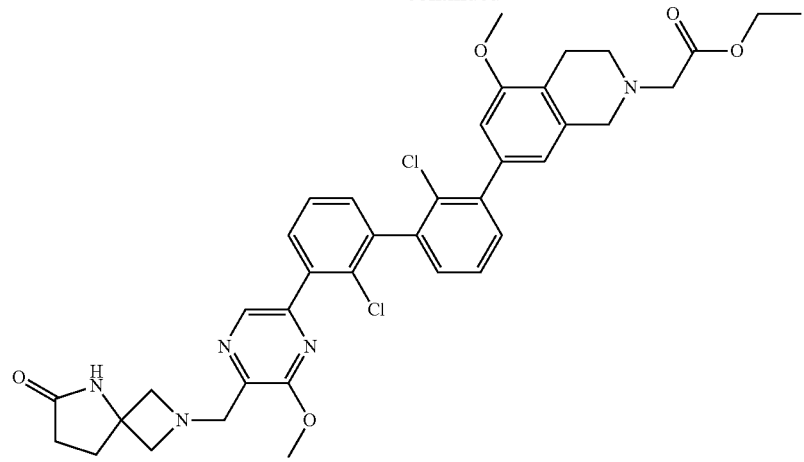
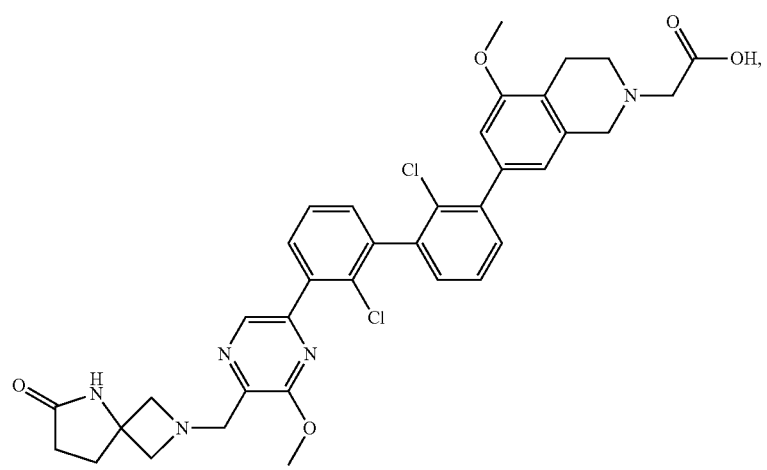
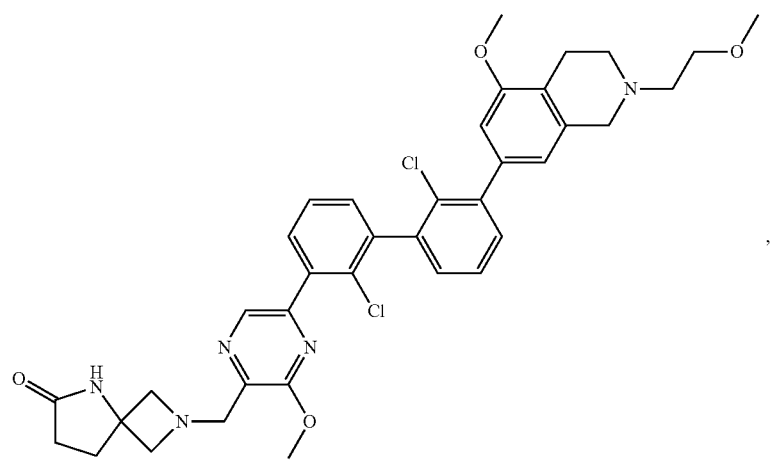

-continued
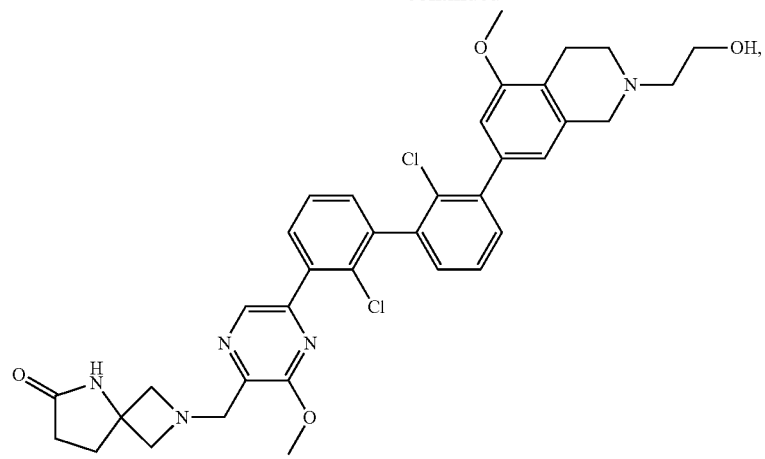
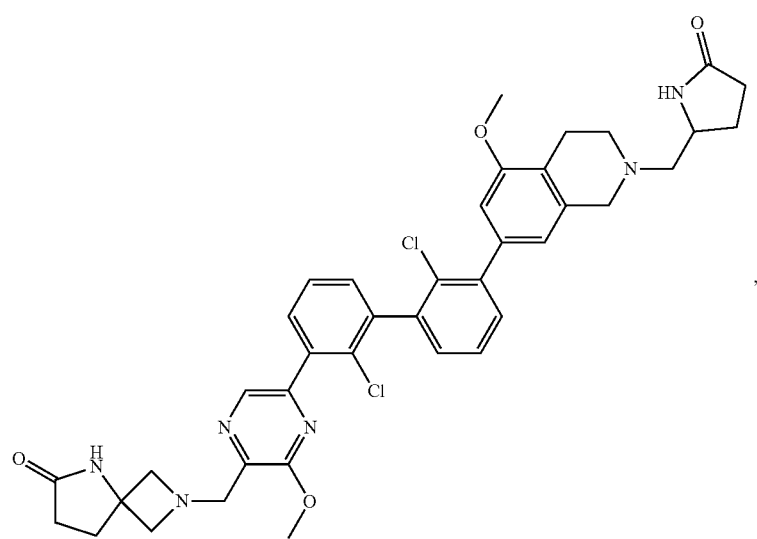
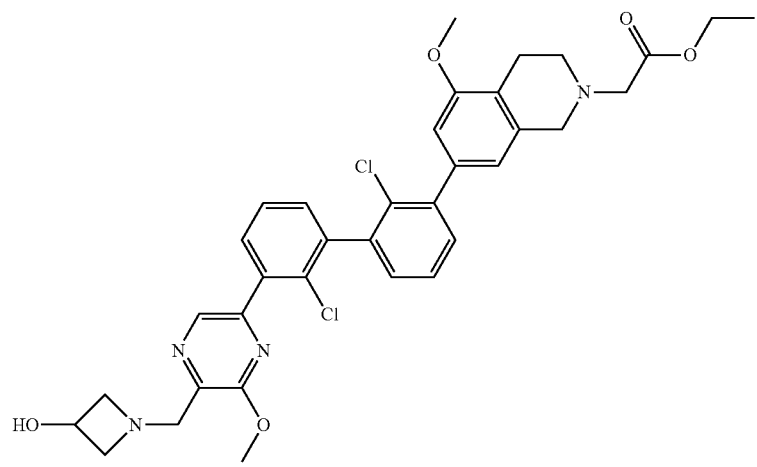

-continued
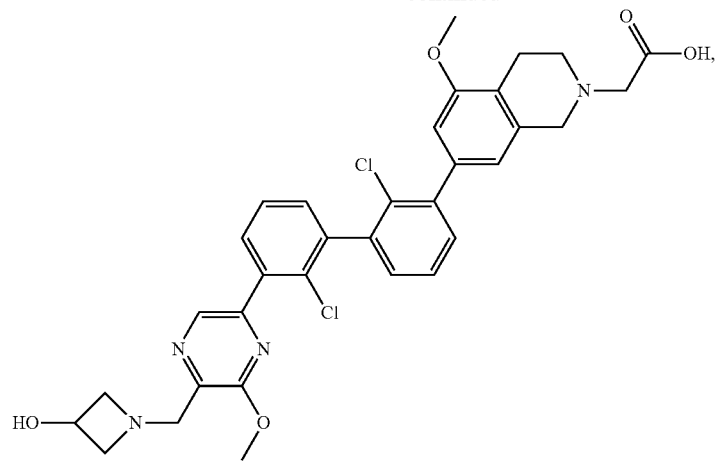
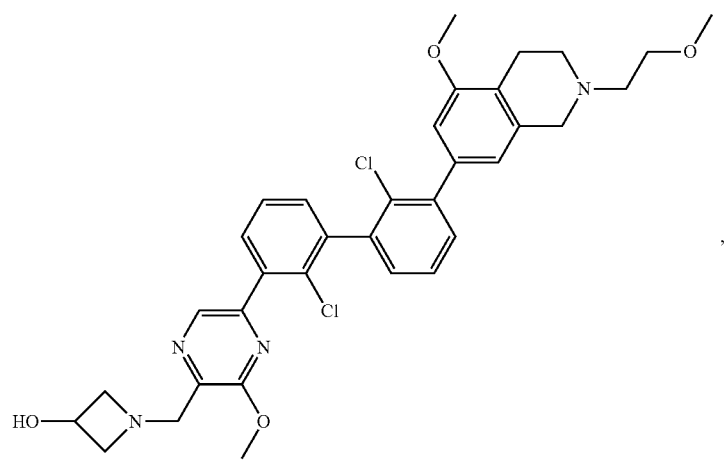
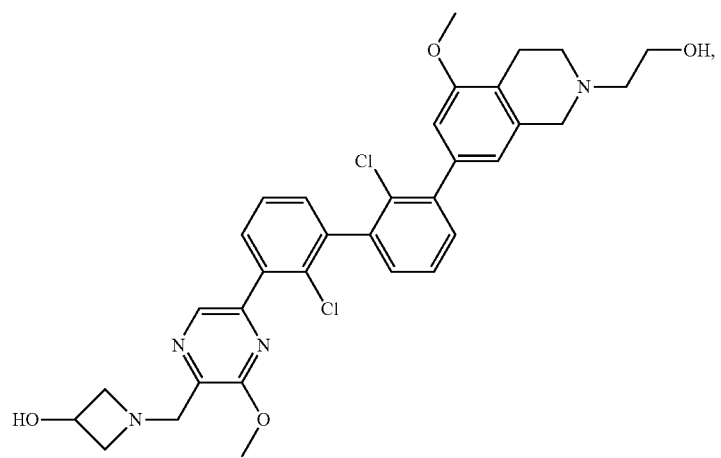

-continued
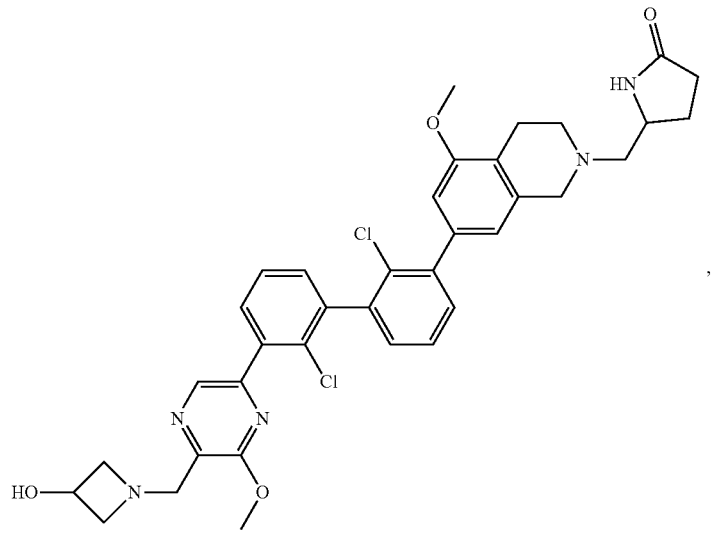
,
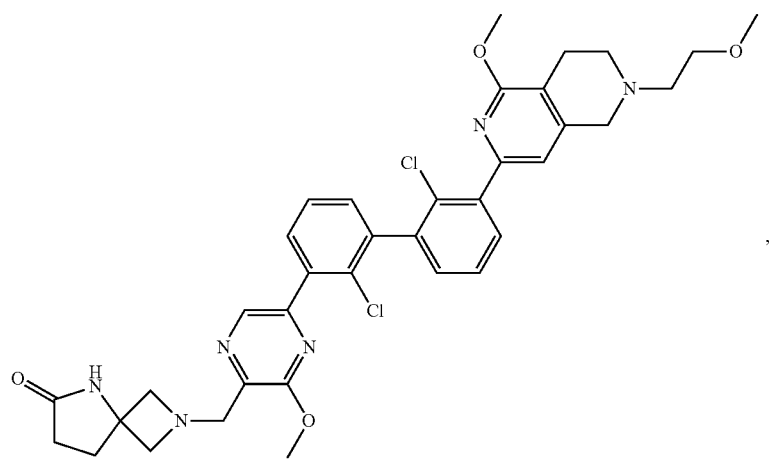
,
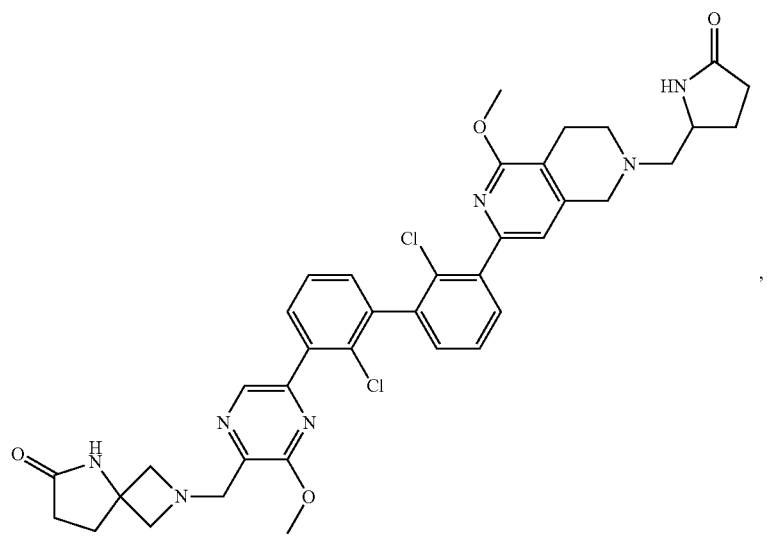
,

-continued
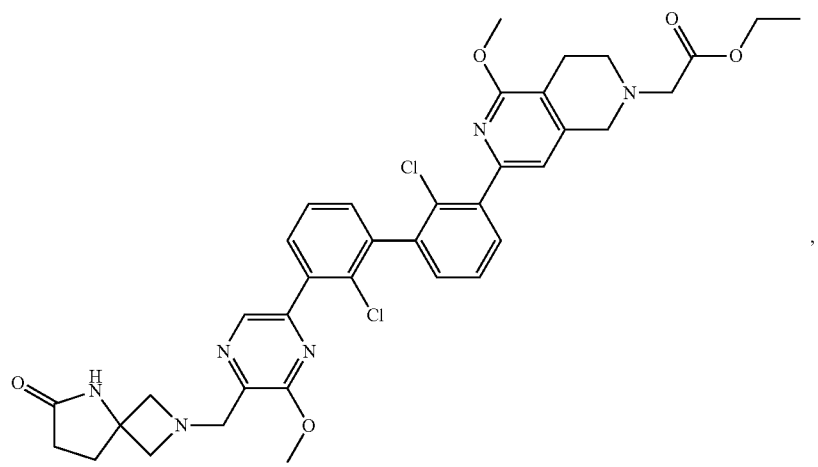
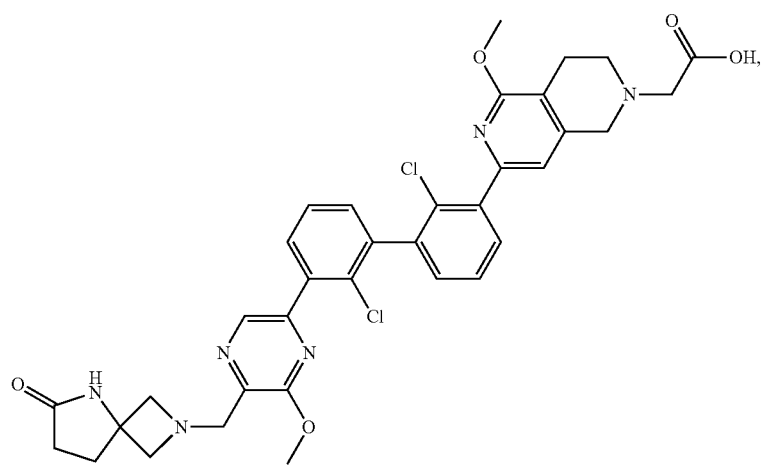
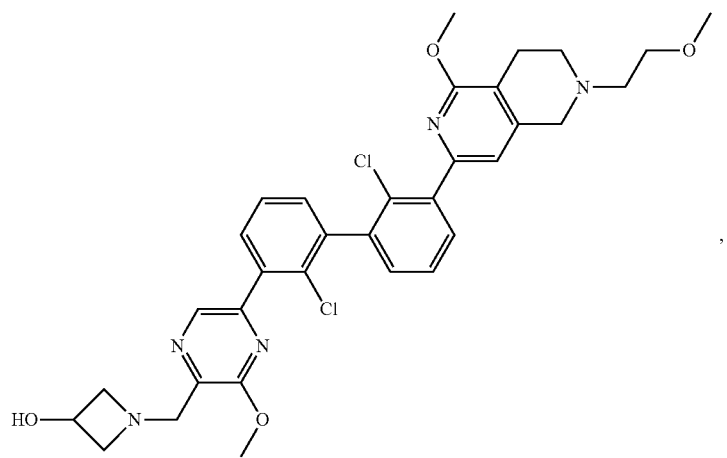

-continued
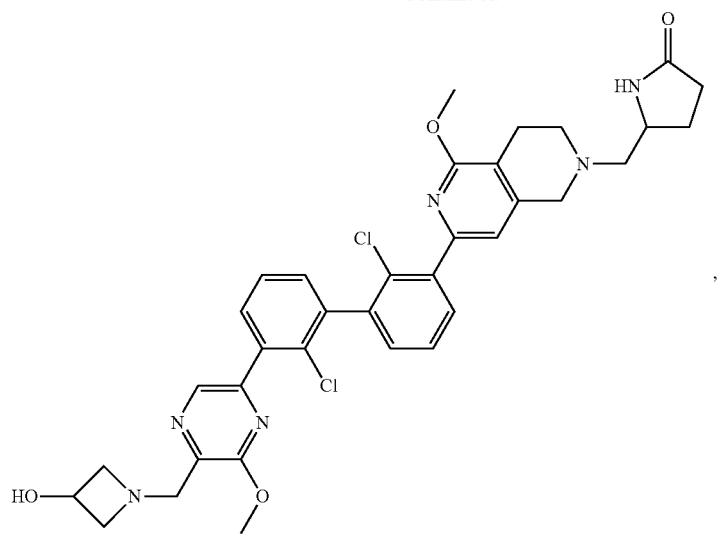
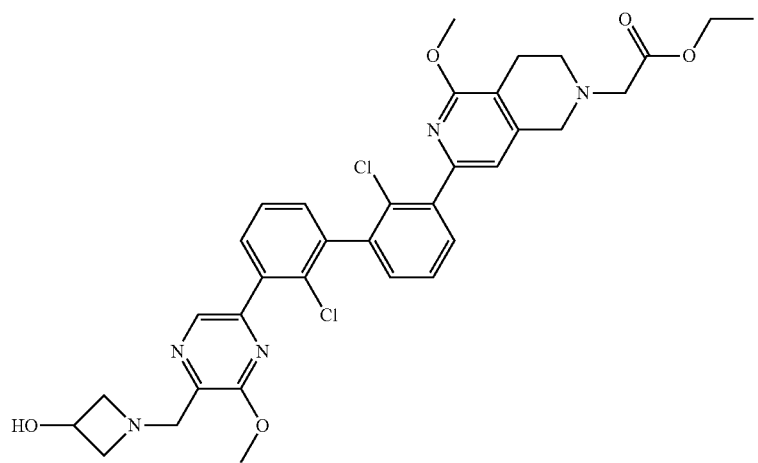
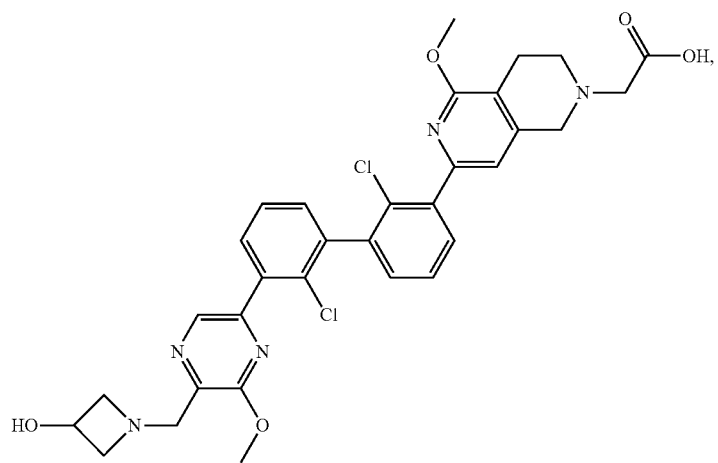

-continued
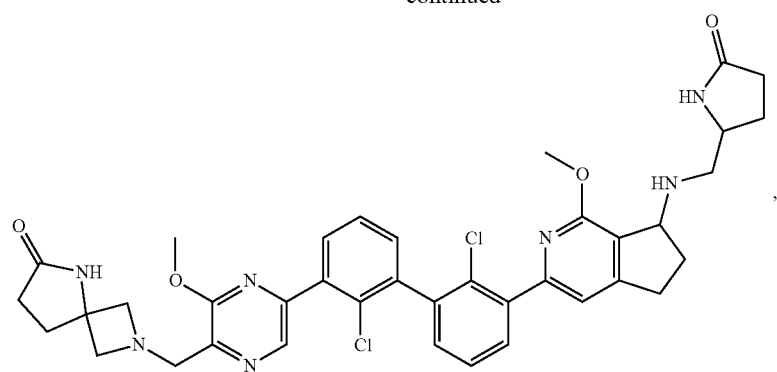
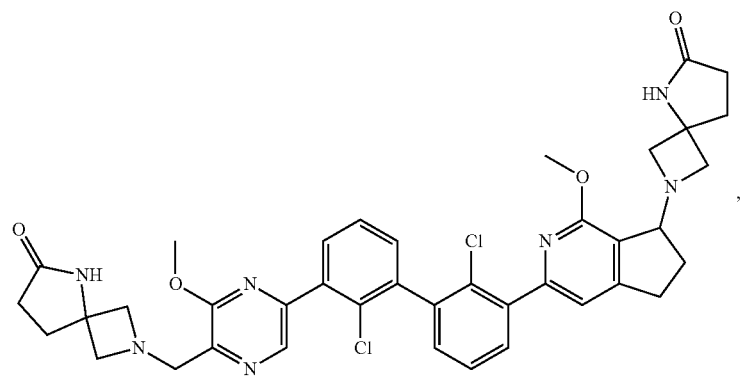
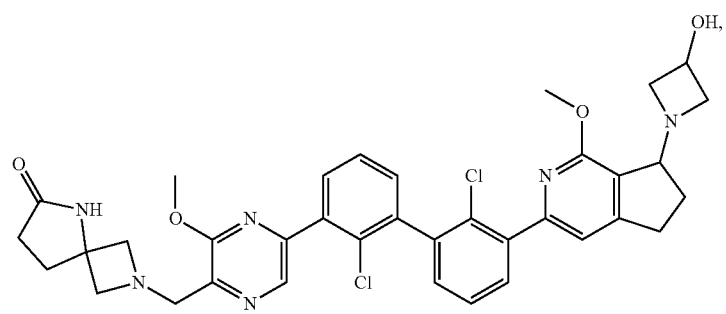
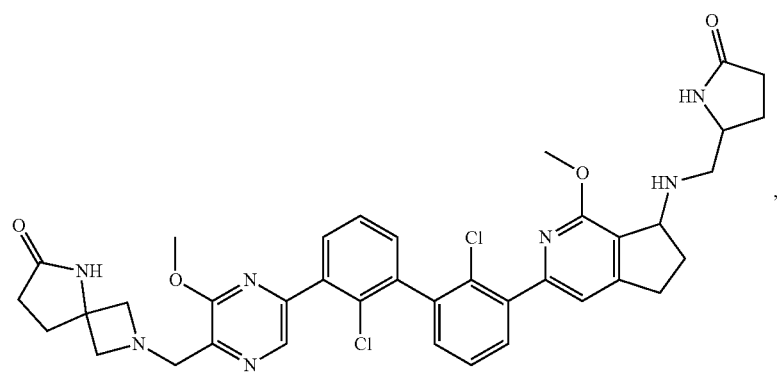

-continued
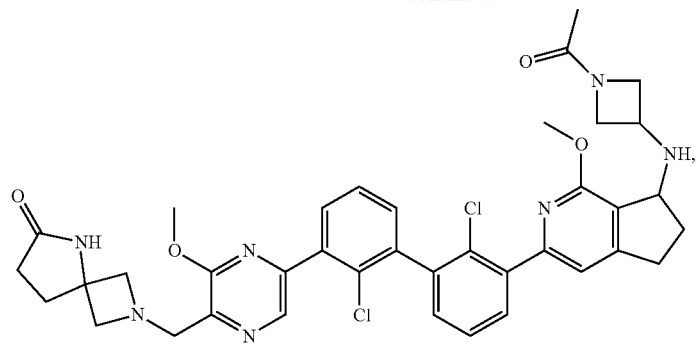
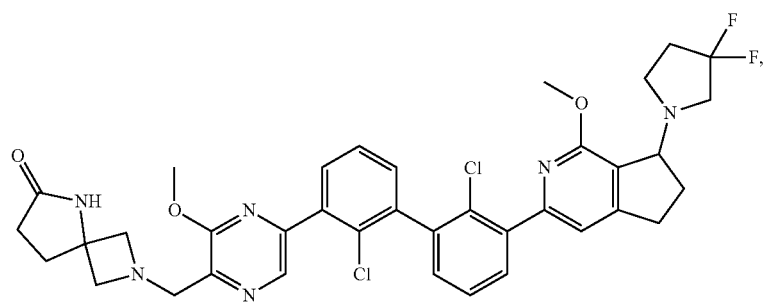
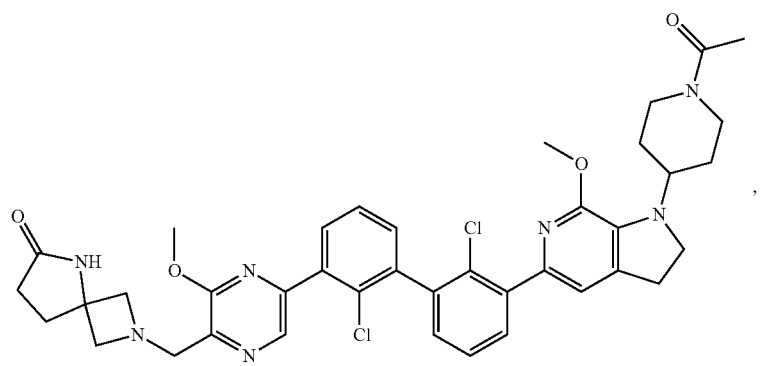
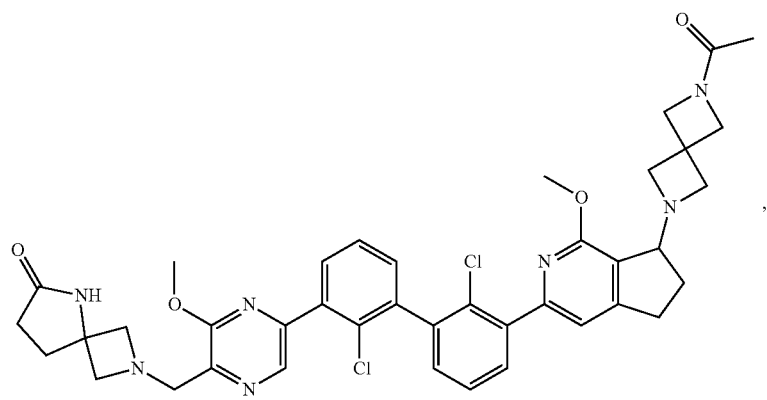

-continued
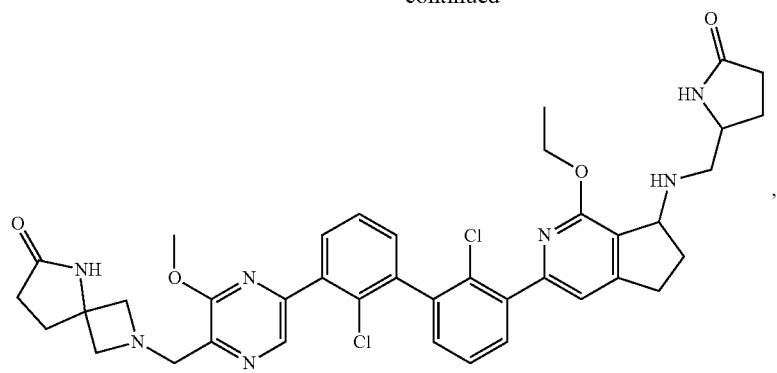
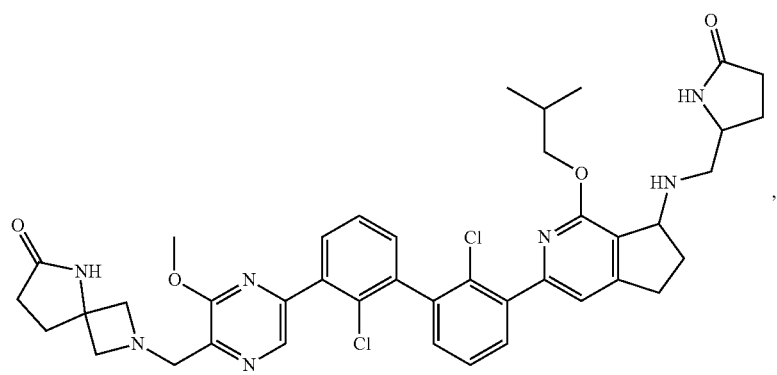
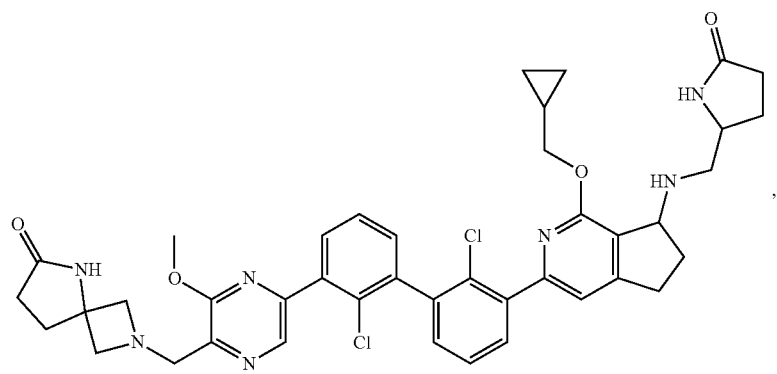
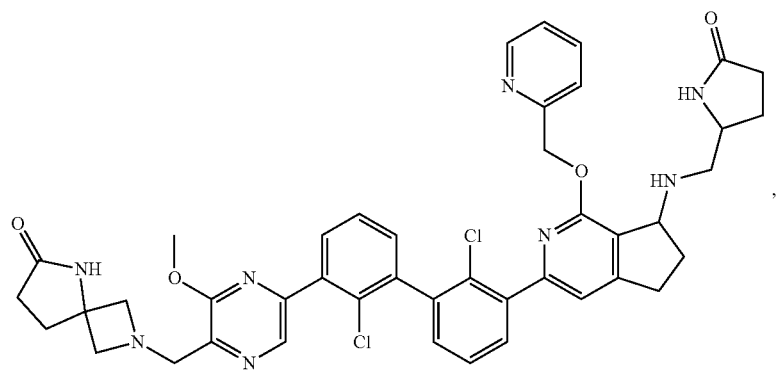

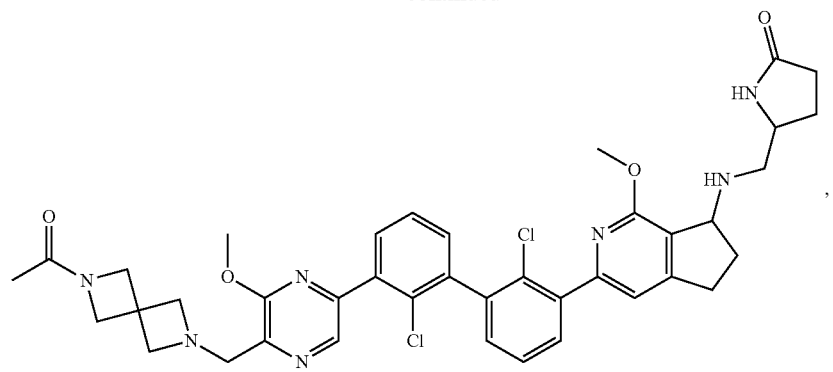
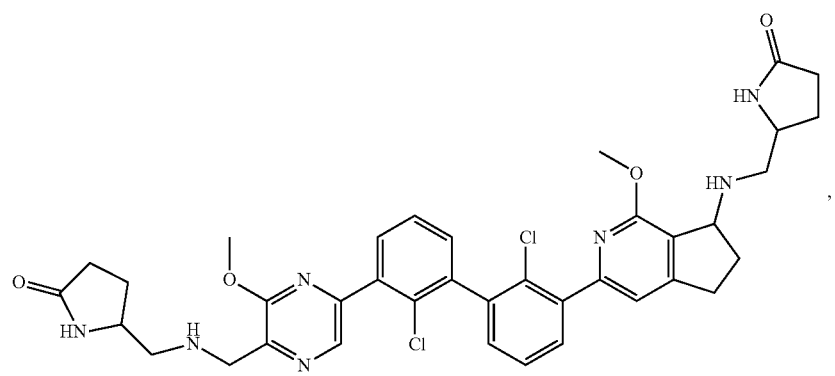
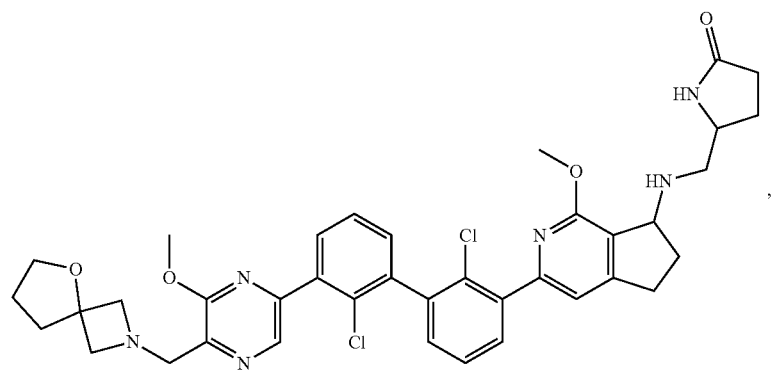
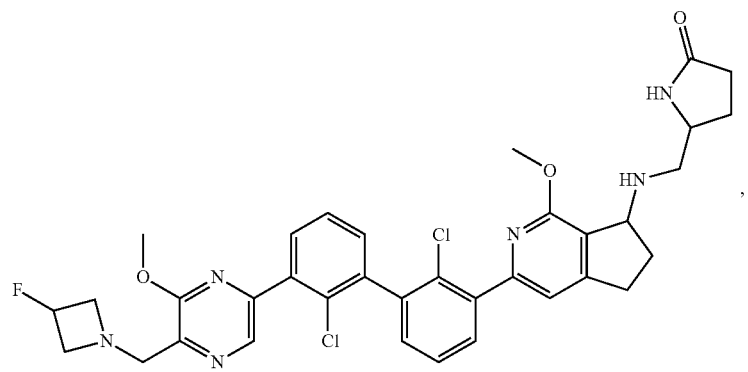

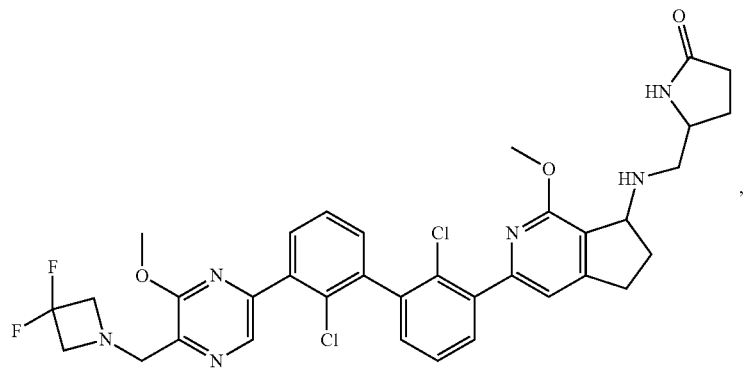
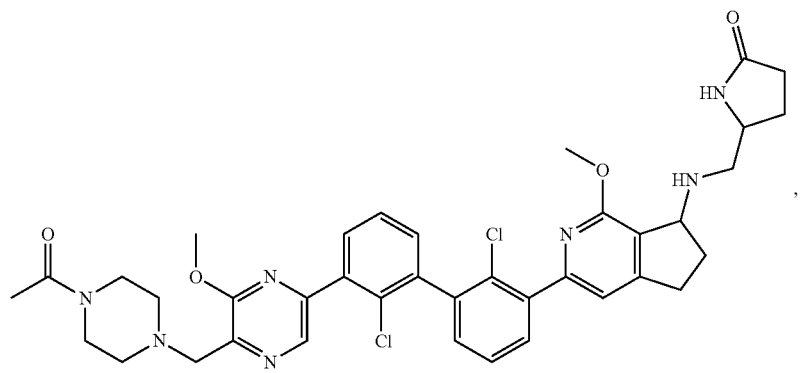
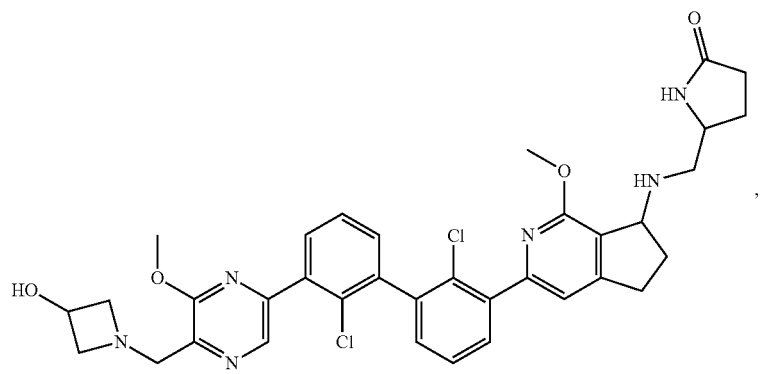
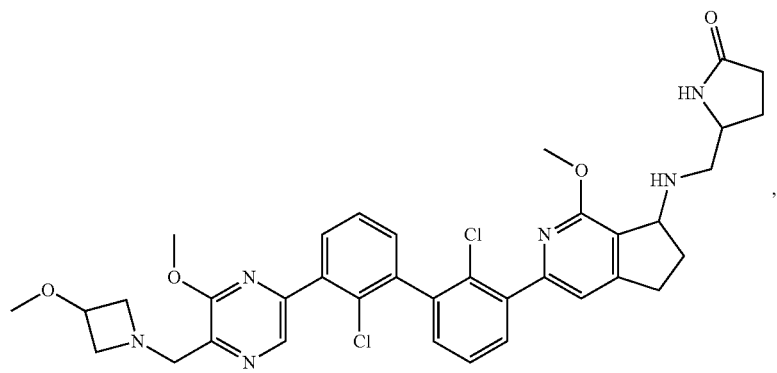

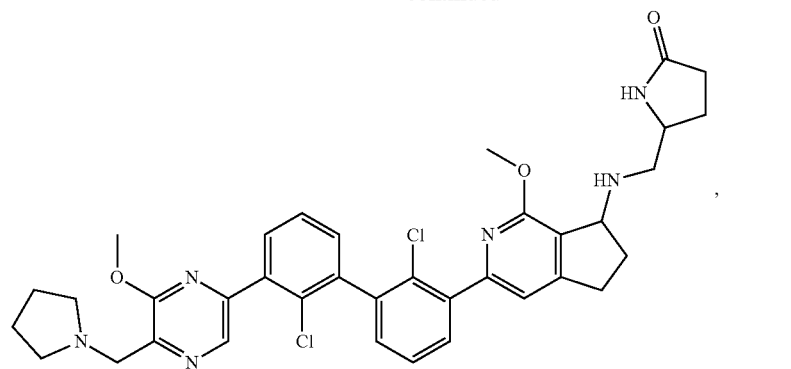
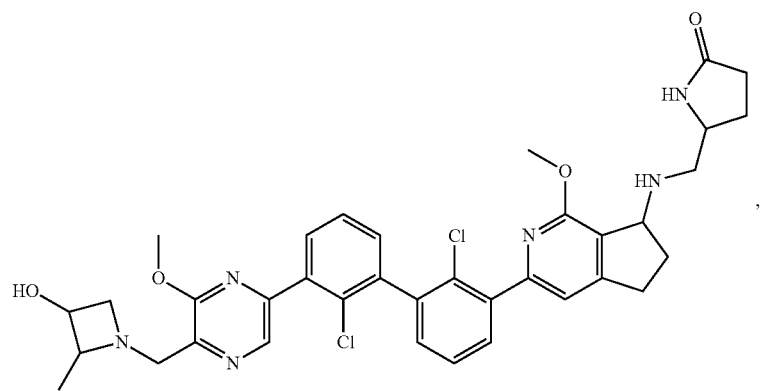
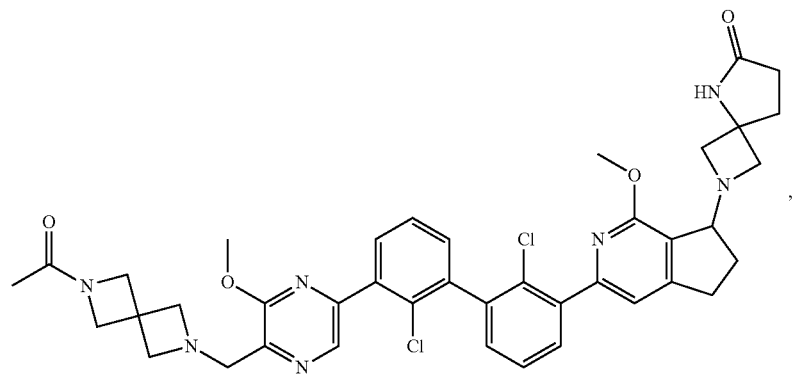
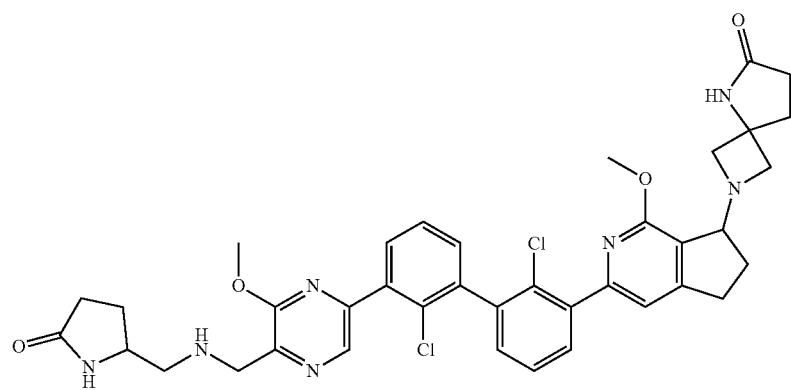

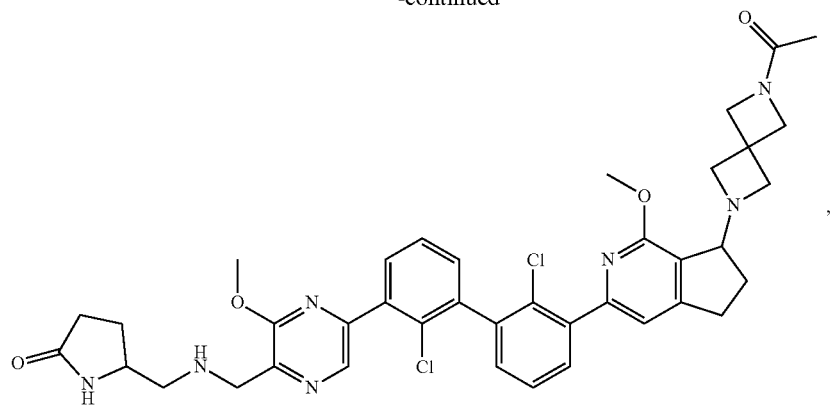
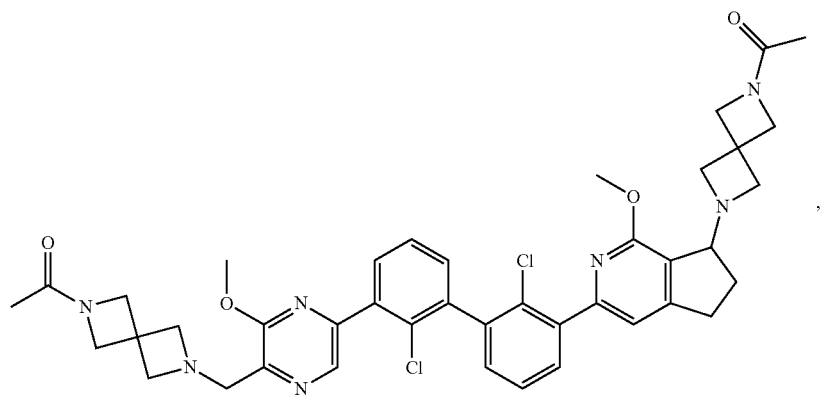
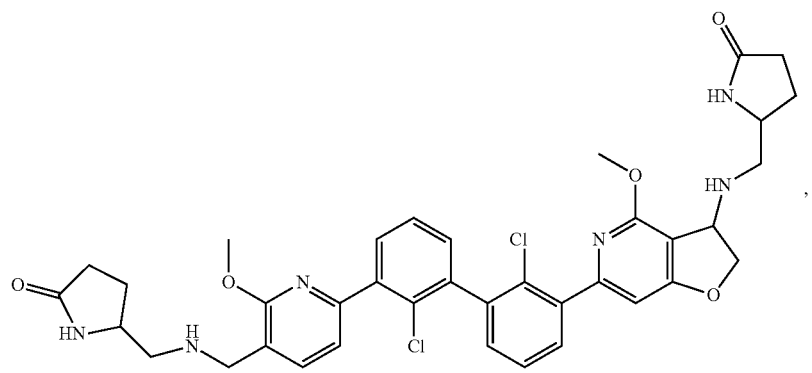
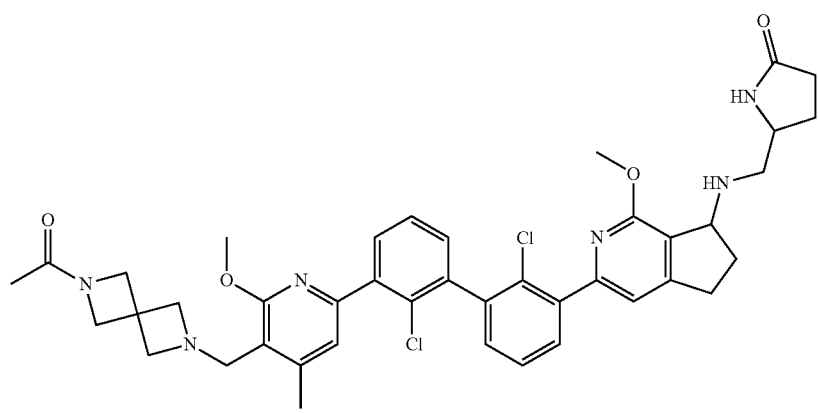

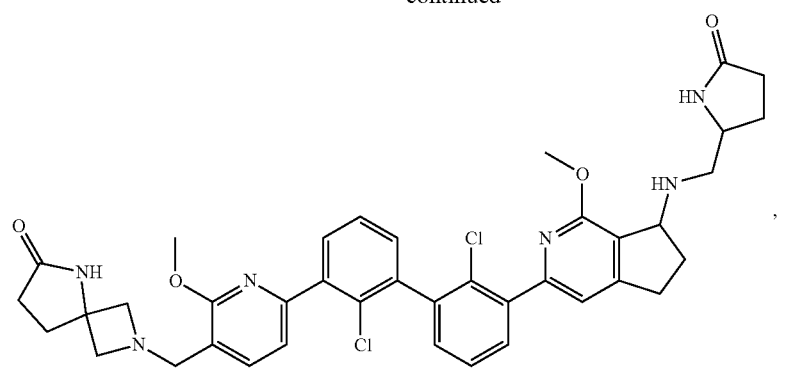
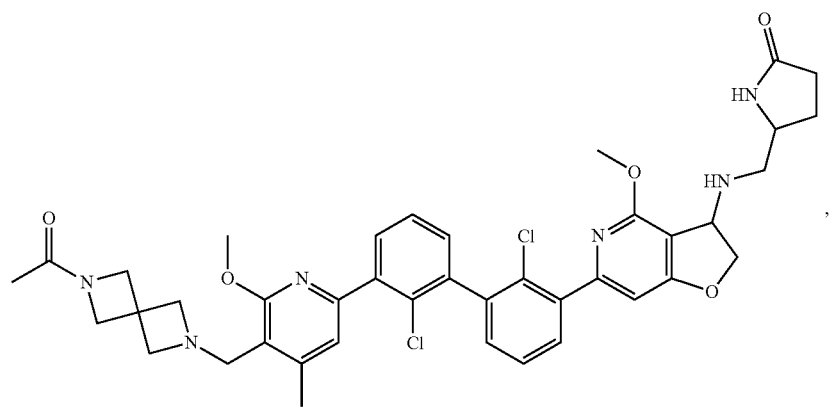
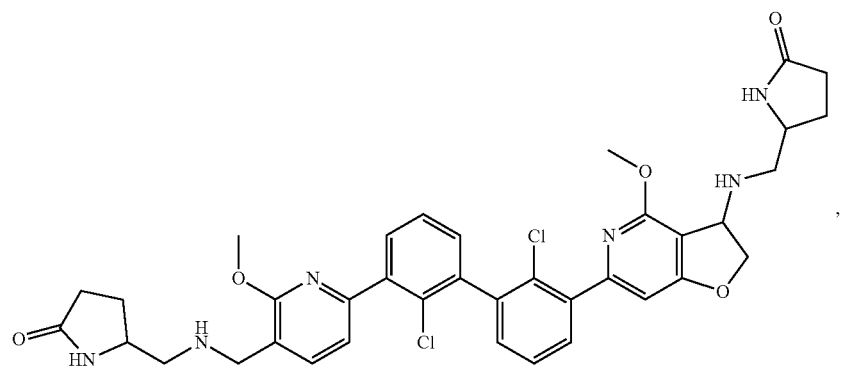
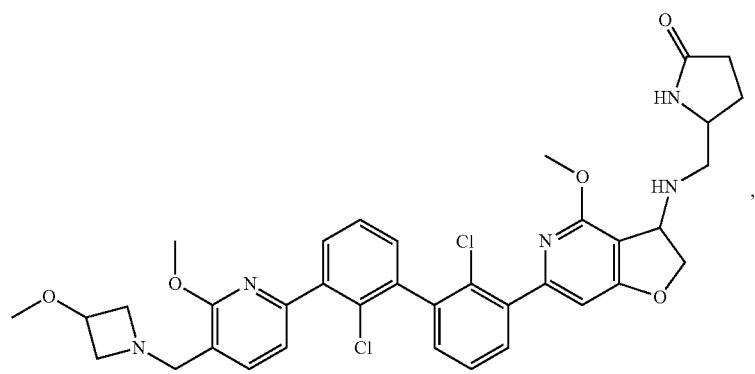

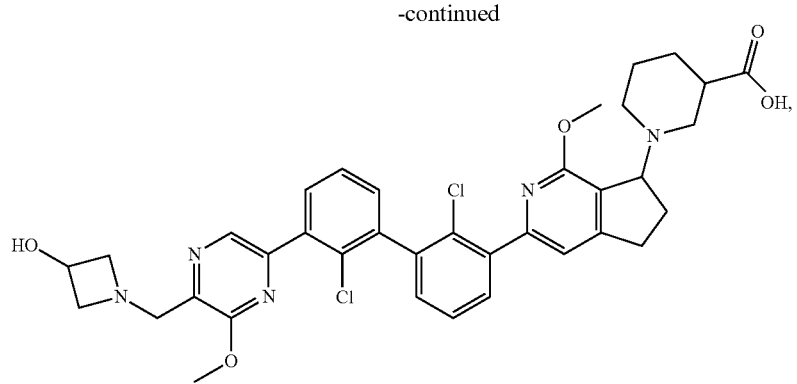
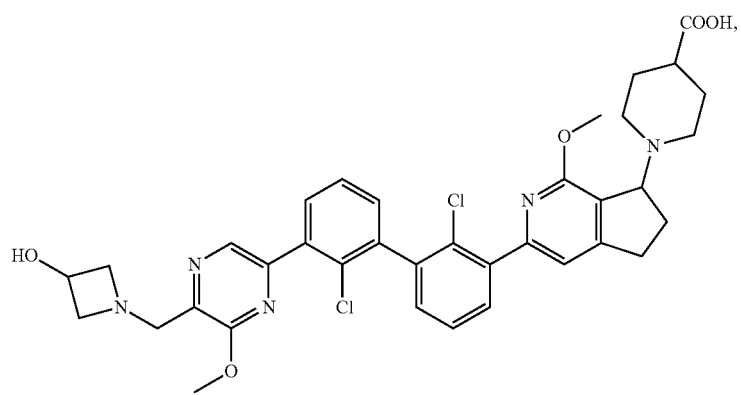
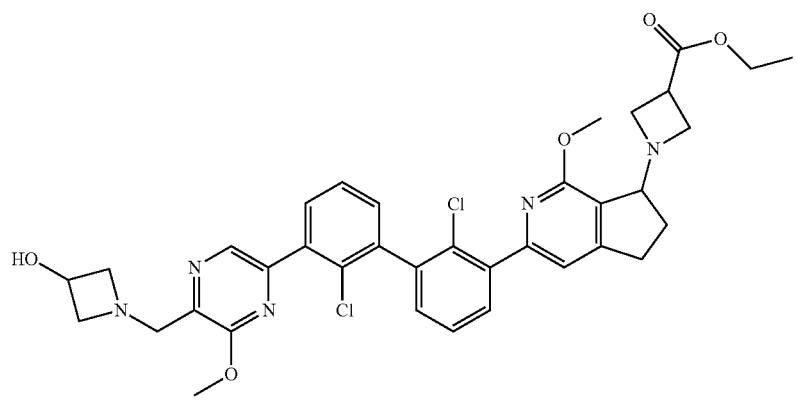
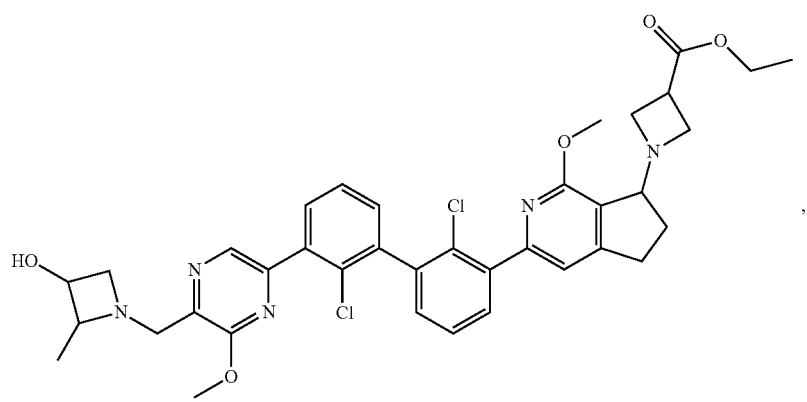

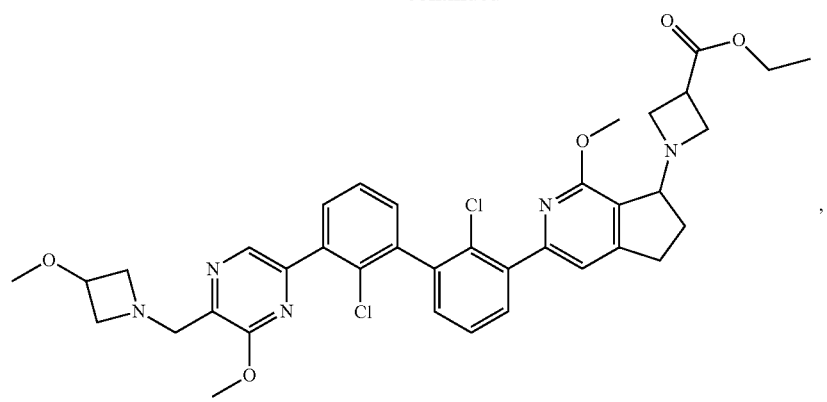
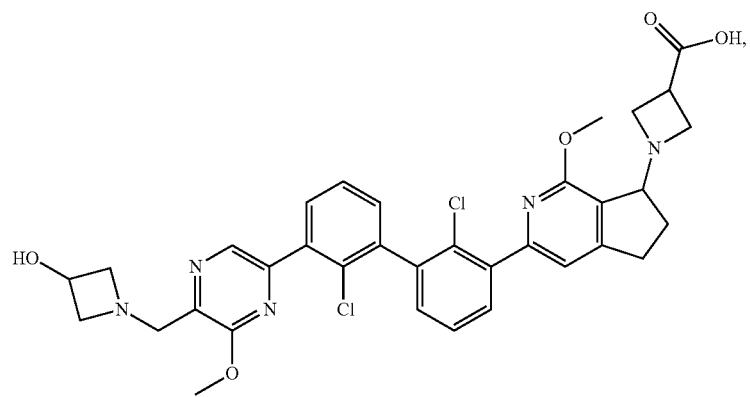
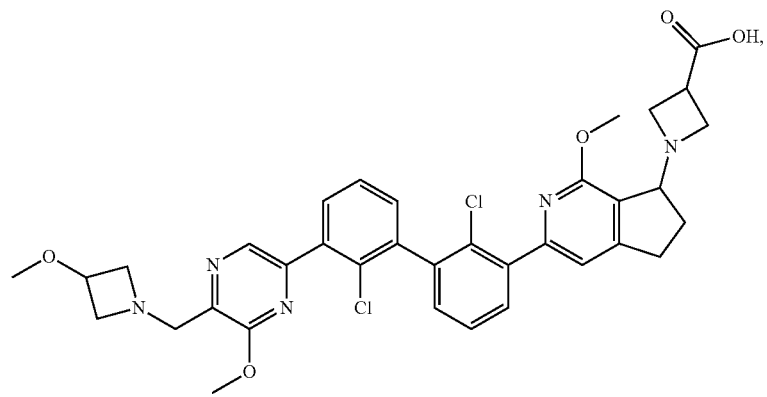
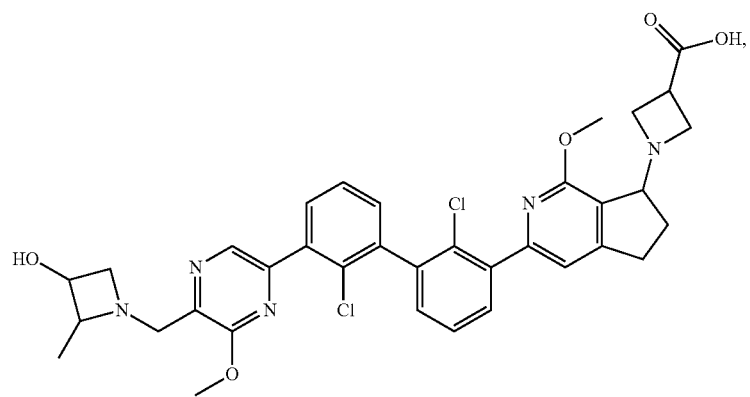

-continued
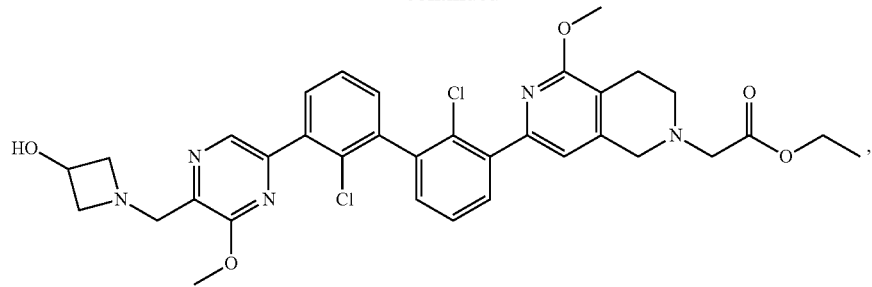
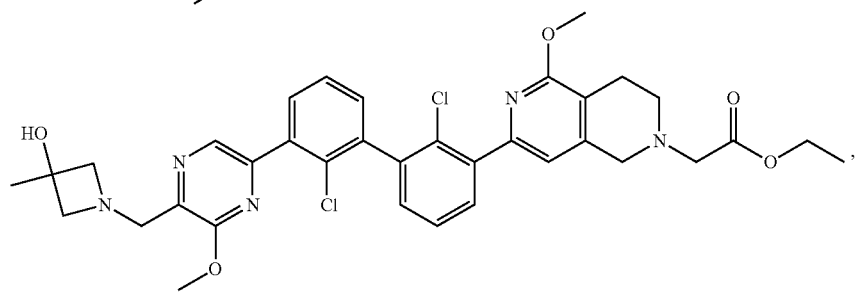
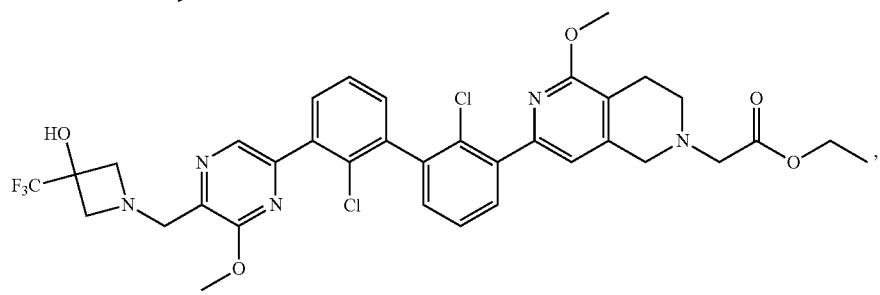
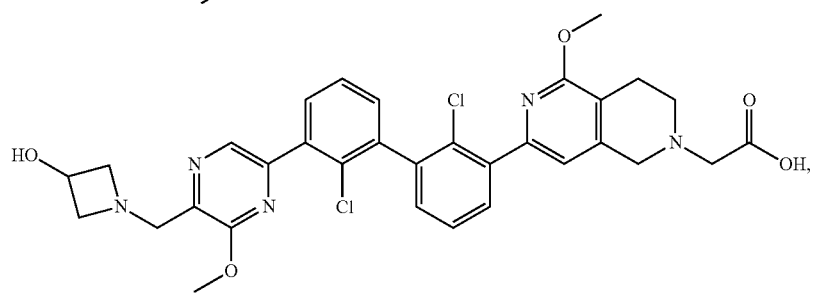
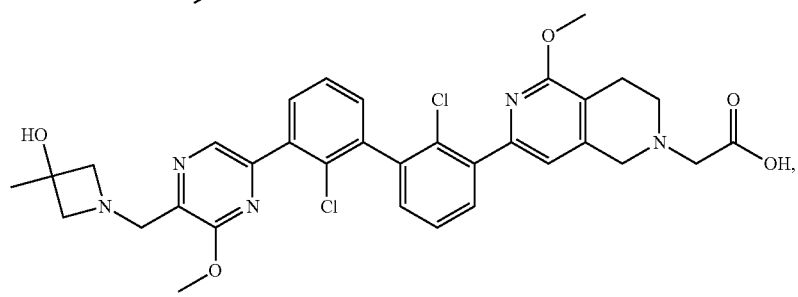
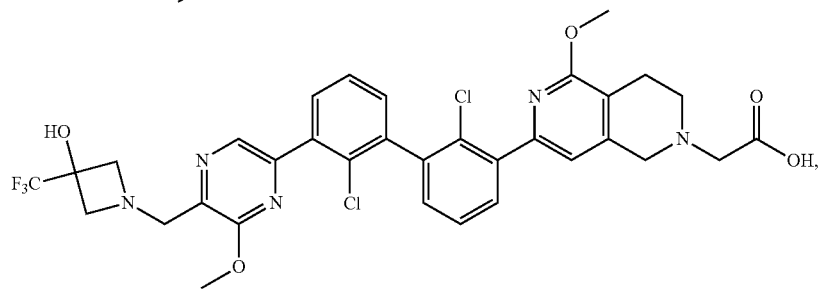

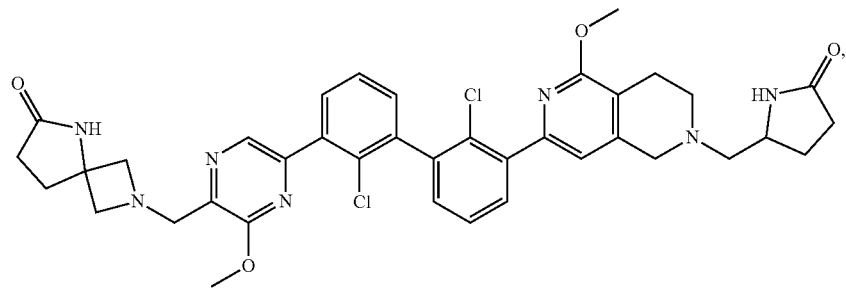
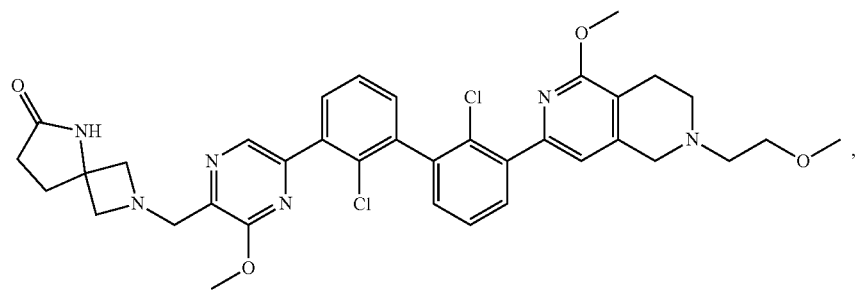
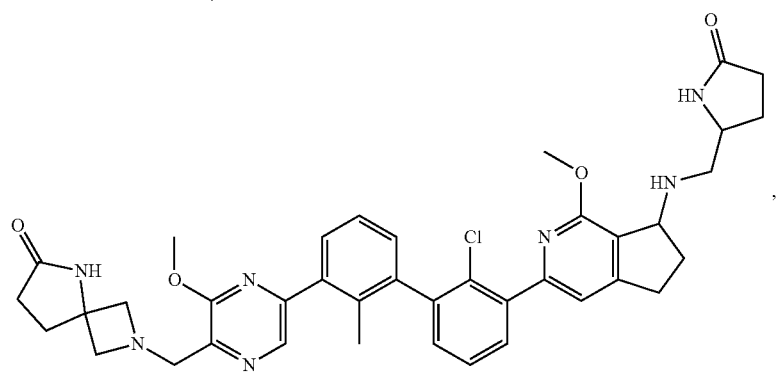
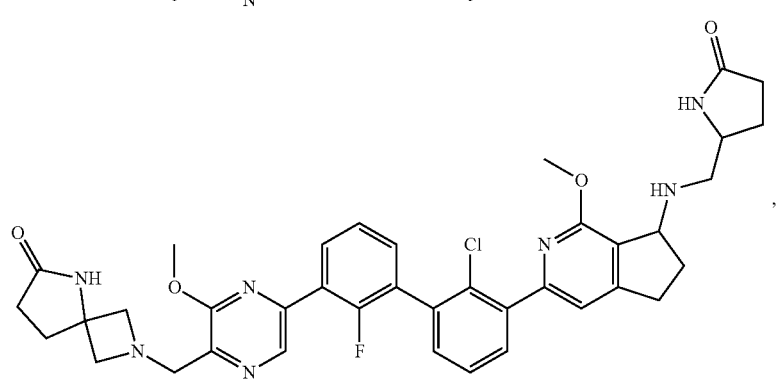
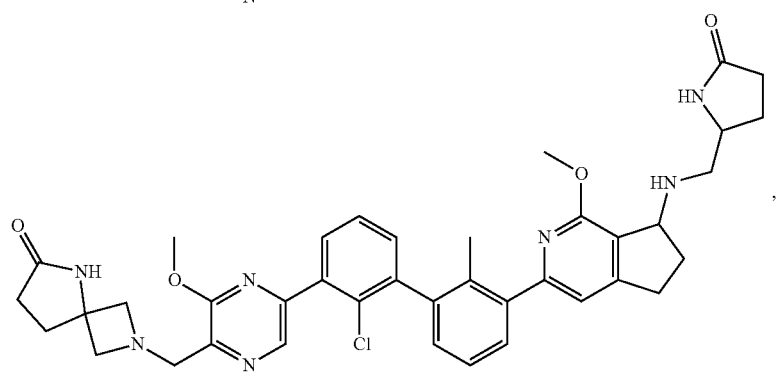

-continued
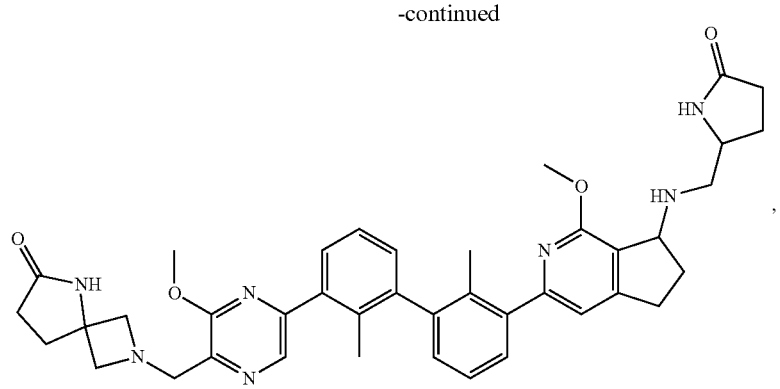
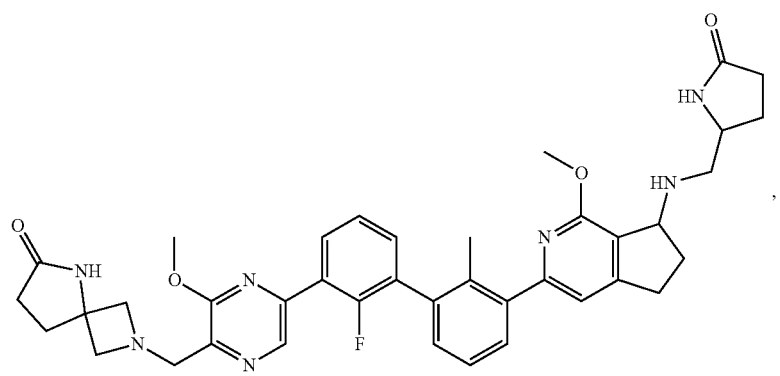
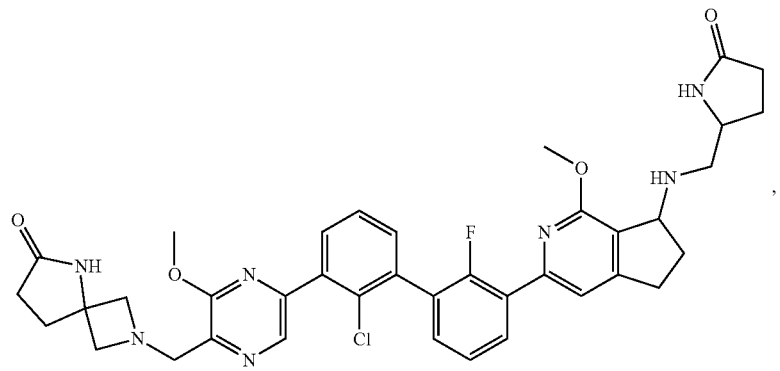
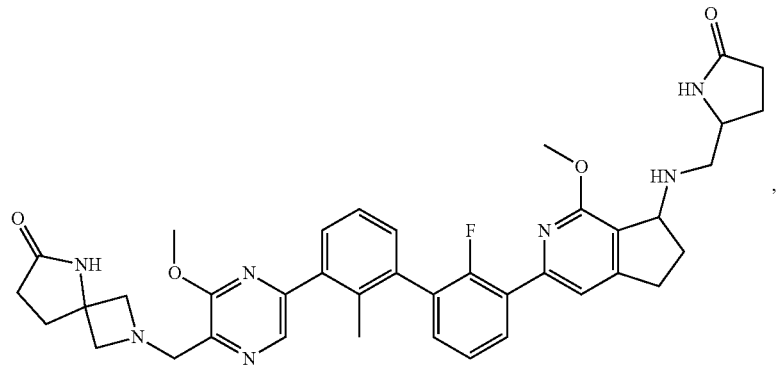

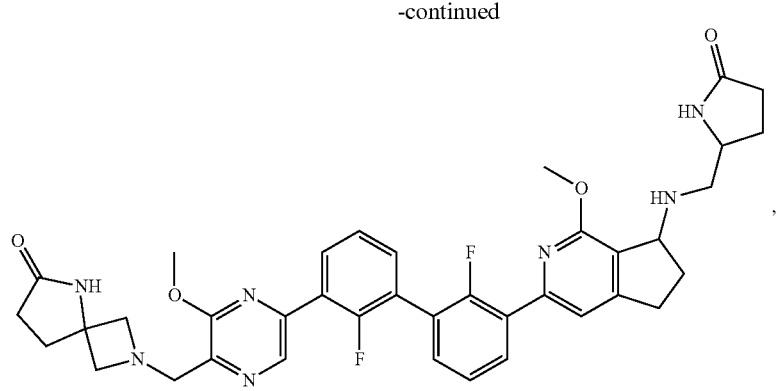,
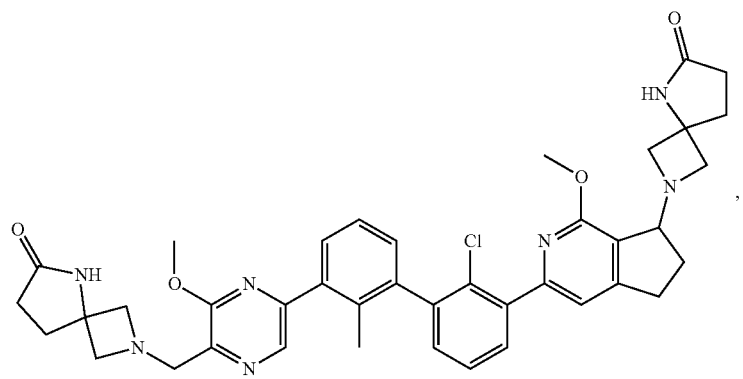,
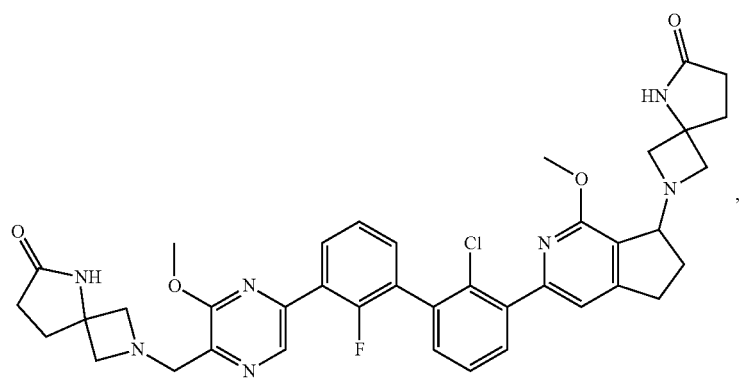,
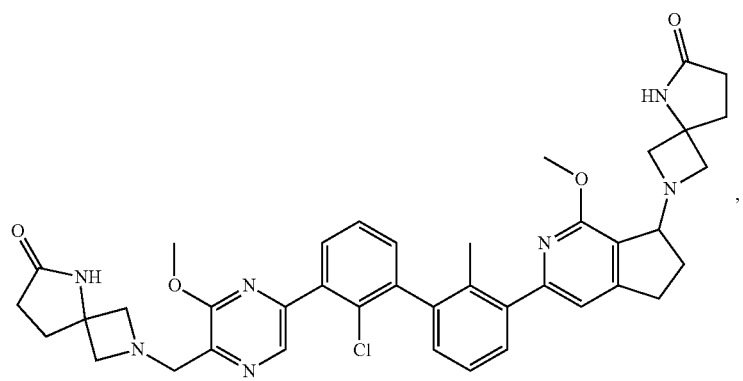,

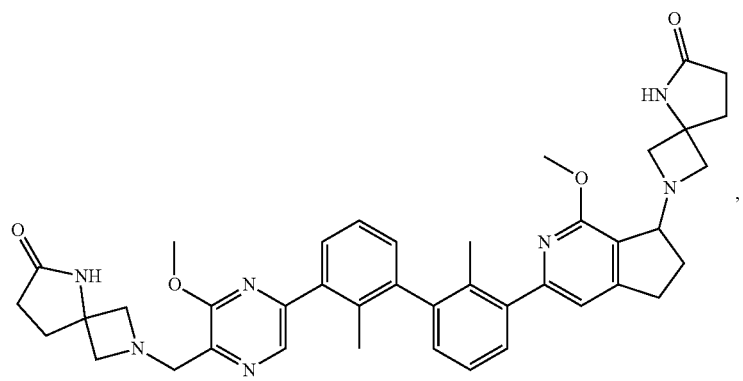
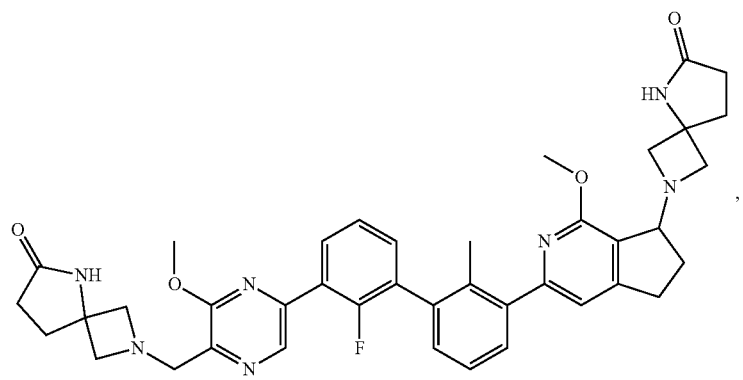
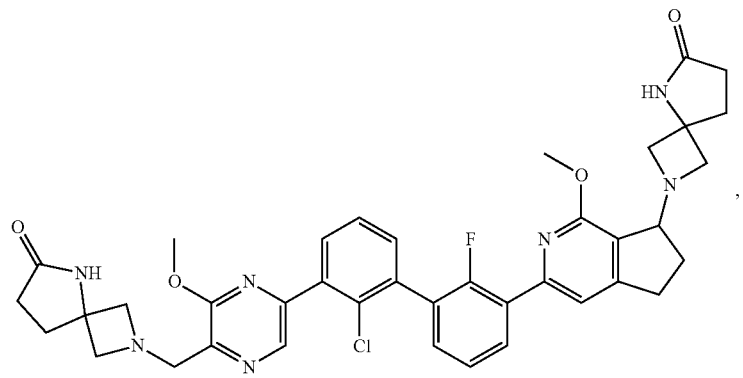
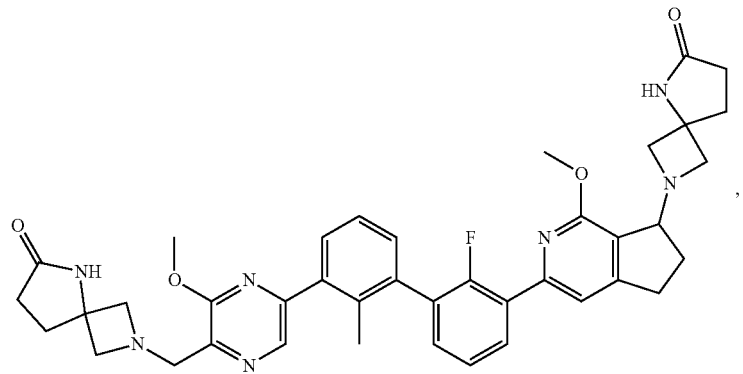

-continued
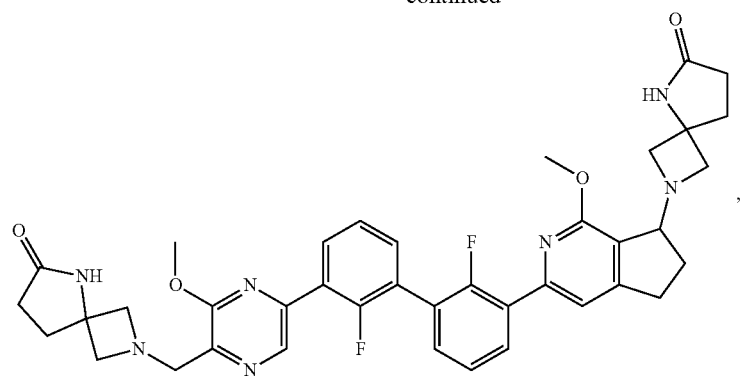
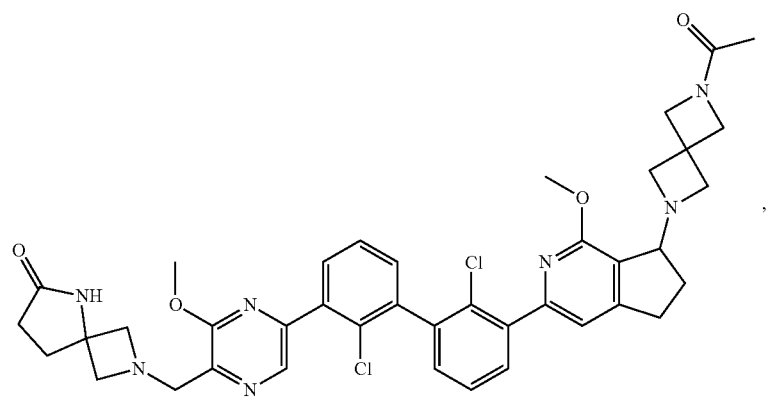
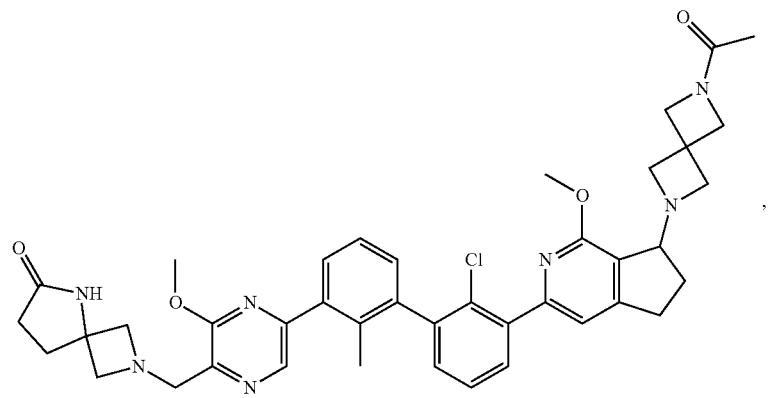
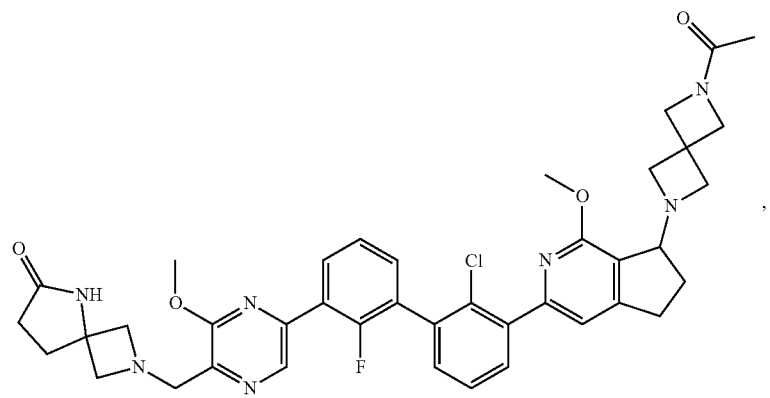

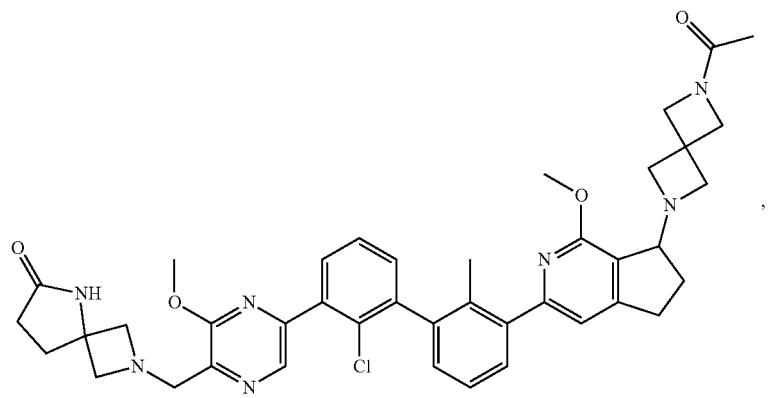
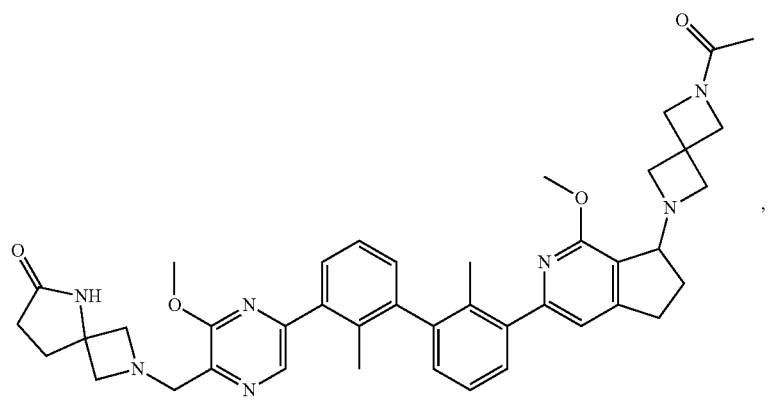
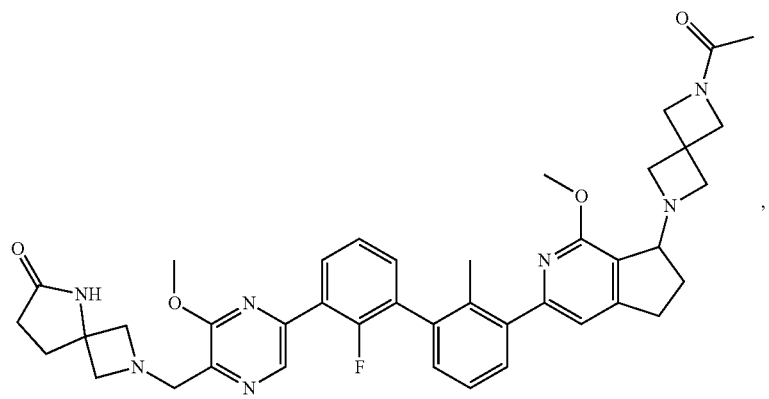
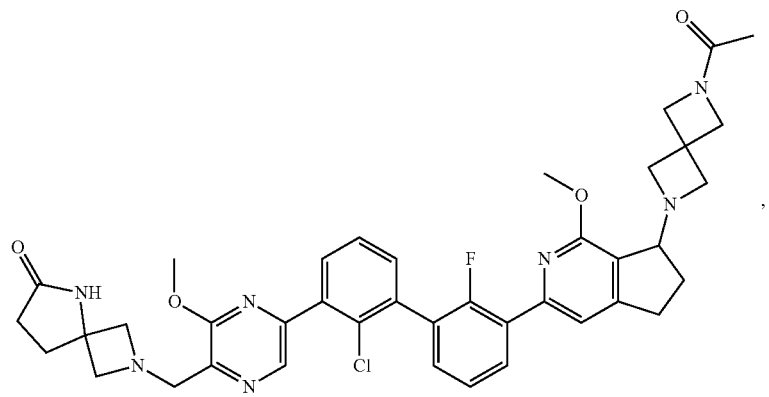

-continued
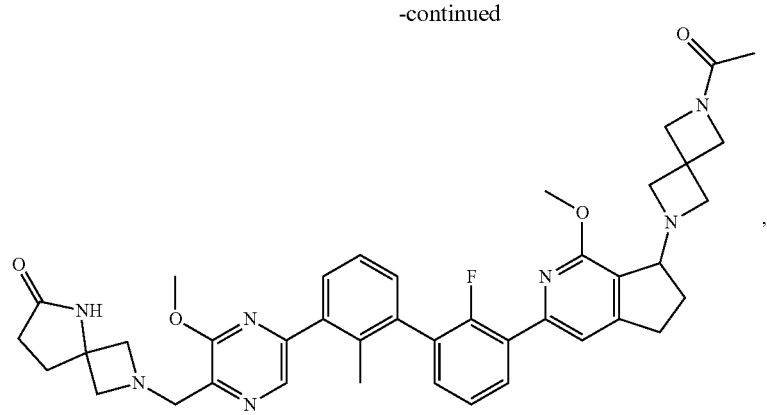
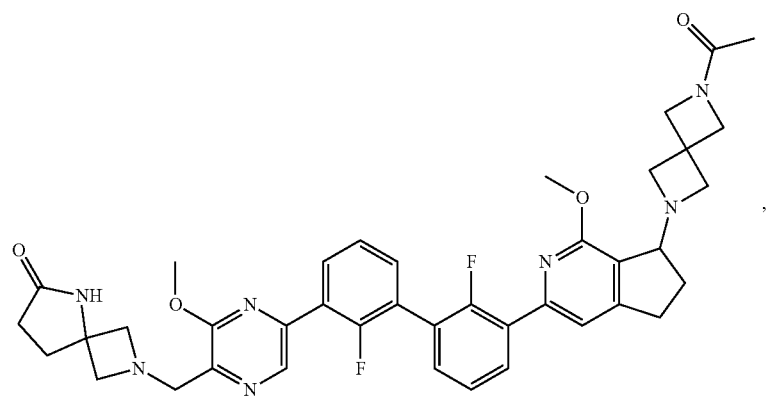
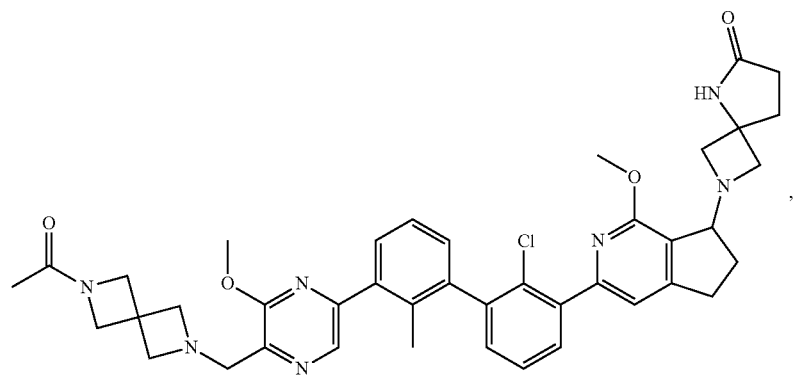
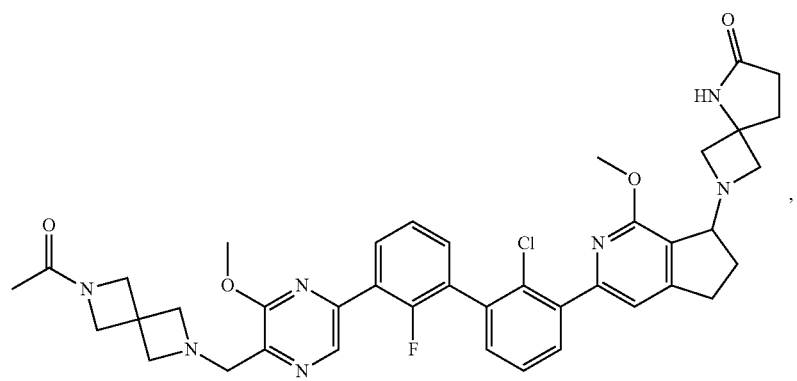

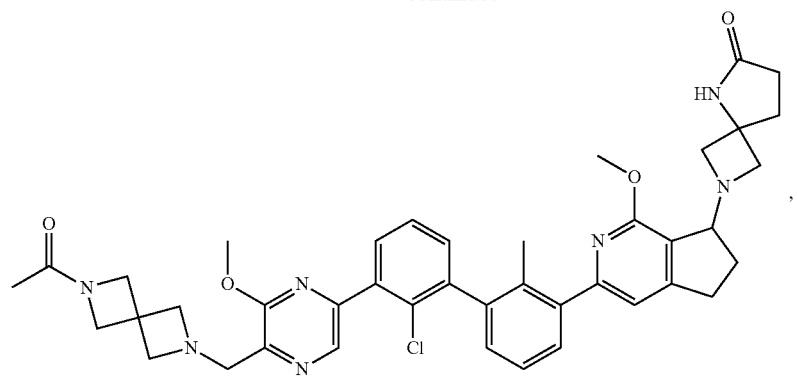
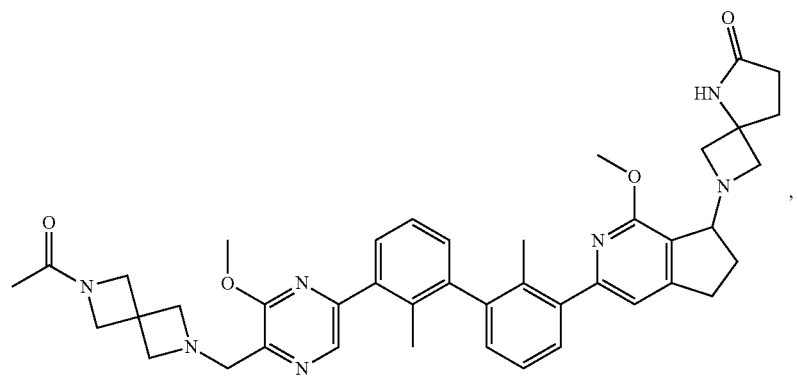
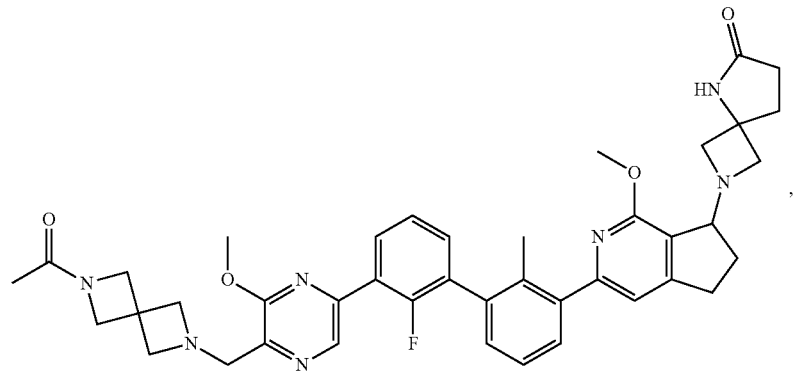
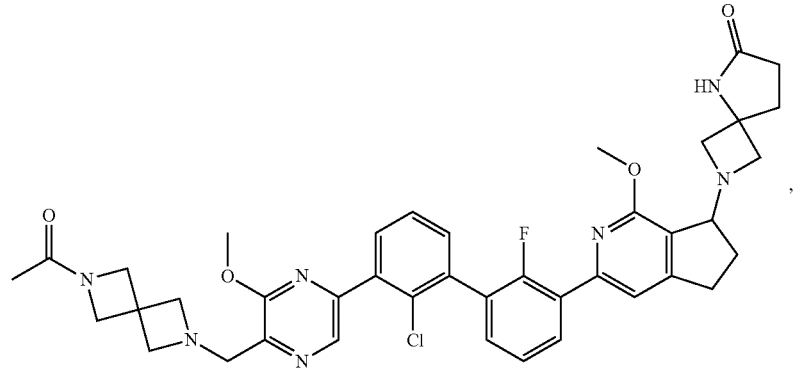

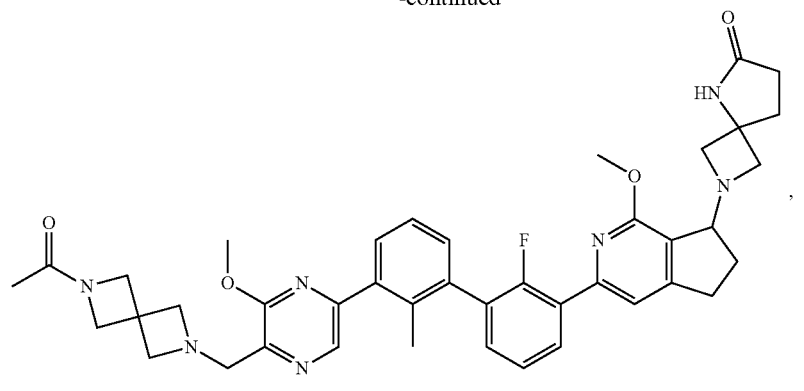
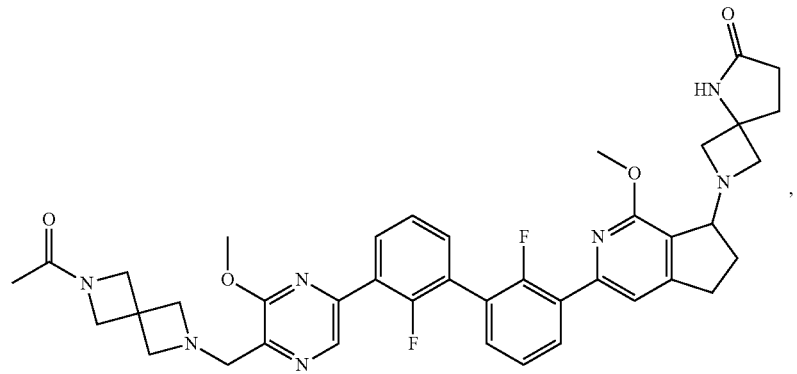
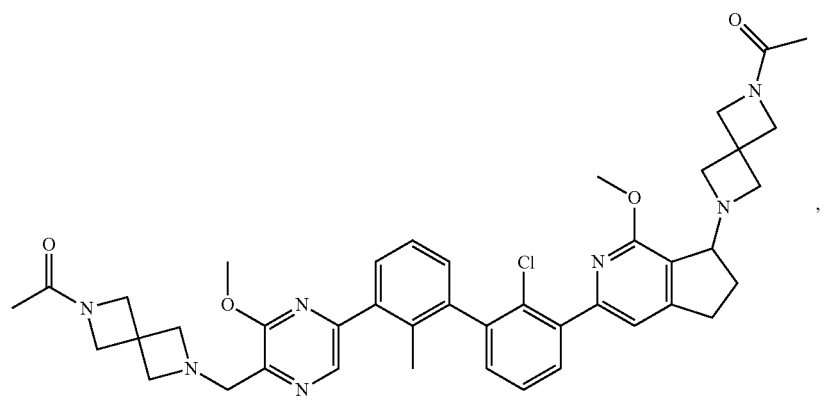
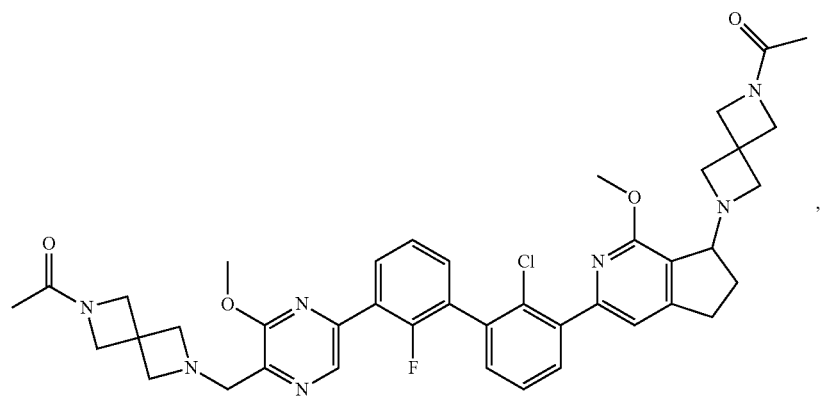

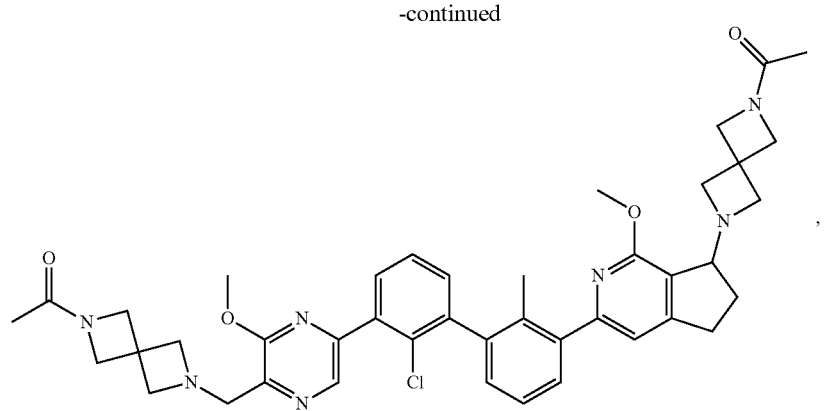
,
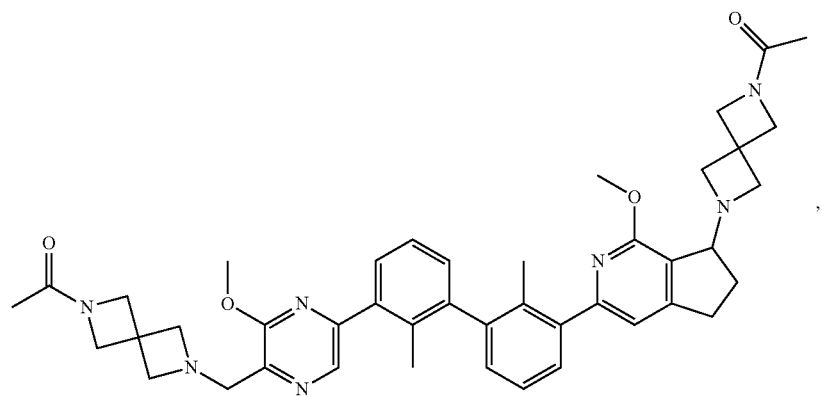
,
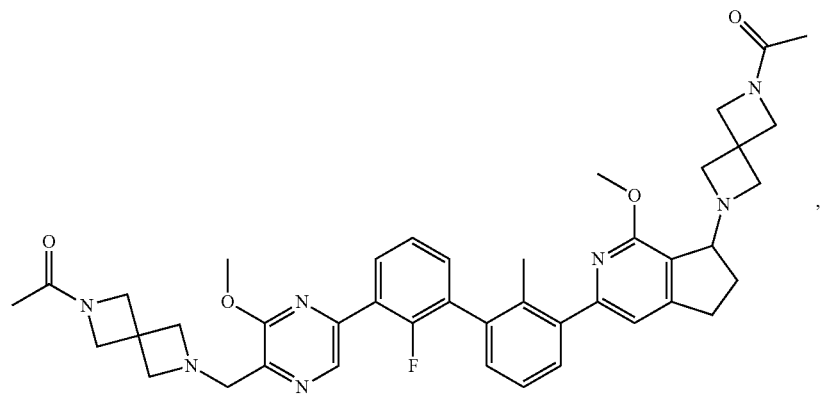
,
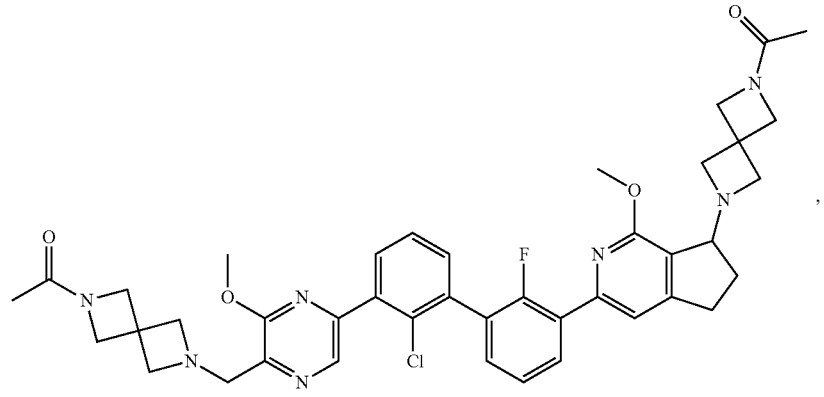
,

-continued
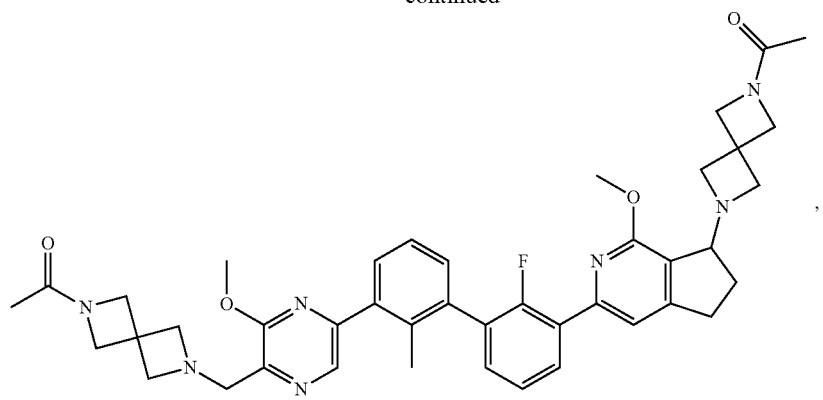
,
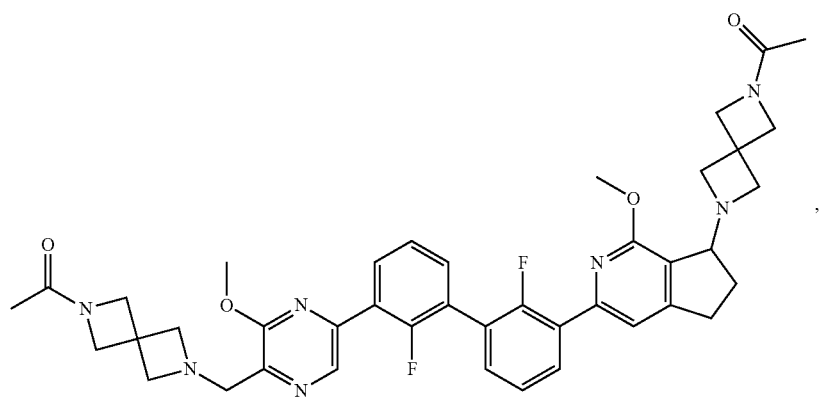
,
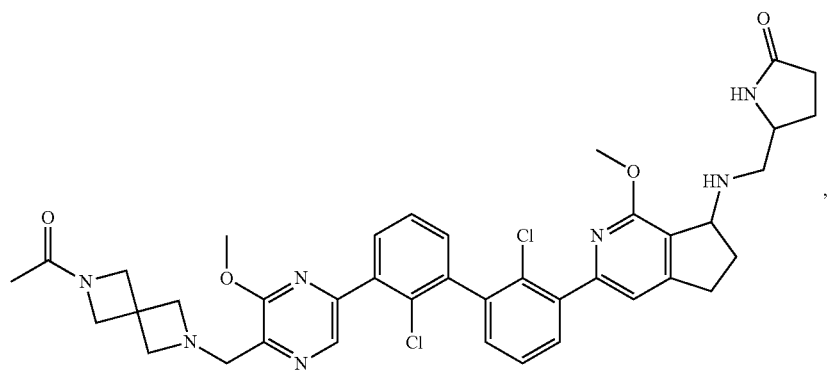
,
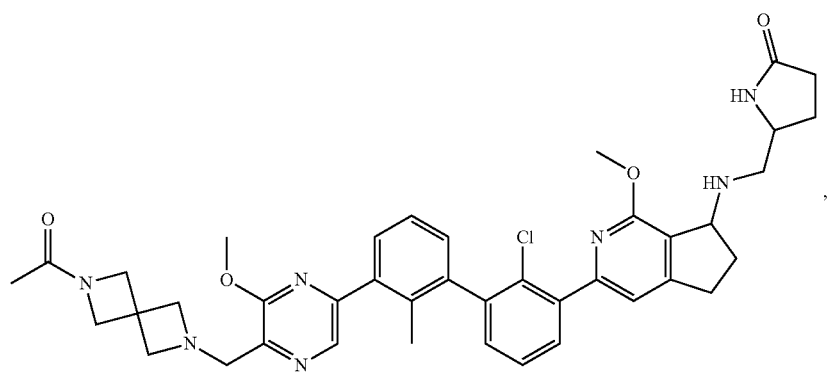
,

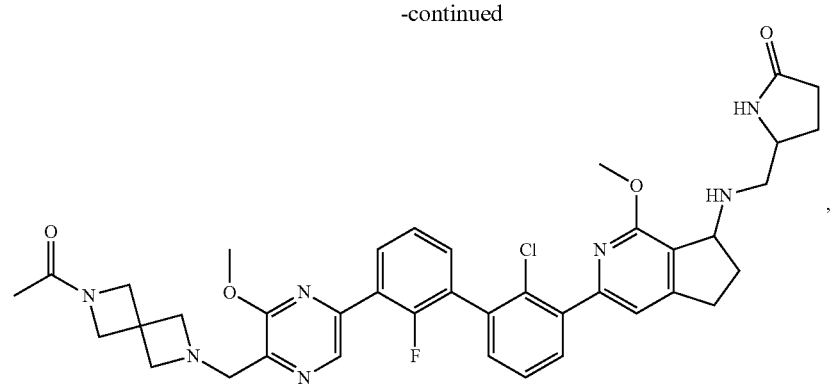
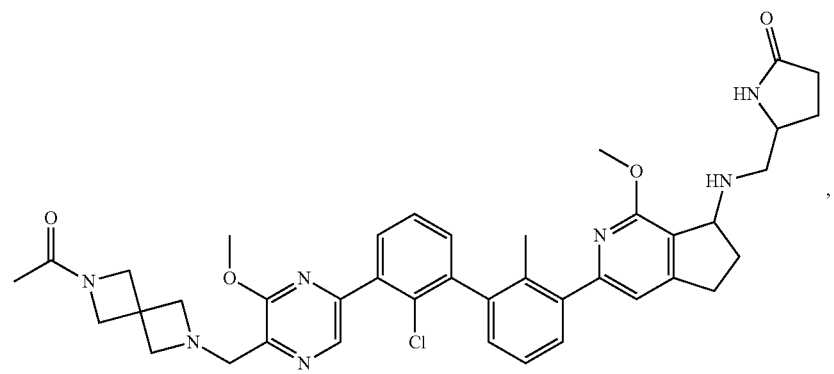
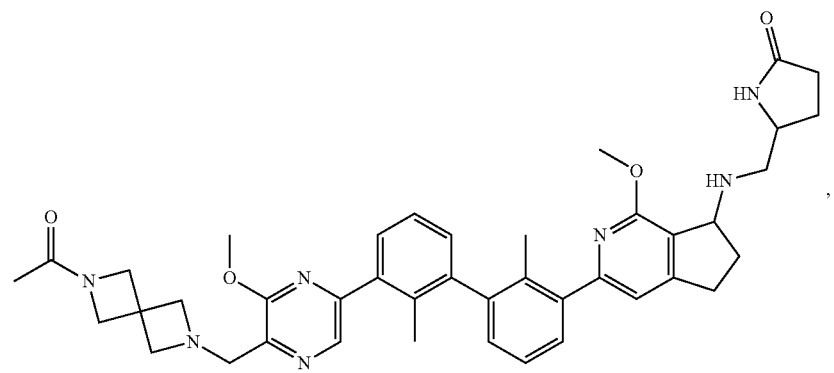
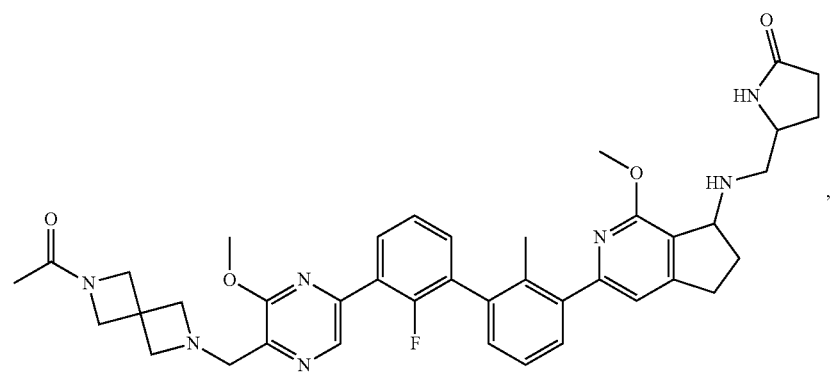

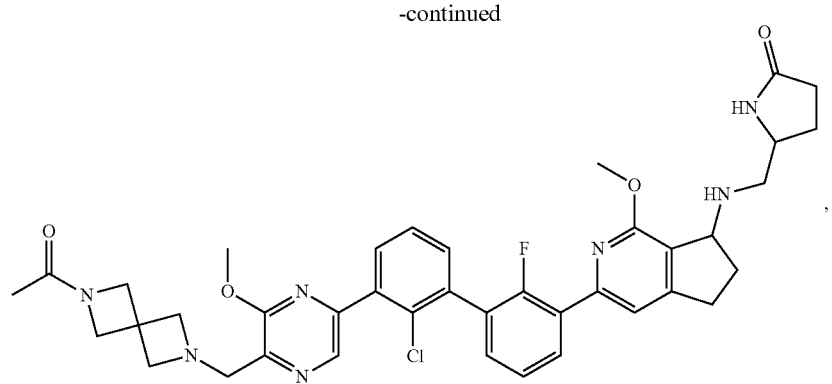
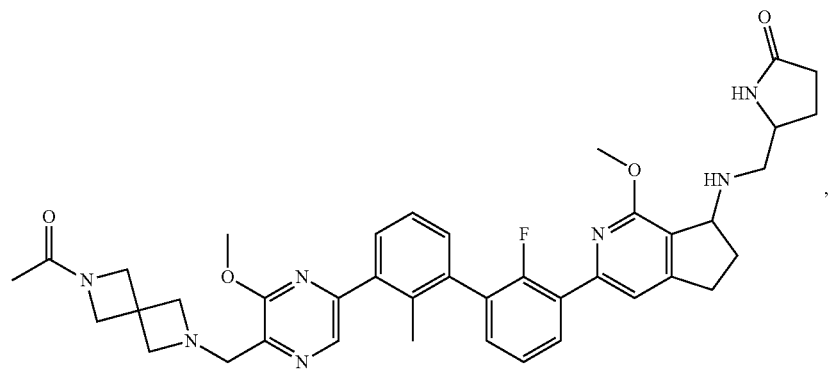
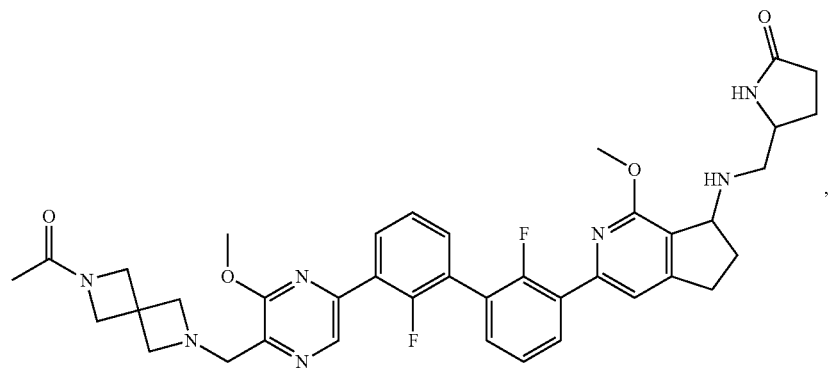
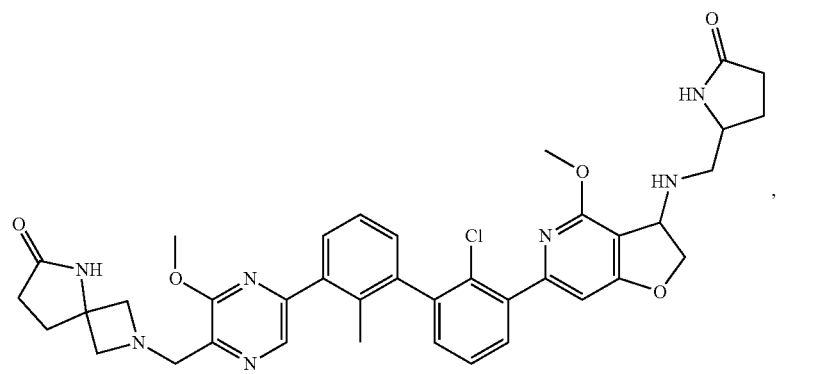

-continued
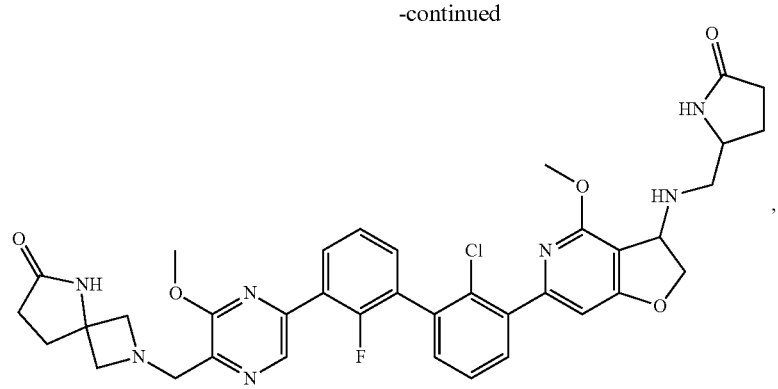
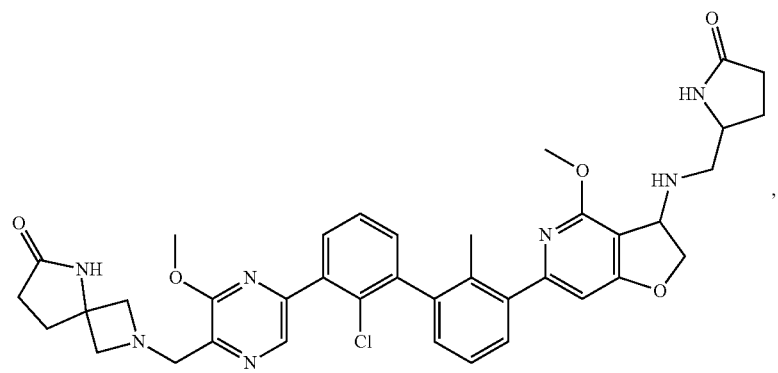
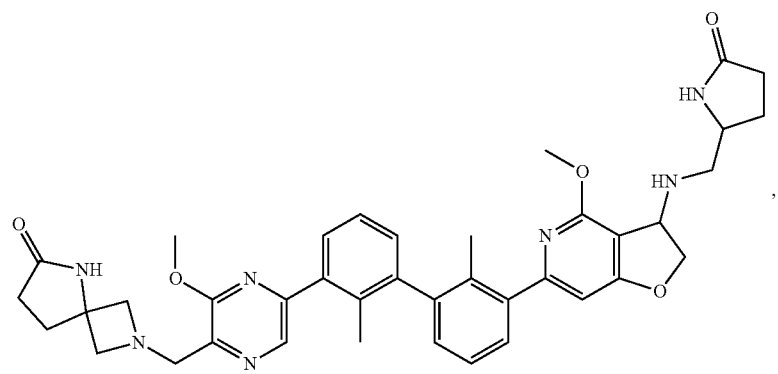
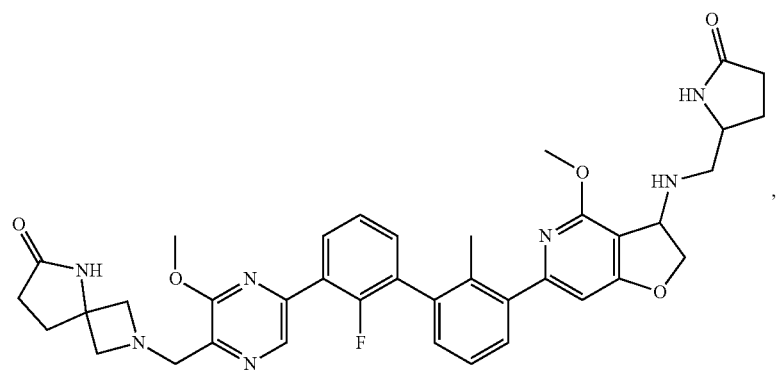

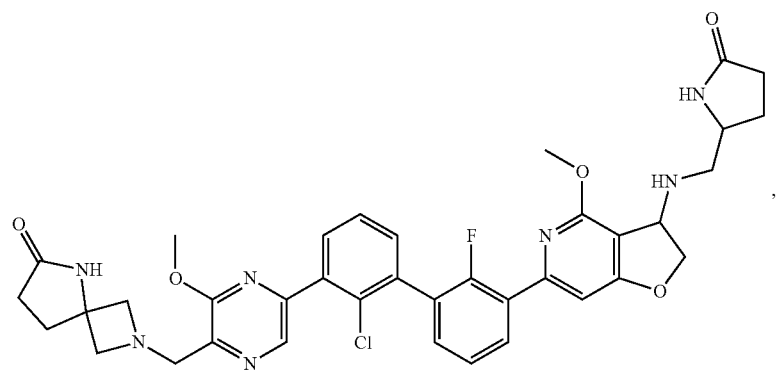
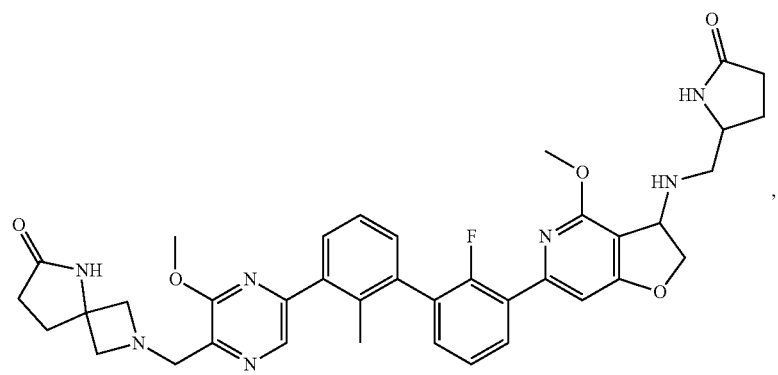
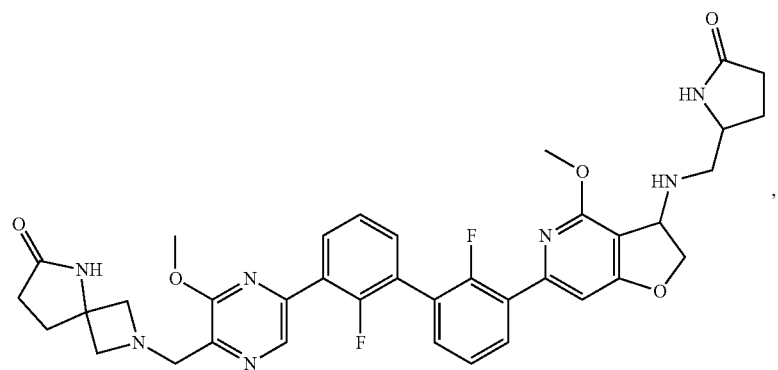
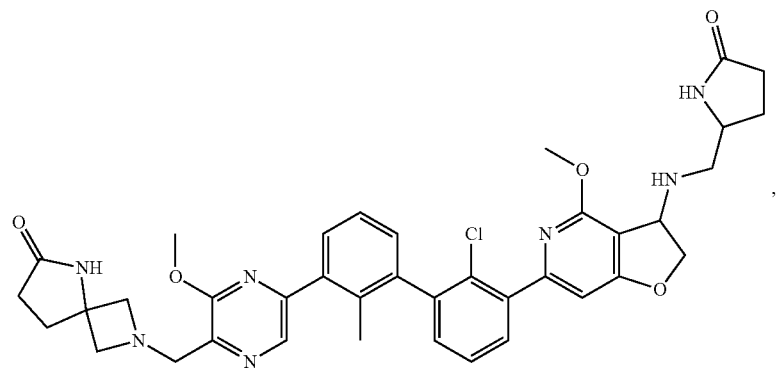

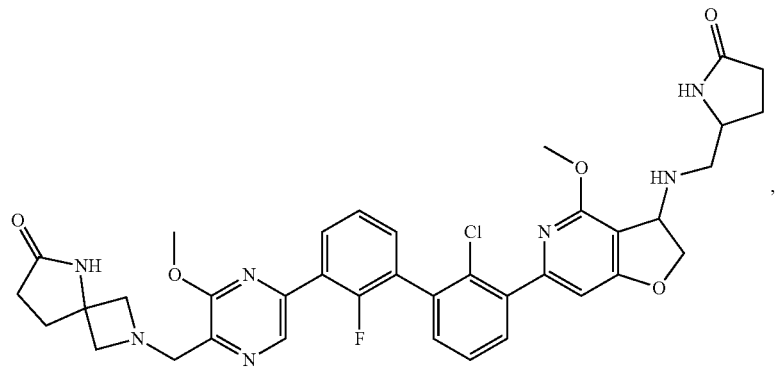 [SMILES: COc1nc(-c2cccc(-c3cccc(-c4cc5c(c(OC)n4)C(NCC4CCC(=O)N4)CC5)c3Cl)c2Cl)cnc1CN1CC2(CCC(=O)N2)C1]
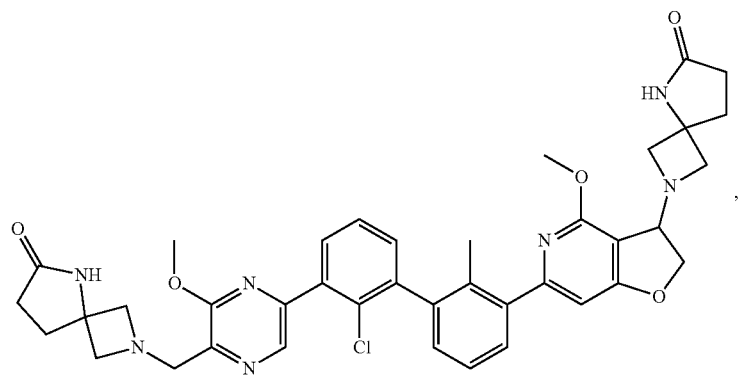
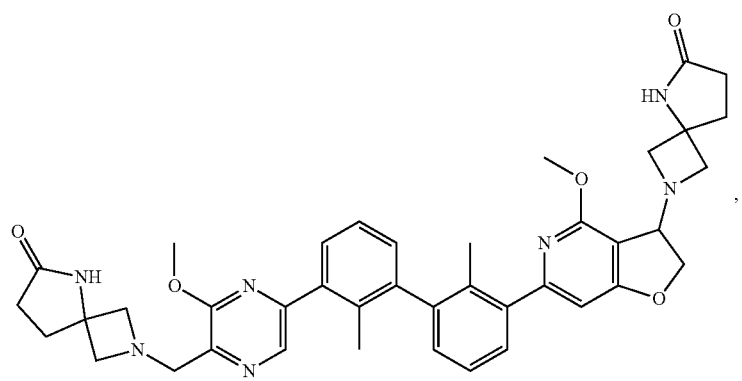
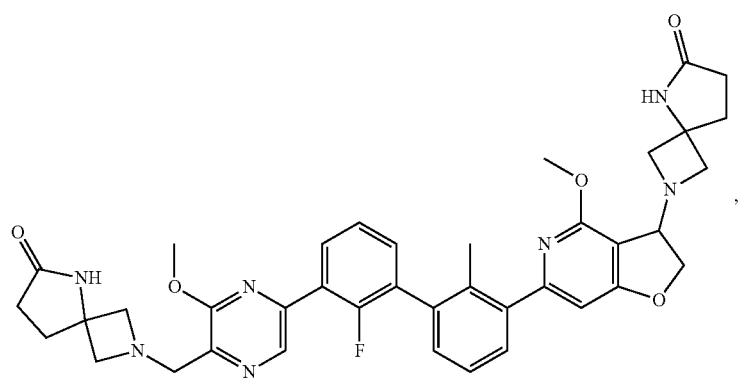

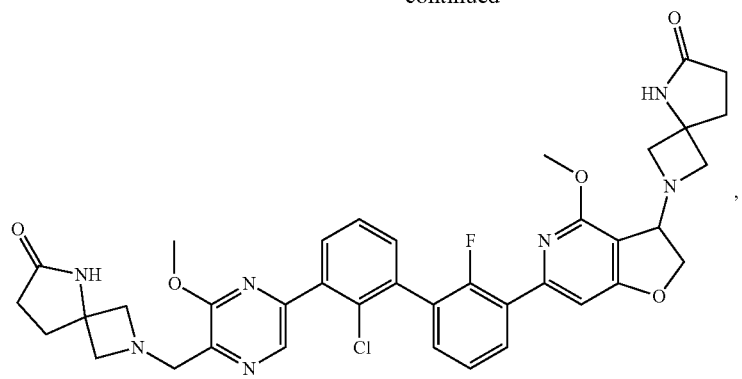
,
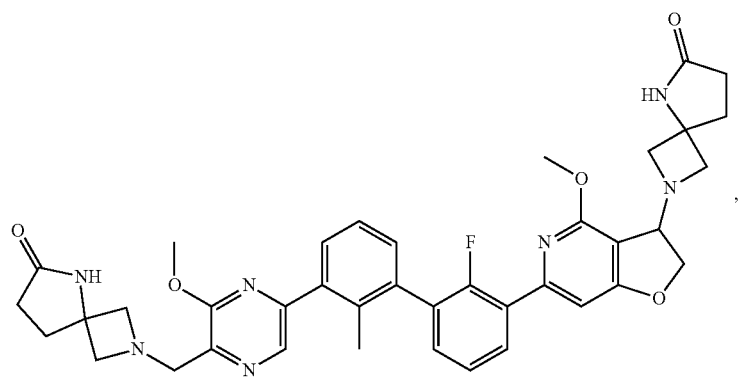
,
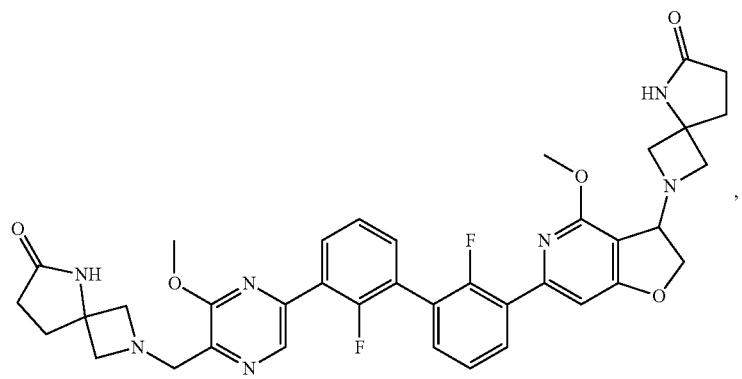
,
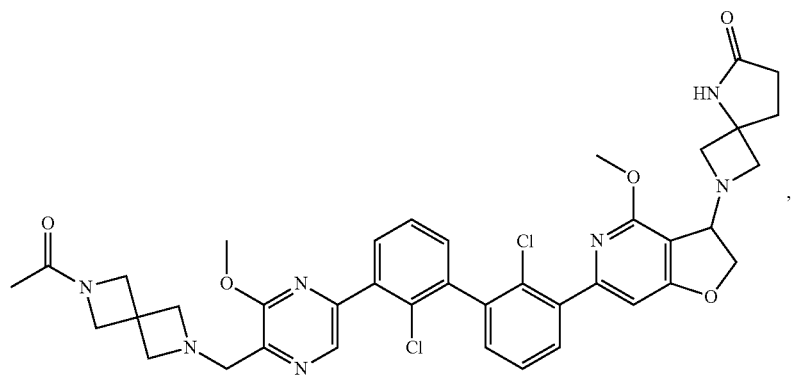
,

-continued
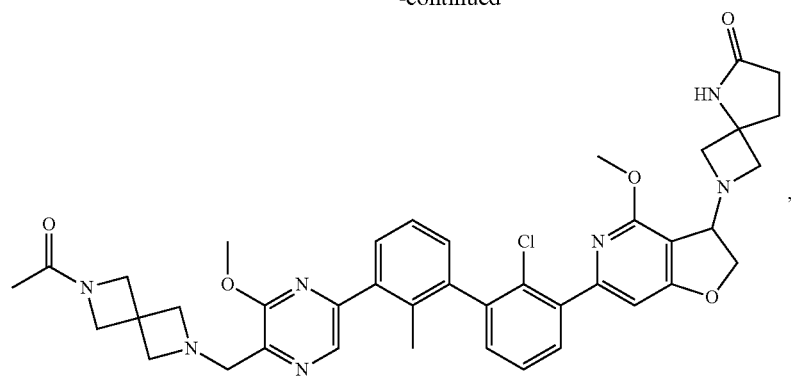
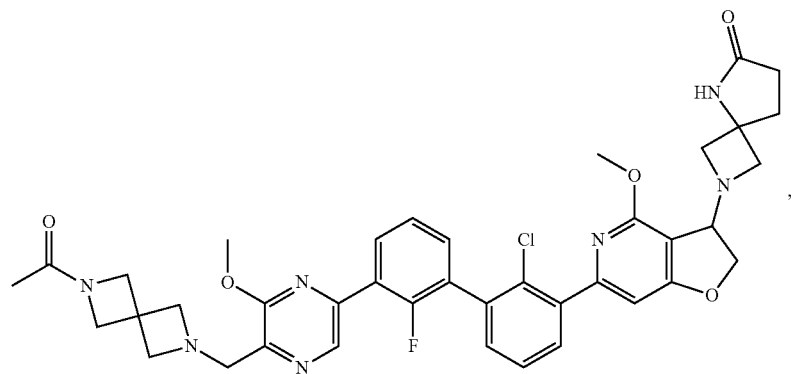
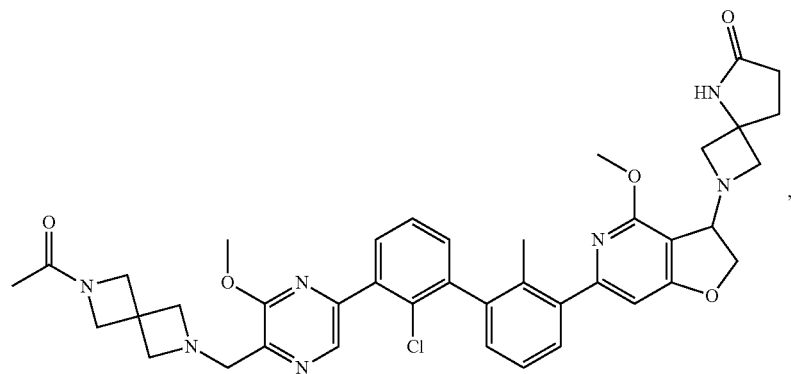
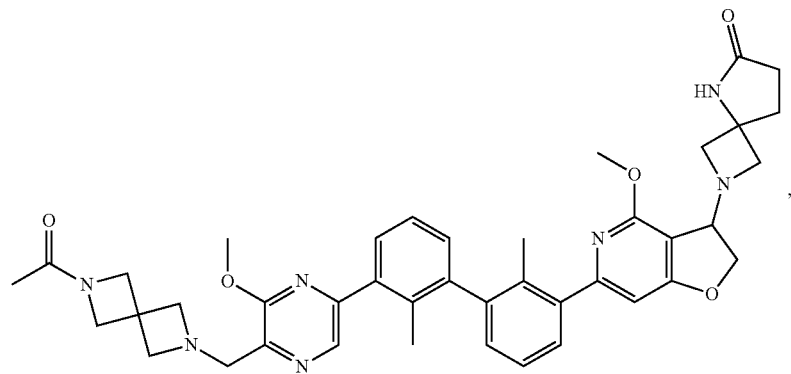

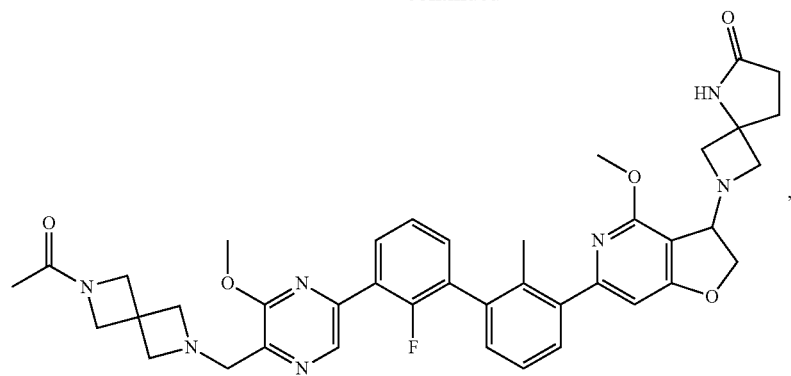,
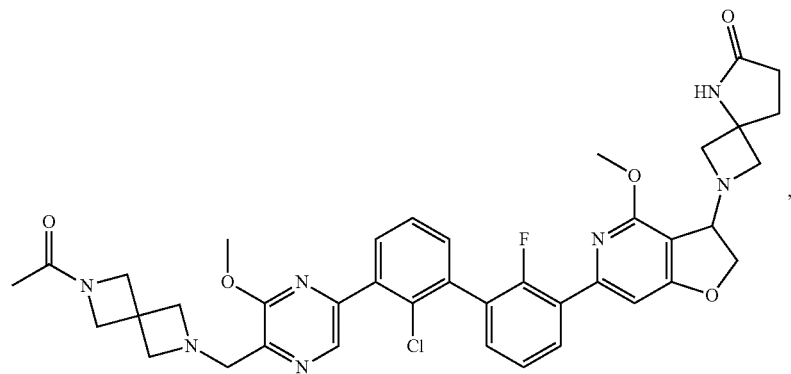,
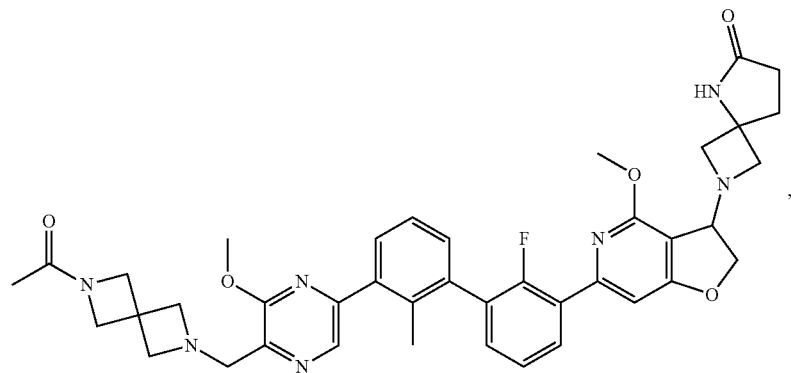,
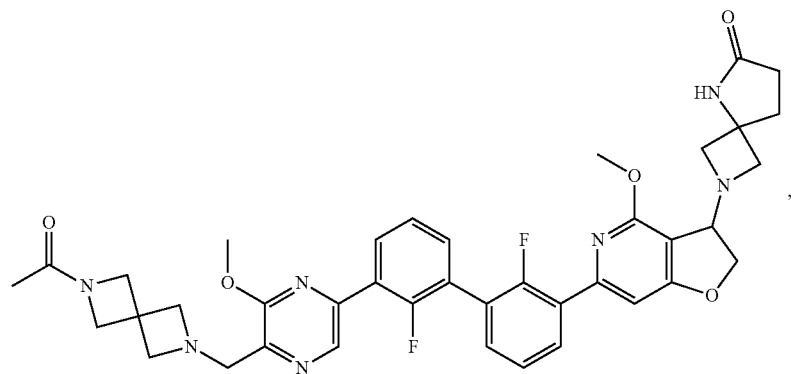,

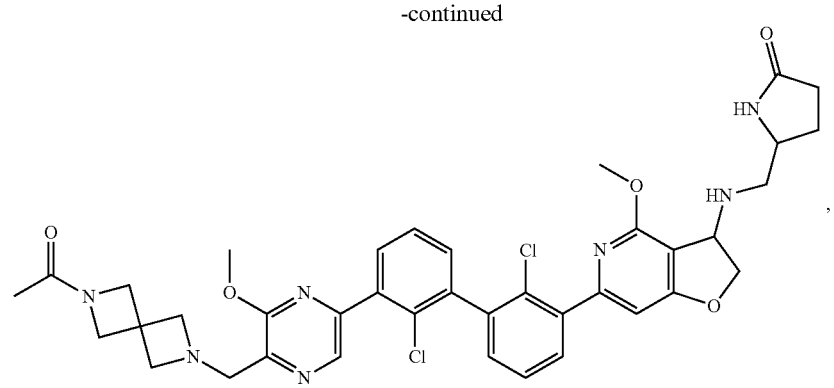
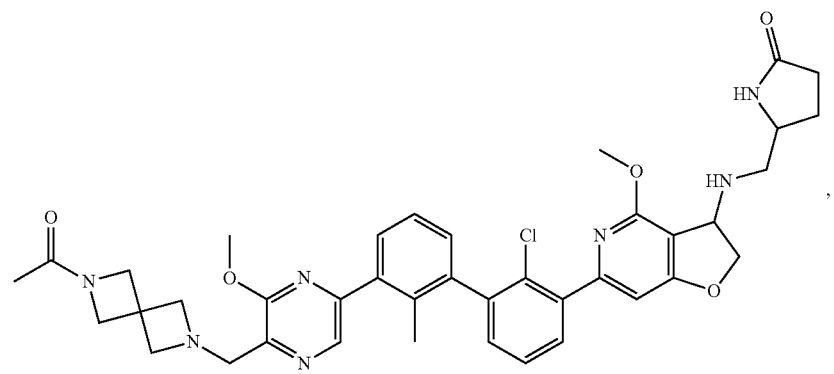
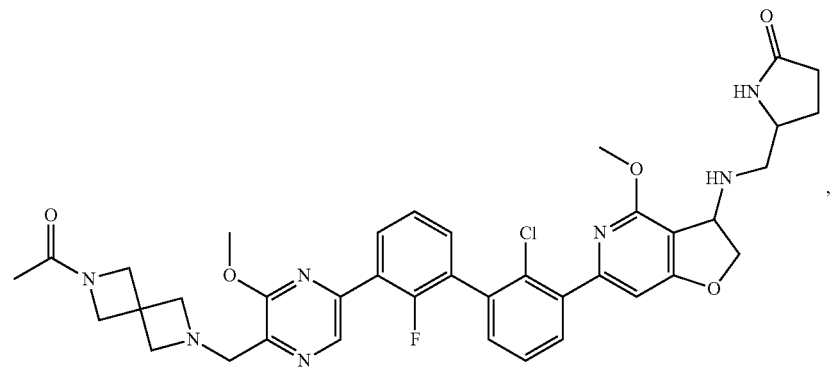
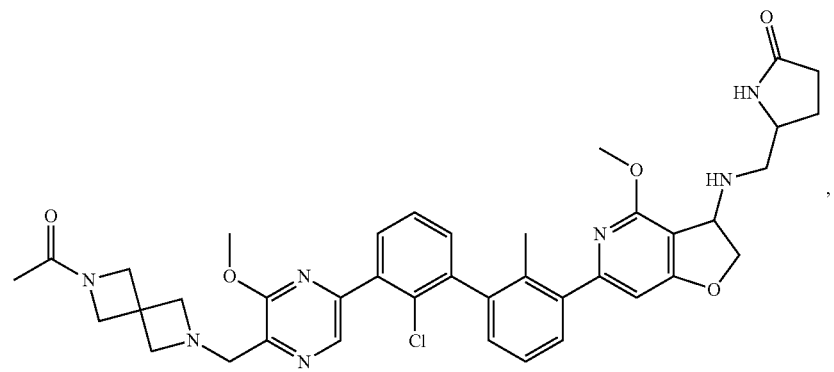

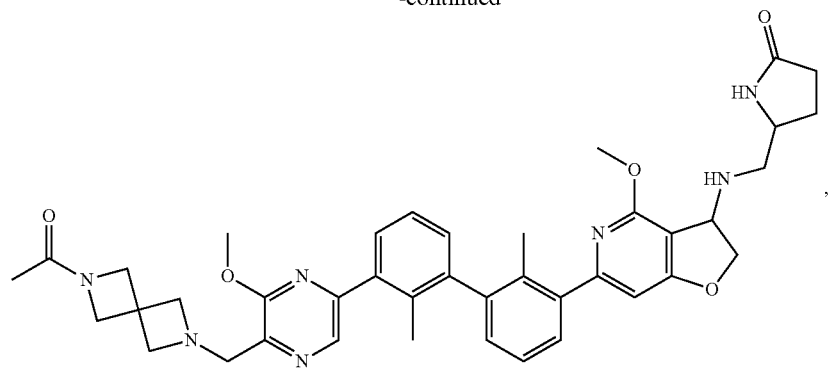
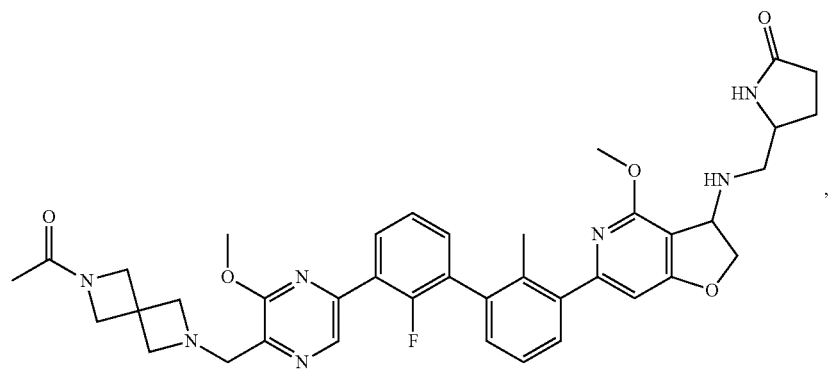
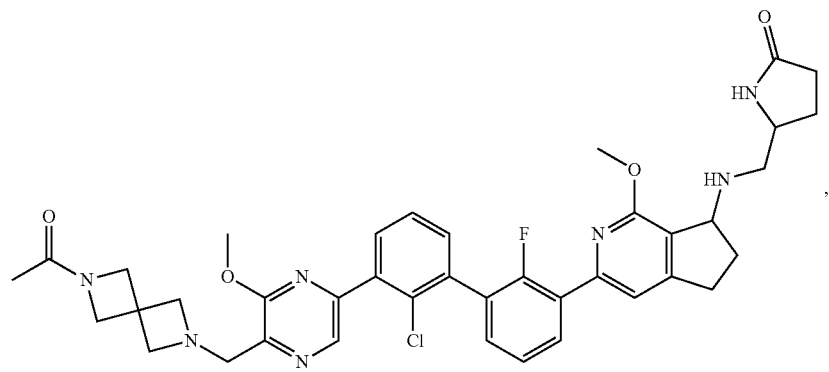
and

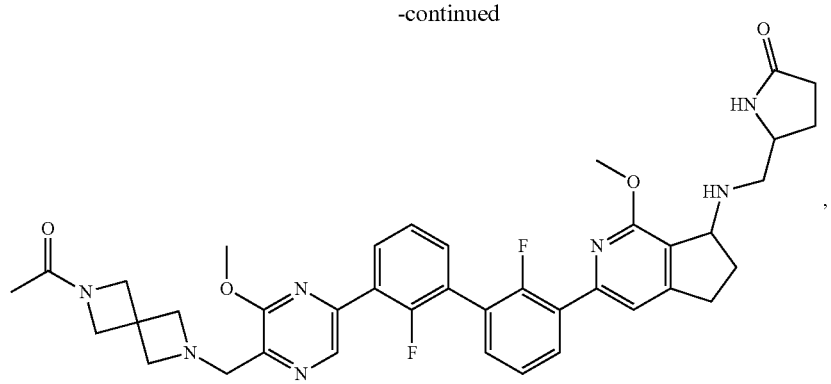
or a pharmaceutically acceptable salt of any of the foregoing.
22. The compound of claim 1 selected from the group consisting of:
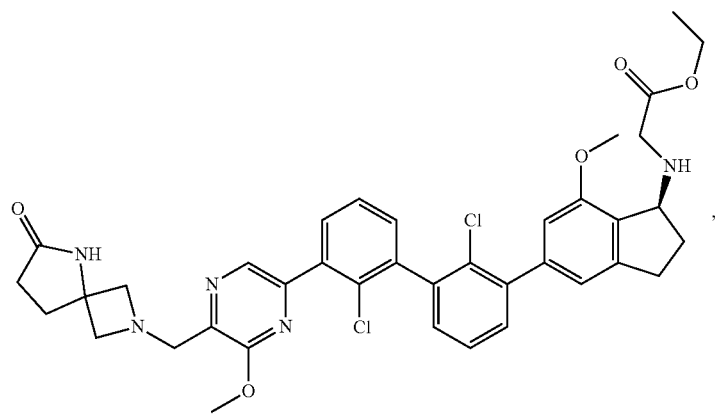
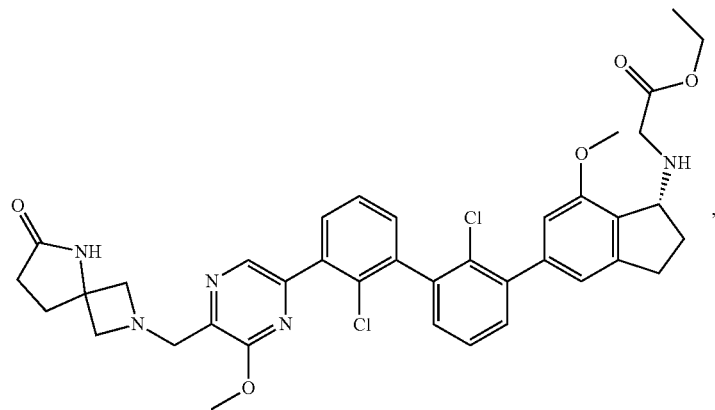
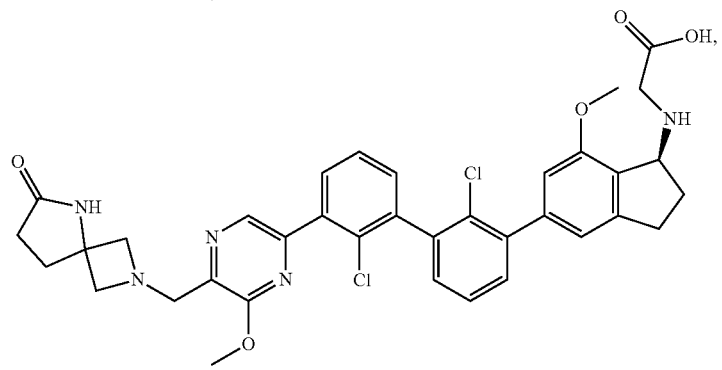

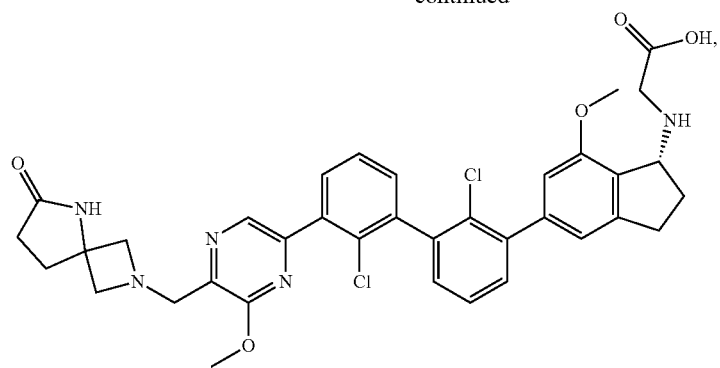
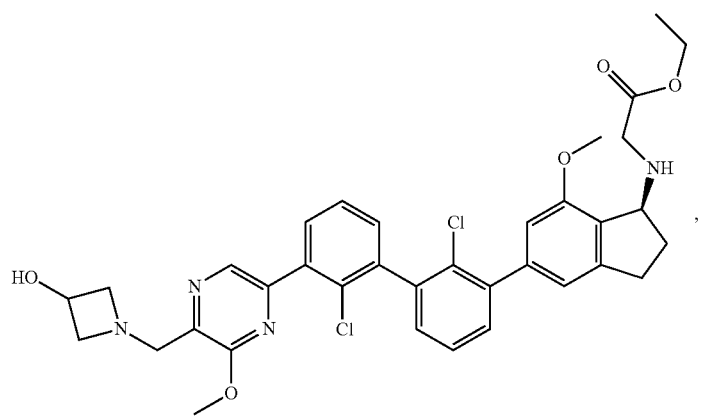
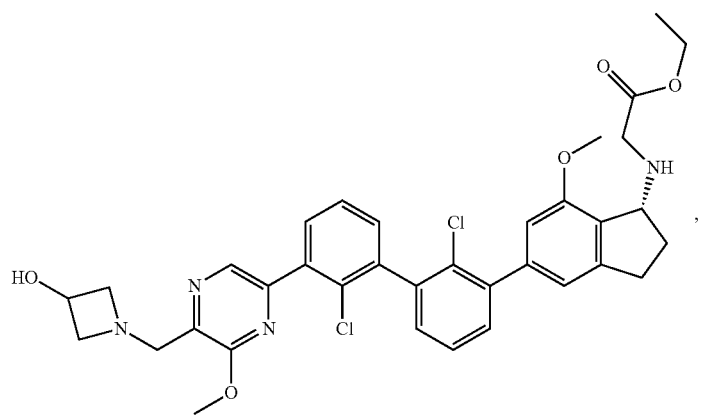
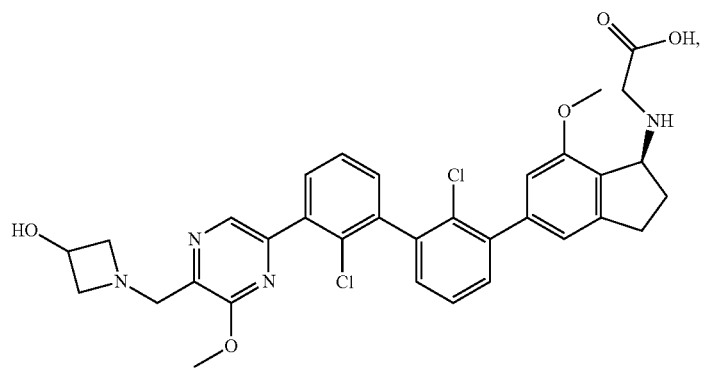

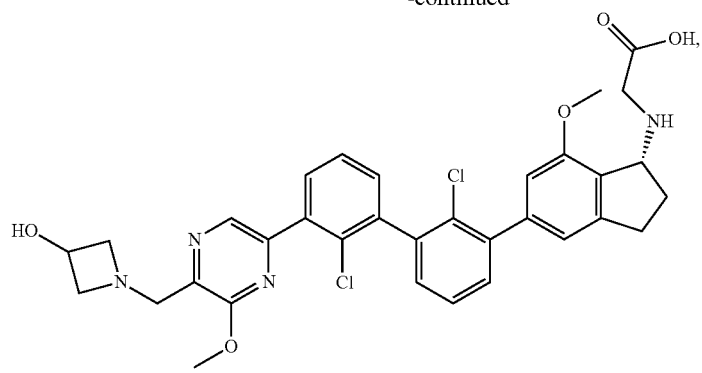
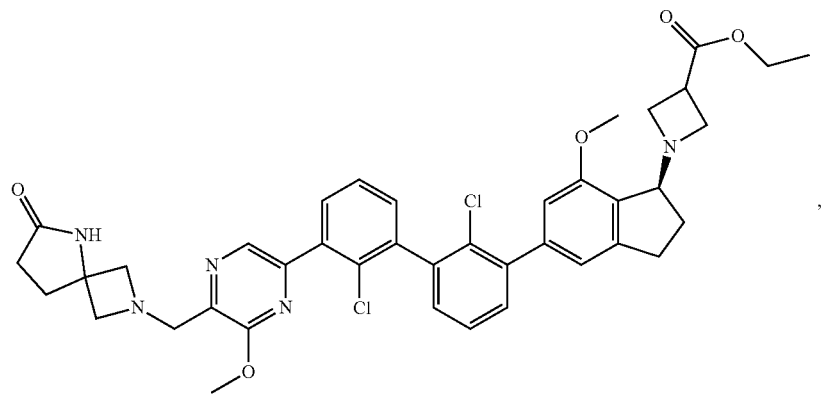
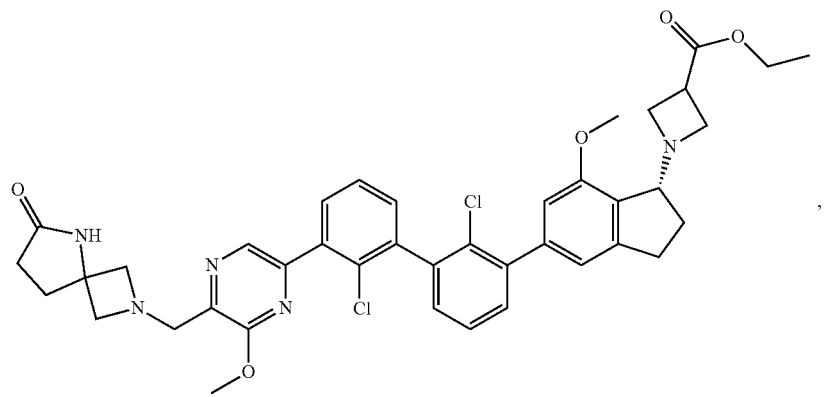
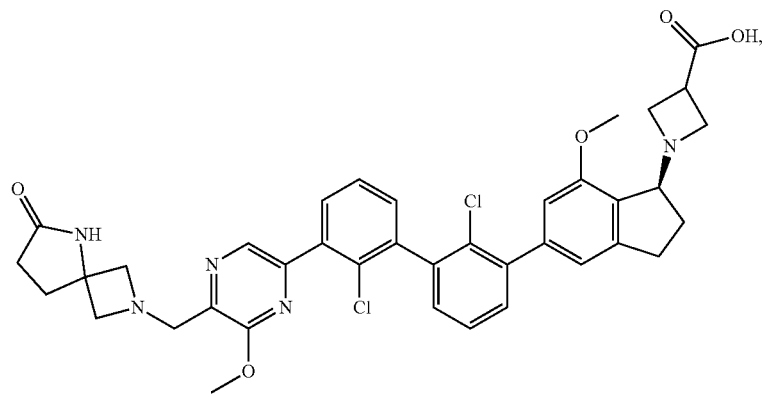

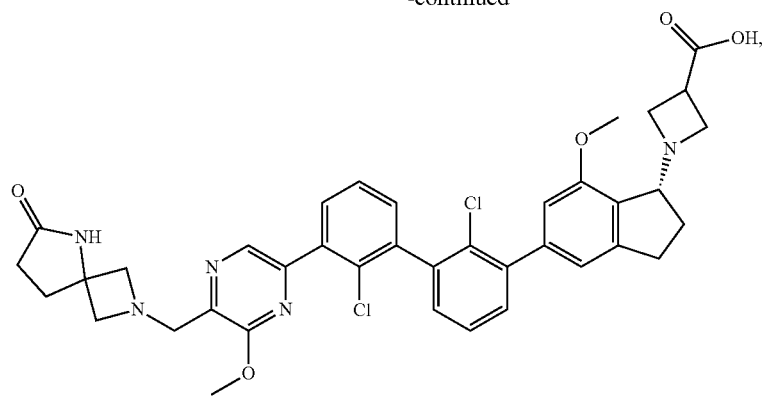
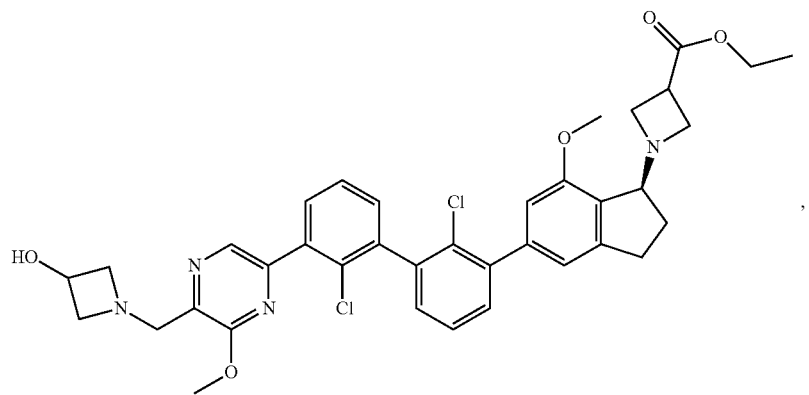
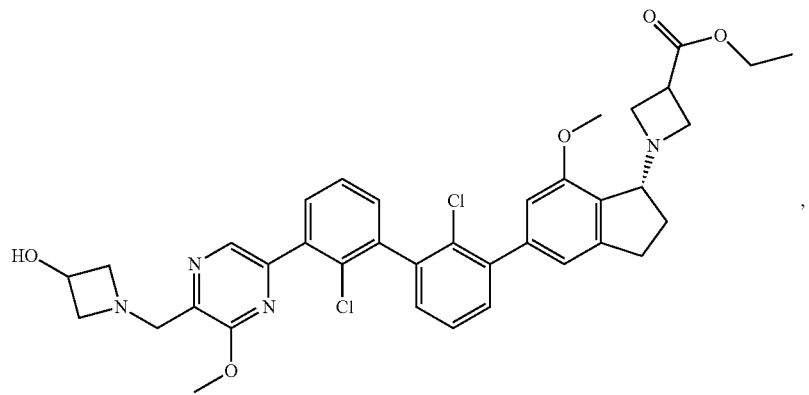
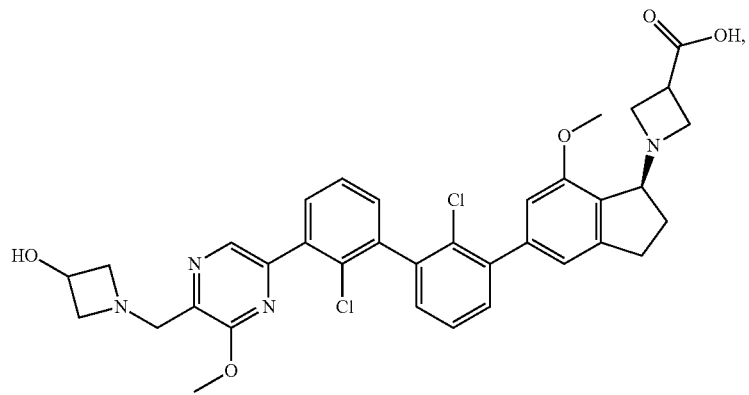

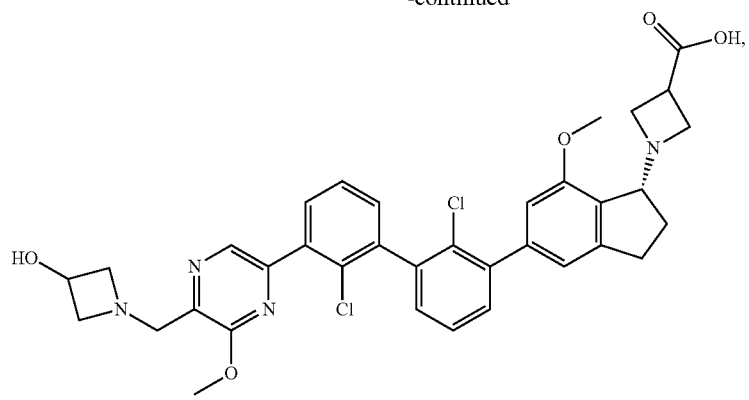
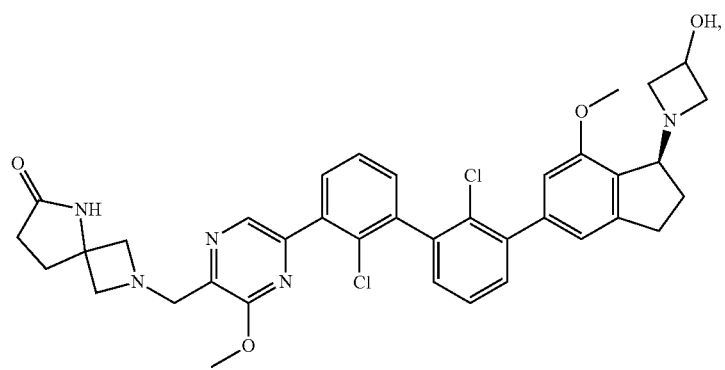
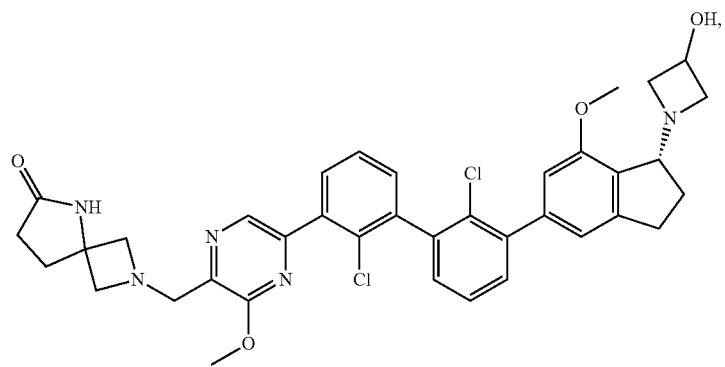
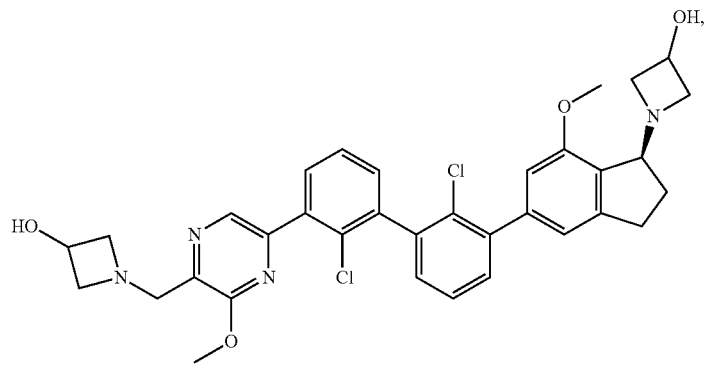

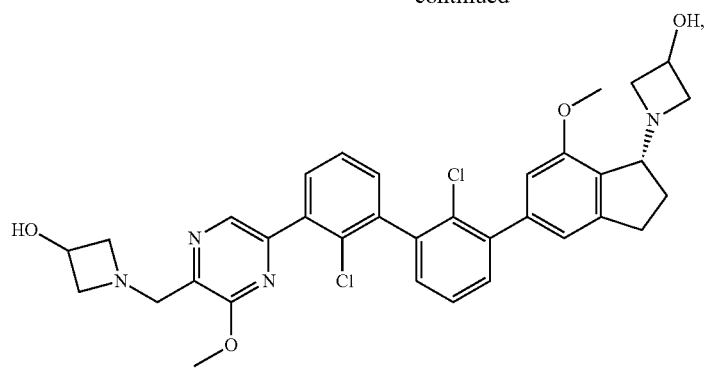
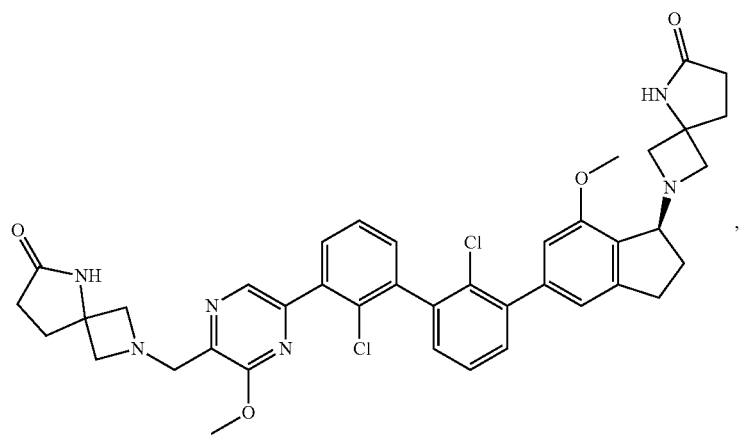
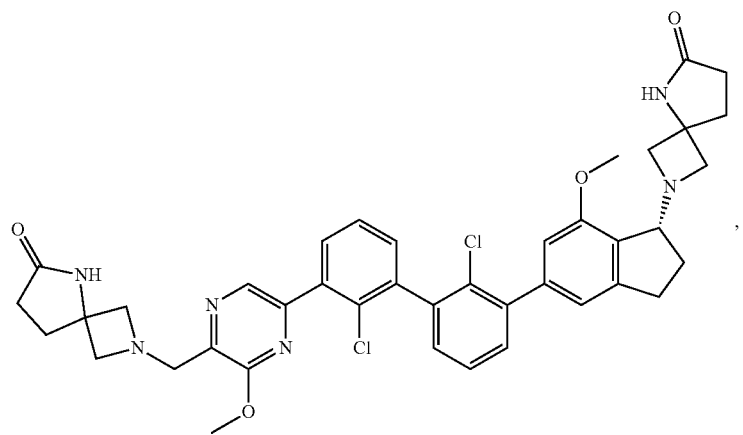
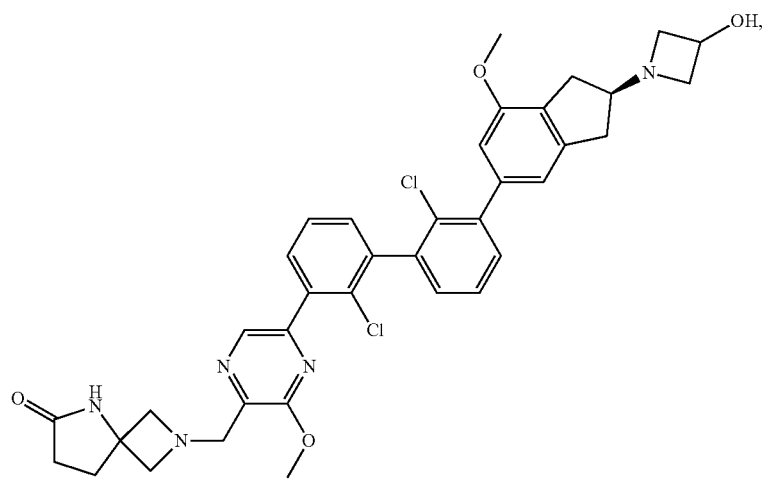

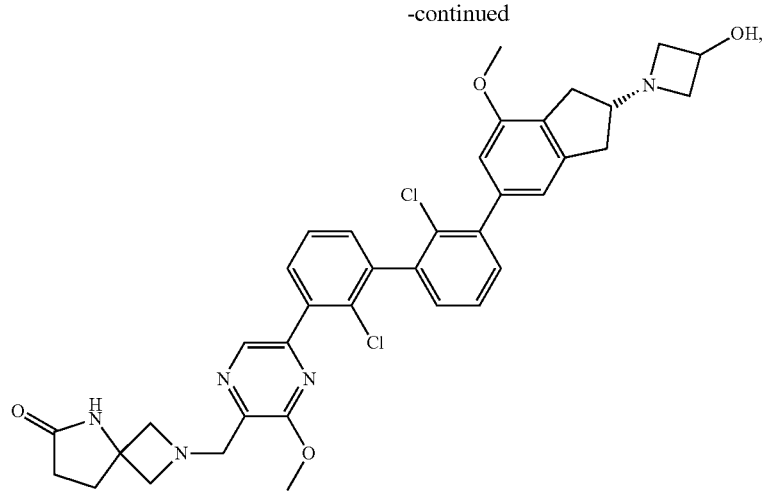
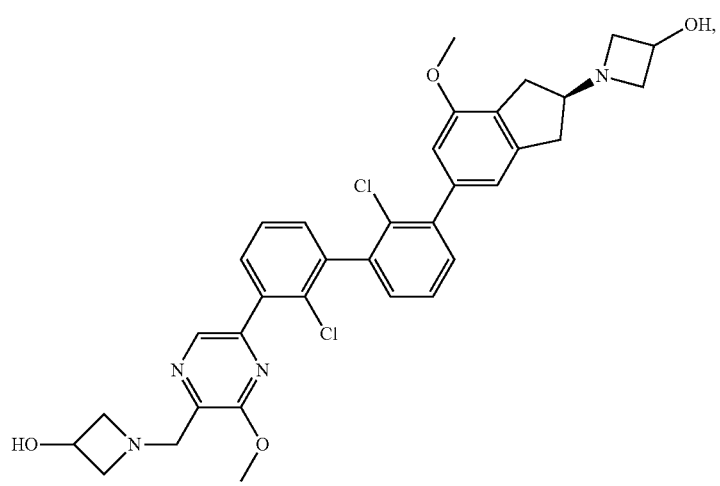
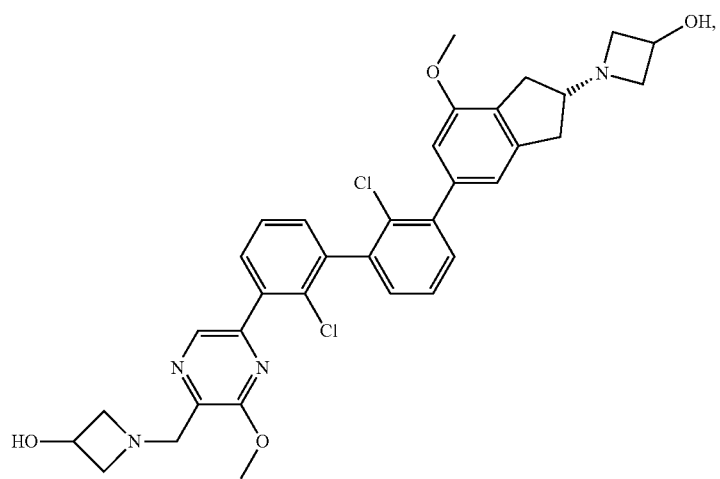

-continued
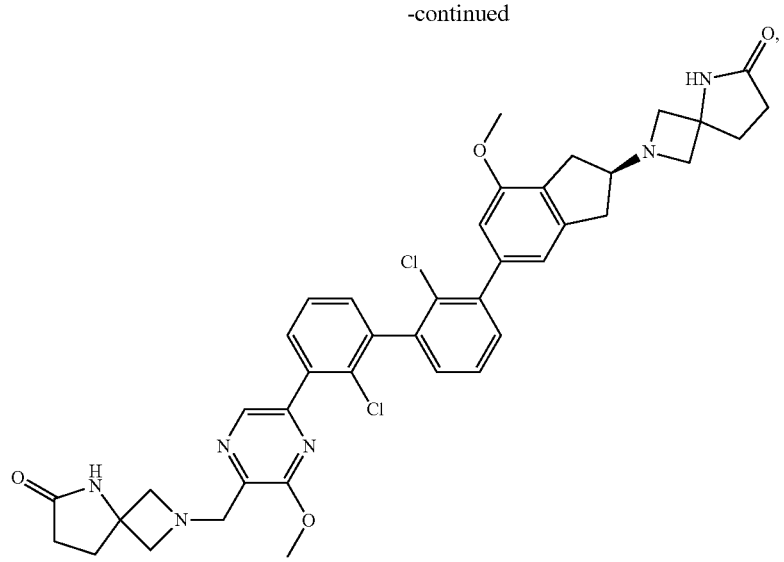
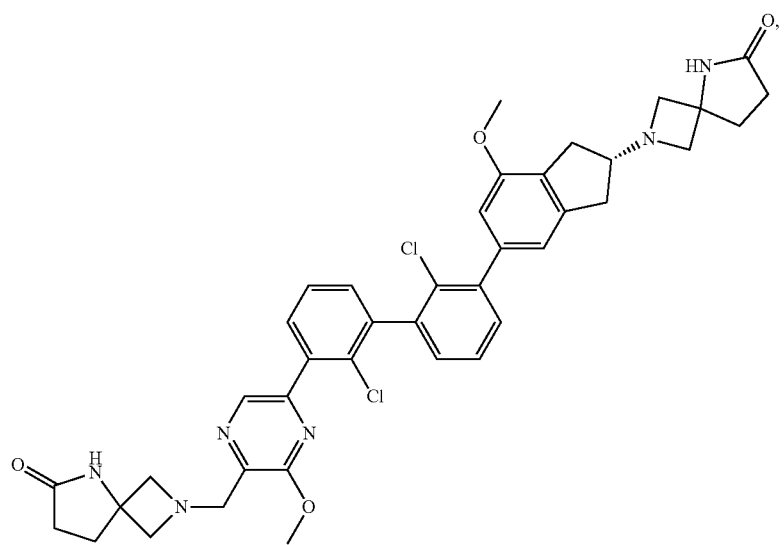
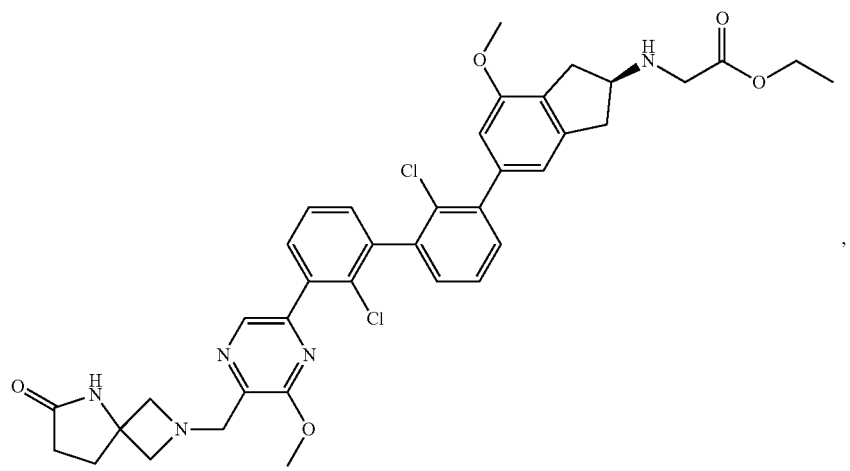

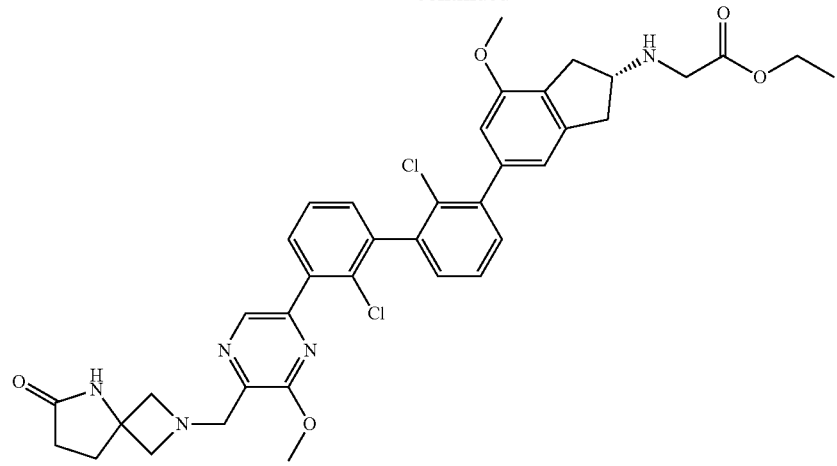
,
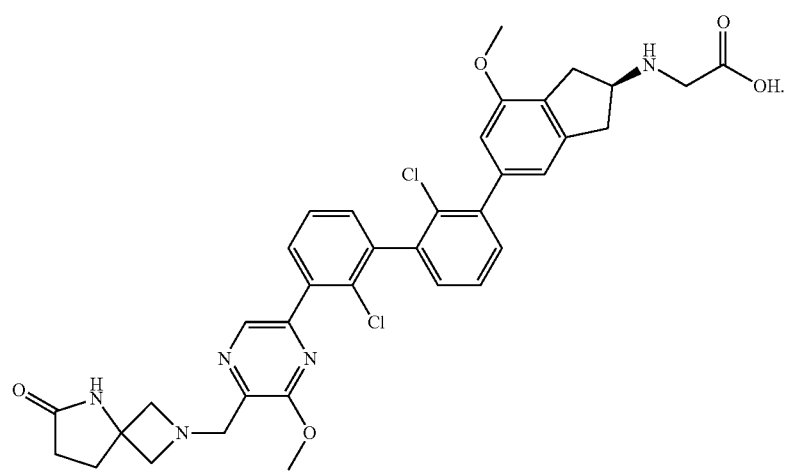
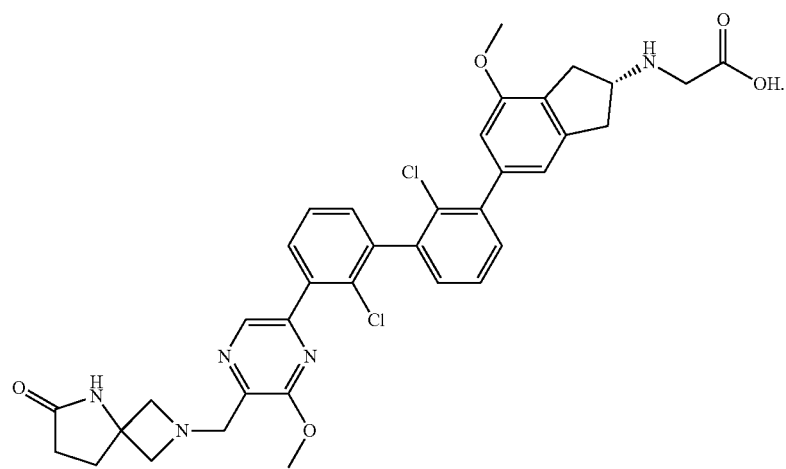

-continued
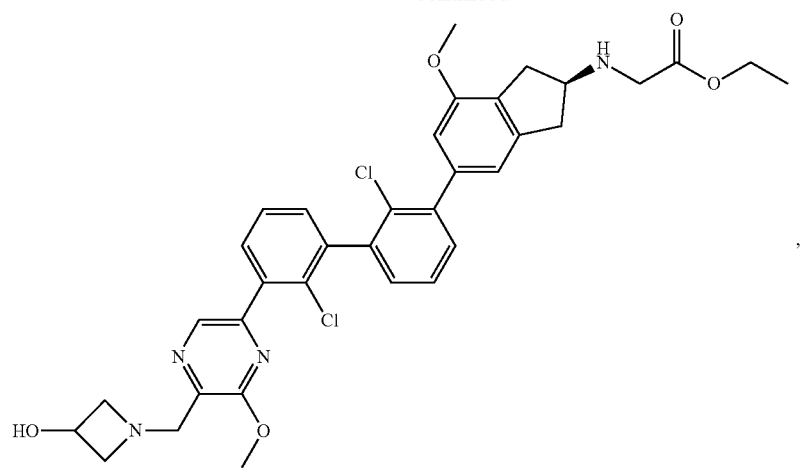
,
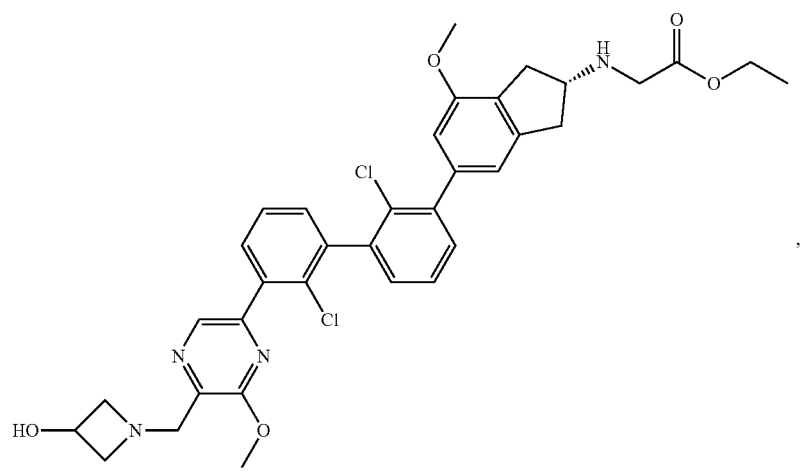
,
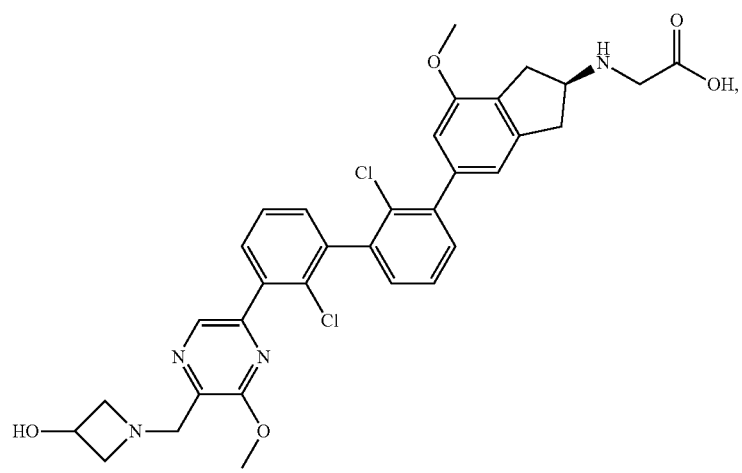

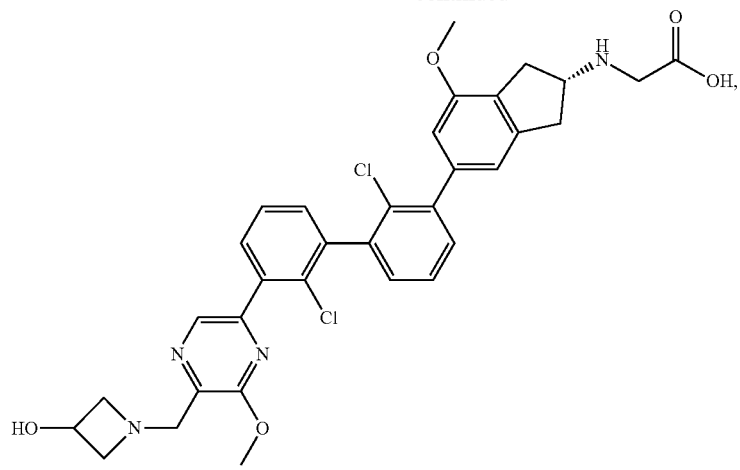
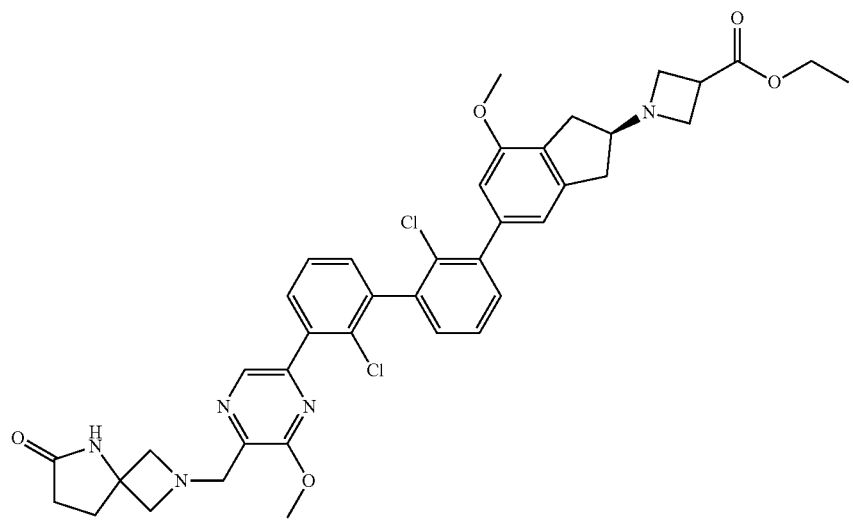
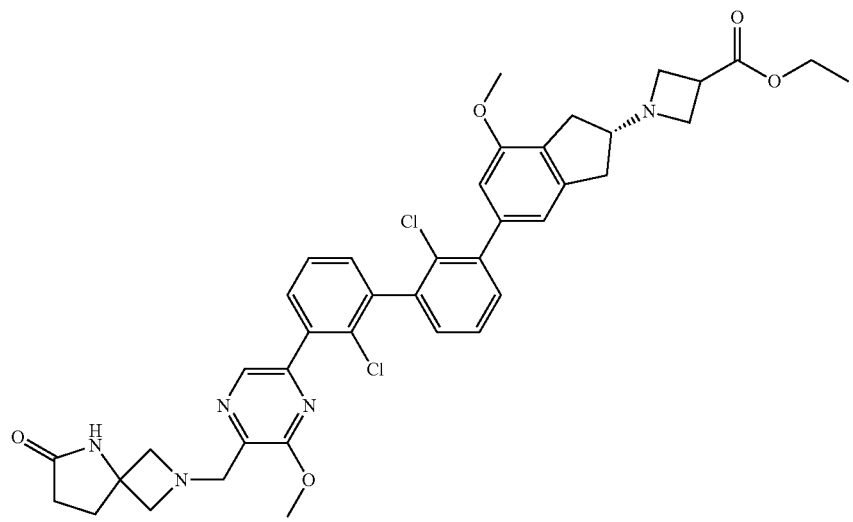

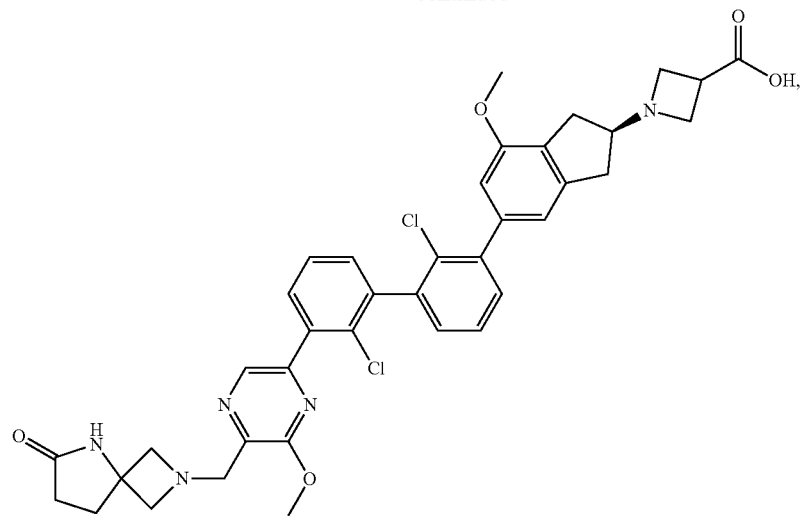
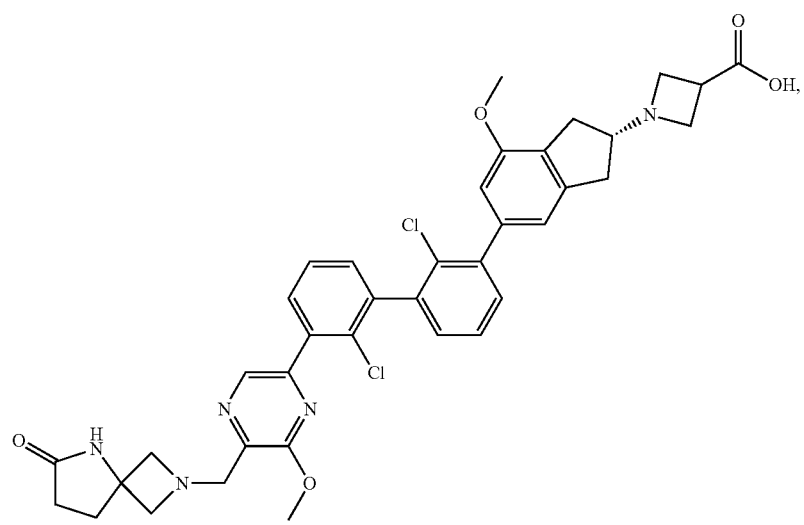
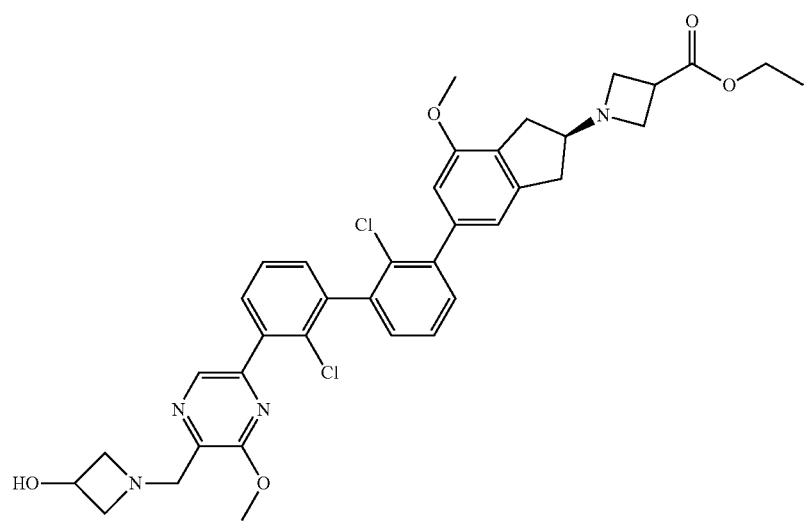

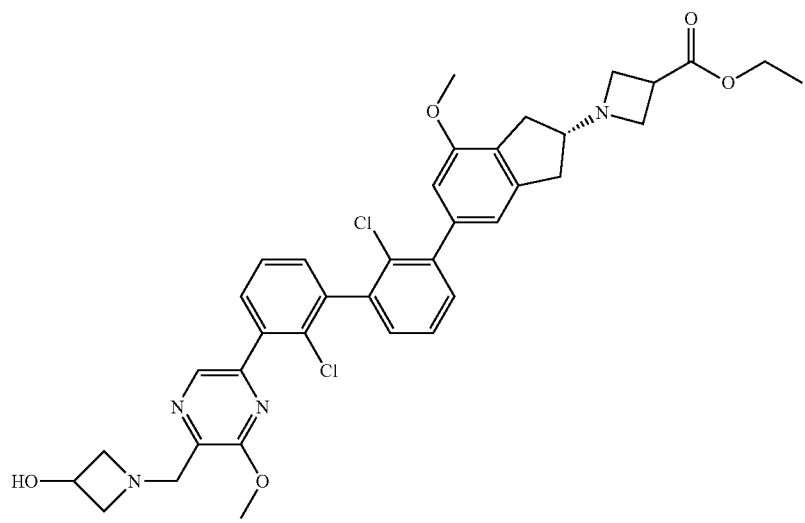
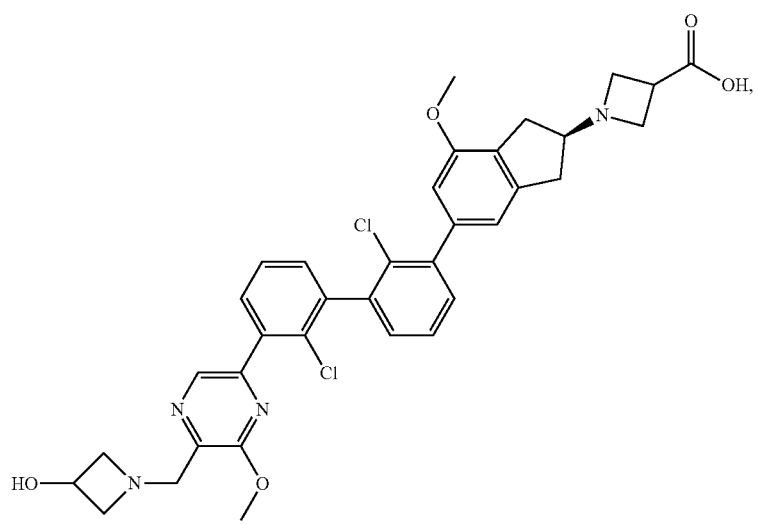
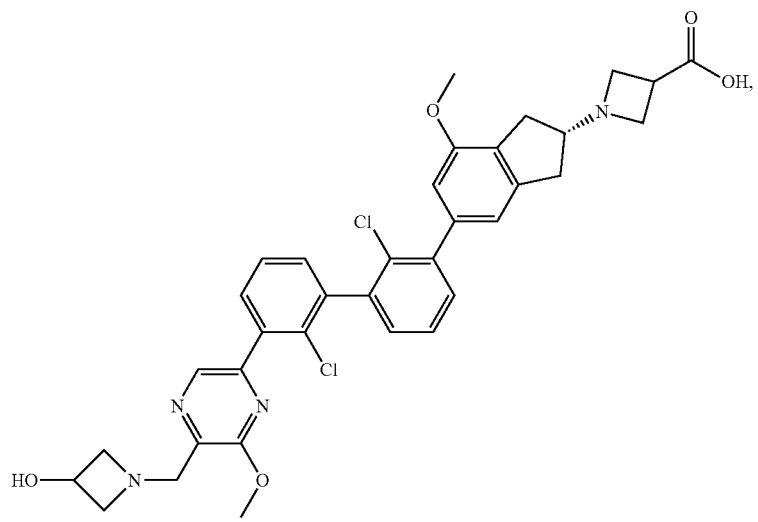

-continued
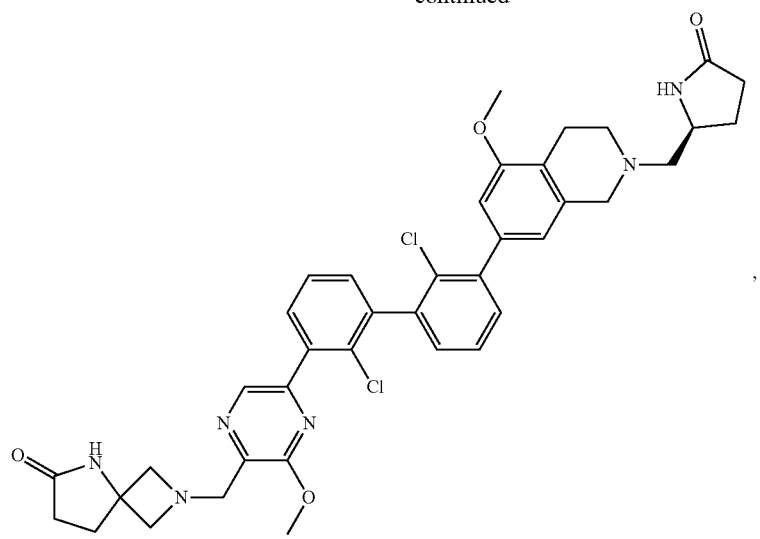
,
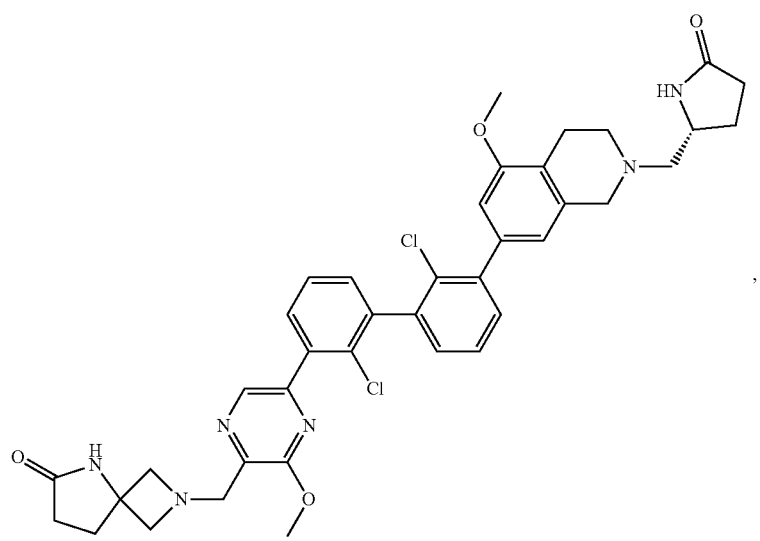
,
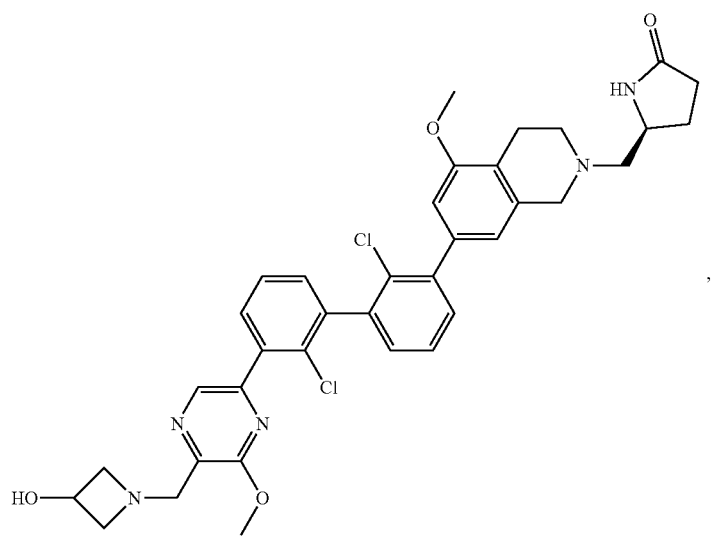
,

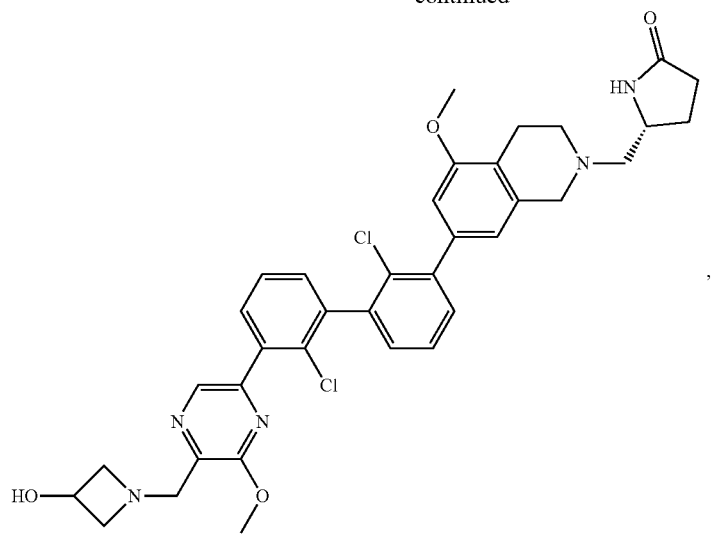
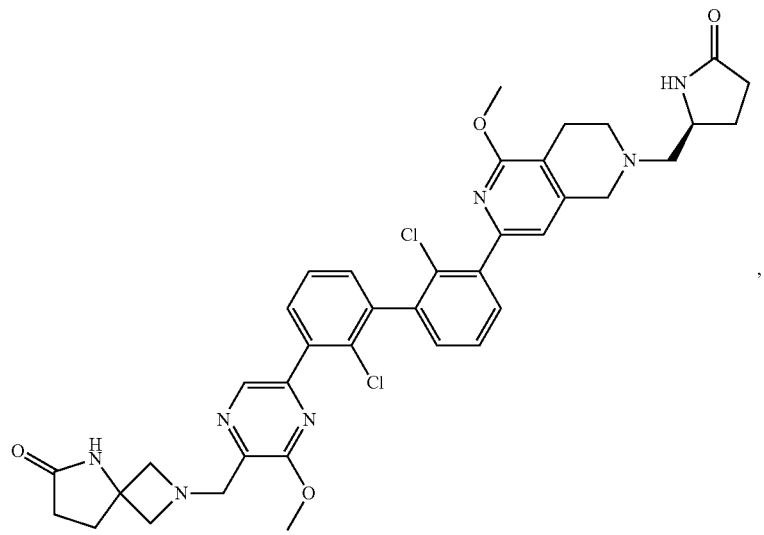
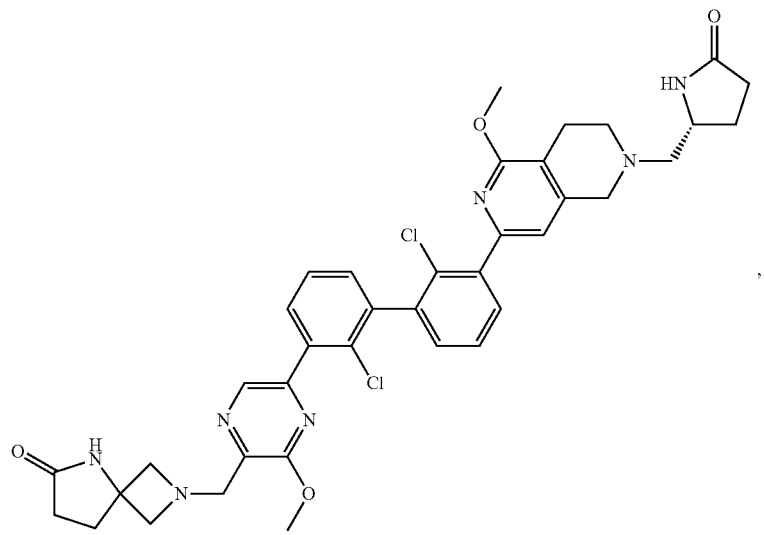

-continued
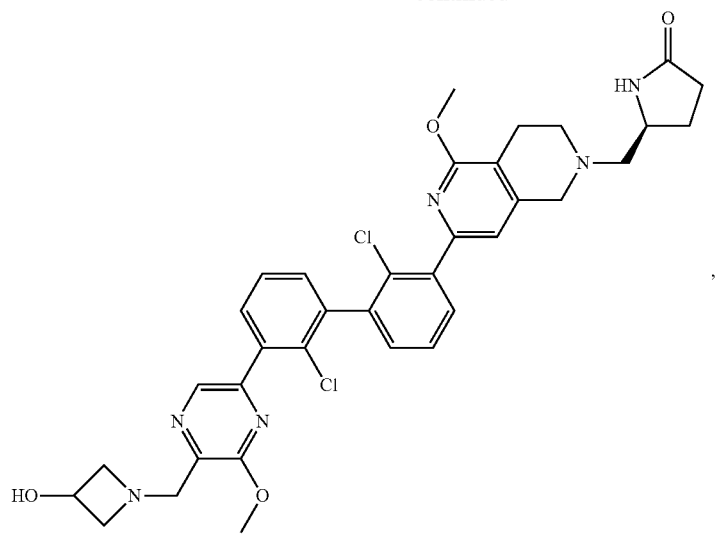
,
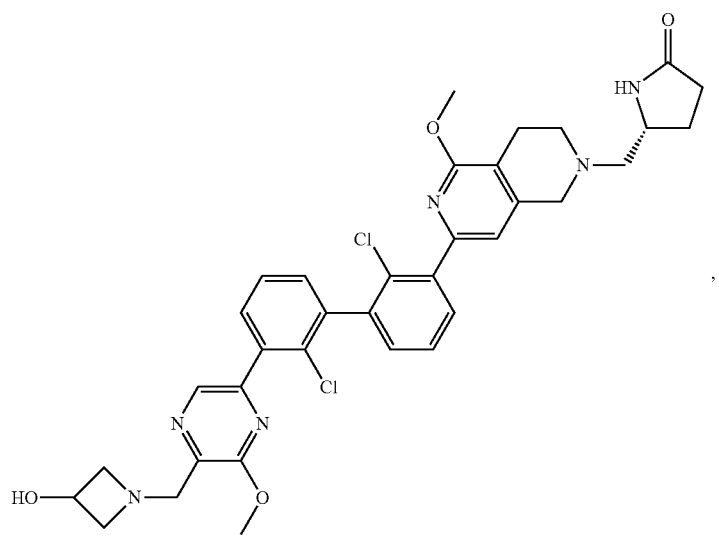
,
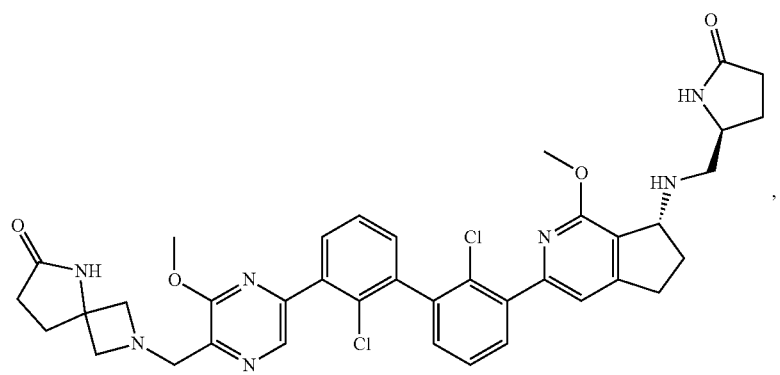
,

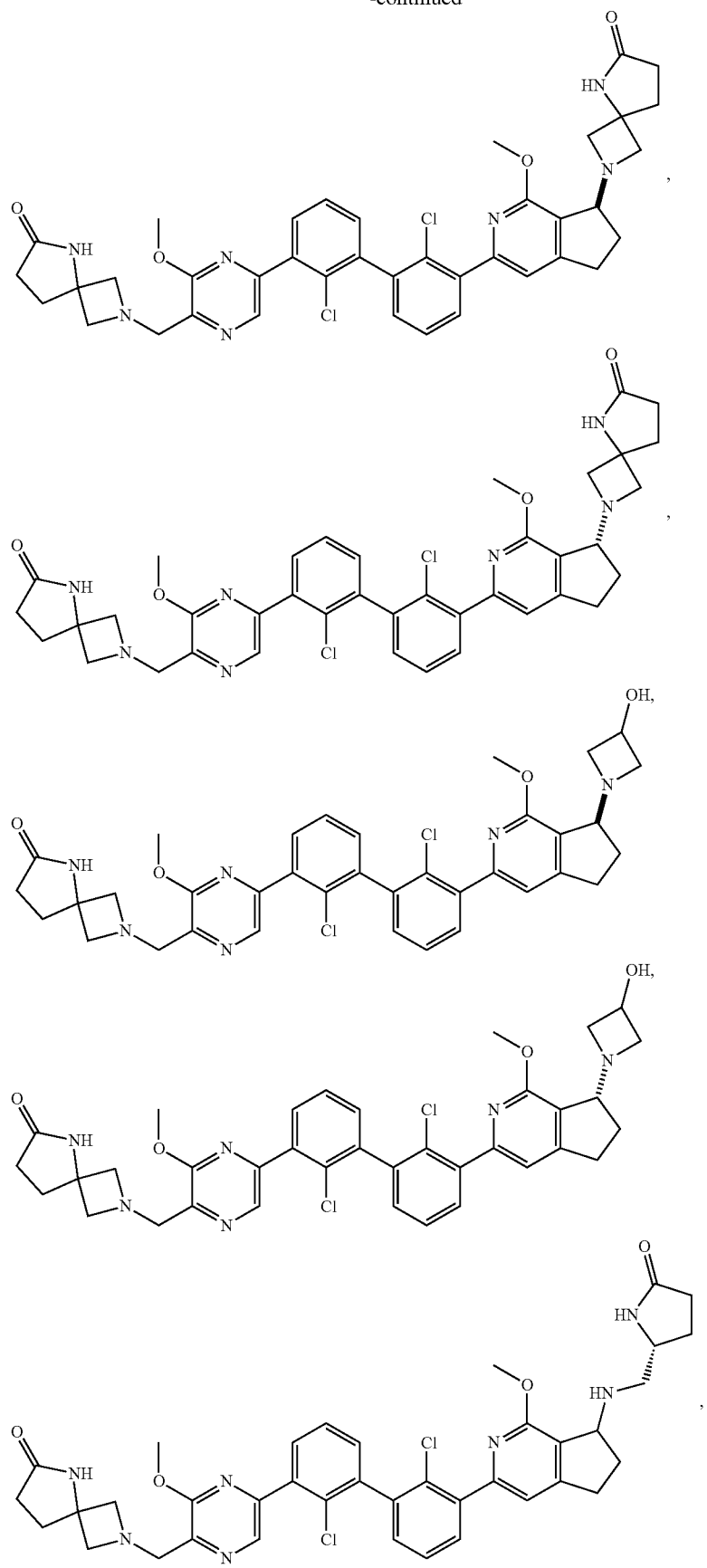

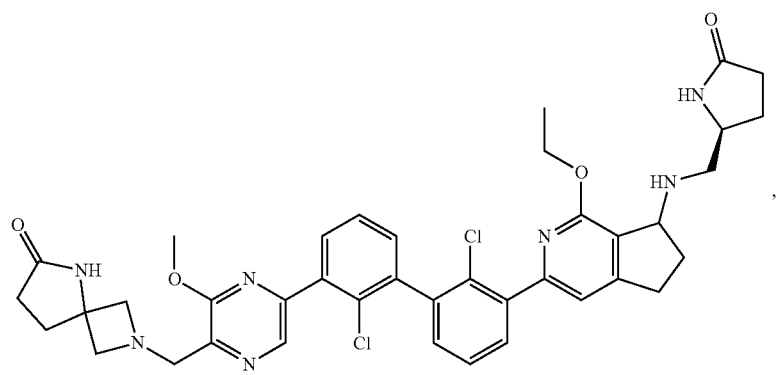
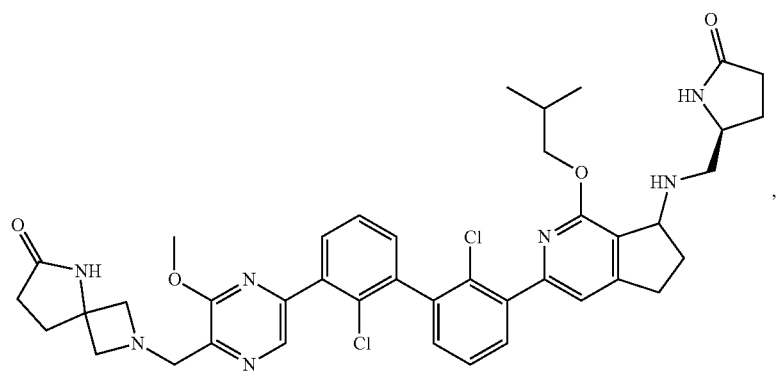
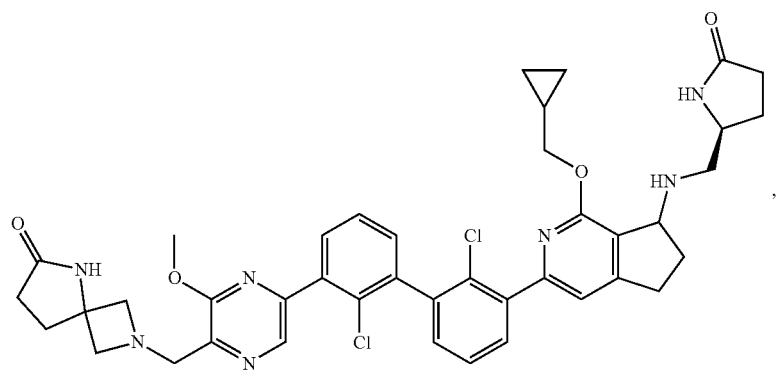
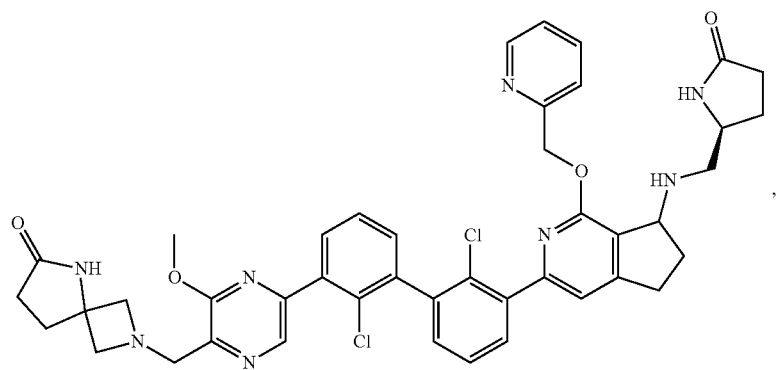

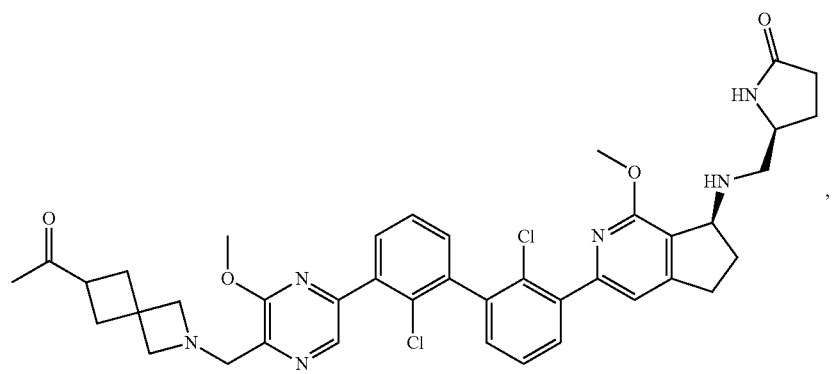
,
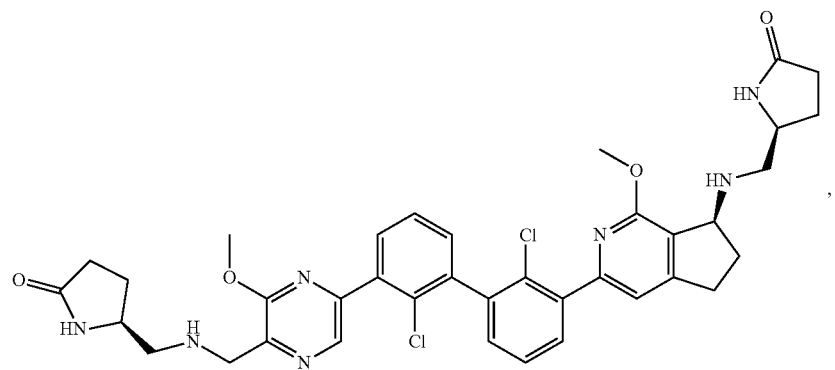
,
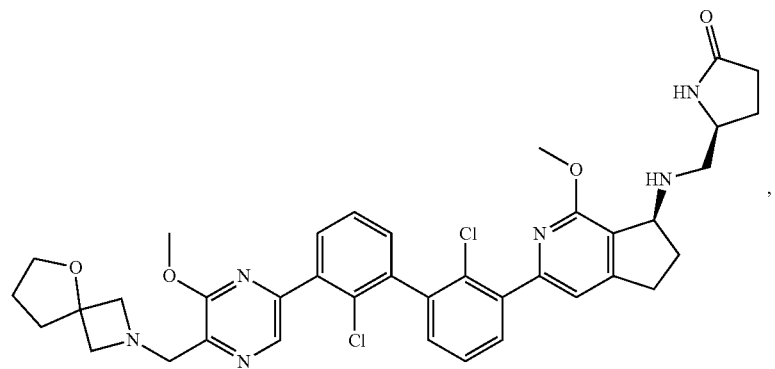
,
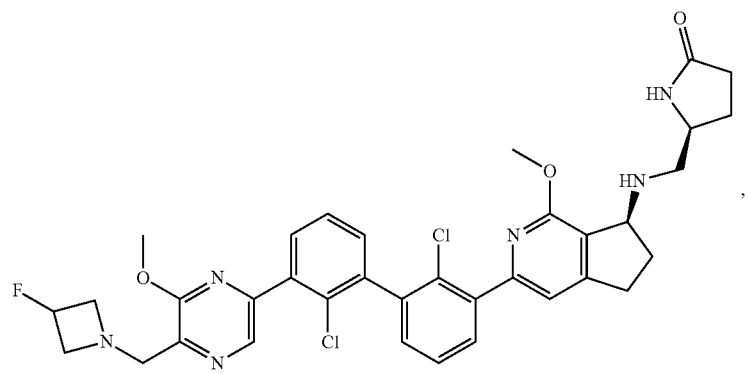
,

-continued
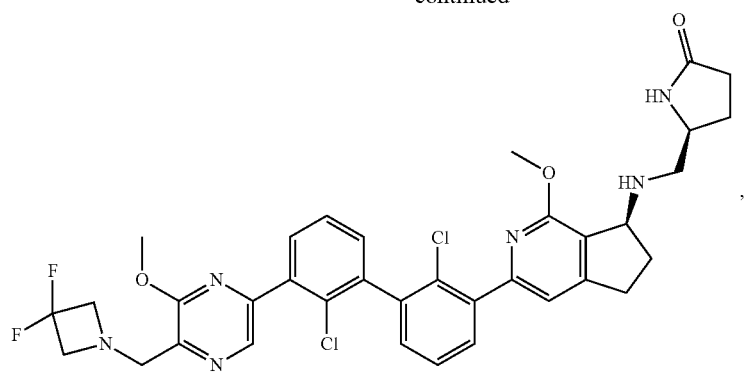
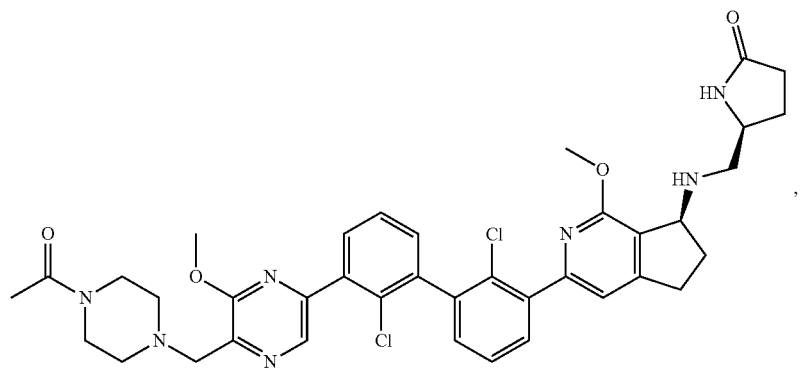
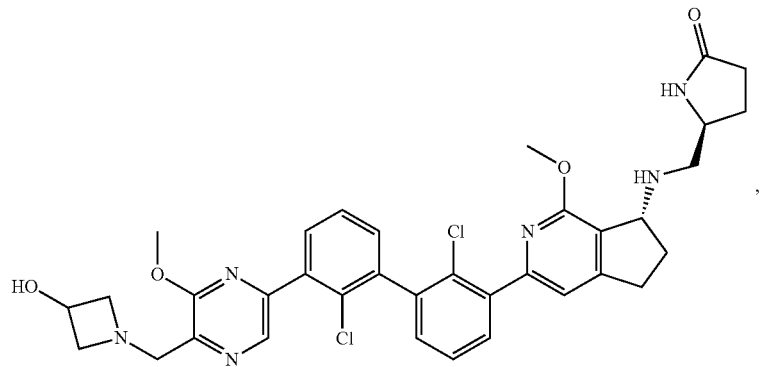
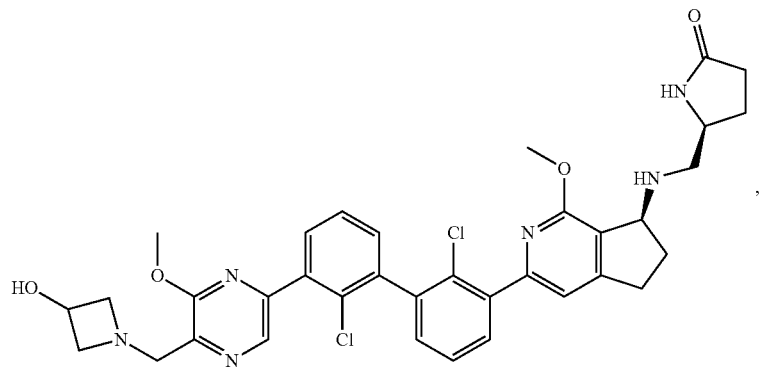

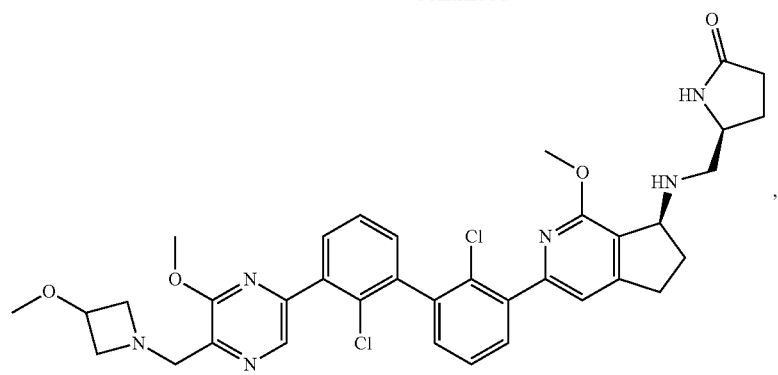,
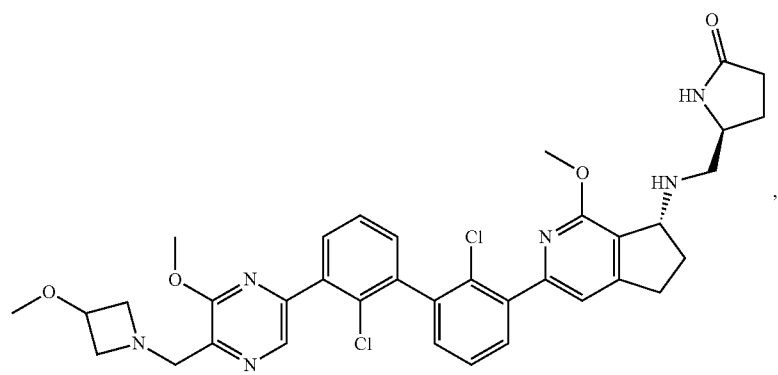,
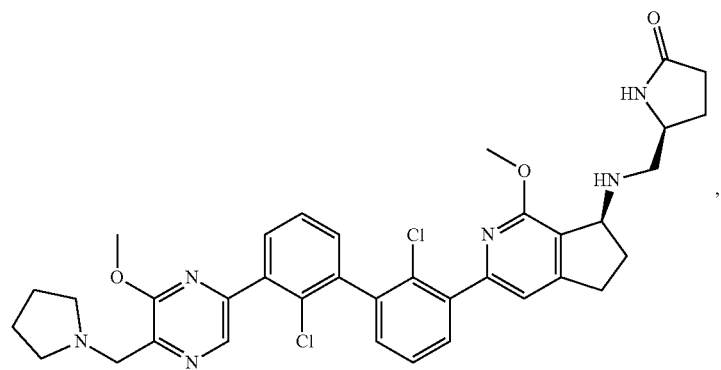,
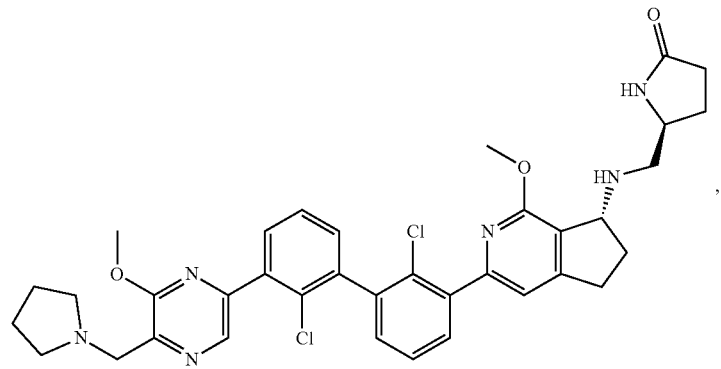,

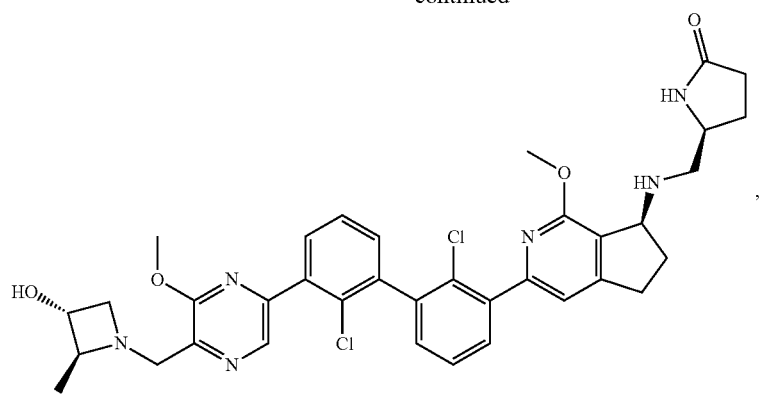
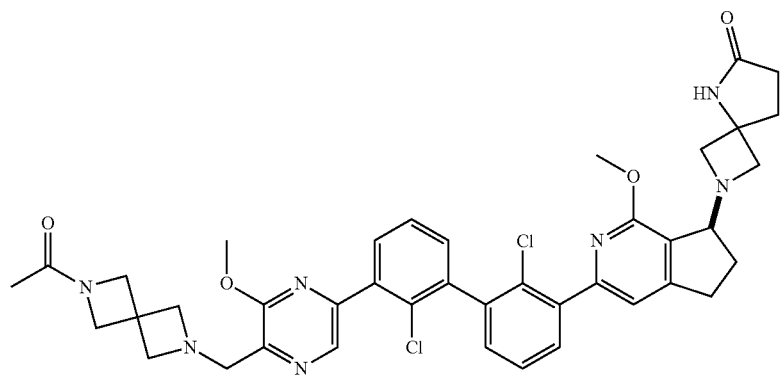
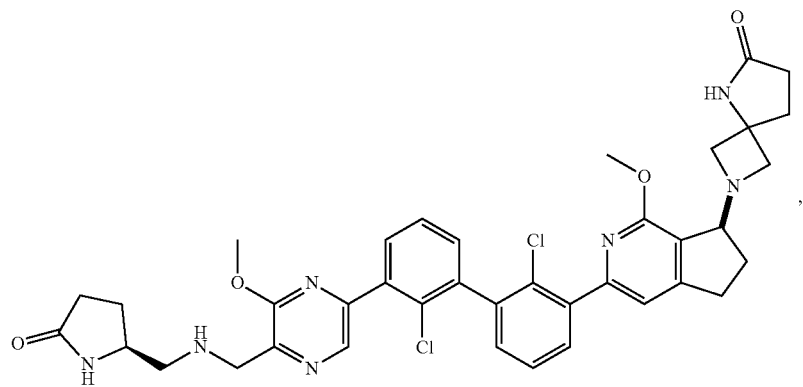
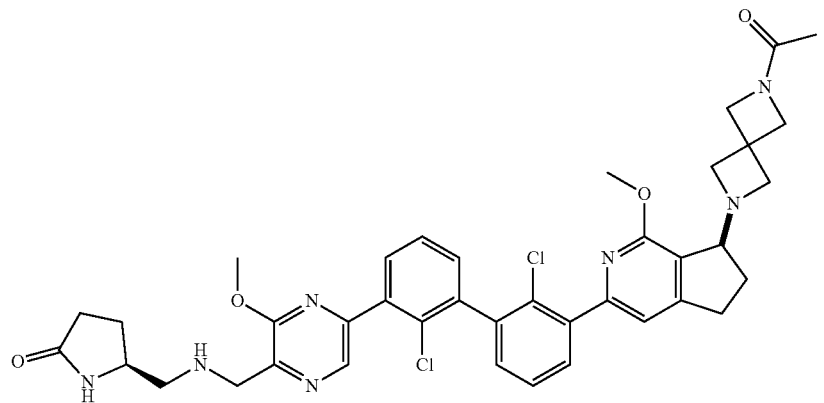

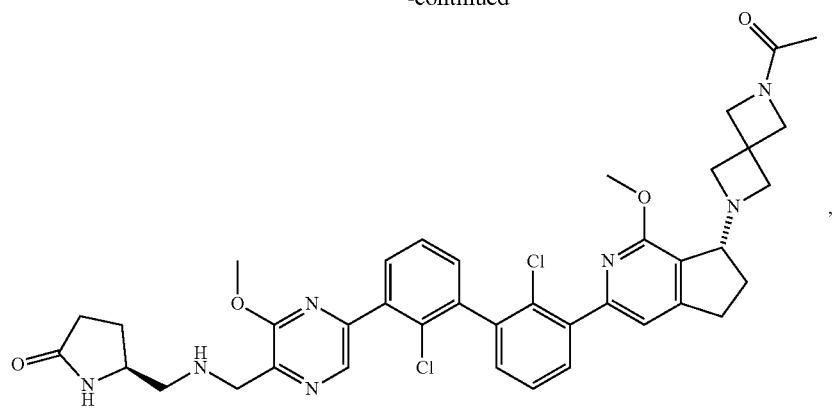
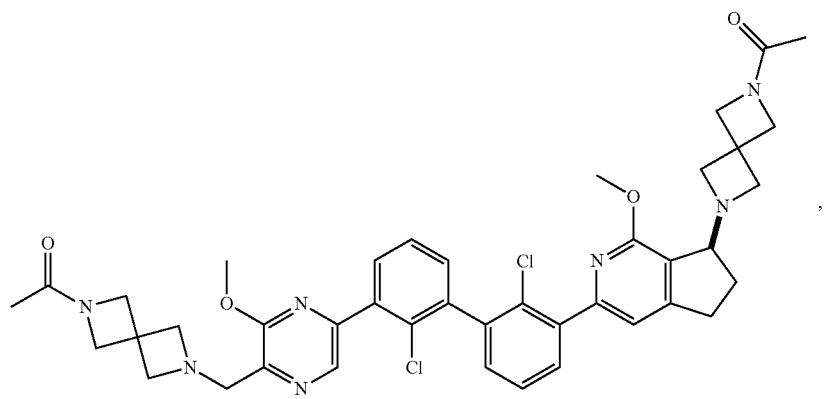
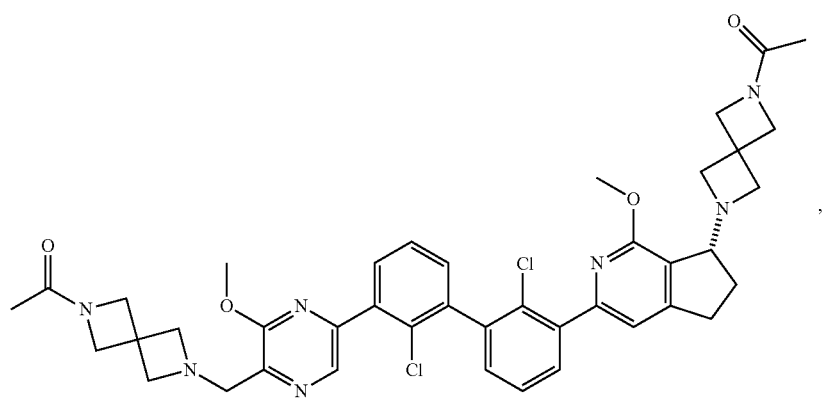
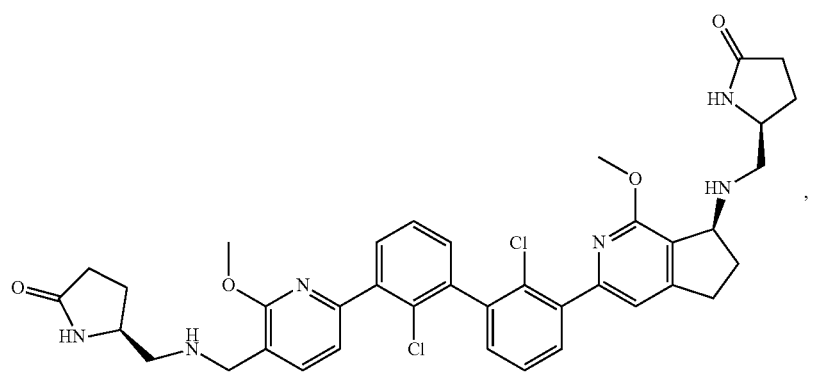

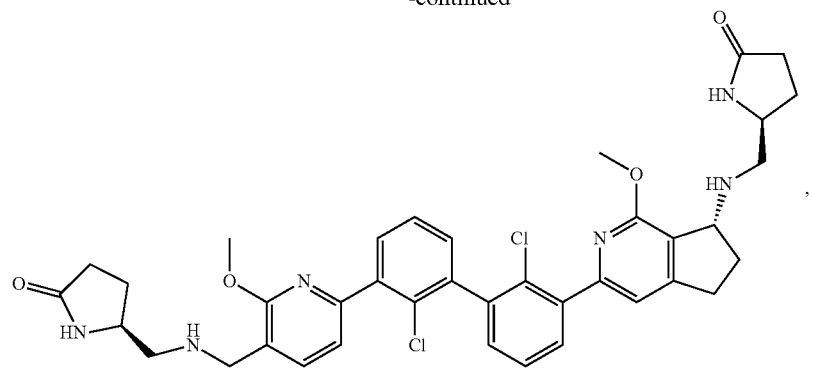
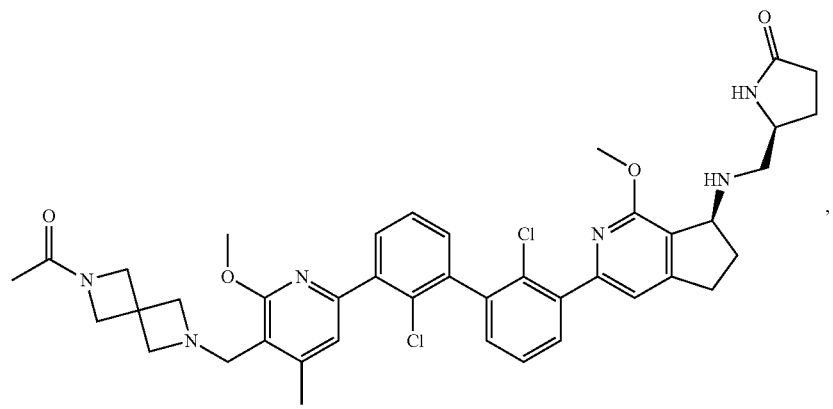
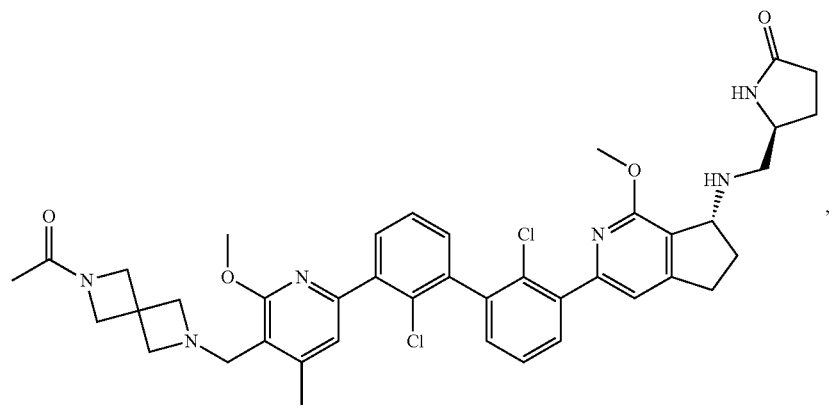
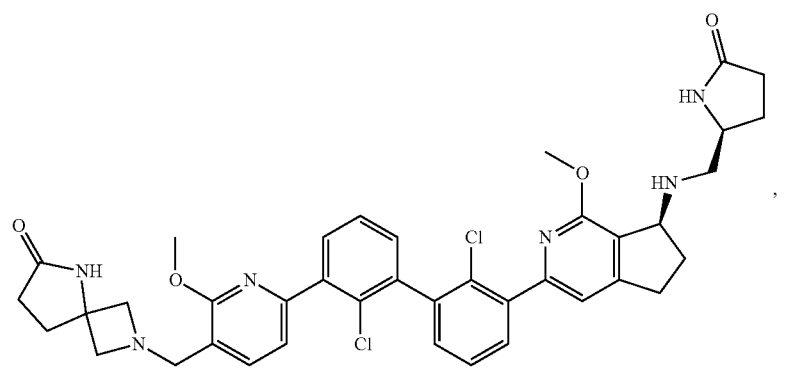

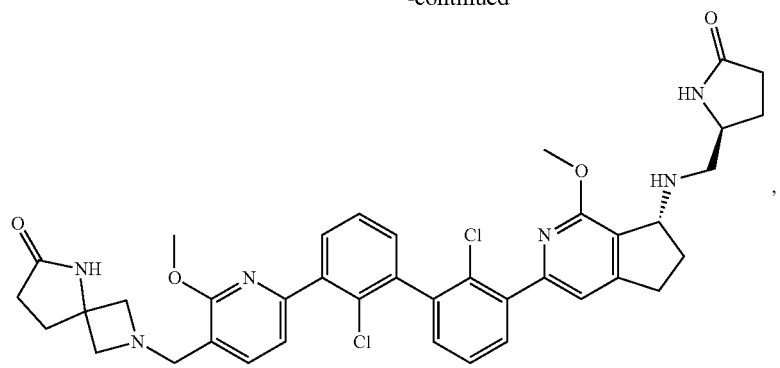
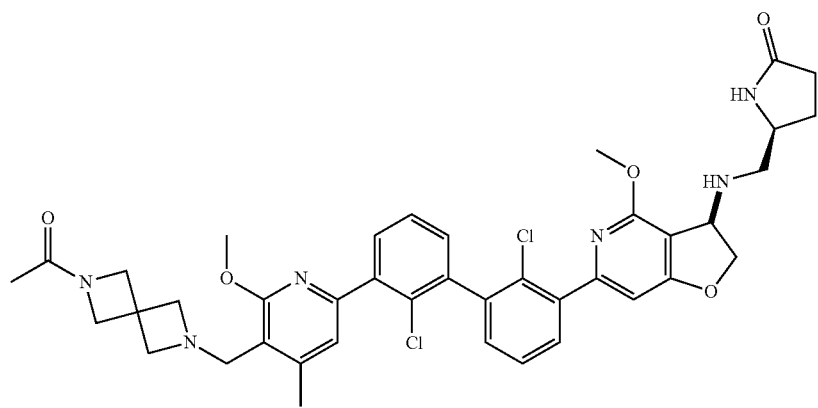
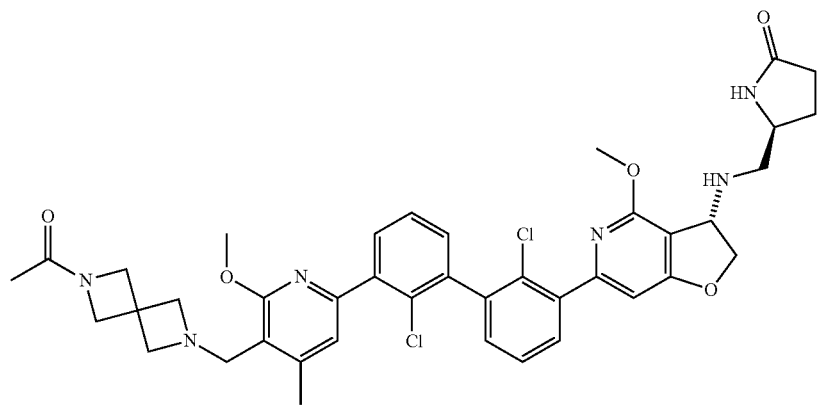
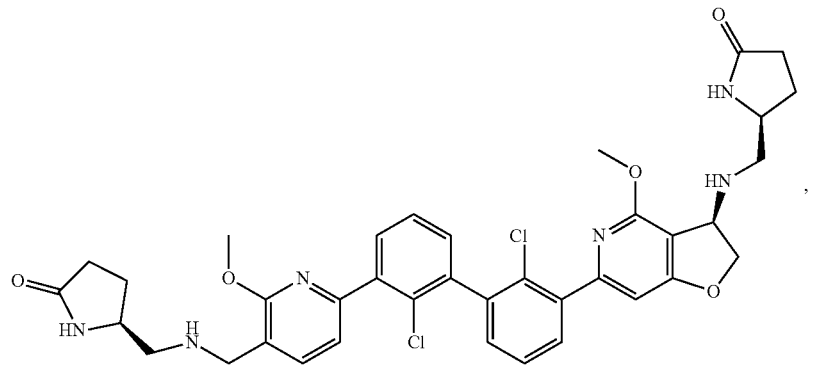

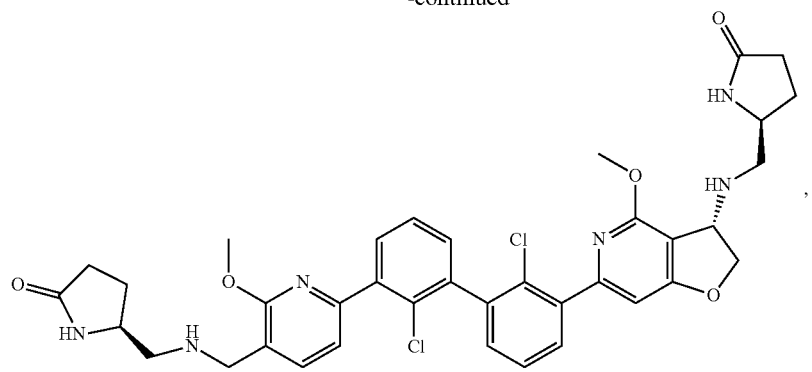
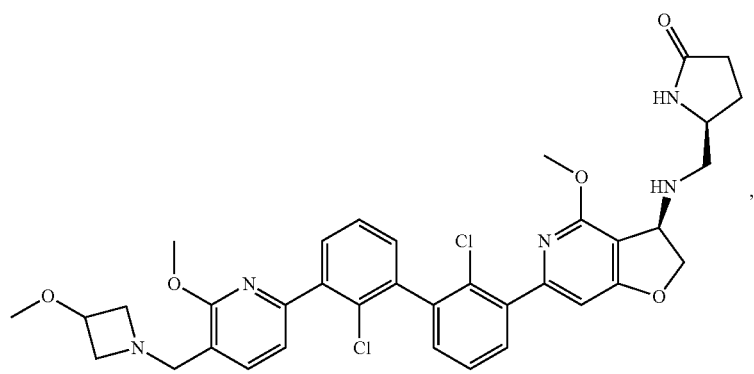
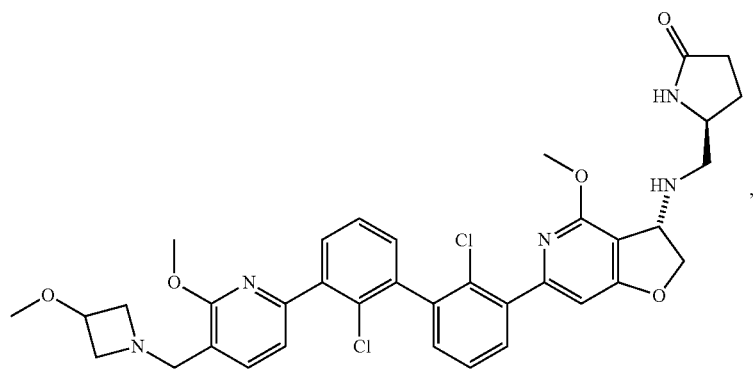
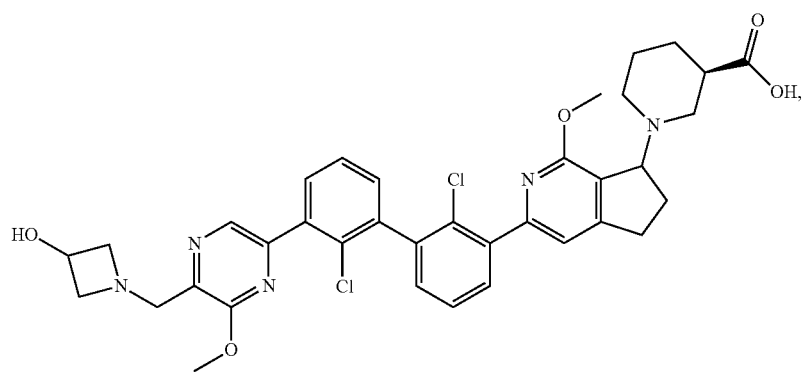

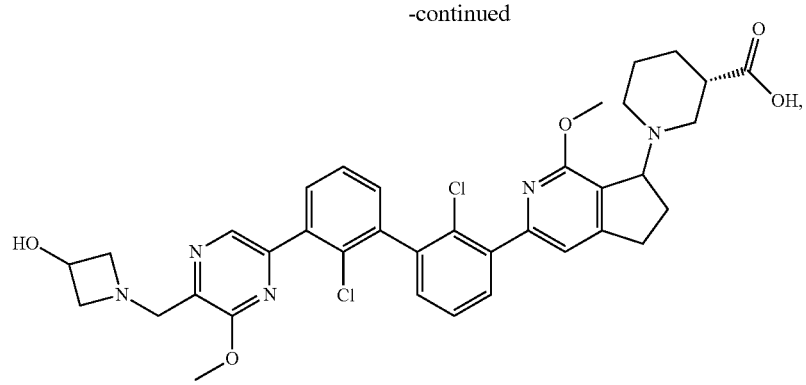
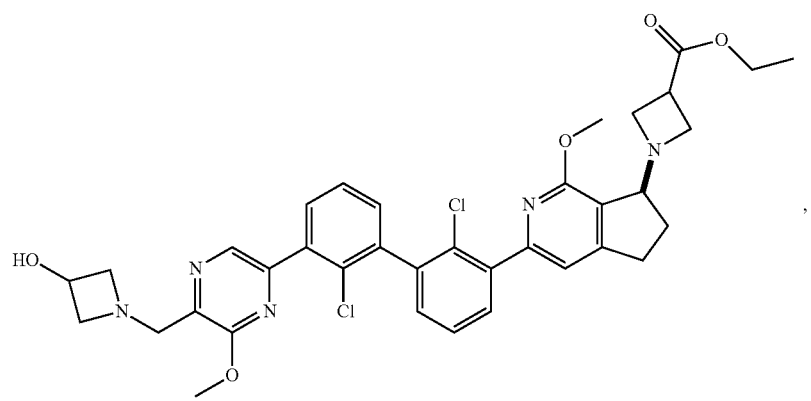
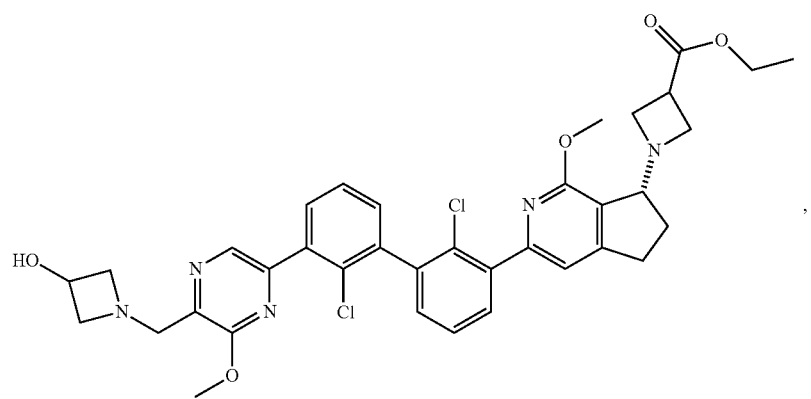
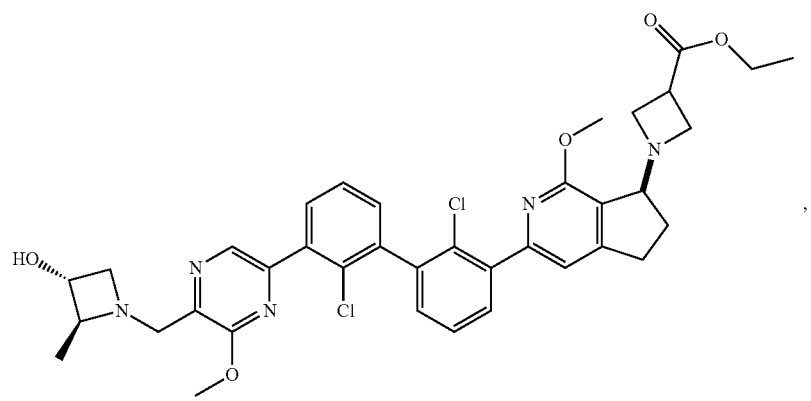

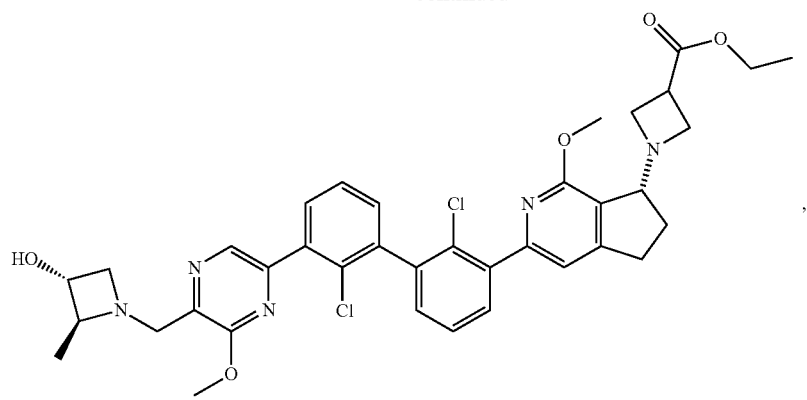,
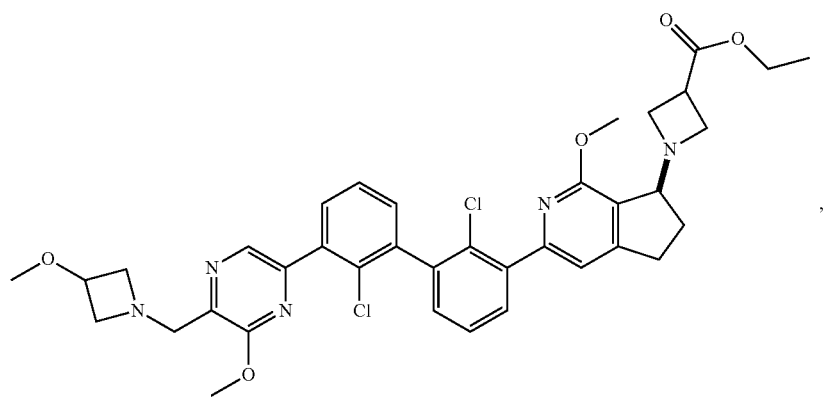,
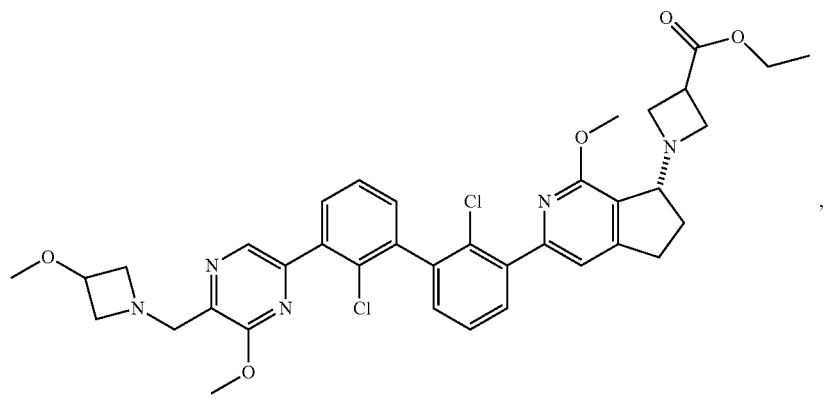,
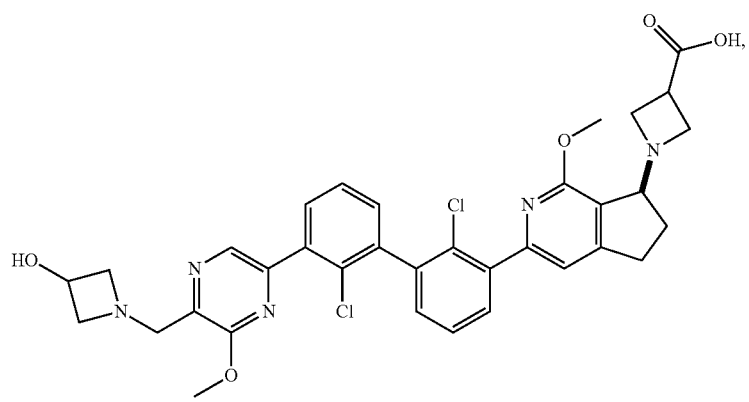

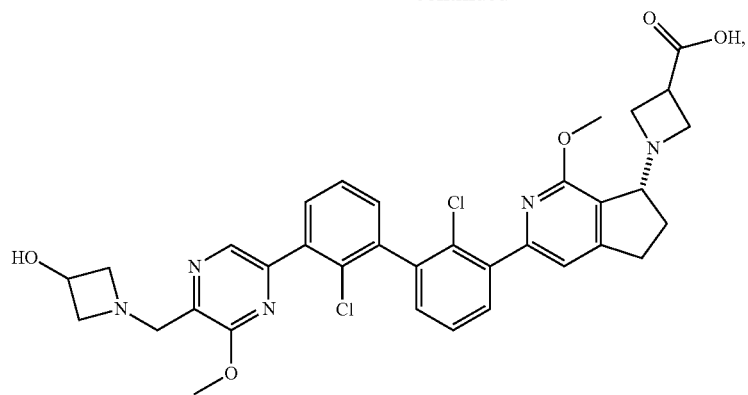
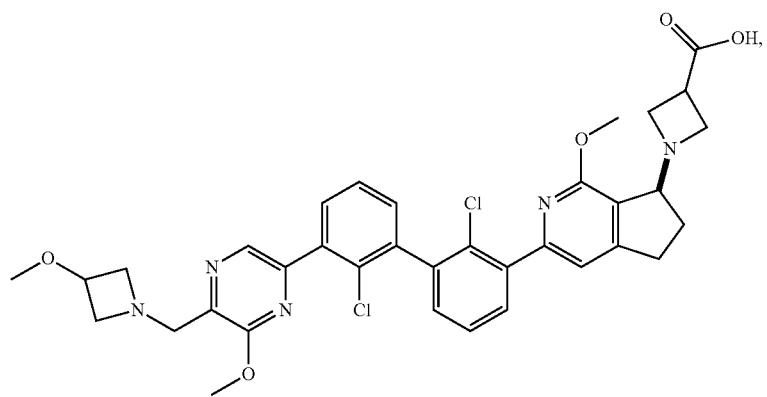
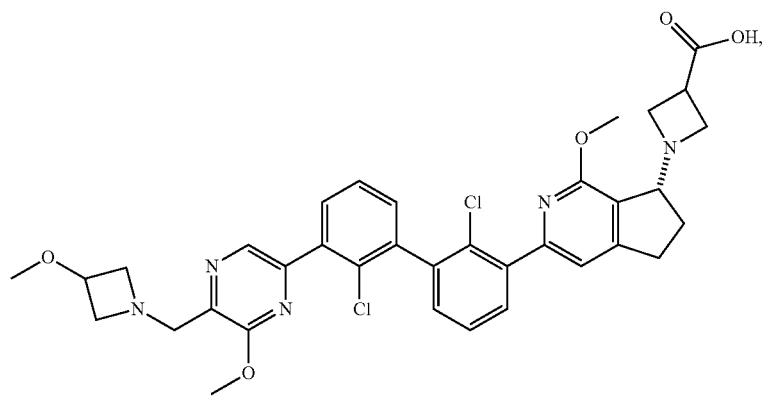
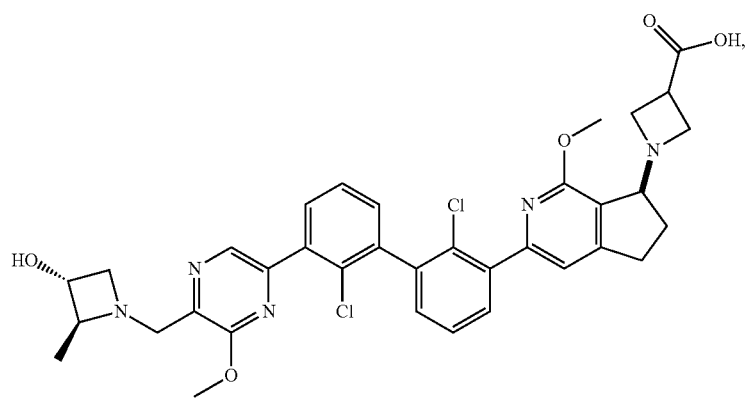

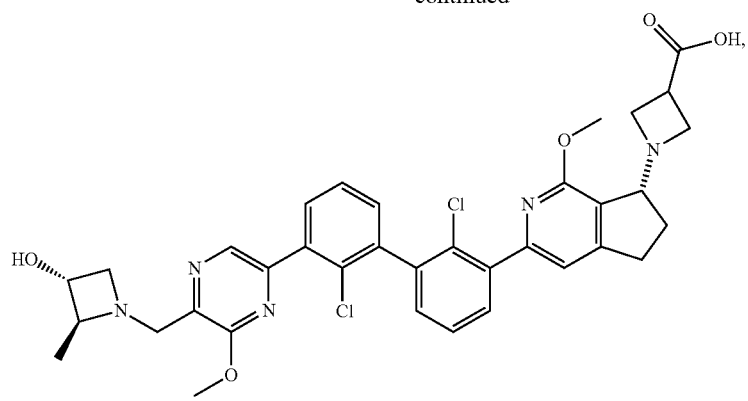
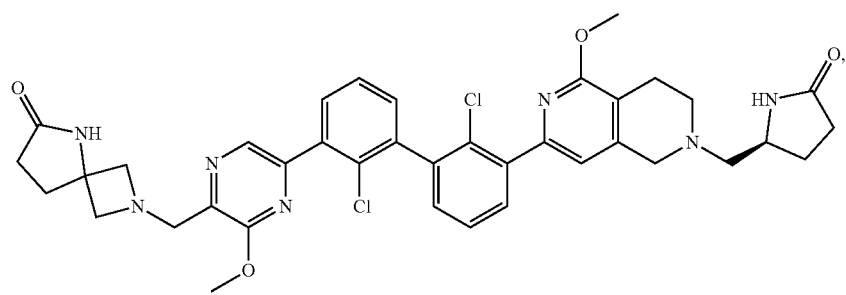
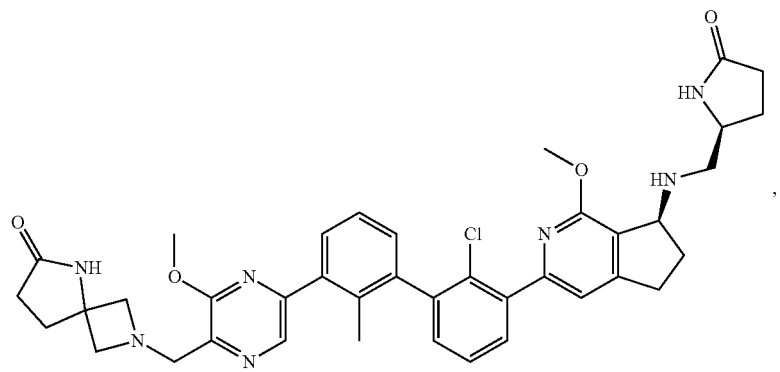
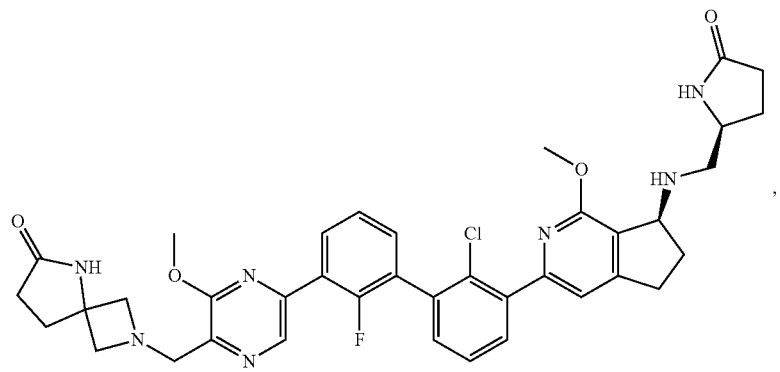

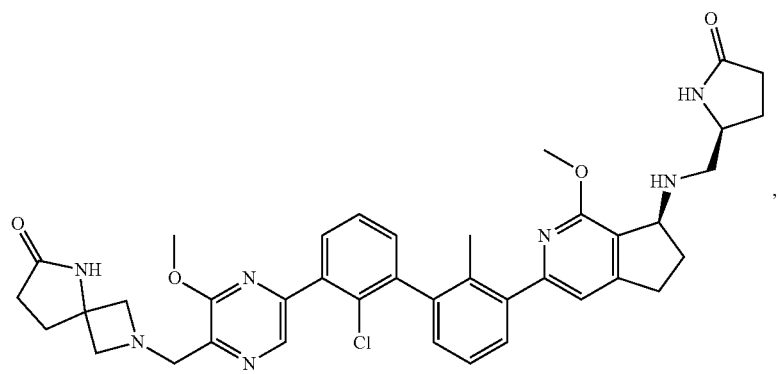
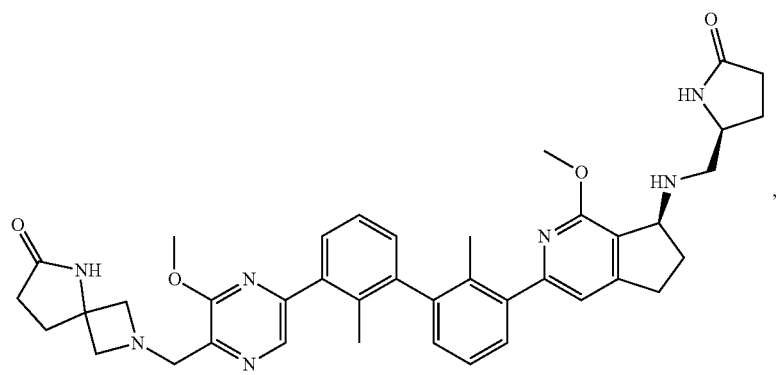
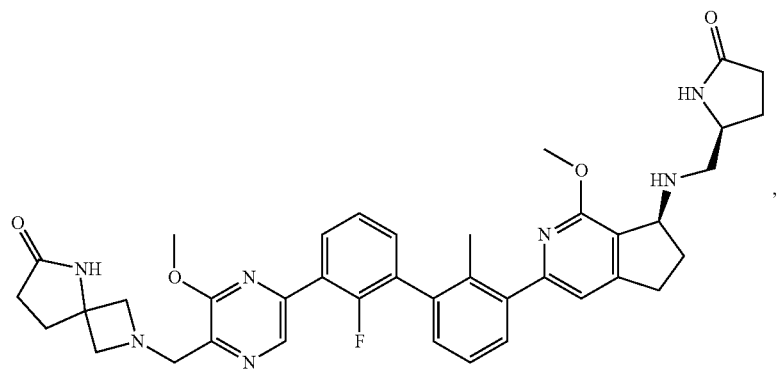
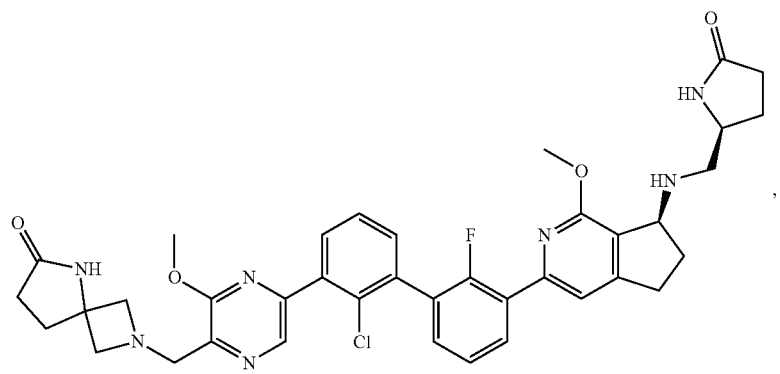

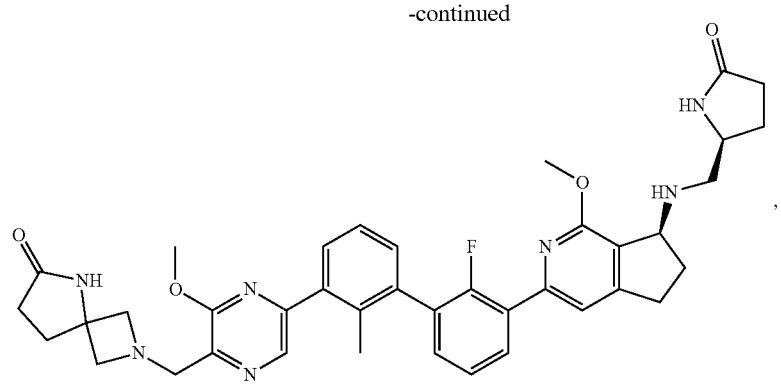
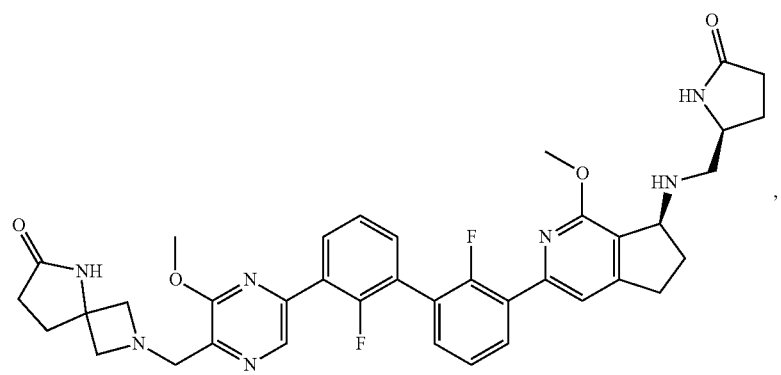
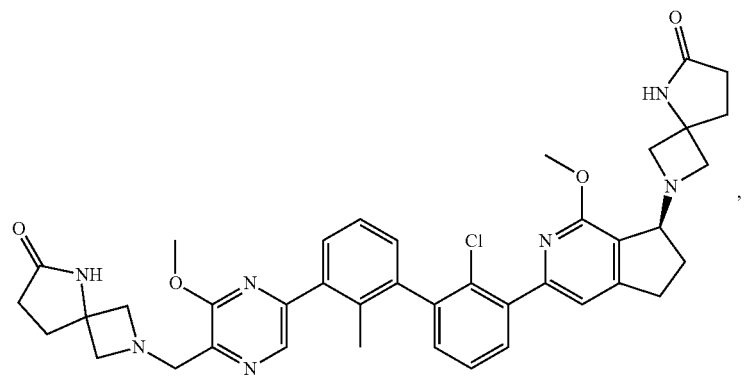
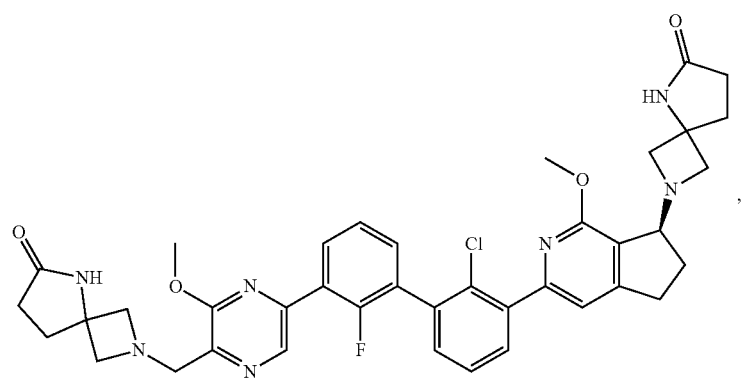

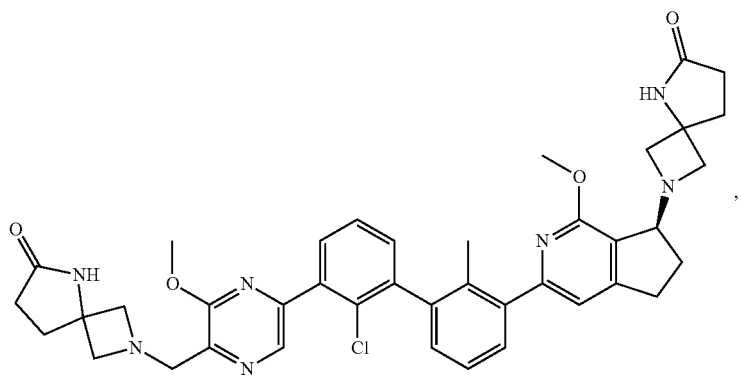
,
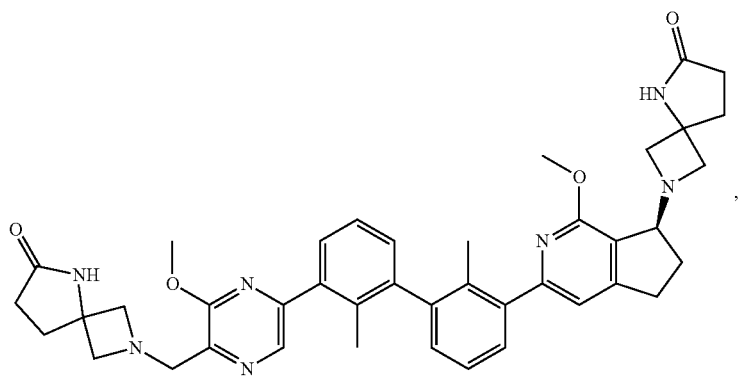
,
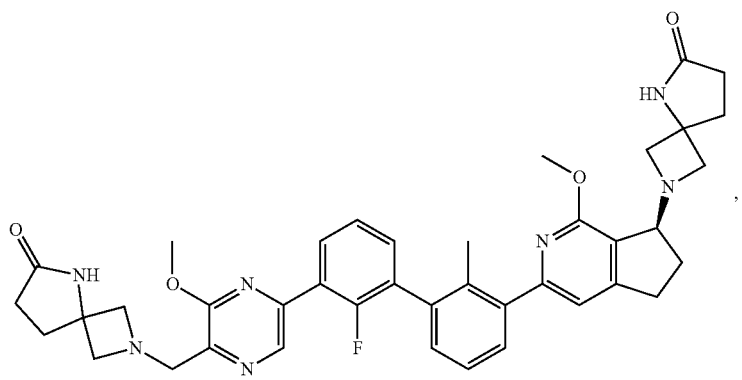
,
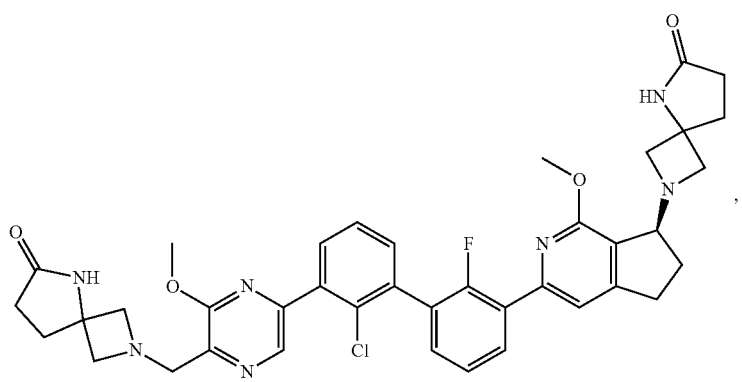
,

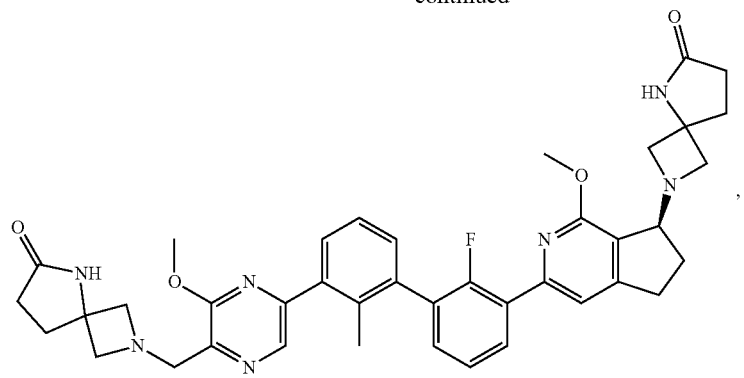
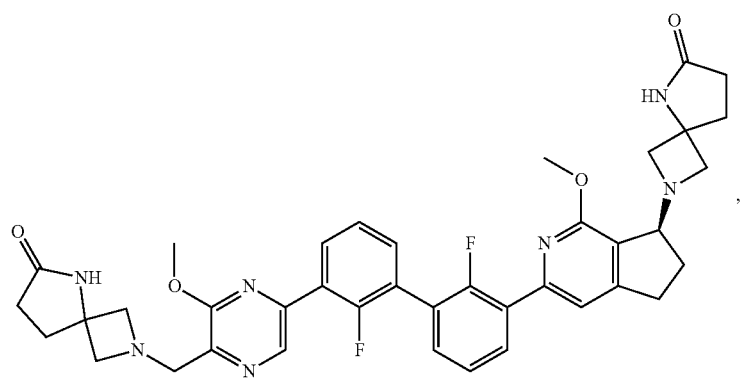
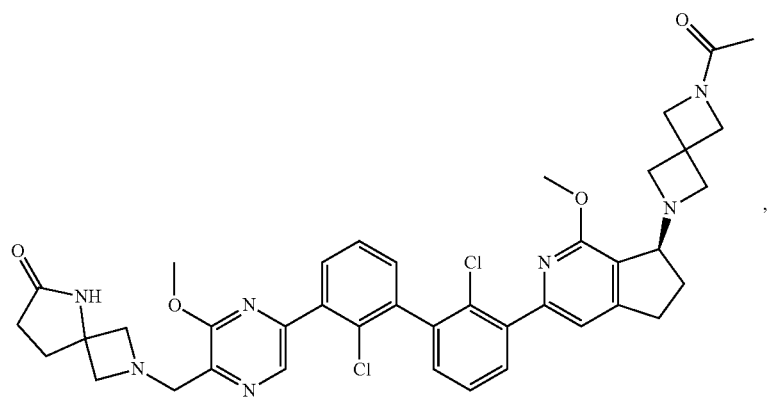
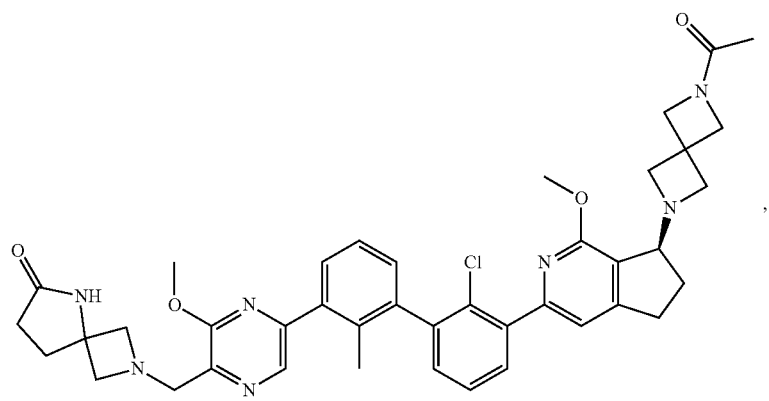

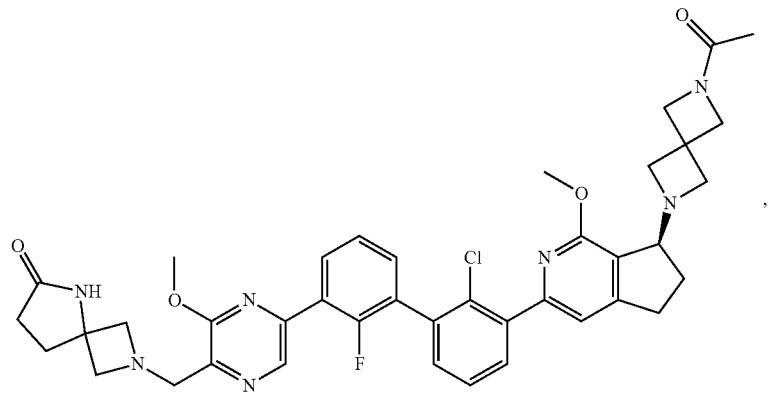
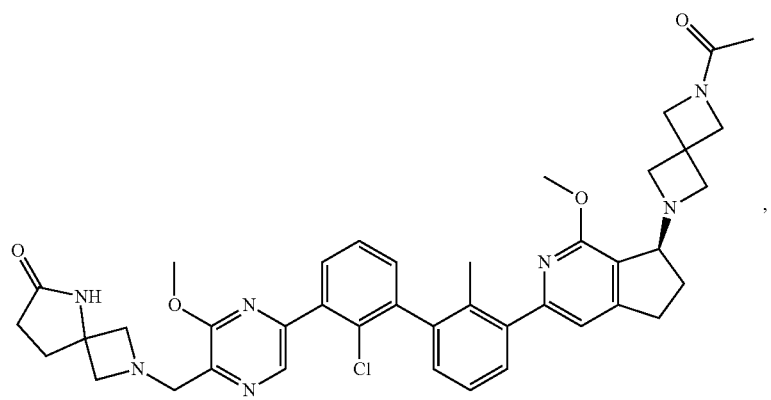
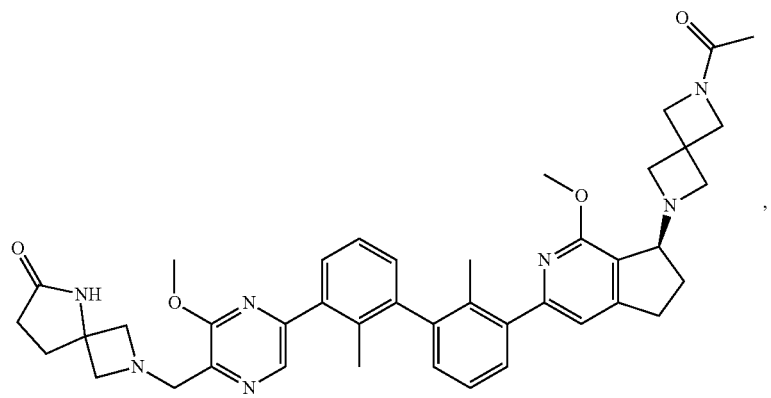
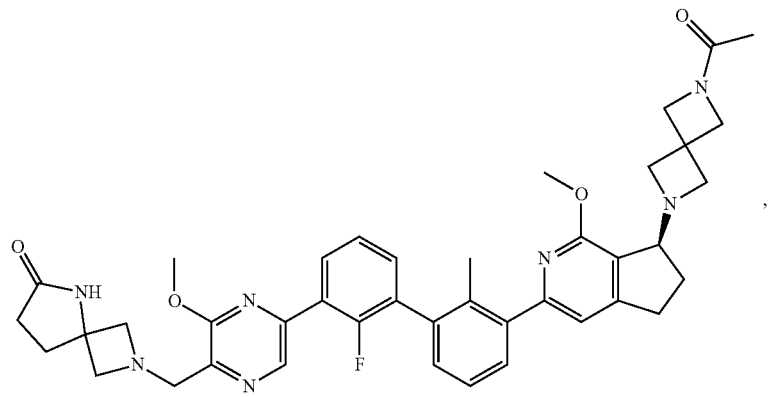

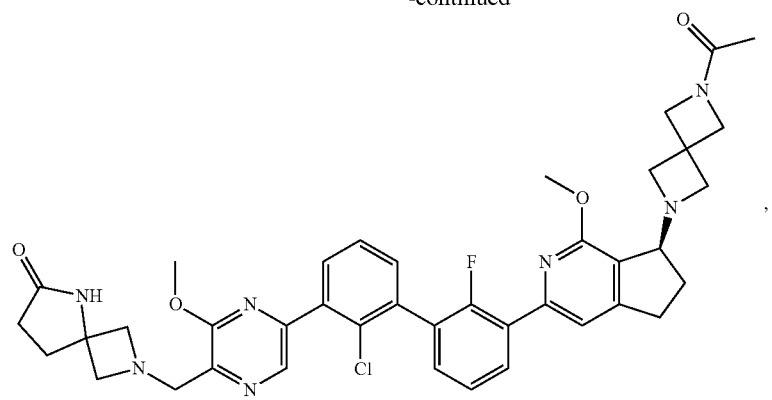
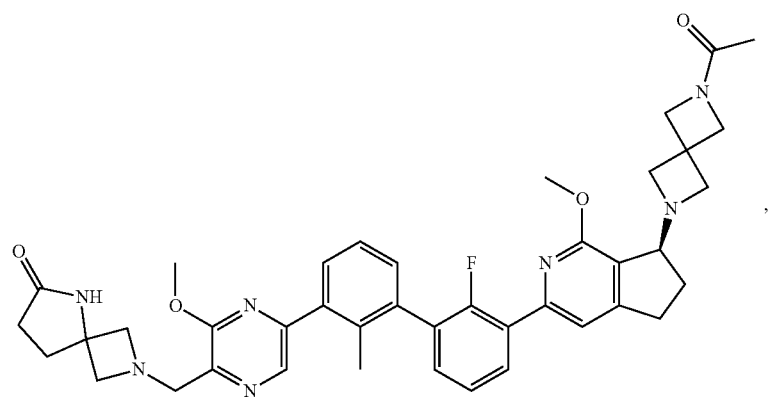
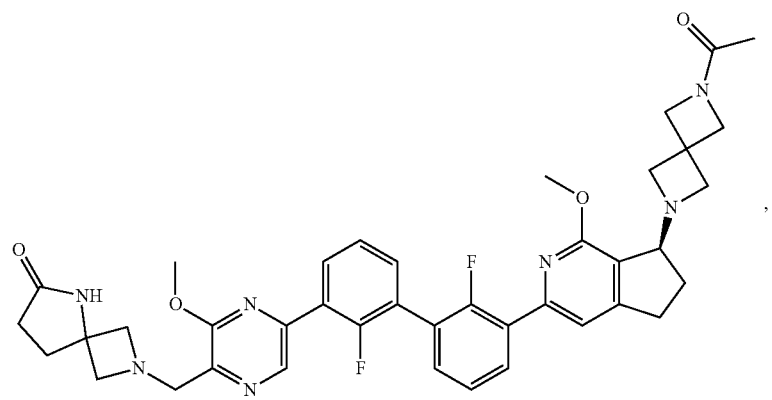
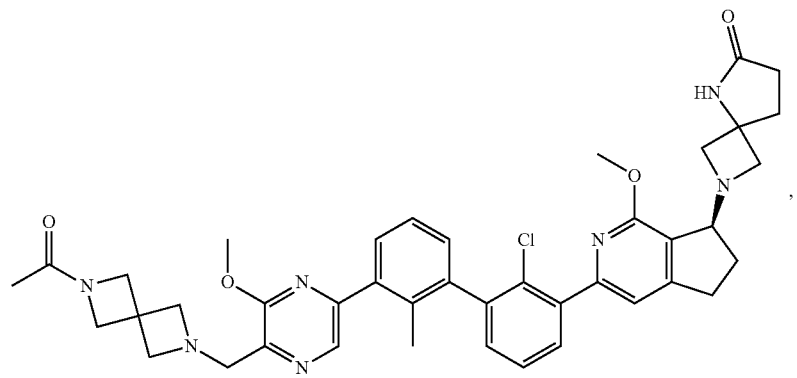

-continued
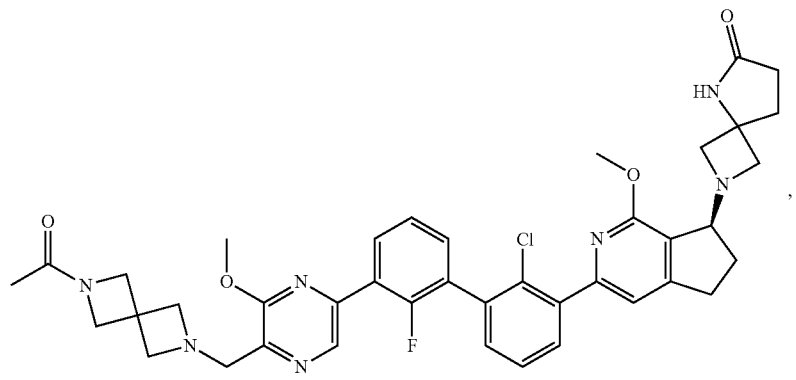
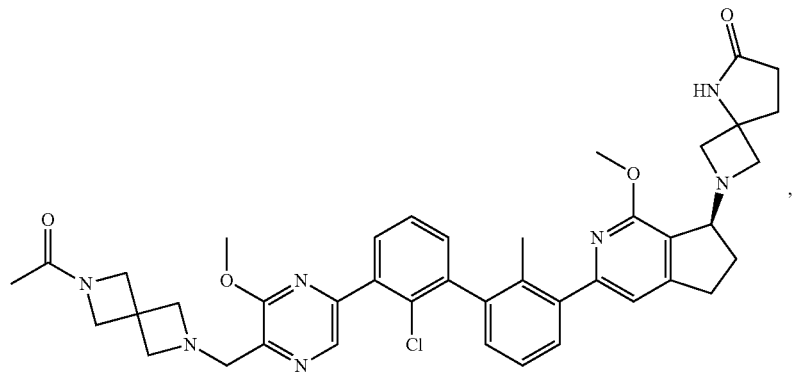
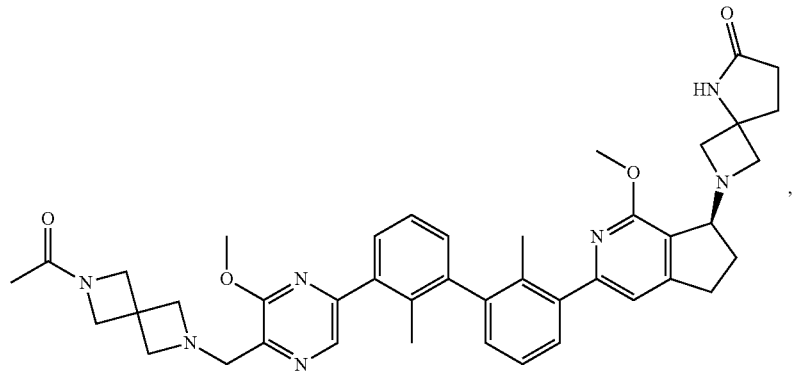
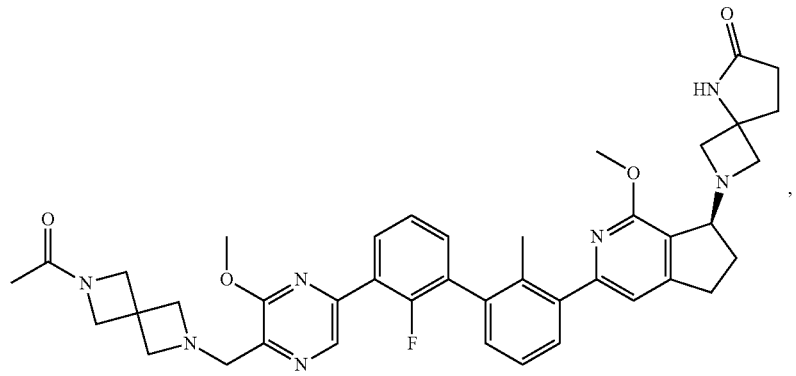

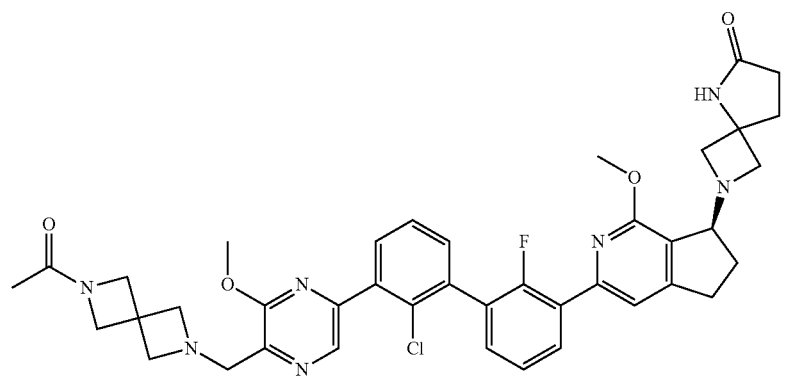,
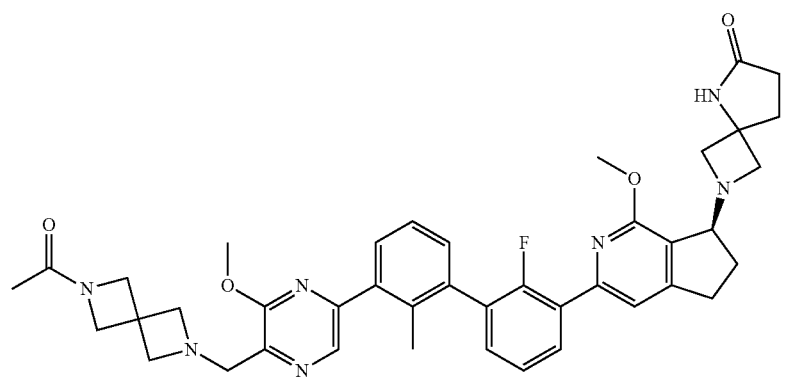,
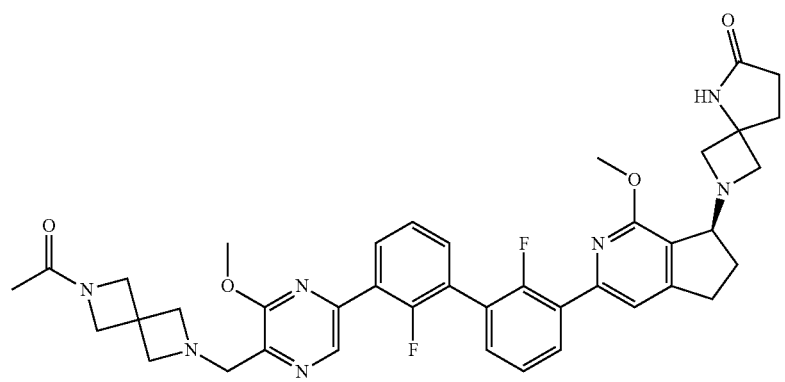,
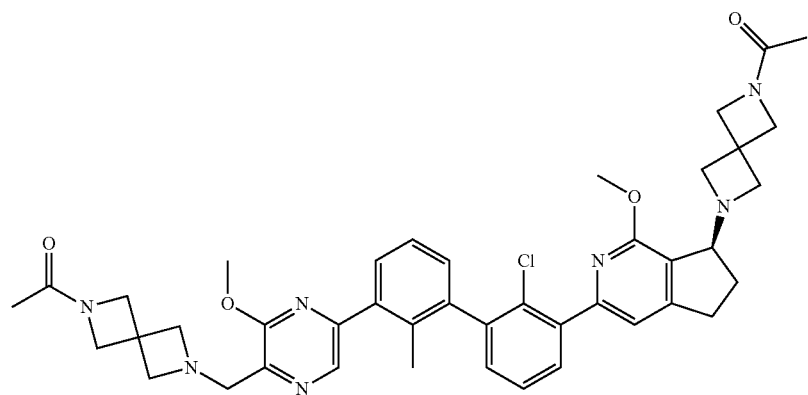,

-continued
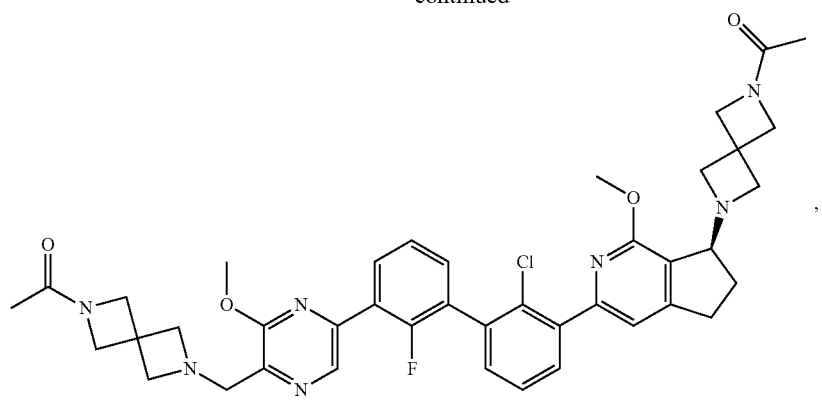
,
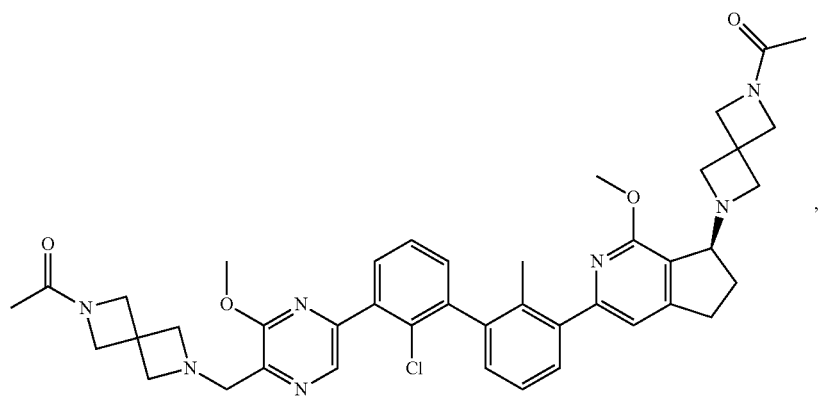
,
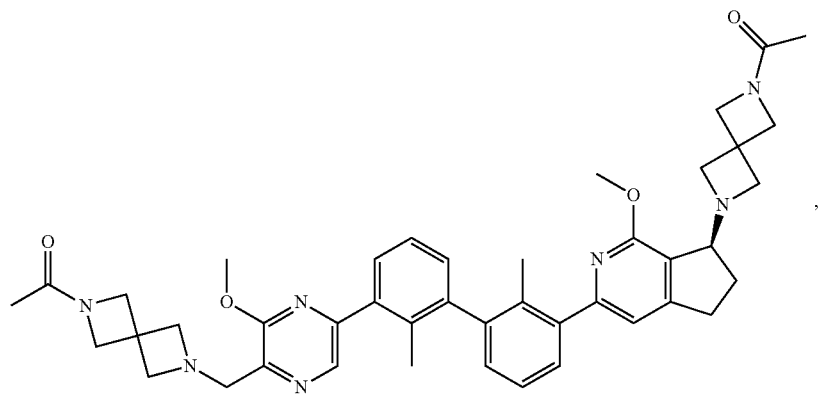
,
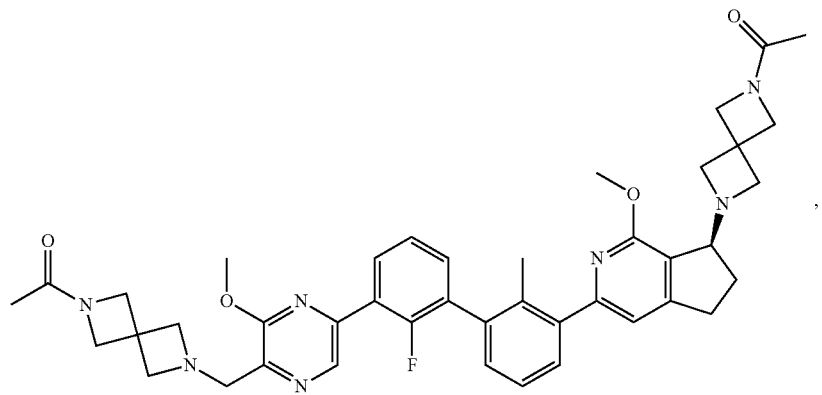
,

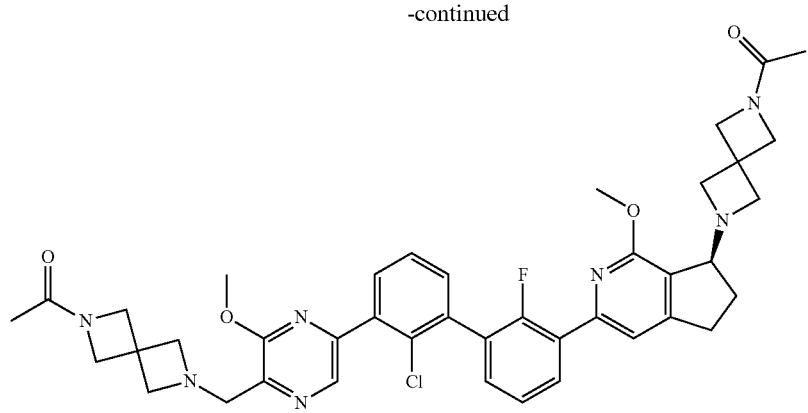
,
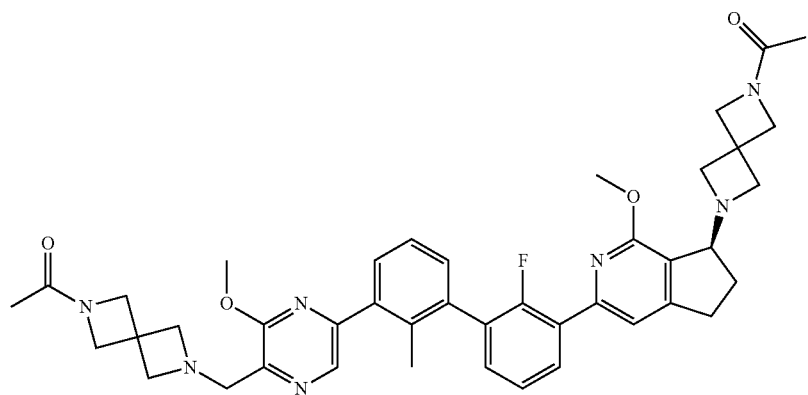
,
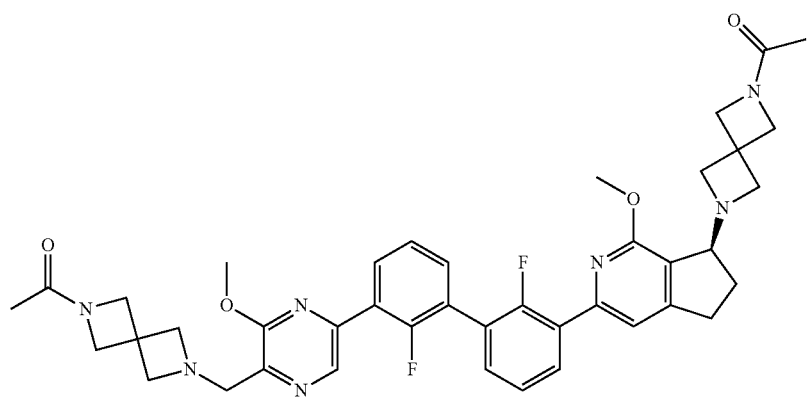
,
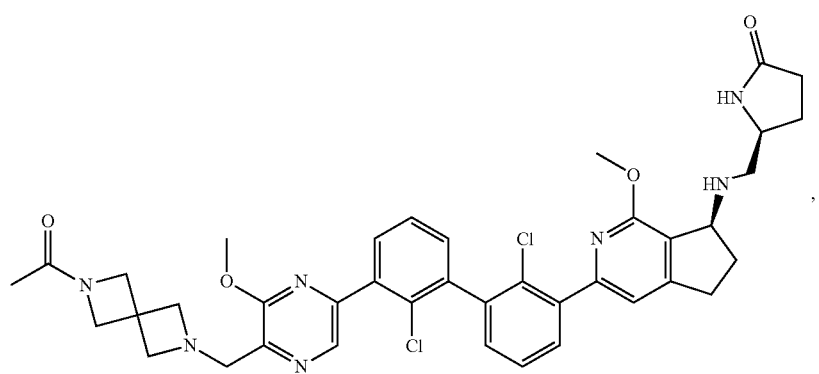
,

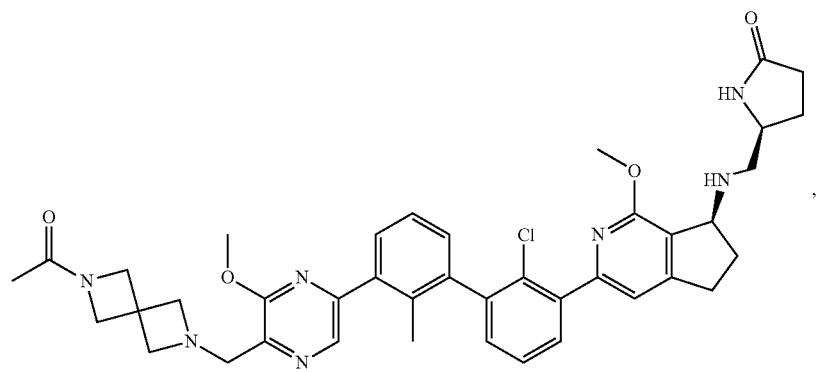
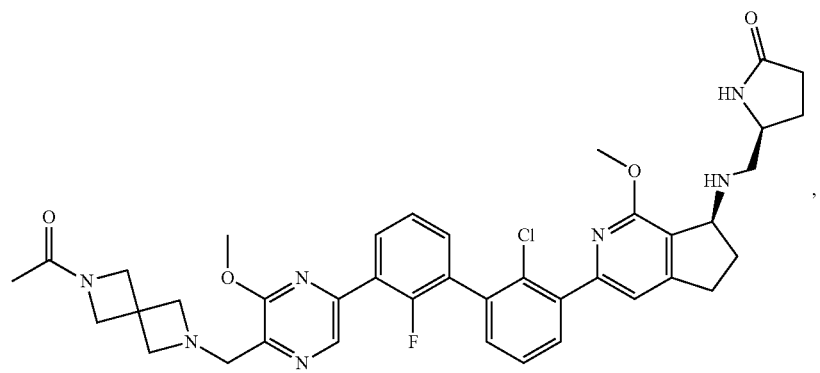
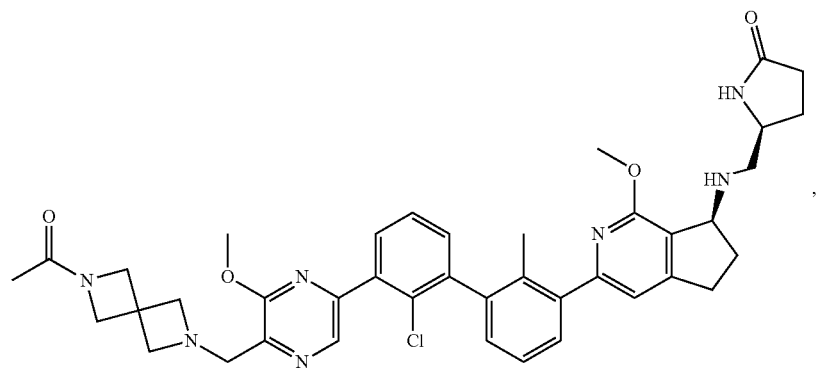
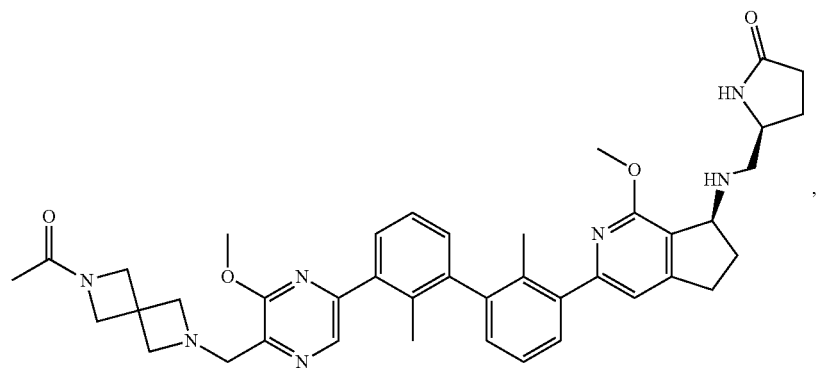

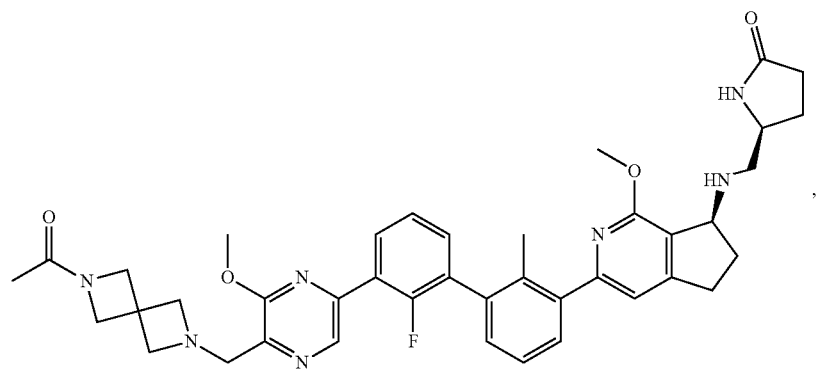
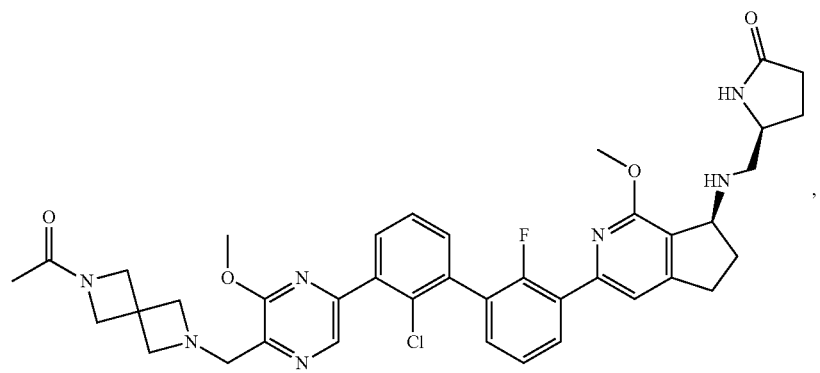
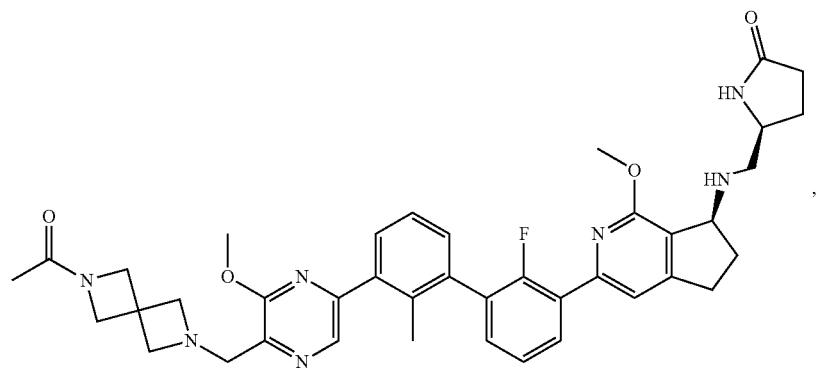
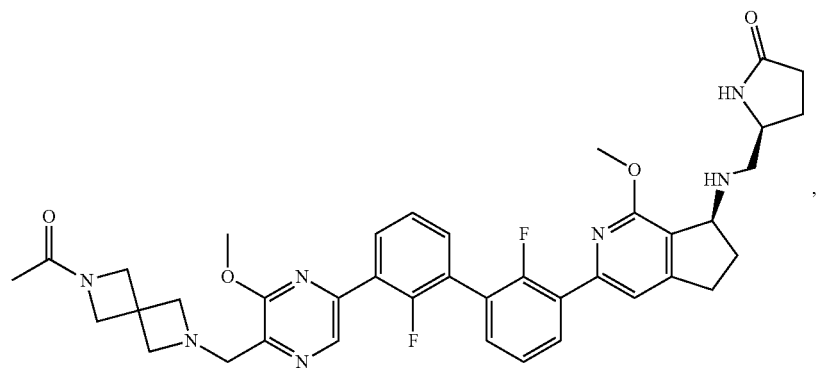

-continued
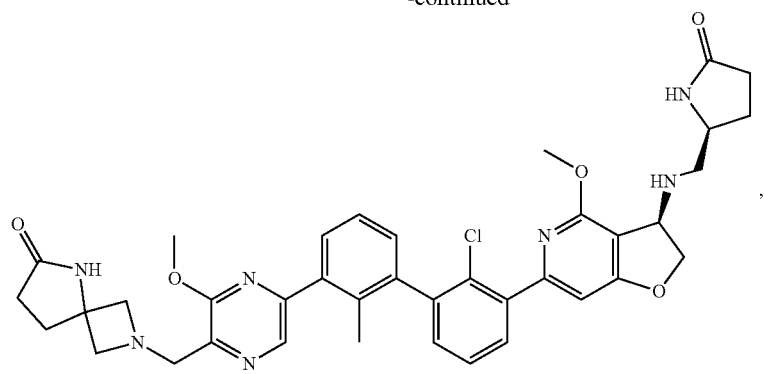
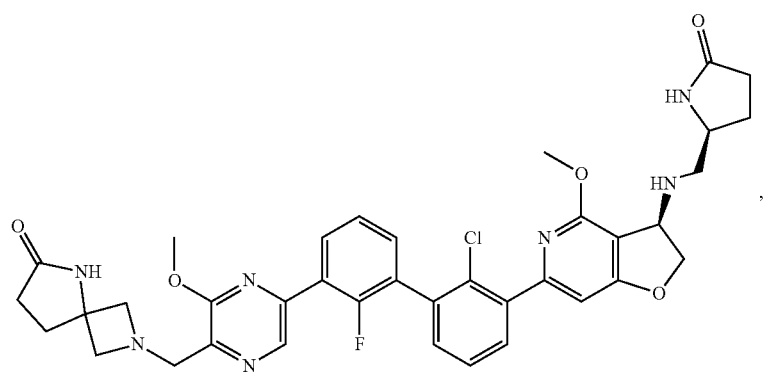
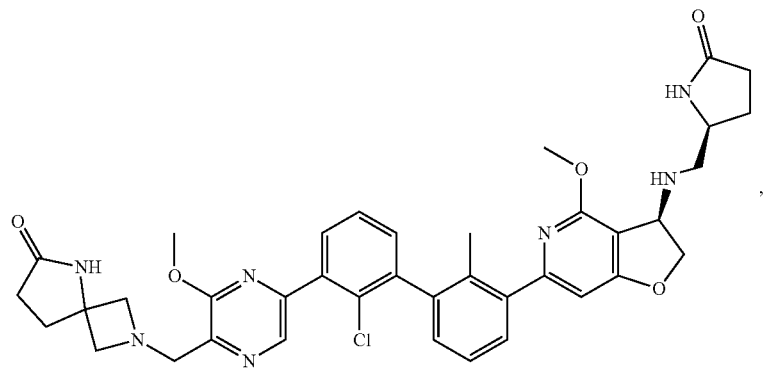
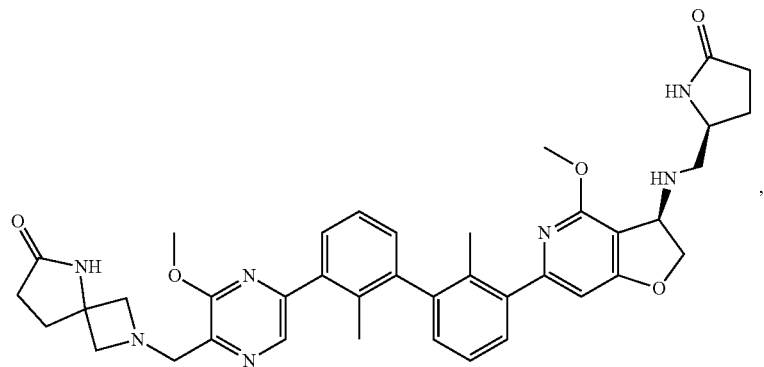

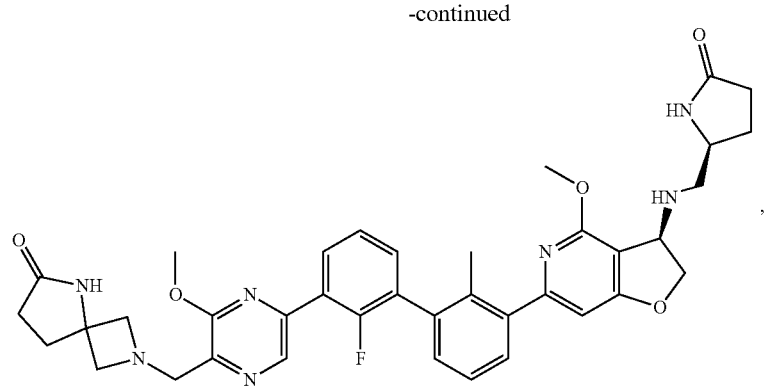
,
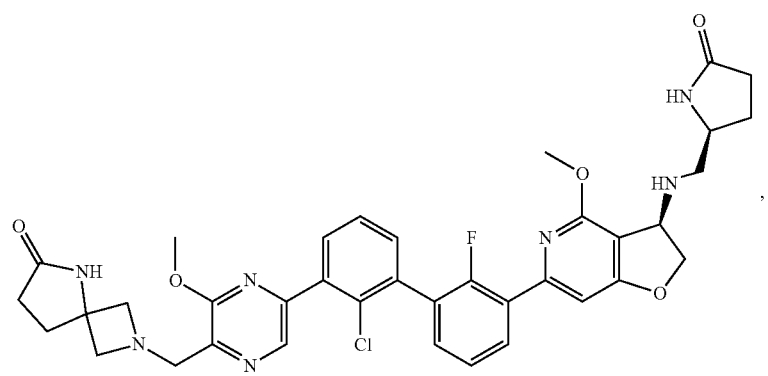
,
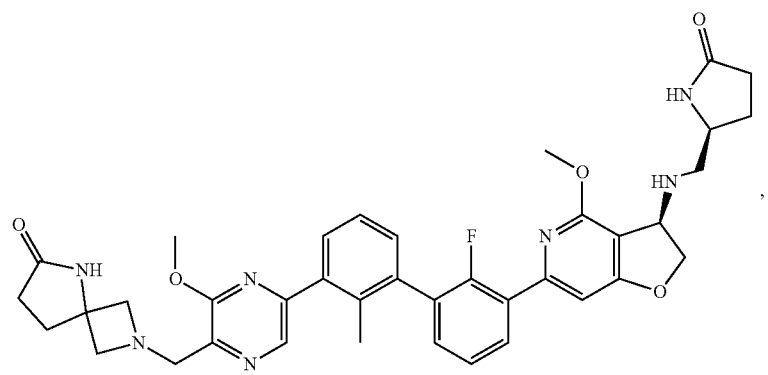
,
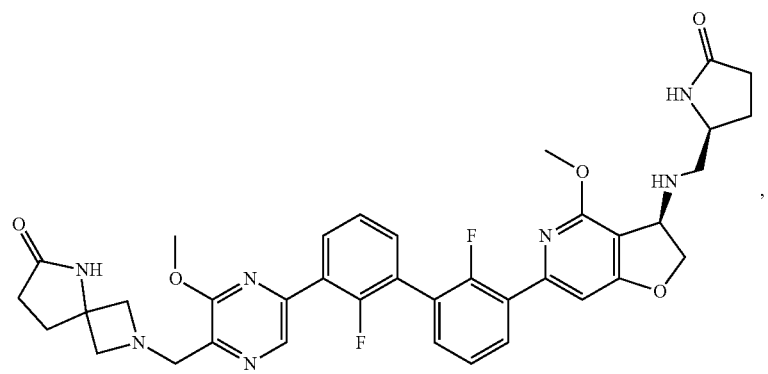
,

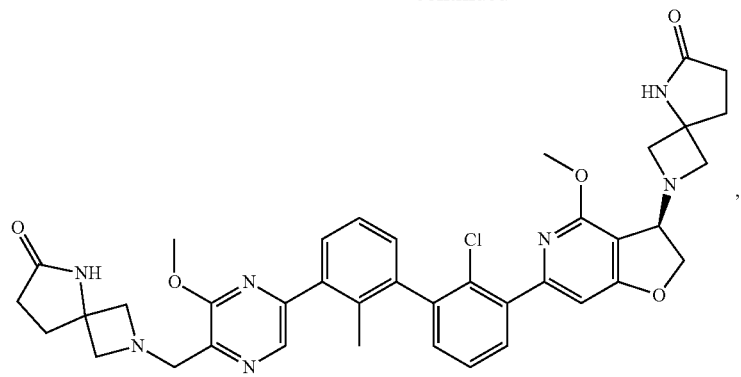
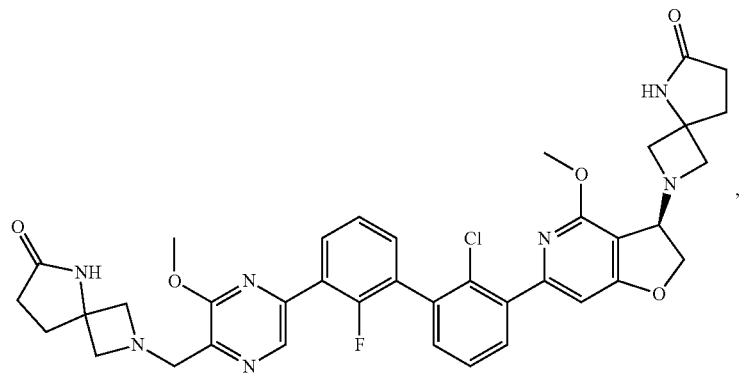
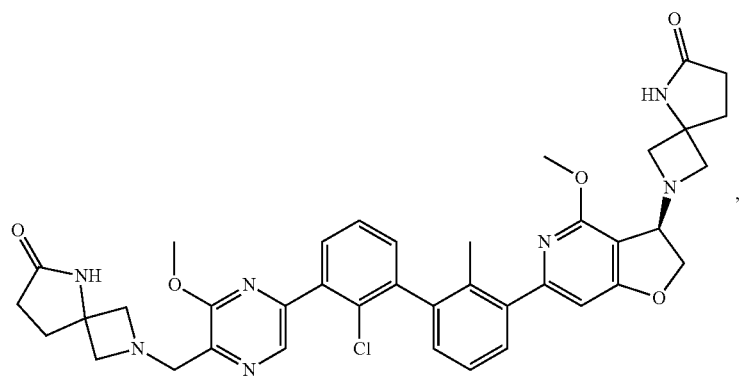
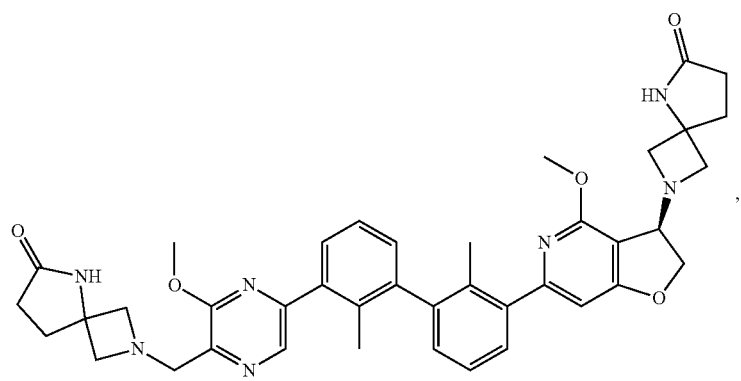

-continued
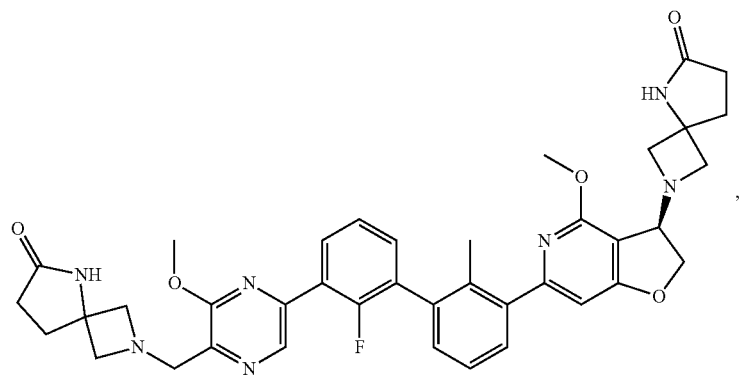
,
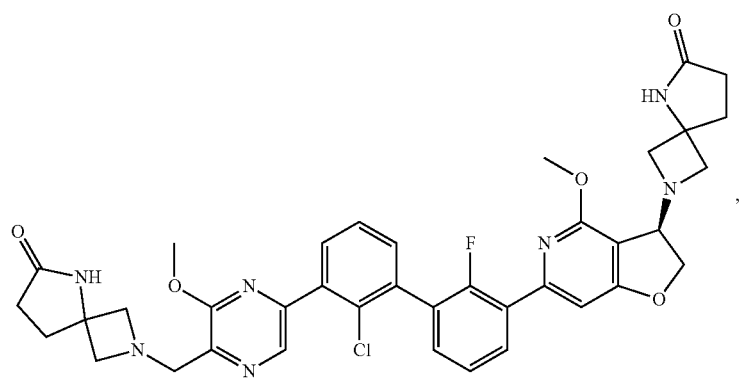
,
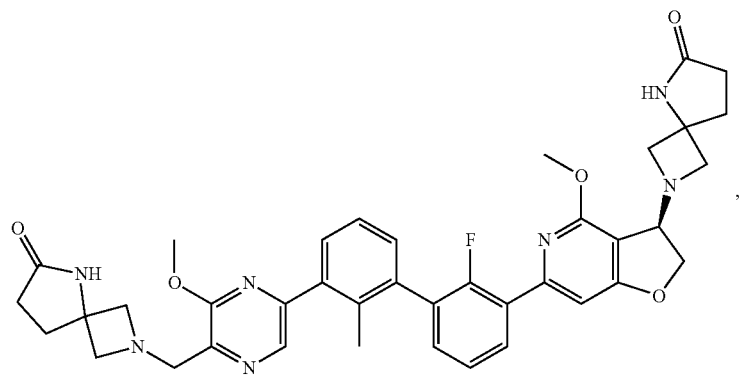
,
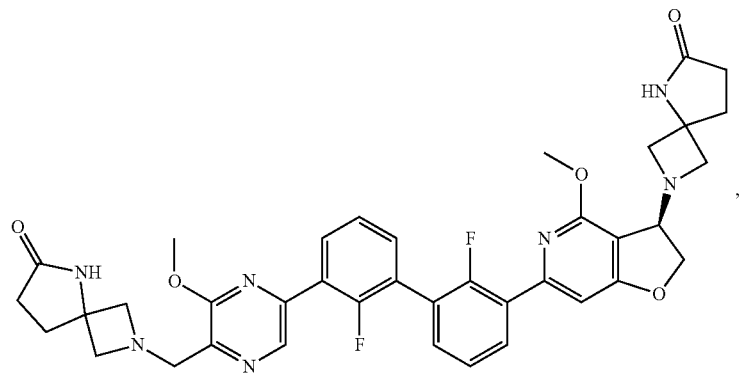
,

-continued
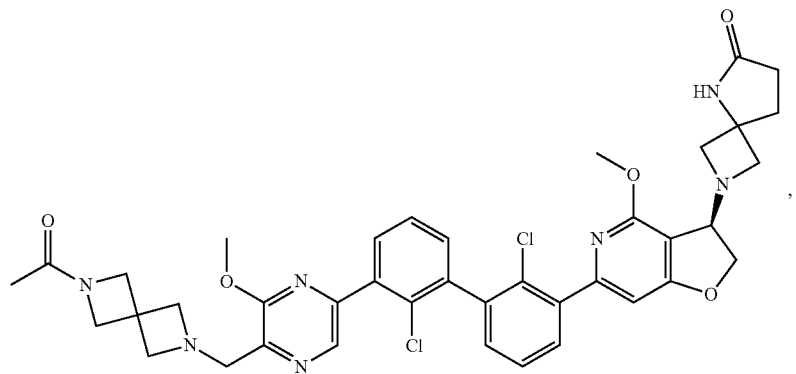
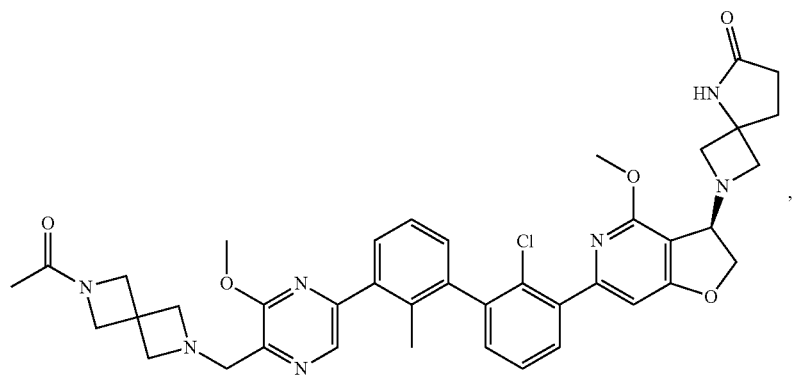
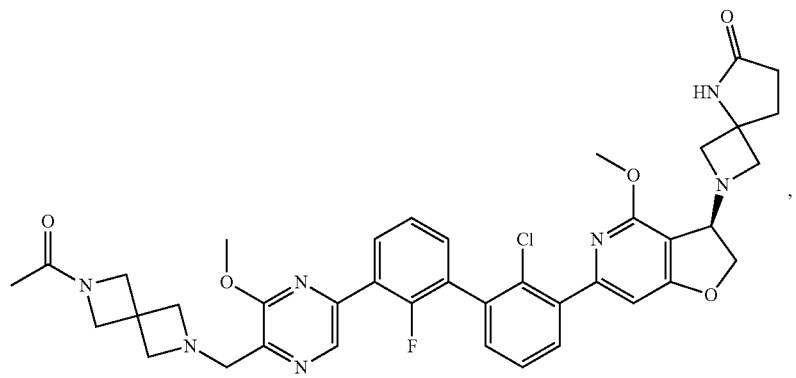
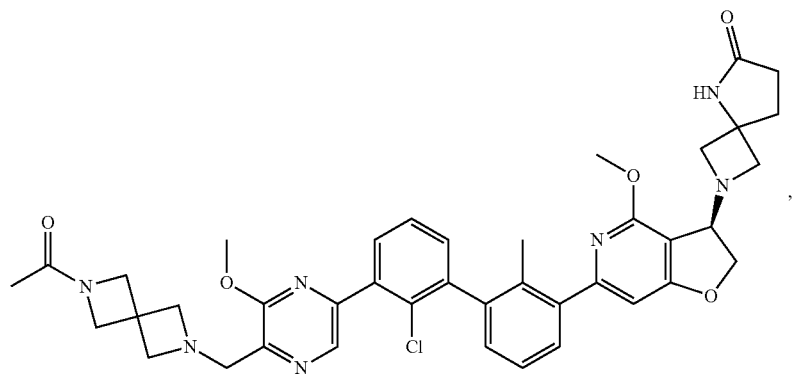

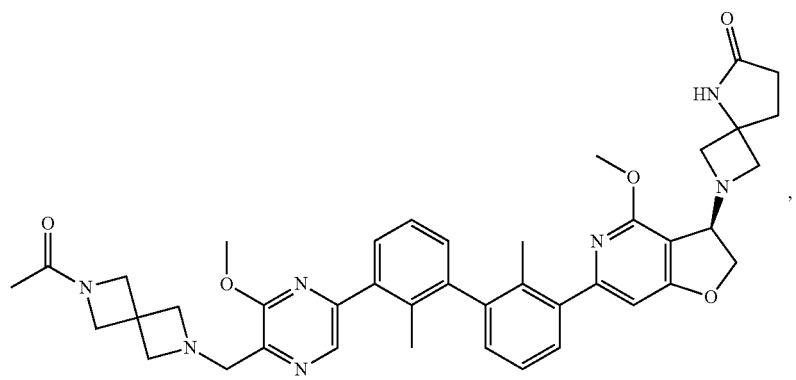,
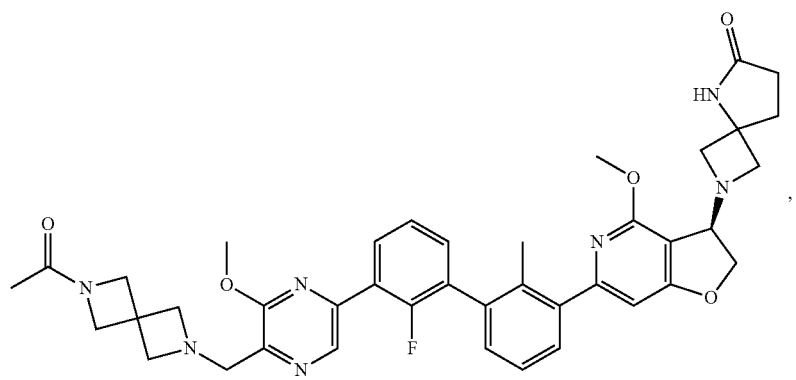,
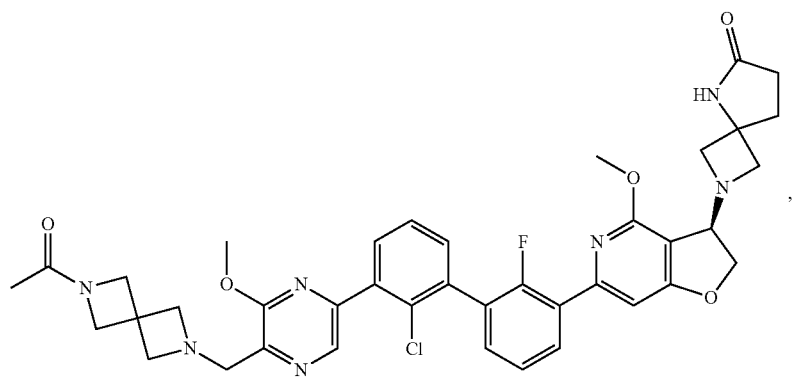,
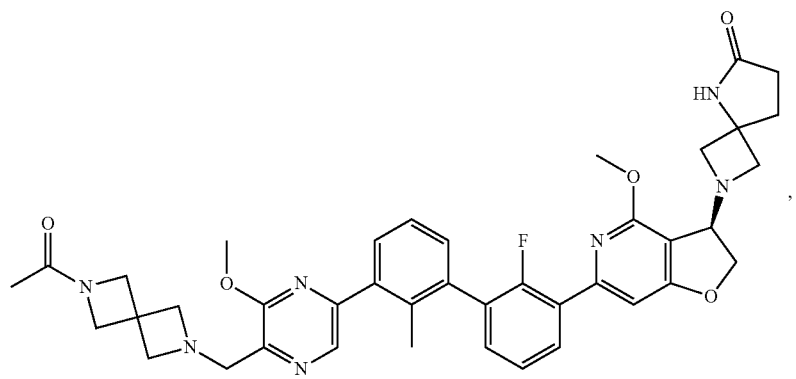,

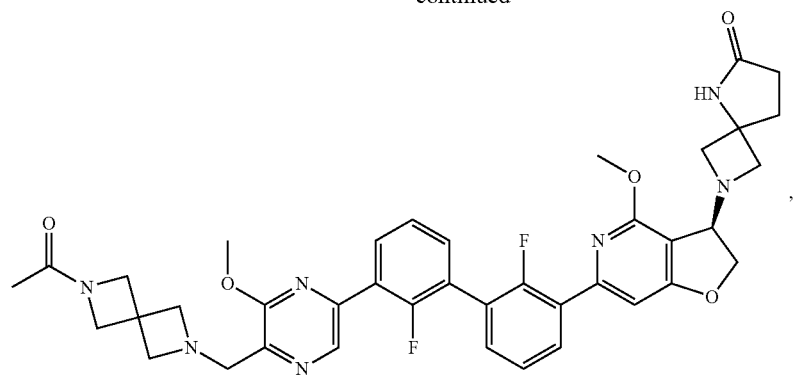
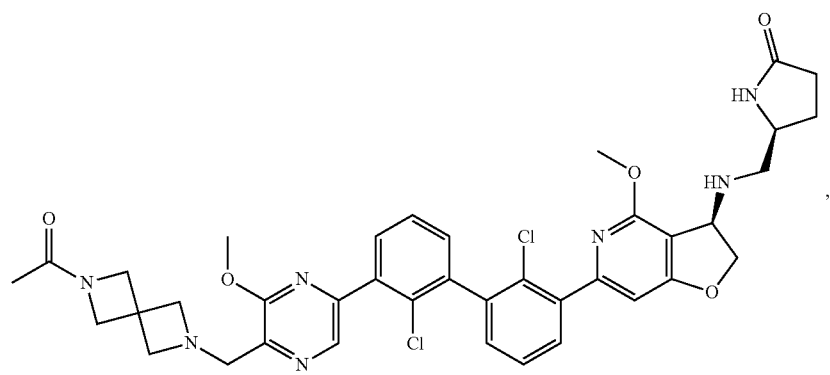
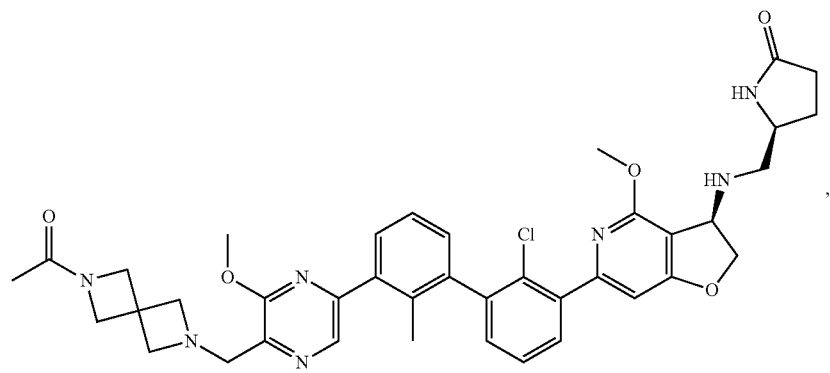
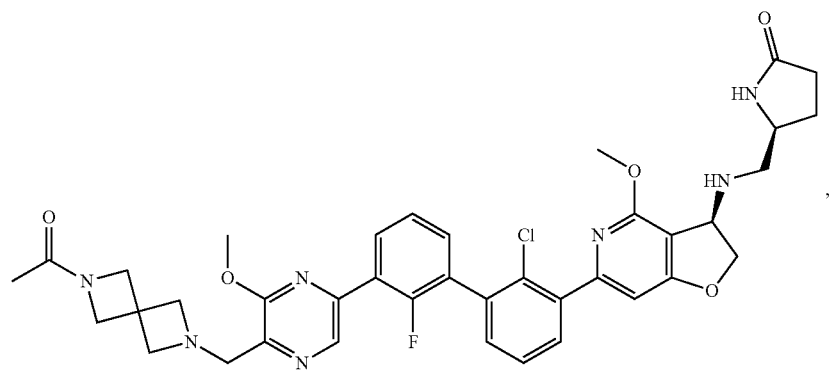

-continued
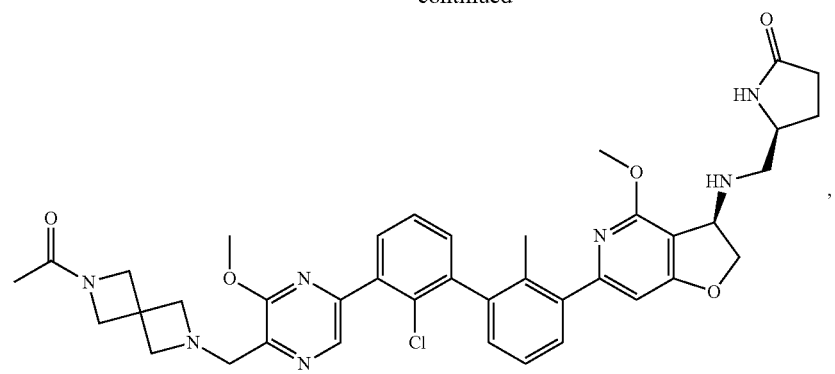
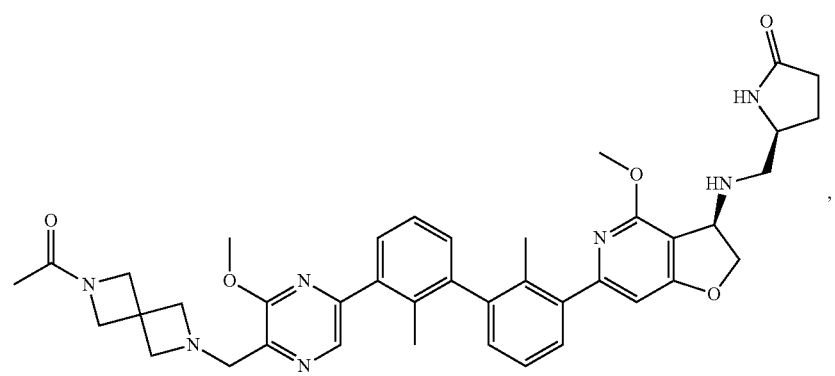
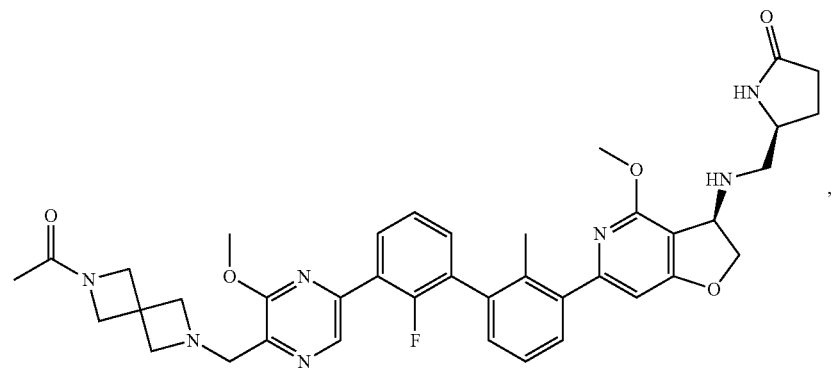
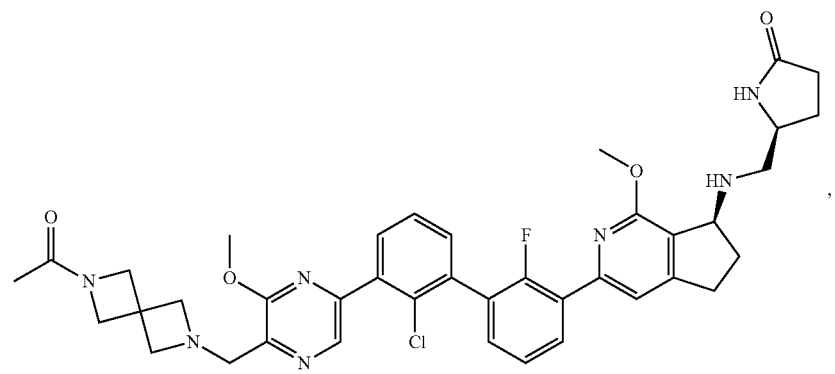

-continued
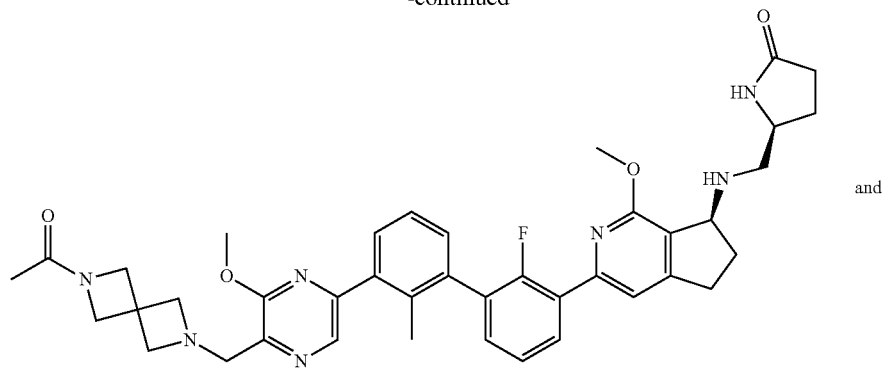
and
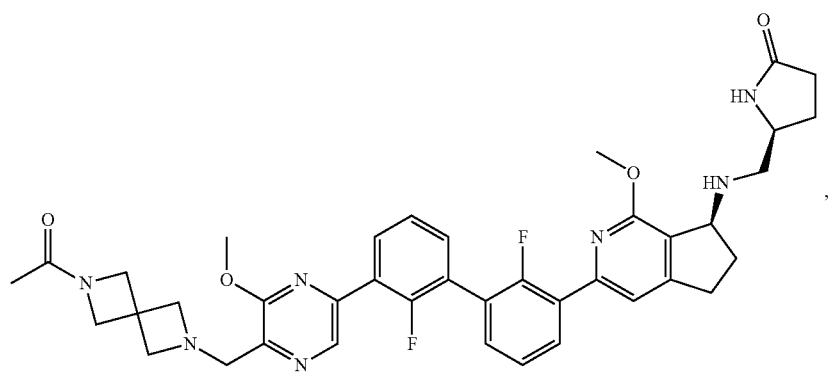
or a pharmaceutically acceptable salt of any of the foregoing.
23. A pharmaceutical composition comprising an effective amount of a compound of claim 1, or a pharmaceutically acceptable salt thereof, and excipient.
24. A compound selected from the group consisting of:
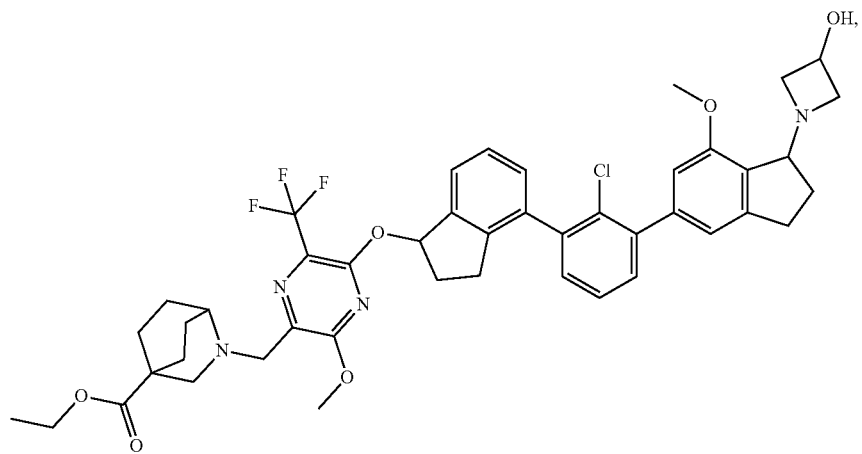

-continued
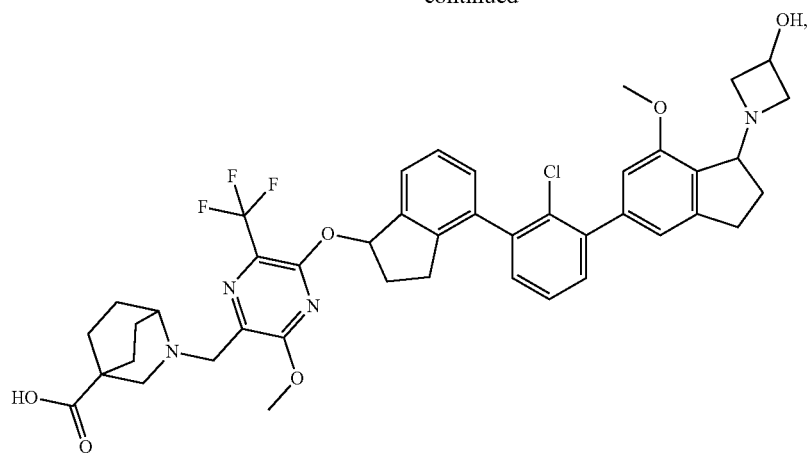
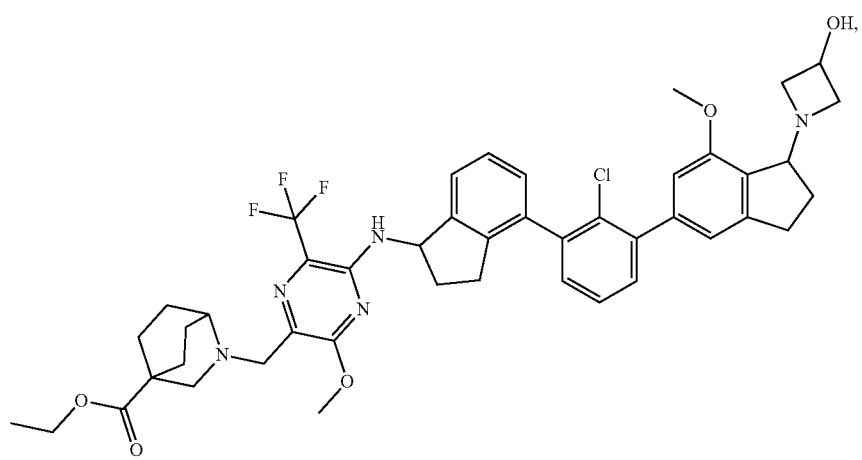
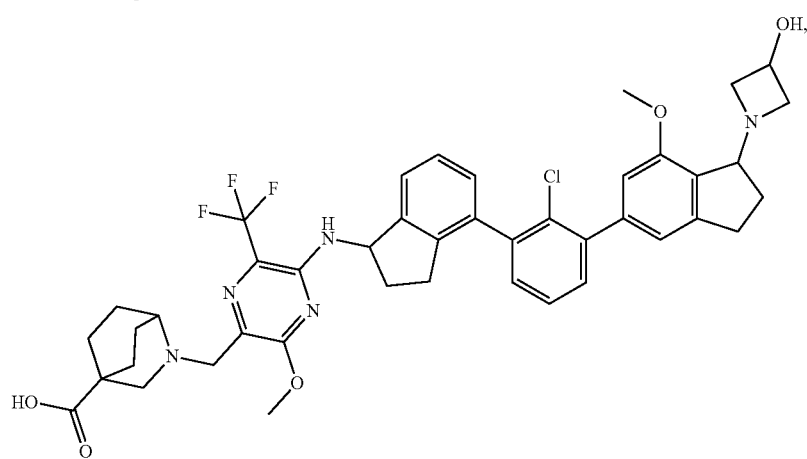
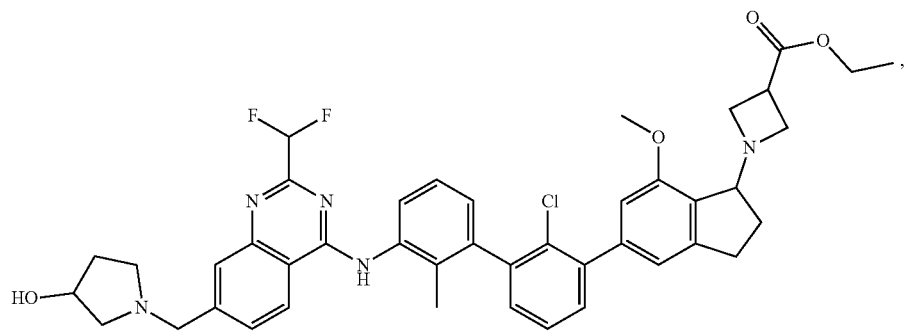

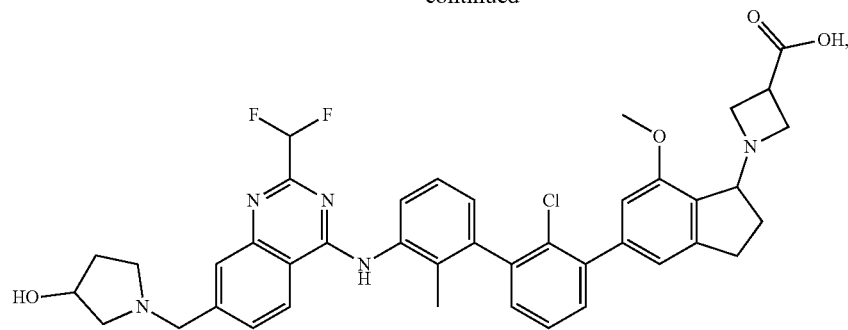
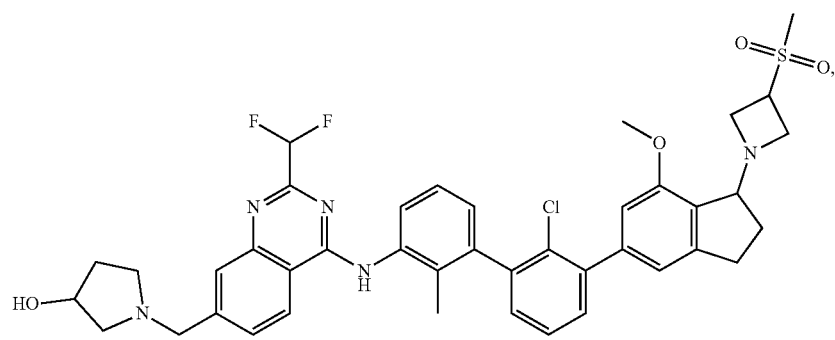
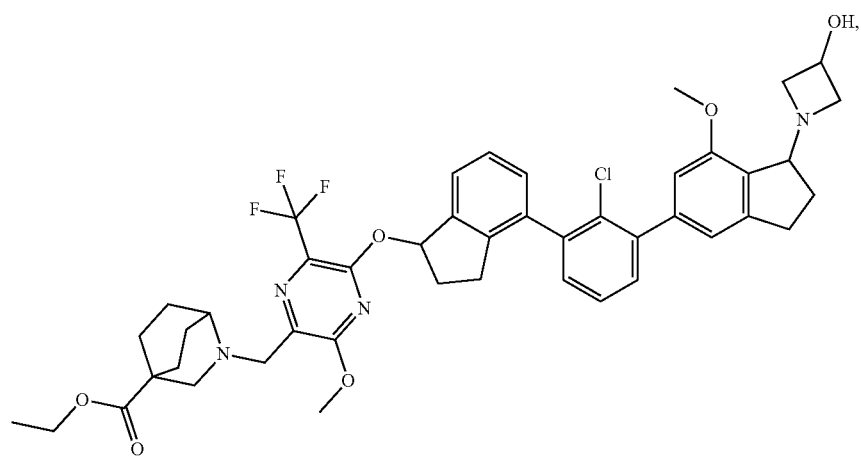
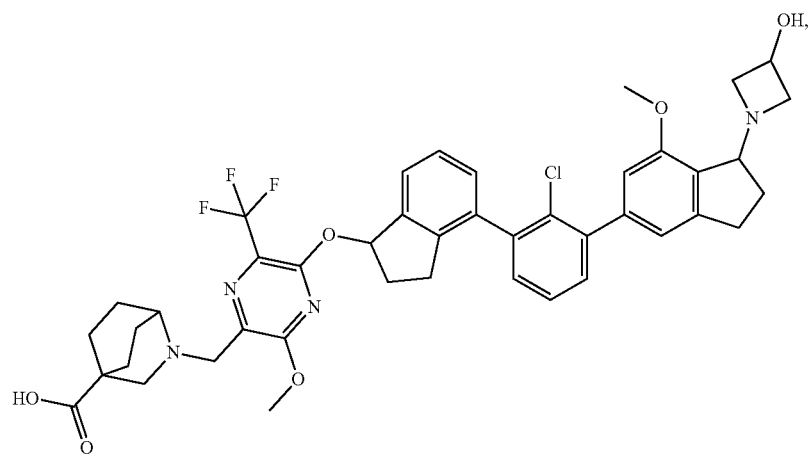

-continued
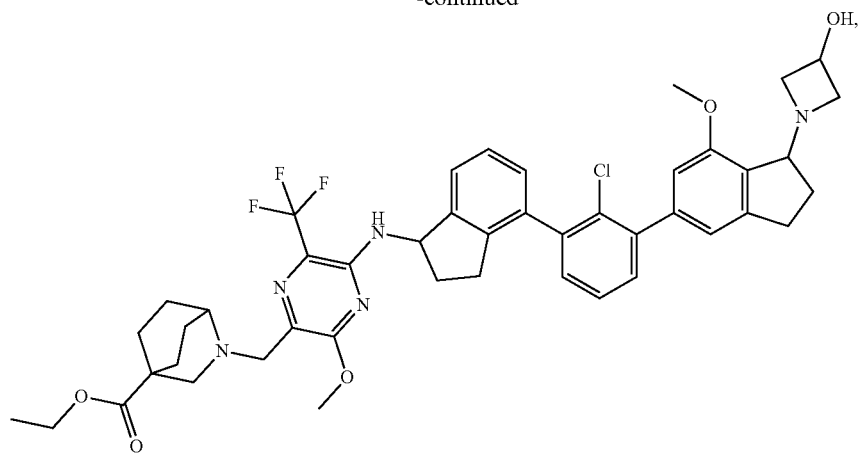
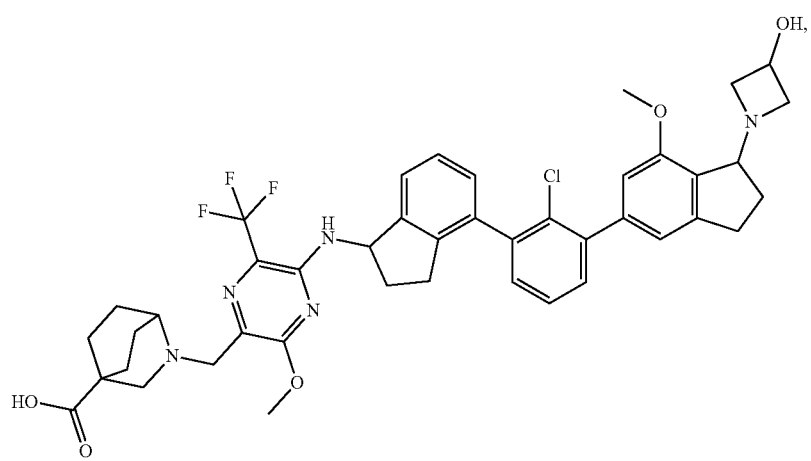
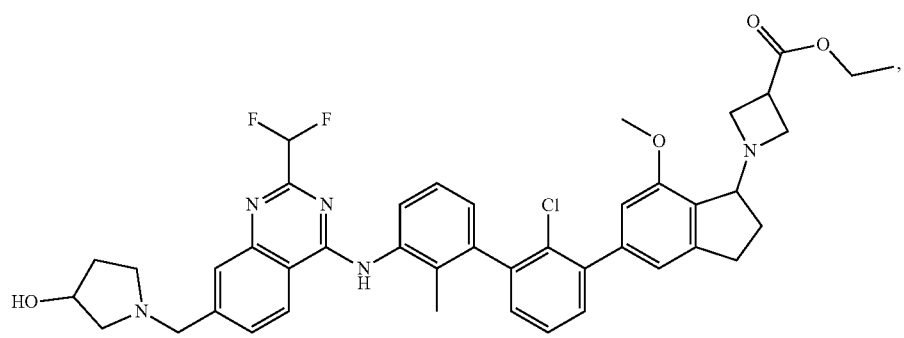
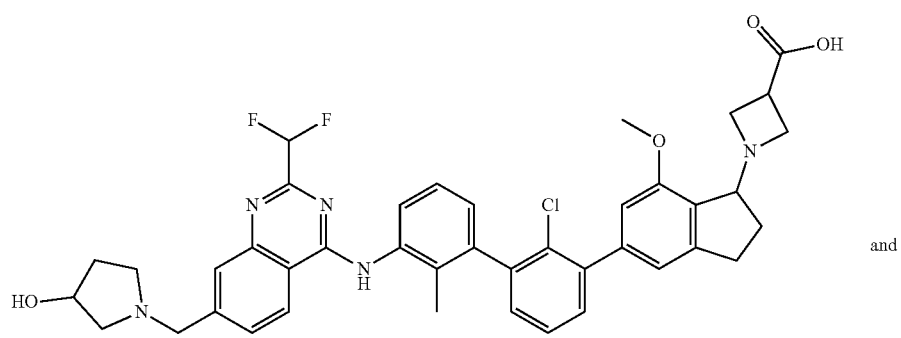
and

-continued

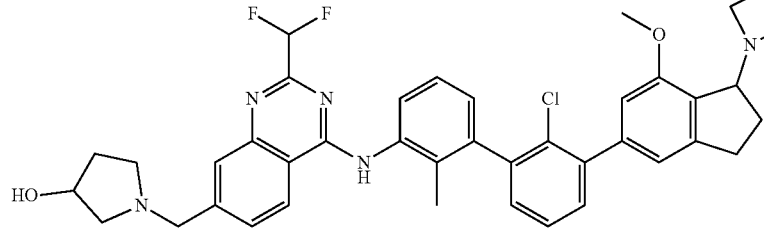

or a pharmaceutically acceptable salt of any of the foregoing.

25. A method for treating hepatitis B comprising administering to a subject suffering from hepatitis B an effective amount of a compound of claim 1, or a pharmaceutically acceptable salt thereof.

26. A method for treating hepatocellular carcinoma (HCC) in a subject comprising administering to a subject suffering from hepatocellular carcinoma (HCC) an effective amount of a compound of claim 1, or a pharmaceutically acceptable salt thereof.

* * * * *